(12) United States Patent
Gieseke et al.

(10) Patent No.: US 11,865,159 B2
(45) Date of Patent: Jan. 9, 2024

(54) THERAPEUTIC RNA

(71) Applicant: Sanofi, Paris (FR)

(72) Inventors: Friederike Gieseke, Mainz (DE); Ugur Sahin, Mainz (DE); Timothy R. Wagenaar, Sudbury, MA (US); Dmitri G. Wiederschain, Bridgewater, NJ (US); Christian Hotz, Mainz (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 17/245,605

(22) Filed: Apr. 30, 2021

(65) Prior Publication Data

US 2021/0290730 A1    Sep. 23, 2021

Related U.S. Application Data

(60) Division of application No. 16/552,248, filed on Aug. 27, 2019, which is a continuation of application No. PCT/US2018/019878, filed on Feb. 27, 2018.

(60) Provisional application No. 62/597,527, filed on Dec. 12, 2017, provisional application No. 62/464,981, filed on Feb. 28, 2017.

(30) Foreign Application Priority Data

Aug. 23, 2017   (EP) ..................... 17306089

(51) Int. Cl.

| | |
|---|---|
| *A61K 38/20* | (2006.01) |
| *A61P 35/00* | (2006.01) |
| *A61K 9/00* | (2006.01) |
| *A61K 38/09* | (2006.01) |
| *A61K 38/21* | (2006.01) |
| *A61K 48/00* | (2006.01) |
| *A61K 39/395* | (2006.01) |
| *A61K 38/19* | (2006.01) |

(52) U.S. Cl.
CPC .......... *A61K 38/208* (2013.01); *A61K 9/0019* (2013.01); *A61K 38/193* (2013.01); *A61K 38/2086* (2013.01); *A61K 38/212* (2013.01); *A61K 39/3955* (2013.01); *A61K 48/00* (2013.01); *A61P 35/00* (2018.01)

(58) Field of Classification Search
CPC ................ A61K 38/208; A61K 38/193; A61K 38/2086; A61K 38/212
See application file for complete search history.

(56) References Cited

U.S. PATENT DOCUMENTS

| | | | |
|---|---|---|---|
| 4,816,567 A | 3/1989 | Cabilly et al. |
| 5,116,964 A | 5/1992 | Capon et al. |
| 5,595,756 A | 1/1997 | Bally et al. |
| 8,008,449 B2 | 8/2011 | Korman et al. |
| 8,067,227 B2 | 11/2011 | Wähler et al. |
| 8,354,509 B2 | 1/2013 | Carven et al. |
| 8,609,089 B2 | 12/2013 | Langermann et al. |
| 9,205,148 B2 | 12/2015 | Langermann et al. |
| 9,987,500 B2 | 6/2018 | Papadopoulos et al. |
| 2003/0118564 A1 | 6/2003 | Molling et al. |
| 2006/0088836 A1 | 4/2006 | Wohlgemuth et al. |
| 2009/0028857 A1 | 1/2009 | Li et al. |
| 2009/0238791 A1 | 9/2009 | Jacques et al. |
| 2013/0259923 A1 | 10/2013 | Bancel et al. |
| 2015/0203579 A1 | 7/2015 | Papadopoulos et al. |
| 2016/0272708 A1 | 9/2016 | Chen |
| 2016/0311879 A1 | 10/2016 | Sopczynski et al. |
| 2016/0331844 A1 | 11/2016 | Fotin-Mleczek et al. |
| 2016/0376367 A1 | 12/2016 | Yuan et al. |
| 2017/0080104 A1 | 3/2017 | Irvine et al. |

FOREIGN PATENT DOCUMENTS

| | | |
|---|---|---|
| CN | 105031630 A | 11/2015 |
| EP | 1442750 A1 | 8/2004 |
| EP | 1537878 A1 | 6/2005 |
| EP | 2623121 A1 | 8/2013 |
| EP | 2700708 B1 | 8/2017 |
| EP | 3173092 B1 | 6/2019 |
| EP | 3492109 B1 | 3/2020 |
| KR | 1020160010398 A | 1/2016 |
| NO | 2003059381 A3 | 1/2004 |
| WO | 2001062274 A1 | 8/2001 |
| WO | 2003051401 A2 | 6/2003 |
| WO | 2002098443 A3 | 11/2003 |
| WO | 2003051401 A3 | 12/2003 |
| WO | 2004035799 A2 | 4/2004 |
| WO | 2006008154 A1 | 1/2006 |
| WO | 2006024518 A1 | 3/2006 |
| WO | 2006121168 A1 | 11/2006 |
| WO | 2007024708 A2 | 3/2007 |
| WO | 2006122828 A3 | 5/2007 |
| WO | 2009014708 A2 | 1/2009 |
| WO | 2009034172 A1 | 3/2009 |
| WO | 2009046738 A1 | 4/2009 |
| WO | 2009046739 A1 | 4/2009 |
| WO | 2009095226 A2 | 8/2009 |
| WO | 2009114816 A2 | 9/2009 |

(Continued)

OTHER PUBLICATIONS

Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000, 10:398-400 (Year: 2000).*

(Continued)

*Primary Examiner* — Vanessa L. Ford
*Assistant Examiner* — Sandra Dillahunt
(74) *Attorney, Agent, or Firm* — McNeill Baur PLLC

(57) ABSTRACT

This disclosure relates to the field of therapeutic RNAs for treatment of solid tumor cancers.

30 Claims, 87 Drawing Sheets

Specification includes a Sequence Listing.

(56) References Cited

FOREIGN PATENT DOCUMENTS

| | | | |
|---|---|---|---|
| WO | 2009149539 A1 | 12/2009 | |
| WO | 2010037408 A1 | 4/2010 | |
| WO | 2011071931 A2 | 6/2011 | |
| WO | 2011119773 A1 | 9/2011 | |
| WO | 2012006376 A2 | 1/2012 | |
| WO | 2012045075 A1 | 4/2012 | |
| WO | 2011161699 A3 | 5/2012 | |
| WO | 2012116714 A1 | 9/2012 | |
| WO | 2012116715 A1 | 9/2012 | |
| WO | 2012145493 A1 | 10/2012 | |
| WO | 2013053775 A1 | 4/2013 | |
| WO | 2013120497 A1 | 8/2013 | |
| WO | 2014066527 A2 | 5/2014 | |
| WO | 2014066527 A3 | 7/2014 | |
| WO | 2014153052 A2 | 9/2014 | |
| WO | 2014179664 A2 | 11/2014 | |
| WO | 2014127917 A8 | 12/2014 | |
| WO | 2014206107 A1 | 12/2014 | |
| WO | 2015024664 A1 | 2/2015 | |
| WO | 2015024666 A1 | 2/2015 | |
| WO | 2015035606 A1 | 3/2015 | |
| WO | 2015048744 A1 | 4/2015 | |
| WO | 2015085847 A1 | 6/2015 | |
| WO | 2015095249 A1 | 6/2015 | |
| WO | WO-2015095249 A1 * | 6/2015 | ......... A61K 31/7088 |
| WO | 2015112800 A1 | 7/2015 | |
| WO | 2015112900 A1 | 7/2015 | |
| WO | 2016005324 A1 | 1/2016 | |
| WO | 2015092419 A1 | 6/2016 | |
| WO | 2016112983 A1 | 7/2016 | |
| WO | 2015095249 A8 | 8/2016 | |
| WO | 2016170176 A1 | 10/2016 | |
| WO | 2016176330 A1 | 11/2016 | |
| WO | 2017019846 A1 | 2/2017 | |
| WO | 2017025016 A1 | 2/2017 | |
| WO | 2017027843 A1 | 2/2017 | |
| WO | 2017040790 A1 | 3/2017 | |
| WO | 2017079112 A1 | 5/2017 | |
| WO | 2017123675 A1 | 7/2017 | |
| WO | 2018033254 A2 | 2/2018 | |
| WO | 2020041655 A1 | 2/2020 | |
| WO | 2020154187 A1 | 7/2020 | |
| WO | 2020154189 A1 | 7/2020 | |

OTHER PUBLICATIONS

Bowie et al. Deciphering the message in protein sequences: tolerance to amino acid substitutuions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Lazar et al. Transforming Growth Factor ox: Mutation of Aspartic Acid 47 and Leucine 48 Results in Different Biological Activities. Mol. Cell. Biol., 8:1247-1252, 1988 (Year: 1988).*

Bork. Powers and Pitfalls in Sequence Analysis: The 70% Hurdle. Genome Research, 2000, 10:398-400 (Year: 2000).*

Berensmeier S. "Magnetic particles for the separation and purification of nucleic acids" Appl Microbiol Biotechnol. 73(3):495-504 (2006).

Bernardo, M. et al. Mechanism of action of a novel mRNA-based cytokine mixture for cancer immunotherapy, Global R&D Science Awards Ceremony, poster (2018).

Bernardo, M. et al. "Generation and characterization of a PD-1 resistant mouse tumormodel. 34th Annual Meeting & Pre-Conference Programs of the Society for for Immunotherapy of Cancer (SITC 2019) : part 1" Journal for Immunotherapy of Cancer, vol. 7, No. S1, P283, Nov. 6, 2019 (Nov. 6, 2019), pp. 152-153.

Bossi L et al., "The influence of codon context on genetic code translation" Nature. 286(5769):123-7 (1980).

Castillo A et al., "Rapid isolation of mycoviral double-stranded RNA from Botrytis cinerea and *Saccharomyces cerevisiae*" Virol J. 8:38 (2011).

Charette and Gray, "Pseudouridine inRNA: What, Where, How, and Why" Life, vol. 49, 2000, pp. 341-351.

Chong et al., 1998, "Tumour cell expression of B7 costimulatory molecules and interleukin-12 or granulocyte-macrophage colony stimulating factor induces a local antitumour response and may generate systemic protective immunity", Gene Therapy 5:223-232.

Coughlin et al., 1995, "B7-1 and Interleukin 12 Synergistically Induce Effective Antitumor Immunity", Cancer Res. 55:4980-4987.

Cross, R. "Can mRNA disrupt the drug industry?" Chemical and Engineering News, vol. 96 (35) Sep. 3, 2018.

Day PR et al., "Double-stranded RNA in Endothia parasitica" Phytopathology 67:1393 (1977).

Floros, T., et al. Anticancer Cytokines: Biology and Clinical Effects of Interferon-[alpha]2, Interleukin (IL)-2, IL-15, L-21, and IL-12', Seminars in Oncology, vol. 42, No. 4, Aug. 1, 2015 (Aug. 1, 2015), pp. 539-548.

Grudzien-Nogalska E. et al. (2013) Synthetic mRNAs with Superior Translation and Stability Properties. In: Rabinovich P. (eds) Synthetic Messenger RNA and Cell Metabolism Modulation. Methods in Molecular Biology (Methods and Protocols), vol. 969:55-72.

Gustave Roussy "Early trial solid tumors" CSET 2900, retrieved from the internet at https://www.gustaveroussy.fr/fr/cset-2900 on Mar. 23, 2020.

Gustave Roussy, "TED15297 The first-in-human phase 1, dose escalation and extension study to evaluate the safety, pharmacokinetics, pharmacodynamics, and antitumor activity of SAR441000, intratumorally administered monotherapy and in combination with cemiplimab in patients with advanced solid tumors" on the web at: https://translate.google.com/translate?hl=en&sl=fr&u=https://www.gustaveroussy.fr/fr/cset-2900&prev=search (accessed Sep. 30, 2019).

Hernandez-Alcoceba et al: "Cytokines for the treatment of gastrointestinal cancers: Clinical experience and new perspectives" Expert Opinion On Investigational D, Informa Healthcare, UK, vol. 22, No. 7, pp. 827-841 (Jan. 1, 2013).

Hoerr, 2006, Abstract OP 57, "Stabilized Messenger RNA (RNActive™) as a Tool for Innovative Gene Delivery", presented at the BioStar 2006 2nd International Congress on Regenerative Biology and ICBN 2006 2nd International Congress on Bio-Nano-Interface held on Oct. 9 to 11, 2006, published in Tissue Engineering 13:886-887, Apr. 2007.

Holtkamp et al., "Modification of antigen-encoding RNA increases stability, translational efficacy, and T-cell stimulatory capacity of dendritic cells" 2006, Blood, vol. 108, pp. 4009-4017.

International Search Report and Written Opinion for PCT/US2018/019878 dated Apr. 19, 2018.

International Search Report and Written Opinion issued in PCT/US2019/047819 dated Dec. 9, 2019.

International Search Report and Written Opinion issued in PCT/US2020/014019 dated May 12, 2020.

International Search Report and Written Opinion issued in PCT/US2020/014039 dated Apr. 29, 2020.

Irwin et al., "Codon pair utilization biases influence translational elongation step times" J Biol Chem. 270(39):22801-6 (1995).

Jaiswal, A. R. et al. "Melanoma Evolves Complete Immunotherapy Resistance through the Acquisition of a Hypermetabolic Phenotype" Cancer Immunol Res 2020;8:1365-80.

Jenkins, R. W., et al. "Ex Vivo Profiling of PD-1 Blockade Using Organotypic Tumor Spheroids", Cancer Discovery, vol. 8, No. 2, Nov. 3, 2017 (Nov. 3, 2017), pp. 196-215.

Jiang,C et al. "Construction of a Single-Chain Interleukin-12-Expressing Retroviral Vector and Its Application in Cytokine Gene Therapy again Experimental Coccidioidomycosis" 1999, Infection and Immunity, 67 (6), 2996-3001.

Karikó et al. "Generating the optimal mRNA for therapy: HPLC purification eliminates immune activation and improves translation of nucleoside-modified, protein-encoding mRNA" Nucleic Acids Res. 39(21):e142 (2011).

(56) References Cited

OTHER PUBLICATIONS

Kuhn AN et al, "Phosphorothioate cap analogs increase stability and translational efficiency of RNA vaccines in Immature dendritic cells and induce superior immune responses in vivo" Gene Ther. 17(8):961-71 (2010).

Mahvi, DM, et al. "Interatumoral injection of IL-12 plasmid DNA—results of a phase I/IB clinical trial" Cancer Gene Therapy (2007) 14, 717-723.

Malkova, N. V. et al. "Combination of local mRNA immunotherapy with systemic immune checkpoint blockade demonstrates antitumor activity across a diverse range of preclinical syngeneic tumor models" AACR Poster, Jun. 2020.

Middleton, M.R., et al."Intratumoural immunotherapies for unresectable and metastatic melanoma: current status and future perspectives" British Journal of Cancer, Jul. 2020, pp. 1-13.

Morris TJ et al., "solation and Analysis of Double-Stranded RNA from Virus-Infected Plant and Fungal Tissue" Phytopathology 69:854-858 (1979).

Neddleman and Wunsch, "A general method applicable to the search for similarities in the amino acid sequence of two proteins" 1970, J. Mol. Biol. 48, 443.

Nowicki, T. S. "Mechanisms of Resistance to PD-1 and PD-L1 blockade" Cancer J., 2018 ; 24(1): 47-53.

Pascola, 2006, "Vaccination with Messenger RNA", Methods in Molecular Medicine 127:23-40.

Pearson and Lipman, "Improved tools for biological sequence comparison" 1988, Proc. Natl Acad. Sci. USA 88, 2444.

Pierce et al., 2015 "In-situ tumor vaccination: Bringing the fight to the tumor" Human Vaccines & Immunotherapeutics, 11:8, 1901-1909.

Pützer et al., 1997, "Interleukin 12 and B7-1 costimulatory molecule expressed by an adenovirus vector act synergistically to facilitate tumor regression", Proc. Natl. Acad. Sei. USA 94:10889-10894.

Pützer et al., 2001, "Large Nontransplanted Hepatocellular Carcinoma in Woodchucks: Treatment With Adenovirus-Mediated Delivery of Interleukin 12/B7.1" Genes, J. Natl. Cancer Institute 93:472-479.

Quetglas, et al., "Virotherapy with a Semliki Forest Virus-Based Vector Encoding IL12 Synergizes with PD-1/PD-L1 Blockade" Cancer Immunol Res May 3, 2015 3 (5) 449-454.

Raab D et al., "The GeneOptimizer Algorithm: using a sliding window approach to cope with the vast sequence space In multiparameter DNA sequence optimization" Syst Synth Biol. 4(3):215-25 (2010).

Rodig, et al. "MHC proteins confer differential sensitivity to CTLA-4 and PD-1 blockade in untreated metastatic melanoma" Sci. Transl. Med 10, Jul. 18, 2018, p. 1-13.

Rodriguez-Madoz et al., "Semliki Forest Virus Vectors Engineered to Express Higher IL-12 Levels Induced Efficient Elimination of Murine Colon Adenocarcinomas" 2005, Molecular therapy, vol. 12,n°1, p. 153-163.

Sade-Feldman, M. et al. "Resistance to checkpoint blockade therapy through inactivation of antigen presentation" , Nature Communications, vol. 8, No. 1, Oct. 26, 2017 (Oct. 26, 2017).

Sahin et al., "mRNA-based therapeutics—developing a new class of drugs" 2014, Nature Reviews, vol. 13, p. 759-780.

Saika et al., 2004, "Route of administration influences the anti tumor effects of bone marrow-derived dendritic cells engineered to produce interleukin-12 in a metastatic mouse prostate cancer model", Cancer Gene Therapy 11:317-324.

Sharma, P., et al. "Primary, Adaptive, and Acquired Resistance to Cancer Immunotherapy", Cell, vol. 168, No. 4, Feb. 9, 2017 (Feb. 9, 2017), pp. 707-723.

Shi, et al., "Single-nucleotide polymorphisms of the IL-12 gene lead to a hight cancer risk: a meta-analysis based on 22.670 subjects" Genes Genet. Syst. (2017) 92:173-187.

Smerdou et al., "Two-Helper RNA Systems for Production of Recombinant Semliki Forest Virus Particles"1999, Journal of Virology, vol. 73, n°2, p. 1092-1098.

Smith and Waterman, "Comparison of biosequences" 1981, Ads App. Math. 2, 482.

Tatsumi et al., 1999, "B7-1 (CD80)-Gene Transfer Combined With Interleukin-12 Administration Elicits Protective and Therapeutic Immunity Against Mouse Hepatocellular Carcinoma", Hepatology 30:422-429.

U.S. Appl. No. 62/314,322, by Dean Falb, et al., entitled Microorganisms Programmed to Produce Immune Modulators and Anti-Cancer Therapeutics in Tumor Cells, filed Mar. 28, 2016.

Van Der Jeught, et al., "Targeting the tumor microenvironment to enhance antitumor immune responses" Oncotarget, 6(3): 1359-1381 (2014).

Van Der Jeught, et al., "Intratumoral delivery of mRNA: Overcoming obstacles for effective immunotherapy" Oncoimmunology, 4 (5), e1005504 (2015).

ViralZone, "Positive stranded RNA virus replication" Retrieved from "https://viralzone.expasy.org/1116", downloaded from the internet Mar. 3, 2020.

Vom Berg, et al., "Intratumoral IL-12 combined with CTLA-4 blockade elicits T cell-mediated glioma rejection" Journal of Experimental Medicine 210 (13), 2803-2811 (2013).

Wagenaar, T. et al "Combinatorial treatment with intratumoral cytokine mRNA's results in high frequencey of tumor rejection and development of anti-tumor immunity across a range of preclinical cancer models" Poster #LB-130, presented at AACR Apr. 14, 2018.

Wikipedia, Jan. 30, 2020, "Alphavirus" Retrived from: https://en.wikipedia.org/wiki/Alphavirus on Mar. 3, 2020.

Yamamoto et al., 2009, "Current prospects for mRNA gene delivery", Euro. J. Pharm. Biopharm. 71 :484-489.

Zitvogel et al., 1996, "Interleukin-12 and B7 .1 co-stimulation cooperate in the induction of effective antitumor immunity and therapy of established tumors", Eur. J. Immunol. 26:1335-1341.

Beans "Targeting metastasis to halt cancer's spread" PNAS 2018; 115(50): 12539-12543.

Bork "Powers and Pitfalls in Sequence Analysis: The 70% Hurdle" Genome Research, 2000, 10:398-400.

Bowie et al. "Deciphering the Message in Protein Sequences: Tolerance to Amino Acid Substitutions." Science, 1990, 247:1306-1310.

Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". J. Cell Biol. 111 :2129-2138, 1990.

Gravanis et al. "The changing world of cancer drug development: the regulatory bodies' perspective" Chin Clin Oneal, 2014, 3, pp. 1-5.

Hait. "Anticancer drug development: the grand challenge" Nature Reviews/Drug Discovery, 2010, 9, pp. 253-254.

Heppner et al. "Tumor heterogeneity: biological implications and therapeutic consequences" Cancer Metastasis Review 2:5-23; 1983.

Jain RK. "Barriers to drug delivery in solid tumors" Scientific American, Jul. 1994, 58-65.

Lazar et al. "Transforming Growth Factor alpha: Mutation of Aspartic Acid 47 and Leucine 48 Results in Different Biological Activities." Mol. Cell. Biol., 8:1247-1252, 1988.

Press Release: "Sanofi and BioNTech Announce Cancer Immunotherapy Collaboration and License Agreement" dated Nov. 3, 2015. Retrieved from: https://www.sanofi.com/en/media-room/press-releases/2015/2015-11-03-07-00-00.

Liechtenstein et al., s (2014) Anti-melanoma vaccines engineered to simultaneouslymodulate cytokine priming and silence PD-L1 characterized using ex_x0001_vivo myeloid-derivedsuppressor cells as a readout of therapeutic efficacy, OncoImmunology, 3:7.

Lundstrom, Alphaviruses in Gene Therapy, Viruses 7 (2015), pp. 2321-2333.

Marabelle, A. et al., Starting the fight in the tumor: expert recommendations for the development of human intratumoral immunotherapy (HIT-IT). Ann. Oncol. 29, 2163-2174 (2018).

Martinon et al., (1993) "Induction of virus-specific cytotoxic T lymphocytes in vivo by liposomeentrapped mRNA", Eur. J. Immunol. 23: 1719-1722.

(56) References Cited

OTHER PUBLICATIONS

MED/1191 program update, D103 from EP opposition in EP16166757.1 as identified on the Consolidated List dated Oct. 15, 2021.
Melero et al. Strict Requirement for Vector-Induced Type I Interferon in Efficacious Antitumor Responses to Virally Encoded IL 12; Cancer Res. 75(3) (2015), pp. 497-507.
Melo-Cardenas et al. Intratumoral delivery of CD154 homo log (Ad-ISF35) induces tumor regression: analysis of vector piodistribution, persistence and gene expression, Cancer Gene Therapy 19 (2012), pp. 336-344.
Momin et al., "Anchoring of intratumorally administered cytokines to collagen safely potentiates systemic cancer immunotherapy" Sci. Transl. Med. 11, eaaw2614 (2019).
Mortier, E. et al., Soluble interleukin-15 receptor a (IL-15R a)-sushi as a selective and potent agonist of IL-15 action through IL-15Rb/g: Hyperagonist IL-15 • IL-15Ra fusion proteins. J. Biol. Chem. 281, 1612-1619 (2006).
Orlandini von Niessen, A. G. et al., Improving mRNA-based therapeutic gene delivery by expression-augmenting 3' UTRs identified by cellular library screening. Mol. Ther. 27, 824-836 (2019).
Pardi et al., 2015 "Expression kinetics of nucleoside-modified mRNA delivered in lipid nanoparticles to mice by various routes" Journal of Controlled Release, accepted manuscript.
Pardoll et al. (2012), "The blockade of immune checkpoints in cancer immunotherapy", Nature Reviews Cancer 12(4): 252-264.
Quesada, J. R. et al., Clinical toxicity of interferons in cancer patients: A review. J. Clin. Oncol. 4, 234-243 (1986).
Quetglas et al. "Alphavirus vectors for cancer therapy" Virus Research, 153 (2010) 179-196.
Rodriguez-Gascon et al. "Development of nucleic acid vaccines: use of self-amplifying RNA in lipid nanoparticles" International Journal of Nanomedicine (2014) 9: 1833-1843.
Rodriguez-Madoz et al. "Semliki Forest Virus Vectors Engineered to Express Higher IL-12 Levels Induce Efficient Elimination of Murine Colon Adenocarcinomas" Molecular Therapy, (2005) 12(1):153-163.
Sahin et al., "mRNA-based therapeutics—developing a new class of drugs." Nat Rev Drug Discov 13, 759-780 (2014).
Sato et al.(2011) "Interleukin 10 in the tumor microenvironment: a target for anticancer immunotherapy", Immunol Res. 51 (2-3):170-82.
Sautès-Fridman, C. et al., Tertiary lymphoid structures in the era of cancer immunotherapy. Nat. Rev. Cancer 19, 307-325 (2019).
Sayour et al. (Apr. 21, 2015), "Bridging infectious disease vaccines with cancer immunotherapy: a role for targeted RNA based immunotherapeutics", Journal for Immuno Therapy of Cancer3:13 (pp. 1-7).
Scheel et al., Toll-like receptor-dependent activation of several human blood cell types by protamine-condensed MRNA; Eur. J. Immunol. 35 (2005), pages.
Schirrmacher, V., Forg, P., Dalemans, W et al. Intra-pinna antitumor vaccination with self-replicating infectious RNA or with DNA encoding a model tumor antigen and a cytokine. Gene Ther 7, 1137-1147 (2000).
Seder, R. A. et al., T-cell quality in memory and protection: Implications for vaccine design. Nat. Rev. Immunol. 8, 247-258 (2008).
Selby, M.J. et al., Anti-CTLA-4 antibodies of IgG2a isotype enhance antitumor activity through reduction of intratumoral regulatory T cells. Cancer Immunol. Res. 1, 32-42 (2013).
Sharma, P. et al., Primary, adaptive, and acquired resistance to cancer immunotherapy. Cell 168, 707-723 (2017).
Singh et al., 2015 "Intratumoral immunotherapy for melanoma" Cancer Immunol Immunother, pp. 1-11.
Singh et al., An alphavirus-based therapeutic cancer vaccine: from design to clinical trial, Cancer Immunology, Immunotherapy 68 (2019), pp. 849-859.
Smerdou et al., 1999, Journal of Virology, vol. 73, n°2, p. 1092-1098.
Stadler et al., 2017 "Elimination of large tumors in mice by mRNA-encoded bispecific antibodies", Nature Medicine, 1-6.
Summary of Product Characteristics for Kymriah, D94 from EP opposition in EP16166757.1 as identified on the Consolidated List dated Oct. 15, 2021.
Summary of Product Characteristics for Yescarta, D95 from EP opposition in EP16166757.1 as identified on the Consolidated List dated Oct. 15, 2021.
Supplementary Figures 1 and (2018), D89 from EP opposition in EP16166757.1 as identified on the Consolidated List dated Oct. 15, 2021.
Tavernier et al. (2011 ), "mRNA as gene therapeutic : how to control protein expression ", J Controlled Release 150:238-247.
Triozzi et al., 2015—Phase I Study of the Intratumoral Administration of Recombinant Canarypox Viruses Expressing B7.1 and Interleukin 12 in Patients with Metastatic.
Tugues et al., "New insights into IL-12-mediated tumor suppression" Cell Death Differ 22, 237-246 (2015).
Ugen, KE et al. "Regression of subcutaneous B16 melanoma tumors after intratumoral delivery of an IL-15-expressing plasmid followed by in vivo electroporation" Cancer Gene Ther. Oct. 2006;13(10):969-74.
Van der Jeught et al., Intratumoral administration of mRNA encoding a fusokine consisting of IFN-p and the ectodomain of the TGF-β receptor II potentiates antitumor immunity; Oncotarget. 5(20) (2014), pp. 10100-10113.
Van Lint et al., 2015—Intratumoral Delivery of TriMix mRNA Results in T-cell Activation by Cross-Presentina Dendritic Cells.
Van Lint et al., The ReNAissanCe of mRNA-based cancer therapy; Expert Rev. Vaccines Early online (2014), pp. 1-17.
Van Lint, S. et al., Intratumoral delivery of TriMix mRNA results in T-cell activation by cross-presenting dendritic cells. Cancer Immunol. Res. 4, 146-156 (2016).
Weber et al., (2010) "Immune Checkpoint Proteins: A New Therapeutic Paradigm for Cancer-Preclinical Background: CTLA-4 and PD-1 Blockade" Seminars in Oncology. 37(5):430-439.
Weiss, JM et al., "Immunotherapy of cancer by IL-12-based cytokine combinations" Expert Opin Biol Ther. Nov. 2007;(11):1705-21.
Wilgenhof et al. (2013), "A phase IB study on intravenous synthetic mRNA electroporated dendritic cell immunotherapy in pretreated advanced melanoma patients", Annals of Oncology 24(10):2686 -2693.
Wulff, H., et al. "Cloning and characterization of an adenoviral vector for highly efficient and doxycycline—suppressible expression of bioactive human single-chain interleukin 12 in colon cancer." BMC biotechnology. Jun. 26, 2007. vol. 7, No. 1, p. 1-9.
Zaidi, M. R. and Merlino, G., The two faces of interferon-g in cancer. Clin. Cancer Res. 17, 6118-6124 (2011).
Zhang, J. et al., In situ administration of cytokine combinations induces tumor regression in mice. EBioMedicine 37, 38-46 (2018).
Ammi et al. (2014), "Poly(I:C) as cancer vaccine adjuvant: Knocking on the door of medical breakthroughs", Pharmacology and Therapeutics 146: 1 20131.
Amos et al. (2011 ), "Adoptive immunotherapy combined with intratumoral TLR agonist delivery eradicates established melanoma in mice", Cancer Immunoloav and Immunotheraov 60(s5):671-683.
Ardolino, M. et al., Cytokine therapy reverses NK cell anergy in MHC-deficient tumors. J. Clin. Invest. 124, 4781-4794 (2014).
Ayers, M. et al., IFN-g-related mRNA profile predicts clinical response to PD-1 blockade. J. Clin. Invest. 127, 2930-2940 (2017).
Baiersdörfer, M. et al., A facile method for the removal of dsRNA contaminant from in vitro-transcribed mRNA. Mol. Ther. Nucleic Acids 15, 26-35 (2019).
Barratt, (2000) "Therapeutic applications of colloidal drug carriers", PSTT 3(5):163-171.
Berraondo, P. et al., Cytokines in clinical cancer immunotherapy. Br. J. Cancer 120, 6-15 (2019).
Bloom et al. "Self-amplifying RNA vaccines for infection diseases" Gene Therapy (2020) pp. 1-13.
Bontkes et al. (2008), "Tumor associated antigen and interleukin-12 mRNA transfected dendritic cells enhance effector function of natural killer cells and antigen specific T-cells", Clinical Immunology 127(3):375-384.

(56) References Cited

OTHER PUBLICATIONS

Brunda. M.J. et al. "Antitumor and antimetastatic activity of interleukin 12 against murine tumors" J. Exp. Med. 178, 1223-1230 (1993).
Chikkana-Gowda et al. Regression of mouse tumours and inhibition of metastases following administration of a Semliki Forest virus vector with enhanced expression of IL-12 Gene Therapy 12 (2005), pp. 1253-1263. (D20 of the OA of Jul. 26, 2018).
Cohen, J., IL-12 deaths: Explanation and a puzzle. Science 270, 908 (1995).
Consolidated List from EP Opposition in EP16166757.1 dated Oct. 15, 2021.
Couzin-Frankel (2013) "Breakthrough of the year 2013. Cancer immunotherapy", Science, 342(6165):1432-1433.
Cronin et al., 2012, Bacterial vectors for imaging and cancer gene theraov: a review, Cancer Gene Therapy 19:731-740.
Dagogo-Jack, I. and Shaw, A. T., Tumour heterogeneity and resistance to cancer therapies. Nat. Rev. Clin. Oncol. 15, 81-94 (2018).
Dalpke and Helm; RNA mediated toll-like receptor stimulation in health and disease rNA Bioloav 9:6, pp. 828-842.
Daud et al., Intratumoral electroporation of plasmid interleukin-12: efficacy and biomarker analyses from a phase 2 study in melanoma (OMS-1100). J Transl Med 13, O11 (2015).
EP request form for EP16166757.1, D2 from EP opposition in EP16166757.1 as identified on the Consolidated List dated Oct. 15, 2021.
EP16166757.1 office action response dated Dec. 5, 2018, D4 from EP opposition in EP16166757.1 as identified on the Consolidated List dated Oct. 15, 2021.
EP16166757.1 office action response dated Mar. 16, 2018, D3 from EP opposition in EP16166757.1 as identified on the Consolidated List dated Oct. 15, 2021.
Experimental results: IL-12 mRNA in CT26 tumor model (2020), D88 from EP opposition in EP16166757.1 as identified on the Consolidated List dated Oct. 15, 2021.
Experimental results: IL-12 mRNA in various tumor models (2020)m D93 from EP opposition in EP16166757.1 as identified on the Consolidated List dated Oct. 15, 2021.
Experimental results: IL-12 protein amounts (2020) D90 from EP opposition in EP16166757.1 as identified on the Consolidated List dated Oct. 15, 2021.
Fotin-Mleczek et al., (2012), Highly potent mRNA based cancer vaccines represent an attractive platform for combination therapies supporting an improved therapeutic effect. J Gene Med, 14: 428-439.
Fowler, "Conversation on CureVac's RNA-Based Therapeutics with CEO Ingmar Hoerr", Medgadget, (May 28, 2014), URL: https://www.medgadget.com/2014/05/conversation-on-curevacs-ma-based-therapeutics-with-ceo-ingmar-hoerr.html.
Frenzel et al., (2013) "Expression of recombinant antibodies" Frontiers in Immunology vol. 4, Artcile 217, p. 1-20.
Front page pf certified priority application No. EP15001191, D1 from EP opposition in EP16166757.1 as identified on the Consolidated List dated Oct. 15, 2021.
Fyfe, G. et al., Results of treatment of 255 patients with metastatic renal cell carcinoma who received high-dose recombinant interleukin-2 therapy. J. Clin. Oncol. 13, 688-696 (1995).
Genbank AAL01442.1, bioactive single-chain murine interleukin 12 [synthetic construct] (2001), pp. 1-2.
Haabeth, O.A.W et al., Local delivery of Ox40l, Cd80, and Cd86 mRNA kindles global anticancer immunity. Cancer Res. 79, 1624-1634 (2019).
Hashimoto, H. et al. "Type I IFN gene delivery suppresses regulatory T cells within tumors" Cancer Gene Ther. Dec. 2014;21(12):532-41.
Heidenreich et al., a novel RNA-based adjuvant combines strong immunostimulatory capacities with a favorable safety profile, Int. J.Cancer 137 (2015), pp. 372-384.
Herndon, T. M. et al, U.S. Food and Drug Administration approval: Peginterferon-alfa-2b for the adjuvant treatment of patients with melanoma. Oncologist 17, 1323-1328 (2012).
Hewitt, S.L. et al., Durable anticancer immunity from intratumoral administration of IL-23, IL-36g, and OX40L mRNAs. Sci. Transl. Med. 11, eaat9143 (2019).
Hill, HC, et al. "Cancer immunotherapy with interleukin 12 and granulocyte-macrophage colony-stimulating factor-encapsulated microspheres: coinduction of innate and adaptive antitumor immunity and cure of disseminated disease" Cancer Res. 2002;62(24):7254-7263).
Hotz, et al., "Local delivery of mRNA-encoding cytokines promotes antitumor immunity and tumor eradication across multiple preclinical tumor models" Sci. Transl. Med. 13, eabc7804 (2021).
Hotz, et al., "Local delivery of mRNA-encoding cytokines promotes antitumor immunity and tumor eradication across multiple preclinical tumor models" Sci. Transl. Med. 13, eabc7804 Suppl Materials (2021).
Jenkins, R.W. et al., Mechanisms of resistance to immune checkpoint inhibitors. Br. J. Cancer 118, 9-16 (2018).
Jiang, C et al. "Construction of a Single-Chain interleukin-12-Expressing Retroviral Vector and Its Application in Cytokine Gene Therapy against Experimental Coccidioidomycosis", 1999, Infection and Immunity, 67 (6), 2993-3001.
Jonasch, E. and Haluska, F.G., Interferon in oncological practice: Review of interferon biology, clinical applications, and toxicities. Oncologist 6, 34-55 (2001).
Kallen et al. A development that may evolve into a revolution in medicine: mRNA as the basis for novel, nucleotide-based vaccines and drugs. Therapeutic Advances in Vaccines. Jan. 2014:10-31.
Kallio et al. Template RNA Length Determines the Size of Replication Complex Spherules for Semliki Forest Virus; J. Viral. 87(16) (2013), oaaes 9125-9134.
Karikó, K. et al., Incorporation of pseudouridine into mRNA yields superior nonimmunogenic vector with increased translational capacity and biological stability. Mol. Ther. 16, 1833-1840 (2008).
Kaufmann, H.L. et al. "Current status of granulocyte-macrophage colony-stimulating factor in the immunotherapy of melanoma" J Immunother Cancer. May 13, 2014;2:11.
Kennedy, M.K. et al., Reversible defects in natural killer and memory CD8 T cell lineages in interleukin 15-deficient mice. J. Exp. Med. 191, 771-780 (2000).
Kirkwood, J. M. et al., Interferon alfa-2b adjuvant therapy of high-risk resected cutaneous melanoma: The Eastern Cooperative Oncology Group Trial EST 1684. J. Clin. Oncol. 14, 7-17 (1996).
Kudo-Saito, C. et al. "Combination therapy of an orthotopic renal cell carcinoma model using intratumoral vector-mediated costimulation and systemic interleukin-2" Clin Cancer Res. Mar. 15, 2007;13(6):1936-46.
Lee, S. and Margolin, K., Cytokines in cancer immunotherapy. Cancers 3, 3856-3893 (2011).
Li, D. et al., Combination nonviral interleukin 2 and interleukin 12 gene therapy for head and neck squamous cell carcinoma. Arch. Otolaryngol. Head Neck Surg. 127, 1319-1324 (2001).
Quetglas et al., "Immunotherapeutic Synergy Between Anti-CD137 mAb and Intratumoral Administration of a Cytopathic Semliki Forest Virus Encoding IL-12", Molecular Therapy, 20(9), pp. 1664-1675 (Sep. 2012).
Rakhmilevich et al., "Cytokine Gene Therapy of Cancer Using Gene Gun Technology: Superior Atitumor Activity of Interleukin-12", Human Gene Therapy, 8, pp. 1303-1311 (Jul. 20, 1997).
Rakhmilevich et al., "Gene Gun-Mediated IL-12 Gene Therapy Induces Antitumor Effects in the Absence of Toxicity: A Direct Comparison with Systemic IL-12 Protein Therapy", Journal of Immunotherapy, 22(2), pp. 135-144 (1999).
Rudnick et al., "Affinity and Avidity in Antibody-Based Tumor Targeting", Cancer Biotherapy and Radiopharmaceuticals, 24(2), pp. 155-161 (2009).
Sabel et al.,"Synergistic effect of intratumoral IL-12 and TNF-alpha microspheres: systemic anti-tumor immunity is mediated by both CDS+ CTL and NK cells", Surgery, 142(5), pp. 749-760 (2007).
Saffran et al., "Immunotherapy of established tumors in mice by intratumoral injection of interleukin-2 plasmid DNA: Induction of CD8+ T-cell immunity", Cancer Gene Therapy, 5(5), pp. 321-330 (1998).

(56) References Cited

OTHER PUBLICATIONS

Scheuplein et al., "Abstract 4871: Two novel anti-PD-1 antibodies, 244C8 and 388D4, elicit in vivo antitumor efficacy in a lung PDX tumorgraft in immuno-humanized NSG mice", Cancer Res, 76(14_Supplment); Abstract 4871 (2016).
Schmidt, S.R., "Fusion-proteins as biopharmaceuticals—Applications and Challenges", Current Opinion in Drug Discovery & Development, 12(2), pp. 1-12 (Apr. 2009).
Selby et al., "Preclinical Development of Ipilimumab and Nivolumab Combination Immunotherapy: Mouse Tumor Models, In Vitro Functional Studies, and Cynomolgus Macaque Toxicology", PLOS One, 11(9), pp. 1-19 (Sep. 9, 2016).
Seliger et al., "The expression, function, and clinical relevance of the B7 family members in cancer", Cancer Immunol. Immunother, 61, pp. 1327-1341 (2012).
Seymour et al., "iRECIST: guidelines for response criteria for use in trials testing immunotherapeutics", Lancet Oncol., 18(3), pp. e143-e152 (Mar. 2017).
Shimizu et al., "Stimulation of CD25+CD4+ regulatory T cells through GITR breaks immunological self-tolerance", Nature Immunology, 3(2), pp. 135-142 (Feb. 2002).
Shirabe et al., "Tumor-infiltrating lymphocytes and hepatocellular carcinoma: pathology and clinical management", International Journal of Clinical Oncology, 15, pp. 552-558 (2010).
Simeone et al., "Immunomodulating antibodies in the treatment of metastatic melanoma: The experience with anti-CTLA-4, anti-CD137, and anti-PD1", Journal of Immunotoxicology, 9(3), pp. 241-247 (2012).
Tahara et al., "Effective Eradication of Established Murine Tumors with IL-12 Gene Therapy Using a Polycistronic Retroviral Vector", The Journal of Immunology, 154, pp. 6466-6474 (1995).
Topalian et al., "Safety, Activity, and Immune Correlates of Anti-PD-1 Antibody in Cancer", N. Engl. J. Med., 366(26), pp. 2443-2454 (Jun. 2012).
Topalian et al., "Targeting the PD-1/B7-H1 (Pd-L 1) pathway to activate anti-tumor immunity", Current Opinion in Immunology, 24(2), pp. 207-212 (Apr. 2012).
Turnis et al., "Enhancement of dendritic cells as vaccines for cancer", Immunotherapy, 2(6), pp. 847-862 (Nov. 2010).
Vacchelli et al., "Trial Watch—Immunostimulation with cytokines in cancer therapy", Oncoimmunology, 5(2), e1115942 (12 pgs) (2016).
Vanneman et al., "Combining Immunotherapy and Targeted Therapies in Cancer Treatment", Nature Reviews Cancer, 12(4), pp. 237-251 (2014).
Vom Berg J., "Interleukin-12 in Combination with CTLA-4 Blockade Leads to T-cell Dependent Rejection of Advanced Stage Glioma", University of Zurich, Faculty of Medicine. ZORA URL: https://doi.org/10.5167/uzh-74786 (134 pages) (2012).
Wang et al., "Suppression of Type I IFN Signaling in Tumors Mediates Resistance to Anti-PD-1 Treatment That Can Be Overcome by Radiotherapy", Cancer Res, 77(4), pp. 839-850 (Feb. 15, 2017).
Watanabe et al., "Intradermal Delivery of IL-12 Naked DNA Induces Systemic NK Cell Activation and Th1 Response In Vivo That is Independent of Endogenous IL-12 Production", The Journal of Immunology, 163, pp. 1943-1950 (1999).
Weber et al., "Interleukin-12 Gene Transfer Results in CD8-Dependent Regression of Murine CT26 Liver Tumors", Annals of Surgical Oncology, 6(2), pp. 186-194 (1999).
Wong et al., "Programmed death-1 blockade enhances expansion and functional capacity of human melanoma antigen-specific CTLs", International Immunology, 19(10), pp. 1223-1234 (2007).
Xu et al., "Regulation of Antitumor Immune Responses by the IL-12 Family Cytokines, IL-12, IL-23, and IL-27", Clinical and Developmental Immunology, vol. 2010, Article ID 832454, pp. 1-9 (2010).
Yamazaki et al., "Blockade of B7-H1 on Macrophages Suppresses CD4+ T Cell Proliferation by Augmenting IFN-gamma-Induced Nitric Oxide Production", J Immunol 175(3), pp. 1586-1592 (2005).
Yu et al., "Simultaneous blockade of multiple immune system inhibitory checkpoints enhances anti-tumour activity mediated by interleukin-15 in a murine metastatic colon carcinoma model", Clin Cancer Res., 16(24), pp. 6019-6028 (Dec. 15, 2010).
Zabala et al., "Induction of immunosuppressive molecules and regulatory T cells counteract the antitumor effect of Interleukin-12-based gene therapy in a transgenic mouse model of liver cancer", Journal of Hepatology, 47, pp. 807-815 (2007).
Zaharoff et al., "Intratumoral immunotherapy of established solid tumors with chitosan/IL-12 ", J Immunother, 33(7), pp. 697-705 (2010).
Zaretsky et al., "Mutations Associated with Acquired Resistance to PD-1 Blockade in Melanoma", N Engl J Med, 375 (9), pp. 819-829 (Sep. 1, 2016).
Zhong et al., "Induction, Selection and Expansion of Acute Myeloid Leukemia Reactive Autologous T Cells for Adoptive Immunotherapy", Blood, 106(11), p. 1061-Abstract (2005).
Ascierto et al., "Clinical experiences with anti-CD137 and anti-PD1 therapeutic antibodies", Seminars in Oncology, 37 (5), pp. 508-516 (2010).
Aydin et al., "Spotlight on atezolizumab and its potential in the treatment of advanced urothelial bladder cancer", OncoTargets and Therapy, 10, pp. 1487-1502 (2017).
Beckman et al. "Antibody Constructs in Cancer Therapy", Cancer, 109(2), pp. 170-179 (Jan. 15, 2007).
Berenbaum, M.C., "Synergy, additivism and antagonism in immunosuppression", Clinical Experimental Immunology, 28, pp. 1-18 (1977).
Berger et al., "Phase I Safety and Pharmacokinetic Study of CT-011, a Humanized Antibody Interacting with PD-1, in Patients with Advanced Hematologic Malignancies", Clin Cancer Res., 14(10), pp. 3044-3051 (2008).
Brahmer et al., "Safety and Activity of Anti-PD-L1 Antibody in Patients with Advanced Cancer", N. Engl. J. Med., 366 (26), pp. 2455-2465 (Jun. 2012).
Bramson et al., "Direct Intratumoral Injection of an Adenovirus Expressing Interleukin-12 Induces Regression and Long-Lasting Immunity that is Associated with Highly Localized Expression of Interleukin-12", Human Gene Therapy, 7, pp. 1995-2002 (Oct. 20, 1996).
Burova et al., "Characterization of the Anti-PD-1 Antibody REGN2810 and Its Antitumor Activity in Human PD-1 Knock-In Mice", Mol. Cancer, 16(5), pp. 861-870 (May 2017).
Carson et al., "Braking Bad: Blockade of Inhibitory Pathways Improves Interleukin-15 Therapy", Clinical Cancer Research, 16(24), pp. 5917-5919 (Dec. 15, 2010).
Chang, CJ, et al., "Combined GM-CSF and IL-12 Gene Therapy Synergistically Suppresses the Growth of Orthotopic Liver Tumors", Hepatology, 45(3), pp. 746-754 (2007).
Chen, L., "Co-inhibitory molecules of the B7-CD28 family in the control of T-cell immunity", Nature Reviews Immunology, 4, pp. 336-347 (May 2004).
Cheng et al., "The PD-1/PD-L pathway is up-regulated during IL-12-induced suppression of EAE mediated by IFN-gamma", Journal of Neuroimmunology, 185(1-2), pp. 75-86 (Apr. 2007).
Cheson et al., "Recommendations for Initial Evaluation, Staging, and Response Assessment of Hodgkin and Non- Hodgkin Lymphoma: The Lugano Classification", J Clin Onc, 32(27), pp. 3059-3068 (Sep. 20, 2014).
Choi et al., "Strengthening of antitumor immune memory and prevention of thymic atrophy mediated by adenovirus expressing IL-12 and GM-CSF", Gene Therapy, 19, pp. 711-723 (2012).
Chothia et al., "Canonical Structures for the Hypervariable Regions of Immunoglobulins", J. Mol. Biol. 196, pp. 901-917 (1987).
Colombo et al., "Amount of Interleukin 12 Available at the Tumor Site is Critical for Tumor Regression", Cancer Research, 56, pp. 2531-2534 (Jun. 1, 1996).
Consolidated List from EP Opposition in EP18160057.8 dated Mar. 2, 2022.
Corzo, J., "Time, the Forgotten Dimension of Ligand Binding Teaching," Biochem Mol Biol Educ.,34(6), pp. 413-416 (2006).

(56) References Cited

OTHER PUBLICATIONS

Del Vecchio et al., "Interleukin-12: Biological Properties and Clinical Application", Clin. Cancer Res., 13(16), pp. 1677-4685 (Aug. 15, 2007).

Dunn et al., "Cancer immunoediting: from immunosurveillance to tumor escape", Nature Immunology, 3(11), pp. 991-998 (Nov. 2002).

Egilmez et al., "Controlled-release Particulate Cytokine Adjuvants for Cancer Therapy", Endocrine, Metabolic & Immune Disorders—Drug Targets, 7, pp. 266-270 (2007).

Egilmez et al., "Tumor-Resident CD8+ T-cell: The Critical Catalyst in IL-12-Mediated Reversal of Tumor Immune Suppression", Arch. Immunol. Ther. Exp., 58, pp. 399-405 (2010).

Eisenhauer et al., "New response evaluation criteria in solid tumours: Revised RECIST guideline (version 1.1)", Eur J Cancer, 45, pp. 228-247 (2009).

Eisenring et al., "IL-12 initiates tumor rejection via lymphoid tissue-inducer cells bearing the natural cytotoxicity receptor NKp46", Nature Immunology, 11(11), pp. 1030-1039 (Nov. 2010).

Falchook et al., "Responses of metastatic basal cell and cutaneous squamous cell carcinomas to anti-PD1 monoclonal antibody REGN2810", J Immuno Ther Cancer, 4:70 (5 pages) (2016).

Fecci et al., "Systemic CTLA-4 Blockade Ameliorates Glioma-Induced Changes to the CD4+ T Cell Compartment without Affecting Regulatory T-Cell Function", Clinical Cancer Research, 13(7), pp. 2158-2467 (2007).

Flemming A., "Cancer: PD1 makes waves in anticancer immunotherapy", Nature Reviews Drug Discovery, 11(8), p. 601 (Aug. 2012).

Gershenwald et al., "Melanoma Staging: Evidence-Based Changes in the American Joint Committee on Cancer Eighth Edition Cancer Staging Manual", CA Cancer J Clin., 67(6), pp. 472-492 (Nov. 2017).

Gettinger et al., "Impaired HLA Class I Antigen Processing and Presentation as a Mechanism of Acquired Resistance to Immune Checkpoint Inhibitors in Lung Cancer", Cancer Discov., 7(12), pp. 1420-1435 (Dec. 2017).

Haile et al., "Tumor Cell Programmed Death Ligand 1-Mediated T Cell Suppression is Overcome by Coexpression of CD80", Journal of Immunol., 186(12), pp. 6822-6829 (Jun. 15, 2011).

Huang et al., "The PD-1/B7-H1 Pathway Modulates the Natural Killer Cells Versus Mouse Glioma Stem Cells", PLoS ONE, 10(8) e0134715 (14 pages) (Aug. 12, 2015).

Hugo et al., "Genomic and Transcriptomic Features of Response to Anti-PD-1 Therapy in Metastatic Melanoma", Cell, 165(1), pp. 35-44 (Mar. 24, 2016).

InvivoGen review: Immunoglobulin G, downloaded from the internet at: https://www.invivogen.com/review-antibody-generation (1 page) (2011).

Kohler et al., "Continuous cultures of fused cells secreting antibody of predefined specificity", Nature, 256, pp. 495-497 (Aug. 7, 1975).

Kumar et al., "Preclinical characterization of dostarlimab, a therapeutic anti-PD-1 antibody with potent activity to enhance immune function in in vitro cellular assays and in vivo animal models", mAbs, 13(1), pp. 1-12 (2021).

Li et al., "Anti-Programmed Death-1 Synergizes with Granulocyte Macrophage Colony-Stimulating Factor—Secreting Tumor Cell Immunotherapy Providing Therapeutic Benefit to Mice with Established Tumors", Clin Cancer Res, 15(5), pp. 1623-1634 (Mar. 1, 2009).

Liu et al., "In situ adenoviral interleukin 12 gene transfer confers potent and long-lasting cytotoxic immunity in glioma", Cancer Gene Therapy, 9(1 ), pp. 9-15 (2002).

Liu et al., "Structural basis of anti-PD-L 1 monoclonal antibody avelumab for tumor therapy", Cell Research, 27, pp. 151-153 (2017).

Liu et al., "Study of the interactions of a novel monoclonal antibody, mAb059c, with the hPD-1 receptor", Scientific Reports, 9: 17830 (10 pages) (2019).

Mangsbo et al., "Enhanced Tumor Eradication by Combining CTLA-4 or PD-1 Blockade with CpG Therapy", J. Immunother., 33(3), pp. 225-235 (2010).

Markham et al., "Cemiplimab: First Global Approval", Drugs, 78, pp. 1841-1846 (2018).

McCafferty et al., "Phage antibodies: filamentous phage displaying antibody variable domains", Nature, 348, pp. 552-554 (Dec. 6, 1990).

Middha et al., "Majority of B2M-Mutant and -Deficient Colorectal Carcinomas Achieve Clinical Benefit From Immune Checkpoint Inhibitor Therapy and Are Microsatellite Instability-High", JCO Precis Oncol. (doi:10.1200/PO.18.00321), published at ascopubs.org/journal/po (14 pages) (Mar. 4, 2019).

Notice of Opposition filed in EP3351261 dated Mar. 2, 2022.

Oshikawa et al., "Synergistic inhibition of tumor growth in a murine mammary adenocarcinoma model by combinational gene therapy using IL-12, pro-IL-18, and IL-1Beta converting enzyme cDNA", Proceedings of the National Academy of the Sciences of the United States of America, 96(23), pp. 13351-13356 (Nov. 9, 1999).

Patnaik et al., "Phase I study of Pembrolizumab (MK-3475; Anti-PD-1 Monoclonal Antibody) in Patients with Advanced Solid Tumors", Clin Cancer Res., 21(19), pp. 4286-4293 (Oct. 1, 2015).

Pavlin et al., "Local and systemic antitumor effect of intratumoral and peritumoral IL-12 electrogene therapy on murine sarcoma", Cancer Biology & Therapy 8(22), pp. 2112-2120 (Nov. 15, 2009).

Perez-Gracia et al., "Clinical development of combination strategies in immunotherapy: are we ready for more than one investigational product in an early clinical trial?", Immunotherapy, 1(5), pp. 845-853 (2009).

Picardo et al., "Structure and Optimization of Checkpoint Inhibitors", Cancers, 12(38), pp. 1-15 (2020).

Powell et al., "Compendium of Excipients for Parenteral Formulations", PDA J Pharm Sci Technol, 52, pp. 238-311 (1998).

Sanofi "Solid Q2 performance and strong pipeline momentum Full-year 2023 business EPS guidance raised" Press Release dated Jul. 28, 2023 retrieved from: https://ml-eu.globenewswire.com/Resource/Download/5d66ecd8-2d1b-4ca1-8a1d-2e426b9aa949 (26 pgs).

Taylor, Nick Paul "Sanofi, BioNTech cull mRNA clinical cytokine cancer candidate based on early data" Fierce Biotech, 2023. Retrieved from: https://www.fiercebiotech.com/biotech/sanofi-biontech-cull-mrna-clinical-cytokine-cancer-candidate-based-early-data (2 pgs).

\* cited by examiner

*Fig. 26A*      *Fig. 26B* lipopolysaccharide
IFNG
TNF
poly rI:rC-RNA
IL1B
NFkB (complex)
Interferon alpha
tretinoin
phorbol myrisitate acetate
E. coli B5 lipopolysaccharide
IRF7
STAT1
IFNA2
TLR3
CD40LG
TLR9
IL2
MYD88
E. coli B4 lipopolysaccharide
TLR4
RELA
IKBKB
IL1
NUPR1
salmonella Minnesota R595 lipopolysaccharide
TLR7
TICAM1
IL1A
IL18
IRF3
RARA
MYCN
FOXM1
VCAN
L-dopa
Bay 11-7082
SOCS1
GFI1
SCAP
N-acetyl-L-cysteine
alefacept
U0126
pyrrolidine dithiocarbamate
TBX2
NKX2-3
Alpha catenin
RABL6
MYC
IL1RN
TRIM24
SB203580
IL10RA

*Fig. 27B*

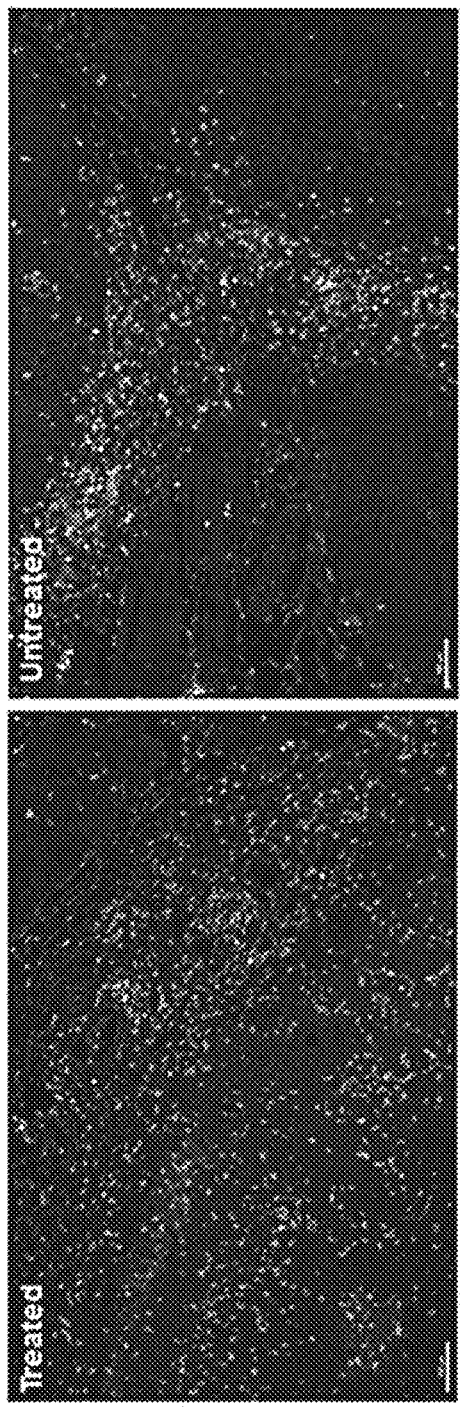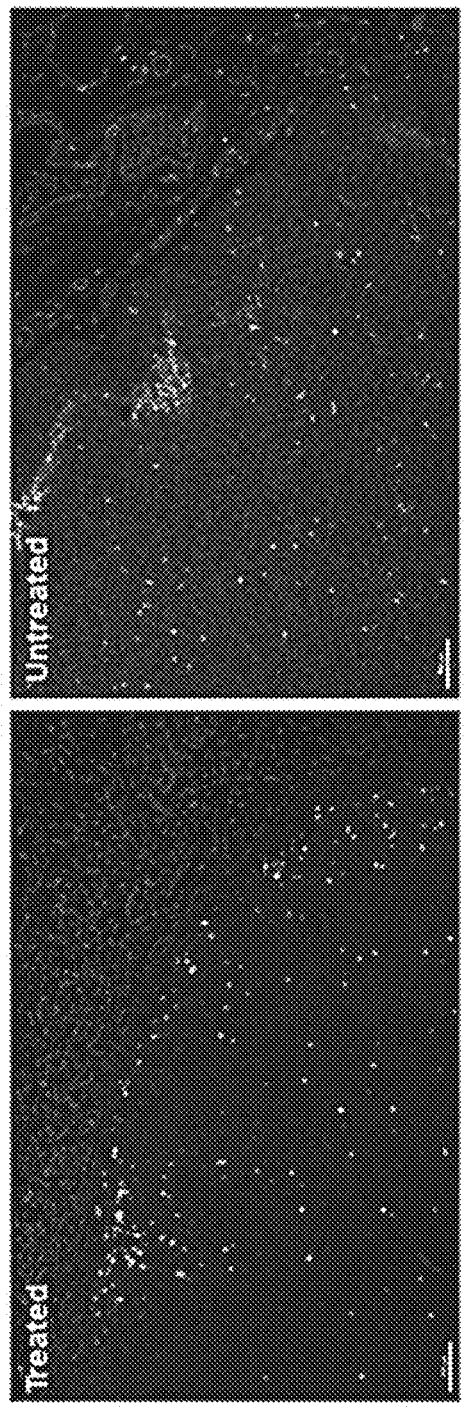
Fig. 28A  Fig. 28B  Fig. 28C  Fig. 28D
CD4+ CD8+ FOXP3 Nuclei

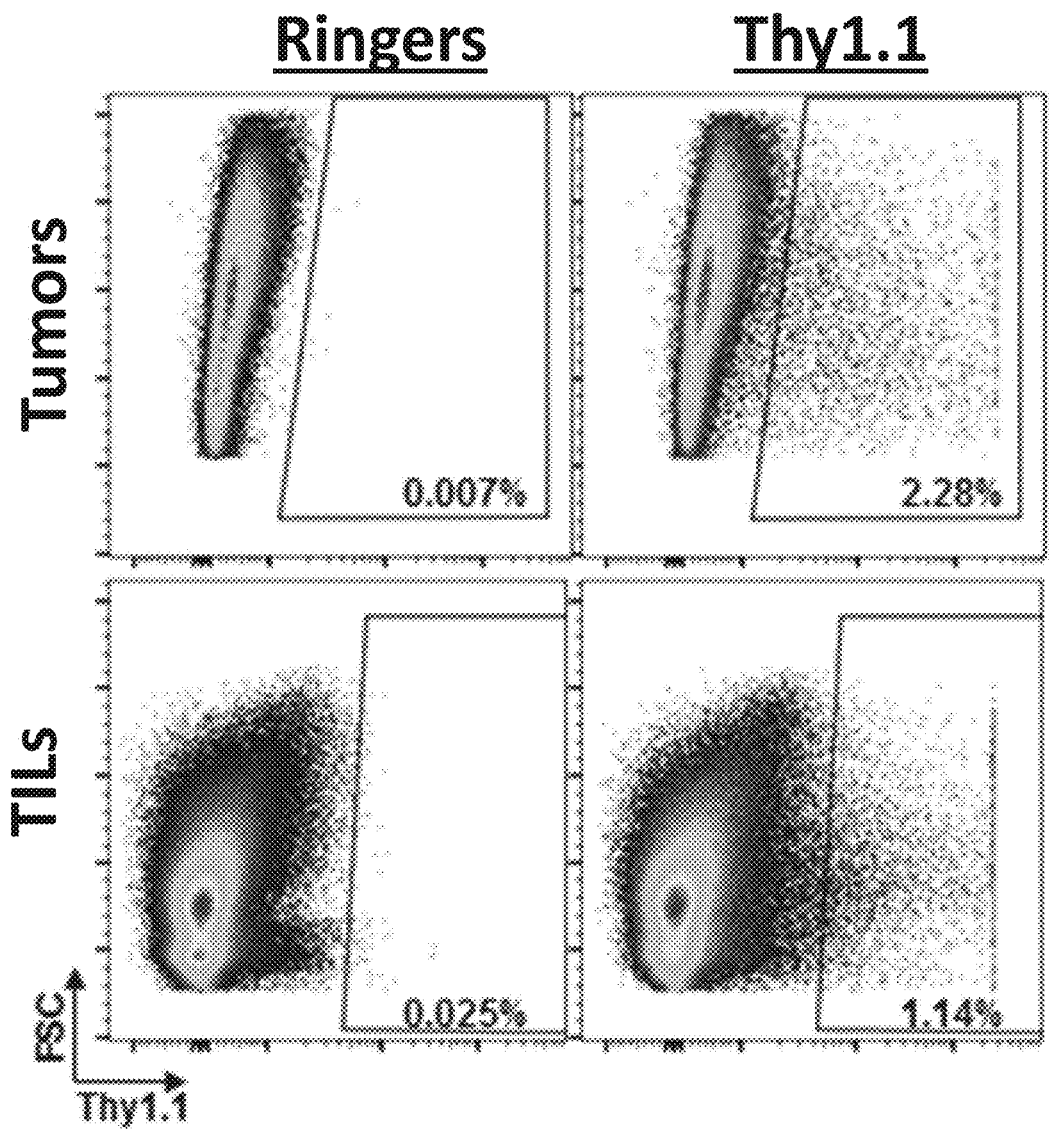

↑PD-L1 on tumor infiltrating cells (CD11B+)

↑PD-1 on tumor infiltrating CD8+

Control mRNA

Cytokine mRNA

SEQUENCE LISTING

```
<160> NUMBER OF SEQ ID NOS: 88

<210> SEQ ID NO 1
<211> LENGTH: 52
<212> TYPE: DNA
<213> ORGANISM: Artificial sequence
<220> FEATURE:
<223> OTHER INFORMATION: ModA 5' UTR

<400> SEQUENCE: 1
gggcgaacta gtattcttct ggtccccaca gactcagaga gaacccgcca cc         52

<210> SEQ ID NO 2
<211> LENGTH: 52
```

```
<212> TYPE: RNA
<213> ORGANISM: Artificial sequence
<220> FEATURE:
<223> OTHER INFORMATION: ModA 5' UTR

<400> SEQUENCE: 2
gggcgaacua guauucuucu gguccccaca gacucagaga gaacccgcca cc        52

<210> SEQ ID NO 3
<211> LENGTH: 145
<212> TYPE: DNA
<213> ORGANISM: Artificial sequence
<220> FEATURE:
<223> OTHER INFORMATION: ModB 5' UTR

<400> SEQUENCE: 3
ggaataaact agtctcaaca caacatatac aaaacaaacg aatctcaagc aatcaagcat    60
tctacttcta ttgcagcaat ttaaatcatt tcttttaaag caaaagcaat tttctgaaaa   120
ttttcaccat ttacgaacga tagcc                                         145

<210> SEQ ID NO 4
<211> LENGTH: 145
<212> TYPE: RNA
<213> ORGANISM: Artificial sequence
<220> FEATURE:
<223> OTHER INFORMATION: ModB 5' UTR

<400> SEQUENCE: 4
ggaauaaacu agucucaaca caacauauac aaaacaaacg aaucucaagc aaucaagcau    60
ucuacuucua uugcagcaau uuaaaucauu ucuuuuaaag caaaagcaau uuucugaaaa   120
uuuucaccau uuacgaacga uagcc                                         145

<210> SEQ ID NO 5
<211> LENGTH: 52
<212> TYPE: DNA
<213> ORGANISM: Artificial sequence
<220> FEATURE:
<223> OTHER INFORMATION: Alternative Mod 5' UTR

<400> SEQUENCE: 5
agacgaacta gtattcttct ggtccccaca gactcagaga gaacccgcca cc        52

<210> SEQ ID NO 6
<211> LENGTH: 52
<212> TYPE: RNA
<213> ORGANISM: Artificial sequence
<220> FEATURE:
<223> OTHER INFORMATION: Alternative Mod 5' UTR

<400> SEQUENCE: 6
agacgaacua guauucuucu gguccccaca gacucagaga gaacccgcca cc        52

<210> SEQ ID NO 7
<211> LENGTH: 427
<212> TYPE: DNA
<213> ORGANISM: Artificial sequence
<220> FEATURE:
<223> OTHER INFORMATION: ModA/B 3' UTR

<400> SEQUENCE: 7
ctcgagctgg tactgcatgc acgcaatgct agctgcccct ttcccgtcct gggtaccccg    60
agtctccccc gacctcgggt cccaggtatg ctcccacctc cacctgcccc actcaccacc   120
```

```
tctgctagtt ccagacacct cccaagcacg cagcaatgca gctcaaaacg cttagcctag    180 ccacacccc acgggaaaca gcagtgatta acctttagca ataaacgaaa gtttaactaa     240
gctatactaa ccccagggtt ggtcaatttc gtgccagcca caccgagacc tggtccagag    300
tcgctagccg cgtcgctaaa aaaaaaaaaa aaaaaaaaaa aaaaaagca tatgactaaa    360 aaaaaaaaaa aaaaaaaaaa aaaaaaaaaa aaaaaaaaaa aaaaaaaaaa aaaaaaaaaa    420
aaaaaaa                                                               427

<210> SEQ ID NO 8
<211> LENGTH: 427
<212> TYPE: RNA
<213> ORGANISM: Artificial sequence
<220> FEATURE:
<223> OTHER INFORMATION: ModA/B 3' UTR

<400> SEQUENCE: 8
cucgagcugg uacugcaugc acgcaaugcu agcugccccu uucccgoccu ggguaccccg     60 agucuccccc gaccucgggu cccagguaug ucccaccuc caccugcccc acucaccacc    120
ucugcuaguu ccagacaccu cccaagcacg cagcaaugca gcucaaaacg cuuagccuag    180 ccacacccc acgggaaaca gcagugauua accuuuagca auaaacgaaa guuuaacuaa    240
gcuauacuaa ccccagggu ggucaauuuc gugccagcca caccgagacc ugguccagag    300
ucgcuagccg cgucgcuaaa aaaaaaaaaa aaaaaaaaaa aaaaaagca uaugacuaaa    360 aaaaaaaaaa aaaaaaaaaa aaaaaaaaaa aaaaaaaaaa aaaaaaaaaa aaaaaaaaaa    420
aaaaaaa                                                               427

<210> SEQ ID NO 9
<211> LENGTH: 153
<212> TYPE: PRT
<213> ORGANISM: Homo sapiens

<400> SEQUENCE: 9

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 10
<211> LENGTH: 465
```

<212> TYPE: DNA
<213> ORGANISM: Homo sapiens

<400> SEQUENCE: 10

```
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat tacaagaatc ccaaactcac caggatgctc   180
acatttaagt tttacatgcc caagaaggcc acagaactga acatcttca gtgtctagaa    240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggattacct tttgtcaaag catcatctca acactgactt gatga                   465
```

<210> SEQ ID NO 11
<211> LENGTH: 465
<212> TYPE: DNA
<213> ORGANISM: Artificial sequence
<220> FEATURE:
<223> OTHER INFORMATION: Human optimized IL-2

<400> SEQUENCE: 11

```
atgtacagaa tgcagctgct gtcttgcatt gctctttctc ttgctcttgt gacaaattct    60
gctccaacat cttcttcaac aaagaaaaca cagcttcagc ttgaacacct tcttcttgat   120
cttcagatga ttctgaatgg aatcaacaat tacaaaaatc caaaactgac aagaatgctg   180
acatttaaat tttacatgcc aaagaaagca acagaactga acaccttca gtgccttgaa    240
gaagaactga aacctctgga agaagtgctg aatctggctc agagcaaaaa ttttcacctg   300
agaccaagag atctgatcag caacatcaat gtgattgtgc tggaactgaa aggatctgaa   360
acaacattca tgtgtgaata tgctgatgaa acagcaacaa ttgtggaatt tctgaacaga   420
tggatcacat tttgccagtc aatcatttca acactgacat gatga                   465
```

<210> SEQ ID NO 12
<211> LENGTH: 465
<212> TYPE: RNA
<213> ORGANISM: Homo sapiens

<400> SEQUENCE: 12

```
auguacagga ugcaacuccu gucuugcauu gcacuaaguc uugcacuugu cacaaacagu    60
gcaccuacuu caaguucuac aaagaaaaca cagcuacaac uggagcauuu acugcuggau   120
uuacagauga uuuugaaugg aauuauaau uacaagaauc ccaaacucac caggaugcuc   180
acauuuaagu uuuacaugcc caagaaggcc acagaacuga acaucuuca gugucuagaa    240
gaagaacuca aaccucugga ggaagugcua aauuuagcuc aaagcaaaaa cuuucacuua   300
agacccaggg acuuaaucag caauaucaac guaauaguuc uggaacuaaa gggaucugaa   360
acaacauuca uguguaauau gcugaugag acagcaacca uuguagaauu ucugaacaga   420
uggauuaccu uuugucaaag caucaucuca acacugacuu gauga                   465
```

<210> SEQ ID NO 13
<211> LENGTH: 465
<212> TYPE: RNA
<213> ORGANISM: Artificial sequence
<220> FEATURE:
<223> OTHER INFORMATION: Human optimized IL-2

<400> SEQUENCE: 13

```
auguacagaa ugcagcugcu gucuugcauu gcucuuucuc uugcucuugu gacaaauucu      60
gcuccaacau cuucuucaac aaagaaaaca cagcuucagc uugaacaccu ucuucuugau     120
cuucagauga uucugaaugg aaucaacauu uacaaaaauc caaaacugac aagaaugcug     180
acauuuaaau uuuacaugcc aaagaaagca acagaacuga acaccuuca gugccuugaa     240 gaagaacuga aaccucugga agaagugcug aaucuggcuc agagcaaaaa uuuucaccug     300
agaccaagag aucugaucag caacaucaau gugauugugc uggaacugaa aggaucugaa     360
acaacauuca gugugaauua gcugaugaa acagcaacaa uuguggaauu ucugaacaga      420
uggaucacau uugccaguc aaucauuuca acacugacau gauga                     465
```

<210> SEQ ID NO 14
<211> LENGTH: 539
<212> TYPE: PRT
<213> ORGANISM: Artificial sequence
<220> FEATURE:
<223> OTHER INFORMATION: Human IL-12sc

<400> SEQUENCE: 14

```
Met Cys His Gln Gln Leu Val Ile Ser Trp Phe Ser Leu Val Phe Leu
1               5                  10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270
```

| | | | | | | | | | | |
|---|---|---|---|---|---|---|---|---|---|---|
|Phe|Cys|Val|Gln|Val|Gln|Gly|Lys|Ser|Lys|Arg|Glu|Lys|Asp|Arg|
| | |275| | | |280| | | |285| | | | |
|Val|Phe|Thr|Asp|Lys|Thr|Ser|Ala|Thr|Val|Ile|Cys|Arg|Lys|Asn|Ala|
| |290| | | | |295| | | | |300| | | | |
|Ser|Ile|Ser|Val|Arg|Ala|Gln|Asp|Arg|Tyr|Tyr|Ser|Ser|Ser|Trp|Ser|
|305| | | | |310| | | | |315| | | | |320|
|Glu|Trp|Ala|Ser|Val|Pro|Cys|Ser|Gly|Ser|Ser|Gly|Gly|Gly|Ser|
| | | | |325| | | | |330| | | | |335|
|Pro|Gly|Gly|Gly|Ser|Ser|Arg|Asn|Leu|Pro|Val|Ala|Thr|Pro|Asp|Pro|
| | | |340| | | | |345| | | | |350| | |
|Gly|Met|Phe|Pro|Cys|Leu|His|His|Ser|Gln|Asn|Leu|Leu|Arg|Ala|Val|
| | |355| | | | |360| | | | |365| | | |
|Ser|Asn|Met|Leu|Gln|Lys|Ala|Arg|Gln|Thr|Leu|Glu|Phe|Tyr|Pro|Cys|
| |370| | | | |375| | | | |380| | | | |
|Thr|Ser|Glu|Glu|Ile|Asp|His|Glu|Asp|Ile|Thr|Lys|Asp|Lys|Thr|Ser|
|385| | | | |390| | | | |395| | | | |400|
|Thr|Val|Glu|Ala|Cys|Leu|Pro|Leu|Glu|Leu|Thr|Lys|Asn|Glu|Ser|Cys|
| | | | |405| | | | |410| | | | |415| |
|Leu|Asn|Ser|Arg|Glu|Thr|Ser|Phe|Ile|Thr|Asn|Gly|Ser|Cys|Leu|Ala|
| | | |420| | | | |425| | | | |430| | |
|Ser|Arg|Lys|Thr|Ser|Phe|Met|Met|Ala|Leu|Cys|Leu|Ser|Ser|Ile|Tyr|
| | |435| | | | |440| | | | |445| | | |
|Glu|Asp|Leu|Lys|Met|Tyr|Gln|Val|Glu|Phe|Lys|Thr|Met|Asn|Ala|Lys|
| |450| | | | |455| | | | |460| | | | |
|Leu|Leu|Met|Asp|Pro|Lys|Arg|Gln|Ile|Phe|Leu|Asp|Gln|Asn|Met|Leu|
|465| | | | |470| | | | |475| | | | |480|
|Ala|Val|Ile|Asp|Glu|Leu|Met|Gln|Ala|Leu|Asn|Phe|Asn|Ser|Glu|Thr|
| | | | |485| | | | |490| | | | |495| |
|Val|Pro|Gln|Lys|Ser|Ser|Leu|Glu|Glu|Pro|Asp|Phe|Tyr|Lys|Thr|Lys|
| | | |500| | | | |505| | | | |510| | |
|Ile|Lys|Leu|Cys|Ile|Leu|Leu|His|Ala|Phe|Arg|Ile|Arg|Ala|Val|Thr|
| | |515| | | | |520| | | | |525| | | |
|Ile|Asp|Arg|Val|Met|Ser|Tyr|Leu|Asn|Ala|Ser|
| |530| | | | |535| | | | |

<210> SEQ ID NO 15
<211> LENGTH: 1623
<212> TYPE: DNA
<213> ORGANISM: Artificial sequence
<220> FEATURE:
<223> OTHER INFORMATION: Human non-optimized IL-12sc

<400> SEQUENCE: 15

```
atgtgtcacc agcagttggt catctcttgg tttccctgg ttttctggc atctcccctc      60
gtggccatat gggaactgaa gaaagatgtt tatgtcgtag aattggattg gtatccggat    120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag cgaggttct aagccattcg    300
ctcctgctgc ttcacaaaaa ggaagatgga atttggtcca ctgatatttt aaaggaccag   360
aaagaaccca aaaataagac ctttctaaga tgcgaggcca gaattattc tggacgtttc   420
acctgctggt ggctgacgac aatcagtact gatttgacat tcagtgtcaa agcagcaga   480
gggtcttctg accccaagg ggtgacgtgc ggagctgcta cactctctgc agagagagtc   540
```

```
agagggggaca caaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca aacctgaccc acccaagaac      720
ttgcagctga agccattaaa gaattctcgg caggtgaggt cagctgggag gtaccctgac      780
acctggagta ctccacattc ctacttctcc ctgacattct gcgttcaggt ccagggcaag      840
agcaagagag aaaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagtggctct agcggagggg gaggctctcc tggcggggga     1020
tctagcagaa acctccccgt ggccactcca gacccaggaa tgttcccatg ccttcaccac     1080
tcccaaaacc tgctgagggc cgtcagcaac atgctccaga aggccagaca aactctagaa     1140
ttttaccctt gcacttctga ggaaattgat catgaagata tcacaaaaga taaaaccagc     1200
acagtggagg cctgtttacc attggaatta accaagaatg agagttgcct aaattccaga     1260
gagacctctt tcataactaa tgggagttgc ctggcctcca gaaagacctc ttttatgatg     1320
gccctgtgcc ttagtagtat ttatgaagac ttgaagatgt accaggtgga gttcaagacc     1380
atgaatgcaa agcttctgat ggatcctaag aggcagatct ttctagatca aaacatgctg     1440
gcagttattg atgagctgat gcaggccctg aatttcaaca gtgagactgt gccacaaaaa     1500
tcctcccttg aagaaccgga ttttatataaa actaaaatca agctctgcat acttcttcat     1560
gctttcagaa ttcgggcagt gactattgat agagtgatga gctatctgaa tgcttcctga     1620
tga                                                                  1623

<210> SEQ ID NO 16
<211> LENGTH: 1623
<212> TYPE: DNA
<213> ORGANISM: Artificial sequence
<220> FEATURE:
<223> OTHER INFORMATION: Human optimized IL-12sc

<400> SEQUENCE: 16
atgtgtcacc agcagctggt gatctcatgg ttctccctgg tatttctggc atctcctctt       60
gtcgcaatct gggaactgaa gaaagacgtg tatgtcgttg agctcgactg gtatccggat      120
gcgcctggcg agatggtggt gctgacctgt gacaccccag aggaggatgg gatcacttgg      180
acccttgatc aatcctccga agtgctcggg tctggcaaga ctctgaccat acaagtgaaa      240
gagtttggcg atgccgggca gtacacttgc cataagggcg agaagttcct gtcccactca      300
ctgctgctgc tgcacaagaa agaggacgga atttggagta ccgatatcct gaaagatcag      360
aaagagccca gaacaaaac cttccttgcg tgcgaagcca gaactactc agggagattt       420 acttgttggt ggctgacgac gatcagcacc gatctgactt tctccgtgaa atcaagtagg      480
ggatcatctg accctcaagg agtcacatgt ggagcggcta ctctgagcgc tgaacgcgta      540
agaggggaca ataaggagta cgagtatagc gttgagtgcc aagaggatag cgcatgcccc      600
gccgccgaag aatcattgcc cattgaagtg atggtggatg ctgtacacaa gctgaagtat      660
gagaactaca caagctcctt cttcatccgt gacatcatca aaccagatcc tcctaagaac      720
ctccagctta aacctctgaa gaactctaga caggtggaag tgtcttggga gtatcccgac      780
acctggtcta caccacattc ctacttcagt ctcacattct gcgttcaggt acagggcaag      840 tccaaagggag agaagaagga tcgggtcttt acagataaaa caagtgccac cgttatatgc      900
cggaagaatg cctctatttc tgtgcgtgcg caggacagat actatagcag ctcttggagt      960
```

```
gaatgggcca gtgtcccatg ttcagggtca tccggtggtg gcggcagccc cggaggcggt    1020
agctccagaa atctccctgt ggctacacct gatccaggca tgtttccctg tttgcaccat    1080
agccaaaacc tcctgagagc agtcagcaac atgctccaga agctagacaa aacactggaa    1140
ttctacccat gcacctccga ggaaatagat cacgaggata tcactaagga caaacaagc     1200 actgtcgaag catgccttcc cttggaactg acaaagaacg agagttgcct taattcaaga    1260
gaaacatctt tcattacaaa cggtagctgc ttggcaagca gaaaaacatc ttttatgatg    1320
gccctttgtc tgagcagtat ttatgaggat ctcaaaatgt accaggtgga gtttaagacc    1380
atgaatgcca agctgctgat ggacccaaag agacagattt tcctcgatca gaatatgctg    1440
gctgtgattg atgaactgat gcaggccttg aatttcaaca gcgaaaccgt tccccagaaa    1500
agcagtcttg aagaacctga cttttataag accaagatca aactgtgtat tctcctgcat    1560
gcctttagaa tcagagcagt cactatagat agagtgatgt cctacctgaa tgcttcctga    1620
tga                                                                  1623

<210> SEQ ID NO 17
<211> LENGTH: 1623
<212> TYPE: RNA
<213> ORGANISM: Artificial sequence
<220> FEATURE:
<223> OTHER INFORMATION: Human non-optimized IL-12sc

<400> SEQUENCE: 17 augucacc agcaguuggu caucucuugg uuuucccugg uuuuucuggc aucuccccuc      60
guggccauau gggaacugaa gaaagauguu uaugucguag aauuggauug guauccggau    120
gccccuggag aaaugguggu ccucaccugu gacaccccug aagaagaugg uaucaccugg    180
accuuggacc agagcaguga ggucuuaggc ucuggcaaaa cccugaccau ccaagucaaa    240
gaguuuggag augcuggcca guacaccugu cacaaaggag cgagguucu aagccauucg    300 cuccugcugc uucacaaaaa ggaagaugga auuuggucca cugauauuuu aaaggaccag    360
aaagaaccca aaauaagac cuuucuaaga ugcgaggcca agaauuauuc uggacguuuc    420
accugcuggu ggcugacgac aaucaguacu gauuugacau ucagucaa aagcagcaga    480 ggucuucug acccccaagg ggugacgugc ggagcugcua cacucucugc agagagaguc    540
agaggggaca caaggaguau gaguacucua guggagugcc aggaggacag ugccugccca    600
gcugcugagg agagucugcc cauugagguc augguggaug ccguucacaa gcucaaguau    660
gaaaacuaca ccagcagcuu cuucaucagg gacaucauca aaccgacccc acccaagaac    720
uugcagcuga agccauuaaa gaauucucgg caggugagg ucagcuggga guacccugac    780
accuggagua cuccacauuc cuacuucccc cugacauucu cguucaggu ccagggcaag    840 agcaagagag aaaagaaaga uagagucuuc acggacaaga ccucagccac ggucaucugc    900
cgcaaaaaug ccagcauuag cgugcgggcc aggaccgcu acauagcuc aucuggagc    960 gaaugggcau cugugcccug caguggcucu agcggagggg gaggcucucc uggcggggga    1020
ucuagcagaa accuccccgu ggccacucca gacccaggaa uguucccaug ccuucaccac    1080
ucccaaaacc gcugagggc cgucagcaac augcuccaga aggccagaca aacucuagaa    1140
uuuuacccuu gcacuucuga ggaaauugau caugaagaua ucacaaaaga uaaaaccagc    1200
acaguggagg ccuguuuacc auuggaauua accaagaaug agaguugccu aaauuccaga    1260
gagaccucuu ucauaacuaa ugggagugc cuggccucca gaaagaccuc uuuuaugaug    1320
```

-continued

```
gcccugugcc uuaguaguau uuaugaagac uugaagaugu accaggugga guucaagacc    1380
augaaugcaa agcuucugau ggauccuaag aggcagaucu uucuagauca aaacaugcug    1440
gcaguuauug augagcugau gcaggcccug aauuucaaca gugagacugu gccacaaaaa    1500
uccucccuug aagaaccgga uuuuauaaa acuaaaauca agcucugcau acuucuucau     1560
gcuuucagaa uucgggcagu gacuauugau agagugauga gcuaucugaa ugcuuccuga    1620
uga                                                                  1623
```

<210> SEQ ID NO 18
<211> LENGTH: 1623
<212> TYPE: RNA
<213> ORGANISM: Artificial sequence
<220> FEATURE:
<223> OTHER INFORMATION: Human optimized IL-12sc

<400> SEQUENCE: 18

```
augucacc agcagcuggu gaucucaugg uucucccugg uauuucggc aucuccucuu        60 gucgcaaucu gggaacugaa gaaagacgug uaugucguug agcucgacug guauccggau   120
gcgccuggcg agauggugu gcugaccugu gacaccccag aggaggaugg gaucacuugg     180
acccuugauc aauccuccga agugcucggg ucuggcaaga cucugaccau acaagugaaa    240
gaguuuggcg augccgggca guacacuugc cauaagggcg agaaguucu gucccacuca    300 cugcugcugc ugcacaagaa agaggacgga auuggagua ccgauauccu gaaagaucag     360
aaagagccca agaacaaaac cuucuugcgg ugcgaagcca agaacuacuc agggagauuu    420
acuuguuggg gcugacgac gaucagcacc gaucugacuu ucuccgugaa ucaaguagg     480 ggaucaucug acccucaagg agucacaugu ggagcggcua cucugagcgc ugaacgcgua    540
agaggggaca auaaggagua cgaguauagc guugagugcc aagaggauag cgcaugcccc    600
gccgccgaag aaucauugcc cauugaagug augguggaug cuguacacaa gcugaaguau   660
gagaacuaca caagcccuu cuucauccgu gacaucauca accagauccu ccuaagaac     720 cuccagcuua aacucugaa gaacucuaga caggugaag ugucuuggga uaucccgac      780 accuggcuua caccacauc cuacuucagu cucacauucu gcuucaggu acagggcaag     840 uccaaaaggg agaagaagga ucgggucuuu acagauaaaa caagugccac cguuauaugc   900
cggaagaaug ccucuauuuc ugugcgugcg caggacagau acuauagcag cucuuggagu    960
gaaugggcca gucccaug uucagggu ucgguggug gcggcagccc cggaggcggu        1020 agcccagaa aucucccgu ggcuacaccu gauccaggca guuucccug uuugcaccau      1080 agccaaaacc uccugagagc agcagcaac augucaaga agcuagaca aacacuggaa      1140 uucuacccau gcaccucca ggaaauagau cacgaggaua ucacuaagga caaacaagc     1200 acugucgaag caugccuucc cuuggaacug acaaagaacg agaguugccu uaauucaaga   1260
gaaacaucuu ucauuacaaa cgguagcugc uuggcaagca gaaaacauc uuuuaugaug   1320 gcccuuuguc ugagcaguau uuaugaggau ucaaaaugu accaggugga guuaagacc      1380 augaaugcca agcugcugau ggacccaaag agacagauuu uccucgauca gaauaugcug    1440
gcugugauug augaacugau gcaggcccug aauuucaaca gcgaaaccgu ucccagaaa   1500 agcagucuug aagaaccuga cuuuuauaag accaagauca aacugugua ucuccugcau    1560 gccuuuagaa ucagagcagu cacuauagau agagugaugu ccuaccgaa ugcuuccuga    1620 uga                                                                 1623
```

<210> SEQ ID NO 19
<211> LENGTH: 188
<212> TYPE: PRT
<213> ORGANISM: Homo sapiens

<400> SEQUENCE: 19

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185
```

<210> SEQ ID NO 20
<211> LENGTH: 570
<212> TYPE: DNA
<213> ORGANISM: Homo sapiens

<400> SEQUENCE: 20

```
atggccttga cctttgcttt actggtggcc ctcctggtgc tcagctgcaa gtcaagctgc    60
tctgtgggct gtgatctgcc tcaaacccac agcctgggta gcaggaggac cttgatgctc   120
ctggcacaga tgaggagaat ctctcttttc cctgcttga aggacagaca tgactttgga    180
tttcccagg aggagtttgg caaccagttc caaaaggctg aaaccatccc tgtcctccat    240
gagatgatcc agcagatctt caaccttttc agcacaaagg actcatctgc tgcttgggat   300
gagaccctcc tagacaaatt ctacactgaa ctctaccagc agctgaatga cctggaagcc   360
tgtgtgatac aggggtgggg ggtgacagag actcccctga tgaaggagga ctccattctg   420
gctgtgagga atacttcca aagaatcact ctctatctga agagaagaa atacagccct     480
tgtgcctggg aggttgtcag agcagaaatc atgagatctt tttctttgtc aacaaacttg   540
caagaaagtt taagaagtaa ggaatgatga                                    570
```

<210> SEQ ID NO 21
<211> LENGTH: 570
<212> TYPE: DNA
<213> ORGANISM: Artificial sequence
<220> FEATURE:
<223> OTHER INFORMATION: Human optimized IFN-alpha-2b

<400> SEQUENCE: 21

```
atggccctga cttttgccct tctcgtggct tgttggtgc tgagttgcaa atcttcctgt    60
agtgtcggat gtgatctgcc tcaaacccac agtctgggat ctaggagaac actgatgctg   120
ttggcacaga tgaggagaat tagcctcttt tcctgcctga aggatagaca tgacttcggc   180
tttccccaag aggagtttgg caatcagttc cagaaagcgg aaacgattcc cgttctgcac   240
gagatgatcc agcagatctt caacctcttt tcaaccaaag acagctcagc agcctgggat   300
gagacactgc tggacaaatt ctacacagaa ctgtatcagc agcttaacga tctggaggca   360
tgcgtgatcc aaggggttgg tgtgactgaa actccgctta tgaaggagga ctccattctg   420
gctgtacgga agtacttcca gagaataacc ctctatctga aggagaagaa gtactcacca   480
tgtgcttggg aagtcgtgag agccgaaatc atgagatcct tcagccttag caccaatctc   540
caggaatctc tgagaagcaa agagtgatga                                    570
```

<210> SEQ ID NO 22
<211> LENGTH: 570
<212> TYPE: RNA
<213> ORGANISM: Homo sapiens

<400> SEQUENCE: 22

```
auggccuuga ccuuugcuuu acugguggcc uccuggugc ucagcugcaa gucaagcugc    60
ucugugggcu gugaucugcc ucaaacccac agcuggguua gcaggaggac cuugaugcuc   120
cuggcacaga ugaggagaau cucucuuuuc ccugcuuga aggacagaca ugacuuugga   180
uuucccagg aggaguuugg caaccaguuc caaaaggcug aaaccauccc uguccuccau   240
gagaugaucc agcagaucuu caaccuuuuc agcacaaagg acucaucugc ugcuugggau   300
gagacccucc uagacaaauu cuacacagaa cucuaccagc agcugaauga ccuggaagcc   360
ugugugauac aggggguggg ggugacagag acucccuga ugaaggagga cuccauucug   420
gcugugagga aauacuucca agaaucacu cucuaucuga agagaagaa auacagcccu   480
ugugccuggg agguugucag agcagaaauc augagaucuu uucuuugc aacaaacuug   540
caagaaaguu uaagaaguaa ggaaugauga                                    570
```

<210> SEQ ID NO 23
<211> LENGTH: 570
<212> TYPE: RNA
<213> ORGANISM: Artificial sequence
<220> FEATURE:
<223> OTHER INFORMATION: Human optimized IFN-alpha-2b

<400> SEQUENCE: 23

```
auggcccuga cuuuugcccu ucucguggcu uguuggugc ugaguugcaa aucuuccugu    60
aguguucggau gugaucugcc ucaaacccac agucugggau cuaggagaac acugaugcug   120
uuggcacaga ugaggagaau uagccucuuu uccugccuga aggauagaca ugacuucggc   180
uuuccccaag aggaguuugg caaucaguuc cagaaagcgg aaacgauucc cguucugcac   240
gagaugaucc agcagaucuu caaccucuuu ucaaccaaag acagcucagc agccugggau   300
gagacacugc uggacaaauu cuacacagaa cuguaucagc agcuuaacga ucuggaggca   360
ugcguugaucc aaggggguugg ugugacugaa acuccgcuua ugaaggagga cuccauucug   420
gcuguacgga aguacuucca gagaauaacc cucuaucuga aggagaagaa guacucacca   480
ugugcuuggg aagucgugag agccgaaauc augagauccu ucagccuuag caccaaucuc   540
caggaaucuc ugagaagcaa agagugauga                                    570
```

<210> SEQ ID NO 24
<211> LENGTH: 241
<212> TYPE: PRT
<213> ORGANISM: Artificial sequence
<220> FEATURE:
<223> OTHER INFORMATION: Human IL-15 sushi

<400> SEQUENCE: 24

Met Ala Pro Arg Arg Ala Arg Gly Cys Arg Thr Leu Gly Leu Pro Ala
1               5                   10                  15

Leu Leu Leu Leu Leu Leu Leu Arg Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Gly Gly Gly Ser Gly
            100                 105                 110

Gly Gly Gly Ser Gly Gly Gly Ser Gly Gly Gly Ser Leu Gln Asn
        115                 120                 125

Trp Val Asn Val Ile Ser Asp Leu Lys Lys Ile Glu Asp Leu Ile Gln
    130                 135                 140

Ser Met His Ile Asp Ala Thr Leu Tyr Thr Glu Ser Asp Val His Pro
145                 150                 155                 160

Ser Cys Lys Val Thr Ala Met Lys Cys Phe Leu Leu Glu Leu Gln Val
                165                 170                 175

Ile Ser Leu Glu Ser Gly Asp Ala Ser Ile His Asp Thr Val Glu Asn
            180                 185                 190

Leu Ile Ile Leu Ala Asn Asn Ser Leu Ser Ser Asn Gly Asn Val Thr
        195                 200                 205

Glu Ser Gly Cys Lys Glu Cys Glu Glu Leu Glu Glu Lys Asn Ile Lys
    210                 215                 220

Glu Phe Leu Gln Ser Phe Val His Ile Val Gln Met Phe Ile Asn Thr
225                 230                 235                 240

Ser

<210> SEQ ID NO 25
<211> LENGTH: 729
<212> TYPE: DNA
<213> ORGANISM: Artificial sequence
<220> FEATURE:
<223> OTHER INFORMATION: Human IL-15 sushi

<400> SEQUENCE: 25
atggccccgc ggcgggcgcg cggctgccgg accctcggtc tcccggcgct gctactgctg      60
ctgctgctcc ggccgccggc gacgcggggc atcacgtgcc ctcccccat gtccgtggaa      120 cacgcagaca tctgggtcaa gagctacagc ttgtactcca gggagcggta catttgtaac      180
tctggtttca gcgtaaagc cggcacgtcc agcctgacgg agtgcgtgtt gaacaaggcc      240
acgaatgtcg cccactggac aaccccagt ctcaaatgca ttagagaccc tgccctggtt      300
caccaaaggc cagcgccacc cggggggagga tctggcggcg gtgggtctgg cgggggatct      360

```
ggcggaggag gaagcttaca gaactgggtg aatgtaataa gtgatttgaa aaaaattgaa    420
gatcttattc aatctatgca tattgatgct actttatata cggaaagtga tgttcacccc    480
agttgcaaag taacagcaat gaagtgcttt ctcttggagt tacaagttat ttcacttgag    540
tccggagatg caagtattca tgatacagta gaaaatctga tcatcctagc aaacaacagt    600
ttgtcttcta atgggaatgt aacagaatct ggatgcaaag aatgtgagga actggaggaa    660
aaaaatatta agaattttt gcagagtttt gtacatattg tccaaatgtt catcaacact    720
tcttgatga                                                           729
```

<210> SEQ ID NO 26
<211> LENGTH: 729
<212> TYPE: RNA
<213> ORGANISM: Artificial sequence
<220> FEATURE:
<223> OTHER INFORMATION: Human IL-15 sushi

<400> SEQUENCE: 26

```
auggccccgc ggcgggcgcg cggcugccgg acccucgguc uccggcgcu gcuacugcug      60 cugcugcucc ggccgccggc gacgcggggc aucacgugcc ucccccau guccguggaa     120 cacgcagaca ucugggucaa gagcuacagc uuguacucca gggagcggua cauuuguaac    180
ucugguuuca gcguaaagc cggcacgucc agccugacgg agugcguguu gaacaaggcc    240
acgaaugucg cccacuggac aaccccagu cucaaaugca uuagagaccc ugcccugguu    300
caccaaaggc cagcgccacc cggggagga ucuggcggcg gugggucugg cggggaucu    360 ggcggaggag gaagcuuaca gaacugggug augaauaa gugauuugaa aaaaauugaa    420
gaucuuauuc aaucuaugca uauugaugcu acuuuauaua cggaaaguga uguucacccc    480
aguugcaaag uaacagcaau gaagugcuuu cucuuggagu uacaaguuau uucacuugag    540
uccggagaug caaguauuca ugauacagua gaaaaucuga ucauccuagc aaacaacagu    600
uugucuucua augggaaugu aacagaaucu ggaugcaaag aaugugagga acuggaggaa    660
aaaaauauua agaauuuuu gcagaguuuu guacauauug uccaaauguu caucaacacu    720
ucuugauga                                                           729
```

<210> SEQ ID NO 27
<211> LENGTH: 144
<212> TYPE: PRT
<213> ORGANISM: Homo sapiens

<400> SEQUENCE: 27

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110
```

```
Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 28
<211> LENGTH: 438
<212> TYPE: DNA
<213> ORGANISM: Homo sapiens

<400> SEQUENCE: 28

```
atgtggctcc agagcctgct gctcttgggc actgtggcct gctccatctc tgcacccgcc      60
cgctcgccca gccccagcac gcagccctgg gagcatgtga atgccatcca ggaggcccgg     120
cgtctgctga acctgagtag agacactgct gctgagatga atgaaacagt agaagtcatc     180
tcagaaatgt ttgacctcca ggagccgacc tgcctacaga cccgcctgga gctgtacaag     240
cagggcctgc ggggcagcct caccaagctc aagggcccct tgaccatgat ggccagccac     300
tacaagcagc actgccctcc aaccccggaa acttcctgtg caacccagat tatcaccttt     360
gaaagtttca agagaaacct gaaggacttt ctgcttgtca tccccttga ctgctgggag     420
ccagtccagg agtgatga                                                    438
```

<210> SEQ ID NO 29
<211> LENGTH: 438
<212> TYPE: RNA
<213> ORGANISM: Homo sapiens

<400> SEQUENCE: 29

```
auguggcucc agagccugcu gcucuugggc acuguggccu gcuccaucuc ugcacccgcc      60
cgcucgccca gccccagcac gcagcccugg gagcauguga augccaucca ggaggcccgg     120
cgucugcuga accugaguag agacacugcu gcugagauga augaaacagu agaagucauc     180
ucagaaaugu uugaccucca ggagccgacc ugccuacaga cccgccugga gcuguacaag     240
cagggccugc ggggcagccu caccaagcuc aagggccccu ugaccaugau ggccagccac     300
uacaagcagc acugcccucc aaccccggaa acuuccugug caacccagau uaucaccuuu     360
gaaaguuuca agagaaaccu gaaggacuuu cugcuuguca ucccuuuga cugcugggag     420
ccaguccagg agugauga                                                    438
```

<210> SEQ ID NO 30
<211> LENGTH: 161
<212> TYPE: PRT
<213> ORGANISM: Artificial sequence
<220> FEATURE:
<223> OTHER INFORMATION: ModA IL-2 (human IL-2 in combination with a
      mouse optimized secretion sequence)

<400> SEQUENCE: 30

```
Met Arg Val Thr Ala Pro Arg Thr Leu Ile Leu Leu Leu Ser Gly Ala
1               5                   10                  15

Leu Ala Leu Thr Glu Thr Trp Ala Gly Ser Gly Ser Ala Pro Thr Ser
            20                  25                  30

Ser Ser Thr Lys Lys Thr Gln Leu Gln Leu Glu His Leu Leu Leu Asp
        35                  40                  45

Leu Gln Met Ile Leu Asn Gly Ile Asn Asn Tyr Lys Asn Pro Lys Leu
    50                  55                  60

Thr Arg Met Leu Thr Phe Lys Phe Tyr Met Pro Lys Lys Ala Thr Glu
```

```
                65                  70                  75                  80
Leu Lys His Leu Gln Cys Leu Glu Glu Glu Leu Lys Pro Leu Glu Glu
                    85                  90                  95

Val Leu Asn Leu Ala Gln Ser Lys Asn Phe His Leu Arg Pro Arg Asp
                100                 105                 110

Leu Ile Ser Asn Ile Asn Val Ile Val Leu Glu Leu Lys Gly Ser Glu
                115                 120                 125

Thr Thr Phe Met Cys Glu Tyr Ala Asp Glu Thr Ala Thr Ile Val Glu
            130                 135                 140

Phe Leu Asn Arg Trp Ile Thr Phe Cys Gln Ser Ile Ile Ser Thr Leu
145                 150                 155                 160

Thr

<210> SEQ ID NO 31
<211> LENGTH: 959
<212> TYPE: DNA
<213> ORGANISM: Artificial sequence
<220> FEATURE:
<223> OTHER INFORMATION: ModA IL-2 (5'UTR-CDS-3'UTR)

<400> SEQUENCE: 31
gggcgaacta gtattcttct ggtccccaca gactcagaga gaacccgcca ccatgagagt     60
gaccgccccc agaaccctga tcctgctgct gtctggcgcc ctggccctga cagagacatg    120
ggccggaagc ggatccgcac ctacttcaag ttctacaaag aaaacacagc tacaactgga    180
gcatttactt ctggatttac agatgatttt gaatggaatt aataattaca agaatcccaa    240
actcaccagg atgctcacat ttaagtttta catgcccaag aaggccacag aactgaaaca    300
tcttcagtgt ctagaagaag aactcaaacc tctggaggaa gtgctaaatt tagctcaaag    360
caaaaacttt cacttaagac ccagggactt aatcagcaat atcaacgtaa tagttctgga    420
actaaaggga tctgaaacaa cattcatgtg tgaatatgct gatgagacag caaccattgt    480
agaatttctg aacagatgga ttaccttttg tcaaagcatc atctcaacac tgacttgact    540
cgagagctcg ctttcttgct gtccaatttc tattaaaggt tcctttgttc cctaagtcca    600
actactaaac tgggggatat tatgaagggc cttgagcatc tggattctgc ctaataaaaa    660
acatttattt tcattgctgc gtcgagagct cgctttcttg ctgtccaatt tctattaaag    720
gttcctttgt tccctaagtc caactactaa actgggggat attatgaagg gccttgagca    780
tctggattct gcctaataaa aacatttat tttcattgct gcgtcgagac ctggtccaga    840
gtcgctagca aaaaaaaaa aaaaaaaaa aaaaaaaag catatgacta aaaaaaaaa    900 aaaaaaaaa aaaaaaaaa aaaaaaaaa aaaaaaaaa aaaaaaaaa aaaaaaaa    959

<210> SEQ ID NO 32
<211> LENGTH: 959
<212> TYPE: RNA
<213> ORGANISM: Artificial sequence
<220> FEATURE:
<223> OTHER INFORMATION: ModA IL-2

<400> SEQUENCE: 32
gggcgaacua guauucuucu gguccccaca gacucagaga gaacccgcca ccaugagagu     60
gaccgccccc agaacccuga uccugcugcu gucuggcgcc cuggcccuga cagagacaug    120
ggccggaagc ggauccgcac cuacuucaag uucuacaaag aaaacacagc uacaacugga    180
gcauuuacuu cuggauuuac agaugauuuu gaauggaauu aauaauuaca agaaucccaa    240
```

| | | |
|---|---|---|
| acucaccagg augcucacau uuaaguuuua caugcccaag aaggccacag aacugaaaca | 300 | |
| ucuucagugu cuagaagaag aacucaaacc ucuggaggaa gugcuaaauu uagcucaaag | 360 | |
| caaaaacuuu cacuuaagac ccagggacuu aaucagcaau aucaacguaa uaguucugga | 420 | |
| acuaaaggga ucugaacaa cauucaugug ugaauaugcu gaugacag caaccauugu | 480 | |
| agaauuucug aacagaugga uuaccuuuug ucaaagcauc aucucaacac ugacuugacu | 540 | |
| cgagagcucg cuucuugcu guccaauuuc uauuaaaggu uccuuuguuc ccuaagucca | 600 | |
| acuacuaaac uggggauau uaugaagggc cuugagcauc uggauucugc cuauaaaaa | 660 | |
| acauuuauuu ucauugcugc gucgagagcu cgcuucuug cuguccaauu ucuauuaaag | 720 | |
| guuccuuugu ucccuaaguc caacuacuaa acuggggau auuaugaagg gccuugagca | 780 | |
| ucuggauucu gccuaauaaa aaacauuuau uuucauugcu gcgucgagac cuggccaga | 840 | |
| gucgcuagca aaaaaaaaa aaaaaaaaa aaaaaaaag cauugacua aaaaaaaaa | 900 | |
| aaaaaaaaa aaaaaaaaa aaaaaaaaa aaaaaaaaa aaaaaaaaa aaaaaaaa | 959 | |

<210> SEQ ID NO 33
<211> LENGTH: 161
<212> TYPE: PRT
<213> ORGANISM: Artificial sequence
<220> FEATURE:
<223> OTHER INFORMATION: ModB IL-2

<400> SEQUENCE: 33

Met Gly Ala Met Ala Pro Arg Thr Leu Leu Leu Leu Ala Ala
1               5                   10                  15

Leu Ala Pro Thr Gln Thr Arg Ala Gly Pro Gly Ser Ala Pro Thr Ser
            20                  25                  30

Ser Ser Thr Lys Lys Thr Gln Leu Gln Leu Glu His Leu Leu Leu Asp
        35                  40                  45

Leu Gln Met Ile Leu Asn Gly Ile Asn Asn Tyr Lys Asn Pro Lys Leu
    50                  55                  60

Thr Arg Met Leu Thr Phe Lys Phe Tyr Met Pro Lys Lys Ala Thr Glu
65                  70                  75                  80

Leu Lys His Leu Gln Cys Leu Glu Glu Glu Leu Lys Pro Leu Glu Glu
                85                  90                  95

Val Leu Asn Leu Ala Gln Ser Lys Asn Phe His Leu Arg Pro Arg Asp
            100                 105                 110

Leu Ile Ser Asn Ile Asn Val Ile Val Leu Glu Leu Lys Gly Ser Glu
        115                 120                 125

Thr Thr Phe Met Cys Glu Tyr Ala Asp Glu Thr Ala Thr Ile Val Glu
    130                 135                 140

Phe Leu Asn Arg Trp Ile Thr Phe Cys Gln Ser Ile Ile Ser Thr Leu
145                 150                 155                 160

Thr

<210> SEQ ID NO 34
<211> LENGTH: 1039
<212> TYPE: DNA
<213> ORGANISM: Artificial sequence
<220> FEATURE:
<223> OTHER INFORMATION: ModB IL-2 (5'UTR-CDS-3'UTR)

<400> SEQUENCE: 34

| | | |
|---|---|---|
| ggaataaact agtctcaaca caacatatac aaaacaaacg aatctcaagc aatcaagcat | 60 | |
| tctacttcta ttgcagcaat ttaaatcatt tcttttaaag caaaagcaat tttctgaaaa | 120 | |

```
ttttcaccat ttacgaacga tagccatggg cgccatggcc cctagaacat tgctcctgct      180
gctggccgct gccctggccc ctacacagac aagagctgga cctggatccg cacctacttc      240
aagttctaca agaaaacac agctacaact ggagcattta cttctggatt tacagatgat       300
tttgaatgga attaataatt acaagaatcc caaactcacc aggatgctca catttaagtt      360
ttacatgccc aagaaggcca cagaactgaa acatcttcag tgtctagaag aagaactcaa      420
acctctggag gaagtgctaa atttagctca aagcaaaaac tttcacttaa gacccaggga      480
cttaatcagc aatatcaacg taatagttct ggaactaaag ggatctgaaa caacattcat      540
gtgtgaatat gctgatgaga cagcaaccat tgtagaattt ctgaacagat ggattacctt      600
ttgtcaaagc atcatctcaa cactgacttg actcgacgtc ctggtactgc atgcacgcaa      660
tgctagctgc cccttttccg tcctgggtac cccgagtctc ccccgacctc gggtccagg       720 tatgctccca cctccacctg ccccactcac cacctctgct agttccagac acctcccaag      780
cacgcagcaa tgcagctcaa aacgcttagc ctagccacac ccccacggga aacagcagtg     840
attaaccttt agcaataaac gaaagtttaa ctaagctata ctaaccccag ggttggtcaa      900
tttcgtgcca gccacaccct cgagctagca aaaaaaaaaa aaaaaaaaaa aaaaaaaag      960 catatgacta aaaaaaaaaa aaaaaaaaaa aaaaaaaaaa aaaaaaaaaa aaaaaaaaaa      1020
aaaaaaaaaa aaaaaaaaa                                                   1039

<210> SEQ ID NO 35
<211> LENGTH: 1039
<212> TYPE: RNA
<213> ORGANISM: Artificial sequence
<220> FEATURE:
<223> OTHER INFORMATION: ModB IL-2

<400> SEQUENCE: 35
ggaauaaacu agucucaaca caacauauac aaaacaaacg aaucucaagc aaucaagcau      60
ucuacuucua uugcagcaau uuaaaucauu ucuuuuaaag caaaagcaau uuucugaaaa      120
uuuucaccau uuacgaacga uagccauggg cgccauggcc ccuagaacau ugcuccugcu      180
gcuggccgcu gcccuggccc cuacacagac aagagcugga ccuggauccg caccuacuuc      240
aaguucuaca agaaaacac agcuacaacu ggagcauuua cuucuggauu uacagaugau      300
uuugaaugga auuaauaauu acaagaaucc caaacucacc aggaugcuca cauuuaaguu      360
uuacaugccc aagaaggcca cagaacugaa acaucuucag ugucuagaag aagaacucaa      420
accucuggag gaagugcuaa auuuagcuca aagcaaaaac uuucacuuaa gacccaggga      480
cuuaaucagc aauaucaacg uaauaguucu ggaacuaaag ggaucugaaa caacauucau      540
gugugaauau gcugaugaga cagcaaccau uguagaauuu cugaacagau ggauuaccuu      600
uugucaaagc aucaucucaa cacugacuug acucgacguc cugguacugc augcacgcaa      660
ugcuagcugc cccuuucccg uccuggguac cccgagucuc ccccgaccuc ggguccagg      720 uaugcuccca ccuccaccug ccccacucac caccucugcu aguuccagac accucccaag      780
cacgcagcaa ugcagcucaa aacgcuuagc cuagccacac ccccacggga aacagcagug     840
auuaaccuuu agcaauaaac gaaaguuuaa cuaagcuaua cuaaccccag gguuggucaa      900
uuucgugcca gccacacccu cgagcuagca aaaaaaaaaa aaaaaaaaaa aaaaaaaag      960 cauaugacua aaaaaaaaaa aaaaaaaaaa aaaaaaaaaa aaaaaaaaaa aaaaaaaaaa     1020
aaaaaaaaaa aaaaaaaaa                                                   1039
```

<210> SEQ ID NO 36
<211> LENGTH: 544
<212> TYPE: PRT
<213> ORGANISM: Artificial sequence
<220> FEATURE:
<223> OTHER INFORMATION: ModA murine IL-12

<400> SEQUENCE: 36

```
Met Arg Val Thr Ala Pro Arg Thr Leu Ile Leu Leu Leu Ser Gly Ala
1               5                   10                  15

Leu Ala Leu Thr Glu Thr Trp Ala Gly Ser Gly Ser Met Trp Glu Leu
            20                  25                  30

Glu Lys Asp Val Tyr Val Val Glu Val Asp Trp Thr Pro Asp Ala Pro
        35                  40                  45

Gly Glu Thr Val Asn Leu Thr Cys Asp Thr Pro Glu Glu Asp Asp Ile
    50                  55                  60

Thr Trp Thr Ser Asp Gln Arg His Gly Val Ile Gly Ser Gly Lys Thr
65                  70                  75                  80

Leu Thr Ile Thr Val Lys Glu Phe Leu Asp Ala Gly Gln Tyr Thr Cys
                85                  90                  95

His Lys Gly Gly Glu Thr Leu Ser His Ser His Leu Leu Leu His Lys
            100                 105                 110

Lys Glu Asn Gly Ile Trp Ser Thr Glu Ile Leu Lys Asn Phe Lys Asn
        115                 120                 125

Lys Thr Phe Leu Lys Cys Glu Ala Pro Asn Tyr Ser Gly Arg Phe Thr
    130                 135                 140

Cys Ser Trp Leu Val Gln Arg Asn Met Asp Leu Lys Phe Asn Ile Lys
145                 150                 155                 160

Ser Ser Ser Ser Ser Pro Asp Ser Arg Ala Val Thr Cys Gly Met Ala
                165                 170                 175

Ser Leu Ser Ala Glu Lys Val Thr Leu Asp Gln Arg Asp Tyr Glu Lys
            180                 185                 190

Tyr Ser Val Ser Cys Gln Glu Asp Val Thr Cys Pro Thr Ala Glu Glu
        195                 200                 205

Thr Leu Pro Ile Glu Leu Ala Leu Glu Ala Arg Gln Gln Asn Lys Tyr
    210                 215                 220

Glu Asn Tyr Ser Thr Ser Phe Phe Ile Arg Asp Ile Ile Lys Pro Asp
225                 230                 235                 240

Pro Pro Lys Asn Leu Gln Met Lys Pro Leu Lys Asn Ser Gln Val Glu
                245                 250                 255

Val Ser Trp Glu Tyr Pro Asp Ser Trp Ser Thr Pro His Ser Tyr Phe
            260                 265                 270

Ser Leu Lys Phe Phe Val Arg Ile Gln Arg Lys Lys Glu Lys Met Lys
        275                 280                 285

Glu Thr Glu Glu Gly Cys Asn Gln Lys Gly Ala Phe Leu Val Glu Lys
    290                 295                 300

Thr Ser Thr Glu Val Gln Cys Lys Gly Gly Asn Val Cys Val Gln Ala
305                 310                 315                 320

Gln Asp Arg Tyr Tyr Asn Ser Ser Cys Ser Lys Trp Ala Cys Val Pro
                325                 330                 335

Cys Arg Val Arg Ser Val Pro Val Gly Val Pro Val Gly Val Gly Arg
            340                 345                 350

Val Ile Pro Val Ser Gly Pro Ala Arg Cys Leu Ser Gln Ser Arg Asn
        355                 360                 365
```

| | | | | | | | | | | | | |
|---|---|---|---|---|---|---|---|---|---|---|---|---|
|Leu|Leu|Lys|Thr|Thr|Asp|Asp|Met|Val|Lys|Thr|Ala|Arg|Glu|Lys|Leu|
| |370| | | |375| | | |380| | | | | | |
|Lys|His|Tyr|Ser|Cys|Thr|Ala|Glu|Asp|Ile|Asp|His|Glu|Asp|Ile|Thr|
|385| | | | |390| | | |395| | | | |400|
|Arg|Asp|Gln|Thr|Ser|Thr|Leu|Lys|Thr|Cys|Leu|Pro|Leu|Glu|Leu|His|
| | | | |405| | | | |410| | | | |415| |
|Lys|Asn|Glu|Ser|Cys|Leu|Ala|Thr|Arg|Glu|Thr|Ser|Ser|Thr|Thr|Arg|
| | | |420| | | | |425| | | | |430| | |
|Gly|Ser|Cys|Leu|Pro|Pro|Gln|Lys|Thr|Ser|Leu|Met|Met|Thr|Leu|Cys|
| | |435| | | | |440| | | | |445| | | |
|Leu|Gly|Ser|Ile|Tyr|Glu|Asp|Leu|Lys|Met|Tyr|Gln|Thr|Glu|Phe|Gln|
| |450| | | | |455| | | | |460| | | | |
|Ala|Ile|Asn|Ala|Ala|Leu|Gln|Asn|His|Asn|His|Gln|Gln|Ile|Ile|Leu|
|465| | | | |470| | | | |475| | | | |480|
|Asp|Lys|Gly|Met|Leu|Val|Ala|Ile|Asp|Glu|Leu|Met|Gln|Ser|Leu|Asn|
| | | | |485| | | | |490| | | | |495| |
|His|Asn|Gly|Glu|Thr|Leu|Arg|Gln|Lys|Pro|Pro|Val|Gly|Glu|Ala|Asp|
| | | |500| | | | |505| | | | |510| | |
|Pro|Tyr|Arg|Val|Lys|Met|Lys|Leu|Cys|Ile|Leu|Leu|His|Ala|Phe|Ser|
| | |515| | | | |520| | | | |525| | | |
|Thr|Arg|Val|Val|Thr|Ile|Asn|Arg|Val|Met|Gly|Tyr|Leu|Ser|Ser|Ala|
| |530| | | | |535| | | | |540| | | | |

<210> SEQ ID NO 37
<211> LENGTH: 2111
<212> TYPE: DNA
<213> ORGANISM: Artificial sequence
<220> FEATURE:
<223> OTHER INFORMATION: ModA murine IL-12 (5'UTR-CDS-3'UTR)

<400> SEQUENCE: 37

```
gggcgaacta gtattcttct ggtccccaca gactcagaga gaacccgcca ccatgagagt     60
gaccgccccc agaaccctga tcctgctgct gtctggcgcc ctggccctga cagagacatg    120
ggccggaagc ggatccatgt gggagctgga gaaagacgtt tatgttgtag aggtggactg    180
gactcccgat gcccctggag aaacagtgaa cctcacctgt gacacgcctg aagaagatga    240
catcacctgg acctcagacc agagacatgg agtcataggc tctggaaaga ccctgaccat    300
cactgtcaaa gagtttctag atgctggcca gtacacctgc cacaaggagg cgagactctc    360
gagccactca catctgctgc tccacaagaa ggaaaatgga atttggtcca ctgaaatttt    420
aaaaaatttc aaaacaaga ctttcctgaa gtgtgaagca ccaaattact ccggacggtt    480
cacgtgctca tggctggtgc aaagaaacat ggacttgaag ttcaacatca agagcagtag    540
cagttcccct gactctcggg cagtgacatg tggaatggcg tctctgtctg cagagaaggt    600
cacactggac caaagggact atgagaagta ttcagtgtcc tgccaggagg atgtcacctg    660
cccaactgcc gaggagaccc tgcccattga actggcgttg gaagcacggc agcagaataa    720
atatgagaac tacagcacca gcttcttcat cagggacatc atcaaaccag acccgcccaa    780
gaacttgcag atgaagcctt tgaagaactc acaggtggag gtcagctggg agtaccctga    840
ctcctggagc actccccatt cctacttctc cctcaagttc tttgttcgaa tccagcgcaa    900
gaaagaaaag atgaaggaga cagaggaggg tgtaaccag aaaggtgcgt tcctcgtaga    960
gaagacatct accgaagtcc aatgcaaagg cgggaatgtc tgcgtgcaag ctcaggatcg   1020
ctattacaat tcctcatgca gcaagtgggc atgtgttccc tgcagagtcc gatcggttcc   1080
```

```
tggagtaggg gtacctggag tgggcagggt cataccggtc tctggacctg ccaggtgtct    1140
tagccagtcc cgaaacctgc tgaagaccac agatgacatg gtgaagacgg ccagagaaaa    1200
gctgaaacat tattcctgca ctgctgaaga catcgatcat gaagacatca cacgggacca    1260
aaccagcaca ttgaagacct gtttaccact ggaactacac aagaacgaga gttgcctggc    1320
tactagagag acttcttcca caacaagagg gagctgcctg cccccacaga agacgtcttt    1380
gatgatgacc ctgtgccttg gtagcatcta tgaggacttg aagatgtacc agacagagtt    1440
ccaggccatc aacgcagcac ttcagaatca caaccatcag cagatcattc tagacaaggg    1500
catgctggtg gccatcgatg agctgatgca gtctctgaat cataatggcg agactctgcg    1560
ccagaaacct cctgtgggag aagcagaccc ttacagagtg aaaatgaagc tctgcatcct    1620
gcttcacgcc ttcagcaccc gcgtcgtgac catcaacagg gtgatgggct atctgtccag    1680
cgcctaatag ctcgagagct cgcttttcttg ctgtccaatt tctattaaag gttcctttgt    1740
tccctaagtc caactactaa actgggggat attatgaagg ccttgagca tctggattct    1800 gcctaataaa aaacatttat tttcattgct gcgtcgagag ctcgctttct tgctgtccaa    1860
tttctattaa aggttccttt gttccctaag tccaactact aaactggggg atattatgaa    1920
gggccttgag catctggatt ctgcctaata aaaaacattt attttcattg ctgcgtcgag    1980
acctggtcca gagtcgctag caaaaaaaaa aaaaaaaaaa aaaaaaaaaa agcatatgac    2040
taaaaaaaaa aaaaaaaaaa aaaaaaaaaa aaaaaaaaaa aaaaaaaaaa aaaaaaaaaa    2100
aaaaaaaaaa a                                                        2111

<210> SEQ ID NO 38
<211> LENGTH: 2111
<212> TYPE: RNA
<213> ORGANISM: Artificial sequence
<220> FEATURE:
<223> OTHER INFORMATION: ModA murine IL-12

<400> SEQUENCE: 38
gggcgaacua guauucuucu gguccccaca gacucagaga gaacccgcca ccaugagagu     60
gaccgccccc agaacccuga uccugcugcu gucuggcgcc cuggcccuga cagagacaug    120
ggccggaagc ggauccaugu gggagcugga gaaagacguu uauguuguag agguggacug    180
gacucccgau gccccuggag aaacagugaa ccucaccugu gacacgccug aagaagauga    240
caucaccugg accucagacc agagacaugg agucauaggc ucuggaaaga cccugaccau    300
cacugucaaa gaguuucuag augcuggcca guacaccugc cacaaggagg cgagacucu     360 gagccacuca caucugcugc uccacaagaa ggaaaaugga auuggucca cugaaauuuu    420 aaaaaauuuc aaaaacaaga cuuuccugaa gugugaagca ccaaauuacu ccggacgguu    480
cacgugcuca uggcugguge aaagaaacau ggacuugaag uucaacauca agagcaguag    540 caguucccu gacucucggg caguga caug uggaauggcg ucucugucug cagagaaggu    600
cacacuggac caaagggacu augagaagua uucagugucc ugccaggagg augucaccug    660
cccaacugcc gaggagaccc ugcccauuga acuggcguug aagcacggc agcagaauaa    720 auaugagaac uacagcacca gcuucuucau caggacauc aucaaaccag acccgcccaa    780
gaacuugcag augaagccuu ugaagaacuc acaggugcag gucagcuggg aguacccuga    840
cuccuggagc acuccccauu ccuacuucuc ccucaaguuc uuuguucgaa uccagcgcaa    900
gaaagaaaag augaaggaga cagaggaggg uguuaaccag aaaggugcgu uccucguaga    960
gaagacaucu accgaaguuc aaugcaaagg cgggaauguc ugcgugcaag cucaggaucg    1020
```

```
cuauuacaau uccucaugca gcaagugggc auguguuccc ugcagagucc gaucgguucc    1080
uggaguaggg guaccuggag ugggcagggu cauaccgguc ucuggaccug ccaggugucu    1140
uagccagucc cgaaaccugc ugaagaccac agaugacaug gugaagacgg ccagagaaaa    1200
gcugaaacau uauuccugca cugcugaaga caucgaucau gaagacauca cacgggacca    1260
aaccagcaca uugaagaccu guuuaccacu ggaacuacac aagaacgaga uugccuggc     1320 uacuagagag acuucuucca caacaagagg gagcugccug cccccacaga agacgucuuu    1380
gaugaugacc cugugccuug guagcaucua ugaggacuug aagauguacc agacagaguu    1440
ccaggccauc aacgcagcac uucagaauca caaccaucag cagaucauuc uagcaagggg   1500
caugcuggug gccaucgaug agcugaugca gucucugaau cauaauggcg agacucugcg    1560
ccagaaaccu ccugugggag aagcagaccc uuacagagug aaaaugaagc ucugcauccu    1620
gcuucacgcc uucagcaccc gcgucgugac caucaacagg gugaugggcu aucuguccag    1680
cgccuaauag cucgagagcu cgcuuucuug cuguccaauu ucuauuaaag guuccuuugu    1740
ucccuaaguc caacuacuaa acuggggau auuaugaagg gccuugagca ucuggauucu    1800
gccuaauaaa aaacauuuau uuucauugcu gcgucgagag cucgcuuucu ugcuguccaa    1860
uuucuauuaa agguuccuuu guucccuaag uccaacuacu aaacuggggg auauuaugaa    1920
gggccuugag caucuggauu cugccuaaua aaaaacauuu auuuucauug cugcgucgag    1980
accuggucca gagucgcuag caaaaaaaaa aaaaaaaaaa aaaaaaaaa agcauaugac     2040 uaaaaaaaaa aaaaaaaaaa aaaaaaaaa aaaaaaaaaa aaaaaaaaa aaaaaaaaa      2100 aaaaaaaaaa a                                                        2111
```

<210> SEQ ID NO 39
<211> LENGTH: 544
<212> TYPE: PRT
<213> ORGANISM: Artificial sequence
<220> FEATURE:
<223> OTHER INFORMATION: ModB murine IL-12

<400> SEQUENCE: 39

```
Met Gly Ala Met Ala Pro Arg Thr Leu Leu Leu Leu Ala Ala Ala
1               5                   10                  15

Leu Ala Pro Thr Gln Thr Arg Ala Gly Pro Gly Ser Met Trp Glu Leu
            20                  25                  30

Glu Lys Asp Val Tyr Val Val Glu Val Asp Trp Thr Pro Asp Ala Pro
        35                  40                  45

Gly Glu Thr Val Asn Leu Thr Cys Asp Thr Pro Glu Glu Asp Asp Ile
    50                  55                  60

Thr Trp Thr Ser Asp Gln Arg His Gly Val Ile Gly Ser Gly Lys Thr
65                  70                  75                  80

Leu Thr Ile Thr Val Lys Glu Phe Leu Asp Ala Gly Gln Tyr Thr Cys
                85                  90                  95

His Lys Gly Gly Glu Thr Leu Ser His Ser His Leu Leu Leu His Lys
            100                 105                 110

Lys Glu Asn Gly Ile Trp Ser Thr Glu Ile Leu Lys Asn Phe Lys Asn
        115                 120                 125

Lys Thr Phe Leu Lys Cys Glu Ala Pro Asn Tyr Ser Gly Arg Phe Thr
    130                 135                 140

Cys Ser Trp Leu Val Gln Arg Asn Met Asp Leu Lys Phe Asn Ile Lys
145                 150                 155                 160
```

-continued

```
Ser Ser Ser Ser Ser Pro Asp Ser Arg Ala Val Thr Cys Gly Met Ala
                165                 170                 175
Ser Leu Ser Ala Glu Lys Val Thr Leu Asp Gln Arg Asp Tyr Glu Lys
            180                 185                 190
Tyr Ser Val Ser Cys Gln Glu Asp Val Thr Cys Pro Thr Ala Glu Glu
        195                 200                 205
Thr Leu Pro Ile Glu Leu Ala Leu Glu Ala Arg Gln Gln Asn Lys Tyr
    210                 215                 220
Glu Asn Tyr Ser Thr Ser Phe Phe Ile Arg Asp Ile Ile Lys Pro Asp
225                 230                 235                 240
Pro Pro Lys Asn Leu Gln Met Lys Pro Leu Lys Asn Ser Gln Val Glu
                245                 250                 255
Val Ser Trp Glu Tyr Pro Asp Ser Trp Ser Thr Pro His Ser Tyr Phe
            260                 265                 270
Ser Leu Lys Phe Phe Val Arg Ile Gln Arg Lys Lys Glu Lys Met Lys
        275                 280                 285
Glu Thr Glu Glu Gly Cys Asn Gln Lys Gly Ala Phe Leu Val Glu Lys
    290                 295                 300
Thr Ser Thr Glu Val Gln Cys Lys Gly Gly Asn Val Cys Val Gln Ala
305                 310                 315                 320
Gln Asp Arg Tyr Tyr Asn Ser Ser Cys Ser Lys Trp Ala Cys Val Pro
                325                 330                 335
Cys Arg Val Arg Ser Val Pro Gly Val Gly Val Pro Gly Val Gly Arg
            340                 345                 350
Val Ile Pro Val Ser Gly Pro Ala Arg Cys Leu Ser Gln Ser Arg Asn
        355                 360                 365
Leu Leu Lys Thr Thr Asp Asp Met Val Lys Thr Ala Arg Glu Lys Leu
    370                 375                 380
Lys His Tyr Ser Cys Thr Ala Glu Asp Ile Asp His Glu Asp Ile Thr
385                 390                 395                 400
Arg Asp Gln Thr Ser Thr Leu Lys Thr Cys Leu Pro Leu Glu Leu His
                405                 410                 415
Lys Asn Glu Ser Cys Leu Ala Thr Arg Glu Thr Ser Ser Thr Thr Arg
            420                 425                 430
Gly Ser Cys Leu Pro Pro Gln Lys Thr Ser Leu Met Met Thr Leu Cys
        435                 440                 445
Leu Gly Ser Ile Tyr Glu Asp Leu Lys Met Tyr Gln Thr Glu Phe Gln
    450                 455                 460
Ala Ile Asn Ala Ala Leu Gln Asn His Asn His Gln Gln Ile Ile Leu
465                 470                 475                 480
Asp Lys Gly Met Leu Val Ala Ile Asp Glu Leu Met Gln Ser Leu Asn
                485                 490                 495
His Asn Gly Glu Thr Leu Arg Gln Lys Pro Pro Val Gly Glu Ala Asp
            500                 505                 510
Pro Tyr Arg Val Lys Met Lys Leu Cys Ile Leu Leu His Ala Phe Ser
        515                 520                 525
Thr Arg Val Val Thr Ile Asn Arg Val Met Gly Tyr Leu Ser Ser Ala
    530                 535                 540
```

<210> SEQ ID NO 40
<211> LENGTH: 2191
<212> TYPE: DNA
<213> ORGANISM: Artificial sequence
<220> FEATURE:
<223> OTHER INFORMATION: ModB murine IL-12 (5'UTR-CDS-3'UTR)

<400> SEQUENCE: 40

```
ggaataaact agtctcaaca caacatatac aaaacaaacg aatctcaagc aatcaagcat      60
tctacttcta ttgcagcaat ttaaatcatt tcttttaaag caaaagcaat tttctgaaaa     120
ttttcaccat ttacgaacga tagccatggg cgccatggcc cctagaacat tgctcctgct     180
gctggccgct gccctggccc ctacacagac aagagctgga cctggatcca tgtgggagct     240
ggagaaagac gtttatgttg tagaggtgga ctggactccc gatgccctg gagaaacagt      300
gaacctcacc tgtgacacgc ctgaagaaga tgacatcacc tggacctcag accagagaca     360
tggagtcata ggctctggaa agaccctgac catcactgtc aaagagtttc tagatgctgg     420
ccagtacacc tgccacaaag gaggcgagac tctgagccac tcacatctgc tgctccacaa     480
gaaggaaaat ggaatttggt ccactgaaat tttaaaaaat ttcaaaaaca agactttcct     540
gaagtgtgaa gcaccaaatt actccggacg gttcacgtgc tcatggctgg tgcaaagaaa     600
catggacttg aagttcaaca tcaagagcag tagcagttcc cctgactctc gggcagtgac     660
atgtggaatg gcgtctctgt ctgcagagaa ggtcacactg gaccaagggg actatgagaa     720
gtattcagtg tcctgccagg aggatgtcac ctgcccaact gccgaggaga ccctgcccat     780
tgaactggcg ttggaagcac ggcagcagaa taaatatgag aactacagca ccagcttctt     840
catcagggac atcatcaaac cagacccgcc caagaacttg cagatgaagc ctttgaagaa     900
ctcacaggtg gaggtcagct gggagtaccc tgactcctgg agcactcccc attcctactt     960
ctccctcaag ttctttgttc gaatccagcg caagaaagaa aagatgaagg agacagagga    1020
ggggtgtaac cagaaaggtg cgttcctcgt agagaagaca tctaccgaag tccaatgcaa    1080
aggcgggaat gtctgcgtgc aagctcagga tcgctattac aattcctcat gcagcaagtg    1140
ggcatgtgtt ccctgcagag tccgatcggt tcctggagta ggggtacctg gagtgggcag    1200
ggtcataccg gtctctggac ctgccaggtg tcttagccag tcccgaaacc tgctgaagac    1260
cacagatgac atggtgaaga cggccagaga aaagctgaaa cattattcct gcactgctga    1320
agacatcgat catgaagaca tcacacggga ccaaaccagc acattgaaga cctgtttacc    1380
actggaacta cacaagaacg agagttgcct ggctactaga gagacttctt ccacaacaag    1440
agggagctgc ctgccccac agaagacgtc tttgatgatg accctgtgcc ttggtagcat     1500
ctatgaggac ttgaagatgt accagacaga gttccaggcc atcaacgcag cacttcagaa    1560
tcacaaccat cagcagatca ttctagacaa gggcatgctg gtggccatcg atgagctgat    1620
gcagtctctg aatcataatg gcgagactct gcgccagaaa cctcctgtgg gagaagcaga    1680
cccttacaga gtgaaaatga agctctgcat cctgcttcac gccttcagca cccgcgtcgt    1740
gaccatcaac agggtgatgg gctatctgtc cagcgcctaa tagctcgacg tcctggtact    1800
gcatgcacgc aatgctagct gcccctttcc cgtcctgggt accccgagtc tcccccgacc    1860
tcgggtccca ggtatgctcc cacctccacc tgcccactc accacctctg ctagttccag     1920
acacctccca agcacgcagc aatgcagctc aaaacgctta gcctagccac accccacgg     1980
gaaacagcag tgattaacct ttagcaataa acgaaagttt aactaagcta tactaacccc    2040
agggttggtc aatttcgtgc cagccacacc ctcgagctag caaaaaaaaa aaaaaaaaa     2100
aaaaaaaaaa agcatatgac taaaaaaaaa aaaaaaaaa aaaaaaaaa aaaaaaaaa       2160
aaaaaaaaaa aaaaaaaaaa aaaaaaaaaa a                                    2191
```

<210> SEQ ID NO 41

<211> LENGTH: 2191
<212> TYPE: RNA
<213> ORGANISM: Artificial sequence
<220> FEATURE:
<223> OTHER INFORMATION: ModB murine IL-12

<400> SEQUENCE: 41

| | | | | | |
|---|---|---|---|---|---|
| ggaauaaacu | agucucaaca | caacauauac | aaaacaaacg | aaucucaagc | aaucaagcau | 60 |
| ucuacuucua | uugcagcaau | uuaaaucauu | ucuuuuaaag | caaaagcaau | uuucugaaaa | 120 |
| uuuucaccau | uuacgaacga | uagccauggg | cgccauggcc | ccuagaacau | ugcuccugcu | 180 |
| gcuggccgcu | gcccuggccc | cuacacagac | aagagcugga | ccuggauccca | uguggggagcu | 240 |
| ggagaaagac | guuuauguug | uagaggugga | cuggacuccc | gaugcccug | gagaaacagu | 300 |
| gaaccucacc | ugugacacgc | cugaagaaga | ugacaucacc | uggaccucag | accagagaca | 360 |
| uggagucaua | ggcucuggaa | agacccugac | caucacaaguc | aaagaguuuc | uagaugcugg | 420 |
| ccaguacacc | ugccacaaag | gaggcgagac | ucugagccac | ucacaucugc | ugcuccacaa | 480 |
| gaaggaaaau | ggaauuuggu | ccacugaaau | uuuaaaaaau | ucaaaaaca | agacuuuccu | 540 |
| gaagugugaa | gcaccaaauu | acuccggacg | guucacgugc | ucauggcugg | ugcaaagaaa | 600 |
| cauggacuug | aaguucaaca | ucaagagcag | uagcaguucc | ccugacucuc | gggcagugac | 660 |
| auguggaaug | gcgucucugu | cugcagagaa | ggucacacug | gaccaagggg | acuaugagaa | 720 |
| guauucagu | uccugccagg | aggaugucac | cugcccaacu | gccgaggaga | cccugccau | 780 |
| ugaacuggcg | uuggaagcac | ggcagcagaa | uaaauaugag | aacuacagca | ccagcuucuu | 840 |
| caucagggac | aucaucaaac | cagacccgcc | caagaacuug | cagaugaagc | cuuugaagaa | 900 |
| cucacaggug | gaggucagcu | gggagauaccc | ugacuccugg | agcacuccccc | auuccuacuu | 960 |
| cucccucaag | uucuuuguuc | gaauccagcg | caagaaagaa | aagaugaagg | agacagagga | 1020 |
| gggguguaac | cagaaagugug | cguuccucgu | agagaagaca | ucuaccgaag | uccaaugcaa | 1080 |
| aggcgggaau | gucugcgugc | aagcucagga | ucgcuauuac | aauucccau | gcagcaagug | 1140 |
| ggcauguguu | cccugcagag | uccgaucggu | uccuggagua | ggguaccug | gagugggcag | 1200 |
| ggucauaccg | gucucuggac | cugccaggug | ucuuagccag | ucccgaaacc | ugcugaagac | 1260 |
| cacagaugac | auggugaaga | cggccagaga | aaagcugaaa | cauuauuccu | gcacugcuga | 1320 |
| agacaucgau | caugaagaca | ucacacggga | ccaaaccagc | acauugaaga | ccuguuacc | 1380 |
| acuggaacua | cacaagaacg | agaguugccu | ggcuacuaga | gagacuucuu | ccacaacaag | 1440 |
| agggagcugc | cugcccccac | agaagacguc | uuugaugaug | acccugugcc | uuggagcau | 1500 |
| cuaugaggac | uugaagaugu | accagacaga | guuccaggcc | aucaacgcag | cacuucagaa | 1560 |
| ucacaaccau | cagcagauca | uucuagacaa | gggcaugcug | guggccaucg | augagcugau | 1620 |
| gcagucucug | aaucauaaug | gcgagacucu | gcgccagaaa | ccuccugugg | gagaagcaga | 1680 |
| cccuuacaga | gugaaaauga | agcucugcau | ccugcuucac | gccuucagca | cccgcgucgu | 1740 |
| gaccaucaac | agggugaugg | gcuaucuguc | cagcgccuaa | uagcucgacg | uccugguacu | 1800 |
| gcaugcacgc | aaugcuagcu | gccccuuucc | cguccugggu | accccgaguc | uccccgacc | 1860 |
| ucggucccca | gguaugcucc | caccuccacc | ugcccacuc | accaccucug | cuaguuccag | 1920 |
| acaccucccca | agcacgcagc | aaugcagcuc | aaaacgcuua | gccuagccac | accccacgg | 1980 |
| gaaacagcag | ugauuaaccu | uuagcaauaa | acgaaaguuu | aacuaagcua | uacuaacccc | 2040 |
| agggguugguc | aauuucgugc | cagccacacc | cucgagcuag | caaaaaaaaa | aaaaaaaaaa | 2100 |
| aaaaaaaaaa | agcauaugac | uaaaaaaaaa | aaaaaaaaaa | aaaaaaaaaa | aaaaaaaaaa | 2160 | aaaaaaaaaa aaaaaaaaaa aaaaaaaaaa a                          2191

<210> SEQ ID NO 42
<211> LENGTH: 190
<212> TYPE: PRT
<213> ORGANISM: Artificial sequence
<220> FEATURE:
<223> OTHER INFORMATION: ModA murine IFN-alpha-4

<400> SEQUENCE: 42

Met Arg Val Thr Ala Pro Arg Thr Leu Ile Leu Leu Leu Ser Gly Ala
1               5                   10                  15

Leu Ala Leu Thr Glu Thr Trp Ala Gly Ser Gly Ser Cys Asp Leu Pro
            20                  25                  30

His Thr Tyr Asn Leu Gly Asn Lys Arg Ala Leu Thr Val Leu Glu Glu
        35                  40                  45

Met Arg Arg Leu Pro Pro Leu Ser Cys Leu Lys Asp Arg Lys Asp Phe
    50                  55                  60

Gly Phe Pro Leu Glu Lys Val Asp Asn Gln Gln Ile Gln Lys Ala Gln
65                  70                  75                  80

Ala Ile Leu Val Leu Arg Asp Leu Thr Gln Gln Ile Leu Asn Leu Phe
                85                  90                  95

Thr Ser Lys Asp Leu Ser Ala Thr Trp Asn Ala Thr Leu Leu Asp Ser
            100                 105                 110

Phe Cys Asn Asp Leu His Gln Gln Leu Asn Asp Leu Lys Ala Cys Val
        115                 120                 125

Met Gln Glu Pro Pro Leu Thr Gln Glu Asp Ser Leu Leu Ala Val Arg
    130                 135                 140

Thr Tyr Phe His Arg Ile Thr Val Tyr Leu Arg Lys Lys Lys His Ser
145                 150                 155                 160

Leu Cys Ala Trp Glu Val Ile Arg Ala Glu Val Trp Arg Ala Leu Ser
                165                 170                 175

Ser Ser Thr Asn Leu Leu Ala Arg Leu Ser Glu Glu Lys Glu
            180                 185                 190

<210> SEQ ID NO 43
<211> LENGTH: 1049
<212> TYPE: DNA
<213> ORGANISM: Artificial sequence
<220> FEATURE:
<223> OTHER INFORMATION: ModA murine IFN-alpha-4 (5'UTR-CDS-3'UTR)

<400> SEQUENCE: 43
gggcgaacta gtattcttct ggtccccaca gactcagaga gaacccgcca ccatgagagt      60
gaccgccccc agaaccctga tcctgctgct gtctggcgcc ctggccctga cagagacatg     120
ggccggaagc ggatcctgtg acctgcctca cacttataac ctcgggaaca agagggcctt     180
gacagtcctg gaagaaatga aagactcccc cctctttcc tgcctgaagg acaggaagga     240
ttttggattc ccccttggaga aggtggataa ccaacagatc cagaaggctc aagccatcct     300
tgtgctaaga gatcttaccc agcagatttt gaacctcttc acatcaaaag acttgtctgc     360
tacttggaat gcaactctcc tagactcatt ctgcaatgac ctccatcagc agctcaatga     420
tctcaaagcc tgtgtgatgc aggaacctcc tctgacccag gaagactccc tgctggctgt     480
gaggacatac ttccacagga tcactgtgta cctgagaaag aagaaacaca gcctctgtgc     540
ctgggaggtg atcagagcag aagtctggag agccctctct tcctcaacca acttgctggc     600

```
aagactgagt gaggagaagg agtgataact cgagagctcg ctttcttgct gtccaatttc    660
tattaaaggt tcctttgttc cctaagtcca actactaaac tggggatat tatgaagggc     720 cttgagcatc tggattctgc ctaataaaaa acatttattt tcattgctgc gtcgagagct    780
cgctttcttg ctgtccaatt tctattaaag gttcctttgt tccctaagtc caactactaa    840
actgggggat attatgaagg gccttgagca tctggattct gcctaataaa aaacatttat    900
tttcattgct gcgtcgagac ctggtccaga gtcgctagca aaaaaaaaa aaaaaaaaa     960 aaaaaaaaag catatgacta aaaaaaaaa aaaaaaaaa aaaaaaaaa aaaaaaaaa      1020 aaaaaaaaaa aaaaaaaaaa aaaaaaaa                                     1049

<210> SEQ ID NO 44
<211> LENGTH: 1049
<212> TYPE: RNA
<213> ORGANISM: Artificial sequence
<220> FEATURE:
<223> OTHER INFORMATION: ModA murine IFN-alpha-4

<400> SEQUENCE: 44
gggcgaacua guauucuucu gguccccaca gacucagaga gaacccgcca ccaugagagu    60
gaccgccccc agaacccuga uccugcugcu gucuggcgcc cuggcccuga cagagacaug    120
ggccggaagc ggauccugug accugccuca cacuuauaac cucgggaaca agagggccuu    180
gacaguccug gaagaaauga gaagacuccc cccucuuucc ugccgaagg acaggaagga    240 uuuuggauuc cccuuggaga aggugggauaa ccaacagauc cagaaggcuc aagccauccu    300
ugugcuaaga gaucuuaccc agcagauuuu gaacccucuu cacaucaaaag acuugucugc    360 uacuuggaau gcaacucucc uagacucauu cugcaaugac cuccaucagc agcucaauga    420
ucucaaagcc ugugugaugc aggaaccucc ucugacccag gaagacuccc ugcuggcugu    480
gaggacauac uuccacagga ucacugugua ccugagaaag aagaaacaca gccucugugc    540
cugggaggug aucagagcag aagucuggag agcccucucu uccucaacca acuugccggc    600
aagacugagu gaggagaagg agugauaacu cgagagcucg cuuucuugcu guccaauuuc    660
uauuaaaggu uccuuguuc ccuaagucca acuacuaaac uggggauau uaugaagggc    720 cuugagcauc uggauucugc cuaauaaaaa acauuauuu ucauugcugc gucgagagcu    780
cgcuuucuug cuguccaauu ucuauuaaag guuccuuugu ucccuaaguc caacuacuaa    840 acuggggau auuaugaagg gccuugagca ucuggauucu gccuaauaaa aaacauuuau    900
uuucauugcu gcgucgagac cugguccaga gucgcuagca aaaaaaaaa aaaaaaaaa     960 aaaaaaaaag cauaugacua aaaaaaaaa aaaaaaaaa aaaaaaaaa aaaaaaaaa      1020 aaaaaaaaaa aaaaaaaaaa aaaaaaaa                                     1049

<210> SEQ ID NO 45
<211> LENGTH: 190
<212> TYPE: PRT
<213> ORGANISM: Artificial sequence
<220> FEATURE:
<223> OTHER INFORMATION: ModB murine IFN-alpha-4

<400> SEQUENCE: 45

Met Gly Ala Met Ala Pro Arg Thr Leu Leu Leu Leu Ala Ala Ala
1               5                   10                  15

Leu Ala Pro Thr Gln Thr Arg Ala Gly Pro Gly Ser Cys Asp Leu Pro
                20                  25                  30

His Thr Tyr Asn Leu Gly Asn Lys Arg Ala Leu Thr Val Leu Glu Glu
```

```
                35                  40                  45
Met Arg Arg Leu Pro Pro Leu Ser Cys Leu Lys Asp Arg Lys Asp Phe
 50                  55                  60

Gly Phe Pro Leu Glu Lys Val Asp Asn Gln Gln Ile Gln Lys Ala Gln
 65                  70                  75                  80

Ala Ile Leu Val Leu Arg Asp Leu Thr Gln Gln Ile Leu Asn Leu Phe
                 85                  90                  95

Thr Ser Lys Asp Leu Ser Ala Thr Trp Asn Ala Thr Leu Leu Asp Ser
                100                 105                 110

Phe Cys Asn Asp Leu His Gln Gln Leu Asn Asp Leu Lys Ala Cys Val
                115                 120                 125

Met Gln Glu Pro Pro Leu Thr Gln Glu Asp Ser Leu Leu Ala Val Arg
130                 135                 140

Thr Tyr Phe His Arg Ile Thr Val Tyr Leu Arg Lys Lys Lys His Ser
145                 150                 155                 160

Leu Cys Ala Trp Glu Val Ile Arg Ala Glu Val Trp Arg Ala Leu Ser
                165                 170                 175

Ser Ser Thr Asn Leu Leu Ala Arg Leu Ser Glu Glu Lys Glu
                180                 185                 190

<210> SEQ ID NO 46
<211> LENGTH: 1129
<212> TYPE: DNA
<213> ORGANISM: Artificial sequence
<220> FEATURE:
<223> OTHER INFORMATION: ModB murine IFN-alpha-4 (5'UTR-CDS-3'UTR)

<400> SEQUENCE: 46
ggaataaact agtctcaaca caacatatac aaaacaaacg aatctcaagc aatcaagcat      60
tctacttcta ttgcagcaat ttaaatcatt tcttttaaag caaaagcaat tttctgaaaa     120
ttttcaccat ttacgaacga tagccatggg cgccatggcc cctagaacat tgctcctgct     180
gctggccgct gccctggccc ctacacagac aagagctgga cctggatcct gtgacctgcc     240
tcacacttat aacctcggga caagagggc cttgacagtc ctggaagaaa tgagaagact     300
cccccctctt tcctgcctga aggacaggaa ggatttttgga ttccccttgg agaaggtgga     360
taaccaacag atccagaagg ctcaagccat ccttgtgcta agagatctta cccagcagat     420
tttgaacctc ttcacatcaa agacttgtc tgctacttgg aatgcaactc tcctagactc     480
attctgcaat gacctccatc agcagctcaa tgatctcaaa gcctgtgtga tgcaggaacc     540
tcctctgacc caggaagact ccctgctggc tgtgaggaca tacttccaca ggatcactgt     600
gtacctgaga aagaagaaac acagcctctg tgcctgggag gtgatcagag cagaagtctg     660
gagagccctc tcttcctcaa ccaacttgct ggcaagactg agtgaggaga aggagtgata     720
actcgacgtc ctggtactgc atgcacgcaa tgctagctgc ccctttcccg tcctgggtac     780
cccgagtctc ccccgacctc gggtcccagg tatgctccca cctccacctg ccccactcac     840
cacctctgct agttccagac acctcccaag cacgcagcaa tgcagctcaa aacgcttagc     900
ctagccacac ccccacggga aacagcagtg attaacccttt agcaataaac gaaagtttaa     960
ctaagctata ctaaccccag ggttggtcaa tttcgtgcca gccacaccct cgagctagca    1020
aaaaaaaaaa aaaaaaaaaa aaaaaaaaag catatgacta aaaaaaaaa aaaaaaaaaa    1080 aaaaaaaaaa aaaaaaaaaa aaaaaaaaaa aaaaaaaaaa aaaaaaaa                 1129

<210> SEQ ID NO 47
```

<211> LENGTH: 1129
<212> TYPE: RNA
<213> ORGANISM: Artificial sequence
<220> FEATURE:
<223> OTHER INFORMATION: ModB murine IFN-alpha-4

<400> SEQUENCE: 47

```
ggaauaaacu agucucaaca caacauauac aaaacaaacg aaucucaagc aaucaagcau      60
ucuacuucua uugcagcaau uuaaaucauu ucuuuuaaag caaaagcaau uuucugaaaa     120
uuuucaccau uuacgaacga uagccauggg cgccauggcc ccuagaacau ugcuccugcu     180
gcuggccgcu gcccuggccc cuacacagac aagagcugga ccuggauccu gugaccugcc     240
ucacacuuau aaccucggga caagagggc cuugacaguc cuggaagaaa ugagaagacu      300
ccccccucuu uccugccuga aggacaggaa ggauuuugga ucccccuugg agaaggugga    360
uaaccaacag auccagaagg cucaagccau ccuugugcua agagaucuua cccagcagau    420
uuugaaccuc uucacaucaa aagacuugcu ugcuacuugg aaugcaacuc uccuagacuc    480
auucugcaau gaccuccauc agcagcucaa ugaucucaaa gccuguguga ugcaggaacc    540
uccucugacc caggaagacu cccugcuggc ugugaggaca uacuuccaca ggaucacugu    600
guaccugaga aagaagaaac acagccucug ugccugggag gugaucagag cagaagucug    660
gagagcccuc ucuuccucaa ccaacuugcu ggcaagacug agugaggaga aggagugaua    720
acucgacguc cugguacugc augcacgcaa ugcuagcugc cccuuucccg uccugggguac   780
cccgagucuc ccccgaccuc gggucccagg uaugcuccca ccuccaccug ccccacucac    840
caccucugcu aguccagac accucccaag cacgcagcaa ugcagcucaa aacgcuuagc     900
cuagccacac ccccacggga aacagcagug auuaaccuuu agcaauaaac gaaaguuuaa    960
cuaagcuaua cuaaccccag gguuggucaa uuucgugcca gccacacccu cgagcuagca   1020
aaaaaaaaa aaaaaaaaa aaaaaaaag cauaugacua aaaaaaaaa aaaaaaaaa         1080
aaaaaaaaaa aaaaaaaaaa aaaaaaaaaa aaaaaaaaa                          1129
```

<210> SEQ ID NO 48
<211> LENGTH: 232
<212> TYPE: PRT
<213> ORGANISM: Artificial sequence
<220> FEATURE:
<223> OTHER INFORMATION: ModA murine IL-15 sushi

<400> SEQUENCE: 48

```
Met Gly Ala Met Ala Pro Arg Thr Leu Leu Leu Leu Ala Ala Ala
1               5                   10                  15

Leu Ala Pro Thr Gln Thr Arg Ala Gly Pro Gly Ser Thr Thr Cys Pro
            20                  25                  30

Pro Pro Val Ser Ile Glu His Ala Asp Ile Arg Val Lys Asn Tyr Ser
        35                  40                  45

Val Asn Ser Arg Glu Arg Tyr Val Cys Asn Ser Gly Phe Lys Arg Lys
    50                  55                  60

Ala Gly Thr Ser Thr Leu Ile Glu Cys Val Ile Asn Lys Asn Thr Asn
65                  70                  75                  80

Val Ala His Trp Thr Thr Pro Ser Leu Lys Cys Ile Arg Asp Pro Ser
                85                  90                  95

Leu Ala Gly Gly Ser Gly Gly Ser Gly Gly Ser Gly Gly Ser Gly Gly
            100                 105                 110

Ser Gly Gly Ser Gly Gly Asn Trp Ile Asp Val Arg Tyr Asp Leu Glu
        115                 120                 125
```

```
Lys Ile Glu Ser Leu Ile Gln Ser Ile His Ile Asp Thr Thr Leu Tyr
        130                 135                 140

Thr Asp Ser Asp Phe His Pro Ser Cys Lys Val Thr Ala Met Asn Cys
145                 150                 155                 160

Phe Leu Leu Glu Leu Gln Val Ile Leu His Glu Tyr Ser Asn Met Thr
                165                 170                 175

Leu Asn Glu Thr Val Arg Asn Val Leu Tyr Leu Ala Asn Ser Thr Leu
            180                 185                 190

Ser Ser Asn Lys Asn Val Ala Glu Ser Gly Cys Lys Glu Cys Glu Glu
        195                 200                 205

Leu Glu Glu Lys Thr Phe Thr Glu Phe Leu Gln Ser Phe Ile Arg Ile
210                 215                 220

Val Gln Met Phe Ile Asn Thr Ser
225                 230

<210> SEQ ID NO 49
<211> LENGTH: 1162
<212> TYPE: DNA
<213> ORGANISM: Artificial sequence
<220> FEATURE:
<223> OTHER INFORMATION: ModA murine IL-15 sushi (5'UTR-CDS-3'UTR)

<400> SEQUENCE: 49
gggcgaacta gtattcttct ggtccccaca gactcagaga gaacccgcca ccatgggcgc    60
catggcccct agaacattgc tcctgctgct ggccgctgcc ctggccccta cacagacaag   120
agctggacct ggatccacca cgtgtccacc tcccgtatct attgagcatg ctgacatccg   180
ggtcaagaat tacagtgtga actccaggga gaggtatgtc tgtaactctg ctttaagcg    240 gaaagctgga acatccaccc tgattgagtg tgtgatcaac aagaacacaa atgttgccca   300
ctggacaact cccagcctca gtgcatcag agacccctcc ctagctggag ggagcggagg   360
ctctggcgga agcggcgggt ctggaggctc cggggg aagc ggcggaaatt ggatcgacgt   420
gcgctacgac ctggaaaaga tcgagagcct gatccagagc atccacatcg acaccaccct   480
gtacaccgac agcgacttcc accccagctg caaagtgacc gctatgaact gcttcctgct   540
ggaactgcaa gtgatcctgc acgagtacag caacatgacc ctgaacgaga cagtgcggaa   600
cgtgctgtac ctggccaaca gcaccctgag cagcaacaag aacgtggccg agagcggctg   660
caaagagtgc gaggaactgg aagaaaagac cttcaccgag tttctgcaga gcttcatcag   720
gatcgtgcag atgttcatca acacctcttg atgagtcgac gtcctggtac tgcatgcacg   780
caatgctagc tgcccctttc ccgtcctggg taccccgagt ctcccccgac ctcgggtccc   840
aggtatgctc ccacctccac ctgccccact caccacctct gctagttcca gacacctccc   900
aagcacgcag caatgcagct caaaacgctt agcctagcca caccccacg ggaaacagca    960 gtgattaacc tttagcaata aacgaaagtt taactaagct atactaaccc cagggttggt  1020
caatttcgtg ccagccacac cctcgagcta gcaaaaaaaa aaaaaaaaaa aaaaaaaaaa  1080
aagcatatga ctaaaaaaaa aaaaaaaaaa aaaaaaaaaa aaaaaaaaaa aaaaaaaaaa  1140
aaaaaaaaaa aaaaaaaaaa aa                                          1162

<210> SEQ ID NO 50
<211> LENGTH: 1162
<212> TYPE: RNA
<213> ORGANISM: Artificial sequence
<220> FEATURE:
<223> OTHER INFORMATION: ModA murine IL-15 sushi
```

<400> SEQUENCE: 50

```
gggcgaacua guauucuucu gguccccaca gacucagaga gaacccgcca ccaugggcgc      60
cauggcsccu agaacauugc uccugcugcu ggccgcugcc cuggcsccua cacagacaag    120
agcuggaccu ggauccacca cguguccacc ucccguaucu auugagcaug cugacauccg    180
ggucaagaau uacagguga acuccaggga gagguaugu cguaaacucug gcuuuaagcg    240
gaaagcugga caucccaccc ugauugagug ugugaucaac aagaacacaa auguugucca    300
cuggacaacu cccagccuca agugcaucag agacccccucc cuagcuggag ggagcggagg    360
cucuggcgga agcggcgggu cuggaggcuc cgggggaagc ggcggaaauu ggaucgacgu    420
gcgcuacgac cuggaaaaga ucgagagccu gauccagagc auccacaucg acaccacccu    480
guacaccgac agcgacuucc accccagcug caaagugacc gcaugaacu gcuuccugcu    540
ggaacugcaa gugauccugc acgaguacag caacaugacc cugaacgaga cagugcggaa    600
cgugcucuac cuggccaaca gcacccugag cagcaacaag aacguggccg agagcggcug    660
caaagagugc gaggaacugg aagaaaagac cuucaccgag uuucugcaga gcuucaucag    720
gaucgugcag auguucauca acaccucuug augagucgac guccugguac ugcaugcacg    780
caaugcuagc ugcccuuuc ccguccuggg uaccccgagu ucccccgac ucgggucccc    840
agguaugcuc ccaccuccac cugcccacuc caccaaccucu gcuaguucca gacaccuccc    900
aagcacgcag caaugcagcu caaaacgcuu agccuagcca ccccccacg ggaaacagca    960
gugauuaacc uuuagcaaua aacgaaaguu uaacuaagcu auacuaaccc caggguuggu   1020
caauuucgug ccagccacac ccucgagcua gcaaaaaaaa aaaaaaaaaa aaaaaaaaaa   1080
aagcauauga cuaaaaaaaa aaaaaaaaaa aaaaaaaaaa aaaaaaaaaa aaaaaaaaaa   1140
aaaaaaaaaa aaaaaaaaaa aa                                            1162
```

<210> SEQ ID NO 51
<211> LENGTH: 232
<212> TYPE: PRT
<213> ORGANISM: Artificial sequence
<220> FEATURE:
<223> OTHER INFORMATION: ModB murine IL-15 sushi

<400> SEQUENCE: 51

```
Met Gly Ala Met Ala Pro Arg Thr Leu Leu Leu Leu Ala Ala Ala
1               5                   10                  15

Leu Ala Pro Thr Gln Thr Arg Ala Gly Pro Gly Ser Thr Thr Cys Pro
            20                  25                  30

Pro Pro Val Ser Ile Glu His Ala Asp Ile Arg Val Lys Asn Tyr Ser
        35                  40                  45

Val Asn Ser Arg Glu Arg Tyr Val Cys Asn Ser Gly Phe Lys Arg Lys
    50                  55                  60

Ala Gly Thr Ser Thr Leu Ile Glu Cys Val Ile Asn Lys Asn Thr Asn
65                  70                  75                  80

Val Ala His Trp Thr Thr Pro Ser Leu Lys Cys Ile Arg Asp Pro Ser
                85                  90                  95

Leu Ala Gly Gly Ser Gly Gly Ser Gly Gly Ser Gly Gly Ser Gly Gly
            100                 105                 110

Ser Gly Gly Ser Gly Gly Asn Trp Ile Asp Val Arg Tyr Asp Leu Glu
        115                 120                 125

Lys Ile Glu Ser Leu Ile Gln Ser Ile His Ile Asp Thr Thr Leu Tyr
    130                 135                 140
```

```
Thr Asp Ser Asp Phe His Pro Ser Cys Lys Val Thr Ala Met Asn Cys
145                 150                 155                 160

Phe Leu Leu Glu Leu Gln Val Ile Leu His Glu Tyr Ser Asn Met Thr
            165                 170                 175

Leu Asn Glu Thr Val Arg Asn Val Leu Tyr Leu Ala Asn Ser Thr Leu
        180                 185                 190

Ser Ser Asn Lys Asn Val Ala Glu Ser Gly Cys Lys Glu Cys Glu Glu
    195                 200                 205

Leu Glu Glu Lys Thr Phe Thr Glu Phe Leu Gln Ser Phe Ile Arg Ile
    210                 215                 220

Val Gln Met Phe Ile Asn Thr Ser
225                 230

<210> SEQ ID NO 52
<211> LENGTH: 1255
<212> TYPE: DNA
<213> ORGANISM: Artificial sequence
<220> FEATURE:
<223> OTHER INFORMATION: ModB murine IL-15 sushi (5'UTR-CDS-3'UTR)

<400> SEQUENCE: 52
ggaataaact agtctcaaca caacatatac aaaacaaacg aatctcaagc aatcaagcat      60
tctacttcta ttgcagcaat ttaaatcatt tcttttaaag caaaagcaat tttctgaaaa    120
ttttcaccat ttacgaacga tagccatggg cgccatggcc cctagaacat tgctcctgct    180
gctggccgct gccctggccc ctacacagac aagagctgga cctggatcca ccacgtgtcc    240
acctcccgta tctattgagc atgctgacat ccgggtcaag aattacagtg tgaactccag    300
ggagaggtat gtctgtaact ctggctttaa gcggaaagct ggaacatcca ccctgattga    360
gtgtgtgatc aacaagaaca caaatgttgc ccactggaca actcccagcc tcaagtgcat    420
cagagacccc tccctagctg agggagcgg aggctctggc ggaagcggcg ggtctggagg    480
ctccggggga agcggcggaa attggatcga cgtgcgctac gacctggaaa agatcgagag    540
cctgatccag agcatccaca tcgacaccac cctgtacacc gacagcgact tccaccccag    600
ctgcaaagtg accgctatga actgcttcct gctggaactg caagtgatcc tgcacgagta    660
cagcaacatg accctgaacg agacagtgcg gaacgtgctg tacctggcca acagcaccct    720
gagcagcaac aagaacgtgg ccgagagcgg ctgcaaagag tgcgaggaac tggaagaaaa    780
gaccttcacc gagtttctgc agagcttcat caggatcgtg cagatgttca tcaacacctc    840
ttgatgagtc gacgtcctgg tactgcatgc acgcaatgct agctgcccct ttcccgtcct    900
gggtaccccg agtctccccc gacctcgggt cccaggtatg ctcccacctc cacctgcccc    960
actcaccacc tctgctagtt ccagacacct cccaagcacg cagcaatgca gctcaaaacg   1020
cttagcctag ccacaccccc acgggaaaca gcagtgatta accttagca ataaacgaaa    1080 gtttaactaa gctatactaa ccccagggtt ggtcaatttc gtgccagcca caccctcgag   1140
ctagcaaaaa aaaaaaaaa aaaaaaaaaa aaaagcata tgactaaaaa aaaaaaaaaa    1200 aaaaaaaaa aaaaaaaaa aaaaaaaaaa aaaaaaaaaa aaaaaaaaaa aaaaa          1255

<210> SEQ ID NO 53
<211> LENGTH: 1255
<212> TYPE: RNA
<213> ORGANISM: Artificial sequence
<220> FEATURE:
<223> OTHER INFORMATION: ModB murine IL-15 sushi
```

<400> SEQUENCE: 53

```
ggaauaaacu aguucucaaca caacauauac aaaacaaacg aaucucaagc aaucaagcau      60
ucuacuucua uugcagcaau uuaaaucauu ucuuuuaaag caaaagcaau uuucugaaaa     120
uuuucaccau uuacgaacga uagccauggg cgccauggcc ccuagaacau ugcuccugcu     180
gcuggccgcu gcccuggccc cuacacagac aagagcugga ccuggauccca ccacgugucc    240 accucccgua ucuauugagc augcugacau ccgggucaag aauuacagug ugaacuccag     300
ggagagguau gucuguaacu cuggcuuuaa gcggaaagcu ggaacaucca cccugauuga     360
gugugugauc aacaagaaca caaauguugc ccacuggaca acucccagcc ucaagugcau     420
cagagacccc ucccuagcug gagggagcgg aggcucuggc ggaagcggcg ggucuggagg     480
cuccggggga agcggcggaa auuggaucga cgugcgcuac gaccuggaaa agaucgagag     540
ccugauccag agcauccaca ucgacaccac ccuguacacc gacagcgacu uccaccccag     600
cugcaaagug accgcuauga acugcuuccu gcuggaacug caagugaucc ugcacgagua     660
cagcaacaug acccugaacg agacagugcg gaacgugcug uaccuggcca acagcacccu     720
gagcagcaac aagaacgugg ccgagagcgg cugcaaagag ugcgaggaac uggaagaaaa     780
gaccuucacc gaguuucugc agagcuucau caggaucgug cagauguuca ucaacaccuc     840
uugaugaguc gacguccugg uacugcaugc acgcaaugcu agcugcccuu uucccguccu     900 gggaccccg aguucucccc gaccucgggu cccagguaug ucuccaccuc caccugcccc     960
acucaccacc ucugcuaguu ccagacaccu cccaagcacg cagcaaugca gcucaaaacg    1020
cuuagccuag ccacacccccc acgggaaaca gcagugauua accuuuagca auaaacgaaa    1080
guuuaacuaa gcuauacuaa ccccagggu ggucaauuuc gugccagcca cacccucgag     1140
cuagcaaaaa aaaaaaaaaa aaaaaaaaaa aaaagcauua ugacuaaaaa aaaaaaaaaa    1200
aaaaaaaaaa aaaaaaaaaa aaaaaaaaaa aaaaaaaaaa aaaaaaaaaa aaaaa         1255
```

<210> SEQ ID NO 54
<211> LENGTH: 141
<212> TYPE: PRT
<213> ORGANISM: Artificial sequence
<220> FEATURE:
<223> OTHER INFORMATION: ModA murine GM-CSF

<400> SEQUENCE: 54

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
```

<210> SEQ ID NO 55
<211> LENGTH: 908
<212> TYPE: DNA
<213> ORGANISM: Artificial sequence
<220> FEATURE:
<223> OTHER INFORMATION: ModA murine GM-CSF (5'UTR-CDS-3'UTR)

<400> SEQUENCE: 55

```
gggcgaacta gtattcttct ggtccccaca gactcagaga gaacccgcca ccatgtggct      60
gcagaacctg ctgttcctgg gcatcgtggt gtacagcctg agcgcccca ccaggagccc     120
catcaccgtg accaggccct ggaagcacgt ggaggccatc aaggaggccc tgaacctgct    180
ggacgacatg cccgtgaccc tgaacgagga ggtggaggtg gtgagcaacg agttcagctt    240
caagaagctg acctgcgtgc agaccaggct gaagatcttc gagcagggcc tgaggggcaa    300
cttcaccaag ctgaagggcg ccctgaacat gaccgccagc tactaccaga cctactgccc    360
ccccacccc gagaccgact gcgagaccca ggtgaccacc tacgccgact tcatcgacag    420
cctgaagacc ttcctgaccg acatccctt cgagtgcaag aagcccggcc agaagtgatg    480
actcgagctg gtactgcatg cacgcaatgc tagctgcccc tttcccgtcc tgggtacccc    540
gagtctcccc cgacctcggg tcccaggtat gctcccacct ccacctgccc cactcaccac    600
ctctgctagt tccagacacc tcccaagcac gcagcaatgc agctcaaaac gcttagccta    660
gccacacccc cacgggaaac agcagtgatt aacctttagc aataaacgaa agtttaacta    720
agctatacta accccagggt tggtcaattt cgtgccagcc acaccgagac ctggtccaga    780
gtcgctagcc gcgtcgctaa aaaaaaaaaa aaaaaaaaa aaaaaaaagc atatgactaa    840
aaaaaaaaa aaaaaaaaa aaaaaaaaa aaaaaaaaa aaaaaaaaa aaaaaaaaa         900
aaaaaaaa                                                              908
```

<210> SEQ ID NO 56
<211> LENGTH: 908
<212> TYPE: RNA
<213> ORGANISM: Artificial sequence
<220> FEATURE:
<223> OTHER INFORMATION: ModA murine GM-CSF

<400> SEQUENCE: 56

```
gggcgaacua guauucuucu gguccccaca gacucagaga gaacccgcca ccauguggcu      60
gcagaaccug cuguuccugg gcaucguggu guacagccug agcgcccca ccaggagccc     120
caucaccgug accaggcccu ggaagcacgu ggaggccauc aaggaggccc ugaaccugcu    180
ggacgacaug cccgugaccc ugaacgagga gguggaggug gugagcaacg aguucagcuu    240
caagaagcug accugcgugc agaccaggcu gaagaucuuc gagcagggcc ugaggggcaa    300
cuucaccaag cugaagggcg cccugaacau gaccgccagc uacuaccaga ccuacugccc    360
ccccacccc gagaccgacu gcgagaccca ggugaccacc uacgccgacu ucaucgacag    420
ccugaagacc uuccugaccg acauccccuu cgagugcaag aagcccggcc agaagugaug    480
acucgagcug guacugcaug cacgcaaugc uagcugcccc uuucccgucc ugggucccc    540
gagucucccc cgaccucggg ucccagguau gcucccaccu ccaccugccc cacucaccac    600
cucugcuagu uccagacacc ucccaagcac gcagcaaugc agcucaaaac gcuuagccua    660
gccacacccc cacgggaaac agcagugauu aaccuuuagc aauaaacgaa aguuuaacua    720
agcuauacua accccagggu uggucaauuu cgugccagcc acaccgagac cugguccaga    780
```

```
gucgcuagcc gcgucgcuaa aaaaaaaaaa aaaaaaaaaa aaaaaaaagc auaugacuaa    840
aaaaaaaaaa aaaaaaaaaa aaaaaaaaaa aaaaaaaaaa aaaaaaaaaa aaaaaaaaaa    900
aaaaaaaa                                                              908
```

<210> SEQ ID NO 57
<211> LENGTH: 141
<212> TYPE: PRT
<213> ORGANISM: Artificial sequence
<220> FEATURE:
<223> OTHER INFORMATION: ModB murine GM-CSF

<400> SEQUENCE: 57

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140
```

<210> SEQ ID NO 58
<211> LENGTH: 1001
<212> TYPE: DNA
<213> ORGANISM: Artificial sequence
<220> FEATURE:
<223> OTHER INFORMATION: ModB murine GM-CSF (5'UTR-CDS-3'UTR)

<400> SEQUENCE: 58

```
ggaataaact agtctcaaca caacatatac aaaacaaacg aatctcaagc aatcaagcat     60
tctacttcta ttgcagcaat ttaaatcatt tcttttaaag caaaagcaat tttctgaaaa    120
ttttcaccat ttacgaacga tagccatgtg gctgcagaac ctgctgttcc tgggcatcgt    180
ggtgtacagc ctgagcgccc ccaccaggag ccccatcacc gtgaccaggc cctggaagca    240
cgtggaggcc atcaaggagg ccctgaacct gctggacgac atgcccgtga ccctgaacga    300
ggaggtggag gtggtgagca acgagttcag cttcaagaag ctgacctgcg tgcagaccag    360
gctgaagatc ttcgagcagg gcctgagggg caacttcacc aagctgaagg gcgccctgaa    420
catgaccgcc agctactacc agacctactg cccccccacc cccgagaccg actgcgagac    480
ccaggtgacc acctacgccg acttcatcga cagcctgaag accttcctga ccgacatccc    540
cttcgagtgc aagaagcccg gccagaagtg atgactcgag ctggtactgc atgcacgcaa    600
tgctagctgc ccctttcccg tcctgggtac ccgagtctc cccgacctc gggtccagg    660 tatgctccca cctccacctg ccccactcac cacctctgct agttccagac acctcccaag    720
cacgcagcaa tgcagctcaa aacgcttagc ctagccacac ccccacggga aacagcagtg    780
```

```
attaaccttt agcaataaac gaaagtttaa ctaagctata ctaacccag ggttggtcaa        840 tttcgtgcca gccacaccga gacctggtcc agagtcgcta gccgcgtcgc taaaaaaaaa       900
aaaaaaaaaa aaaaaaaaaa agcatatgac taaaaaaaaa aaaaaaaaaa aaaaaaaaaa       960
aaaaaaaaaa aaaaaaaaaa aaaaaaaaaa aaaaaaaaaa a                          1001
```

<210> SEQ ID NO 59
<211> LENGTH: 1001
<212> TYPE: RNA
<213> ORGANISM: Artificial sequence
<220> FEATURE:
<223> OTHER INFORMATION: ModB murine GM-CSF

<400> SEQUENCE: 59

```
ggaauaaacu agucucaaca caacauauac aaaacaaacg aaucucaagc aaucaagcau        60
ucuacuucua uugcagcaau uuaaaucauu ucuuuuaaag caaaagcaau uuucugaaaa       120
uuuucaccau uuacgaacga uagccaugug gcugcagaac cugcuguucc ugggcaucgu       180
gguguacagc cugagcgccc ccaccaggag ccccaucacc gugaccaggc ccuggaagca       240
cguggaggcc aucaaggagg cccugaaccu gcuggacgac augcccguga cccugaacga       300
ggagguggag guggugagca acgaguucag cuucaagaag cugaccugcg ugcagaccag       360
gcugaagauc uucgagcagg gccugagggg caacuucacc aagcugaagg gcgcccugaa       420
caugaccgcc agcuacuacc agaccuacug cccccccacc cccgagaccg acugcgagac       480
ccaggugacc accuacgccg acuucaucga cagccugaag accuuccuga ccgacauccc       540
cuucgagugc aagaagcccg ccagaagug augacucgag cugguacugc augcacgcaa       600
ugcuagcugc cccuuucccg uccugggua cccgagucuc ccccgaccuc gggucccagg       660 uaugcucca ccuccaccug ccccacucac caccucugcu aguucagac accucccaag       720 cacgcagcaa ugcagcucaa aacgcuuagc cuagccacac ccccacggga aacagcagug       780
auuaaccuuu agcaauaaac gaaaguuuaa cuaagcuaua cuaaccccag gguuggucaa       840
uuucgugcca gccacaccga gaccuggucc agagucgcua gccgcgucgc uaaaaaaaaa       900
aaaaaaaaaa aaaaaaaaaa agcauaugac uaaaaaaaaa aaaaaaaaaa aaaaaaaaaa       960
aaaaaaaaaa aaaaaaaaaa aaaaaaaaaa aaaaaaaaaa a                          1001
```

<210> SEQ ID NO 60
<211> LENGTH: 187
<212> TYPE: PRT
<213> ORGANISM: Artificial sequence
<220> FEATURE:
<223> OTHER INFORMATION: ModA FLT3L (human FLT3L in combination with a
      mouse optimized secretion sequence)

<400> SEQUENCE: 60

```
Met Gly Ala Met Ala Pro Arg Thr Leu Leu Leu Leu Leu Ala Ala Ala
1               5                   10                  15

Leu Ala Pro Thr Gln Thr Arg Ala Gly Pro Gly Ser Thr Gln Asp Cys
            20                  25                  30

Ser Phe Gln His Ser Pro Ile Ser Ser Asp Phe Ala Val Lys Ile Arg
        35                  40                  45

Glu Leu Ser Asp Tyr Leu Leu Gln Asp Tyr Pro Val Thr Val Ala Ser
    50                  55                  60

Asn Leu Gln Asp Glu Glu Leu Cys Gly Gly Leu Trp Arg Leu Val Leu
65                  70                  75                  80
```

Ala Gln Arg Trp Met Glu Arg Leu Lys Thr Val Ala Gly Ser Lys Met
                85                  90                  95

Gln Gly Leu Leu Glu Arg Val Asn Thr Glu Ile His Phe Val Thr Lys
            100                 105                 110

Cys Ala Phe Gln Pro Pro Pro Ser Cys Leu Arg Phe Val Gln Thr Asn
        115                 120                 125

Ile Ser Arg Leu Leu Gln Glu Thr Ser Glu Gln Leu Val Ala Leu Lys
    130                 135                 140

Pro Trp Ile Thr Arg Gln Asn Phe Ser Arg Cys Leu Glu Leu Gln Cys
145                 150                 155                 160

Gln Pro Asp Ser Ser Thr Leu Pro Pro Pro Trp Ser Pro Arg Pro Leu
                165                 170                 175

Glu Ala Thr Ala Pro Thr Ala Pro Gln Pro Pro
                180                 185

<210> SEQ ID NO 61
<211> LENGTH: 1027
<212> TYPE: DNA
<213> ORGANISM: Artificial sequence
<220> FEATURE:
<223> OTHER INFORMATION: ModA FLT3L (5'UTR-CDS-3'UTR)

<400> SEQUENCE: 61
gggcgaacta gtattcttct ggtccccaca gactcagaga gaacccgcca ccatgggcgc      60
catggcccct agaacattgc tcctgctgct ggccgctgcc ctggcccctta cacagacaag    120 agctggacct ggatccaccc aggactgcag cttccagcac tcccctatct cctccgactt    180
cgccgtgaag atccgggagc tgtccgatta cctgctgcag gactaccctg tgaccgtggc    240
cagcaacctg caggacgaag aactgtgtgg cggcctgtgg cggctggtgc tggcccagcg    300
gtggatggaa cggctgaaaa ccgtggccgg ctccaagatg cagggcctgc tcgagcgggt    360
gaacaccgag atccacttcg tgaccaagtg cgccttccag cctcctcctt cctgcctgcg    420
gttcgtgcag accaacatct cccggctgct gcaggaaacc tccgagcagc tggtcgccct    480
gaagccttgg atcaccccgg cagaacttct ccggtgtctg gaactccagt gtcagcccga    540
ctcctccacc ctgcctcctc cctggtcccc caggcctctg gaagccaccg ccctaccgc     600 cccacagcct ccttgatagg tcgacgtcct ggtactgcat gcacgcaatg ctagctgccc    660
ctttcccgtc ctgggtaccc cgagtctccc ccgacctcgg gtcccaggta tgctcccacc    720
tccacctgcc ccactcacca cctctgctag ttccagacac ctcccaagca cgcagcaatg    780
cagctcaaaa cgcttagcct agccacaccc cacgggaaaa cagcagtgat taacctttag    840
caataaacga aagtttaact aagctatact aaccccaggg ttggtcaatt tcgtgccagc    900
cacaccctcg agctagcaaa aaaaaaaaaa aaaaaaaaaa aaaaaagca tatgactaaa    960 aaaaaaaaaa aaaaaaaaaa aaaaaaaaaa aaaaaaaaaa aaaaaaaaaa aaaaaaaaaa   1020
aaaaaaa                                                            1027

<210> SEQ ID NO 62
<211> LENGTH: 1027
<212> TYPE: RNA
<213> ORGANISM: Artificial sequence
<220> FEATURE:
<223> OTHER INFORMATION: ModA FLT3L

<400> SEQUENCE: 62
gggcgaacua guauucuucu gguccccaca gacucagaga gaacccgcca ccaugggcgc     60

```
cauggccccu agaacauugc uccugcugcu ggccgcugcc cuggcccuua cacagacaag    120
agcuggaccu ggauccaccc aggacugcag cuuccagcac uccccuaucu ccuccgacuu    180
cgccgugaag auccgggagc uguccgauua ccugcugcag acuacccug  ugaccgugcc    240 cagcaaccug caggacgaag aacugugugg cggccugugg cggcuggugc uggcccagcg    300
guggauggaa cggcugaaaa ccguggccgg uccaagaug  cagggccugc ucgagcgggu    360
gaacaccgag auccacuucg ugaccaagug cgccuuccag ccuccuccuu ccugccugcg    420
guucgugcag accaacaucu cccggcugcu gcaggaaacc uccgagcagc uggucgcccu    480
gaagccuugg aucaccccgg cagaacuucuc ccggugucug aacuccagu gucagcccga    540 cuccuccacc cugccuccuc ccuggucccc caggccucug gaagccaccg ccccuaccgc    600
cccacagccu ccuugauagg ucgacgaucc gguacugcau gcacgcaaug cuagcugccc    660
cuuucccguc cuggguaccc cgagucuccc ccgaccucgg gucccaggua ugcucccacc    720
uccaccugcc ccacucacca ccucugcuag uucagacac  cucccaagca cgcagcaaug    780
cagcucaaaa cgcuuagccu agccacaccc ccacgggaaa cagcagugau uaaccuuuag    840
caauaaacga aaguuuaacu aagcuauacu aaccccaggg uuggucaauu cgugccagc    900 cacacccucg agcuagcaaa aaaaaaaaaa aaaaaaaaaa aaaaaaagca uaugacuaaa    960
aaaaaaaaaa aaaaaaaaaa aaaaaaaaaa aaaaaaaaaa aaaaaaaaaa aaaaaaaaaa  1020
aaaaaaa                                                            1027
```

<210> SEQ ID NO 63
<211> LENGTH: 187
<212> TYPE: PRT
<213> ORGANISM: Artificial sequence
<220> FEATURE:
<223> OTHER INFORMATION: ModB FLT3L (human FLT3L in combination with a mouse optimized secretion sequence)

<400> SEQUENCE: 63

```
Met Gly Ala Met Ala Pro Arg Thr Leu Leu Leu Leu Ala Ala Ala
1               5                   10                  15

Leu Ala Pro Thr Gln Thr Arg Ala Gly Pro Gly Ser Thr Gln Asp Cys
            20                  25                  30

Ser Phe Gln His Ser Pro Ile Ser Ser Asp Phe Ala Val Lys Ile Arg
        35                  40                  45

Glu Leu Ser Asp Tyr Leu Leu Gln Asp Tyr Pro Val Thr Val Ala Ser
    50                  55                  60

Asn Leu Gln Asp Glu Glu Leu Cys Gly Gly Leu Trp Arg Leu Val Leu
65                  70                  75                  80

Ala Gln Arg Trp Met Glu Arg Leu Lys Thr Val Ala Gly Ser Lys Met
                85                  90                  95

Gln Gly Leu Leu Glu Arg Val Asn Thr Glu Ile His Phe Val Thr Lys
            100                 105                 110

Cys Ala Phe Gln Pro Pro Ser Cys Leu Arg Phe Val Gln Thr Asn
        115                 120                 125

Ile Ser Arg Leu Leu Gln Glu Thr Ser Glu Gln Leu Val Ala Leu Lys
    130                 135                 140

Pro Trp Ile Thr Arg Gln Asn Phe Ser Arg Cys Leu Glu Leu Gln Cys
145                 150                 155                 160

Gln Pro Asp Ser Ser Thr Leu Pro Pro Pro Trp Ser Pro Arg Pro Leu
                165                 170                 175

Glu Ala Thr Ala Pro Thr Ala Pro Gln Pro Pro
            180                 185
```

<210> SEQ ID NO 64
<211> LENGTH: 1120
<212> TYPE: DNA
<213> ORGANISM: Artificial sequence
<220> FEATURE:
<223> OTHER INFORMATION: ModB FLT3L (5'UTR-CDS-3'UTR)

<400> SEQUENCE: 64

```
ggaataaaact agtctcaaca caacatatac aaaacaaacg aatctcaagc aatcaagcat      60
tctacttcta ttgcagcaat ttaaatcatt tcttttaaag caaaagcaat tttctgaaaa     120
ttttcaccat ttacgaacga tagccatggg cgccatggcc cctagaacat tgctcctgct     180
gctggccgct gccctggccc ctacacagac aagagctgga cctggatcca cccaggactg     240
cagcttccag cactccccta tctcctccga cttcgccgtg aagatccggg agctgtccga     300
ttacctgctg caggactacc ctgtgaccgt ggccagcaac ctgcaggacg aagaactgtg     360
tggcggcctg tggcggctgg tgctggccca gcggtggatg aacggctga aaaccgtggc     420
cggctccaag atgcagggcc tgctcgagcg ggtgaacacc gagatccact tcgtgaccaa     480
gtgcgccttc cagcctcctc cttcctgcct gcggttcgtg cagaccaaca tctcccggct     540
gctgcaggaa acctccgagc agctggtcgc cctgaagcct tggatcaccc ggcagaactt     600
ctccggtgt ctggaactcc agtgtcagcc cgactcctcc accctgcctc ctccctggtc     660
ccccaggcct ctggaagcca ccgcccctac cgccccacag cctccttgat aggtcgacgt     720
cctggtactg catgcacgca atgctagctg cccctttccc gtcctgggta ccccgagtct     780
ccccgaccct cgggtcccag gtatgctccc acctccacct gccccactca ccacctctgc     840
tagttccaga cacctcccaa gcacgcagca atgcagctca aaacgcttag cctagccaca     900
cccccacggg aaacagcagt gattaacctt tagcaataaa cgaaagttta actaagctat     960
actaacccca gggttggtca atttcgtgcc agccacaccc tcgagctagc aaaaaaaaa    1020
aaaaaaaaa aaaaaaaaaa gcatatgact aaaaaaaaa aaaaaaaaa aaaaaaaaaa    1080
aaaaaaaaaa aaaaaaaaaa aaaaaaaaaa aaaaaaaaaa                         1120
```

<210> SEQ ID NO 65
<211> LENGTH: 1120
<212> TYPE: RNA
<213> ORGANISM: Artificial sequence
<220> FEATURE:
<223> OTHER INFORMATION: ModB murine FLT3L

<400> SEQUENCE: 65

```
ggaauaaaacu agucucaaca caacauauac aaaacaaacg aaucucaagc aaucaagcau      60
ucuacuucua uugcagcaau uuaaaucauu ucuuuuaaag caaaagcaau uuucugaaaa     120
uuuucaccau uuacgaacga uagccauggg cgccauggcc ccuagaacau ugcuccugcu     180
gcuggccgcu gcccuggccc cuacacagac aagagcugga ccuggaucca cccaggacug     240
cagcuuccag cacuccccua ucuccuccga cuucgccgug aagauccggg agcugpuccga     300
uuaccugcug caggacuacc cugugaccgu ggccagcaac cugcaggacg aagaacugug     360
uggcggccug uggcggcugg ugcuggccca gcgguggaug aacggcuga aaaccguggc     420
cggcuccaag augcagggcc ugcucgagcg ggugaacacc gagauccacu ucgugaccaa     480
gugcgccuuc cagccuccuc cuuccugccu gcgguucgug cagaccaaca ucucccggcu     540
gcugcaggaa accuccgagc agcuggucgc ccugaagccu uggaucaccc ggcagaacuu     600
```

```
cucccggugu cuggaacucc agugucagcc cgacuccucc acccugccuc cucccugguc    660
ccccaggccu cuggaagcca ccgcccuac  cgccccacag ccuccuugau aggucgacgu    720 ccuguacug  caugcacgca augcuagcug ccccuuuccc guccugggua ccccgagucu    780 ccccgaccu  cgggucccag guaugcuccc accuccaccu gccccacuca ccaccucugc    840
uaguuccaga caccucccaa gcacgcagca augcagcuca aaacgcuuag ccuagccaca    900
cccccacggg aaacagcagu gauuaaccuu uagcaauaaa cgaaaguuua acuaagcuau    960 acuaaccccca ggguuggguca auuucgugcc agccacaccc ucgagcuagc aaaaaaaaaa   1020
aaaaaaaaaa aaaaaaaaaa gcauaugacu aaaaaaaaaa aaaaaaaaaa aaaaaaaaaa   1080
aaaaaaaaaa aaaaaaaaaa aaaaaaaaaa aaaaaaaaa                          1120

<210> SEQ ID NO 66
<211> LENGTH: 309
<212> TYPE: PRT
<213> ORGANISM: Artificial sequence
<220> FEATURE:
<223> OTHER INFORMATION: ModA murine 41BBL

<400> SEQUENCE: 66

Met Asp Gln His Thr Leu Asp Val Glu Asp Thr Ala Asp Ala Arg His
1               5                   10                  15

Pro Ala Gly Thr Ser Cys Pro Ser Asp Ala Ala Leu Leu Arg Asp Thr
            20                  25                  30

Gly Leu Leu Ala Asp Ala Ala Leu Leu Ser Asp Thr Val Arg Pro Thr
        35                  40                  45

Asn Ala Ala Leu Pro Thr Asp Ala Ala Tyr Pro Ala Val Asn Val Arg
    50                  55                  60

Asp Arg Glu Ala Ala Trp Pro Pro Ala Leu Asn Phe Cys Ser Arg His
65                  70                  75                  80

Pro Lys Leu Tyr Gly Leu Val Ala Leu Val Leu Leu Leu Ile Ala
                85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Ala Asp Gln
        115                 120                 125

Val Thr Pro Val Ser His Ile Gly Cys Pro Asn Thr Thr Gln Gln Gly
130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
            180                 185                 190

Asp Ser Pro Gly Leu Tyr Tyr Val Phe Leu Glu Leu Lys Leu Ser Pro
        195                 200                 205

Thr Phe Thr Asn Thr Gly His Lys Val Gln Gly Trp Val Ser Leu Val
    210                 215                 220

Leu Gln Ala Lys Pro Gln Val Asp Asp Phe Asp Asn Leu Ala Leu Thr
225                 230                 235                 240

Val Glu Leu Phe Pro Cys Ser Met Glu Asn Lys Leu Val Asp Arg Ser
                245                 250                 255

Trp Ser Gln Leu Leu Leu Leu Lys Ala Gly His Arg Leu Ser Val Gly
            260                 265                 270
```

Leu Arg Ala Tyr Leu His Gly Ala Gln Asp Ala Tyr Arg Asp Trp Glu
     275                 280                 285

Leu Ser Tyr Pro Asn Thr Thr Ser Phe Gly Leu Phe Leu Val Lys Pro
     290                 295                 300

Asp Asn Pro Trp Glu
305

<210> SEQ ID NO 67
<211> LENGTH: 1393
<212> TYPE: DNA
<213> ORGANISM: Artificial sequence
<220> FEATURE:
<223> OTHER INFORMATION: ModA murine 41BBL (5'UTR-CDS-3'UTR)

<400> SEQUENCE: 67

| | | |
|---|---|---|
| gggcgaacta gtattcttct ggtccccaca gactcagaga gaacccgcca ccatggacca | 60 |
| gcacacactt gatgtggagg ataccgcgga tgccagacat ccagcaggta cttcgtgccc | 120 |
| ctcggatgcg gcgctcctca gagataccgg gctcctcgcg gacgctgcgc tcctctcaga | 180 |
| tactgtgcgc cccacaaatg ccgcgctccc cacggatgct gcctaccctg cggttaatgt | 240 |
| tcgggatcgc gaggccgcgt ggccgcctgc actgaacttc tgttcccgcc acccaaagct | 300 |
| ctatggccta gtcgctttgg ttttgctgct tctgatcgcc gcctgtgttc ctatcttcac | 360 |
| ccgcaccgag cctcggccag cgctcacaat caccacctcg cccaacctgg taccccgaga | 420 |
| gaataatgca gaccaggtca cccctgtttc ccacattggc tgccccaaca ctacacaaca | 480 |
| gggctctcct gtgttcgcca agctactggc taaaaaccaa gcatcgttgt gcaatacaac | 540 |
| tctgaactgg cacagccaag atggagctgg gagctcatac ctatctcaag gtctgaggta | 600 |
| cgaagaagac aaaaaggagt tggtggtaga cagtcccggg ctctactacg tattttttgga | 660 |
| actgaagctc agtccaacat tcacaaacac aggccacaag gtgcagggct gggtctctct | 720 |
| tgtttttgcaa gcaaagcctc aggtagatga ctttgacaac ttggccctga cagtggaact | 780 |
| gttcccttgc tccatggaga acaagttagt ggaccgttcc tggagtcaac tgttgctcct | 840 |
| gaaggctggc caccgcctca gtgtgggtct gagggcttat ctgcatggag cccaggatgc | 900 |
| atacagagac tgggagctgt cttatcccaa caccaccagc tttggactct tcttgtgaa | 960 |
| acccgacaac ccatgggaat gatagggatc cgatctggta ctgcatgcac gcaatgctag | 1020 |
| ctgccccttt cccgtcctgg gtaccccgag tctcccccga cctcgggtcc caggtatgct | 1080 |
| cccacctcca cctgccccac tcaccacctc tgctagttcc agacacctcc caagcacgca | 1140 |
| gcaatgcagc tcaaaacgct tagcctagcc acaccccac gggaaacagc agtgattaac | 1200 |
| ctttagcaat aaacgaaagt ttaactaagc tatactaacc caggggttgg tcaatttcgt | 1260 |
| gccagccaca ccctcgagct agcaaaaaaa aaaaaaaaaa aaaaaaaaaa aaagcatatg | 1320 |
| actaaaaaaa aaaaaaaaaa aaaaaaaaaa aaaaaaaaaa aaaaaaaaaa aaaaaaaaaa | 1380 |
| aaaaaaaaaa aaa | 1393 |

<210> SEQ ID NO 68
<211> LENGTH: 1393
<212> TYPE: RNA
<213> ORGANISM: Artificial sequence
<220> FEATURE:
<223> OTHER INFORMATION: ModA murine 41BBL

<400> SEQUENCE: 68
gggcgaacua guauucuucu gguccccaca gacucagaga gaacccgcca ccauggacca     60

| | | |
|---|---|---|
| gcacacacuu gaugugggagg auaccgcgga ugccagacau ccagcaggua cuucgugccc | | 120 |
| cucggaugcg gcgcuccuca gagauaccgg gcuccucgcg gacgcugcgc uccucucaga | | 180 |
| uacugugcgc cccacaaaug ccgcgcuccc cacggaugcu gccuacccug cgguuaaugu | | 240 |
| ucgggaucgg gaggccgcgu ggccgccugc acugaacuuc uguucccgcc acccaaagcu | | 300 |
| cuauggccua gucgcuuugg uuugcugcu cugaucgcc gccuguguuc cuaucuucac | | 360 |
| ccgcaccgag ccucggccag cgcucacaau caccaccucg cccaaccugg guacccgaga | | 420 |
| gaauaaugca gaccagguca ccccuguuuc ccacauuggc ugcccaaaca cuacacaaca | | 480 |
| gggcucuccu guguucgcca agcuacggcu aaaaaccaa gcaucguugu gcaauacaac | | 540 |
| ucugaacugg cacagccaag auggagcugg gagcucauac cuaucucaag gucugaggua | | 600 |
| cgaagagagac aaaaaggagu uggugguaga cagucccggg cucuacuacg uauuuuugga | | 660 |
| acugaagcuc aguccaacau ucacaaacac aggccacaag gugcagggcu gggucucucu | | 720 |
| uguuuugcaa gcaaagccuc agguagauga cuuugacaac uuggcccuga caguggaacu | | 780 |
| guucccuugc uccauggaga acaaguuagu ggaccguucc uggagucaac guugcuccu | | 840 |
| gaaggcuggc caccgccuca gugugggucu gagggcuuau cugcauggag cccaggaugc | | 900 |
| auacagagac ugggagcugu cuuaucccaa caccaccagc uuuggacucu uucugugaa | | 960 |
| acccgacaac ccaugggaau gauagggauc cgaucuggua cugcaugcac gcaaugcuag | | 1020 |
| cugccccuuu cccguccugg uaccccgag ucuccccga ccucgggucc cagguaugcu | | 1080 |
| cccaccucca ccugcccac ucaccacccuc ugcuaguucc agacacccuc caagcacgca | | 1140 |
| gcaaugcagc ucaaaacgcu uagccuagcc acacccccac gggaaacagc agugauuaac | | 1200 |
| cuuuagcaau aaacgaaagu uuaacuaagc uauacuaacc ccaggguugg ucaauuucgu | | 1260 |
| gccagccaca cccucgagcu agcaaaaaaa aaaaaaaaaa aaaaaaaaa aaagcauaug | | 1320 |
| acuaaaaaaaa aaaaaaaaaa aaaaaaaaa aaaaaaaaa aaaaaaaaa aaaaaaaaa | | 1380 |
| aaaaaaaaaa aaa | | 1393 |

<210> SEQ ID NO 69
<211> LENGTH: 309
<212> TYPE: PRT
<213> ORGANISM: Artificial sequence
<220> FEATURE:
<223> OTHER INFORMATION: ModB murine 41BBL

<400> SEQUENCE: 69

Met Asp Gln His Thr Leu Asp Val Glu Asp Thr Ala Asp Ala Arg His
1               5                   10                  15

Pro Ala Gly Thr Ser Cys Pro Ser Asp Ala Ala Leu Leu Arg Asp Thr
            20                  25                  30

Gly Leu Leu Ala Asp Ala Ala Leu Leu Ser Asp Thr Val Arg Pro Thr
        35                  40                  45

Asn Ala Ala Leu Pro Thr Asp Ala Ala Tyr Pro Ala Val Asn Val Arg
    50                  55                  60

Asp Arg Glu Ala Ala Trp Pro Pro Ala Leu Asn Phe Cys Ser Arg His
65                  70                  75                  80

Pro Lys Leu Tyr Gly Leu Val Ala Leu Val Leu Leu Leu Ile Ala
                85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Asn Ala Asp Gln

|  |  |  | 115 |  |  |  | 120 |  |  |  | 125 |  |
|---|---|---|---|---|---|---|---|---|---|---|---|---|
| Val | Thr | Pro | Val | Ser | His | Ile | Gly | Cys | Pro | Asn | Thr | Thr | Gln | Gln | Gly |
| 130 | | | | | 135 | | | | | 140 | | | | | |

Ser Pro Val Phe Ala Lys Leu Leu Ala Lys Asn Gln Ala Ser Leu Cys
145                 150                   155                   160

Asn Thr Thr Leu Asn Trp His Ser Gln Asp Gly Ala Gly Ser Ser Tyr
                   165                   170                   175

Leu Ser Gln Gly Leu Arg Tyr Glu Glu Asp Lys Lys Glu Leu Val Val
            180                   185                   190

Asp Ser Pro Gly Leu Tyr Tyr Val Phe Leu Glu Leu Lys Leu Ser Pro
         195                   200                   205

Thr Phe Thr Asn Thr Gly His Lys Val Gln Gly Trp Val Ser Leu Val
210                   215                   220

Leu Gln Ala Lys Pro Gln Val Asp Asp Phe Asp Asn Leu Ala Leu Thr
225                 230                   235                   240

Val Glu Leu Phe Pro Cys Ser Met Glu Asn Lys Leu Val Asp Arg Ser
                  245                   250                   255

Trp Ser Gln Leu Leu Leu Leu Lys Ala Gly His Arg Leu Ser Val Gly
            260                   265                   270

Leu Arg Ala Tyr Leu His Gly Ala Gln Asp Ala Tyr Arg Asp Trp Glu
         275                   280                   285

Leu Ser Tyr Pro Asn Thr Thr Ser Phe Gly Leu Phe Leu Val Lys Pro
        290                   295                   300

Asp Asn Pro Trp Glu
305

<210> SEQ ID NO 70
<211> LENGTH: 1486
<212> TYPE: DNA
<213> ORGANISM: Artificial sequence
<220> FEATURE:
<223> OTHER INFORMATION: ModB murine 41BBL (5'UTR-CDS-3'UTR)

<400> SEQUENCE: 70

```
ggaataaact agtctcaaca caacatatac aaaacaaacg aatctcaagc aatcaagcat      60
tctacttcta ttgcagcaat ttaaatcatt tcttttaaag caaaagcaat tttctgaaaa     120
ttttcaccat ttacgaacga tagccatgga ccagcacaca cttgatgtgg aggataccgc     180
ggatgccaga catccagcag gtacttcgtg cccctcggat gcggcgctcc tcagagatac     240
cgggctcctc gcggacgctg cgctcctctc agatactgtg cgcccacaa atgccgcgct     300
ccccacggat gctgcctacc ctgcggttaa tgttcgggat cgcgaggccg cgtggccgcc     360
tgcactgaac ttctgttccc gccacccaaa gctctatggc ctagtcgctt tggttttgct     420
gcttctgatc gccgcctgtg ttcctatctt cacccgcacc gagcctcggc cagcgctcac     480
aatcaccacc tcgcccaacc tgggtacccg agagaataat gcagaccagg tcacccctgt     540
ttcccacatt ggctgcccca acactacaca acagggctct cctgtgttcg ccaagctact     600
ggctaaaaac caagcatcgt tgtgcaatac aactctgaac tggcacagcc aagatggagc     660
tgggagctca tacctatctc aaggtctgag gtacgaagaa dacaaaaagg agttggtggt     720
agacagtccc gggctctact acgtattttt ggaactgaag ctcagtccaa cattcacaaa     780
cacaggccac aaggtgcagg gctgggtctc tcttgttttg caagcaaagc ctcaggtaga     840
tgactttgac aacttggccc tgacagtgga actgttccct gctccatgg agaacaagtt     900
agtggaccgt tcctggagtc aactgttgct cctgaaggct ggccaccgcc tcagtgtggg     960
```

```
tctgagggct tatctgcatg gagcccagga tgcatacaga gactgggagc tgtcttatcc    1020
caacaccacc agctttggac tctttcttgt gaaacccgac aacccatggg aatgataggg    1080
atccgatctg gtactgcatg cacgcaatgc tagctgcccc tttcccgtcc tgggtacccc    1140
gagtctcccc cgacctcggg tcccaggtat gctcccacct ccacctgccc cactcaccac    1200
ctctgctagt tccagacacc tcccaagcac gcagcaatgc agctcaaaac gcttagccta    1260
gccacacccc cacgggaaac agcagtgatt aacctttagc aataaacgaa agtttaacta    1320
agctatacta accccagggt tggtcaattt cgtgccagcc acaccctcga gctagcaaaa    1380
aaaaaaaaaa aaaaaaaaaa aaaaagcat atgactaaaa aaaaaaaaaa aaaaaaaaa    1440 aaaaaaaaaa aaaaaaaaaa aaaaaaaaaa aaaaaaaaaa aaaaaa                  1486
```

<210> SEQ ID NO 71
<211> LENGTH: 1486
<212> TYPE: RNA
<213> ORGANISM: Artificial sequence
<220> FEATURE:
<223> OTHER INFORMATION: ModB murine 41BBL

<400> SEQUENCE: 71

```
ggaauaaacu agucucaaca caacauauac aaaacaaacg aaucucaagc aaucaagcau      60
ucuacuucua uugcagcaau uuaaaucauu ucuuuuaaag caaaagcaau uuucugaaaa     120
uuuucaccau uuacgaacga uagccaugga ccagcacaca cuugaugugg aggauaccgc     180
ggaugccaga cauccagcag guacuucgug ccccucggau gcggcgcucc ucagagauac     240
cgggcuccuc gcggacgcug cgcuccucuc agauacugug cgcccacaa augccgcgcu     300 ccccacggau gcugccuacc cugcgguuaa uguucgggau cgcgaggccg cguggccgcc     360
ugcacugaac uucuguuccc gccacccaaa gcucuauggc cuagucgcuu ugguuuugcu     420 gcuucgauc gccgccugug uuccuaucuu cacccgcacc gagccucggc cagcgcucac     480
aaucaccacc ucgcccaacc uggguacccg agagaauaau gcagaccagg ucaccccugu     540
uucccacauu ggcugcccca acacuacaca cagggcucu ccuguguucg ccaagcuacu     600
ggcuaaaaac caagcaucgu ugugcaauac aacucugaac uggcacagcc aagauggagc     660
ugggagcuca uaccuaucuc aaggucugag guacgaagaa cacaaaaagg aguugguggu     720
agacaguccc gggcucuacu acguauuuuu ggaacugaag cucagcccaa cauucacaaa     780
cacaggccac aaggugcagg gcuggguucu ucuuguuug caagcaaagc cucagguaga     840
ugacuuugac aacuuggccc ugacaguugga acuguuccu ugcuccaugg agaacaaguu     900
aguggaccgu uccuggagguc aacuguugcu ccugaaggcu ggccaccgcc ucagugugg     960 ucugagggcu uaucugcaug gagcccagga ugcauacaga gacugggagc ugucuuaucc    1020
caacaccacc agcuuuggac ucuuucuugu gaaacccgac aacccauggg aaugauaggg    1080
auccgaucug guacugcaug cacgcaaugc uagcugcccc uuucccguccu ggguaccccc   1140 gagucucccc cgaccucggg uccagguau gcucccaccu ccaccugcc cacucaccac     1200 cucugcuagu uccagacacc ucccaagcac gcagcaaugc agcucaaaac gcuuagccua    1260
gccacacccc cacgggaaac agcaguagu aaccuuuagc aauaaacgaa aguuuaacua    1320
agcuauacua accccagggu ugguucaauuu cgugccagcc acaccucga gcuagcaaaa   1380 aaaaaaaaaa aaaaaaaaaa aaaaagcau augacuaaaa aaaaaaaaaa aaaaaaaaa    1440 aaaaaaaaaa aaaaaaaaaa aaaaaaaaaa aaaaaaaaaa aaaaaa                 1486
```

<210> SEQ ID NO 72
<211> LENGTH: 935
<212> TYPE: PRT
<213> ORGANISM: Artificial sequence
<220> FEATURE:
<223> OTHER INFORMATION: ModA murine CD27L-CD40L

<400> SEQUENCE: 72

```
Met Arg Val Thr Ala Pro Arg Thr Leu Ile Leu Leu Ser Gly Ala
1               5                   10                  15

Leu Ala Leu Thr Glu Thr Trp Ala Gly Ser Gly Ser His Pro Glu Pro
            20                  25                  30

His Thr Ala Glu Leu Gln Leu Asn Leu Thr Val Pro Arg Lys Asp Pro
        35                  40                  45

Thr Leu Arg Trp Gly Ala Gly Pro Ala Leu Gly Arg Ser Phe Thr His
    50                  55                  60

Gly Pro Glu Leu Glu Glu Gly His Leu Arg Ile His Gln Asp Gly Leu
65              70                  75                  80

Tyr Arg Leu His Ile Gln Val Thr Leu Ala Asn Cys Ser Ser Pro Gly
                85                  90                  95

Ser Thr Leu Gln His Arg Ala Thr Leu Ala Val Gly Ile Cys Ser Pro
            100                 105                 110

Ala Ala His Gly Ile Ser Leu Leu Arg Gly Arg Phe Gly Gln Asp Cys
        115                 120                 125

Thr Val Ala Leu Gln Arg Leu Thr Tyr Leu Val His Gly Asp Val Leu
    130                 135                 140

Cys Thr Asn Leu Thr Leu Pro Leu Leu Pro Ser Arg Asn Ala Asp Glu
145                 150                 155                 160

Thr Phe Phe Gly Val Gln Trp Ile Cys Pro Gly Gly Ser Gly Gly
                165                 170                 175

Gly His Pro Glu Pro His Thr Ala Glu Leu Gln Leu Asn Leu Thr Val
            180                 185                 190

Pro Arg Lys Asp Pro Thr Leu Arg Trp Gly Ala Gly Pro Ala Leu Gly
        195                 200                 205

Arg Ser Phe Thr His Gly Pro Glu Leu Glu Glu Gly His Leu Arg Ile
    210                 215                 220

His Gln Asp Gly Leu Tyr Arg Leu His Ile Gln Val Thr Leu Ala Asn
225                 230                 235                 240

Cys Ser Ser Pro Gly Ser Thr Leu Gln His Arg Ala Thr Leu Ala Val
                245                 250                 255

Gly Ile Cys Ser Pro Ala Ala His Gly Ile Ser Leu Leu Arg Gly Arg
            260                 265                 270

Phe Gly Gln Asp Cys Thr Val Ala Leu Gln Arg Leu Thr Tyr Leu Val
        275                 280                 285

His Gly Asp Val Leu Cys Thr Asn Leu Thr Leu Pro Leu Leu Pro Ser
    290                 295                 300

Arg Asn Ala Asp Glu Thr Phe Phe Gly Val Gln Trp Ile Cys Pro Gly
305                 310                 315                 320

Gly Gly Ser Gly Gly Gly His Pro Glu Pro His Thr Ala Glu Leu Gln
                325                 330                 335

Leu Asn Leu Thr Val Pro Arg Lys Asp Pro Thr Leu Arg Trp Gly Ala
            340                 345                 350

Gly Pro Ala Leu Gly Arg Ser Phe Thr His Gly Pro Glu Leu Glu Glu
        355                 360                 365
```

```
Gly His Leu Arg Ile His Gln Asp Gly Leu Tyr Arg Leu His Ile Gln
370                 375                 380
Val Thr Leu Ala Asn Cys Ser Ser Pro Gly Ser Thr Leu Gln His Arg
385                 390                 395                 400
Ala Thr Leu Ala Val Gly Ile Cys Ser Pro Ala Ala His Gly Ile Ser
                405                 410                 415
Leu Leu Arg Gly Arg Phe Gly Gln Asp Cys Thr Val Ala Leu Gln Arg
                420                 425                 430
Leu Thr Tyr Leu Val His Gly Asp Val Leu Cys Thr Asn Leu Thr Leu
            435                 440                 445
Pro Leu Leu Pro Ser Arg Asn Ala Asp Glu Thr Phe Phe Gly Val Gln
450                 455                 460
Trp Ile Cys Pro Gly Gly Gly Ser Gly Gly Gly Ser Gly Gly
465                 470                 475                 480
Gly Gly Ser Gly Asp Glu Asp Pro Gln Ile Ala Ala His Val Val Ser
                485                 490                 495
Glu Ala Asn Ser Asn Ala Ala Ser Val Leu Gln Trp Ala Lys Lys Gly
                500                 505                 510
Tyr Tyr Thr Met Lys Ser Asn Leu Val Met Leu Glu Asn Gly Lys Gln
            515                 520                 525
Leu Thr Val Lys Arg Glu Gly Leu Tyr Tyr Val Tyr Thr Gln Val Thr
530                 535                 540
Phe Cys Ser Asn Arg Glu Pro Ser Ser Gln Arg Pro Phe Ile Val Gly
545                 550                 555                 560
Leu Trp Leu Lys Pro Ser Ser Gly Ser Glu Arg Ile Leu Leu Lys Ala
                565                 570                 575
Ala Asn Thr His Ser Ser Ser Gln Leu Cys Glu Gln Gln Ser Val His
                580                 585                 590
Leu Gly Gly Val Phe Glu Leu Gln Ala Gly Ala Ser Val Phe Val Asn
            595                 600                 605
Val Thr Glu Ala Ser Gln Val Ile His Arg Val Gly Phe Ser Ser Phe
610                 615                 620
Gly Leu Leu Lys Leu Gly Gly Ser Gly Gly Gly Gly Asp Glu Asp
625                 630                 635                 640
Pro Gln Ile Ala Ala His Val Val Ser Glu Ala Asn Ser Asn Ala Ala
                645                 650                 655
Ser Val Leu Gln Trp Ala Lys Lys Gly Tyr Tyr Thr Met Lys Ser Asn
                660                 665                 670
Leu Val Met Leu Glu Asn Gly Lys Gln Leu Thr Val Lys Arg Glu Gly
            675                 680                 685
Leu Tyr Tyr Val Tyr Thr Gln Val Thr Phe Cys Ser Asn Arg Glu Pro
690                 695                 700
Ser Ser Gln Arg Pro Phe Ile Val Gly Leu Trp Leu Lys Pro Ser Ser
705                 710                 715                 720
Gly Ser Glu Arg Ile Leu Leu Lys Ala Ala Asn Thr His Ser Ser Ser
                725                 730                 735
Gln Leu Cys Glu Gln Gln Ser Val His Leu Gly Gly Val Phe Glu Leu
                740                 745                 750
Gln Ala Gly Ala Ser Val Phe Val Asn Val Thr Glu Ala Ser Gln Val
            755                 760                 765
Ile His Arg Val Gly Phe Ser Ser Phe Gly Leu Leu Lys Leu Gly Gly
770                 775                 780
Gly Ser Gly Gly Gly Gly Asp Glu Asp Pro Gln Ile Ala Ala His Val
```

```
                785              790               795              800
Val Ser Glu Ala Asn Ser Asn Ala Ala Ser Val Leu Gln Trp Ala Lys
                    805                 810                 815
Lys Gly Tyr Tyr Thr Met Lys Ser Asn Leu Val Met Leu Glu Asn Gly
                820                 825                 830
Lys Gln Leu Thr Val Lys Arg Glu Gly Leu Tyr Tyr Val Tyr Thr Gln
            835                 840                 845
Val Thr Phe Cys Ser Asn Arg Glu Pro Ser Ser Gln Arg Pro Phe Ile
        850                 855                 860
Val Gly Leu Trp Leu Lys Pro Ser Ser Gly Ser Glu Arg Ile Leu Leu
865                 870                 875                 880
Lys Ala Ala Asn Thr His Ser Ser Ser Gln Leu Cys Glu Gln Gln Ser
                885                 890                 895
Val His Leu Gly Gly Val Phe Glu Leu Gln Ala Gly Ala Ser Val Phe
            900                 905                 910
Val Asn Val Thr Glu Ala Ser Gln Val Ile His Arg Val Gly Phe Ser
        915                 920                 925
Ser Phe Gly Leu Leu Lys Leu
    930                 935

<210> SEQ ID NO 73
<211> LENGTH: 3281
<212> TYPE: DNA
<213> ORGANISM: Artificial sequence
<220> FEATURE:
<223> OTHER INFORMATION: ModA murine CD27L-CD40L (5'UTR-CDS-3'UTR)

<400> SEQUENCE: 73
gggcgaacta gtattcttct ggtccccaca gactcagaga gaacccgcca ccatgagagt      60
gaccgccccc agaaccctga tcctgctgct gtctggcgcc ctggccctga cagagacatg     120
ggccggaagc ggatcccacc ccgagcccca caccgccgaa ctgcagctga acctgaccgt     180
gcccagaaag gaccccaccc tgagatgggg agctggccct gctctgggca gatccttta c    240
acacggcccc gagctggaag aaggccacct gagaatccac caggacggcc tgtacagact     300
gcacatccaa gtgaccctgg ccaactgcag cagccctggc tctaccctgc agcacagagc     360
cacactggcc gtgggcatct gtagccctgc tgctcacgga atcagcctgc tgagaggcag     420
attcggccag gactgtaccg tggccctgca gaggctgacc tatctggtgc atggcgacgt     480
gctgtgcacc aacctgacac tgcctctgct gcccagcaga aacgccgacg aaacattctt     540
tggagtgcag tggatttgtc ctggcggagg gtccggggga ggacacccag aacctcatac     600
agctgaactg cagctgaacc tgaccgtgcc cagaaaggac ccacccctga tggggagc       660
tggccctgct ctgggcagat cctttacaca cggccccgag ctggaagaag gccacctgag     720
aatccaccag gacggcctgt acagactgca catccaagtg accctggcca actgcagcag     780
ccctggctct accctgcagc acagagccac actggccgtg gcatctgta gccctgctgc      840
tcacggaatc agcctgctga gaggcagatt cggccaggac tgtaccgtgg ccctgcagag     900
gctgacctat ctggtgcatg gcgacgtgct gtgcaccaac ctgacactgc ctctgctgcc     960
cagcagaaac gccgacgaaa cattctttgg agtgcagtgg atttgtcctg ggggaggctc    1020
cggaggcgga caccctgaac ctcatacagc tgaactgcag ctgaacctga ccgtgcccag    1080
aaaggacccc accctgagat ggggagctgg ccctgctctg gcagatcct ttacacacgg     1140
ccccgagctg gaagaaggcc acctgagaat ccaccaggac ggcctgtaca gactgcacat    1200
```

| | |
|---|---|
| ccaagtgacc ctggccaact gcagcagccc tggctctacc ctgcagcaca gagccacact | 1260 |
| ggccgtgggc atctgtagcc ctgctgctca cggaatcagc ctgctgagag cagattcgg | 1320 |
| ccaggactgt accgtggccc tgcagaggct gacctatctg gtgcatggcg acgtgctgtg | 1380 |
| caccaacctg acactgcctc tgctgcccag cagaaacgcc gacgagacct tcttcggcgt | 1440 |
| ccagtggatc tgccccggag gcggtggtag tggaggtggc gggtccggtg gaggtggaag | 1500 |
| cggcgacgag gacccccaga tcgccgccca cgtggtgtct gaggccaaca gcaacgccgc | 1560 |
| ctctgtgctg cagtgggcca agaaaggcta ctacaccatg aagtccaacc tcgtgatgct | 1620 |
| ggaaaacggc aagcagctga ccgtgaagcg cgagggcctg tactatgtgt acacccaagt | 1680 |
| gacattctgc agcaaccgcg agcccagcag ccagaggcct tttatcgtgg gcctgtggct | 1740 |
| gaagcctagc agcggcagcg agagaatcct gctgaaggcc gccaacaccc acagcagctc | 1800 |
| tcagctgtgc gagcagcagt ctgtgcacct gggaggcgtg ttcgagctgc aagctggcgc | 1860 |
| ttccgtgttc gtgaacgtga ccgaggccag ccaagtgatc cacagagtgg gcttcagcag | 1920 |
| ctttggactg ctcaaactgg gcggagggtc cggcggaggc ggagatgaag atcctcagat | 1980 |
| tgctgcccac gtggtgtctg aggccaacag caacgccgcc tctgtgctgc agtgggccaa | 2040 |
| gaaaggctac tacaccatga agtccaacct cgtgatgctg gaaaacggca agcagctgac | 2100 |
| cgtgaagcgc gagggcctgt actatgtgta cacccaagtg acattctgca gcaaccgcga | 2160 |
| gcccagcagc cagaggcctt ttatcgtggg cctgtggctg aagcctagca gcggcagcga | 2220 |
| gagaatcctg ctgaaggccg ccaacaccca cagcagctct cagctgtgcg agcagcagtc | 2280 |
| tgtgcacctg ggaggcgtgt tcgagctgca agctggcgct tccgtgttcg tgaacgtgac | 2340 |
| cgaggccagc caagtgatcc acagagtggg cttcagcagc tttggactgc tcaaactggg | 2400 |
| aggcggctcc ggaggcggag gagatgaaga tcctcagatt gctgcccacg tggtgtctga | 2460 |
| ggccaacagc aacgccgcct ctgtgctgca gtgggccaag aaaggctact acaccatgaa | 2520 |
| gtccaacctc gtgatgctgg aaaacggcaa gcagctgacc gtgaagcgcg agggcctgta | 2580 |
| ctatgtgtac acccaagtga cattctgcag caaccgcgag cccagcagcc agaggccttt | 2640 |
| tatcgtgggc ctgtggctga agcctagcag cggcagcgag agaatcctgc tgaaggccgc | 2700 |
| caacacccac agcagctctc agctgtgcga gcagcagtct gtgcacctgg gaggcgtgtt | 2760 |
| cgagctgcaa gctggcgctt ccgtgttcgt gaacgtgacc gaggccagcc aagtgatcca | 2820 |
| cagagtgggc ttcagcagct ttggactgct caaactgggc ggagggtcag gcggaggcgg | 2820 |
| cagagtgggc ttctcctcct tcggcctcct gaagctgtga ctcgagagct cgctttcttg | 2880 |
| ctgtccaatt tctattaaag gttcctttgt tccctaagtc caactactaa actgggggat | 2940 |
| attatgaagg gccttgagca tctggattct gcctaataaa aacatttat tttcattgct | 3000 |
| gcgtcgagag ctcgctttct tgctgtccaa tttctattaa aggttccttt gttccctaag | 3060 |
| tccaactact aaactggggg atattatgaa gggccttgag catctggatt ctgcctaata | 3120 |
| aaaaacattt attttcattg ctgcgtcgag acctggtcca gagtcgctag caaaaaaaaa | 3180 |
| aaaaaaaaaa aaaaaaaaaa agcatatgac taaaaaaaaa aaaaaaaaaa aaaaaaaaaa | 3240 |
| aaaaaaaaaa aaaaaaaaaa aaaaaaaaaa aaaaaaaaa a | 3281 |

```
<210> SEQ ID NO 74
<211> LENGTH: 3281
<212> TYPE: RNA
<213> ORGANISM: Artificial sequence
<220> FEATURE:
<223> OTHER INFORMATION: ModA murine CD27L-CD40L

<400> SEQUENCE: 74
```

-continued

```
gggcgaacua guauucuucu ggucgccaca gacucagaga gaacccgcca ccaugagagu    60
gaccgccccc agaacccuga uccugcugcu gucuggcgcc cuggcccuga cagagacaug   120
ggccggaagc ggaucccacc ccgagcccca caccgccgaa cugcagcuga accugaccgu   180
gcccagaaag gaccccaccc ugagauggg agcuggcccu gcucugggca gauccuuuac   240
acacggcccc gagcuggaag aaggccaccu gagaauccac caggacggcc uguacagacu   300
gcacauccaa gugacccugg ccaacugcag cagcccuggc ucuacccugc agcacagagc   360
cacacuggcc gugggcaucu uagcccugc ugcucacgga aucagccugc ugagaggcag   420
auucggccag acuguaccg uggcccugca gaggcugacc uaucggguc auggcgacgu    480
gcugugcacc aaccugacac ugccucugcu gcccagcaga aacgccgacg aaacauucuu   540
uggagugcag uggauuuguc cuggcggagg guccggggga ggacacccag aaccucauac   600
agcugaacug cagcugaacc ugaccgugcc cagaaaggac cccacccuga gauggggagc   660
uggcccugcu cugggcagau ccuuuacaca cggccccgag cuggaagaag gccaccugag   720
aauccaccag gacggccugu acagacugca cauccaagug acccuggcca acugcagcag   780
cccuggcucu acccugcagc acagagccac acuggccgug ggcaucugua gcccugcugc   840
ucacggaauc agccugcuga gaggcagauu cggccaggac uguaccgugg cccugcagag   900
gcugaccuau cuggugcaug gcgacgugcu gugcaccaac cugacacugc cucugcugcc   960
cagcagaaac gccgacgaaa cauucuuugg agugcagugg auuugccug ggggaggcuc  1020
cggaggcgga cacccugaac cucauacagc ugaacugcag cugaaccuga ccgugcccag  1080
aaaggacccc acccugagau ggggagcugg cccugcucug gcagauccu uuacacacgg  1140
ccccgagcug gaagaaggcc accugagaau ccaccaggac ggccuguaca gacugcacau  1200
ccaagugacc cuggccaacu gcagcagccc uggcucuacc cugcagcaca gagccacacu  1260
ggccgugggc aucuuagcc cugcugcuca cggaaucagc cugcugagag gcagauucgg  1320
ccaggacugu accgugggcc ugcagaggcu gaccuaucug gugcauggcg acgugcugug  1380
caccaaccug acacugccuc ugcugcccag cagaaacgcc gacgagaccu cuucggcgu  1440
ccaguggauc ugccccggag gcggugguag uggaggugc gggucggug gaggugaag  1500
cggcgacgag gaccccaga ucgccgccca cguggugucu gaggccaaca gcaacgccgc  1560
cucugugcug cagugggcca agaaaggcua cuacaccaug aaguccaacc ucgugaugcu  1620
ggaaaacggc aagcagcuga ccgugaagcg cgagggccug uacuaugugu acacccaagu  1680
gacauucugc agcaaccgcg agcccagcag ccagaggccu uuuaucgugg ccuguggcu  1740
gaagccuagc agcggcagcg agagaauccu gcugaaggcc gccaacaccc acagcagcuc  1800
ucagcugugc gagcagcagu cugugcaccu ggggaggcgug uucagcugc aagcuggcgc  1860
uuccgguguc gugaacguga ccgaggccag ccaagugauc cacagagugg cuucagcag  1920
cuuuggacug cucaaacugg gcggagggu cggcggaggc ggagaugaag auccucagau  1980
ugcugccac gugugucug aggccaacag caacgccgcc ucugugcugc agugggccaa  2040
gaaaggcuac uacaccauga aguccaaccu cgugaugcug gaaaacggca agcagcugac  2100
cgugaagcgc gagggccugu acuaugugua cacccaagug acauucugca gcaaccgcga  2160
gcccagcagc cagaggccuu uuaucguggg ccuguggcug aagccuagca gcggcagcga  2220
gagaauccug cugaaggccg ccaacaccca cagcagcucu cagcugugcg agcagcaguc  2280
ugugcaccug ggaggcgugu ucagcugca agcuggcgcu uccguguucg ugaacgugac  2340
```

-continued

```
cgaggccagc caagugaucc acagaguggg cuucagcagc uuuggacugc ucaaacuggg    2400
aggcggcucc ggaggcggag gagaugaaga uccucagauu gcugcccacg uggugucuga    2460
ggccaacagc aacgccgccu cugugcugca gugggccaag aaaggcuacu acaccaugaa    2520
guccaaccuc gugaugcugg aaaacggcaa gcagcgcgcg gugaagcgcg agggccugua    2580
cuauguguac acccaaguga cauucugcag caaccgcgag cccagcagcc agaggccuuu    2640
uaucgugggc cuguggcuga agccuagcag cggcagcgag agaauccugc ugaaggccgc    2700
caacacccac agcagcucuc agcugugcga gcagcagucu gugcaccugg aggcguguu    2760 cgagcugcaa gcuggcgcuu ccguguucgu gaacgugacc gaggccagcc aagugauccagagugggc uucuccuccu ucggccuccu gaagcuguga cucgagagcu cgcuuucuug    2820
cagagugggc uucuccuccu ucggccuccu gaagcuguga cucgagagcu cgcuuucuug    2880 cguccaauu ucuauuaaag guuccuuugu ucccuaaguc caacuacuaa acuggggau     2940 auuaugaagg gccuugagca ucuggauucu gccuauaaa aaacauuuau uucauugcu     3000 gcgucgagag cucgcuuucu ugcuguccaa uuucuauuaa agguuccuuu guucccuaag    3060
uccaacuacu aaacuggggg auauuaugaa gggccuugag caucuggauu cugccuaaua    3120
aaaaacauuu auuuucauug cugcgucgag accuggucca gagucgcuag caaaaaaaaa    3180
aaaaaaaaaa aaaaaaaaaa agcauaugac uaaaaaaaaa aaaaaaaaaa aaaaaaaaaa    3240
aaaaaaaaaa aaaaaaaaaa aaaaaaaaaa aaaaaaaaa a                          3281
```

<210> SEQ ID NO 75
<211> LENGTH: 935
<212> TYPE: PRT
<213> ORGANISM: Artificial sequence
<220> FEATURE:
<223> OTHER INFORMATION: ModB murine CD27L-CD40L

<400> SEQUENCE: 75

```
Met Gly Ala Met Ala Pro Arg Thr Leu Leu Leu Leu Ala Ala
1               5                   10                  15

Leu Ala Pro Thr Gln Thr Arg Ala Gly Pro Gly Ser His Pro Glu Pro
            20                  25                  30

His Thr Ala Glu Leu Gln Leu Asn Leu Thr Val Pro Arg Lys Asp Pro
        35                  40                  45

Thr Leu Arg Trp Gly Ala Gly Pro Ala Leu Gly Arg Ser Phe Thr His
    50                  55                  60

Gly Pro Glu Leu Glu Glu Gly His Leu Arg Ile His Gln Asp Gly Leu
65                  70                  75                  80

Tyr Arg Leu His Ile Gln Val Thr Leu Ala Asn Cys Ser Ser Pro Gly
                85                  90                  95

Ser Thr Leu Gln His Arg Ala Thr Leu Ala Val Gly Ile Cys Ser Pro
                100                 105                 110

Ala Ala His Gly Ile Ser Leu Leu Arg Gly Arg Phe Gly Gln Asp Cys
            115                 120                 125

Thr Val Ala Leu Gln Arg Leu Thr Tyr Leu Val His Gly Asp Val Leu
    130                 135                 140

Cys Thr Asn Leu Thr Leu Pro Leu Leu Pro Ser Arg Asn Ala Asp Glu
145                 150                 155                 160

Thr Phe Phe Gly Val Gln Trp Ile Cys Pro Gly Gly Ser Gly Gly
                165                 170                 175

Gly His Pro Glu Pro His Thr Ala Glu Leu Gln Leu Asn Leu Thr Val
            180                 185                 190

Pro Arg Lys Asp Pro Thr Leu Arg Trp Gly Ala Gly Pro Ala Leu Gly
```

```
            195                 200                 205
Arg Ser Phe Thr His Gly Pro Glu Leu Glu Gly His Leu Arg Ile
210                 215                 220

His Gln Asp Gly Leu Tyr Arg Leu His Ile Gln Val Thr Leu Ala Asn
225                 230                 235                 240

Cys Ser Ser Pro Gly Ser Thr Leu Gln His Arg Ala Thr Leu Ala Val
                245                 250                 255

Gly Ile Cys Ser Pro Ala Ala His Gly Ile Ser Leu Leu Arg Gly Arg
                260                 265                 270

Phe Gly Gln Asp Cys Thr Val Ala Leu Gln Arg Leu Thr Tyr Leu Val
                275                 280                 285

His Gly Asp Val Leu Cys Thr Asn Leu Thr Leu Pro Leu Pro Ser
290                 295                 300

Arg Asn Ala Asp Glu Thr Phe Phe Gly Val Gln Trp Ile Cys Pro Gly
305                 310                 315                 320

Gly Gly Ser Gly Gly Gly His Pro Glu Pro His Thr Ala Glu Leu Gln
                325                 330                 335

Leu Asn Leu Thr Val Pro Arg Lys Asp Pro Thr Leu Arg Trp Gly Ala
                340                 345                 350

Gly Pro Ala Leu Gly Arg Ser Phe Thr His Gly Pro Glu Leu Glu Glu
                355                 360                 365

Gly His Leu Arg Ile His Gln Asp Gly Leu Tyr Arg Leu His Ile Gln
                370                 375                 380

Val Thr Leu Ala Asn Cys Ser Ser Pro Gly Ser Thr Leu Gln His Arg
385                 390                 395                 400

Ala Thr Leu Ala Val Gly Ile Cys Ser Pro Ala Ala His Gly Ile Ser
                405                 410                 415

Leu Leu Arg Gly Arg Phe Gly Gln Asp Cys Thr Val Ala Leu Gln Arg
                420                 425                 430

Leu Thr Tyr Leu Val His Gly Asp Val Leu Cys Thr Asn Leu Thr Leu
                435                 440                 445

Pro Leu Leu Pro Ser Arg Asn Ala Asp Glu Thr Phe Phe Gly Val Gln
450                 455                 460

Trp Ile Cys Pro Gly Gly Gly Gly Ser Gly Gly Gly Gly Ser Gly Gly
465                 470                 475                 480

Gly Gly Ser Gly Asp Glu Asp Pro Gln Ile Ala Ala His Val Val Ser
                485                 490                 495

Glu Ala Asn Ser Asn Ala Ala Ser Val Leu Gln Trp Ala Lys Lys Gly
                500                 505                 510

Tyr Tyr Thr Met Lys Ser Asn Leu Val Met Leu Glu Asn Gly Lys Gln
                515                 520                 525

Leu Thr Val Lys Arg Glu Gly Leu Tyr Tyr Val Tyr Thr Gln Val Thr
                530                 535                 540

Phe Cys Ser Asn Arg Glu Pro Ser Ser Gln Arg Pro Phe Ile Val Gly
545                 550                 555                 560

Leu Trp Leu Lys Pro Ser Ser Gly Ser Glu Arg Ile Leu Leu Lys Ala
                565                 570                 575

Ala Asn Thr His Ser Ser Ser Gln Leu Cys Glu Gln Gln Ser Val His
                580                 585                 590

Leu Gly Gly Val Phe Glu Leu Gln Ala Gly Ala Ser Val Phe Val Asn
                595                 600                 605

Val Thr Glu Ala Ser Gln Val Ile His Arg Val Gly Phe Ser Ser Phe
610                 615                 620
```

| Gly | Leu | Leu | Lys | Leu | Gly | Gly | Ser | Gly | Gly | Gly | Asp | Glu | Asp |
| --- | --- | --- | --- | --- | --- | --- | --- | --- | --- | --- | --- | --- | --- |
| 625 | | | | 630 | | | | 635 | | | | | 640 |

Pro Gln Ile Ala Ala His Val Val Ser Glu Ala Asn Ser Asn Ala Ala
              645                 650                 655

Ser Val Leu Gln Trp Ala Lys Lys Gly Tyr Tyr Thr Met Lys Ser Asn
        660                 665                 670

Leu Val Met Leu Glu Asn Gly Lys Gln Leu Thr Val Lys Arg Glu Gly
    675                 680                 685

Leu Tyr Tyr Val Tyr Thr Gln Val Thr Phe Cys Ser Asn Arg Glu Pro
690                 695                 700

Ser Ser Gln Arg Pro Phe Ile Val Gly Leu Trp Leu Lys Pro Ser Ser
705                 710                 715                 720

Gly Ser Glu Arg Ile Leu Leu Lys Ala Ala Asn Thr His Ser Ser Ser
            725                 730                 735

Gln Leu Cys Glu Gln Gln Ser Val His Leu Gly Gly Val Phe Glu Leu
        740                 745                 750

Gln Ala Gly Ala Ser Val Phe Val Asn Val Thr Glu Ala Ser Gln Val
    755                 760                 765

Ile His Arg Val Gly Phe Ser Ser Phe Gly Leu Leu Lys Leu Gly Gly
770                 775                 780

Gly Ser Gly Gly Gly Gly Asp Glu Asp Pro Gln Ile Ala Ala His Val
785                 790                 795                 800

Val Ser Glu Ala Asn Ser Asn Ala Ala Ser Val Leu Gln Trp Ala Lys
            805                 810                 815

Lys Gly Tyr Tyr Thr Met Lys Ser Asn Leu Val Met Leu Glu Asn Gly
        820                 825                 830

Lys Gln Leu Thr Val Lys Arg Glu Gly Leu Tyr Tyr Val Tyr Thr Gln
    835                 840                 845

Val Thr Phe Cys Ser Asn Arg Glu Pro Ser Ser Gln Arg Pro Phe Ile
850                 855                 860

Val Gly Leu Trp Leu Lys Pro Ser Ser Gly Ser Glu Arg Ile Leu Leu
865                 870                 875                 880

Lys Ala Ala Asn Thr His Ser Ser Ser Gln Leu Cys Glu Gln Gln Ser
            885                 890                 895

Val His Leu Gly Gly Val Phe Glu Leu Gln Ala Gly Ala Ser Val Phe
        900                 905                 910

Val Asn Val Thr Glu Ala Ser Gln Val Ile His Arg Val Gly Phe Ser
    915                 920                 925

Ser Phe Gly Leu Leu Lys Leu
930                 935

<210> SEQ ID NO 76
<211> LENGTH: 3361
<212> TYPE: DNA
<213> ORGANISM: Artificial sequence
<220> FEATURE:
<223> OTHER INFORMATION: ModB murine CD27L-CD40L (5'UTR-CDS-3'UTR)

<400> SEQUENCE: 76

```
ggaataaact agtctcaaca caacatatac aaaacaaacg aatctcaagc aatcaagcat      60
tctacttcta ttgcagcaat ttaaatcatt tcttttaaag caaaagcaat tttctgaaaa     120 ttttccaccat ttacgaacga tagccatggg cgccatggcc cctagaacat tgctcctgct    180
gctggccgct gccctggccc ctacacagac aagagctgga cctggatccc accccgagcc    240
```

```
ccacaccgcc gaactgcagc tgaacctgac cgtgcccaga aaggacccca ccctgagatg    300
gggagctggc cctgctctgg gcagatcctt tacacacggc cccgagctgg aagaaggcca    360
cctgagaatc caccaggacg gcctgtacag actgcacatc caagtgaccc tggccaactg    420
cagcagccct ggctctaccc tgcagcacag agccacactg gccgtgggca tctgtagccc    480
tgctgctcac ggaatcagcc tgctgagagg cagattcggc caggactgta ccgtggccct    540
gcagaggctg acctatctgg tgcatggcga cgtgctgtgc accaacctga cactgcctct    600
gctgcccagc agaaacgccg acgaaacatt ctttggagtg cagtggattt gtcctggcgg    660
agggtccggg ggaggacacc cagaacctca tacagctgaa ctgcagctga acctgaccgt    720
gcccagaaag gaccccaccc tgagatgggg agctggccct gctctgggca gatcctttac    780
acacggcccc gagctggaag aaggccacct gagaatccac caggacggcc tgtacagact    840
gcacatccaa gtgaccctgg ccaactgcag cagcctggc tctaccctgc agcacagagc    900
cacactggcc gtgggcatct gtagccctgc tgctcacgga atcagcctgc tgagaggcag    960
attcggccag gactgtaccg tggccctgca gaggctgacc tatctggtgc atggcgacgt   1020
gctgtgcacc aacctgacac tgcctctgct gcccagcaga aacgccgacg aaacattctt   1080
tggagtgcag tggatttgtc ctggggagg ctccggaggc ggacccctg aacctcatac   1140 agctgaactg cagctgaacc tgaccgtgcc cagaaaggac cccaccctga tggggagc   1200 tggccctgct ctgggcagat cctttacaca cggccccgag ctggaagaag gccacctgag   1260
aatccaccag gacggcctgt acagactgca catccaagtg accctggcca actgcagcag   1320
ccctggctct accctgcagc acagagccac actggccgtg ggcatctgta gccctgctgc   1380
tcacggaatc agcctgctga gaggcagatt cggccaggac tgtaccgtgg ccctgcagag   1440
gctgacctat ctggtgcatg gcgacgtgct gtgcaccaac ctgacactgc ctctgctgcc   1500
cagcagaaac gccgacgaga ccttcttcgg cgtccagtgg atctgccccg aggcggtgg   1560 tagtggaggt ggcgggtccg gtggaggtgg aagcggcgac gaggaccccc agatcgccgc   1620
ccacgtggtg tctgaggcca acagcaacgc cgcctctgtg ctgcagtggg ccaagaaagg   1680
ctactacacc atgaagtcca acctcgtgat gctggaaaac ggcaagcagc tgaccgtgaa   1740
gcgcgagggc ctgtactatg tgtacaccca agtgacattc tgcagcaacc gcgagcccag   1800
cagccagagg cctttttatcg tgggcctgtg gctgaagcct agcagcggca gcgagagaat   1860
cctgctgaag gccgccaaca cccacagcag ctctcagctg tgcgagcagc agtctgtgca   1920
cctgggaggc gtgttcgagc tgcaagctgg cgcttccgtg ttcgtgaacg tgaccgaggc   1980
cagccaagtg atccacagag tgggcttcag cagctttgga ctgctcaaac tgggcggagg   2040
gtccggcgga ggcggagatg aagatcctca gattgctgcc cacgtggtgt ctgaggccaa   2100
cagcaacgcc gcctctgtgc tgcagtgggc caagaaaggc tactacacca tgaagtccaa   2160
cctcgtgatg ctggaaaacg gcaagcagct gaccgtgaag cgcgagggcc tgtactatgt   2220
gtacacccaa gtgacattct gcagcaaccg cgagcccagc agcagaggc ttttatcgt   2280 gggcctgtgg ctgaagccta gcagcggcag cgagagaatc ctgctgaagg ccgccaacac   2340
ccacagcagc tctcagctgt gcgagcagca gtctgtgcac ctgggaggcg tgttcgagct   2400
gcaagctggc gcttccgtgt tcgtgaacgt gaccgaggcc agccaagtga tccacagagt   2460
gggcttcagc agctttggac tgctcaaact gggcggag cccggaggcg aggagatga   2520 agatcctcag attgctgccc acgtggtgtc tgaggccaac agcaacgccg cctctgtgct   2580
gcagtgggcc aagaaaggct actacaccat gaagtccaac ctcgtgatgc tggaaaacgg   2640
```

```
caagcagctg accgtgaagc gcgagggcct gtactatgtg tacacccaag tgacattctg    2700
cagcaaccgc gagcccagca gccagaggcc ttttatcgtg ggcctgtggc tgaagcctag    2760
cagcggcagc gagagaatcc tgctgaaggc cgccaacacc cacagcagct ctcagctgtg    2820
cgagcagcag tctgtgcacc tgggaggcgt gttcgagctg caagctggcg cttccgtgtt    2880
cgtgaacgtg accgaggcca gccaagtgat ccacagagtg ggcttctcct ccttcggcct    2940
cctgaagctg tgactcgacg tcctggtact gcatgcacgc aatgctagct gcccctttcc    3000
cgtcctgggt accccgagtc tcccccgacc tcgggtccca ggtatgctcc cacctccacc    3060
tgccccactc accacctctg ctagttccag acacctccca agcacgcagc aatgcagctc    3120
aaaacgctta gcctagccac accccacgg gaaacagcag tgattaacct ttagcaataa    3180
acgaaagttt aactaagcta tactaacccc agggttggtc aatttcgtgc cagccacacc    3240
ctcgagctag caaaaaaaaa aaaaaaaaa aaaaaaaaa agcatatgac taaaaaaaa     3300 aaaaaaaaaa aaaaaaaaaa aaaaaaaaa aaaaaaaaaa aaaaaaaaa aaaaaaaa      3360 a                                                                    3361
```

<210> SEQ ID NO 77
<211> LENGTH: 3361
<212> TYPE: RNA
<213> ORGANISM: Artificial sequence
<220> FEATURE:
<223> OTHER INFORMATION: ModB murine CD27L-CD40L

<400> SEQUENCE: 77

```
ggaauaaacu agucucaaca caacauauac aaaacaaacg aaucucaagc aaucaagcau     60
ucuacuucua uugcagcaau uuaaaucauu ucuuuuaaag caaaagcaau uuucugaaaa    120
uuuucaccau uuacgaacga uagccauggg cgccauggcc ccuagaacau ugcuccugcu    180
gcuggccgcu gcccuggccc cuacacagac aagagcugga ccuggauccc accccgagcc    240
ccacaccgcc gaacugcagc ugaaccugac cgugcccaga aaggacccca cccugagaug    300
gggagcuggc ccugcucugg gcagauccuu uacacacggc cccgagcugg aagaaggcca    360
ccugagaauc caccaggacg gccuguacag acugcacauc caagugaccc uggccaacug    420
cagcagcccu ggcucuaccc ugcagcacag agccacacug gccgugggca ucuguagccc    480
ugcugcucac ggaaucagcc ugcugagagg cagauucggc caggacugua ccgugggccu    540
gcagaggcug accaucaugg ugcaauggcg acgugcugug ccaaccacug acacugccucu    600 gcugcccagc agaaacgccg acgaaacauu cuuuggagug caguggauuu guccuggcgg    660
aggguccggg ggaggacacc cagaaccuca uacagcugaa cugcagcuga accugaccgu    720
gcccagaaag gacccccacc ugagauggggg agcuggccuu gcucugggca gauccuuuac    780
acacggcccc gagcuggaag aaggccaccu gagaauccac caggacggcc uguacagacu    840
gcacauccaa gugacccugg ccaacugcag cagcccuggc ucuacccugc agcacagagc    900
cacacuggcc gugggcaucu guagcccugc ugcucacgga aucagccugc ugagaggcag    960
auucggccag gacuguaccg uggcccuga gaggcugacc uaucuggugc auggcgacgu   1020
gcugugcacc aaccugacac ugccucugcu gcccagcaga aacgccgacg aaacauucuu   1080
uggagugcag uggauuguc cuggggagg ucccggaggc ggacacccug aaccucauac   1140
agcugaacug cagcugaacc ugaccgugcc cagaaaggac cccacccuga ugggggagc   1200 uggcccugcu cugggcagau ccuuuacaca cggccccgag cuggaagaag gccaccugag   1260
```

| | |
|---|---|
| aauccaccag gacggccugu acagacugca cauccaagug acccuggcca acugcagcag | 1320 |
| cccuggcucu acccugcagc acagagccac acuggccgug ggcaucugua gcccugcugc | 1380 |
| ucacggaauc agccugcuga gaggcagauu cggccaggac uguaccgugg cccugcagag | 1440 |
| gcugaccuau cuggugcaug gcgacgcgcu gugcaccaac cugacacugc ucucgcugcc | 1500 |
| cagcagaaac gccgacgaga ccuucuucgg cguccagugg aucugccccg gaggcggugg | 1560 |
| uaguggaggu ggcggguccg guggaggugg aagcggcgac gaggaccccc agaucgccgc | 1620 |
| ccacguggug ucugaggcca acagcaacgc cgccucugug cugcagugg ccaagaaagg | 1680 |
| cuacuacacc augaaguccaaccucgugau gcuggaaaac ggcaagcagc ugaccgugaa | 1740 |
| gcgcgagggc cuguacuaug uguacaccca agugacauuc ugcagcaacc gcgagcccag | 1800 |
| cagccagagg ccuuuuaucg ugggccugug gcugaagccu agcagcggca gcgagagaau | 1860 |
| ccugcugaag gccgccaaca cccacagcag cucucagcug ugcgagcagc agucugugca | 1920 |
| ccugggaggc guguucgagc ugcaagcugg cgcuuccgug uucgugaacg ugaccgaggc | 1980 |
| cagccaagug auccacagag uggguucag cagcuuugga cugcucaaac ugggcggagg | 2040 |
| guccggcgga ggcggagaug aagauccuca gauugcugcc cacguggugu cugaggccaa | 2100 |
| cagcaacgcc gccucugugc ugcagugggc caagaaaggc uacuacacca ugaaguccaa | 2160 |
| ccucgugaug cuggaaaacg gcaagcagcu gaccgugaag cgcgagggcc uguacuaugu | 2220 |
| guacacccaa gugacauucu gcagcaaccg cgagcccagc agccagaggc uuuuaucgu | 2280 |
| gggccugugg cugaagccua gcagcggcag cgagagaauc cugcugaagg ccgccaacac | 2340 |
| ccacagcagc ucucagcugu gcgagcagca gucugugcac cugggaggcg uguucgagcu | 2400 |
| gcaagcuggc gcuuccgugu cgugaacgu gaccgaggcc agccaaguga uccacagagu | 2460 |
| gggcuucagc agcuuggac ugcucaaacu ggaggcggc uccggaggcg aggagauga | 2520 |
| agauccucag auugcugccc acguggguc ugaggccaac agcaacgccg ccucugugcu | 2580 |
| gcagugggcc aagaaaggcu acuacaccau gaaguccaac cucgugaugc uggaaaacgg | 2640 |
| caagcagcug accgugaagc gcgagggccu guacuaugug uacacccaag ugacauucug | 2700 |
| cagcaaccgc gagcccagca gccagaggcc uuuuaucgug ggccugugc ugaagccuag | 2760 |
| cagcggcagc gagagaaucc ugcugaaggc cgccaacacc cacagcagcu cucagcugug | 2820 |
| cgagcagcag ucugugcacc ugggaggcgu guucgagcug caagcuggcg cuuccguguu | 2880 |
| cgugaacgug accgaggcca gccaagugau ccacagagug ggcuucuccu ccuucggccu | 2940 |
| ccugaagcug ugacucgacg uccugguacu gcaugcacgc aaugcuagcu gccccuuucc | 3000 |
| cguccugggu accccgaguc uccccgaccu cggguccca gguaugcucc caccuccacc | 3060 |
| ugccccacuc accaccucug cuaguuccag acacccccca agcacgcagc aaugcagcuc | 3120 |
| aaaacgcuua gccuagccac accccacgg gaaacagcag ugauuaaccu uuagcaauaa | 3180 |
| acgaaaguuu aacuaagcua acuaacccc agggunguc aauucgugc cagccacacc | 3240 |
| cucgagcuag caaaaaaaaa aaaaaaaaaa aaaaaaaaaa agcauaugac uaaaaaaaaa | 3300 |
| aaaaaaaaaa aaaaaaaaaa aaaaaaaaaa aaaaaaaaaa aaaaaaaaaa aaaaaaaaaa | 3360 |
| a | 3361 |

<210> SEQ ID NO 78
<211> LENGTH: 110
<212> TYPE: RNA
<213> ORGANISM: Artificial sequence
<220> FEATURE:
<223> OTHER INFORMATION: Poly-A

<400> SEQUENCE: 78
aaaaaaaaaa aaaaaaaaaa aaaaaaaaaa gcauaugacu aaaaaaaaaa aaaaaaaaaa    60
aaaaaaaaaa aaaaaaaaaa aaaaaaaaaa aaaaaaaaaa aaaaaaaaaa              110

<210> SEQ ID NO 79
<211> LENGTH: 444
<212> TYPE: PRT
<213> ORGANISM: Artificial sequence
<220> FEATURE:
<223> OTHER INFORMATION: Anti-PD1 Mab heavy chain

<400> SEQUENCE: 79

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

```
Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440
```

<210> SEQ ID NO 80
<211> LENGTH: 214
<212> TYPE: PRT
<213> ORGANISM: Artificial sequence
<220> FEATURE:
<223> OTHER INFORMATION: Anti-PD1 Mab light chain

<400> SEQUENCE: 80

```
Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 81
<211> LENGTH: 8
<212> TYPE: PRT
<213> ORGANISM: Artificial sequence

```
<220> FEATURE:
<223> OTHER INFORMATION: HCDR1

<400> SEQUENCE: 81

Gly Phe Thr Phe Ser Asn Phe Gly
1               5

<210> SEQ ID NO 82
<211> LENGTH: 8
<212> TYPE: PRT
<213> ORGANISM: Artificial sequence
<220> FEATURE:
<223> OTHER INFORMATION: HCDR2

<400> SEQUENCE: 82

Ile Ser Gly Gly Gly Arg Asp Thr
1               5

<210> SEQ ID NO 83
<211> LENGTH: 10
<212> TYPE: PRT
<213> ORGANISM: Artificial sequence
<220> FEATURE:
<223> OTHER INFORMATION: HCDR3

<400> SEQUENCE: 83

Val Lys Trp Gly Asn Ile Tyr Phe Asp Tyr
1               5                   10

<210> SEQ ID NO 84
<211> LENGTH: 6
<212> TYPE: PRT
<213> ORGANISM: Artificial sequence
<220> FEATURE:
<223> OTHER INFORMATION: LCDR1

<400> SEQUENCE: 84

Leu Ser Ile Asn Thr Phe
1               5

<210> SEQ ID NO 85
<211> LENGTH: 3
<212> TYPE: PRT
<213> ORGANISM: Artificial sequence
<220> FEATURE:
<223> OTHER INFORMATION: LCDR2

<400> SEQUENCE: 85

Ala Ala Ser
1

<210> SEQ ID NO 86
<211> LENGTH: 9
<212> TYPE: PRT
<213> ORGANISM: Artificial sequence
<220> FEATURE:
<223> OTHER INFORMATION: LCDR3

<400> SEQUENCE: 86

Gln Gln Ser Ser Asn Thr Pro Phe Thr
1               5

<210> SEQ ID NO 87
<211> LENGTH: 117
<212> TYPE: PRT
<213> ORGANISM: Artificial sequence
<220> FEATURE:
```

```
<223> OTHER INFORMATION: Anti-PD1 Mab VH

<400> SEQUENCE: 87

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
                100                 105                 110

Val Thr Val Ser Ser
            115

<210> SEQ ID NO 88
<211> LENGTH: 107
<212> TYPE: PRT
<213> ORGANISM: Artificial sequence
<220> FEATURE:
<223> OTHER INFORMATION: Anti-PD1 Mab VL

<400> SEQUENCE: 88

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
            35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
                100                 105
```

THERAPEUTIC RNA

This application is a Divisional of U.S. application Ser. No. 16/552,248, filed on Aug. 27, 2019, which is a Continuation of International Application No. PCT/US2018/019878, filed on Feb. 27, 2018, which claims the benefit of priority to U.S. Provisional Application No. 62/464,981, filed Feb. 28, 2017; U.S. Provisional Application No. 62/597,527, filed Dec. 12, 2017; and European Patent Application No. 17306089.8, filed Aug. 23, 2017; all of the contents of which are incorporated by reference in their entirety.

The instant application contains a Sequence Listing which has been submitted electronically in ASCII format and is hereby incorporated by reference in its entirety. The ASCII copy, created on Apr. 23, 2021, is named 2021-04-23_01183-0001-01US-T1_sequence_listing_ST25.txt and is 159,800 bytes in size.

This disclosure relates to the field of therapeutic RNA to treat solid tumors. The National Cancer Institute defines solid tumors as abnormal masses of tissue that do not normally contain cysts or liquid areas. Solid tumors include benign and malignant (cancerous) sarcomas, carcinomas, and lymphomas, and can be physically located in any tissue or organ including the brain, ovary, breast, colon, and other tissues. Cancer is often divided into two main types: solid tumor cancer and hematological (blood) cancers. It is estimated that more than 1.5 million cases of cancer are diagnosed in the United States each year, and more than 500,000 people in the United States will die each year from cancer.

Solid tumor cancers are particularly difficult to treat. Current treatments include surgery, radiotherapy, immunotherapy and chemotherapy. Surgery alone may be an appropriate treatment for small localized tumors, but large invasive tumors and most metastatic malignancies are usually unresectable by surgery. Other common treatments such as radiotherapy and chemotherapy are associated with undesirable side effects and damage to healthy cells.

While surgery and current therapies sometimes are able to kill the bulk of the solid tumor, additional cells (including potentially cancer stem cells) may survive therapy. These cells, over time, can form a new tumor leading to cancer recurrence. In spite of multimodal conventional therapies, disease-free survival is less than 25% for many types of solid tumors. Solid tumors that are resistant to multi-modal therapy or that have recurred following therapy are even more difficult to treat, and long-term survival is less than 10%.

Disclosed herein are compositions, uses, and methods that can overcome present shortcomings in treatment of solid tumors. Administration of therapeutic RNAs disclosed herein can reduce tumor size, extend survival time, and/or protect against metastasis and/or recurrence of the tumor.

SUMMARY

Embodiment 1. A composition comprising RNA encoding an IL-12sc protein that is at least 99%, 98%, 97%, 96%, 95%, 90%, 85%, or 80% identical to the amino acids of SEQ ID NO: 14 and RNA encoding a GM-CSF protein that is at least 99%, 98%, 97%, 96%, 95%, 90%, 85%, or 80% identical to the amino acids of SEQ ID NO: 27.

Embodiment 2. The composition of embodiment 1, further comprising RNA encoding an IL-15 sushi protein that is at least 99%, 98%, 97%, 96%, 95%, 90%, 85%, or 80% identical to the amino acids of SEQ ID NO: 24.

Embodiment 3. The composition of embodiment 1, further comprising RNA encoding an IL-2 protein that is at least 99%, 98%, 97%, 96%, 95%, 90%, 85%, or 80% identical to the amino acids of SEQ ID NO: 9.

Embodiment 4. The composition of embodiment 1, further comprising RNA encoding an IFNα2b protein that is at least 99%, 98%, 97%, 96%, 95%, 90%, 85%, or 80% identical to the amino acids of SEQ ID NO: 19.

Embodiment 5. A composition comprising:
  a. RNA encoding an IL-12sc protein that is at least 99%, 98%, 97%, 96%, 95%, 90%, 85%, or 80% identical to the amino acids of SEQ ID NO: 14;
  b. RNA encoding a GM-CSF protein that is at least 99%, 98%, 97%, 96%, 95%, 90%, 85%, or 80% identical to the amino acids of SEQ ID NO: 27; and
  c. RNA encoding an IFNα2b protein that is at least 99%, 98%, 97%, 96%, 95%, 90%, 85%, or 80% identical to the amino acids of SEQ ID NO: 19.

Embodiment 6. The composition of embodiment 5, further comprising RNA encoding an IL-15sushi protein that is at least 99%, 98%, 97%, 96%, 95%, 90%, 85%, or 80% identical to the amino acids of SEQ ID NO: 24.

Embodiment 7. The composition of embodiment 5, further comprising RNA encoding an IL-2 protein that is at least 99%, 98%, 97%, 96%, 95%, 90%, 85%, or 80% identical to the amino acids of SEQ ID NO: 9.

Embodiment 8. The composition of any one of embodiments 1-7, wherein at least one RNA comprises a modified nucleobase in place of at least one uridine.

Embodiment 9. The composition of any one of embodiments 1-7, wherein each RNA comprises a modified nucleobase in place of each uridine.

Embodiment 10. The composition of any one of embodiments 8-9, wherein the modified nucleobase is pseudouridine (ψ), N1-methyl-pseudouridine (m$^1$ψ) or 5-methyl-uridine (m$^5$U).

Embodiment 11. The composition of embodiment 10, wherein the modified nucleobase is N1-methyl-pseudouridine (m$^1$ψ).

Embodiment 12. The composition of any one of embodiments 1-11, wherein at least one RNA further comprises a 5' cap.

Embodiment 13. The composition of any one of embodiments 1-11, wherein each RNA further comprises a 5' cap.

Embodiment 14. The composition of any one of embodiments 12-13, wherein the 5' cap is m$_2^{7,3'-O}$Gppp(m$_1^{2'-O}$)ApG or 3'-O-Me-m$^7$G(5')ppp(5')G.

Embodiment 15. The composition of any one of embodiments 1-14, wherein at least one RNA further comprises a 5' UTR.

Embodiment 16. The composition of any one of embodiments 1-14, wherein each RNA further comprises a 5' UTR.

Embodiment 17. The composition of any one of embodiments 15-16, wherein the 5' UTR comprises or consists of the nucleotides of SEQ ID NOs: 2, 4, or 6, or nucleotides having at least 99%, 98%, 97%, 96%, 95%, 90%, or 85% identity to SEQ ID NOs: 2, 4, or 6.

Embodiment 18. The composition of any one of embodiments 1-17, wherein at least one RNA further comprises a 3' UTR.

Embodiment 19. The composition of any one of embodiments 1-17, wherein each RNA further comprises a 3' UTR.

Embodiment 20. The composition of any one of embodiments 18-19, wherein the 3' UTR comprises or consists of the nucleotides of SEQ ID NO: 8, or nucleotides having at least 99%, 98%, 97%, 96%, 95%, 90%, or 85% identity to SEQ ID NO: 8.

Embodiment 21. The composition of any one of embodiments 1-20, wherein at least one RNA further comprises a poly-A tail.

Embodiment 22. The composition of any one of embodiments 1-20, wherein each RNA further comprises a poly-A tail.

Embodiment 23. The composition of any one of embodiments 21-22, wherein the poly-A tail comprises at least 100 nucleotides.

Embodiment 24. The composition of any one of embodiments 1-23, wherein at least one RNA comprises a 5' cap, 5' UTR, 3' UTR, and poly-A tail.

Embodiment 25. The composition of any one of embodiments 1-23, wherein each RNA comprises a 5' cap, 5' UTR, 3' UTR, and poly-A tail.

Embodiment 26. The composition of any one of embodiments 24-25, wherein
  a. the 5' cap is $m_2^{7,3'-O}Gppp(m_1^{2'-O})ApG$ or 3'-O-Me-$m^7G(5')ppp(5')G$;
  b. the 5' UTR comprises or consists of the nucleotides of SEQ ID NOs: 2, 4, or 6, or nucleotides having at least 99%, 98%, 97%, 96%, 95%, 90%, or 85% identity to SEQ ID NOs: 2, 4, or 6;
  c. the 3' UTR comprises or consists of the nucleotides of SEQ ID NO: 8, or nucleotides having at least 99%, 98%, 97%, 96%, 95%, 90%, or 85% identity to SEQ ID NO: 8; and
  d. the poly-A tail comprises at least 100 nucleotides.

Embodiment 27. A method for treating or preventing cancer, reducing the size of a tumor, preventing the reoccurrence of cancer in remission, or preventing cancer metastasis in a subject comprising administering the composition of any one of embodiments 1-26 to the subject.

Embodiment 28. A method for treating or preventing cancer, reducing the size of a tumor, preventing the reoccurrence of cancer in remission, or preventing cancer metastasis in a subject comprising administering to the subject:
  a. an RNA encoding an IL-12sc protein that is at least 99%, 98%, 97%, 96%, 95%, 90%, 85%, or 80% identical to the amino acids of SEQ ID NO: 14, and/or comprising nucleotides having at least 99%, 98%, 97%, 96%, 95%, 90%, 85%, or 80% identity to the nucleotides of SEQ ID NOs: 17 or 18; and
  b. an RNA encoding a GM-CSF protein that is at least 99%, 98%, 97%, 96%, 95%, 90%, 85%, or 80% identical to the amino acids of SEQ ID NO: 27, and/or comprising nucleotides having at least 99%, 98%, 97%, 96%, 95%, 90%, 85%, or 80% identity to the nucleotides of SEQ ID NO: 29,
thereby treating or preventing cancer, reducing the size of a tumor, preventing the reoccurrence of cancer in remission, or preventing cancer metastasis in the subject.

Embodiment 29. The method of embodiment 28, further comprising administering RNA encoding an IFNα2b protein that is at least 99%, 98%, 97%, 96%, 95%, 90%, 85%, or 80% identical to the amino acids of SEQ ID NO: 19, and/or comprising nucleotides having at least 99%, 98%, 97%, 96%, 95%, 90%, 85%, or 80% identity to the nucleotides of SEQ ID NOs: 22 or 23.

Embodiment 30. The method of embodiment 28, further comprising administering RNA encoding an IL-15 sushi protein that is at least 99%, 98%, 97%, 96%, 95%, 90%, 85%, or 80% identical to the amino acids of SEQ ID NO: 24, and/or comprising nucleotides having at least 99%, 98%, 97%, 96%, 95%, 90%, 85%, or 80% identity to the nucleotides of SEQ ID NO: 26.

Embodiment 31. The method of embodiment 28, further comprising administering RNA encoding an IL-2 protein that is at least 99%, 98%, 97%, 96%, 95%, 90%, 85%, or 80% identical to the amino acids of SEQ ID NO: 9, and/or comprising nucleotides having at least 99%, 98%, 97%, 96%, 95%, 90%, 85%, or 80% identity to the nucleotides of SEQ ID NOs: 12 or 13.

Embodiment 32. The method of embodiment 28, further comprising administering RNA encoding
  a. an IL-15 sushi protein that is at least 99%, 98%, 97%, 96%, 95%, 90%, 85%, or 80% identical to the amino acids of SEQ ID NO: 24, and/or comprising nucleotides having at least 99%, 98%, 97%, 96%, 95%, 90%, 85%, or 80% identity to the nucleotides of SEQ ID NO: 26; and
  b. an IFNα2b protein that is at least 99%, 98%, 97%, 96%, 95%, 90%, 85%, or 80% identical to the amino acids of SEQ ID NO: 19, and/or comprising nucleotides having at least 99%, 98%, 97%, 96%, 95%, 90%, 85%, or 80% identity to the nucleotides of SEQ ID NOs: 22 or 23.

Embodiment 33. The method of embodiment 28, further comprising administering RNA encoding
  a. an IL-2 protein that is at least 99%, 98%, 97%, 96%, 95%, 90%, 85%, or 80% identical to the amino acids of SEQ ID NO: 9, and/or comprising nucleotides having at least 99%, 98%, 97%, 96%, 95%, 90%, 85%, or 80% identity to the nucleotides of SEQ ID NOs: 12 or 13; and
  b. an IFNα2b protein that is at least 99%, 98%, 97%, 96%, 95%, 90%, 85%, or 80% identical to the amino acids of SEQ ID NO: 19, and/or comprising nucleotides having at least 99%, 98%, 97%, 96%, 95%, 90%, 85%, or 80% identity to the nucleotides of SEQ ID NOs: 22 or 23.

Embodiment 34. The method of any one of embodiments 27-33, wherein the cancer is a sarcoma, carcinoma, or lymphoma.

Embodiment 35. The method of any one of embodiments 27-33, wherein the cancer is a solid tumor.

Embodiment 36. The method of embodiment 35, wherein the solid tumor is in the lung, colon, ovary, cervix, uterus, peritoneum, testicles, penis, tongue, lymph node, pancreas bone, breast, prostate, soft tissue, connective tissue, kidney, liver, brain, thyroid, or skin.

Embodiment 37. The method of embodiment 35, wherein the solid tumor is an epithelial tumor, Hodgkin lymphoma (HL), non-Hodgkin lymphoma, prostate tumor, ovarian tumor, renal cell tumor, gastrointestinal tract tumor, hepatic tumor, colorectal tumor, tumor with vasculature, mesothelioma tumor, pancreatic tumor, breast tumor, sarcoma tumor, lung tumor, colon tumor, brain tumor, melanoma tumor, small cell lung tumor, neuroblastoma, testicular tumor, carcinoma, adenocarcinoma, glioma tumor, seminoma tumor, retinoblastoma, or osteosarcoma tumor.

Embodiment 38. The method of any one of embodiments 27-37, wherein the composition is administered intratumorally or peri-tumorally.

Embodiment 39. The method of embodiment 38, wherein the injected tumor and a non-injected tumor are both reduced in size after intra- or peri-tumoral injection into or near the first tumor.

Embodiment 40. The method of any one of embodiments 27-39, wherein the subject is human.

Embodiment 41. The method of any one of embodiments 27-40, wherein another therapy is also administered.

Embodiment 42. The method of embodiment 41, wherein the other therapy is surgery to excise, resect, or debulk the tumor.

Embodiment 43. The method of embodiment 41, wherein the other therapy is immunotherapy, radiotherapy or chemotherapy.

Embodiment 44. The method of any one of embodiments 27-43, wherein at least one RNA comprises a modified nucleobase in place of at least one uridine.

Embodiment 45. The method of any one of embodiments 27-43, wherein each RNA comprises a modified nucleobase in place of each uridine.

Embodiment 46. The method of any one of embodiments 44-45, wherein the modified nucleobase is pseudouridine ($\psi$), N1-methyl-pseudouridine ($m^1\psi$), or 5-methyl-uridine ($m^5U$).

Embodiment 47. The method of embodiment 46, wherein the modified nucleobase is N1-methyl-pseudouridine ($m^1\psi$).

Embodiment 48. The method of any one of embodiments 27-47, wherein at least one RNA further comprises a 5' cap.

Embodiment 49. The method of any one of embodiments 27-47, wherein each RNA further comprises a 5' cap.

Embodiment 50. The method of any one of embodiments 48-49, wherein the 5' cap is $m_2^{7,3'-O}Gppp(m_1^{2'-O})ApG$ or 3'-O-Me-$m^7G(5')ppp(5')G$.

Embodiment 51. The method of any one of embodiments 27-50, wherein at least one RNA further comprises a 5' UTR.

Embodiment 52. The method of any one of embodiments 27-50, wherein each RNA further comprises a 5' UTR.

Embodiment 53. The method of any one of embodiments 51-52, wherein the 5' UTR comprises or consists of the nucleotides of SEQ ID NOs: 2, 4, or 6, or nucleotides having at least 99%, 98%, 97%, 96%, 95%, 90%, or 85% identity to SEQ ID NOs: 2, 4, or 6.

Embodiment 54. The method of any one of embodiments 27-54, wherein at least one RNA further comprises a 3' UTR.

Embodiment 55. The method of any one of embodiments 27-54, wherein each RNA further comprises a 3' UTR.

Embodiment 56. The method of any one of embodiments 54-55, wherein the 3' UTR comprises or consists of the nucleotides of SEQ ID NO: 8, or nucleotides having at least 99%, 98%, 97%, 96%, 95%, 90%, or 85% identity to SEQ ID NO: 8.

Embodiment 57. The method of any one of embodiments 27-56, wherein at least one RNA further comprises a poly-A tail.

Embodiment 58. The method of any one of embodiments 27-56, wherein each RNA further comprises a poly-A tail.

Embodiment 59. The method of any one of embodiments 57-58, wherein the poly-A tail comprises at least 100 nucleotides.

Embodiment 60. The method of any one of embodiments 27-59, wherein at least one RNA comprises a 5' cap, 5' UTR, 3' UTR, and poly-A tail.

Embodiment 61. The method of any one of embodiments 27-59, wherein each RNA comprises a 5' cap, 5' UTR, 3' UTR, and poly-A tail.

Embodiment 62. The method of any one of embodiments 60-61, wherein
a. the 5' cap is $m_2^{7,3'-O}Gppp(m_1^{2'-O})ApG$ or 3'-O-Me-$m^7G(5')ppp(5')G$;
b. the 5' UTR comprises or consists of the nucleotides of SEQ ID NOs: 2, 4, or 6, or nucleotides having at least 99%, 98%, 97%, 96%, 95%, 90%, or 85% identity to SEQ ID NOs: 2, 4, or 6;
c. the 3' UTR comprises or consists of the nucleotides of SEQ ID NO: 8, or nucleotides having at least 99%, 98%, 97%, 96%, 95%, 90%, or 85% identity to SEQ ID NO: 8; and
d. the poly-A tail comprises at least 100 nucleotides.

Embodiment 63. A codon-optimized DNA comprising or consisting of contiguous nucleotides having at least 83% identity to SEQ ID NO: 11.

Embodiment 64. The DNA of embodiment 63, comprising or consisting of contiguous nucleotides having at least 99%, 98%, 97%, 96%, 95%, 90%, or 85% identity to SEQ ID NO: 11.

Embodiment 65. A codon-optimized RNA comprising or consisting of contiguous nucleotides having at least 83% identity to SEQ ID NO: 13.

Embodiment 66. The RNA of embodiment 65, comprising or consisting of contiguous nucleotides having at least 99%, 98%, 97%, 96%, 95%, 90%, or 85% identity to SEQ ID NO: 13.

Embodiment 67. An RNA produced from the DNA of any one of embodiments 63 or 64.

Embodiment 68. A codon-optimized DNA comprising or consisting of:
a. contiguous nucleotides having at least 78% identity to nucleotides 1-984 of SEQ ID NO: 16;
b. contiguous nucleotides having at least 81% identity to nucleotides 1027-1623 of SEQ ID NO: 16; and
c. nucleotides encoding a linker between the nucleotides of a) and b).

Embodiment 69. The DNA of embodiment 68, wherein the linker comprises nucleotides 985-1026 of SEQ ID NO: 16.

Embodiment 70. The DNA of any one of embodiments 68 and 69, wherein part a) comprises contiguous nucleotides having at least 99%, 98%, 97%, 96%, 95%, 90%, 85%, 80%, or 75% identity to nucleotides 1-984 of SEQ ID NO: 16; and part b) comprises contiguous nucleotides having at least 99%, 98%, 97%, 96%, 95%, 90%, or 85% identity to nucleotides 1027-1623 of SEQ ID NO: 16.

Embodiment 71. A codon-optimized RNA comprising or consisting of:
a. contiguous nucleotides having at least 78% identity to nucleotides 1-984 of SEQ ID NO: 18;
b. contiguous nucleotides having at least 81% identity to nucleotides 1027-1623 of SEQ ID NO: 18; and
c. nucleotides encoding a linker between the nucleotides of a) and b).

Embodiment 72. The RNA of embodiment 71, wherein the linker comprises nucleotides 985-1026 of SEQ ID NO: 18.

Embodiment 73. The RNA of any one of embodiments 71 and 72, wherein part a) comprises contiguous nucleotides having at least 99%, 98%, 97%, 96%, 95%, 90%, 85%, 80%, or 75% identity to nucleotides 1-984 of SEQ ID NO: 18; and part b) comprises contiguous nucleotides having at least 99%, 98%, 97%, 96%, 95%, 90%, or 85% identity to nucleotides 1027-1623 of SEQ ID NO: 18.

Embodiment 74. An RNA produced from the DNA of any one of embodiments 68-70.

Embodiment 75. A codon-optimized DNA comprising or consisting of contiguous nucleotides having at least 80% identity to SEQ ID NO: 21.

Embodiment 76. The DNA of embodiment 75, comprising or consisting of contiguous nucleotides having at least 99%, 98%, 97%, 96%, 95%, 90%, or 85% identity to SEQ ID NO: 21.

Embodiment 77. A codon-optimized RNA comprising or consisting of contiguous nucleotides having at least 80% identity to SEQ ID NO: 23.

Embodiment 78. The RNA of embodiment 77, comprising or consisting of contiguous nucleotides having at least 99%, 98%, 97%, 96%, 95%, 90%, or 85% identity to SEQ ID NO: 23.

Embodiment 79. An RNA produced from the DNA of any one of embodiments 75-76.

Embodiment 80. A DNA comprising or consisting of:
  a. contiguous nucleotides comprising or consisting of contiguous nucleotides having at least 99%, 98%, 97%, 96%, 95%, 90%, or 85% identity to nucleotides 1-321 of SEQ ID NO: 25;
  b. contiguous nucleotides comprising or consisting of contiguous nucleotides having at least 99%, 98%, 97%, 96%, 95%, 90%, or 85% identity to nucleotides 382-729 of SEQ ID NO: 25; and
  c. nucleotides encoding a linker between the nucleotides of a) and b).

Embodiment 81. An RNA produced from the DNA of embodiment 80.

Embodiment 82. A RNA comprising or consisting of:
  a. contiguous nucleotides comprising or consisting of contiguous nucleotides having at least 99%, 98%, 97%, 96%, 95%, 90%, or 85% identity to nucleotides 1-321 of SEQ ID NO: 26;
  b. contiguous nucleotides comprising or consisting of contiguous nucleotides having at least 99%, 98%, 97%, 96%, 95%, 90%, or 85% identity to nucleotides 382-729 of SEQ ID NO: 26; and
  c. nucleotides encoding a linker between the nucleotides of a) and b).

Embodiment 83. A DNA comprising or consisting of contiguous nucleotides having at least 99%, 98%, 97%, 96%, 95%, 90%, or 85% identity to SEQ ID NO: 28.

Embodiment 84. An RNA produced from the DNA of embodiment 83.

Embodiment 85. An RNA comprising or consisting of contiguous nucleotides having at least 99%, 98%, 97%, 96%, 95%, 90%, or 85% identity to SEQ ID NO: 29.

Embodiment 86. The RNA of any one of embodiments 67, 74, 79, 81, and 84 wherein the RNA is transcribed from the DNA in vitro.

Embodiment 87. The RNA of any one of embodiments 65-67, 71-74, 78-79, 81-82, and 84-85, wherein at least one uridine is replaced with a modified nucleobase.

Embodiment 88. The RNA of any one of embodiments 65-67, 71-74, 78-79, 81-82, and 84-85, wherein each uridine is replaced with a modified nucleobase.

Embodiment 89. The RNA of embodiment 87 or 88, wherein the modified nucleobase is pseudouridine ($\psi$), N1-methyl-pseudouridine ($m^1\psi$), or 5-methyl-uridine ($m^5U$).

Embodiment 90. The RNA of embodiment 89, wherein the modified nucleobase is N1-methyl-pseudouridine ($m^1\psi$).

Embodiment 91. The RNA of any one of embodiments 65-67, 71-74, 78-79, 81-82, and 84-90, further comprising a 5' cap.

Embodiment 92. The RNA of embodiment 91, wherein the 5' cap is $m_2^{7,3'-O}Gppp(m_1^{2'-O})ApG$ or 3'-O-Me-$m^7G(5')ppp(5')G$.

Embodiment 93. The RNA of any one of embodiments 65-67, 71-74, 78-79, 81-82, and 84-92, further comprising a 5' UTR.

Embodiment 94. The RNA of embodiment 93, wherein the 5' UTR comprises or consists of the nucleotides of SEQ ID NOs: 2, 4, or 6, or nucleotides having at least 99%, 98%, 97%, 96%, 95%, 90%, or 85% identity to SEQ ID NOs: 2, 4, or 6.

Embodiment 95. The RNA of any one of embodiments 65-67, 71-74, 78-79, 81-82, and 84-94, further comprising a 3' UTR.

Embodiment 96. The RNA of embodiment 95, wherein the 3' UTR comprises or consists of the nucleotides of SEQ ID NO: 8, or nucleotides having at least 99%, 98%, 97%, 96%, 95%, 90%, or 85% identity to SEQ ID NO: 8.

Embodiment 97. The RNA of any one of embodiments 65-67, 71-74, 78-79, 81-82, and 84-96, further comprising a poly-A tail.

Embodiment 98. The RNA of embodiment 97, wherein the poly-A tail comprises at least 100 nucleotides.

Embodiment 99. The RNA of any one of embodiments 65-67, 71-74, 78-79, 81-82, and 84-97, further comprising a 5' cap, 5' UTR, 3' UTR, and poly-A tail.

Embodiment 100. The RNA of embodiment 99, wherein
  a. the 5' cap is $m_2^{7,3'-O}Gppp(m_1^{2'-O})ApG$ or 3'-O-Me-$m^7G(5')ppp(5')G$;
  b. the 5' UTR comprises or consists of the nucleotides of SEQ ID NOs: 2, 4, or 6, or nucleotides having at least 99%, 98%, 97%, 96%, 95%, 90%, or 85% identity to SEQ ID NOs: 2, 4, or 6;
  c. the 3' UTR comprises or consists of the nucleotides of SEQ ID NO: 8, or nucleotides having at least 99%, 98%, 97%, 96%, 95%, 90%, or 85% identity to SEQ ID NO: 8 and;
  d. the poly-A tail comprises at least 100 nucleotides.

Embodiment 101. A DNA comprising or consisting of:
  a. contiguous nucleotides comprising or consisting of nucleotides having at least 99%, 98%, 97%, 96%, 95%, 90%, 85% or 83% identity to SEQ ID NO: 11; and
  b. contiguous nucleotides comprising or consisting of nucleotides having at least 99%, 98%, 97%, 96%, 95%, 90%, 85% or 80% identity to SEQ ID NOs: 1, 3, or 5, wherein when transcribed, the nucleotides of parts a) and b) form a single transcript.

Embodiment 102. A DNA comprising or consisting of:
  a. contiguous nucleotides comprising or consisting of nucleotides having at least 99%, 98%, 97%, 96%, 95%, 90%, 85%, 80% or 78% identity to nucleotides 1-984 of SEQ ID NO: 16;
  b. contiguous nucleotides comprising or consisting of nucleotides having at least 99%, 98%, 97%, 96%, 95%, 90%, 85%, 80% or 81% identity to nucleotides 1027-1623 of SEQ ID NO: 16; and
  c. contiguous nucleotides comprising or consisting of nucleotides having at least 99%, 98%, 97%, 96%, 95%, 90%, 85% or 80% identity to SEQ ID NOs: 1, 3, or 5, wherein when transcribed, the nucleotides of part a), b) and c) form a single transcript.

Embodiment 103. A DNA comprising or consisting of:
  a. contiguous nucleotides comprising or consisting of nucleotides having at least 99%, 98%, 97%, 96%, 95%, 90%, 85% or 80% identity to SEQ ID NO: 21; and
  b. contiguous nucleotides comprising or consisting of nucleotides having at least 99%, 98%, 97%, 96%, 95%, 90%, 85% or 80% identity to SEQ ID NOs: 1, 3, or 5, wherein when transcribed, the nucleotides of part a) and b) form a single transcript.

Embodiment 104. A DNA comprising or consisting of:
  a. contiguous nucleotides comprising or consisting of nucleotides having at least 99%, 98%, 97%, 96%, 95%, 90%, 85% or 80% identity to SEQ ID NO: 28; and
  b. contiguous nucleotides comprising or consisting of nucleotides having at least 99%, 98%, 97%, 96%, 95%, 90%, 85% or 80% identity to SEQ ID NOs: 1, 3, or 5, wherein when transcribed, the nucleotides of part a) and b) form a single transcript.

Embodiment 105. A DNA comprising or consisting of:
  a. contiguous nucleotides comprising or consisting of nucleotides having at least 99%, 98%, 97%, 96%, 95%, 90%, 85% or 80% identity to nucleotides 1-321 of SEQ ID NO: 25;
  b. contiguous nucleotides comprising or consisting of nucleotides having at least 99%, 98%, 97%, 96%, 95%, 90%, 85% or 80% identity to nucleotides 382-729 of SEQ ID NO: 25; and
  c. contiguous nucleotides having at least 80% identity to SEQ ID NOs: 1, 3, or 5, wherein when transcribed, the nucleotides of part a), b), and c) form a single transcript.

Embodiment 106. A DNA comprising or consisting of:
  a. contiguous nucleotides comprising or consisting of nucleotides having at least 99%, 98%, 97%, 96%, 95%, 90%, 85% or 83% identity to SEQ ID NO: 11; and
  b. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a) and b) form a single transcript.

Embodiment 107. A DNA comprising or consisting of:
  a. contiguous nucleotides comprising or consisting of nucleotides having at least 99%, 98%, 97%, 96%, 95%, 90%, 85%, 80% or 78% identity to nucleotides 1-984 of SEQ ID NO: 16;
  b. contiguous nucleotides comprising or consisting of nucleotides having at least 99%, 98%, 97%, 96%, 95%, 90%, 85%, 80% or 81% identity to nucleotides 1027-1623 of SEQ ID NO: 16; and
  c. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b) and c) form a single transcript.

Embodiment 108. A DNA comprising or consisting of:
  a. contiguous nucleotides comprising or consisting of nucleotides having at least 99%, 98%, 97%, 96%, 95%, 90%, 85% or 80% identity to SEQ ID NO: 21; and
  b. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a) and b) form a single transcript.

Embodiment 109. A DNA comprising or consisting of:
  a. contiguous nucleotides comprising or consisting of nucleotides having at least 99%, 98%, 97%, 96%, 95%, 90%, 85% or 80% identity to SEQ ID NO: 28; and
  b. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a) and b) form a single transcript.

Embodiment 110. A DNA comprising or consisting of:
  a. contiguous nucleotides comprising or consisting of nucleotides having at least 99%, 98%, 97%, 96%, 95%, 90%, 85% or 80% identity to nucleotides 1-321 of SEQ ID NO: 25;
  b. contiguous nucleotides comprising or consisting of nucleotides having at least 99%, 98%, 97%, 96%, 95%, 90%, 85% or 80% identity to nucleotides 382-729 of SEQ ID NO: 25; and
  c. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b), and c) form a single transcript.

Embodiment 111. A DNA comprising or consisting of:
  a. contiguous nucleotides comprising or consisting of nucleotides having at least 99%, 98%, 97%, 96%, 95%, 90%, 85% or 83% identity to SEQ ID NO: 11;
  b. contiguous nucleotides comprising or consisting of nucleotides having at least 99%, 98%, 97%, 96%, 95%, 90%, 85% or 80% identity to SEQ ID NOs: 1, 3, or 5; and
  c. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b), and c) form a single transcript.

Embodiment 112. A DNA comprising or consisting of:
  a. contiguous nucleotides comprising or consisting of nucleotides having at least 99%, 98%, 97%, 96%, 95%, 90%, 85%, 80% or 78% identity to nucleotides 1-984 of SEQ ID NO: 16;
  b. contiguous nucleotides comprising or consisting of nucleotides having at least 99%, 98%, 97%, 96%, 95%, 90%, 85%, 80% or 81% identity to nucleotides 1027-1623 of SEQ ID NO: 16;
  c. contiguous nucleotides comprising or consisting of nucleotides having at least 99%, 98%, 97%, 96%, 95%, 90%, 85% or 80% identity to SEQ ID NOs: 1, 3, or 5; and
  d. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b), c), and d) form a single transcript.

Embodiment 113. A DNA comprising or consisting of:
  a. contiguous nucleotides comprising or consisting of nucleotides having at least 99%, 98%, 97%, 96%, 95%, 90%, 85% or 80% identity to SEQ ID NO: 21;
  b. contiguous nucleotides comprising or consisting of nucleotides having at least 99%, 98%, 97%, 96%, 95%, 90%, 85% or 80% identity to SEQ ID NOs: 1, 3, or 5, wherein the nucleotides of part b) regulate the expression of the nucleotides of part a); and
  c. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b) and c) form a single transcript.

Embodiment 114. A DNA comprising or consisting of:
a. contiguous nucleotides comprising or consisting of nucleotides having at least 99%, 98%, 97%, 96%, 95%, 90%, 85% or 80% identity to SEQ ID NO: 28;
b. contiguous nucleotides comprising or consisting of nucleotides having at least 99%, 98%, 97%, 96%, 95%, 90%, 85% or 80% identity to SEQ ID NOs: 1, 3, or 5; and
c. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b), and c) form a single transcript.

Embodiment 115. A DNA comprising or consisting of:
a. contiguous nucleotides comprising or consisting of nucleotides having at least 99%, 98%, 97%, 96%, 95%, 90%, 85% or 80% identity to nucleotides 1-321 of SEQ ID NO: 25;
b. contiguous nucleotides comprising or consisting of nucleotides having at least 99%, 98%, 97%, 96%, 95%, 90%, 85% or 80% identity to nucleotides 382-729 of SEQ ID NO: 25;
c. contiguous nucleotides comprising or consisting of nucleotides having at least 99%, 98%, 97%, 96%, 95%, 90%, 85% or 80% identity to SEQ ID NOs: 1, 3, or 5; and
d. contiguous nucleotides comprising or consisting of nucleotides having at least 99%, 98%, 97%, 96%, 95%, 90%, 85% or 80% identity to SEQ ID NO: 7, wherein when transcribed, the nucleotides of part a), b), c), and d) form a single transcript.

Embodiment 116. An RNA produced from any one of the DNAs of embodiments 101-115.

Embodiment 117. The RNA of embodiment 116, wherein at least one uridine is replaced with a modified nucleobase.

Embodiment 118. The RNA of embodiment 116, wherein each uridine is replaced with a modified nucleobase.

Embodiment 119. The RNA of any one of embodiments 117-118, wherein the modified nucleobase is pseudouridine ($\psi$), N1-methyl-pseudouridine ($m^1\psi$), or 5-methyl-uridine ($m^5U$).

Embodiment 120. The RNA of embodiment 119, wherein the modified nucleobase is N1-methyl-pseudouridine ($m^1\psi$).

Embodiment 121. The RNA of any one of embodiments 116-120, wherein the RNA further comprises a 5' cap.

Embodiment 122. The RNA of embodiment 121, wherein the 5' cap is $m_2^{7,3'-O}Gppp(m_1^{2'-O})ApG$ or 3'-O-Me-$m^7G(5')ppp(5')G$.

Embodiment 123. The RNA of any of embodiments 116-122, wherein the RNA is substantially free of double-stranded RNA.

Embodiment 124. The RNA of any of embodiments 116-122, wherein double stranded RNA has been removed from the RNA.

Embodiment 125. The RNA of any one of embodiments 123-124, wherein the RNA has been purified via HPLC or cellulose-based chromatography.

Embodiment 126. A pharmaceutical formulation comprising any one of the DNA or RNAs of embodiments 63-125 and a pharmaceutically acceptable excipient.

Embodiment 127. A method for treating or preventing cancer, reducing the size of a tumor, preventing the reoccurrence of cancer in remission, or preventing cancer metastasis in a subject comprising administering any one or more of the RNAs or DNAs of embodiments 63-125, or the pharmaceutical formulation of embodiment 126.

Embodiment 128. A method of producing a polypeptide encoding IL-2, IL-12sc, IL-15 sushi, GM-CSF and IFNα2b in vivo comprising administering to a subject one or more of the DNAs or RNAs of any one of embodiment 63-125, the composition of any one of embodiments 1-26, or the pharmaceutical formulation of embodiment 126.

Embodiment 129. A composition comprising at least two RNAs, wherein the RNAs encode different proteins, and wherein the RNAs are selected from the RNAs of any one of embodiments 65-67, 71-74, 78-79, 81-82, 84-100, and 116-125.

Embodiment 130. The composition of embodiment 129, wherein the composition comprises two RNAs encoding GM-CSF and IL-12sc.

Embodiment 131. The composition of embodiment 129, wherein the composition comprises three RNAs encoding GM-CSF, IL-12sc, and IFNα2b.

Embodiment 132. The composition of embodiment 129, wherein the composition comprises three RNAs encoding GM-CSF, IL-2, and IFNα2b.

Embodiment 133. The composition of embodiment 129, wherein the composition comprises four RNAs encoding GM-CSF, IL-12sc, IL-2 and IFNα2b.

Embodiment 134. The composition of embodiment 129, wherein the composition comprises four RNAs encoding GM-CSF, IL-12sc, IL-15 sushi and IFNα2b.

Embodiment 135. The composition of any one of embodiments 130-134, wherein the RNA encoding GM-CSF is selected from the RNA of any one of embodiments 84-85.

Embodiment 136. The composition of any one of embodiments 130-134, wherein the RNA encoding IL-12sc is selected from the RNA of any one of embodiments 71-74.

Embodiment 137. The composition of any one of embodiments 131-134, wherein the RNA encoding IFNα2b is selected from the RNA of any one of embodiments 77-79.

Embodiment 138. The composition of embodiment 134, wherein the RNA encoding IL-15 sushi is selected from the RNA of any one of embodiments 81-82.

Embodiment 139. The composition of any one of embodiments 132-133, wherein the RNA encoding IL-2 is selected from the RNA of any one of embodiments 65-67.

Embodiment 140. A method of treating or preventing solid tumor cancer comprising administering a therapeutically effective amount of each of the following RNAs directly into a tumor:
a. an RNA comprising an RNA encoding IL-12sc (SEQ ID NOs: 17 or 18);
b. an RNA comprising an RNA encoding GM-CSF (SEQ ID NO: 29); and
c. an RNA comprising an RNA encoding IFNα2b (SEQ ID NOs: 22 or 23), wherein each RNA comprises a modified nucleobase in place of each uridine, and wherein each RNA comprises a 5' UTR (SEQ ID NOs: 2, 4, or 6), a 3' UTR (SEQ ID NO: 8), a 5' cap, and a poly-A tail.

Embodiment 141. A method of treating or preventing solid tumor cancer comprising administering a therapeutically effective amount of each of the following RNAs directly into a tumor:
a. an RNA comprising an RNA encoding IL-12sc (SEQ ID NOs: 17 or 18);
b. an RNA comprising an RNA encoding GM-CSF (SEQ ID NO: 29);
c. an RNA comprising an RNA encoding IFNα2b (SEQ ID NOs: 22 or 23); and
d. an RNA comprising an RNA encoding IL-2 (SEQ ID NOs: 12 or 13), wherein each RNA comprises a modified nucleobase in place of each uridine, and wherein each RNA comprises a 5' UTR (SEQ ID NOs: 2, 4, or 6), a 3' UTR (SEQ ID NO: 8), a 5' cap, and a poly-A tail.

Embodiment 142. A method of treating or preventing solid tumor cancer comprising administering a therapeutically effective amount of each of the following RNAs directly into a tumor:
a. an RNA comprising an RNA encoding IL-12sc (SEQ ID NOs: 17 or 18);
b. an RNA comprising an RNA encoding GM-CSF (SEQ ID NO: 29);
c. an RNA comprising an RNA encoding IFNα2b (SEQ ID NOs: 22 or 23); and
d. an RNA comprising an RNA encoding IL-15 sushi (SEQ ID NO: 26), wherein each RNA comprises a modified nucleobase in place of each uridine, and wherein each RNA comprises a 5' UTR (SEQ ID NOs: 2, 4, or 6), a 3' UTR (SEQ ID NO: 8), a 5' cap, and a poly-A tail.

Embodiment 143. A composition comprising an RNA encoding an IL-2 protein having at least 95% identity to the amino acids of SEQ ID NO: 9, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 144. A composition comprising an RNA encoding an IL-12sc protein having at least 95% identity to the amino acids of SEQ ID NO: 14, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 145. A composition comprising an RNA encoding a GM-CSF protein having at least 95% identity to the amino acids of SEQ ID NO: 27, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 146. A composition comprising an RNA encoding an IFNα2b protein having at least 95% identity to the amino acids of SEQ ID NO: 19, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 147. A composition comprising an RNA encoding an IL-15 sushi protein having at least 95% identity to the amino acids of SEQ ID NO: 24, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 148. An IL-12sc RNA composition comprising or consisting of nucleotides having at least 95% identity to SEQ ID NOs: 17 or 18, wherein each uridine is replaced with a modified nucleobase and further comprising a 5' UTR (SEQ ID NOs: 2, 4, or 6), a 3' UTR (SEQ ID NO: 8), a 5' cap, and a poly-A tail.

Embodiment 149. A GM-CSF RNA composition comprising or consisting of nucleotides having at least 95% identity to SEQ ID NO: 29, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 150. An IFNα2b RNA composition comprising or consisting of nucleotides having at least 95% identity to SEQ ID NOs: 22 or 23, wherein each uridine is replaced with a uridine analog, and further comprising a 5' UTR (SEQ ID NOs: 2, 4, or 6), a 3' UTR (SEQ ID NO: 8), a 5' cap, and a poly-A tail.

Embodiment 151. An IL-15 sushi RNA composition comprising or consisting of nucleotides having at least 95% identity to SEQ ID NO: 26, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 152. An IL-2 RNA composition comprising or consisting of nucleotides having at least 95% identity to SEQ ID NOs: 12 or 13, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 153. An IL-12sc RNA composition comprising or consisting of the nucleotides of SEQ ID NOs: 17 or 18, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 154. A GM-CSF RNA composition comprising or consisting of the nucleotides of SEQ ID NO: 29, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 155. An IFNα2b RNA composition comprising or consisting of the nucleotides of SEQ ID NOs: 22 or 23, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 156. An IL-15 sushi RNA composition comprising or consisting of the nucleotides of SEQ ID NO: 26, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 157. An IL-2 RNA composition comprising or consisting of the nucleotides of SEQ ID NOs: 12 or 13, wherein each uridine is replaced with a modified nucleobase, and further comprising a 5' UTR (SEQ ID NOs: 2, 4, or 6), a 3' UTR (SEQ ID NO: 8), a 5' cap, and a poly-A tail.

Embodiment 158. The composition of any of embodiments 143-157, wherein the modified nucleobase is pseudouridine (ψ), N1-methyl-pseudouridine ($m^1\psi$), or 5-methyl-uridine ($m^5U$).

Embodiment 159. A composition comprising an RNA encoding IFNα2b, wherein the RNA is altered to have reduced immunogenicity as compared to un-altered RNA.

Embodiment 160. The composition of embodiment 159, wherein the alteration comprises substitution of at least one uridine with a modified nucleobase.

Embodiment 161. The composition of embodiment 159, wherein the modified nucleobase is pseudouridine (ψ), N1-methyl-pseudouridine (m¹ψ), or 5-methyl-uridine (m⁵U).

Embodiment 162. The composition of embodiment 161, wherein the modified nucleobase is N1-methyl-pseudouridine (m¹ψ).

Embodiment 163. The composition of any one of embodiments 159-162, wherein the alteration comprises a reduction in the amount of double-stranded RNA.

Embodiment 164. The composition of embodiment 163, wherein the reduction in double-stranded RNA is the result of purification via HPLC or cellulose-based chromatography.

Embodiment 165. The composition of any one of embodiments 159-164, wherein the alteration reduces RNA recognition by an innate immune system as compared to un-altered RNA.

Embodiment 166. The composition of any one of embodiments 159-165, wherein the alteration comprises addition of a 5' cap to the RNA.

Embodiment 167. The composition of embodiment 166, wherein the 5' cap is $m_2^{7,3'-O}Gppp(m_1^{2'-O})ApG$ or 3'-O-Me-m⁷G(5')ppp(5')G.

Embodiment 168. The composition of any one of embodiments 159-167, further comprising a second RNA encoding a peptide or protein of interest.

Embodiment 169. The composition of embodiment 168, wherein the peptide or protein of interest is a peptide or protein selected or derived from cytokines, chemokines, suicide gene products, immunogenic proteins or peptides, apoptosis inducers, angiogenesis inhibitors, heat shock proteins, tumor antigens, β-catenin inhibitors, activators of the STING pathway, activators of the retinoic inducible gene (RIG)-I pathway, agonists of toll-like receptor (TLR) pathways, checkpoint modulators, innate immune activators, antibodies, dominant negative receptors and decoy receptors, inhibitors of myeloid derived suppressor cells (MDSCs), IDO pathway inhibitors, and proteins or peptides that bind inhibitors of apoptosis.

Embodiment 170. The composition of embodiment 168 or 169, wherein the second RNA is altered to have reduced immunogenicity as compared to un-altered RNA.

Embodiment 171. The composition of embodiment 170, wherein the alteration comprises substitution of at least one uridine with a modified nucleobase.

Embodiment 172. The composition of embodiment 171, wherein the modified nucleobase is pseudouridine (ψ), N1-methyl-pseudouridine (m¹ψ) or 5-methyl-uridine (m⁵U).

Embodiment 173. The composition of embodiment 172, wherein the modified nucleobase is N1-methyl-pseudouridine (m¹ψ).

Embodiment 174. The composition of any one of embodiments 168-173, wherein the alteration comprises a reduction in the amount of double-stranded RNA.

Embodiment 175. The composition of embodiment 174, wherein the reduction in double-stranded RNA is the result of purification via HPLC or cellulose-based chromatography.

Embodiment 176. The composition of any one of embodiments 168-173, wherein the alteration comprises addition of a 5' cap to the RNA.

Embodiment 177. The composition of embodiment 176, wherein the 5' cap is $m_2^{7,3'-O}Gppp(m_1^{2'-O})ApG$ or 3'-O-Me-m⁷G(5')ppp(5')G.

Embodiment 178. The composition of any one of embodiments 168-177, wherein the second RNA comprises:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29;
c. an RNA encoding an IL-15 sushi protein having at least 95% identity to the amino acid sequence of SEQ ID NO: 24, and/or comprising nucleotides having at least 95% identity to the nucleotides of SEQ ID NO: 26; or
d. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 179. A method for treating or preventing cancer, reducing the size of a tumor, preventing the reoccurrence of cancer in remission, or preventing cancer metastasis in a subject comprising administering any one of the compositions of embodiments 159-178.

Embodiment 180. The composition of any one of embodiments 159-178 for use in a method of treating or preventing cancer, reducing the size of a tumor, preventing the reoccurrence of cancer in remission, or preventing cancer metastasis.

Embodiment 181. A composition comprising an RNA encoding an IL-12sc protein having at least 95% identity to the amino acid sequence of SEQ ID NO: 14.

Embodiment 182. A composition comprising an RNA encoding a GM-CSF protein having at least 95% identity to the amino acid sequence of SEQ ID NO: 27.

Embodiment 183. A composition comprising an RNA encoding an IFNα2b protein having at least 95% identity to the amino acid sequence of SEQ ID NO: 19.

Embodiment 184. A composition comprising an RNA encoding an IL-15 sushi protein having at least 95% identity to the amino acid sequence of SEQ ID NO: 24.

Embodiment 185. A composition comprising an RNA encoding an IL-2 protein having at least 95% identity to the amino acid sequence of SEQ ID NO: 9.

Embodiment 186. A composition comprising an RNA encoding an IL-12sc protein, wherein the RNA comprises nucleotides having at least 95% identity to the nucleotides of SEQ ID NOs: 17 or 18.

Embodiment 187. A composition comprising an RNA encoding a GM-CSF protein, wherein the RNA comprises nucleotides having at least 95% identity to the nucleotides of SEQ ID NO: 29.

Embodiment 188. A composition comprising an RNA encoding an IFNα2b protein, wherein the RNA comprises nucleotides having at least 95% identity to the nucleotides of SEQ ID NOs: 22 or 23.

Embodiment 189. A composition comprising an RNA encoding an IL-15 sushi protein, wherein the RNA comprises nucleotides having at least 95% identity to the nucleotides of SEQ ID NO: 26.

Embodiment 190. A composition comprising an RNA encoding an IL-2 protein, wherein the RNA comprises nucleotides having at least 95% identity to the nucleotides of SEQ ID NOs: 12 or 13.

Embodiment 191. A composition comprising any two of the following RNAs:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
  b. an RNA encoding a GM-CSF protein having at least 95% identity to the amino acid sequence of SEQ ID NO: 27, and/or comprising nucleotides having at least 95% identity to the nucleotides of SEQ ID NO: 29;
  c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
  d. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
  e. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 192. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18; and
  b. an RNA encoding a GM-CSF protein having at least 95% identity to the amino acid sequence of SEQ ID NO: 27, and/or comprising nucleotides having at least 95% identity to the nucleotides of SEQ ID NO: 29.

Embodiment 193. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18; and
  b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23.

Embodiment 194. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18; and
  b. an RNA encoding an IL-15 sushi protein having at least 95% identity to the amino acid sequence of SEQ ID NO: 24, and/or comprising nucleotides having at least 95% identity to the nucleotides of SEQ ID NO: 26.

Embodiment 195. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18; and
  b. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 196. A composition comprising:
  a. an RNA encoding a GM-CSF protein having at least 95% identity to the amino acid sequence of SEQ ID NO: 27, and/or comprising nucleotides having at least 95% identity to the nucleotides of SEQ ID NO: 29; and
  b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23.

Embodiment 197. A composition comprising:
  a. an RNA encoding a GM-CSF protein having at least 95% identity to the amino acid sequence of SEQ ID NO: 27, and/or comprising nucleotides having at least 95% identity to the nucleotides of SEQ ID NO: 29; and
  b. an RNA encoding an IL-15 sushi protein having at least 95% identity to the amino acid sequence of SEQ ID NO: 24, and/or comprising nucleotides having at least 95% identity to the nucleotides of SEQ ID NO: 26.

Embodiment 198. A composition comprising:
  a. an RNA encoding a GM-CSF protein having at least 95% identity to the amino acid sequence of SEQ ID NO: 27, and/or comprising nucleotides having at least 95% identity to the nucleotides of SEQ ID NO: 29; and
  b. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 199. A composition comprising:
  a. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
  b. an RNA encoding an IL-15 sushi protein having at least 95% identity to the amino acid sequence of SEQ ID NO: 24, and/or nucleotides having at least 95% identity to the nucleotides of SEQ ID NO: 26.

Embodiment 200. A composition comprising:
  a. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
  b. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 201. A composition comprising:
  a. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
b. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 202. A composition comprising any three of the following:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29;
c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
d. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
a. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 203. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29; and
c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23.

Embodiment 204. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29; and
c. an RNA encoding an IL-15 sushi protein having at least 95% identity to the amino acid sequence of SEQ ID NO: 24, and/or comprising nucleotides having at least 95% identity to the nucleotides of SEQ ID NO: 26.

Embodiment 205. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29; and
c. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 206. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
c. an RNA encoding an IL-15 sushi protein having at least 95% identity to the amino acid sequence of SEQ ID NO: 24, and/or comprising nucleotides having at least 95% identity to the nucleotides of SEQ ID NO: 26.

Embodiment 207. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
c. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 208. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
c. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 209. A composition comprising:
a. an RNA encoding a GM-CSF protein having at least 95% identity to the amino acid sequence of SEQ ID NO: 27, and/or comprising nucleotides having at least 95% identity to the nucleotides of SEQ ID NO: 29;
b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
c. an RNA encoding an IL-15 sushi protein having at least 95% identity to the amino acid sequence of SEQ ID NO: 24, and/or comprising nucleotides having at least 95% identity to the nucleotides of SEQ ID NO: 26.

Embodiment 210. A composition comprising:
a. an RNA encoding a GM-CSF protein having at least 95% identity to the amino acid sequence of SEQ ID NO: 27, and/or comprising nucleotides having at least 95% identity to the nucleotides of SEQ ID NO: 29;
b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
c. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 211. A composition comprising:
a. an RNA encoding a GM-CSF protein having at least 95% identity to the amino acid sequence of SEQ ID NO: 27, and/or comprising nucleotides having at least 95% identity to the nucleotides of SEQ ID NO: 29;
b. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
c. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 212. A composition comprising:
a. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
b. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
c. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 213. A composition comprising any four of the following:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29;
c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
d. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
e. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 214. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29;
c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
d. an RNA encoding an IL-15 sushi protein having at least 95% identity to the amino acid sequence of SEQ ID NO: 24, and/or comprising nucleotides having at least 95% identity to the nucleotides of SEQ ID NO: 26.

Embodiment 215. A composition comprising:
a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
b. an RNA encoding a GM-CSF protein having at least 95% identity to the amino acid sequence of SEQ ID NO: 27, and/or comprising nucleotides having at least 95% identity to the nucleotides of SEQ ID NO: 29;
c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23; and
d. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 216. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
  b. an RNA encoding a GM-CSF protein having at least 95% identity to the amino acid sequence of SEQ ID NO: 27, and/or comprising nucleotides having at least 95% identity to the nucleotides of SEQ ID NO: 29;
  c. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
  d. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 217. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
  b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
  c. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
  d. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 218. A composition comprising:
  a. an RNA encoding a GM-CSF protein having at least 95% identity to the amino acid sequence of SEQ ID NO: 27, and/or comprising nucleotides having at least 95% identity to the nucleotides of SEQ ID NO: 29;
  b. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
  c. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
  d. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 219. A composition comprising:
  a. an RNA encoding an IL-12sc protein having at least 95% identity to the amino acid sequence of SEQ ID NO: 14, and/or comprising nucleotides having at least 95% identity to the nucleotides of SEQ ID NOs: 17 or 18;
  b. an RNA encoding a GM-CSF protein having at least 95% identity to the amino acid sequence of SEQ ID NO: 27, and/or comprising nucleotides having at least 95% identity to the nucleotides of SEQ ID NO: 29;
  c. an RNA encoding an IFNα2b protein having at least 95% identity to the amino acid sequence of SEQ ID NO: 19, and/or comprising nucleotides having at least 95% identity to the nucleotides of SEQ ID NOs: 22 or 23;
  d. an RNA encoding an IL-15 sushi protein having at least 95% identity to the amino acid sequence of SEQ ID NO: 24, and/or comprising nucleotides having at least 95% identity to the nucleotides of SEQ ID NO: 26; and
  e. an RNA encoding an IL-2 protein having at least 95% identity to the amino acid sequence of SEQ ID NO: 9, and/or comprising nucleotides having at least 95% identity to the nucleotides of SEQ ID NOs: 12 or 13.

Embodiment 220. A pharmaceutical formulation comprising any one of the compositions of embodiments 181-219.

Embodiment 221. A pharmaceutical formulation comprising any one of the compositions of embodiments 181-219 and a pharmaceutically acceptable excipient.

Embodiment 222. The composition of any one of embodiments 181-219, or the pharmaceutical formulation of embodiment 220 or 221, for use in a method of treating or preventing cancer.

Embodiment 223. The composition of any one of embodiments 181-219, or the pharmaceutical formulation of embodiment 220 or 221 for use in a method of reducing the size of a tumor.

Embodiment 224. The composition of any one of embodiments 181-219, or the pharmaceutical formulation of embodiment 220 or 221 for use in a method of preventing the reoccurrence of cancer in remission.

Embodiment 225. The composition of any one of embodiments 181-219, or the pharmaceutical formulation of embodiment 220 or 221 for use in a method of preventing cancer metastasis.

Embodiment 226. A method for treating or preventing cancer comprising administering the composition of any one of embodiments 181-219, or the pharmaceutical formulation of embodiment 220 or 221.

Embodiment 227. A method for reducing the size of a tumor comprising administering the composition of any one of embodiments 181-219, or the pharmaceutical formulation of embodiment 220 or 221.

Embodiment 228. A method for preventing the reoccurrence of cancer in remission comprising administering the composition of any one of embodiments 181-219, or the pharmaceutical formulation of embodiment 220 or 221.

Embodiment 229. A method for preventing cancer metastasis comprising administering the composition of any one of embodiments 181-219, or the pharmaceutical formulation of embodiment 220 or 221.

Further embodiments of the present invention are as follows:

Embodiment A1. A medical preparation comprising RNA encoding an IL-12sc protein and RNA encoding a GM-CSF protein.

Embodiment A 2. The medical preparation of embodiment A 1, further comprising RNA encoding an IL-15 sushi protein.

Embodiment A 3. The medical preparation of embodiment A 1 or 2, further comprising RNA encoding an IL-2 protein.

Embodiment A 4. The medical preparation of any one of embodiments A 1 to 3, further comprising RNA encoding an IFNα protein.

Embodiment A 5. The medical preparation of embodiment A 4, wherein the IFNα protein is an IFNα2b protein.

Embodiment A 6. The medical preparation of embodiment A 2, comprising RNA encoding an IL-12sc protein, RNA encoding a GM-CSF protein, and RNA encoding an IL-15 sushi protein.

Embodiment A 7. The medical preparation of embodiment A 3, comprising RNA encoding an IL-12sc protein, RNA encoding a GM-CSF protein, and RNA encoding an IL-2 protein.

Embodiment A 8. The medical preparation of embodiment A 4 or 5, comprising RNA encoding an IL-12sc protein, RNA encoding a GM-CSF protein, and RNA encoding an IFNα protein.

Embodiment A 9. The medical preparation of embodiment A 4 or 5, comprising RNA encoding an IL-12sc protein, RNA encoding a GM-CSF protein, RNA encoding an IL-15 sushi protein, and RNA encoding an IFNα protein.

Embodiment A 10. The medical preparation of embodiment A 4 or 5, comprising RNA encoding an IL-12sc protein, RNA encoding a GM-CSF protein, RNA encoding an IL-2 protein, and RNA encoding an IFNα protein.

Embodiment A 11. The medical preparation of any one of embodiments A 1-10, wherein (i) the RNA encoding an IL-12sc protein comprises the nucleotide sequence of SEQ ID NO: 17 or 18, or a nucleotide sequence having at least 99%, 98%, 97%, 96%, 95%, 90%, 85%, or 80% identity to the nucleotide sequence of SEQ ID NO: 17 or 18 and/or (ii) the IL-12sc protein comprises the amino acid sequence of SEQ ID NO: 14, or an amino acid sequence having at least 99%, 98%, 97%, 96%, 95%, 90%, 85%, or 80% identity to the amino acid sequence of SEQ ID NO: 14.

Embodiment A 12. The medical preparation of any one of embodiments A 1-11, wherein (i) the RNA encoding a GM-CSF protein comprises the nucleotide sequence of SEQ ID NO: 29, or a nucleotide sequence having at least 99%, 98%, 97%, 96%, 95%, 90%, 85%, or 80% identity to the nucleotide sequence of SEQ ID NO: 29 and/or (ii) the GM-CSF protein comprises the amino acid sequence of SEQ ID NO: 27, or an amino acid sequence having at least 99%, 98%, 97%, 96%, 95%, 90%, 85%, or 80% identity to the amino acid sequence of SEQ ID NO: 27.

Embodiment A 13. The medical preparation of any one of embodiments A 2-12, wherein (i) the RNA encoding an IL-15 sushi protein comprises the nucleotide sequence of SEQ ID NO: 26, or a nucleotide sequence having at least 99%, 98%, 97%, 96%, 95%, 90%, 85%, or 80% identity to the nucleotide sequence of SEQ ID NO: 26 and/or (ii) the IL-15 sushi protein comprises the amino acid sequence of SEQ ID NO: 24, or an amino acid sequence having at least 99%, 98%, 97%, 96%, 95%, 90%, 85%, or 80% identity to the amino acid sequence of SEQ ID NO: 24.

Embodiment A 14. The medical preparation of any one of embodiments A 3-13, wherein (i) the RNA encoding an IL-2 protein comprises the nucleotide sequence of SEQ ID NO: 12 or 13, or a nucleotide sequence having at least 99%, 98%, 97%, 96%, 95%, 90%, 85%, or 80% identity to the nucleotide sequence of SEQ ID NO: 12 or 13 and/or (ii) the IL-2 protein comprises the amino acid sequence of SEQ ID NO: 9, or an amino acid sequence having at least 99%, 98%, 97%, 96%, 95%, 90%, 85%, or 80% identity to the amino acid sequence of SEQ ID NO: 9.

Embodiment A 15. The medical preparation of any one of embodiments 4-14, wherein (i) the RNA encoding an IFNα protein comprises the nucleotide sequence of SEQ ID NO: 22 or 23, or a nucleotide sequence having at least 99%, 98%, 97%, 96%, 95%, 90%, 85%, or 80% identity to the nucleotide sequence of SEQ ID NO: 22 or 23 and/or (ii) the IFNα protein comprises the amino acid sequence of SEQ ID NO: 19, or an amino acid sequence having at least 99%, 98%, 97%, 96%, 95%, 90%, 85%, or 80% identity to the amino acid sequence of SEQ ID NO: 19.

Embodiment A 16. The medical preparation of any one of embodiments A 1-15, wherein at least one RNA comprises a modified nucleobase in place of at least one uridine.

Embodiment A 17. The medical preparation of any one of embodiments A 1-16, wherein each RNA comprises a modified nucleobase in place of at least one uridine.

Embodiment A 18. The medical preparation of any one of embodiments A 1-17, wherein each RNA comprises a modified nucleobase in place of each uridine.

Embodiment A 19. The medical preparation of any one of embodiments A 16-18, wherein the modified nucleobase is pseudouridine (ψ), N1-methyl-pseudouridine (m1ψ) or 5-methyl-uridine (m5U).

Embodiment A 20. The medical preparation of embodiment A 19, wherein the modified nucleobase is N1-methyl-pseudouridine (m1ψ).

Embodiment A 21. The medical preparation of any one of embodiments A 1-20, wherein at least one RNA comprises a 5' cap.

Embodiment A 22. The medical preparation of any one of embodiments A 1-21, wherein each RNA comprises a 5' cap.

Embodiment A 23. The medical preparation of embodiment A 21 or 22, wherein the 5' cap is $m_2^{7,3'-O}Gppp(m_1^{2'-O})ApG$ or 3'-O-Me-$m^7G(5')ppp(5')G$.

Embodiment A 24. The medical preparation of any one of embodiments A 1-23, wherein at least one RNA comprises a 5' UTR.

Embodiment A 25. The medical preparation of any one of embodiments A 1-24, wherein each RNA comprises a 5' UTR.

Embodiment A 26. The medical preparation of embodiment A 24 or 25, wherein the 5' UTR comprises a nucleotide sequence selected from the group consisting of SEQ ID NOs: 2, 4, and 6, or a nucleotide sequence having at least 99%, 98%, 97%, 96%, 95%, 90%, 85%, or 80% identity to a nucleotide sequence selected from the group consisting of SEQ ID NOs: 2, 4, and 6.

Embodiment A 27. The medical preparation of any one of embodiments A 1-26, wherein at least one RNA comprises a 3' UTR.

Embodiment A 28. The medical preparation of any one of embodiments A 1-27, wherein each RNA comprises a 3' UTR.

Embodiment A 29. The medical preparation of embodiment A 27 or 28, wherein the 3' UTR comprises the nucleotide sequence of SEQ ID NO: 8, or a nucleotide sequence having at least 99%, 98%, 97%, 96%, 95%, 90%, 85%, or 80% identity to the nucleotide sequence of SEQ ID NO: 8.

Embodiment A 30. The medical preparation of any one of embodiments A 1-29, wherein at least one RNA comprises a poly-A tail.

Embodiment A 31. The medical preparation of any one of embodiments A 1-30, wherein each RNA comprises a poly-A tail.

Embodiment A 32. The medical preparation of embodiment A 30 or 31, wherein the poly-A tail comprises at least 100 nucleotides.

Embodiment A 33. The medical preparation of any one of embodiments A 1-32, wherein at least one RNA comprises a 5' cap, a 5' UTR, a 3' UTR, and a poly-A tail.

Embodiment A 34. The medical preparation of any one of embodiments A 1-33, wherein each RNA comprises a 5' cap, a 5' UTR, a 3' UTR, and a poly-A tail.

Embodiment A 35. The medical preparation of embodiment A 33 or 34, wherein
a. the 5' cap is $m_2^{7,3'-O}Gppp(m_1^{2'-O})ApG$ or 3'-O-Me-m$^7$G (5')ppp(5')G;
b. the 5' UTR comprises a nucleotide sequence selected from the group consisting of SEQ ID NOs: 2, 4, and 6, or a nucleotide sequence having at least 99%, 98%, 97%, 96%, 95%, 90%, 85%, or 80% identity to a nucleotide sequence selected from the group consisting of SEQ ID NOs: 2, 4, and 6;
c. the 3' UTR comprises the nucleotide sequence of SEQ ID NO: 8, or a nucleotide sequence having at least 99%, 98%, 97%, 96%, 95%, 90%, 85%, or 80% identity to the nucleotide sequence of SEQ ID NO:8; and
d. the poly-A tail comprises at least 100 nucleotides.

Embodiment A 36. The medical preparation of any one of embodiments A 1 to 35, wherein the RNA is mRNA.

Embodiment A 37. The medical preparation of any one of embodiments A 1 to 36, which comprises a further therapeutic agent.

Embodiment A 38. The medical preparation of embodiment A 37, wherein the further therapeutic agent is an anti-cancer therapeutic agent.

Embodiment A 39. The medical preparation of embodiment A 37 or 38, wherein the further therapeutic agent is a checkpoint modulator.

Embodiment A 40. The medical preparation of embodiment A 39, wherein the checkpoint modulator is an anti-PD1 antibody, an anti-CTLA-4 antibody, or a combination of an anti-PD1 antibody and an anti-CTLA-4 antibody.

Embodiment A 41. The medical preparation of any one of embodiments A 1 to 40, which is a kit comprising at least two containers, each container comprising at least one of said RNAs.

Embodiment A 42. The medical preparation of embodiment A 41, which comprises each RNA in a separate container.

Embodiment A 43. The medical preparation of embodiment A 41 or 42, wherein the further therapeutic agent is in a container not comprising the RNA.

Embodiment A 44. The medical preparation of any one of embodiments A 41-43, further comprising instructions for use of the medical preparation for treating or preventing cancer.

Embodiment A 45. The medical preparation of any one of embodiments A 1 to 40, which is a pharmaceutical composition comprising the RNAs.

Embodiment A 46. The medical preparation of embodiment A 45, wherein the pharmaceutical composition further comprises one or more pharmaceutically acceptable carriers, diluents and/or excipients.

Embodiment A 47. The medical preparation of any one of embodiments A 1 to 46, wherein the RNA is present in a form selected from a liquid form, a solid form, or a combination thereof.

Embodiment A 48. The medical preparation of embodiment A 47, wherein the solid form is a frozen form or a dehydrated form.

Embodiment A 49. The medical preparation of embodiment A 48, wherein the dehydrated form is a freeze-dried or spray-dried form.

Embodiment A 50. The medical preparation of any one of embodiments A 1 to 49 for pharmaceutical use.

Embodiment A 51. The medical preparation of embodiment A 50, wherein the pharmaceutical use comprises a therapeutic or prophylactic treatment of a disease or disorder.

Embodiment A 52. The medical preparation of any one of embodiments A 1 to 51 for use in a method for treating or preventing cancer.

Embodiment A 53. The medical preparation of any one of embodiments A 38-52, wherein the cancer is a sarcoma, carcinoma, or lymphoma.

Embodiment A 54. The medical preparation of any one of embodiments A 38-53, wherein the cancer is a solid tumor.

Embodiment A 55. The medical preparation of embodiment A 54, wherein the solid tumor is in the lung, colon, ovary, cervix, uterus, peritoneum, testicles, penis, tongue, lymph node, pancreas, bone, breast, prostate, soft tissue, connective tissue, kidney, liver, brain, thyroid, or skin.

Embodiment A 56. The medical preparation of embodiment A 54 or 55, wherein the solid tumor is an epithelial tumor, Hodgkin lymphoma (HL), non-Hodgkin lymphoma, prostate tumor, ovarian tumor, renal cell tumor, gastrointestinal tract tumor, hepatic tumor, colorectal tumor, tumor with vasculature, mesothelioma tumor, pancreatic tumor, breast tumor, sarcoma tumor, lung tumor, colon tumor, brain tumor, melanoma tumor, small cell lung tumor, neuroblastoma tumor, testicular tumor, carcinoma tumor, adenocarcinoma tumor, glioma tumor, seminoma tumor, retinoblastoma, or osteosarcoma tumor.

Embodiment A 57. The medical preparation of any one of embodiments A 1-56, wherein the RNA is for intra-tumoral or peri-tumoral administration.

Embodiment A 58. The medical preparation of any one of embodiments A 37-57, wherein the further therapeutic agent is for systemic administration.

Embodiment A 59. The medical preparation of any one of embodiments A 1-58, which is for administration to a human.

Embodiment A 60. The medical preparation of any one of embodiments A 44 and 47-59, wherein treating or preventing cancer comprises reducing the size of a tumor, preventing the reoccurrence of cancer in remission, or preventing cancer metastasis in a subject.

Further embodiments of the present invention are as follows:

Embodiment B 1. RNA for use in a method for treating or preventing cancer in a subject, wherein the method comprises administering RNA encoding an IL-12sc protein and RNA encoding a GM-CSF protein.

Embodiment B 2. The RNA of Embodiment B 1, wherein the method further comprises administering RNA encoding an IL-15 sushi protein.

Embodiment B 3. The RNA of Embodiment B 1 or 2, wherein the method further comprises administering RNA encoding an IL-2 protein.

Embodiment B 4. The RNA of any one of embodiments B 1 to 3, wherein the method further comprises administering RNA encoding an IFNα protein.

Embodiment B 5. The RNA of Embodiment B 4, wherein the IFNα protein is an IFNα2b protein.

Embodiment B 6. The RNA of Embodiment B 2, wherein the method comprises administering RNA encoding an IL-12sc protein, RNA encoding a GM-CSF protein, and RNA encoding an IL-15 sushi protein.

Embodiment B 7. The RNA of Embodiment B 3, wherein the method comprises administering RNA encoding an IL-12sc protein, RNA encoding a GM-CSF protein, and RNA encoding an IL-2 protein.

Embodiment B 8. The RNA of Embodiment B 4 or 5, wherein the method comprises administering RNA encoding an IL-12sc protein, RNA encoding a GM-CSF protein, and RNA encoding an IFNα protein.

Embodiment B 9. The RNA of Embodiment B 4 or 5, wherein the method comprises administering RNA encoding an IL-12sc protein, RNA encoding a GM-CSF protein, RNA encoding an IL-15 sushi protein, and RNA encoding an IFNα protein.

Embodiment B 10. The RNA of Embodiment B 4 or 5, wherein the method comprises administering RNA encoding an IL-12sc protein, RNA encoding a GM-CSF protein, RNA encoding an IL-2 protein, and RNA encoding an IFNα protein.

Embodiment B 11. The RNA of any one of embodiments B 1-10, wherein (i) the RNA encoding an IL-12sc protein comprises the nucleotide sequence of SEQ ID NO: 17 or 18, or a nucleotide sequence having at least 99%, 98%, 97%, 96%, 95%, 90%, 85%, or 80% identity to the nucleotide sequence of SEQ ID NO: 17 or 18 and/or (ii) the IL-12sc protein comprises the amino acid sequence of SEQ ID NO: 14, or an amino acid sequence having at least 99%, 98%, 97%, 96%, 95%, 90%, 85%, or 80% identity to the amino acid sequence of SEQ ID NO: 14.

Embodiment B 12. The RNA of any one of embodiments B 1-11, wherein (i) the RNA encoding a GM-CSF protein comprises the nucleotide sequence of SEQ ID NO: 29, or a nucleotide sequence having at least 99%, 98%, 97%, 96%, 95%, 90%, 85%, or 80% identity to the nucleotide sequence of SEQ ID NO: 29 and/or (ii) the GM-CSF protein comprises the amino acid sequence of SEQ ID NO: 27, or an amino acid sequence having at least 99%, 98%, 97%, 96%, 95%, 90%, 85%, or 80% identity to the amino acid sequence of SEQ ID NO: 27.

Embodiment B 13. The RNA of any one of embodiments B 2-12, wherein (i) the RNA encoding an IL-15 sushi protein comprises the nucleotide sequence of SEQ ID NO: 26, or a nucleotide sequence having at least 99%, 98%, 97%, 96%, 95%, 90%, 85%, or 80% identity to the nucleotide sequence of SEQ ID NO: 26 and/or (ii) the IL-15 sushi protein comprises the amino acid sequence of SEQ ID NO: 24, or an amino acid sequence having at least 99%, 98%, 97%, 96%, 95%, 90%, 85%, or 80% identity to the amino acid sequence of SEQ ID NO: 24.

Embodiment B 14. The RNA of any one of embodiments B 3-13, wherein (i) the RNA encoding an IL-2 protein comprises the nucleotide sequence of SEQ ID NO: 12 or 13, or a nucleotide sequence having at least 99%, 98%, 97%, 96%, 95%, 90%, 85%, or 80% identity to the nucleotide sequence of SEQ ID NO: 12 or 13 and/or (ii) the IL-2 protein comprises the amino acid sequence of SEQ ID NO: 9, or an amino acid sequence having at least 99%, 98%, 97%, 96%, 95%, 90%, 85%, or 80% identity to the amino acid sequence of SEQ ID NO: 9.

Embodiment B 15. The RNA of any one of embodiments B 4-14, wherein (i) the RNA encoding an IFNα protein comprises the nucleotide sequence of SEQ ID NO: 22 or 23, or a nucleotide sequence having at least 99%, 98%, 97%, 96%, 95%, 90%, 85%, or 80% identity to the nucleotide sequence of SEQ ID NO: 22 or 23 and/or (ii) the IFNα protein comprises the amino acid sequence of SEQ ID NO: 19, or an amino acid sequence having at least 99%, 98%, 97%, 96%, 95%, 90%, 85%, or 80% identity to the amino acid sequence of SEQ ID NO: 19.

Embodiment B 16. The RNA of any one of embodiments B 1-15, wherein at least one RNA comprises a modified nucleobase in place of at least one uridine.

Embodiment B 17. The RNA of any one of embodiments B 1-16, wherein each RNA comprises a modified nucleobase in place of at least one uridine.

Embodiment B 18. The RNA of any one of embodiments B 1-17, wherein each RNA comprises a modified nucleobase in place of each uridine.

Embodiment B 19. The RNA of any one of embodiments B 16-18, wherein the modified nucleobase is pseudouridine (ψ), N1-methyl-pseudouridine (m1ψ) or 5-methyl-uridine (m5U).

Embodiment B 20. The RNA of Embodiment B 19, wherein the modified nucleobase is N1-methyl-pseudouridine (m1ψ).

Embodiment B 21. The RNA of any one of embodiments B 1-20, wherein at least one RNA comprises a 5' cap.

Embodiment B 22. The RNA of any one of embodiments B 1-21, wherein each RNA comprises a 5' cap.

Embodiment B 23. The RNA of Embodiment B 21 or 22, wherein the 5' cap is $m_2^{7,3'-O}Gppp(m_1^{2'-O})ApG$ or 3'-O-Me-$m^7$G(5')ppp(5')G.

Embodiment B 24. The RNA of any one of embodiments B 1-23, wherein at least one RNA comprises a 5' UTR.

Embodiment B 25. The RNA of any one of embodiments B 1-24, wherein each RNA comprises a 5' UTR.

Embodiment B 26. The RNA of Embodiment B 24 or 25, wherein the 5' UTR comprises a nucleotide sequence selected from the group consisting of SEQ ID NOs: 2, 4, and 6, or a nucleotide sequence having at least 99%, 98%, 97%, 96%, 95%, 90%, 85%, or 80% identity to a nucleotide sequence selected from the group consisting of SEQ ID NOs: 2, 4, and 6.

Embodiment B 27. The RNA of any one of embodiments B 1-26, wherein at least one RNA comprises a 3' UTR.

Embodiment B 28. The RNA of any one of embodiments B 1-27, wherein each RNA comprises a 3' UTR.

Embodiment B 29. The RNA of embodiment B 27 or 28, wherein the 3' UTR comprises the nucleotide sequence of SEQ ID NO: 8, or a nucleotide sequence having at least 99%, 98%, 97%, 96%, 95%, 90%, 85%, or 80% identity to the nucleotide sequence of SEQ ID NO: 8.

Embodiment B 30. The RNA of any one of embodiments B 1-29, wherein at least one RNA comprises a poly-A tail.

Embodiment B 31. The RNA of any one of embodiments B 1-30, wherein each RNA comprises a poly-A tail.

Embodiment B 32. The RNA of embodiment B 30 or 31, wherein the poly-A tail comprises at least 100 nucleotides.

Embodiment B 33. The RNA of any one of embodiments B 1-32, wherein at least one RNA comprises a 5' cap, a 5' UTR, a 3' UTR, and a poly-A tail.

Embodiment B 34. The RNA of any one of embodiments B 1-33, wherein each RNA comprises a 5' cap, a 5' UTR, a 3' UTR, and a poly-A tail.

Embodiment B 35. The RNA of embodiment B 33 or 34, wherein
a. the 5' cap is $m_2^{7,3'\text{-}O}Gppp(m_1^{2'\text{-}O}ApG$ or 3'-O-Me-$m^7G(5')ppp(5')G$;
b. the 5' UTR comprises a nucleotide sequence selected from the group consisting of SEQ ID NOs: 2, 4, and 6, or a nucleotide sequence having at least 99%, 98%, 97%, 96%, 95%, 90%, 85%, or 80% identity to a nucleotide sequence selected from the group consisting of SEQ ID NOs: 2, 4, and 6;
c. the 3' UTR comprises the nucleotide sequence of SEQ ID NO: 8, or a nucleotide sequence having at least 99%, 98%, 97%, 96%, 95%, 90%, 85%, or 80% identity to the nucleotide sequence of SEQ ID NO:8; and
d. the poly-A tail comprises at least 100 nucleotides.

Embodiment B 36. The RNA of any one of embodiments B 1 to 35, wherein the RNA is mRNA.

Embodiment B 37. The RNA of any one of embodiments B 1 to 36, wherein the method further comprises administering a further therapy.

Embodiment B 38. The RNA of embodiment B 37, wherein the further therapy comprises one or more selected from the group consisting of: (i) surgery to excise, resect, or debulk a tumor, (ii) immunotherapy, (iii) radiotherapy, and (iv) chemotherapy.

Embodiment B 39. The RNA of embodiment B 37 or 38, wherein the further therapy comprises administering a further therapeutic agent.

Embodiment B 40. The RNA of embodiment B 39, wherein the further therapeutic agent is an anti-cancer therapeutic agent.

Embodiment B 41. The RNA of embodiment B 39 or 40, wherein the further therapeutic agent is a checkpoint modulator.

Embodiment B 42. The RNA of embodiment B 41, wherein the checkpoint modulator is an anti-PD1 antibody, an anti-CTLA-4 antibody, or a combination of an anti-PD1 antibody and an anti-CTLA-4 antibody.

Embodiment B 43. The RNA of any one of embodiments B 1-42, wherein the cancer is a sarcoma, carcinoma, or lymphoma.

Embodiment B 44. The RNA of any one of embodiments B 1-43, wherein the cancer is a solid tumor.

Embodiment B 45. The RNA of embodiment B 44, wherein the solid tumor is in the lung, colon, ovary, cervix, uterus, peritoneum, testicles, penis, tongue, lymph node, pancreas, bone, breast, prostate, soft tissue, connective tissue, kidney, liver, brain, thyroid, or skin.

Embodiment B 46. The RNA of embodiment B 44 or 45, wherein the solid tumor is an epithelial tumor, Hodgkin lymphoma (HL), non-Hodgkin lymphoma, prostate tumor, ovarian tumor, renal cell tumor, gastrointestinal tract tumor, hepatic tumor, colorectal tumor, tumor with vasculature, mesothelioma tumor, pancreatic tumor, breast tumor, sarcoma tumor, lung tumor, colon tumor, brain tumor, melanoma tumor, small cell lung tumor, neuroblastoma tumor, testicular tumor, carcinoma tumor, adenocarcinoma tumor, glioma tumor, seminoma tumor, retinoblastoma, or osteosarcoma tumor.

Embodiment B 47. The RNA of any one of embodiments B 1-46, wherein the RNA is administered intra-tumorally or peri-tumorally.

Embodiment B 48. The RNA of any one of embodiments B 39 to 47, wherein the further therapeutic agent is administered systemically.

Embodiment B 49. The RNA of any one of embodiments B 1-48, wherein the subject is a human.

Embodiment B 50. The RNA of any one of embodiments B 1-49, wherein the RNAs are administered at the same time.

Embodiment B 51. The RNA of any one of embodiments B 1-50, wherein the RNAs are administered by administering a composition comprising a combination of the RNAs.

Embodiment B 52. The RNA of any one of embodiments B 1-49, wherein at least two of the RNAs are administered at different times.

Embodiment B 53. The RNA of any one of embodiments B 1-49 and 52, wherein the RNAs are administered by administering at least two compositions, each composition comprising at least one of said RNAs.

Embodiment B 54. The RNA of any one of embodiments B 1 to 53, wherein treating or preventing cancer comprises reducing the size of a tumor, preventing the reoccurrence of cancer in remission, or preventing cancer metastasis in a subject.

Embodiment B 55. The RNA of any one of embodiments B 1 to 54, which is or comprises one or more of the RNAs administered in said method.

Embodiment B 56. The RNA of embodiment B 55, which is or comprises one or more selected from the group consisting of the RNA encoding an IL-12sc protein, the RNA encoding a GM-CSF protein, the RNA encoding an IL-15 sushi protein, the RNA encoding an IL-2 protein, and the RNA encoding an IFNα protein.

Embodiment B 57. The RNA of embodiment B 55 or 56, which is or comprises the RNA encoding an IL-12sc protein.

Embodiment B 58. The RNA of embodiment B 55 or 56, which is or comprises the RNA encoding a GM-CSF protein.

Embodiment B 59. The RNA of embodiment B 55 or 56, which is or comprises the RNA encoding an IL-15 sushi protein.

Embodiment B 60. The RNA of embodiment B 55 or 56, which is or comprises the RNA encoding an IL-2 protein.

Embodiment B 61. The RNA of embodiment B 55 or 56, which is or comprises the RNA encoding an IFNα protein.

Embodiment B 62. The RNA of embodiment B 55 or 56, which is or comprises the RNA encoding an IL-12sc protein and the RNA encoding a GM-CSF protein.

Embodiment B 63. The RNA of embodiment B 55 or 56, which is or comprises the RNA encoding an IL-12sc protein, the RNA encoding a GM-CSF protein, and the RNA encoding an IL-15 sushi protein.

Embodiment B 64. The RNA of embodiment B 55 or 56, which is or comprises the RNA encoding an IL-12sc protein, the RNA encoding a GM-CSF protein, and the RNA encoding an IL-2 protein.

Embodiment B 65. The RNA of embodiment B 55 or 56, which is or comprises the RNA encoding an IL-12sc protein, the RNA encoding a GM-CSF protein, and the RNA encoding an IFNα protein.

Embodiment B 66. The RNA of embodiment B 55 or 56, which is or comprises the RNA encoding an IL-12sc protein, the RNA encoding a GM-CSF protein, the RNA encoding an IL-15 sushi protein, and the RNA encoding an IFNα protein.

Embodiment B 67. The RNA of embodiment B 55 or 56, which is or comprises the RNA encoding an IL-12sc protein, the RNA encoding a GM-CSF protein, the RNA encoding an IL-2 protein, and the RNA encoding an IFNα protein.

FIGURE LEGENDS

FIGS. 1A-1G shows results of experiments where B16F10 tumor bearing mice were injected intratumorally with mRNA on days 8, 10, 12, 14 and individual tumor growth was monitored to day 41. FIG. 1A and FIG. 1D show results when using IL-2, IL-12sc, and GM-CSF (ModA) mRNA. FIG. 1B and FIG. 1E show IL-2, IL-12sc, and GM-CSF (ModB) mRNA. FIG. 1C and FIG. 1F show results when using luciferase mRNA (ModA). FIG. 1G shows results when using luciferase mRNA (ModB). (N=10 mice/group for A-C and N=9 mice/group for D-G).

FIGS. 2A-2D show results of experiments where CT26 tumor bearing mice were injected intratumorally with mRNA on day 19, 21, 24, 26, 28 and 31 and individual tumor growth was monitored to day 48. FIG. 2A shows GM-CSF, IL-2, IL-12sc (ModA). FIG. 2B shows GM-CSF, IL-2, IL-12sc (ModB). FIG. 2C shows luciferase mRNA (ModA) as a control. FIG. 2D shows Ringer's solution as a control.

FIGS. 3A-3C show results of experiments where CT26 tumor bearing mice were injected intratumorally with mRNA on day 13, 15, 18, 20 and 22 and tumor growth was monitored to day 42. FIG. 3A shows IL-2, GM-CSF, IL-12sc (ModB). FIG. 3B shows IL-15 sushi, GM-CSF, IL-12sc (ModB). FIG. 3C shows luciferase mRNA (ModB) as a control.

FIGS. 4A-4F show results of experiments where B16F10 tumor bearing mice were injected intratumorally with cytokine mRNA mixtures on days 11, 13, 15, 17 and individual tumor growth was monitored to day 45. FIG. 4A shows IL-2, IL-12sc, and GM-CSF (ModA). FIG. 4B is a duplicate in the same experiment as described in FIG. 5A, showing IL-2, IL-12sc, and GM-CSF (ModB). FIG. 4C shows IL-15 sushi, IL-12sc, and GM-CSF (ModA). FIG. 4D is a duplicate in the same experiment as described in FIG. 5B, showing IL-15 sushi, IL-12sc, and GM-CSF (ModB). FIG. 4E shows control luciferase mRNA (ModA). FIG. 4F is a duplicate in the same experiment as described in FIGS. 5D and 6D showing control luciferase mRNA (ModB). (N=8 mice/group).

FIGS. 5A-5D show results of experiments where B16F10 tumor bearing mice were injected intratumorally with cytokine mRNA mixtures on days 11, 13, 15, 17 and individual tumor growth was monitored to day 45. FIG. 5A is a duplicate in the same experiment as described in FIG. 4B, showing IL-2, IL-12sc, and GM-CSF (ModB). FIG. 5B is a duplicate in the same experiment as described in FIG. 4D, showing IL-15 sushi, IL-12sc, and GM-CSF (ModB). FIG. 5C is a duplicate in the same experiment as described in FIG. 6C, showing IL-2, IL-12sc, GM-CSF, and IFNα (ModB). FIG. 5D is a duplicate in the same experiment as described in FIGS. 4F and 6D, showing luciferase mRNA (ModB) as control. (N=8 mice/group).

FIGS. 6A and 6B show results of experiments where CT26 tumor bearing mice were injected intratumorally with cytokine mRNA mixtures on days 13, 15, 17, 19, 21, 23 and individual tumor growth was plotted. FIG. 6A is a duplicate in the same experiment as described in FIG. 7A, showing GM-CSF, IL-2, IL-12sc, IFNα (ModB). FIG. 6B is a duplicate in the same experiment as described in FIG. 7C, showing luciferase mRNA (ModB). N=8 mice/group.

FIGS. 6C and 6D show results of experiments where B16F10 tumor bearing mice were injected intratumorally with mRNA on days 11, 13, 15, 17 and individual tumor growth was plotted. FIG. 6C is a duplicate in the same experiment as described in FIG. 5C, showing GM-CSF, IL-2, IL-12sc, IFNα (ModB). FIG. 6D is a duplicate in the same experiment as described in FIGS. 4F and 5D, showing luciferase mRNA (ModB). N=8 mice/group.

FIGS. 6E and 6F show results of experiments where MC38 tumor bearing mice were injected intratumorally with cytokine mRNA mixtures on days 11, 15, 19, 23 and individual tumor growth was plotted. FIG. 6E shows GM-CSF, IL-2, IL-12sc, IFNα (ModB). FIG. 6F shows luciferase mRNA (ModB). N=5 mice/group.

FIGS. 7A-7F show results of experiments where CT26 tumor bearing mice were injected intratumorally with cytokine mRNA mixtures on days 13, 15, 17, 19, 21, 23 and individual tumor growth was plotted. FIG. 7A is a duplicate in the same experiment as described in FIG. 6A, showing IL-2, IL-12sc, GM-CSF, IFNα (ModB). FIG. 7B shows IL-15 sushi, IL-12sc, GM-CSF, IFNα (ModB). FIG. 7C is a duplicate in the same experiment as described in FIG. 6B, showing a luciferase mRNA (ModB) control. In a repeat study of similar design, CT26 tumor bearing mice were injected intratumorally with cytokine mRNA mixtures on days 19, 21, 23, 26, 28 and 30 and individual tumor growth was plotted. FIG. 7D is a duplicate of the same experiment as described in FIG. 9A, showing IL-2, IL-12sc, GM-CSF, IFNα (ModB). FIG. 7E shows IL-15 sushi, IL-12sc, GM-CSF, IFNα (ModB). FIG. 7F is a duplicate of the same experiment as described in FIG. 9F, showing a luciferase mRNA (ModB) control. N=8 mice/group for Figures A-C and N=10-11 mice/group for Figures D-F.

FIGS. 8A-8H show results of experiments where CT26 tumor bearing mice were injected intratumorally with mRNA on days 12, 15, 19 and 22 and individual tumor growth was monitored and plotted to day 35. FIG. 8A shows IL-15 sushi, IL-12sc, GM-CSF, IFNα (ModB). FIG. 8B shows IL-15 sushi, IL-12sc, IFNα (ModB). FIG. 8C shows IL-15 sushi, GM-CSF, IFNα (ModB). FIG. 8D shows GM-CSF, IL-12sc, IFNα (ModB). FIG. 8E shows IL-15 sushi, GM-CSF, IL-12sc (ModB). FIG. 8F shows a luciferase mRNA (ModB) control. (N=10/group). FIGS. 8G and 8H show tumor growth kinetics of the study shown in FIGS. 8A-8F. FIG. 8G shows mean tumor volumes up to day 33 for all treatment groups. FIG. 8H shows tumor growth repression. T/C (Tumor/Control based on mean tumor volume) was calculated up to day 19.

FIGS. 9A-9F show experiments where CT26 tumor bearing mice were injected intratumorally with mRNA on days 19, 21, 23, 26, 28 and 30 and tumor growth was monitored to day 50. FIG. 9A is a duplicate in the same experiment as described in FIG. 7D, showing GM-CSF, IL-2, IL-12sc, IFNα (ModB). FIG. 9B shows IL-2, IL-12sc, IFNα (ModB). FIG. 9C shows GM-CSF, IL-2, IFNα (ModB). FIG. 9D shows GM-CSF, IL-12sc, IFNα (ModB). FIG. 9E shows GM-CSF, IL-2, IL-12sc (ModB). FIG. 9F is a duplicate in the same experiment as described in FIG. 7F, showing shows luciferase mRNA (ModA) as control. (N=11/group for FIG. 9A-E; luciferase mRNA group N=10 for FIG. 9F).

FIGS. 10A-10B shows tumor growth kinetics of the study shown in FIG. 9. FIG. 10A shows mean tumor volumes up to day 36 for all treatment groups. FIG. 10B shows tumor growth repression. T/C (Tumor/Control based on mean tumor volume) was calculated up to day 30.

FIG. 11 shows a bar graph of data from the experiments shown in FIG. 9 showing mRNA mixtures with significant reduction in tumor volume, where the number of mice in each of the treatment groups with significant tumor reduction was compared to the luciferase control group based on Z score of tumor volume and the ratio between tumor volume change and the mean of the control group.

FIGS. 12A-12D show the results of experiments where mice that were 1) tumor naïve, or 2) had been previously injected subcutaneously with $5 \times 10^5$ B16F10 cells and rejected the original tumor following intratumoral cytokine mRNA treatment. Both groups were re-challenged with B16F10 tumors. FIG. 12A shows tumor naïve host mice. FIG. 12B shows mice that had previously rejected B16F10 tumors following intratumoral cytokine mRNA treatment with GM-CSF, IL-15sushi, IL-12sc, IFNα (ModB). Mice were monitored for 55 days following B16F10 injection and tumor growth for each mouse was plotted. All nine naïve mice engrafted with B16F10 cells developed tumors (FIG. 12A), whereas all eight tumor-free mice rejected the B16F10 cells and did not exhibit growth of B16F10 tumors (FIG. 12B). The graph in FIG. 12B has no visible data trace because all observations were zero, i.e., overlapping the horizontal axis. FIG. 12C shows an example of localized vitiligo at the tumor site. FIG. 12D shows the results of experiments where mice that were tumor naïve (triangle symbol), or had been previously injected subcutaneously with CT26 tumor cells and rejected the original tumor following intratumoral cytokine mRNA treatment (circle symbol). Both groups were re-challenged with either CT26 tumor cells (CT26-WT) or with CT26-Δgp70 tumor cells, in which the gp70-epitope had been knocked out. Mice were monitored for 21 days following tumor cell injection. All nine but one naïve mice engrafted with CT26-WT cells and all naïve mice engrafted with CT26-Δgp70 cells developed tumors, whereas all three tumor-free mice rejected the CT26 tumor cells and did not exhibit growth of CT26 and CT26-Δgp70 tumors, respectively.

FIGS. 13A-13D show the results of experiments where mice were implanted with B16F10 tumor cells on day 0 on the right (injected) and left flanks (uninjected) (FIG. 13A). Mice received a series of 4 intratumoral injections with ModB cytokine mRNA (IL-15 sushi, IL-12sc, GM-CSF and IFNα) or ModB control mRNA (luciferase) in the right tumor on days 11, 15, 19, and 23. Mean tumor volumes+/− SEM (n=12) are shown for the injected (FIG. 13B) and the contralateral uninjected tumors (FIG. 13C). Median survival is shown in FIG. 13D.

FIGS. 14A-14F show results of experiments where human HEK293 (FIG. 14B) and melanoma cell lines (A101D (FIG. 14C), A2058 (FIG. 14D), A375 (FIG. 14E), and Hs294T (FIG. 14F)) were transfected with human cytokine mRNA mixture (IL-12sc, GM-CSF, IL-15 sushi and IFNα2b) in a range of mRNA doses. Supernatants were collected 24 hrs after transfection and protein concentrations were determined with cytokine specific ELISAs. FIG. 14A shows a schematic of the experiment.

FIGS. 15A-15B show a schematic (FIG. 15A) and results (FIG. 15B) from a study where a human cytokine mRNA mixture encoding IL-15 sushi, IL-12sc, GM-CSF and IFNα2b, or individual cytokine mRNAs, were transfected in HEK293 cells and the conditioned media was collected at 24 hrs, diluted and added to human PBMCs. IFNγ was measured in the PBMC culture supernatant at 24 hrs. (N=6 donors, Mean).

FIGS. 16A-16E show the results of experiments where immune compromised mice bearing human A375 tumor xenografts received a single injection with the ModB mRNA mixture encoding the human cytokines (IL-15 sushi, IL-12sc, GM-CSF and IFNα2b; "the IL15 sushi mixture") or (IL-2, IL-12sc, GM-CSF and IFNα2b; "the IL2 mixture"). Tumor cell lysates were prepared at 2 hrs, 4 hrs, 8 hrs, 24 hrs, 48 hrs, and 72 hrs after injection and the concentration of each cytokine was measured with respect to the total protein in the tumor lysates (n=3 mice/time point, +/−SEM). FIG. 16A shows IFNα2b, FIG. 16B shows IL-2, FIG. 16C shows IL-12sc, FIG. 16D shows IL-15 sushi, and FIG. 16E shows GM-CSF.

FIGS. 17A-17C show the results of experiments where mRNA was isolated from A375 tumors at 2 hrs, 4 hrs, 8 hrs, 24 hrs, 48 hrs, and 72 hrs after injection of ModB cytokine mRNA mixture (IL-15 sushi, IL-12sc, GM-CSF, IFNα2b) or (IL-2, IL-12sc, GM-CSF, IFNα2b). Expression of interferon alpha response genes were monitored by qPCR. FIG. 17A shows human ISG15, FIG. 17B shows human ISG54, and FIG. 17C shows human MX1.

FIGS. 18A-18E show the results of experiments where mice were implanted with B16F10 tumor cells and treated with mRNA mixtures (FLT3L, IL-2, 41BBL, and CD27L-CD40L) with or without IFNα. mRNA mixtures without IFNα in standard (ModA, FIG. 18B) and modified forms (ModB, FIG. 18C) were compared to those including IFNα in standard (ModA, FIG. 18D) and modified forms (ModB, FIG. 18E). FIG. 18A is a negative control where Ringer's media without mRNA was provided.

FIGS. 19A-19E show the results of experiments where mice were implanted with tumors on one flank and received an IV injection of luciferase-expressing tumor cells that homed to the lung (FIG. 19A). Mice in the treatment group received intratumoral injections of mRNA mixtures IL-15 sushi, IL-12sc, GM-CSF and IFNα into the flank tumor only while tumors in the lung were untreated. FIG. 19B shows exemplarily bioluminescence measurements in lungs and pictures of the according lungs taken out on the same day (day 20); tumor nodes are visual as black marks; FIG. 19C shows mean tumor volume of flank tumors as determined by caliper measurements; FIG. 19D shows total flux analysis of bioluminescence measurements on day 20; FIG. 19E shows lung weights.

FIGS. 20A-20G show the results of experiments designed to assess the effect of intratumoral injection of mRNA mixtures in combination with systemic administration of antibodies in dual flank tumor models. Mice implanted with either the B16F10 tumor on the left and right flank or MC38 tumors on the left and right flank received intratumoral injections with an mRNA mixture of IL-15 sushi, IL-12sc, GM-CSF and IFNα (Mod B) into only one flank tumor, while the other flank tumor was untreated. Mice also received intraperitoneal (systemic) injection of an anti-PD1 antibody. FIG. 20 shows overall survival in the B16F10 (FIG. 20A) and MC38 (FIG. 20B) tumor models. FIGS.

20C-G show the results of an experiment evaluating the anti-PD-1 antibody where mice were implanted with B16F10 tumors on one flank and received an IV injection of luciferase-expressing B16F10 tumor cells that homed to the lung. Mice received three intratumoral injections with an mRNA mixture of IL-15 sushi, IL-12sc, GM-CSF and IFNα and also received three intraperitoneal (systemic) injection of an anti-PD-1 antibody. Tumor growth of the SC tumors is depicted in FIG. 20C-F. FIG. 20C shows control mRNA and control antibody; FIG. 20D shows control mRNA plus anti-PD1 antibody; FIG. 20E shows cytokine mRNA mixture plus isotype control antibody. FIG. 20F shows cytokine mRNA plus anti-PD-1 antibody. FIG. 20G shows percent survival of all four treatment groups until day 70 after IV tumor inoculation; the treatment group that received mRNA plus anti-PD-1 antibody showed strongest anti-tumoral activity with 6 out of 15 mice being tumor-free on day 40 after tumor inoculation.

FIGS. 21A-21I show the results of additional experiments designed to assess the effect of intratumoral injection of mRNA mixtures in combination with systemic administration of antibodies. Mice bearing CT26 tumors received intratumoral injections with an mRNA mixture of IL-15 sushi, IL-12sc, GM-CSF and IFNα. Mice also received intraperitoneal (systemic) injection of an anti-CTLA-4 antibody. FIG. 21A shows that the combination therapy of intratumoral cytokine mRNA and IP-injected anti-CTLA-4 resulted in strongest anti-tumoral activity with 12 out of 16 mice being tumor-free on day 55 after tumor inoculation. FIG. 21B shows cytokine mRNA mixture plus isotype control antibody; FIG. 21C shows control mRNA plus anti-CTLA-4 antibody; FIG. 21D shows control mRNA and control antibody. FIGS. 21E-21I show the results of additional experiments designed to assess the effect of intratumoral injection of mRNA mixtures in combination with anti-CTLA-4 antibody in B16F10 tumor model. Mice bearing B16F10 tumors received intratumoral injections with an mRNA mixture of IL-15 sushi, IL-12sc, GM-CSF and IFNα. Mice also received intraperitoneal (systemic) injection of an anti-CTLA-4 antibody. FIG. 21E shows that the combination therapy of intratumoral cytokine mRNA and IP-injected anti-CTLA-4 resulted in strongest anti-tumoral activity with 6 out of 9 mice being tumor-free on day 70 after tumor inoculation. FIG. 21F shows cytokine mRNA mixture plus isotype control antibody; FIG. 21G shows control mRNA plus anti-CTLA-4 antibody; FIG. 21H shows control mRNA and control antibody. FIG. 21I shows percent survival of all four treatment groups until day 70 after tumor inoculation.

Figure 24A:
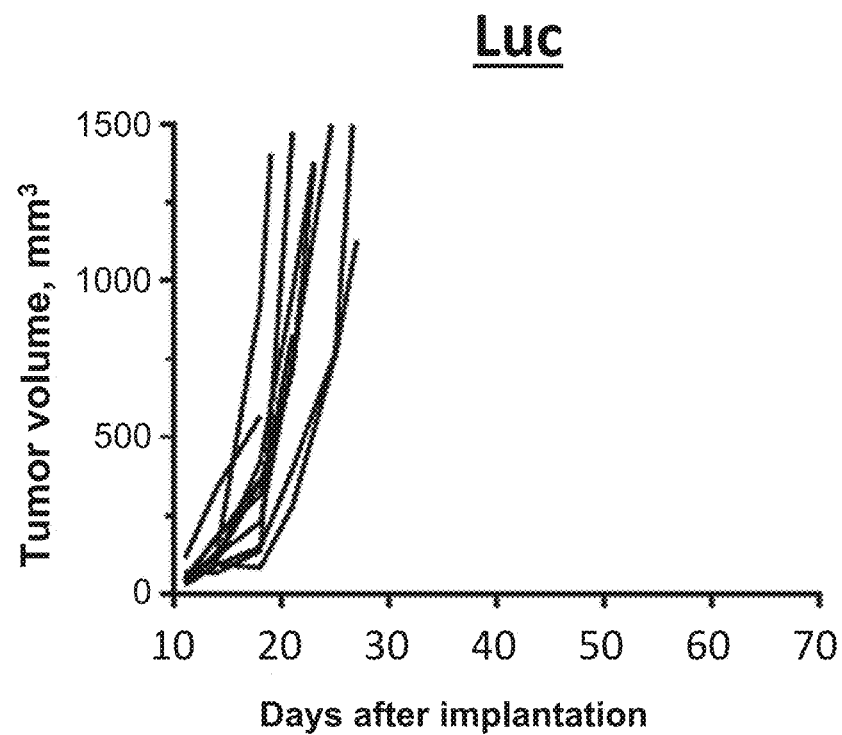
Figure 24B:
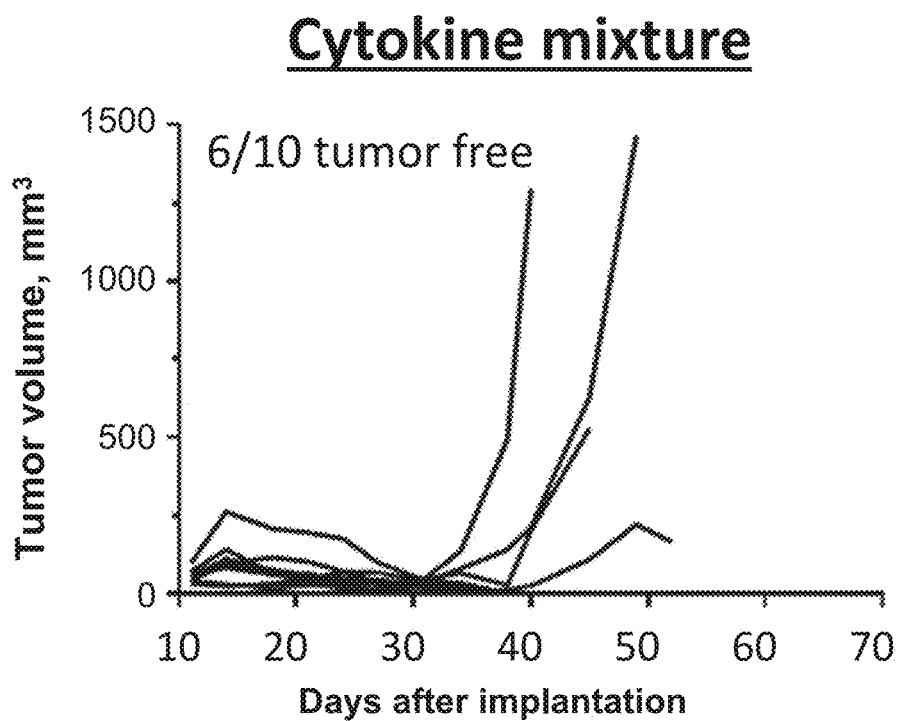
Figure 24C:
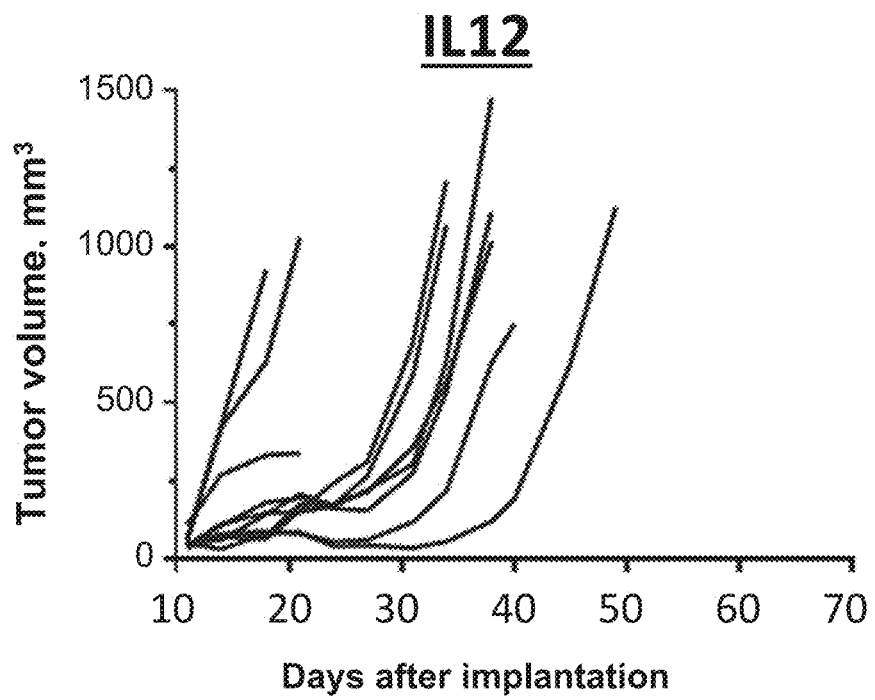
Figure 24D:
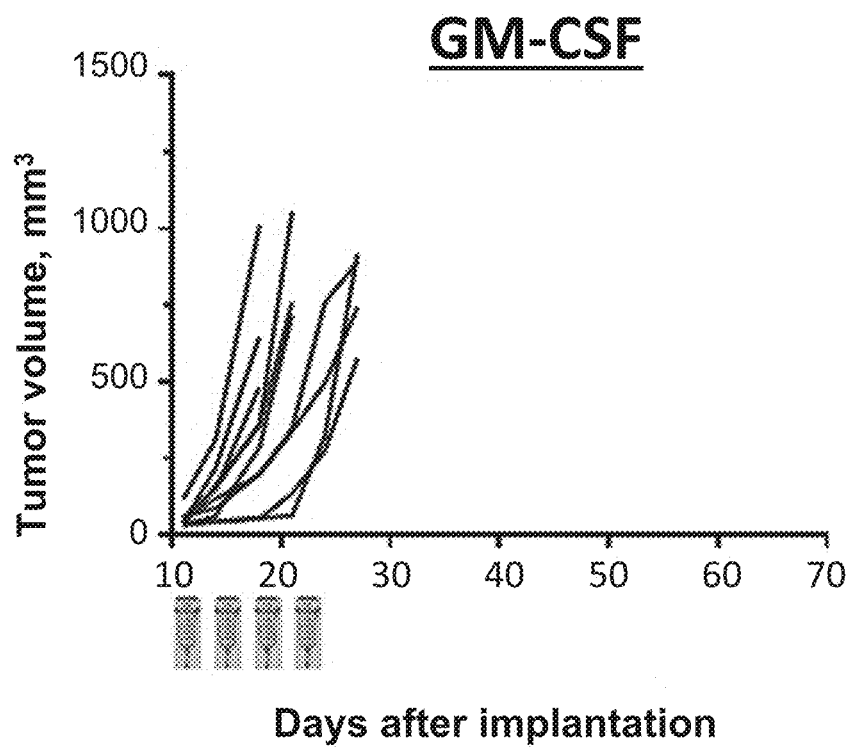
Figure 24E:
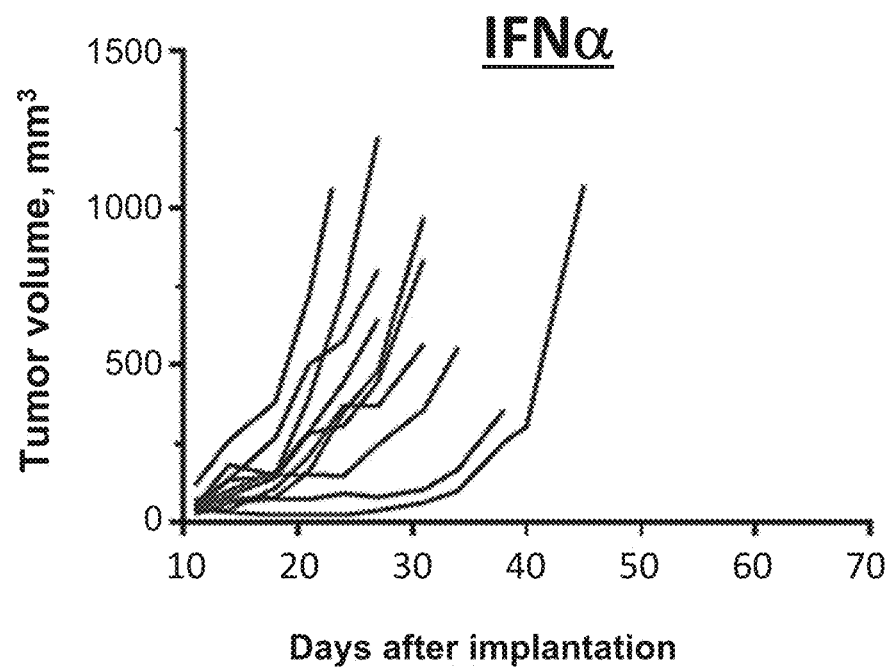
Figure 24F:
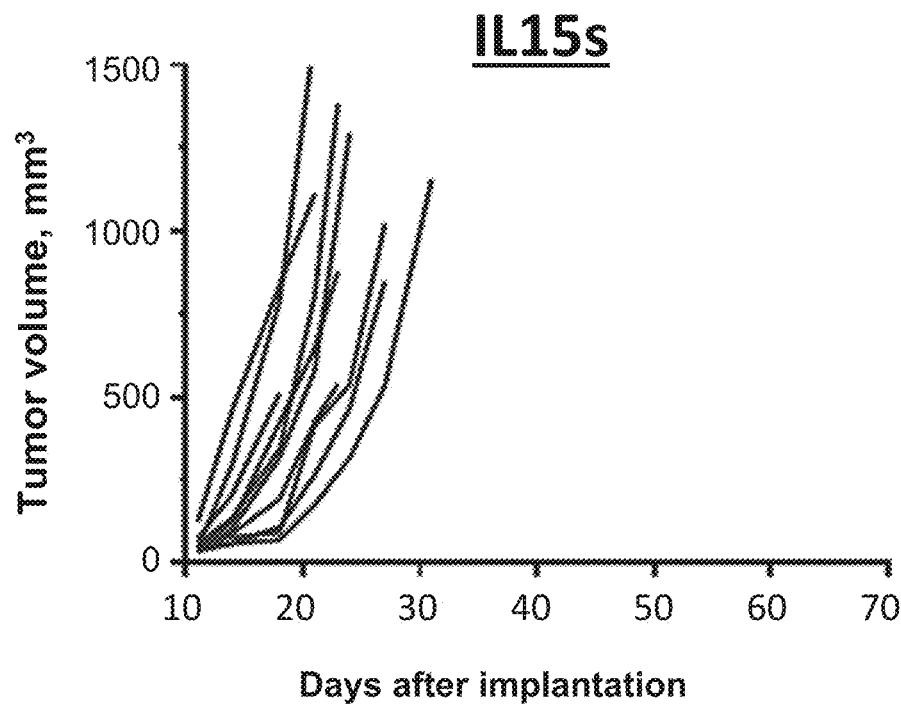
Figure 24G:
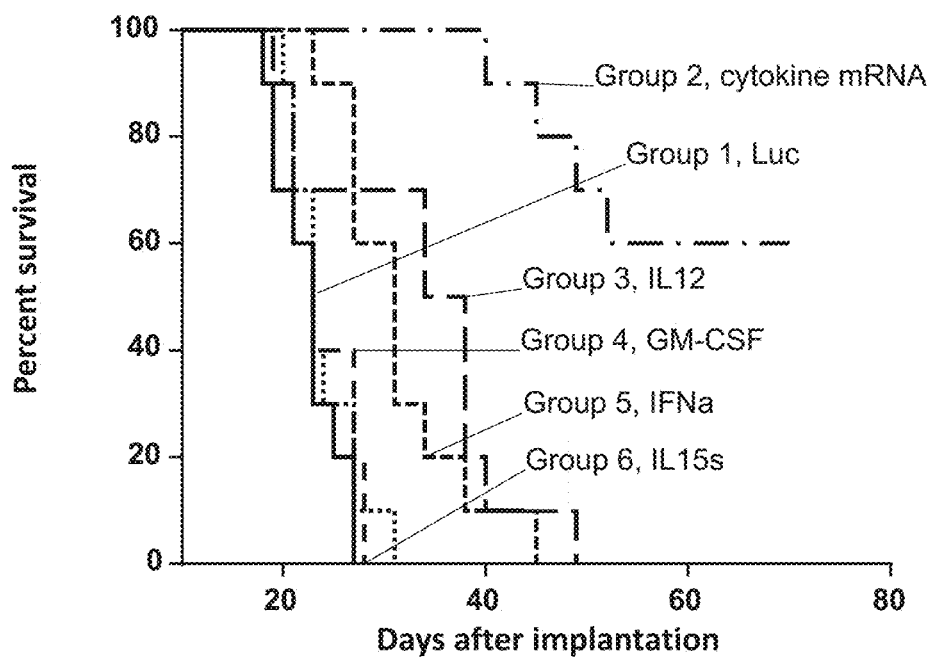

FIGS. 24A-24G show the results of experiments where mice were implanted with B16F10 tumor, and treated with four intratumoral injections of cytokine mRNA mixture of IL-15 sushi, IL-12sc, GM-CSF, IFNα (ModB) or mRNA encoding a single cytokine. Tumor volume out to approximately day 70 was measured. FIG. 24A shows luciferase control; FIG. 24B shows the four-cytokine mixture; FIG. 24C shows IL-12sc mRNA only; FIG. 24D shows GM-CSF mRNA only; FIG. 24E shows IFNα mRNA only; and FIG. 24F shows IL-15 sushi only. FIG. 24G shows overall survival of B16F10 tumors treated with cytokine mRNA mixture or individual mRNA encoded cytokines. Survival data is from experiment presented in FIG. 24A-F.

Figure 25:
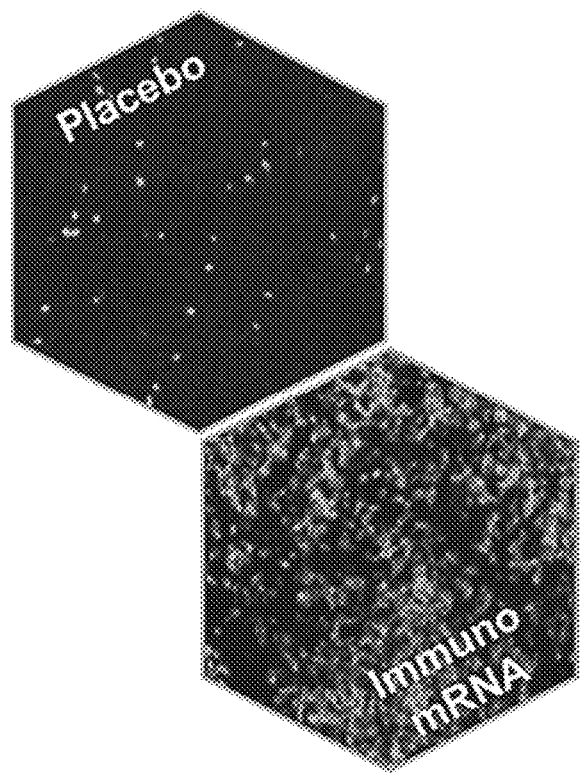

FIG. 25 shows CD8+ immune cell infiltrate in subcutaneous tumors after control mRNA ("placebo") and cytokine mRNA treatment.

Figure 26C:
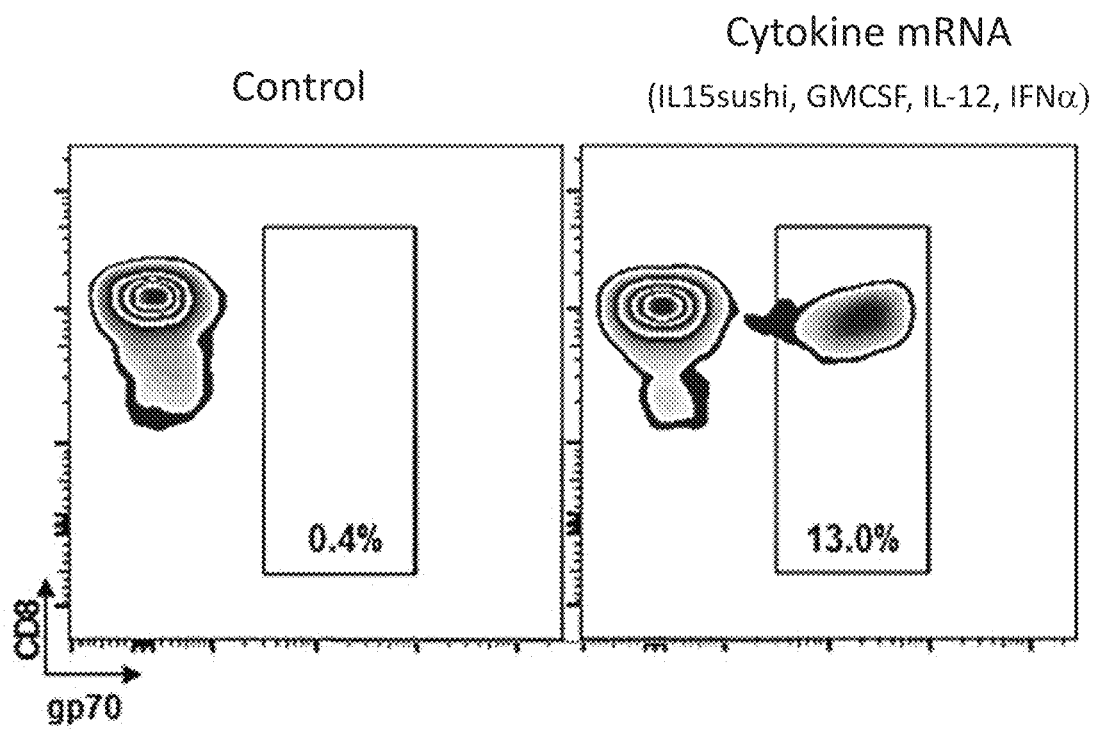
Figure 26C:
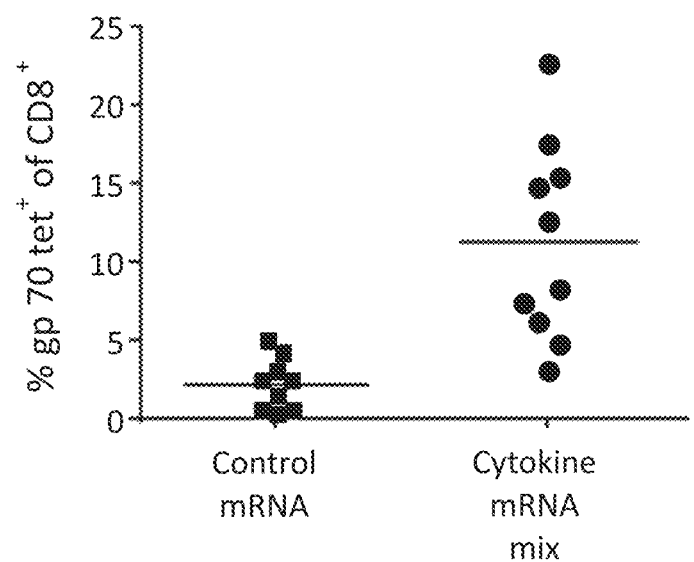

FIGS. 26A-26C show results of measurements of CD8+ T cells specific for the gp70 tumor antigen of gp70 in blood of CT26 tumor bearing mice that had received intratumoral administration of cytokine mRNA treatment and control mRNA, respectively. FIG. 26C shows exemplarily a FACS histogram of CD8+ T cells stained with anti-mouse CD8 antibody and with the gp70-specific tetramer derived from an animal that had received control mRNA and FIG. 26B shows the example from one animal treated with cytokine mRNA. FIG. 26C shows the analysis of percentage of gp70-specific CD8+ T-cells in blood 13 days after treatment start from 9 mice that had received four injections of control mRNA and 10 mice that had received 4 injections of cytokine mRNA.

Figure 27A:
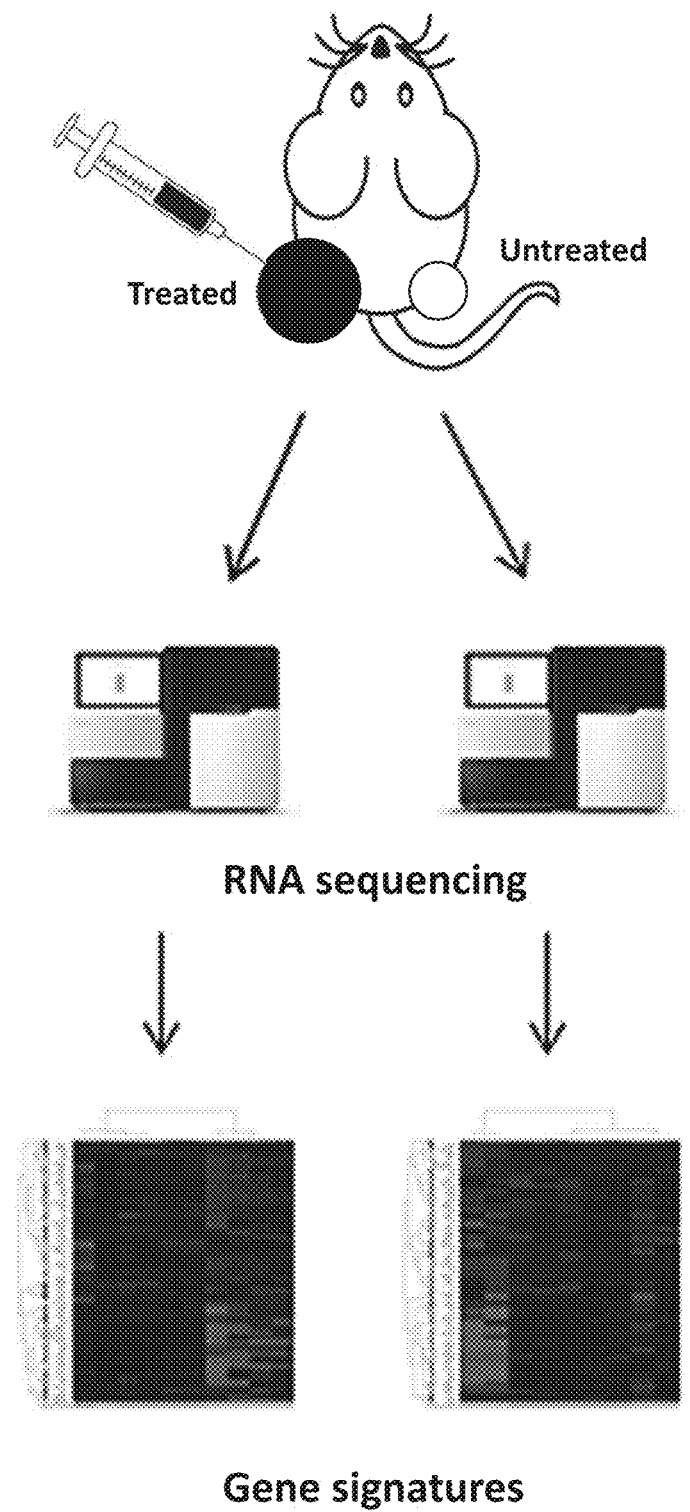
Figure 27C:
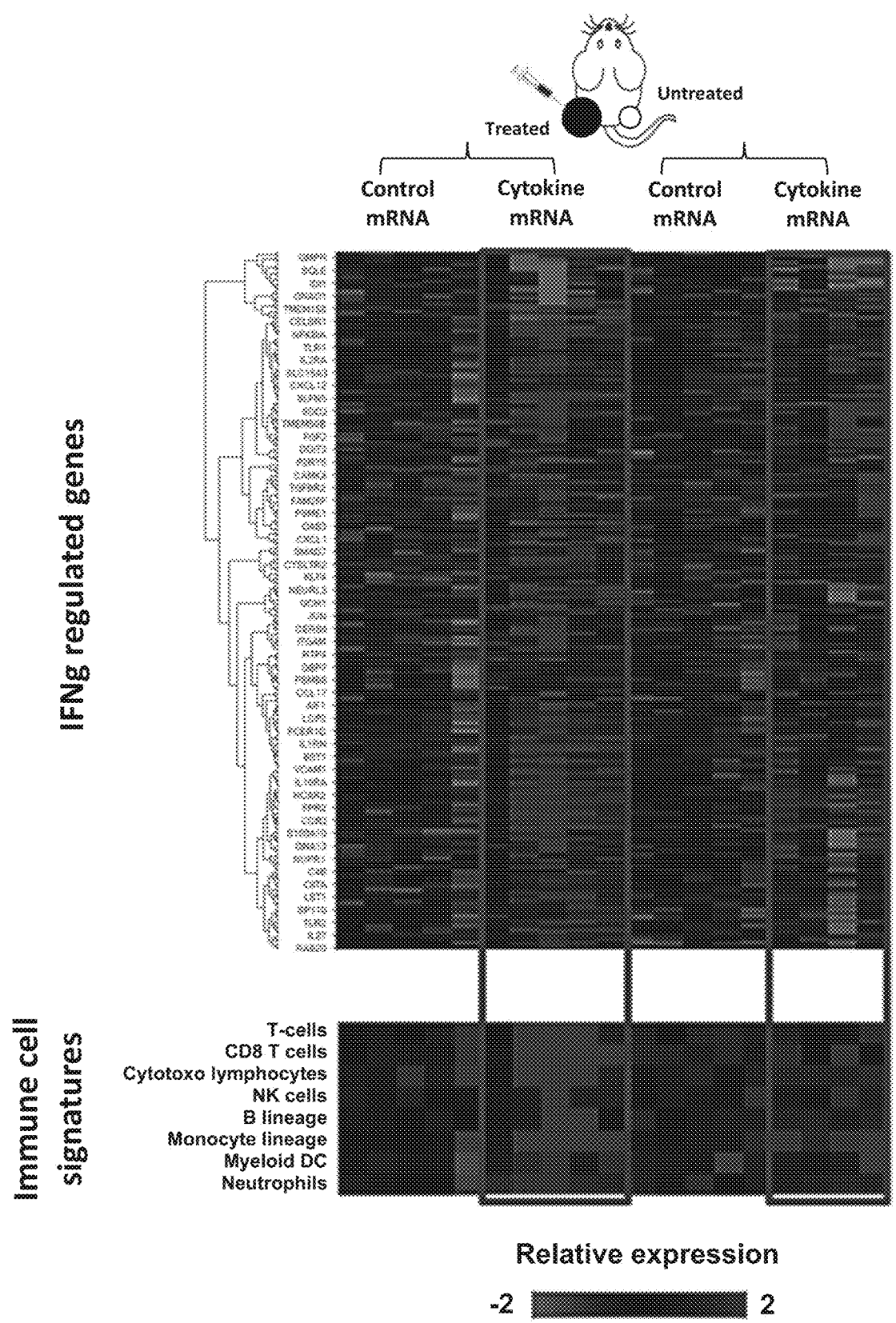

FIGS. 27A-27C show experiments where mice bearing B16F10 tumors on the left and right flanks received a single intratumoral mRNA injection with cytokine mRNA or control mRNA in only one tumor. On day 7 following the mRNA injection the left and right tumors were collected and subjected to RNA sequencing. FIG. 27B shows the results of ingenuity pathway analysis comparing the gene expression changes between the cytokine mRNA treatment vs control mRNA treated tumors. Causal network analysis for treated tumor side (Column 1) and untreated tumor side (Column 2) was performed and Activation Z score (Top half) and Inhibition Z score (Lower half) was analyzed to define pathways up and down regulated, respectively. FIG. 27 shows cluster analysis of injected and non-injected tumors was performed based on 327 interferon gamma regulated genes. Both the injected and non-injected tumors of mice treated with cytokine mRNA showed upregulation of multiple IFN gamma genes in comparison to mice treated with control mRNA.

FIGS. 28A-28D show fluorescence micrographs of cells from a B16F10 dualtumor model. Panel A shows the injected tumor treated with cytokine mRNA and panel B shows the corresponding uninjected tumor. Panel C shows the injected tumor treated with control mRNA and panel D shows the corresponding uninjected tumor. The slides were stained for CD4+, CD8+, and FoxP3+ cells.

Figure 28E:
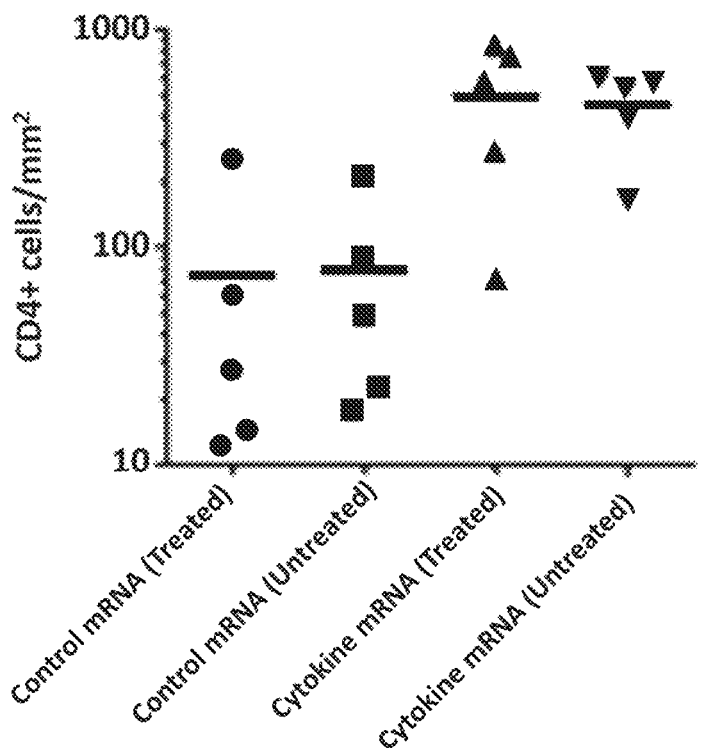
Figure 28F:
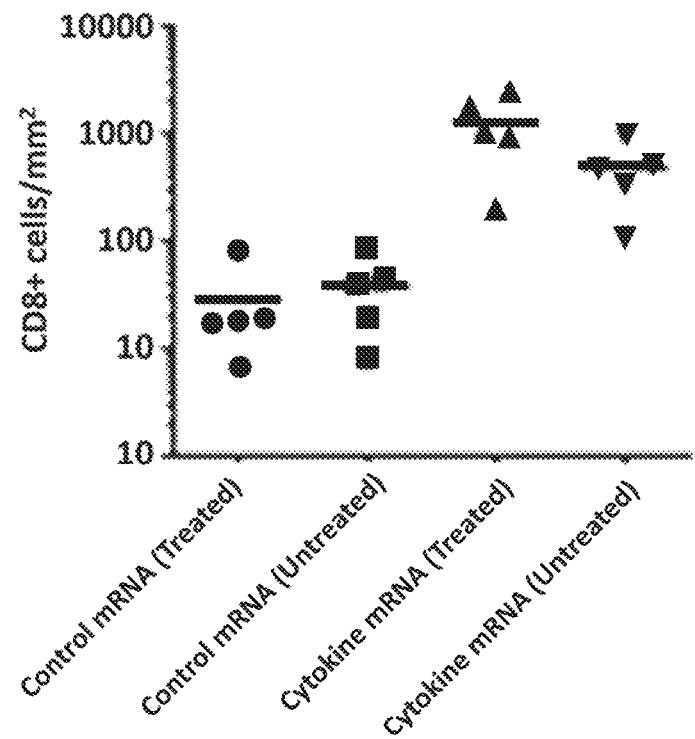
Figure 28G:
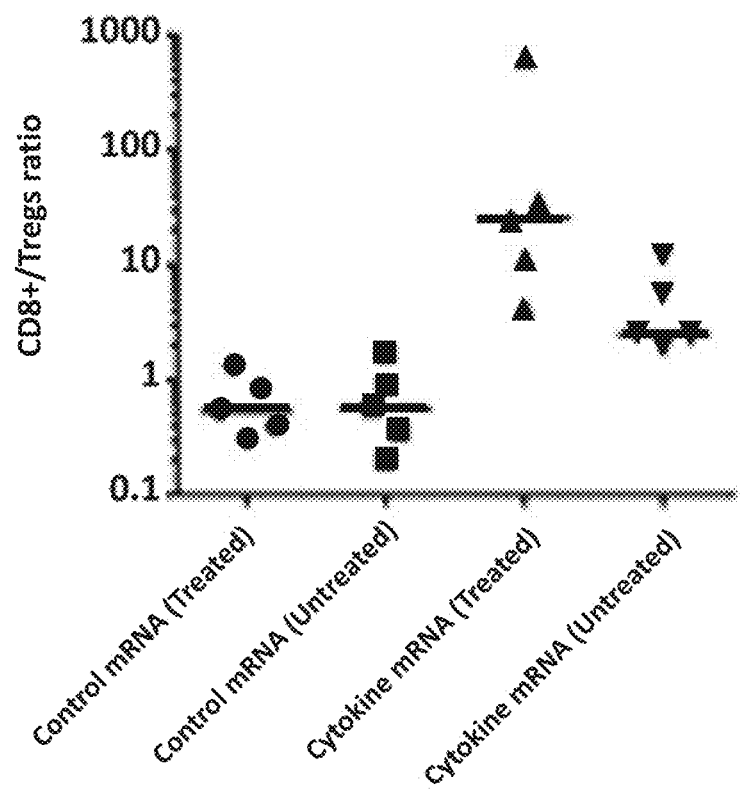
Figure 29A:
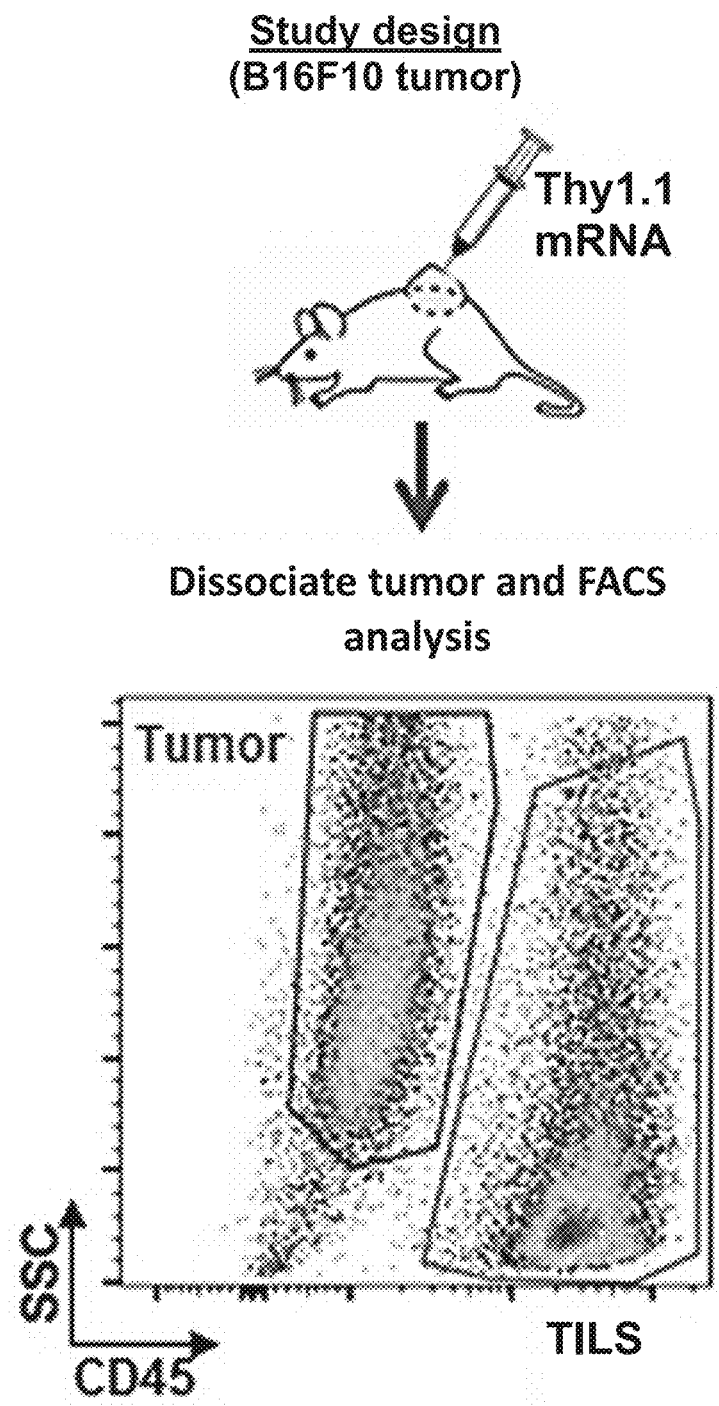
Figure 29F:
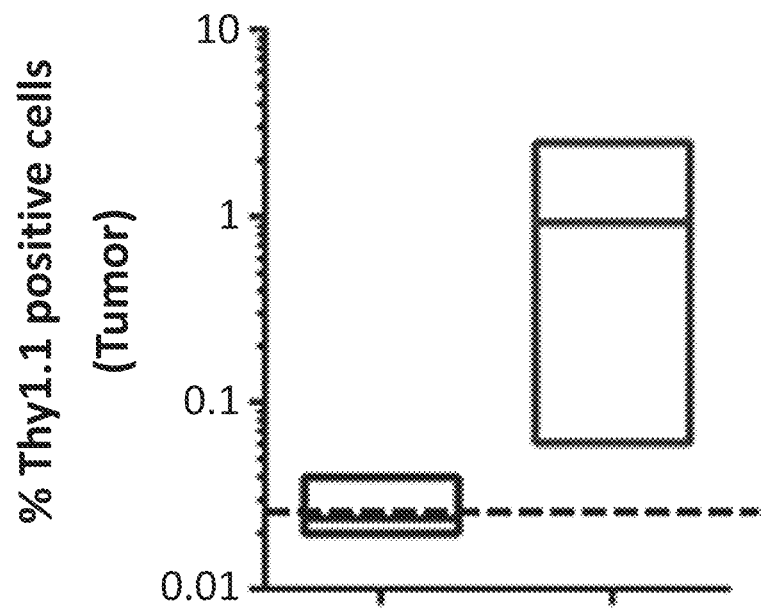
Figure 29G:
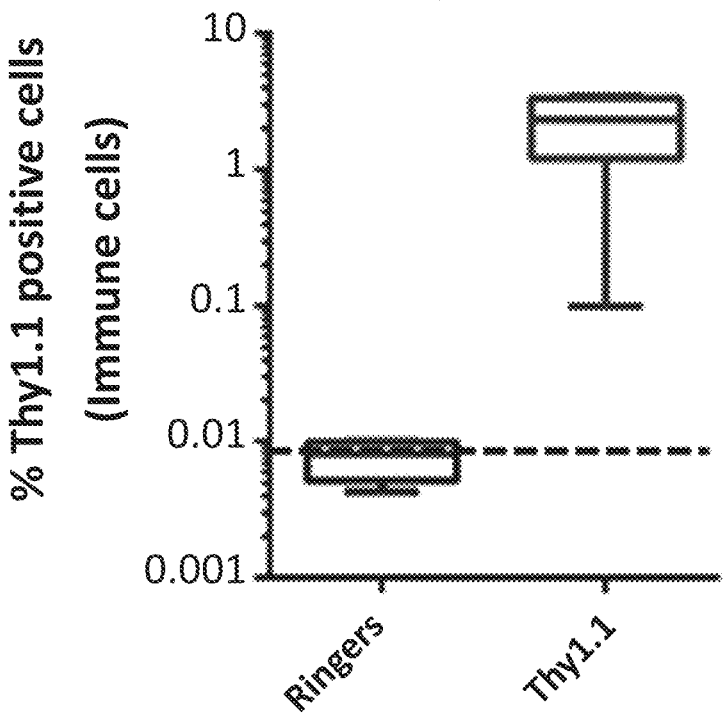
Figure 30A:
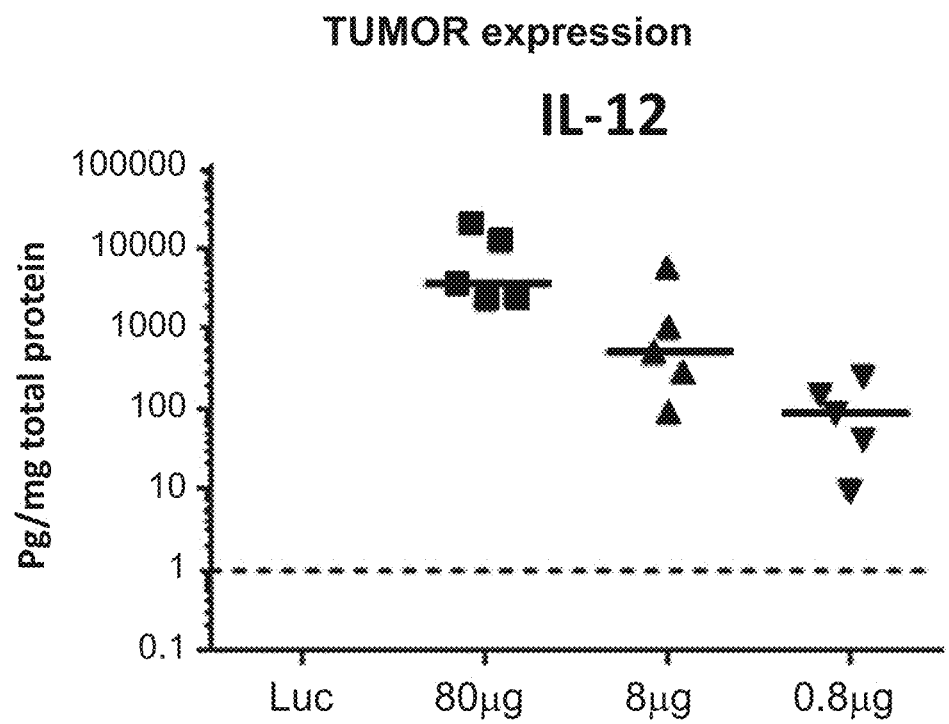
Figure 30B:
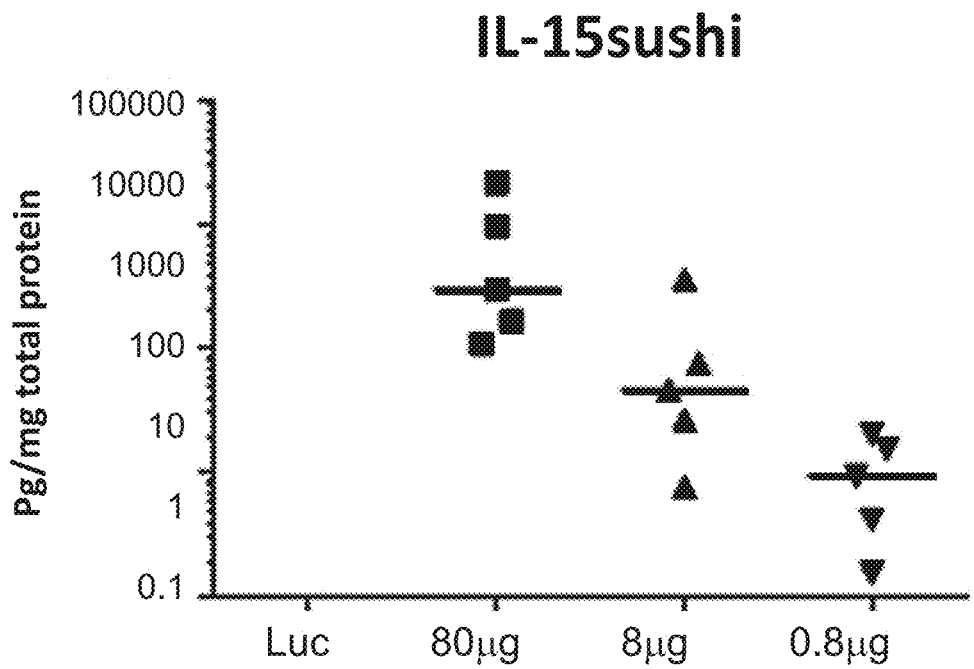
Figure 30C:
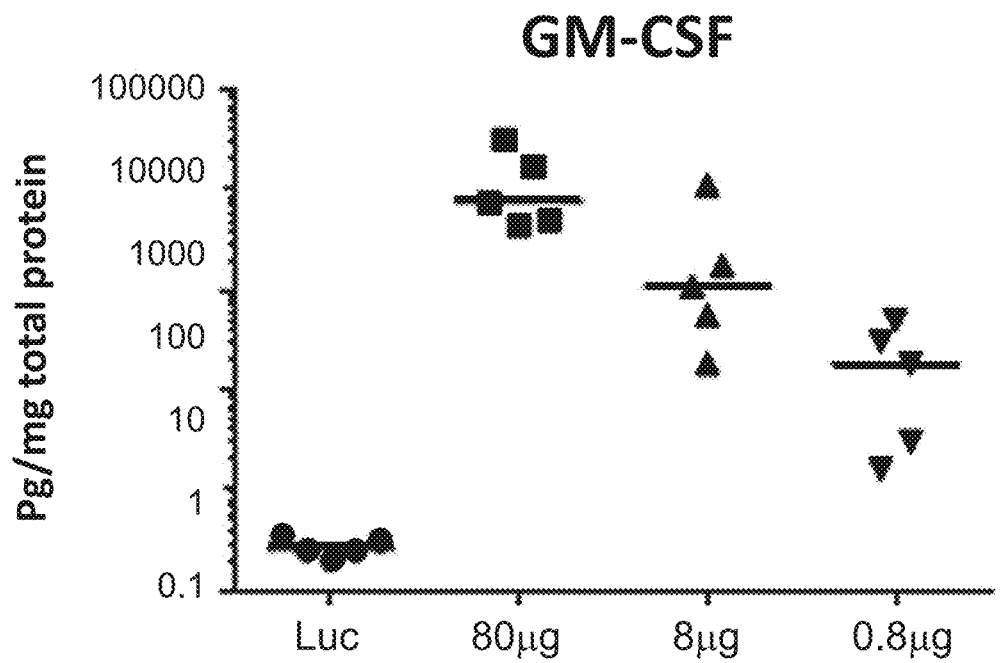
Figure 30D:
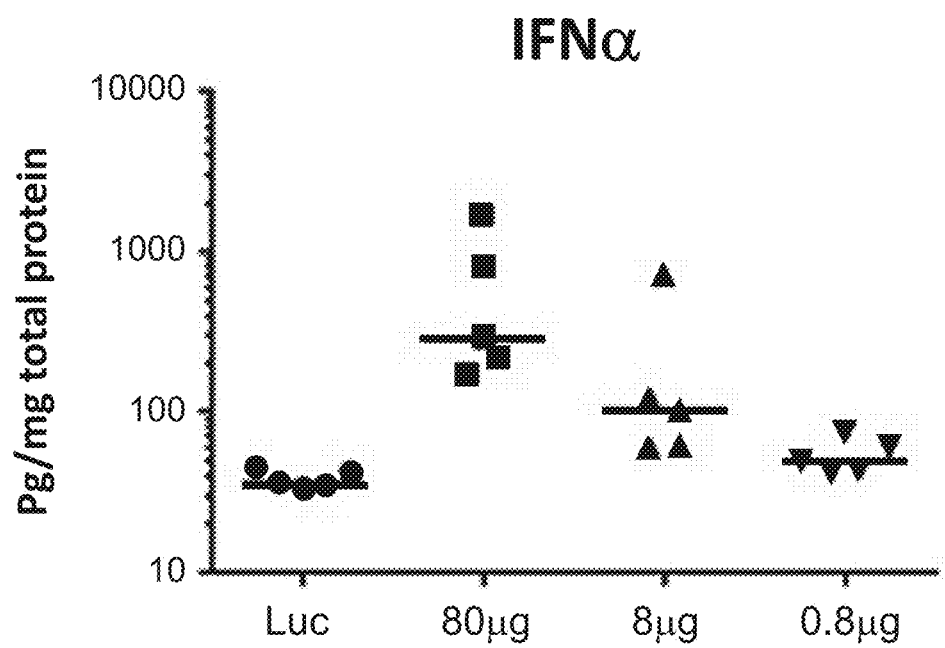
Figure 30E:
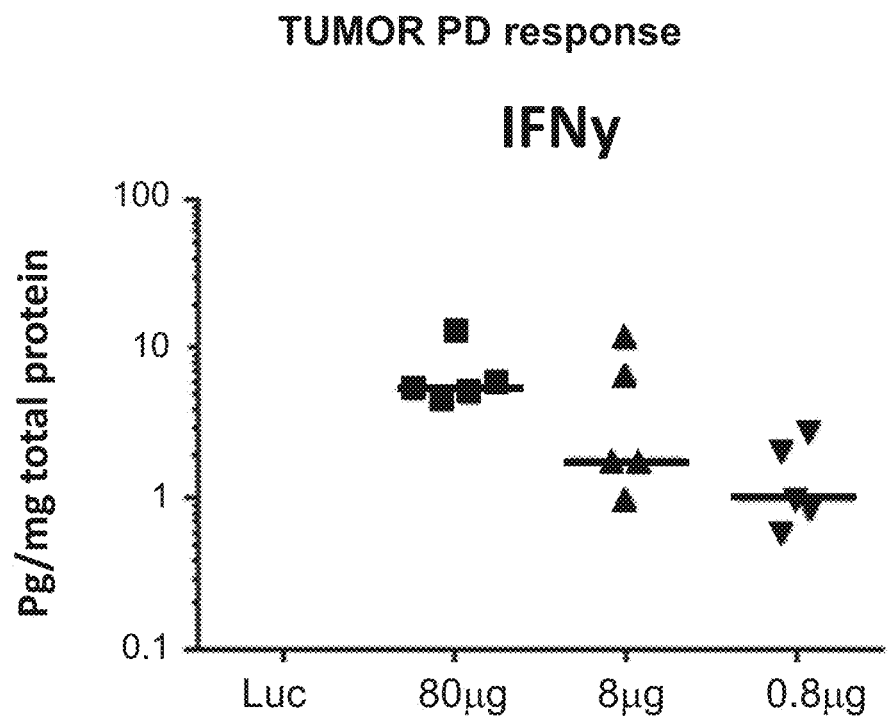
Figure 30F:
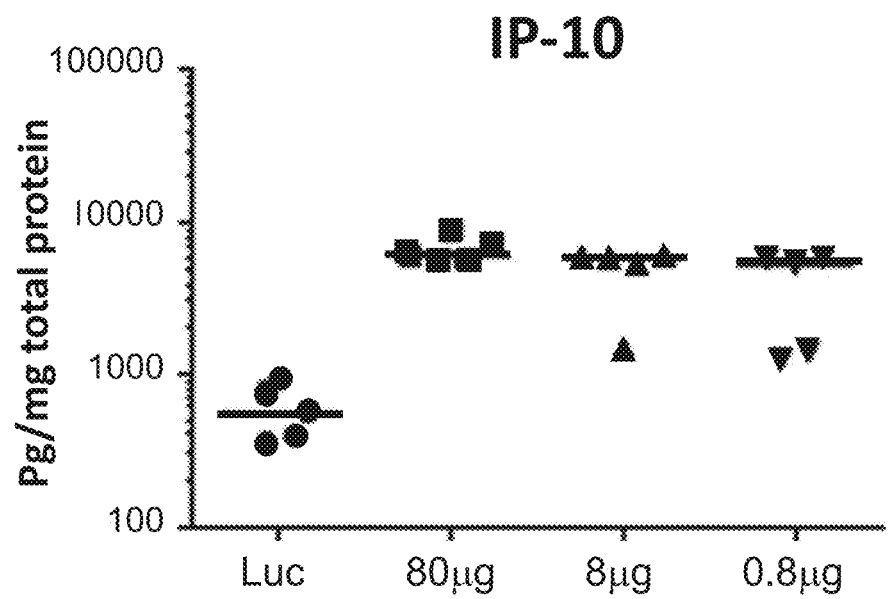

FIGS. 28E-G show frequency of CD4+, CD8+ and FOXP3+ cells quantified in the immunofluorescent images. The frequency of CD4+ and CD8+ cells/mm$^2$ is presented in FIGS. 28E and 28F. The ratio of the CD8+ frequency divided by FOXP3+ frequency is presented in FIG. 28G.

FIGS. 29A-29G show mice with a single B16F10 tumor received a single injection with either mRNA encoding the Thy1.1 cell surface protein or vehicle alone (Ringer's solution). At approximately 16-18 hours following intratumoral injection the tumor was excised, digested, stained with a panel of antibodies and analyzed by flow cytometry. The cell type and frequency of cells expressing Thy1.1 were characterized.

FIGS. 30A-30F show expression of the indicated proteins following various doses of cytokine mRNA or luciferase control mRNA detected in tumor lysates as described in Example 15. "IFNy" in FIG. 30E indicates IFNγ.

Figures 31A, 31B:
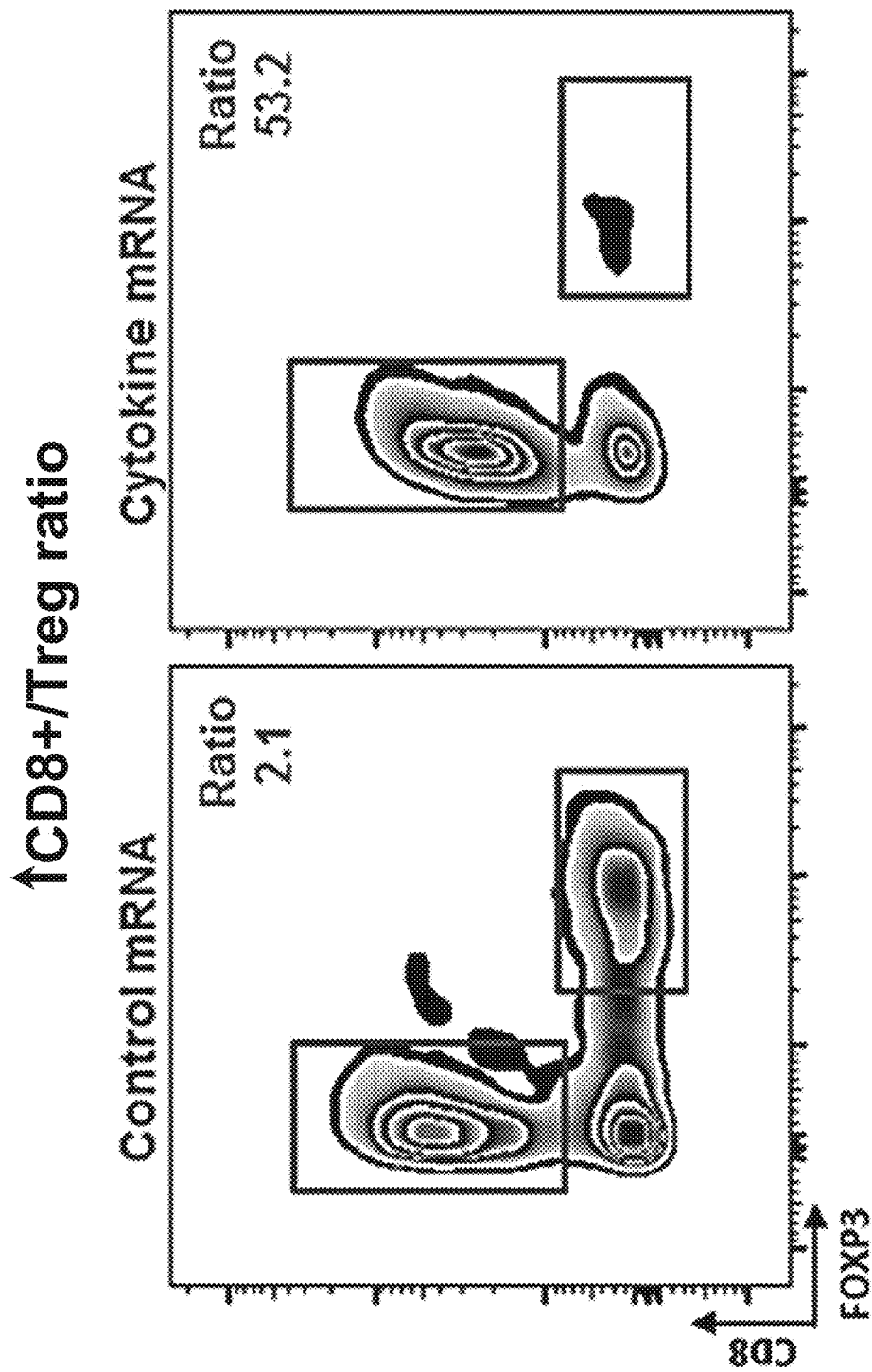

FIGS. 31A-31B show flow cytometry results for CD8+ and FOXP3+ (Treg) cells following control or cytokine mRNA treatments as described in Example 15. The observed ratio of CD8+ to Treg cells is shown in each panel.

Figures 31C, 31D:
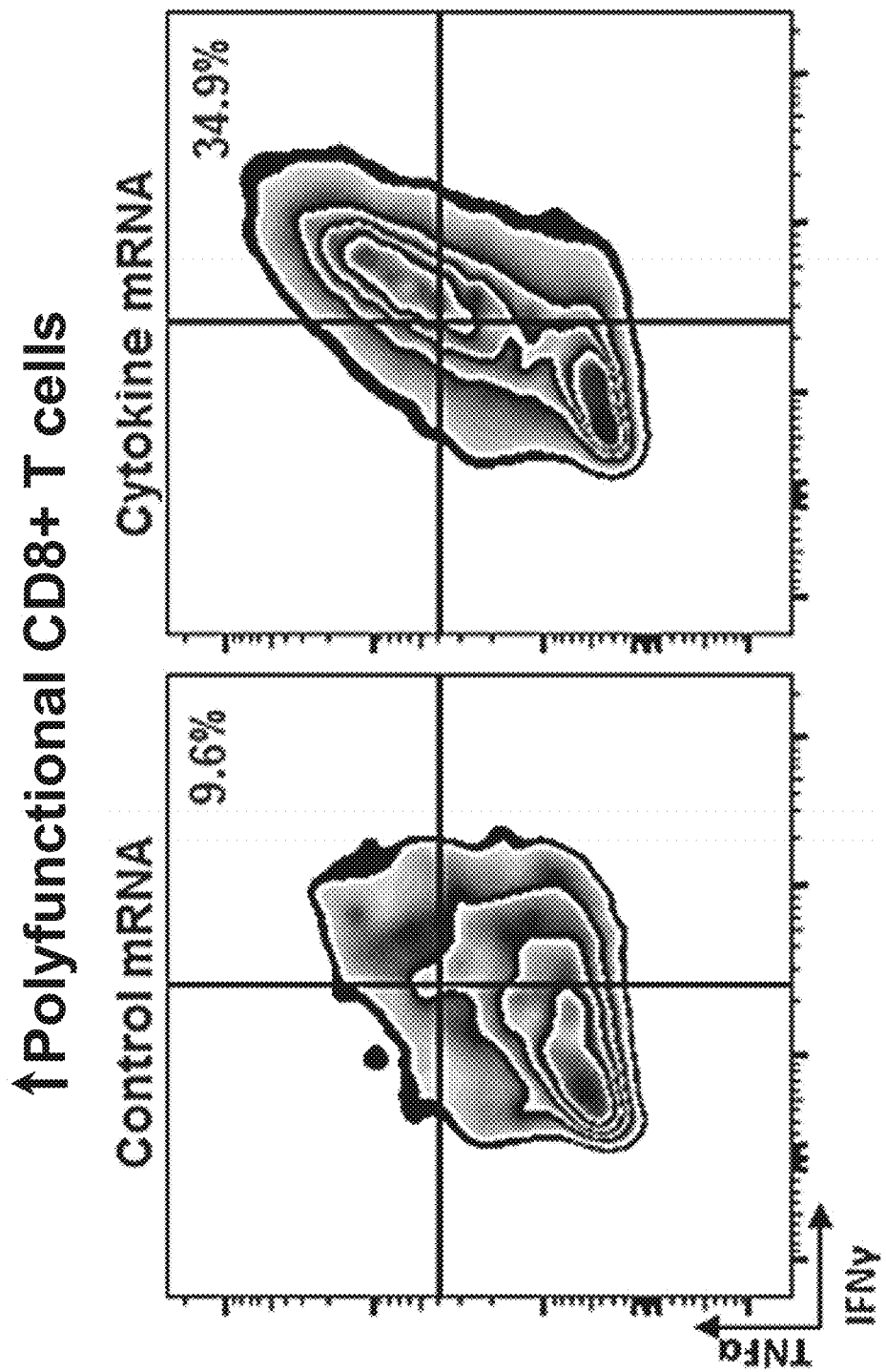

FIGS. 31C-31D show flow cytometry results for polyfunctional CD8+ T cells following control or cytokine mRNA treatments as described in Example 15. The proportion of polyfunctional CD8+ T cells is shown in each panel.

Figure 31E:
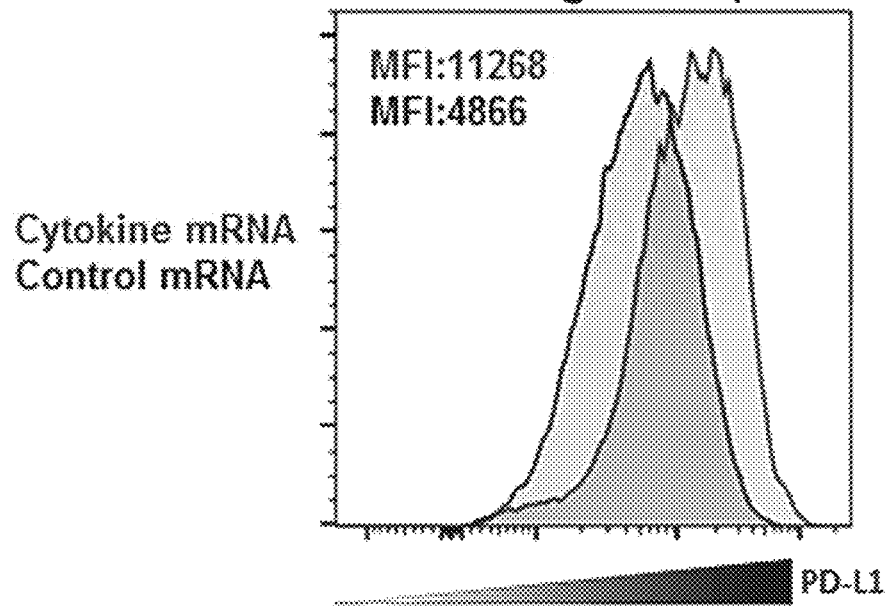

FIG. 31E shows the level of PD-L1 on infiltrating myeloid cells following control or cytokine mRNA treatments as described in Example 15.

Figure 31F:
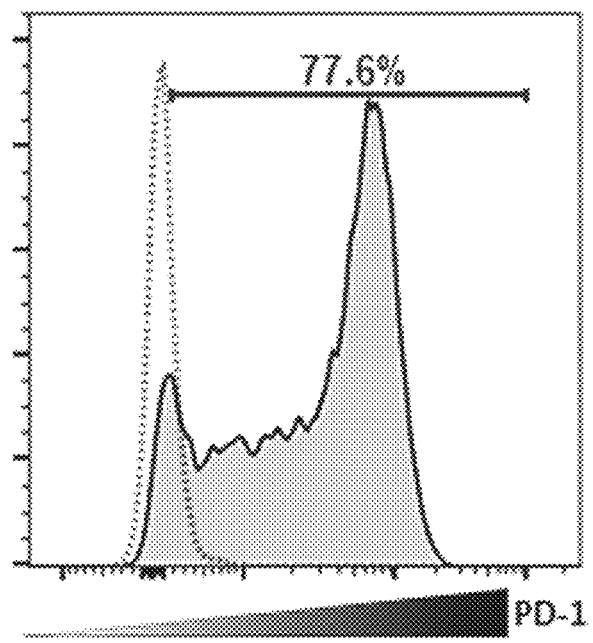

FIG. 31F shows the level of PD-1 on infiltrating CD8+ cells following control or cytokine mRNA treatments as described in Example 15.

Figure 31G:
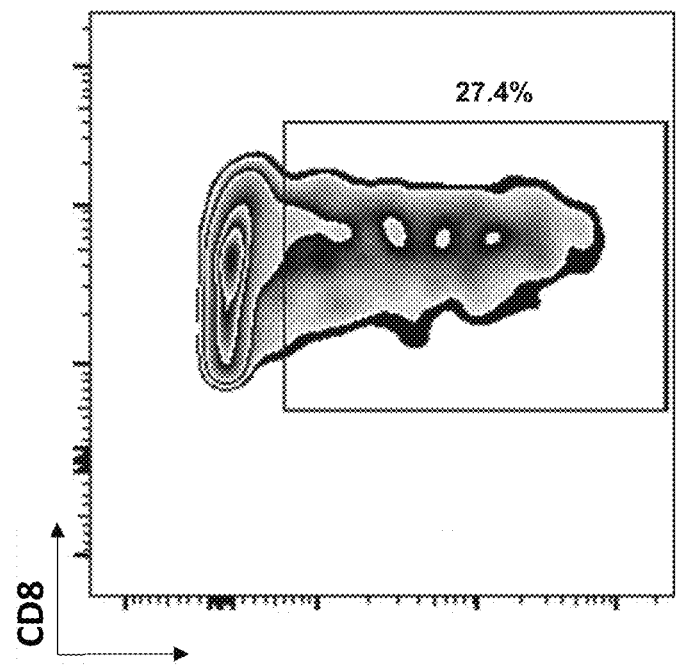
Figure 31H:
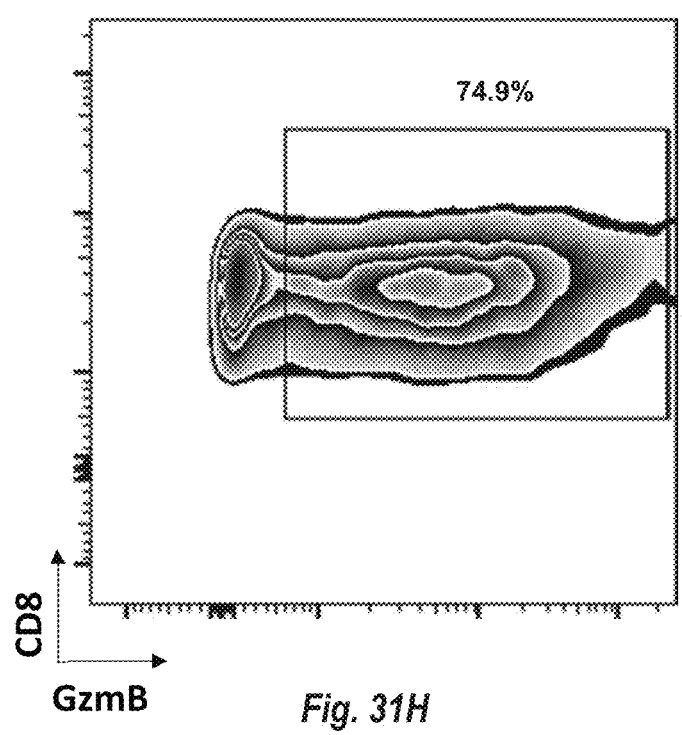

FIGS. 31G-H show the frequency of intratumoral Granzyme B CD8+ T cells following control or cytokine mRNA treatments as described in Example 15.

Figure 32A:
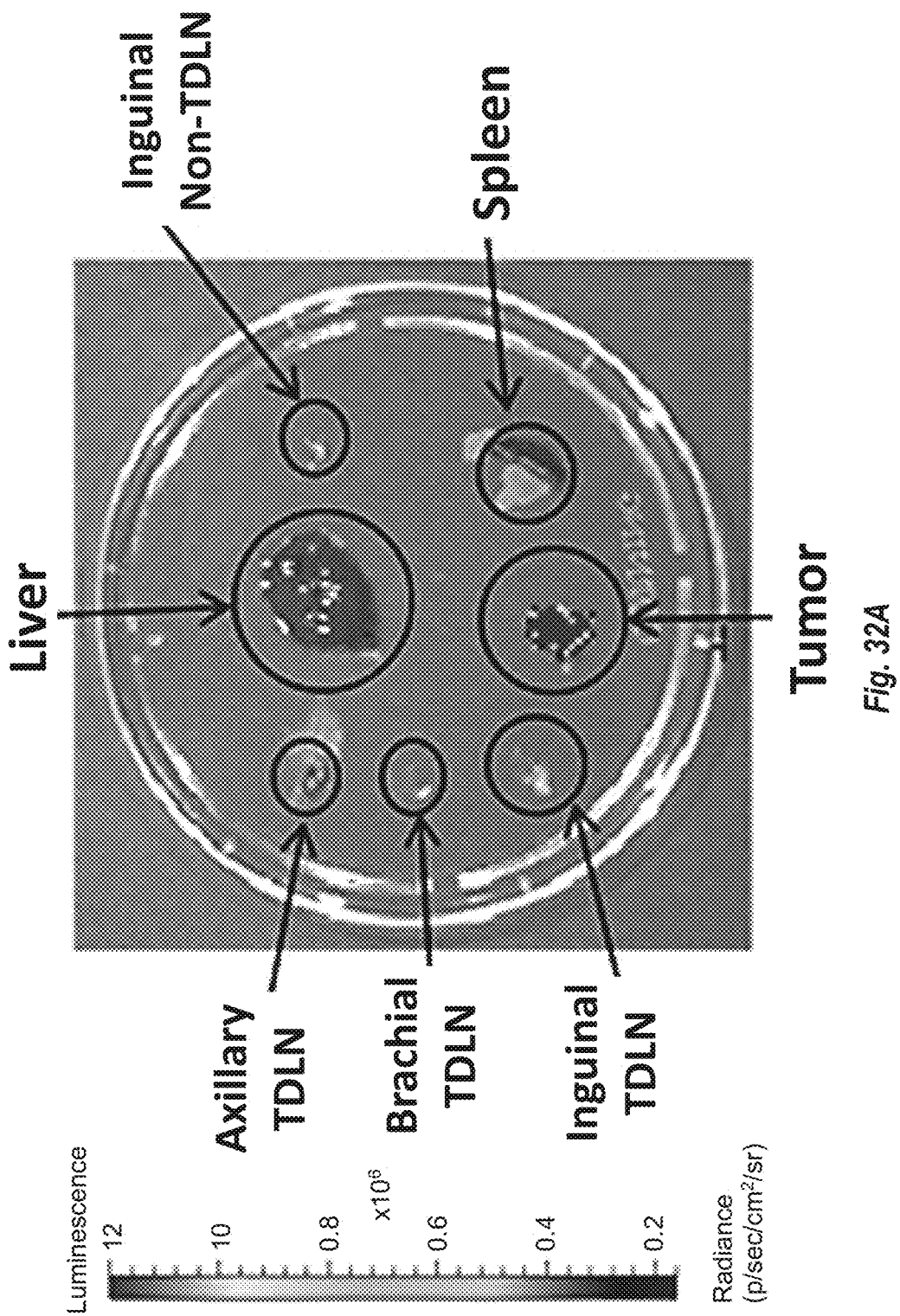
Figure 32B:
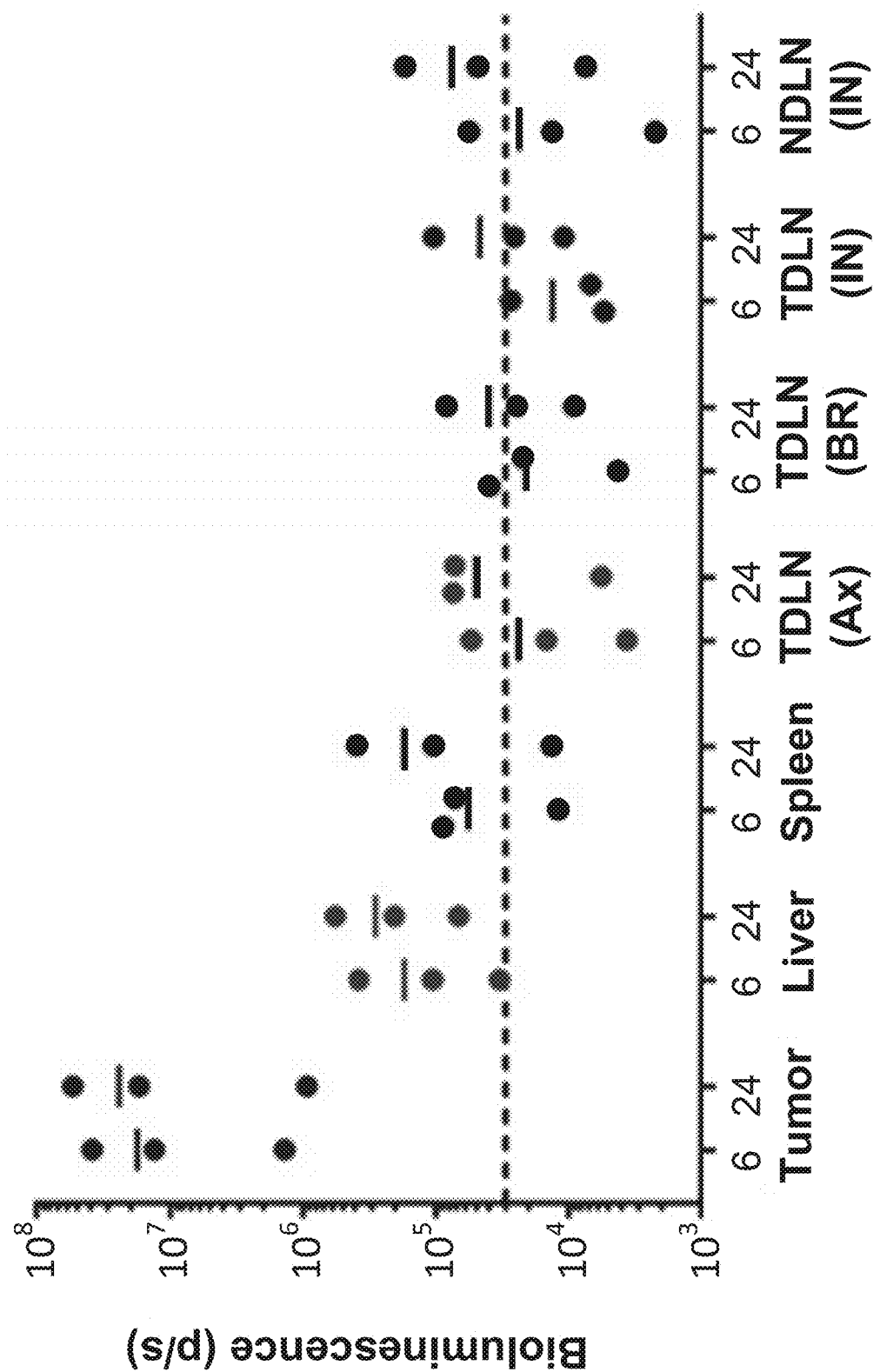

FIGS. 32A-32B show luciferase expression in various tissues following intratumoral injection of 50 μg mRNA encoding firefly luciferase as described in Example 16.

Figure 33:
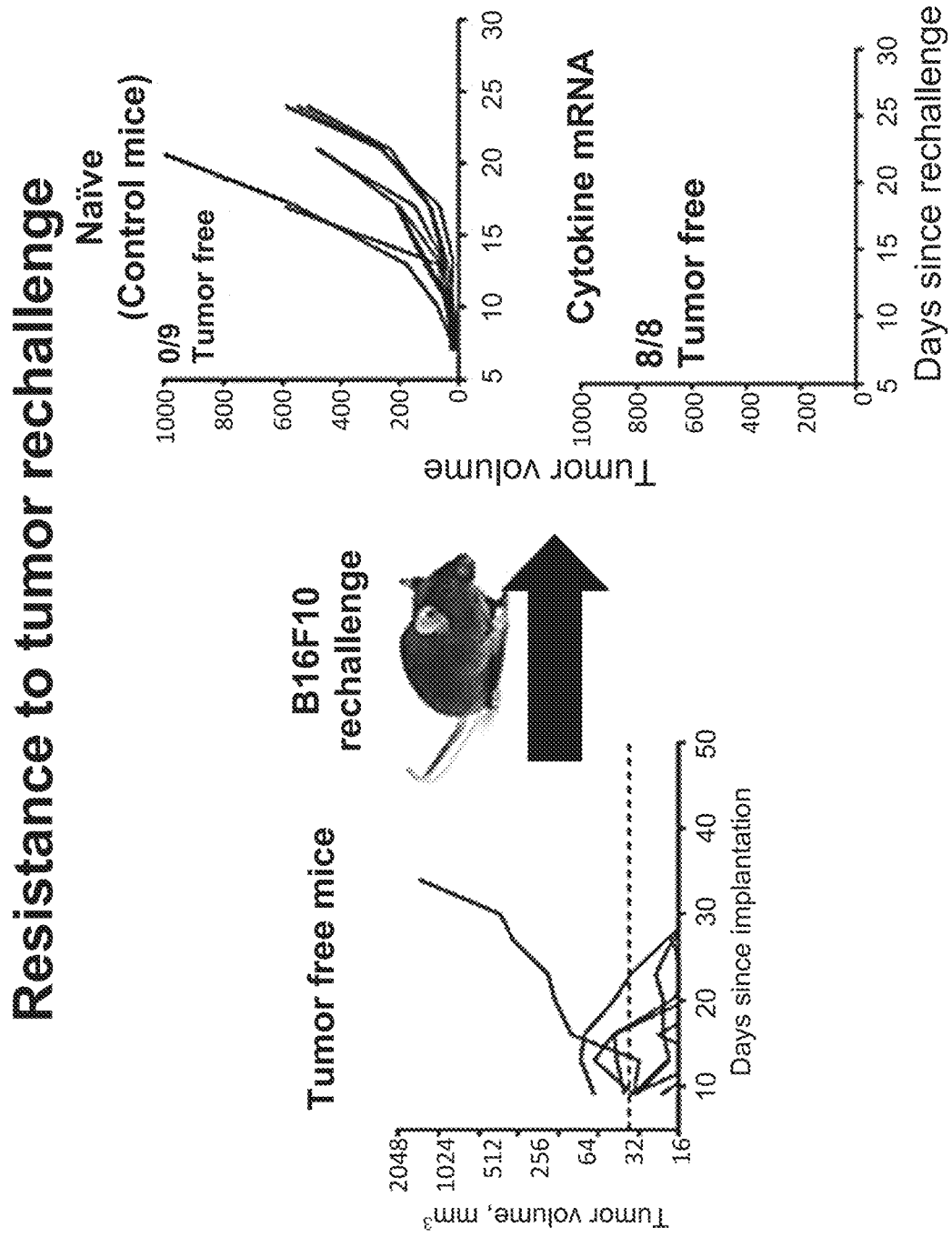

FIG. 33 shows data relating to an experiment essentially as shown in FIG. 12.

Figure 34:
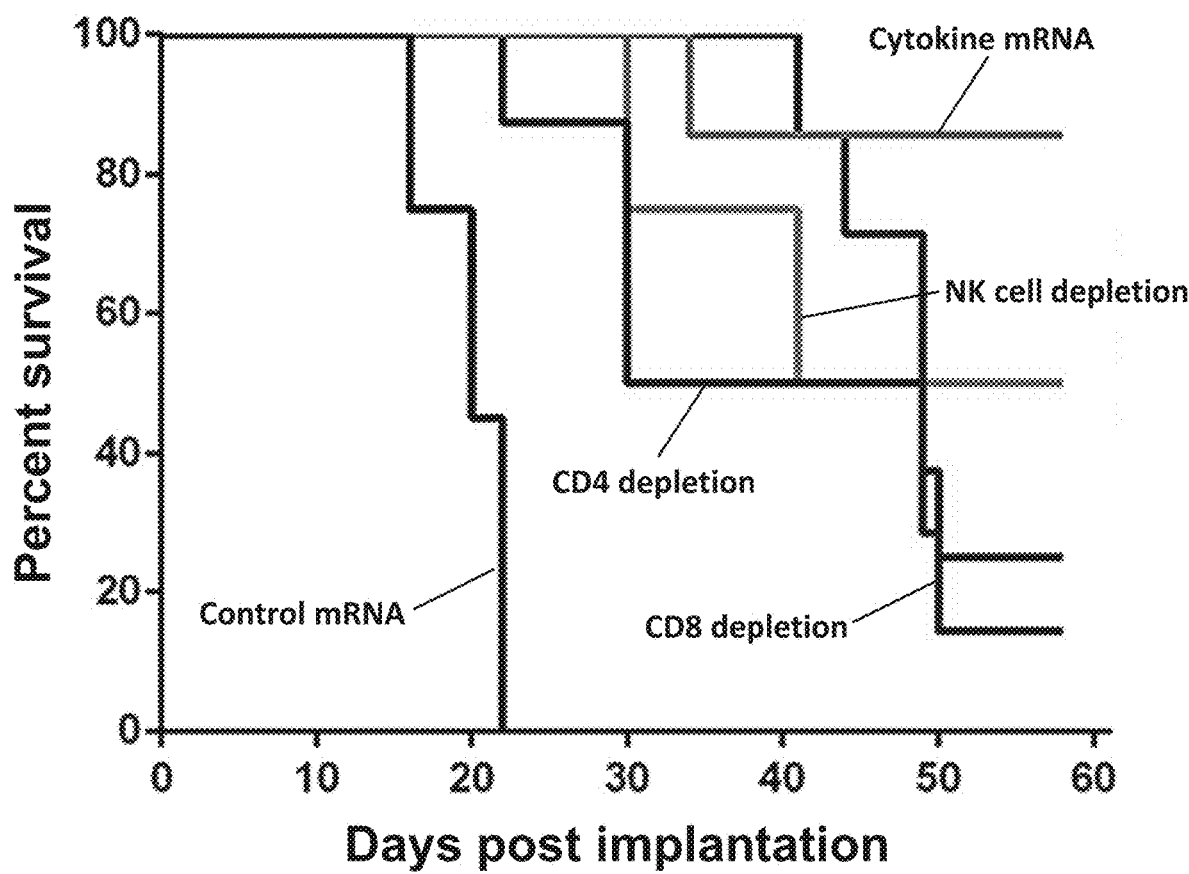

FIG. 34 shows the effect of depleting CD8+ T cells, CD4+ T cells or NK cells before treatment with cytokine mRNAs on survival in mice bearing B16F10 tumors as described in Example 17.

Figure 35:
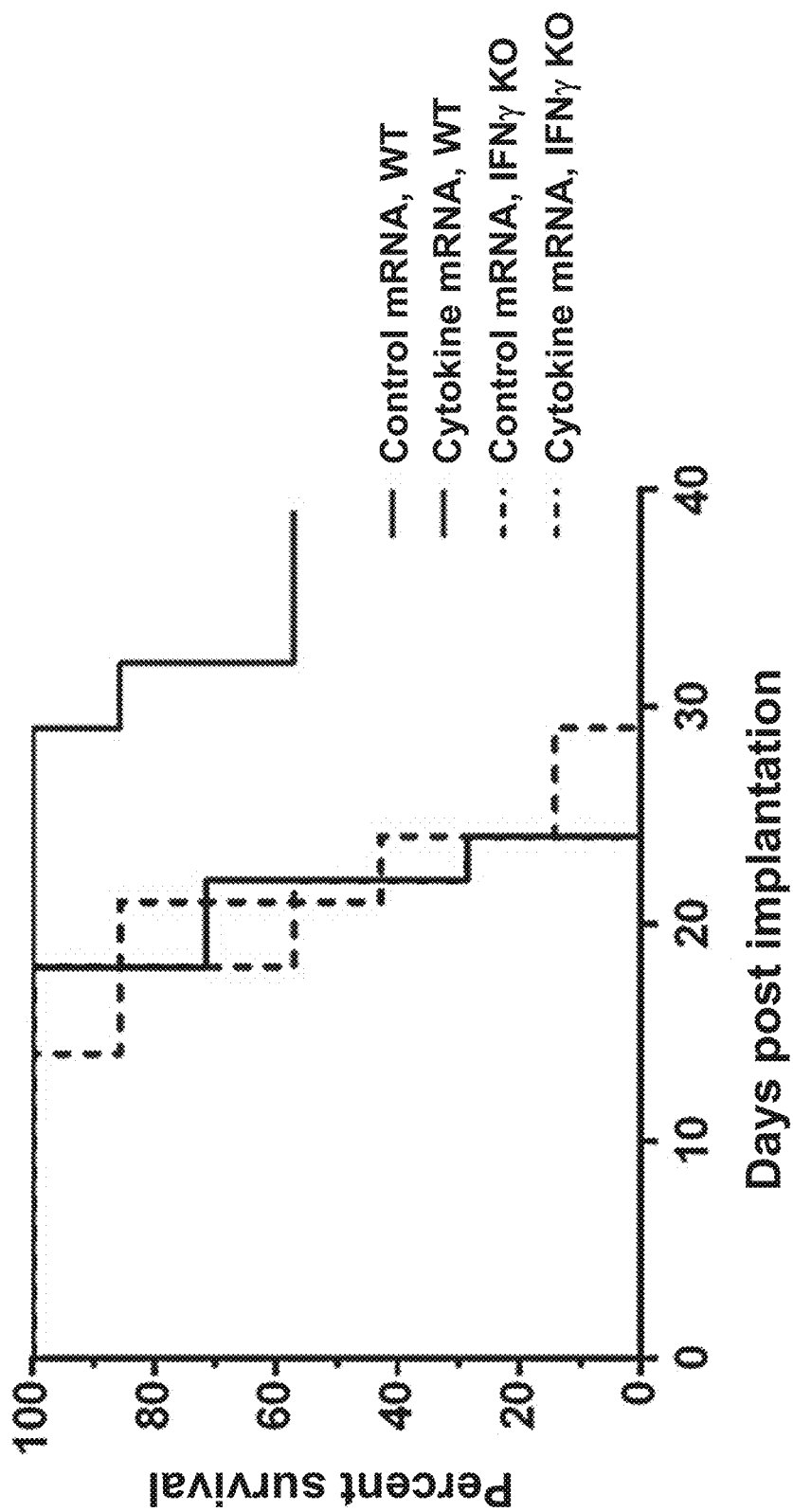

FIG. 35 shows survival of WT and IFNγ KO mice implanted with B16F10 tumor cells as described in Example 1 and treated with control or cytokine mRNAs as described in Example 18.

Figure 36:
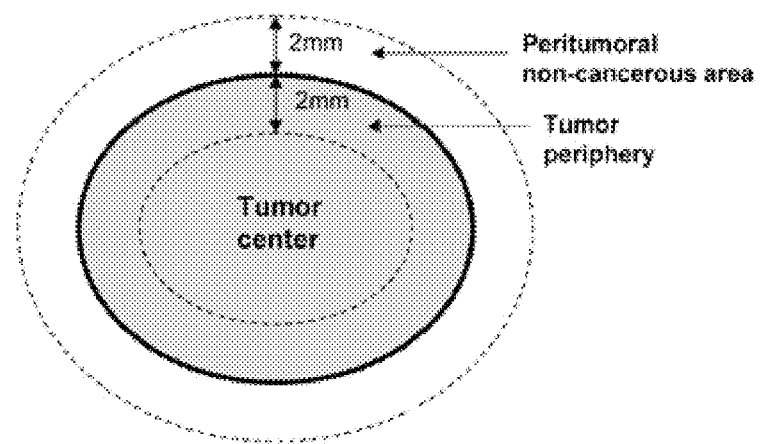

FIG. 36 shows a "peri-tumorally," or "peri-tumoral," area that is about 2-mm wide and is adjacent to the invasive front of the tumor periphery. The peri-tumoral area comprises host tissue.

DESCRIPTION OF THE SEQUENCES

Tables 1 and 2 provide a listing of certain sequences referenced herein.

TABLE 1

DESCRIPTION OF THE SEQUENCES (human sequences)

| SEQ ID NO: | Description | SEQUENCE |
|---|---|---|
| | | 5' UTR |
| 1 | ModA 5' UTR (DNA) | GGGCGAACTAGTATTCTTCTGGTCCCCACAGACTCAGAGAGAACCCGCCACC |
| 2 | ModA 5' UTR (RNA) | GGGCGAACUAGUAUUCUUCUGGUCCCCACAGACUCAGAGAGAACCCGCCACC |
| 3 | ModB 5' UTR (DNA) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCC |
| 4 | ModB 5' UTR (RNA) | GGAAUAAACUAGUCUCAACACAACAUAUACAAAACAAACGAAUCUCAAGCAAUCAAGCAUUCUACUUCUAUUGCAGCAAUUUAAAUCA UUUCUUUUAAAGCAAAAGCAAUUUUCUGAAAAUUUUCACCAUUUACGAACGAUAGCC |
| 5 | Alternative Mod 5' UTR (DNA) | AGACGAACTAGTATTCTTCTGGTCCCCACAGACTCAGAGAGAACCCGCCACC |
| 6 | Alternative Mod 5' UTR (RNA) | AGACGAACUAGUAUUCUUCUGGUCCCCACAGACUCAGAGAGAACCCGCCACC |
| | | 3' UTR |
| 7 | ModA/B 3' UTR (DNA) | CTCGAGCTGGTACTGCATGCACGCAATGCTAGCTGCCCCTTTCCCGTCCTGGGTACCCCGAGTCTCCCCCGACCTCGGGTCCCAGGTA TGCTCCCACCTCCACCTGCCCCACTCACCACCTCTGCTAGTTCCAGACACCTCCCAAGCACGCAGCAATGCAGCTCAAAACGCTTAGC CTAGCCACACCCCCACGGGAAACAGCAGTGATTAACCTTTAGCAATAAACGAAAGTTTAACTAAGCTATACTAACCCCAGGGTTGGTC AATTTCGTGCCAGCCACACCGAGACCTGGTCCAGAGTCGCTAGCCGCGTCGCTAAAAAAAAAAAAAAAAAAAAAAAAAAAAAAGCATA TGACTAAAAAAAAAAAAAAAAAAAAAAAAAAAAAAAAAAAAAAAAAAAAAAAAAAAAAAAAAAAAAAAAAAAAAAAAA |
| 8 | ModA/B 3' UTR (RNA) | CUCGAGCUGGUACUGCAUGCACGCAAUGCUAGCUGCCCCUUUCCCGUCCUGGGUACCCCGAGUCUCCCCCGACCUCGGGUCCCAGGUA UGCUCCCACCUCCACCUGCCCCACUCACCACCUCUGCUAGUUCCAGACACCUCCCAAGCACGCAGCAAUGCAGCUCAAAACGCUUAGC CUAGCCACACCCCCACGGGAAACAGCAGUGAUUAACCUUUAGCAAUAAACGAAAGUUUAACUAAGCUAUACUAACCCCAGGGUUGGUC AAUUUCGUGCCAGCCACACCGAGACCUGGUCCAGAGUCGCUAGCCGCGUCGCUAAAAAAAAAAAAAAAAAAAAAAAAAAAAAAGCAUA UGACUAAAAAAAAAAAAAAAAAAAAAAAAAAAAAAAAAAAAAAAAAAAAAAAAAAAAAAAAAAAAAAAAAAAAAAAAA |
| | | IL-2 |
| 9 | Human IL-2 (amino acid) | MYRMQLLSCIALSLALVTNSAPTSSSTKKTQLQLEHLLLDLQMILNGINNYKNPKLTRMLTFKFYMPKKATELKHLQCLEEELKPLEE VLNLAQSKNFHLRPRDLISNINVIVLELKGSETTFMCEYADETATIVEFLNRWITFCQSIISTLT |
| 10 | Human non-optimized IL-2 (CDS DNA) | ATGTACAGGATGCAACTCCTGTCTTGCATTGCACTAAGTCTTGCACTTGTCACAAACAGTGCACCTACTTCAAGTTCTACAAAGAAAA CACAGCTACAACTGGAGCATTTACTGCTGGATTTACAGATGATTTTGAATGGAATTAATAATTACAAGAATCCCAAACTCACCAGGAT GCTCACATTTAAGTTTTACATGCCCAAGAAGGCCACAGAACTGAAACATCTTCAGTGTCTAGAAGAAGAACTCAAACCTCTGGAGGAA GTGCTAAATTTAGCTCAAAGCAAAAACTTTCACTTAAGACCCAGGGACTTAATCAGCAATATCAACGTAATAGTTCTGGAACTAAAGG GATCTGAAACAACATTCATGTGTGAATATGCTGATGAGACAGCAACCATTGTAGAATTTCTGAACAGATGGATTACCTTTTGTCAAAG CATCATCTCAACACTGACTTGATGA |

TABLE 1-continued

DESCRIPTION OF THE SEQUENCES (human sequences)

| SEQ ID NO: | Description | SEQUENCE |
|---|---|---|
| 11 | Human optimized IL-2 (CDS DNA) | ATGTACAGAATGCAGCTGCTGTCTTGCATTGCTCTTTCTCTTGCTCTTGTGACAAATTCTGCTCCAACATCTTCTTCAACAAAGAAA<br>CACAGCTTCAGCTTGAACACCTTCTTCTTGATCTTCAGATGATTCTGAATGGAATCAACAATTACAAAAATCCAAAACTGACAAGAAT<br>GCTGACATTTAAATTTTACATGCCAAAGAAAGCAACGAACTGAAACACCTTCAGTGCCTTGAAGAAGAACTGAAACCTCTGGAAGAA<br>GTGCTGAATCTGGCTCAGAGCAAAAATTTTCACCTGAGACCAAGAGATCTGATCAGCAACATCAATGTGATTGTGCTGGAACTGAAAG<br>GATCTGAAACAACATTCATGTGTGAATATGCTGATGAAACAGCAACAATTGTGGAATTTCTGAACAGATGGATCACATTTTGCCAGTC<br>AATCATTTCAACACTGACATGATGA |
| 12 | Human non-optimized IL-2 (RNA encoding CDS) | AUGUACAGGAUGCAACUCCUGCUCUUGCAUUGCACUAAGUCUUGCACUUGUCACAAACAGUGCACCUACUUCAAGUUCUACAAAGAAAA<br>CACAGCUACAACUGGAGCAUUUACUGCUGGAUUUACAGAUGAUUUUGAAUGGAAUUAAUAAUUACAAGAAUCCCAAACUCACCAGGAU<br>GCUCACAUUUAAGUUUUACAUGCCCAAGAAGGCCACAGAACUGAAACUUCAGUGCUCUAGAAGAAGAACUCAAACCUCUGGAGGAA<br>GUGCUAAAUUUAGCUCAAAGCAAAAACUUUCACUUAAGACCCAGGGACUUAAUCAGCAAUAUCAACGUAAAUAGUUCUGGAACUAAAGG<br>GAUCUGAAACAACAUUCAUGUGUGAAUAUGCUGAUGAGACAGCAACAAUUGUAGAAUUUCUGAACAGAUGGAUUACCUUUUGUCAAAG<br>CAUCAUCUCAACACUGACUUGAUGA |
| 13 | Human optimized IL-2 (RNA encoding CDS) | AUGUACAGAAUGCAGCUGCUGUCUUGCAUUGCUCUUUCUCUUGCUCUUGUGACAAAUUCUGCUCCAACAUCUUCUUCAACAAAGAAAA<br>CACAGCUUCAGCUUGAACACCUUCUUCUUGAUCUUCAUGAUUCUGAAUGGAAUCAACAAUUACAAAAAUCCAAAACUGACAAGAAU<br>GCUGACAUUUAAAUUUUACAUGCCAAAGAAAGCAACAGAACUGAAACACCUUCAGUGCCUUGAAGAAGAACUGAAACCUCUGGAAGAA<br>GUGCUGAAUCUGGCUCAGAGCAAAAAUUUUCACCUGAGACCAAGAGAUCUGAUCAGCAACAUCAAUGUGAUUGUGCUGGAACUGAAAG<br>GAUCUGAAACAACAUUCAUGUGUGAAUAUGCUGAUGAAACAGCAACAAUUGUGGAAUUUCUGAACAGAUGGAUCACAUUUUGCCAGUC<br>AAUCAUUUCAACACUGACAUGAUGA |

IL-12sc

| SEQ ID NO: | Description | SEQUENCE |
|---|---|---|
| 14 | Human IL-12sc (amino acid) | MCHQQLVISWFSLVFLASPLVAIWELKKDVYVVELDWYPDAPGEMVVLTCDTPEEDGITWTLDQSSEVLGSGKTLTIQVKEFGDAGQY<br>TCHKGGEVLSHSLLLLHKKEDGIWSTDILKDQKEPKNKTFLRCEAKNYSGRFTCWWLTTISTDLTFSVKSSRGSSDPQGVTCGAATLS<br>AERVRGDNKEYEYSVECQEDSACPAAEESLPIEVMVDAVHKLKYENYTSSFFIRDIIKPDPPKNLQLKPLKNSRQVEVSWEYPDTWST<br>PHSYFSLTFCVQVQGKSKREKKDRVFTDKTSATVICRKNASISVRAQDRYYSSSWSEWASVPCSGSSGGGGSPGGGSSRNLPVATPDP<br>GMFPCLHHSQNLLRAVSNMLQKARQTLEFYPCTSEEIDHEDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQALNFNSETVPQKSSLEEPDFYKTKIKLCILLHAFRIRAVT<br>IDRVMSYLNAS |
| 15 | Human non-optimized IL-12sc (CDS DNA) Sequence annotation CAPS: p40 domain; CAPS: linker; CAPS: p35. | ATGTGTCACCAGCAGTTGGTCATCTCTTGGTTTTCCCTGGTTTTTCTGGCATCTCCCCTCGTGGCCATATGGGAACTGAAGAAAGATG<br>TTTATGTCGTAGAATTGGATTGGTATCCGGATGCCCCTGGAGAAATGGTGGTCCTCACCTGTGACACCCCTGAAGAAGATGGTATCAC<br>CTGGACCTTGGACCAGAGCAGTGAGGTCTTAGGCTCTGGCAAAACCCTGACCATCCAAGTCAAAGAGTTTGGAGATGCTGGCCAGTAC<br>ACCTGTCACAAAGGAGGCGAGGTTCTAAGCCATTCGCTCCTGCTGCTTCACAAAAAGGAAGATGGAATTTGGTCCACTGATATTTTAA<br>AGGACCAGAAAGAACCCAAAAATAAGACCTTTCTAAGATGCGAGGCCAAGAATTATTCTGGACGTTTCACCTGCTGGTGGCTGACGAC<br>AATCAGTACTGATTTGACATTCAGTGTCAAAAGCAGCAGAGGGTCTTCTGACCCCCAAGGGGTGACGTGCGGAGCTGCTACACTCTCT<br>GCAGAGAGAGTCAGAGGGGACAACAAGGAGTATGAGTACTCAGTGGAGTGCCAGGAGGACAGTGCCTGCCCAGCTGCTGAGGAGAGTC<br>TGCCCATTGAGGTCATGGTGGATGCCGTTCACAAGCTCAAGTATGAAAACTACACCAGCAGCTTCTTCATCAGGGACATCATCAAACC<br>TGACCCACCCAAGAACTTGCAGCTGAAGCCATTAAAGAATTCTCGGCAGGTGGAGGTCAGCTGGGAGTACCCTGACACCTGGAGTACT<br>CCACATTCCTACTTCTCCCTGACATTCTGCGTTCAGGTCCAGGGCAAGAGCAAGAGAGAAAAGAAAGATAGAGTCTTCACGGACAAGA<br>CCTCAGCCACGGTCATCTGCCGCAAAAATGCCAGCATTAGCGTGCGGGCCCAGGACCGCTACTATAGCTCATCTTGGAGCGAATGGGC<br>ATCTGTGCCCTGCAGTGGCTCTAGCGGAGGGGGAGGCTCTCCTGGCGGGGGATCTAGCAGAAATCTCCCCGTGGCCACTCCAGACCCA<br>GGAATGTTCCCATGCCTTCACCACTCCCAAAACCTGCTGAGGGCCGTCAGCAACATGCTCCAGAAGGCCAGACAAACTCTAGAATTTT<br>ACCCTTGCACTTCTGAGGAAATTGATCATGAAGATATCACAAAAGATAAAACCAGCACAGTGGAGGCCTGTTTACCATTGGAATTAAC<br>CAAGAATGAGAGTTGCCTAAATTCCAGAGAGACCTCTTTCATAACTAATGGGAGTTGCCTGGCCTCCAGAAAGACCTCTTTTATGATG<br>GCCCTGTGCCTTAGTAGTATTTATGAAGACTTGAAGATGTACCAGGTGGAGTTCAAGACCATGAATGCAAAGCTTCTGATGGATCCTA<br>AGAGGCAGATCTTTCTAGATCAAAACATGCTGGCAGTTATTGATGAGCTGATGCAGGCCCTGAATTTCAACAGTGAGACTGTGCCACA<br>AAAATCCTCCCTTGAAGAACCGGATTTTTATAAAACTAAAATCAAGCTCTGCATACTTCTTCATGCTTTCAGAATTCGGGCAGTGACT<br>ATTGATAGAGTGATGAGCTATCTGAATGCTTCCTGATGA |
| 16 | Human optimized IL-12sc (CDS DNA) Sequence annotation CAPS: p40 domain; CAPS: linker; CAPS: p35. | ATGTGTCACCAGCAGCTGGTGATCTCATGGTTCTCCCTGGTATTTCTGGCATCTCCTCTTGTCGCAATCTGGGAACTGAAGAAAGACG<br>TGTATGTCGTTGAGCTCGACTGGTATCCGGATGCGCCTGGCGAGATGGTGGTGCTGACCTGTGACACCCCAGAGGAGGATGGGATCAC<br>TTGGACCCTTGATCAATCCTCCGAAGTGCTCGGGTCTGGCAAGACTCTGACCATACAAGTGAAAGAGTTTGGCGACGCCGGTCAGTAC<br>ACTTGCCATAAGGGCGGAGAAGTTCTGTCCCACTCACTGCTGCTGCTGCACAAGAAAGAGGACGGAATTTGGAGTACCGATATCCTGA<br>AAGATCAGAAAGAGCCCAAGAACAAAACCTTCTTGCGGTGCGAAGCCAAGAACTACTCAGGGAGATTTACTTGTTGGTGGCTGACGAC<br>GATCAGCACCGATCTGACTTTCTCCGTGAAATCAAGTAGGGGATCATCTGACCCTCAAGGAGTCACATGTGGAGCGGCTACTCTGAGC<br>GCTGAACGCGTAAGAGGGGACAATAAGGAGTACGAGTATAGCGTTGAGTGCCAAGAGGATAGCGCATGCCCCGCCGCCGAAGAATCAT<br>TGCCCATTGAAGTGATGGTGGATGCTGTACACAAGCTGAAGTATGAGAACTACACAAGCTCCTTCTTCATCCGTGACATCATCAAACC<br>AGATCCTCCTAAGAACCTCCAGCTTAAACCTCTGAAGAATCTAGACAGGTGGAAGTGTCTTGGGAGTATCCCGACACCTGGTCTACA<br>CCACATTCCTACTTCAGTCTCACATTCTGCGTTCAGGTACAGGGCAAGTCCAAAAGGGAGAAGAAGGATCGGGTCTTTACAGATAAAA<br>CAAGTGCCACCGTTATATGCCGGAAGAATGCCTCTATTTCTGTGCGTGCGCAGGACAGATACTATAGCAGCTCTTGGAGTGAATGGGC<br>CAGTGTCCCATGTTCAGGGTCATCCGGTGGTGGCGGCAGCCCCGGAGGCGGTAGCTCCAGAAATCTCCCTGTGGCTACACCTGATCCA<br>GGCATGTTTCCCTGTTTGCACCATAGCCAAAACCTTCTGAGAGCAGTCAGCAACATGCTCCAGAAAGCTAGACAAACACTGGAATTCT<br>ACCCATGCACCTCCGAGGAAATAGATCACGAGGATATCACTAAGGACAAAACAAGCACTGTCGAAGCATGCCTTCCCTTGGAACTGAC<br>AAAGAACGAGAGTTGCCTTAATTCAAGAGAAACATCTTTCATTACAAACGGTAGCGCTTGGCAAGCAGAAAAACATCTTTTATGATG<br>GCCCTTTGTCTGAGCAGTATTTATGAGGATCTCAAAATGTACCAGGTGGAATTTAAGACCATGAATGCCAAGCTGCTGATGGACCCAA<br>AGAGACAGATTTTCCTCGATCAGAATATGCTGGCTGTGATTGATGAACTGATGCAGGCCTTGAATTTCAACAGCGAAACCGTTCCCCA<br>GAAAAGCAGTCTTGAAGAACCTGACTTTTATAAGACCAAGATCAAACTGTGTATTCTCCTGCATGCCTTTAGAATCAGAGCAGTCACT<br>ATAGATAGAGTGATGTCCTACCTGAATGCTTCCTGATGA |

TABLE 1-continued

DESCRIPTION OF THE SEQUENCES (human sequences)

SEQ ID NO: Description SEQUENCE

| | | |
|---|---|---|
| 17 | Human non-optimized IL-12sc (RNA encoding CDS) | AUGUGUCACCAGCAGUUGGUCAUCUCUUGGUUUUCCCUGGUUUUUCUGGCAUCUCCCCUCGUGGCCAUAUGGGAACUGAAGAAAGAUG UUUAUGUCGUAGAAUUGGAUUGGUAUCCGGAUGCCCCUGGAGAAAUGGUGGUCCUCACCUGUGACACCCCUGAAGAAGAUGGUAUCAC CUGGACCUUGGACCAGAGCAGUGAGGUCUUAGGCUCUGGCAAAACCCUGACCAUCCAAGUCAAAGAGUUUGGAGAUGCUGGCCAGUAC ACCUGUCACAAAGGAGGCGAGGUUCUAAGCCAUUCGCUCCUGCUGCUUCACAAAAAGGAAGAUGGAAUUUGGUCCACUGAUAUUUUAA AGGACCAGAAAGAACCCAAAAAUAAGACCUUUCUAAGAUGCGAGGCCAAGAAUUAUUCUGGACGCUUUUCACCUGCUGGUGGCUGACGAC AAUCAGUACUGAUUUGACAUUCAGUGUGCAAAAGCAGCAGAGGGUCUUCUGACCCCCAAGGGGUGACGUGCGGAGCUGCUACACUCUCU GCAGAGAGAGUCAGAGGGGACAACAAGGAGUAUGAGUACUCAGUGGACAUGCCAGGAGGACAGUGCCUGCCCAGCUGCUGAGGAGAGUC UGCCCAUUGAGGUCAUGGUGGAUGCCGUUCACAAGCUCAAGUAUGAAAACUACACCAGCAGCUUCUUCAUCAGGGACAUCAUCAAACC UGACCCACCCAAGAACUUGCAGCUGAAGCCAUUAAAGAAUUCUCGGCAGGUGGAGGUCAGCUGGGAGUACCCUGACACCUGGAGUACU CCACAUUCCUACUUCUCCCUGACAUUCUGCGUUCAGGUCAGGCAAGUCCAGGGCAAGAAGAGAAAAGAGAAGAUAGAGUCUUCACGGACAAGA CCUCAGCCACGGUCAUCUGCCGCAAAAAUGCCAGCAUUAGCGUGCGGGCCCAGGACCGCUACUAUAGCUCAUCUUGGAGCGAAUGGGC AUCUGUGCCCUGCAGUGGCUCUAGCGGAGGGGAGGCUCUCCUGGCGGGGAUCUAGCAGAAACCUCCCCGUGGCCACUCCAGACCCA GGAAUGUUCCCAUGCCUUCACCACUCCCAAAACCUGCUGAGGGCCGUCAGCAACAUGCUCCAGAAGGCCAGACAAACUCUAGAAUUUU ACCCGUGCACUUCUGAGGAAAAUGAUCAUGAAGAUAUCCAAAAGAUAGCAGUGGAGGCCUGUUUUACCAUGGGAAUUAAC CAAGAAUGAGAGUUGCCUAAAUUCCAGAGAUCCUCUUUCAUAACUAAUGGGAGUUGCCUGGCCUCCAGAAAGACUCUUUUUAUGAUG GCCCUGUGCCUUAGUAGUAUUUAUGAAGACUUGAAGAUGUACCAGGUGGAGUUCAAGACCAUGAAUGCAAAGCUUCUGAUGGAUCCUA AGAGGCAGAUCUUUCUAGAUCAAAACAUGCUGGCAGUUAUUGAUGAGCUGAUGCAGGCCCUGAAUUUCAACAGUGAGACUGUGCCACA AAAUCCUCCCCUUGAAGAACCGGAUUUUUAUAAAACUAAAAUCAAGCUCUGCAUACUUCUUCAUGCUUUCAGAAUUCGGGCAGUGACU AUUGAUAGAGUGAUGAGCUAUCUGAAUGCUUCCUGAUGA |
| 18 | Human optimized IL-12sc (RNA encoding CDS) | AUGUGUCACCAGCAGCUGGUGAUCUCAUGGUUCUCCCUGGUAUUUCUGGCAUCUCCUCUUGUCGCAAUCUGGGAACUGAAGAAAGACG UGUAUGUCGUUGAGCUCGACUGGUAUCCGGAUGCGCCUGGCGAGAUGGUGGUGCUGACCUGUGACACCCCAGAGGAGGAUGGGAUCAC UUGGACCCUUGAUCAAUCCUCCGAAGUGCUCGGUCUGGGCAAGACUCUGACCAUACAGGUGAAAGAGUUUGGCGAUGCCGGCCAGUAC ACUUGCCAUAAGGGCGGAGAAGUUCUGUCCCACUCACUGCUGCUGCUGCACAAAAAGGAGGACGGAAUUUGGAGUACCGAUAUCCUGA AGGAUCAGAAAGAGCCCAAGAACAAAACCUUCUUGCGUGCGAAGCCAAGAACUACUCAGGGAGAUUUACUUGUUGGUGGCUGACGAC GAUCAGCACCGAUCUGAUUUCUCCCGUGAAAUCAAGUAGGGGGAUCAUCUGACCCUCAAGGAGUCACAUGUGGAGCGGCUACUCUGAGC GCUGAACGCGUAAGAGGGGACAAUAAGGAGUACGAGUAUAGCGUUGAGUGCCAAGAGGAUAGCGCAUGCCCCGCCGCCGAAGAAUCAU UGCCCAUUGAAGUGAUGGUGGAUGCUGUACACAAGCUCAAGUACGAAAACUACACAAGCUCCUUCUUCAUCCGUGACAUCAUCAAACC AGAUCCUCCUAAGAACCUCCAGCUUAAACCUCUGAAGAACUCUAGACAGGUGGAAGUGUCUUGGGAGUAUCCCGACACCUGGUCUACA CCACAUUCCUACUUCAGUCUCACAUUCUGCGUUCAGGUACAGGGCAAGUCCAAAAGGGAGAAGAAGGAUCGGGUCUUUACAGAUAAAA CAAGUGCCACCGUUAUAUGCCGGAAGAAUGCCUCUAUUUCUGUGCGUCGCAGGACAGAUACUAUAGCAGCUCUUGGAGUGAAUGGGC CAGUGUCCCAUGUUCAGGGUCAUCCGGUGGUGGCGGCAGCCCCGGAGGCGGUAGCUCCAGAAAUCUCCCCGUGGCUACACCUGAUCCA GGCAUGUUUCCCGUUUGCCACUAGCCAAAACCUCCGAGAGCCAUCAGCAACAUGCUCCAGAAAGUAGACAAACUGGAAUUCU ACCCCAUGCACCUCCGAGGAAAUGAUCACGAGGAUAUCACUAAGGACAAAACAAGCACGUCGAAGCAUGCCUUCCCUUGGAACUAC AAGAACGAGAGUUGCCUUAAUUCAAGAGAAACAUCUUUCAUUACAAACGGUAGCUGCUUGGCAAGCAGAAAACAUCUUUUAUGAUG GCCCUUUGUCUGAGCAGUAUUUAUGAGGAUCUCAAAAUGUACCAGGUGGAGUUUAAGACCAUGAAUGCCAAGCUGCUGAUGGACCCAA AGAGACAGAUUUCCUCGAUCAGAAUAUGCUGGCUGUGAUUGAUGAACUGAUGCAGGCCUUGAAUUUCAACAGCGAAACCGUUCCCCA GAAAAGCAGCUUGAAGAACCUGACUUUUAUAAGACCAAGAUCAAACUGUAUUCUCCGCAUGCCUUUAGAAUCAGAGCAGUCACU AUAGAUAGAGUGAUGUCCUACCUGAAUGCUUCCUGAUGA |

IFNalpha2b (IFNα2b)

| | | |
|---|---|---|
| 19 | Human IFNα2b (amino acid) | MALTFALLVALLVLSCKSSCSVGCDLPQTHSLGSRRTLMLLAQMRRISLFSCLKDRHDFGFPQEEFGNQFQKAETIPVLHEMIQQIFN LFSTKDSSAAWDETLLDKFYTELYQQLNDLEACVIQGVGVTETPLMKEDSILAVRKYFQRITLYLKEKKYSPCAWEVVRAEIMRSFSL STNLQESLRSKE |
| 20 | Human non-optimized IFNα2b (CDS DNA) | ATGGCCTTGACCTTTGCTTTACTGGTGGCCCTCCTGGTGCTCAGCTGCAAGTCAAGCTGCTCTGTGGGCTGTGATCTGCCTCAAACCC ACAGCCTGGGTAGCAGGAGGACCTTGATGCTCCTGGCACAGATGAGGAGAATCTCTCTTTTCTCCTGCTTGAAGGACAGACATGACTT TGGATTTCCCCAGGAGGAGTTTGGCAACCAGTTCCAAAAGGCTGAAACCATCCCTGTCCTCCATGAGATGATCCAGCAGATCTTCAAC CTTTTCAGCACAAAGGACTCATCTGCTGCTTGGGATGAGACCCTCCTAGACAAATTCTACACTGAACTCTACCAGCAGCTGAATGACC TGGAAGCCTGTGTGATACAGGGGGTGGGGGTGACAGAGACTCCCCTGATGAAGGAGGACTCCATTCTGGCTGTGAGGAAATACTTCCA AAGAATCACTCTCTATCTGAAAGAGAAGAAATACAGCCCTTGTGCCTGGGAGGTTGTCAGAGCAGAAATCATGAGATCTTTTTCTTTG TCAACAAACTTGCAAGAAAGTTTAAGAAGTAAGGAATGATGA |
| 21 | Human optimized IFNα2b (CDS DNA) | ATGGCCCTGACTTTTGCCCTTCTCGTGGCTTTGTTGGTGCTGAGTTGCAAATCTTCCTGTAGTGTCGGATGTGATCTGCCTCAAACCC ACAGTCTGGGATCTAGGAGAACACTGATGCTGTTGGCACAGATGAGGAGAATTAGCCTCTTTTCCTGCCTGAAGGATAGACATGACTT CGGCTTTCCCCAAGAGGAGTTTGGCAATCAGTTCCAGAAAGCGGAAACCATTCCCGTTCTGCACGAGATGATCCAGCAGATCTTCAAC CTCTTTTCAACCAAAGACAGCTCAGCAGCCTGGGATGAGACACACTGCTTGACAAATTCTACACAGAACTGTATCAGCAGCTTAACGATC TGGAGGCATGCGTGATCCAAGGGGTTGGTGTGACTGAAACTCCGCTTATGAAGGAGGACTCCATTCTGGCTGTGCGGAAGTACTTCCA GAGAATAACCCTCTATCTGAAGGAGAAGAAGTACTCACCATGCGCTTGGGAAGTCGTGAGAGCCGAAATCATGAGATCCTTCAGCCTT AGCACCAATCTCCAGGAATCTCTGAGAAGCAAAGAGTGATGA |
| 22 | Human non-optimized IFNα2b (RNA encoding CDS) | AUGGCCUUGACCUUUGCUUUACUGGUGGCCCUCCUGGUGCUCAGCUGCAAGUCAAGCUGCUCUGUGGGCUGUGAUCUGCCUCAAACCC ACAGCCUGGGUAGCAGGAGGACCUUGAUGCUCCUGGCACAGAUGAGGAGAAUCUCUCUUUUCUCCUGCUUGAAGGACAGACAUGACUU UGGAUUUCCCCAGGAGGAGUUUGGCAACCAGUUCCAAAAGGCUGAAACCAUCCCUGUCCUCCAUGAGAUGAUCCAGCAGAUCUUCAAC CUUUUCAGCACAAAGGACUCAUCUGCUGCUUGGGAUGAGACCCUCCUAGACAAAUUCUACACUGAACUCUACCAGCAGCUGAAUGACC UGGAAGCCUGUGUGAUACAGGGGGUGGGGGUGACAGAGACUCCCCUGAUGAAGGAGGACUCCAUUCUGGCUGUGAGGAAAUACUUCCA AAGAAUCACUCUCUAUCUGAAAGAGAAGAAAUACAGCCCUUGUGCCUGGGAGGUUGUCAGAGCAGAAAUCAUGAGAUCUUUUUCUUUG UCAACAAACUUGCAAGAAAGUUUAAGAAGUAAGGAAUGAUGA |

TABLE 1-continued

DESCRIPTION OF THE SEQUENCES (human sequences)

| SEQ ID NO: | Description | SEQUENCE |
|---|---|---|
| 23 | Human optimized IFNα2b (RNA encoding CDS) | AUGGCCCUGACUUUUGCCCUUCUCGUGGCUUUGUUGGUGCUGAGUUGCAAAUCUUCCUGUAGUGUCGGAUGUGAUCUGCCUCAAACCC ACAGUCUGGGAUCUAGGAGAACACUGAUGCUGUUGGCACAGAUGAGGAGAAUUAGCCUCUUUUCCUGCCUGAAGGAUAGACAUGACUU CGGCUUUCCCAAGAGGAGUUUGGCAAUCAGUUCCAGAAAGCGGAAACGAUUCCCGUUCUGCACGAGAUGAUCCAGCAGAUCUUCAAC CUCUUUUCAACCAAAGACAGCUCAGCAGCCUGGGAUGAGACACUGCUGGACAAAUUCUACACAGAACUGUAUCAGCAGCUUAACGAUC UGGAGGCAUGCGUGAUCCAAGGGGUUGGUGUGACUGAAACUCCGCUUAUGAAGGAGGACUCCAUUCUGGCUGUACGGAAGUACUUCCA GAGAAUAACCCUCUAUCUGAAGGAGAAGAAGUACACCACCUGUGCUUGGGAAGUCGUGAGAGCCGAAAUCAUGAGAUCCUUCAGCCUU AGCACCAAUCUCCAGGAAUCUCUGAGAAGCAAAGAGUGAUGA |

IL-15 sushi

| 24 | Human IL-15 sushi (amino acid) | MAPRRARGCRTLGLPALLLLLLLRPPATRGITCPPPMSVEHADIWVKSYSLYSRERYICNSGFKRKAGTSSLTECVLNKATNVAHWTT PSLKCIRDPALVHQRPAPPGGGSGGGSGGGSGGGGSLQNWVISDLKKIEDLIQSMHIDATLYTESDVHPSCKVTAMKCFLLELQV ISLESGDASIHDTVENLIILANNSLSSNGNVTESGCKECEELEEKNIKEFLQSFVHIVQMFINTS |
| 25 | Human IL-15 sushi (CDS DNA) Sequence annotations CAPS: IL-15 sushi; CAPS: linker; CAPS: mature IL-15 | ATGGCCCCGCGGCGGGCGCGCGGCTGCCGGACCCTCGGTCTCCCGGCGCTGCTACTGCTGCTGCTGCTCCGGCCGCCGGCGACGCGGG GCATCACGTGCCCTCCCCCCATGTCCGTGGAACACGCAGACATCTGGGTCAAGAGCTACAGCTTGTACTCCAGGGAGCGGTACATTTG TAACTCTGGTTTCAAGCGTAAAGCCGGCACGTCCAGCCTGACGGAGTGCGTGTTGAACAAGGCCACGAATGTCGCCCACTGGACAACC CCCAGTCTCAAATGCATTAGAGACCCTGCCCTGGTTCACCAAAGGCCAGCGCCACCCGGGGGAGGATCTGGCGGCGGTGGGTCTGGCG GGGATCTGGCGGAGGAGGAAGCTTACAGAACTGGGTGAATGTAATAAGTGATTTGAAAAAAATTGAAGATCTTATTCAATCTATGCA TATTGATGCTACTTTATATACGGAAAGTGATGTTCACCCCAGTTGCAAAGTAACAGCAATGAAGTGCTTTCTCTTGGAGTTACAAGTT ATTTCACTTGAGTCCGGAGATGCAAGTATTCATGACAGTAGAAAATCTGATCATCCTAGCAAACAACAGTTTGTCTTCTAATGGGA ATGTAACAGAATCTGGATGCAAAGAATGTGAGGAACTGGAGGAAAAAAATATTAAAGAATTTTTGCAGAGTTTTGTACATATTGTCCA AATGTTCATCAACACTTCTTGATGA |
| 26 | Human IL-15 sushi (RNA encoding CDS) | AUGGCCCCGCGGCGGGCGCGCGGCUGCCGGACCCUCGGUCUCCCGGCGCUGCUACUGCUGCUGCUGCUCCGGCCGCCGGCGACGCGGG GCAUCACGUGCCCUCCCCCCAUGUCCGUGGAACACGCAGACAUCUGGGUCAAGAGCUACAGCUUGUACUCCAGGGAGCGGUACAUUUG UAACUCUGGUUUCAAGCGUAAAGCCGGCACGUCCAGCCUGACGGAGUGCGUGUUGAACAAGGCCACGAAUGUCGCCCACUGGACAACC CCCAGUCUCAAAUGCAUUAGAGACCCUGCCCUGGUUCACCAAAGGCCAGCGCCACCCGGGGGAGGAUCUGGCGGCGGUGGGUCUGGCG GGGAUCUGGCGGAGGAGGAAGCUUACAGAACUGGGUGAAUGUAAUAAGUGAUUUGAAAAAAAUUGAAGAUCUUAUUCAAUCUAUGCA UAUUGAUGCUACUUUAUAUACGGAAAGUGAUGUUCACCCCAGUUGCAAAGUAACAGCAAUGAAGUGCUUUCUCUUGGAGUUACAAGUU AUUUCACUUGAGUCCGGAGAUGCAAGUAUUCAUGACAGUAGAAAAUCUGAUCAUCCUAGCAAACAACAGUUUGUCUUCUAAUGGGA AUGUAACAGAAUCUGGAUGCAAAGAAUGUGAGGAACUGGAGGAAAAAAAUAUUAAAGAAUUUUUGCAGAGUUUUGUACAUAUUGUCCA AAUGUUCAUCAACACUUCUUGAUGA |

GM-CSF

| 27 | Human GM-CSF (amino acid) | MWLQSLLLLGTVACSISAPARSPSPSTQPWEHVNAIQEARRLLNLSRDTAAEMNETVEVISEMFDLQEPTCLQTRLELYKQGLRGSLT KLKGPLTMMASHYKQHCPPTPETSCATQIITFESFKENLKDFLLVIPFDCWEPVQE |
| 28 | Human GM-CSF (CDS DNA) | ATGTGGCTCCAGAGCCTGCTGCTCTTGGGCACTGTGGCCTGCTCCATCTCTGCACCCGCCCGCTCGCCCAGCCCCAGCACGCAGCCCT GGGAGCATGTGAATGCCATCCAGGAGGCCCGGCGTCTGCTGAACCTGAGTAGAGACACTGCTGCTGAGATGAATGAAACAGTAGAAGT CATCTCAGAAATGTTTGACCTCCAGGAGCCGACCTGCCTACAGACCCGCCTGGAGCTGTACAAGCAGGGCCTGCGGGGCAGCCTCACC AAGCTCAAGGGCCCCTTGACCATGATGGCCAGCCACTACAAGCAGCACTGCCCTCCAACCCCGGAAACTTCCTGTGCAACCCAGATTA TCACCTTTGAAAGTTTCAAAGAGAACCTGAAGGACTTTCTGCTTGTCATCCCCTTTGACTGCTGGGAGCCAGTCCAGGAGTGATGA |
| 29 | Human GM-CSF (RNA encoding CDS) | AUGUGGCUCCAGAGCCUGCUGCUCUUGGGCACUGUGGCCUGCUCCAUCUCUGCACCCGCCCGCUCGCCCAGCCCCAGCACGCAGCCCU GGGAGCAUGUGAAUGCCAUCCAGGAGGCCCGGCGUCUGCUGAACCUGAGUAGAGACACUGCUGCUGAGAUGAAUGAAACAGUAGAAGU CAUCUCAGAAAUGUUUGACCUCCAGGAGCCGACCUGCCUACAGACCCGCCUGGAGCUGUACAAGCAGGGCCUGCGGGGCAGCCUCACC AAGCUCAAGGGCCCCUUGACCAUGAUGGCCAGCCACUACAAGCAGCACUGCCCUCCAACCCCGGAAACUUCCUGUGCAACCCAGAUUA UCACCUUUGAAAGUUUCAAAGAGAACCUGAAGGACUUUCUGCUUGUCAUCCCCUUUGACUGCUGGGAGCCAGUCCAGGAGUGAUGA |

TABLE 2

DESCRIPTION OF THE SEQUENCES (mouse sequences and other sequences of the invention)

| SEQ ID NO: | Description | SEQUENCE |
|---|---|---|

IL-2 mouse

| 30 | ModA IL-2 (amino acid, human | MRVTAPRTLILLLSGALALTETWAGSGSAPTSSSTKKTQLQLEHLLLDLQMILNGINNYKNPKLTRMLTFKFYMPKKATELKHLQCLE EELKPLEEVLNLAQSKNFHLRPRDLISNINVIVLELKGSETTFMCEYADETATIVEFLNRWITFCQSIISTLT |

TABLE 2-continued

DESCRIPTION OF THE SEQUENCES (mouse sequences and other sequences of the invention)

| SEQ ID NO: | Description | SEQUENCE |
|---|---|---|
| | IL-2 in combination with a mouse optimized secretion sequence) | |
| 31 | ModA IL-2 (DNA: 5' UTR-CDS-3' UTR) | GGGCGAACTAGTATTCTTCTGGTCCCCACAGACTCAGAGAGAACCCGCCACCATGAGAGTGACCGCCCCCAGAACCCTGATCCTGCTG<br>CTGTCTGGCGCCCTGGCCCTGACAGAGACATGGGCCGGAAGCGGATCCGCACCTACTTCAAGTTCTACAAAGAAAACACAGCTACAAC<br>TGGAGCATTTACTTCTGGATTTACAGATGATTTTGAATGGAATTAATAATTACAAGAATCCCAAACTCACCAGGATGCTCACATTTAA<br>GTTTTACATGCCCAAGAAGGCCACAGAACTGAAACATCTTCAGTGTCTAGAAGAAGAACTCAAACCTCTGGAGGAAGTGCTAAATTTA<br>GCTCAAAGCAAAAACTTTCACTTAAGACCCAGGGACTTAATCAGCAATATCAACGTAATAGTTCTGGAACTAAAGGGATCTGAAACAA<br>CATTCATGTGTGAATATGCTGATGAGACAGCAACCATTGTAGAATTTCTGAACAGATGGATTACCTTTTGTCAAAGCATCATCTCAAC<br>ACTGACTTGACTCGAGAGCTCGCTTTCTTGCTGTCCAATTTCTATTAAAGGTTCCTTTGTTCCCTAAGTCCAACTACTAAACTGGGGG<br>ATATTATGAAGGGCCTTGAGCATCTGGATTCTGCCTAATAAAAAACATTTATTTTCATTGCTGCGTCGAGAGCTCGCTTTCTTGCTGT<br>CCAATTTCTATTAAAGGTTCCTTTGTTCCCTAAGTCCAACTACTAAACTGGGGGATATTATGAAGGGCCTTGAGCATCTGGATTCTGC<br>CTAATAAAAAACATTTATTTTCATTGCTGCGTCGAGACCTGGTCCAGAGTCGCTAGCAAAAAAAAAAAAAAAAAAAAAAAAAAAAAAG<br>CATATGACTAAAAAAAAAAAAAAAAAAAAAAAAAAAAAAAAAAAAAAAAAAAAAAAAAAAAAAAAAAAAAAAA |
| 32 | ModA IL-2 (RNA) | GGGCGAACUAGUAUUCUUCUGGUCCCCACAGACUCAGAGAGAACCCGCCACCAUGAGAGUGACCGCCCCCAGAACCCUGAUCCUGCUG<br>CUGUCUGGCGCCCUGGCCCUGACAGAGACAUGGGCCGGAAGCGGAUCCGCACCUACUUCAAGUUCUACAAAGAAAACACAGCUACAAC<br>UGGAGCAUUUACUUCUGGAUUUACAGAUGAUUUUGAAUGGAAUUAAUAAUUACAAGAAUCCCAAACUCACCAGGAUGCUCACAUUUAA<br>GUUUUACAUGCCCAAGAAGGCCACAGAACUGAAACAUCUUCAGUGUCUAGAAGAAGAACUCAAACCUCUGGAGGAAGUGCUAAAUUUA<br>GCUCAAAGCAAAAACUUUCACUUAAGACCCAGGGACUUAAUCAGCAAUAUCAACGUAAUAGUUCUGGAACUAAAGGGAUCUGAAACAA<br>CAUUCAUGUGUGAAUAUGCUGAUGAGACAGCAACCAUUGUAGAAUUUCUGAACAGAUGGAUUACCUUUUGUCAAAGCAUCAUCUCAAC<br>ACUGACUUGACUCGAGAGCUCGCUUUCUUGCUGUCCAAUUUCUAUUAAAGGUUCCUUUGUUCCCUAAGUCCAACUACUAAACUGGGGG<br>AUAUUAUGAAGGGCCUUGAGCAUCUGGAUUCUGCCUAAUAAAAAACAUUUAUUUUCAUUGCUGCGUCGAGAGCUCGCUUUCUUGCUGU<br>CCAAUUUCUAUUAAAGGUUCCUUUGUUCCCUAAGUCCAACUACUAAACUGGGGGAUAUUAUGAAGGGCCUUGAGCAUCUGGAUUCUGC<br>CUAAUAAAAAACAUUUAUUUUCAUUGCUGCGUCGAGACCUGGUCCAGAGUCGCUAGCAAAAAAAAAAAAAAAAAAAAAAAAAAAAAAG<br>CAUAUGACUAAAAAAAAAAAAAAAAAAAAAAAAAAAAAAAAAAAAAAAAAAAAAAAAAAAAAAAAAAAAAAAA |
| 33 | ModB IL-2 (amino acid) | MGAMAPRTLLLLLAAALAPTQTRAGPGSAPTSSSTKKTQLQLEHLLLDLQMILNGINNYKNPKLTRMLTFKFYMPKKATELKHLQCLE<br>EELKPLEEVLNLAQSKNFHLRPRDLISNINVIVLELKGSETTFMCEYADETATIVEFLNRWITFCQSIISTLT |
| 34 | ModB IL-2 (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA<br>TTTCTTTTAAAGCAAAAGCAATTTTCTGAAAATTTTCACCATTTACGAACGATAGCCATGGGCGCCATGGCCCCTAGAACATTGCTCC<br>TGCTGCTGGCCGCTGCCCTGGCCCCTACACAGACAAGAGCTGGACCTGGATCCGCACCTACTTCAAGTTCTACAAAGAAAACACAGCT<br>ACAACTGGAGCATTTACTTCTGGATTTACAGATGATTTTGAATGGAATTAATAATTACAAGAATCCCAAACTCACCAGGATGCTCACA<br>TTTAAGTTTTACATGCCCAAGAAGGCCACAGAACTGAAACATCTTCAGTGTCTAGAAGAAGAACTCAAACCTCTGGAGGAAGTGCTAA<br>ATTTAGCTCAAAGCAAAAACTTTCACTTAAGACCCAGGGACTTAATCAGCAATATCAACGTAATAGTTCTGGAACTAAAGGGATCTGA<br>AACAACATTCATGTGTGAATATGCTGATGAGACAGCAACCATTGTAGAATTTCTGAACAGATGGATTACCTTTTGTCAAAGCATCATC<br>TCAACACTGACTTGACTCGACGTCCTGGTACTGCATGCACGCAATGCTAGCTGCCCCTTTCCCGTCCTGGGTACCCCGAGTCTCCCCC<br>GACCTCGGGTCCCAGGTATGCTCCCACCTCCACCTGCCCCACTCACCACCTCTGCTAGTTCCAGACACCTCCCAAGCACGCAGCAATG<br>CAGCTCAAAACGCTTAGCCTAGCCACACCCCCACGGGAAACAGCAGTGATTAACCTTTAGCAATAAACGAAAGTTTAACTAAGCTATA<br>CTAACCCCAGGGTTGGTCAATTTCGTGCCAGCCACACCCTCGAGCTAGCAAAAAAAAAAAAAAAAAAAAAAAAAAAAAAAGCATATGAC<br>TAAAAAAAAAAAAAAAAAAAAAAAAAAAAAAAAAAAAAAAAAAAAAAAAAAAAAAAAAAAAAAA |
| 35 | ModB IL-2 (RNA) | GGAAUAAACUAGUCUCAACACAACAUAUACAAAACAAACGAAUCUCAAGCAAUCAAGCAUUCUACUUCUAUUGCAGCAAUUUAAAUCA<br>UUUCUUUUAAAGCAAAAGCAAUUUUCUGAAAAUUUUCACCAUUUACGAACGAUAGCCAUGGGCGCCAUGGCCCCUAGAACAUUGCUCC<br>UGCUGCUGGCCGCUGCCCUGGCCCCUACACAGACAAGAGCUGGACCUGGAUCCGCACCUACUUCAAGUUCUACAAAGAAAACACAGCU<br>ACAACUGGAGCAUUUACUUCUGGAUUUACAGAUGAUUUUGAAUGGAAUUAAUAAUUACAAGAAUCCCAAACUCACCAGGAUGCUCACA<br>UUUAAGUUUUACAUGCCCAAGAAGGCCACAGAACUGAAACAUCUUCAGUGUCUAGAAGAAGAACUCAAACCUCUGGAGGAAGUGCUAA<br>AUUUAGCUCAAAGCAAAAACUUUCACUUAAGACCCAGGGACUUAAUCAGCAAUAUCAACGUAAUAGUUCUGGAACUAAAGGGAUCUGA<br>AACAACAUUCAUGUGUGAAUAUGCUGAUGAGACAGCAACCAUUGUAGAAUUUCUGAACAGAUGGAUUACCUUUUGUCAAAGCAUCAUC<br>UCAACACUGACUUGACUCGACGUCCUGGUACUGCAUGCACGCAAUGCUAGCUGCCCCUUUCCCGUCCUGGGUACCCCGAGUCUCCCCC<br>GACCUCGGGUCCCAGGUAUGCUCCCACCUCCACCUGCCCCACUCACCACCUCUGCUAGUUCCAGACACCUCCCAAGCACGCAGCAAUG<br>CAGCUCAAAACGCUUAGCCUAGCCACACCCCCACGGGAAACAGCAGUGAUUAACCUUUAGCAAUAAACGAAAGUUUAACUAAGCUAUA<br>CUAACCCCAGGGUUGGUCAAUUUCGUGCCAGCCACACCCUCGAGCUAGCAAAAAAAAAAAAAAAAAAAAAAAAAAAAAAAGCAUAUGAC<br>UAAAAAAAAAAAAAAAAAAAAAAAAAAAAAAAAAAAAAAAAAAAAAAAAAAAAAAAAAAAAAAA |

IL-12 mouse

| 36 | ModA murine IL-12 (amino acid) | MRVTAPRTLILLLLSGALALTETWAGSGSMWELEKDVYVVEVDWTPDAPGETVNLTCDTPEEDDITWTSDQRHGVIGSGKTLTITVKEF<br>LDAGQYTCHKGGETLSHSHLLLHKKENGIWSTEILKNFKNKTFLKCEAPNYSGRFTCSWLVQRNMDLKFNIKSSSSSPDSRAVTCGMA<br>SLSAEKVTLDQRDYEKYSVSCQEDVTCPTAEETLPIELALEARQQNKYENYSTSFFIRDIIKPDPPKNLQMKPLKNSQVEVSWEYPDS<br>WSTPHSYFSLKFFVRIQRKKEKMKETEEGCNQKGAFLVEKTSTEVQCKGGNVCVQAQDRYYNSSCSKWACVPCRVRSVPGVGVPGVGR<br>VIPVSGPARCLSQSRNLLKTTDDMVKTAREKLKHYSCTAEDIDHEDITRDQTSTLKTCLPLELHKNESCLATRETSSTTRGSCLPPQK |

TABLE 2-continued

DESCRIPTION OF THE SEQUENCES (mouse sequences and other sequences of the invention)

| SEQ ID NO: | Description | SEQUENCE |
|---|---|---|
| | | TSLMMTLCLGSIYEDLKMYQTEFQAINAALQNHNHQQIILDKGMLVAIDELMQSLNHNGETLRQKPPVGEADPYRVKMKLCILLHAFS TRVVTINRVMGYLSSA |
| 37 | ModA murine IL-12 (DNA: 5' UTR-CDS-3' UTR) | GGGCGAACTAGTATTCTTCTGGTCCCCACAGACTCAGAGAGAACCCGCCACCATGAGAGTGACCGCCCCCAGAACCCTGATCCTGCTG CTGTCTGGCGCCCTGGCCCTGACAGAGACATGGGCCGGAAGCGGATCCATGTGGGAGCTGGAGAAAGACGTTTATGTTGTAGAGGTGG ACTGGACTCCCGATGCCCCTGGAGAAACAGTGAACCTCACCTGTGACACGCCTGAAGAAGATGACATCACCTGGACCTCAGACCAGAG ACATGGAGTCATAGGCTCTGGAAAGACCCTGACCATCACTGTCAAAGAGTTTCTAGATGCTGGCCAGTACACCTGCCACAAAGGAGGC GAGACTCTGAGCCACTCACATCTGCTGCTCCAAGAAGGAAAATGGAATTTGGTCCACTGAAATTTTAAAAAATTTCAAAAACAAGA CTTTCCTGAAGTGTGAAGCACCCAAATTACTCCGGACGGTTCACGTGCTCATGGCTGGTGCAAAGAAACATGGACTTGAAGTTCAACAT CAAGAGCAGTAGCAGTTCCCCTGACTCTCGGGCAGTGACATGTGGAATGGCGTCTCTGTCTGCAGAGAAGGTCACACTGGACCAAAGG GACTATGAGAAGTATTCAGTGTCCTGCCAGGAGATGTCACCTGCCCAACTGCCGAGGAGACCCTGCCCATTGAACTGGCGTTGGAAG CACGGCAGCAGAATAAATATGAGAACTACAGCACCAGCTTCTTCATCAGGGACATCATCAAACCAGACCCGCCCAAGAACTTGCAGAT GAAGCCTTTGAAGAACTCACAGGTGGAGGTCAGCTGGGAGTACCCTGACTCCTGGAGCACTCCCCATTCCTACTTCTCCCTCAAGTTC TTTGTTCGAATCCAGCGCAAGAAAGAAAAGATGAAGGAGACAGAGGAGGGGTGTAACCAGAAAGGTGCGTTCCTCGTAGAAGACAT CTACCGAAGTCCAATGCAAAGGCGGGAATGTCTGCGTGCAAGCTCAGGATCGCTATTACAATTCCTCATGCAGCAAGTGGGCATGTGT TCCCTGCAGAGTCCGATCGGTTCCTGGAGTAGGGGTACCTGGAGTGGGCAGGGTCATACCGGTCTCTGGACCTGCCAGGTGTCTTAGC CAGTCCCGAAACCTGCTGAAGACCACAGATGACATGGTGAAGACGGCCAGAGAAAAGCTGAAACATTATTCCTGCACTGCTGAAGACA TCGATCATGAAGCATCACACGGGACCAAACCAGCACATTGAAGACCTGTTTACCACTGGAACTACACAAGAACGAGAGTTGCCTGGC TACTAGAGAGACTTCTTCCACAACAAGAGGGAGCTGCCTGCCCCCACAGAAGACGTCTTTGATGATGACCGTGTGCCTTGGTAGCATC TATGAGGACTTGAAGATGTACCAGACAGAGTTCCAGGCCATCAACGCAGCACTTCAGAATCAACCATCAGCAGATCATTCTAGACA AGGGCATGCTGGTGGCCATCGATGAGCTGATGCAGTCTCTGAATCATAATGGCGAGACTCTGCGCCAGAAACCTCCTGTGGGAGAAGC AGACCCTTACAGAGTGAAAATGAAGCTCTGCATCCTGCTTCACGCCTTCAGCACCCGCGTCGTGACCATCAACAGGGTGATGGGCTAT CTGTCCAGCGCCTAATAGCTCGAGACTCGCTTTCTTGCTGTCCAATTTCTATTAAAGGTTCCTTTGTTCCCTAAGTCCAACTACTAA ACTGGGGATATTATGAAGGGCCTTGAGCATCTGGATTCTGCCTAATAAAAAACATTTATTTTCATTGCTGCGTCGAGAGCTCGCTTT CTTGCTGTCCAATTTCTATTAAAGGTTCCTTTGTTCCCTAAGTCCAACTACTAAACTGGGGATATTATGAAGGGCCTTGAGCATCTG GATTCTGCCTAATAAAAAACATTTATTTTCATTGCTGCGTCGAGACCTGGTCCAGAGTCGCTAGCAAAAAAAAAAAAAAAAAAAAAA AAAAAAGCATATGACTAAAAAAAAAAAAAAAAAAAAAAAAAAAAAAAAAAAAAAAAAAAAAAAAAAAAAAAAAAAAAAAAAAAAAAA |
| 38 | ModA murine IL-12 (RNA) | GGGCGAACUAGUAUUCUUCUGGUCCCCACAGACUCAGAGAGAACCCGCCACCAUGAGAGUGACCGCCCCCAGAACCCUGAUCCUGCUG CUGUCUGGCGCCCUGGCCCUGACAGAGACAUGGGCCGGAAGCGGAUCCAUGUGGGAGCUGGAGAAAGACGUUUAUGUUGUAGAGGUGG ACUGGACUCCCGAUGCCCCUGGAGAAACAGUGAACCUCACCUGUGACACGCCUGAAGAAGAUGACAUCACCUGGACCUCAGACCAGAG ACAUGGAGUCAUAGGCUCUGGAAAGACCCUGACCAUCACUGUCAAAGAGUUUCUAGAUGCUGGCCAGUACACCUGCCACAAAGGAGGC GAGACUCUGAGCCACUCACAUCUGCUGCUCCAAGAAGGAAAAUGGAAUUUGGUCCACUGAAAUUUUAAAAAAUUUCAAAAACAAGA CUUUCCUGAAGUGUGAAGCACCCAAAUUACUCCGGACGGUUCACGUGCUCAUGGCUGGUGCAAAGAAACAUGGACUUGAAGUUCAACAU CAAGAGCAGUAGCAGUUCCCCUGACUCUCGGGCAGUGACAUGUGGAAUGGCGUCUCUGUCUGCAGAGAAGGUCACACUGGACCAAAGG GACUAUGAGAAGUAUUCAGUGUCCUGCCAGGAGAUGUCACCUGCCCAACUGCCGAGGAGACCCUGCCCAUUGAACUGGCGUUGGAAG CACGGCAGCAGAAUAAAUAUGAGAACUACAGCACCAGCUUCUUCAUCAGGGACAUCAUCAAACCAGACCCGCCCAAGAACUUGCAGAU GAAGCCUUUGAAGAACUCACAGGUGGAGGUCAGCUGGGAGUACCCUGACUCCUGGAGCACUCCCCAUUCCUACUUCUCCCUCAAGUUC UUUGUUCGAAUCCAGCGCAAGAAAGAAAAGAUGAAGGAGACAGAGGAGGGGUGUAACCAGAAAGGUGCGUUCCUCGUAGAAGACAU CUACCGAAGUCCAAUGCAAAGGCGGGAAUGUCUGCGUGCAAGCUCAGGAUCGCUAUUACAAUUCCUCAUGCAGCAAGUGGGCAUGUGU UCCCUGCAGAGUCCGAUCGGUUCCUGGAGUAGGGGUACCUGGAGUGGGCAGGGUCAUACCGGUCUCUGGACCUGCCAGGUGUCUUAGC CAGUCCCGAAACCUGCUGAAGACCACAGAUGACAUGGUGAAGACGGCCAGAGAAAAGCUGAAACAUUAUUCCUGCACUGCUGAAGACA UCGAUCAUGAAGCAUCACACGGGACCAAACCAGCACAUUGAAGACCUGUUUACCACUGGAACUACACAAGAACGAGAGUUGCCUGGC UACUAGAGAGACUUCUUCCACAACAAGAGGGAGCUGCCUGCCCCCACAGAAGACGUCUUUGAUGAUGACCGUGUGCCUUGGUAGCAUC UAUGAGGACUUGAAGAUGUACCAGACAGAGUUCCAGGCCAUCAACGCAGCACUUCAGAAUCAACCAUCAGCAGAUCAUUCUAGACA AGGGCAUGCUGGUGGCCAUCGAUGAGCUGAUGCAGUCUCUGAAUCAUAAUGGCGAGACUCUGCGCCAGAAACCUCCUGUGGGAGAAGC AGACCCUUACAGAGUGAAAAUGAAGCUCUGCAUCCUGCUUCACGCCUUCAGCACCCGCGUCGUGACCAUCAACAGGGUGAUGGGCUAU CUGUCCAGCGCCUAAUAGCUCGAGACUCGCUUUCUUGCUGUCCAAUUUCUAUUAAAGGUUCCUUUGUUCCCUAAGUCCAACUACUAA ACUGGGGAUAUUAUGAAGGGCCUUGAGCAUCUGGAUUCUGCCUAAUAAAAAACAUUUAUUUUCAUUGCUGCGUCGAGAGCUCGCUUU CUUGCUGUCCAAUUUCUAUUAAAGGUUCCUUUGUUCCCUAAGUCCAACUACUAAACUGGGGAUAUUAUGAAGGGCCUUGAGCAUCUG GAUUCUGCCUAAUAAAAAACAUUUAUUUUCAUUGCUGCGUCGAGACCUGGUCCAGAGUCGCUAGCAAAAAAAAAAAAAAAAAAAAAA AAAAAAGCAUAUGACUAAAAAAAAAAAAAAAAAAAAAAAAAAAAAAAAAAAAAAAAAAAAAAAAAAAAAAAAAAAAAAAAAAAAAAA |
| 39 | ModB murine IL-12 (amino acid) | MGAMAPRTLLLLLAAALAPTQTRAGPGSMWELEKDVYVVEVDWTPDAPGETVNLTCDTPEEDDITWTSDQRHGVIGSGKTLTITVKEF LDAGQYTCHKGGETLSHSHLLLHKKENGIWSTEILKNFKNKTFLKCEAPNYSGRFTCSWLVQRNMDLKFNIKSSSSSPDSRAVTCGMA SLSAEKVTLDQRDYEKYSVSCQEDVTCPTAEETLPIELALEARQQNKYENYSTSFFIRDIIKPDPPKNLQMKPLKNSQVEVSWEYPDS WSTPHSYFSLKFFVRIQRKKEKMKETEEGCNQKGAFLVEKTSTEVQCKGGNVCVQAQDRYYNSSCSKWACVPCRVRSVPGVGVPGVGR VIPVSGPARCLSQSRNLLKTTDDMVKTAREKLKHYSCTAEDIDHEDITRDQTSTLKTCLPLELHNESCLATRETSSTTRGSCLPPQK TSLMMTLCLGSIYEDLKMYQTEFQAINAALQNHNHQQIILDKGMLVAIDELMQSLNHNGETLRQKPPVGEADPYRVKMKLCILLHAFS TRVVTINRVMGYLSSA |
| 40 | ModB murine IL-12 (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTTACGAACGATAGCCATGGGCGCCATGGCCCCTAGAACATTGCTCC TGCTGCTGGCCGCTGCCCTGGCCCCTACACAGACAAGAGCTGGACCTGGATCCATGTGGGAGCTGGAGAAAGACGTTTATGTTGTAGA GGTTGACTGGACTCCCGATGCCCCTGGAGAAACAGTGAACCTCACCTGTGACACGCCTGAAGAAGATGACATCACCTGGACCTCAGAC CAGAGACATGGAGTCATAGGCTCTGGAAAGACCCTGACCATCACTGTCAAAGAGTTTCTAGATGCTGGCCAGTACACCTGCCACAAAG GAGGCGAGACTCTGAGCCACTCACATCTGCTGCTCCAAGAAGGAAAATGGAATTTGGTCCACTGAAATTTTAAAAAATTTCAAAAA CAAGACTTTCCTGAAGTGTGAAGCACCCAAATTACTCCGGACGGTTCACGTGCTCATGGCTGGTGCAAAGAAACATGGACTTGAAGTTC AACATCAAGAGCAGTAGCAGTTCCCCTGACTCTCGGGCAGTGACATGTGGAATGGCGTCTCTGTCTGCAGAGAAGGTCACACTGGAC CAAAGGGACTATGAGAAGTATTCAGTGTCCTGCCAGGATGTCACCTGCCCAACTGCCGAGGAGACCCTGCCCATTGAACTGGCGTT GGAAGCACGGCAGCAGAATAAATATGAGAACTACAGCACCAGCTTCTTCATCAGGGACATCATCAAACCAGACCCGCCCAAGAACTTG CAGATGAAGCCTTTGAAGAACTCACAGGTGGAGGTCAGCTGGGAGTACCCTGACTCCTGGAGCACTCCCCATTCCTACTTCTCCCTCA AGTTCTTTGTTCGAATCCAGCGCAAGAAAGAAAAGATGAAGGAGACAGAGGAGGGGTGTAACCAGAAAGGTGCGTTCCTCGTAGAA GACATCTACCGAAGTCCAATGCAAAGGCGGGAATGTCTGCGTGCAAGCTCAGGATCGCTATTACAATTCCTCATGCAGCAAGTGGGCA |

TABLE 2-continued

DESCRIPTION OF THE SEQUENCES (mouse sequences and other sequences of the invention)

| SEQ ID NO: | Description | SEQUENCE |
|---|---|---|
| | | TGTGTTCCCTGCAGAGTCCGATCGGTTCCTGGAGTAGGGGTACCTGGAGTGGGCAGGGTCATACCGGTCTCTGGACCTGCCAGGTGTC<br>TTAGCCAGTCCCGAAACCTGCTGAAGACCACAGATGACATGGTGAAGACGGCCAGAGAAAAGCTGAAACATTATTCCTGCACTGCTGA<br>AGACATCGATCATGAAGACATCACACGGGACCAAACCAGCACATTGAAGACCTGTTTACCACTGGAACTACACAAGAACGAGAGTTGC<br>CTGGCTACTAGAGAGACTTCTTCCACAACAAGAGGGAGCTGCCTGCCCCCACAGAAGACGTCTTTGATGATGACCCTGTGCCTTGGTA<br>GCATCTATGAGGACTTGAAGATGTACCAGACAGAGTTCCAGGCCATCAACGCAGCACTTCAGAATCACAACCATCAGCAGATCATTCT<br>AGACAAGGGCATGCTGGTGGCCATCGATGAGCTGATGCAGTCTCTGAATCATAATGGCGAGACTCTGCGCCAGAAACCTCCTGTGGGA<br>GAAGCAGACCCTTACAGAGTGAAAATGAAGCTCTGCACTCCTGCTTCACGCCTTCAGCACCCGCGTCGTGACCATCAACAGGGTGATGG<br>GCTATCTGTCCAGCGCCTAATAGCTCGACGTCCTGGTACTGCATGCACGCAATGCTAGCTGCCCCTTTCCCGTCCTGGGTACCCCGAG<br>TCTCCCCCGACCTCGGGTCCCAGGTATGCTCCCACCTCCACCTGCCCCACTCACCACCTCTGCTAGTTCCAGACACCTCCCAAGCACG<br>CAGCAATGCAGCTCAAAACGCTTAGCCTAGCCACACCCCCACGGGAAACAGCAGTGATTAACCTTTAGCAATAAACGAAAGTTTAACT<br>AAGCTATACTAACCCCAGGGTTGGTCAATTTCGTGCCAGCCACACCCTCGAGCTAGCAAAAAAAAAAAAAAAAAAAAAAAAAAAAAAG<br>CATATGACTAAAAAAAAAAAAAAAAAAAAAAAAAAAAAAAAAAAAAAAAAAAAAAAAAAAAAAAAAAAAAAA |
| 41 | ModB murine IL-12 (RNA) | GGAAUAAACUAGUCUCAACACAACAUAUACAAAACAAACGAAUCUCAAGCAAUCAAGCAUUCUACUUCUAUUGCAGCAAUUUAAAUCA<br>UUUCUUUUAAAGCAAAAGCAAUUUUCUGAAAAUUUUCACCAUUUACGAACGAUAGCCAUGGGCCAUGGCCCUAGAACAUUUGCUCC<br>UGCUGCUGGCCGCUGCCCUGGCCCCUACACAGACAAGAGCUGGACCUGGAUCCAUGUGGGAGCUGGAGAAGACGUUUAUGUUGUAGA<br>GGUGGACUGGACUCCCGAUGCCCUGGAGAAACAGUGAACCUCACCUGUGACACGCCUGAAGAAGAUGAACAUCACCUGGACCUCAGAC<br>CAGAGACAUGGAGUCAUAGGCUCUGGAAAGACCCUGCCAUCACUGUCAAAGAGUUUCUAGAUGCUGGCCAGUACACCUGCCACAAAG<br>CAAGAACCUCUGAAGUGUGAAGGCACCAAAUUGACUCCGGACGGCUUCAGUGCUGGCUGGUGCAAAGAAACAUGGACUUGAAGUUC<br>AACAUCAAGAGCAGUAGCAGUUCCCCUGACUCUCGGGCAGUGACAUGGGAAUGGCGUCUCUGUCUGCAGAGAAGGUCACACUGGACC<br>AAAGGGACUAUGAGAAGUAUUCAGUGUCCUGCCAGGAGGAUGUCACCUGCCCAACUGCCGAGGAGACCCUGCCCAUUGAACUGGCGUU<br>GGAAGCACGGCAGCAGAAUAAAUAUGAACUACAGCACCAGCUUCUUCAUCAGGGACAUCAUCAAACCAGACCCGCCCAAGAACUUG<br>CAGAUGAAGCCUUUGAAGAACUCACAGGUGGAGGUCAGCUGGGAGUACCCUGACUCCUGGAGCACUCCCCAUUCCUACUUCUCCCUCA<br>AGUUCUUUGUUCGAAUCCAGCGCAAGAAAGAAAAGAUGAAGGAGACAGAGGAGGGGGUGUAACCAGAAAGGGUGCGUUCUCGUAGAGAA<br>GACAUCUACCGAAGUCCAAUGCAAAGGCGGAAAUGUCUGCGUGCAAGCUCAGGAUCGCUAUUACAAUUCCUCAUGCAGCAAGUGGGCA<br>UGUGUUCCCUGCAGAGUCCGAUCGGUUCCUGGAGUAGGGGUACCUGGAGUGGGCAGGGUCAUACCGGUCUCUGGACCUGCCAGGUGUC<br>UUAGCCAGUCCCGAAACCUGCUGAAGACCACAGAUGACAUGGUGAAGACGGCCAGAGAAAAGCUGAAACAUUAUUCCUGCACUGCUGA<br>AGACAUCGAUCAUGAAGACAUCACACGGGACCAAACCAGCACAUUGAAGACCUGUUUACCACUGGAACUACACAAGAACGAGAGUUGC<br>CUGGCUACUAGAGAGACUUCUUCCACAACAAGAGGGAGCUGCCUGCCCCCACAGAAGACGUCUUUGAUGAUGACCCUGUGCCUUGGUA<br>GCAUCUAUGAGGACUUGAAGAUGUACCAGACAGAGUUCCAGGCCAUCAACGCAGCACUUCAGAAUCACAACCAUCAGCAGAUCAUUCU<br>AGACAAGGGCAUGCUGGUGGCCAUCGAUGAGCUGAUGCAGUCUCUGAAUCAUAAUGGCGAGACUCUGCGCCAGAAACCUCCUGUGGGA<br>GAAGCAGACCCUUACAGAGUGAAAAUGAAGCUCUGCAUCCUGCUUCACGCCUUCAGCACCCGCGUCGUGACCAUCAACAGGGUGAUGG<br>GCUAUCUGUCCAGCGCCUAAUAGCUCGACGUCCUGGUACUGCAUGCACGCAAUGCUAGCUGCCCCUUUCCCGUCCUGGGUACCCCGAG<br>UCUCCCCCGACCUCGGGUCCCAGGUAUGCUCCCACCUCCACCUGCCCCACUCACCACCUCUGCUAGUUCCAGACACCUCCCAAGCACG<br>CAGCAAUGCAGCUCAAAACGCUUAGCCUAGCCACACCCCCACGGGAAACAGCAGUGAUUAACCUUUAGCAAUAAACGAAAGUUUAACU<br>AAGCUAUACUAACCCCAGGGUUGGUCAAUUUCGUGCCAGCCACACCCUCGAGCUAGCAAAAAAAAAAAAAAAAAAAAAAAAAAAAAAG<br>CAUAUGACUAAAAAAAAAAAAAAAAAAAAAAAAAAAAAAAAAAAAAAAAAAAAAAAAAAAAAAAAAAAAAAA |

IFNα (IFNα4) mouse

| SEQ ID NO: | Description | SEQUENCE |
|---|---|---|
| 42 | ModA murine IFNα4 (amino acid) | MRVTAPRTLILLLSGALALTETWAGSGSCDLPHTYNLGNKRALTVLEEMRRLPPLSCLKDRKDFGFPLEKVDNQQIQKAQAILVLRDL<br>TQQILNLFTSKDLSATWNATLLDSFCNDLHQQLNDLKACVMQEPPLTQEDSLLAVRTYFHRITVYLRKKKHSLCAWEVIRAEVWRALS<br>SSTNLLARLSEEKE |
| 43 | ModA murine IFNα4 (DNA: 5' UTR-CDS-3' UTR) | GGGCGAACTAGTATTCTTCTGGTCCCCACAGACTCAGAGAGAACCCGCCACCATGAGAGTGACCGCCCCAGAACCCTGATCCTGCTG<br>CTGTCTGGCGCCCTGGCCCTGACAGAGACATGGGCCGGAAGCGGATCCTGTGACCTGCCTCACACTTATAACCTCGGGAACAAGAGGG<br>CCTTGACAGTCCTGGAAGAAATGAGAAGACTCCCCCCTCTTTCCTGCCTGAAGGACAGGAAGGATTTTGGATTCCCCTTGGAGAAGGT<br>GGATAACCAACAGATCCAGAAGGCTCAAGCCATCCTTGTGCTAAGAGATCTTACCCAGCAGATTTTGAACCTCTTCACATCAAAAGAC<br>TTGTCTGCTACTTGGAATGCAACTCTCCTAGACTCATTCTGCAATGACCTCCATCAGCAGCTCAATGATCTCAAAGCCTGTGTGATGC<br>AGGAACCTCCTCTGACCCAGGAAGACTCCCTGCTGGCTGTGAGGACATACTTCCACAGGATCACTGTGTACCTGAGAAAGAAGAAACA<br>CAGCCTCTGTGCCTGGGAGGTGATCAGAGCAGAAGTCTGGAGAGCCCTCTCTTCCTCAACCAACTTGCTGGCAAGACTGAGTGAGGAG<br>AAGGAGTGATAACTCGAGAGCTCGCTTTCTTGCTGTCCAATTTCTATTAAAGGTTCCTTTGTTCCCTAAGTCCAACTACTAAACTGGG<br>GGATATTATGAAGGGCCTTGAGCATCTGGATTCTGCCTAATAAAAACATTTATTTTCATTGCTGCGTCGAGACCTGGTCCAGAGTCGCTAGCAAAAAAAAAAAAAAAAAAAAAAAA<br>GTCCAATTTCTATTAAAGGTTCCTTTGTTCCCTAAGTCCAACTACTAAACTGGGGGATATTATGAAGGGCCTTGAGCATCTGGATTCT<br>GCCTAATAAAAACATTTATTTTCATTGCTGCGTCGAGACCTGGTCCAGAGTCGCTAGCAAAAAAAAAAAAAAAAAAAAAAAAAAAAAA<br>AGCATATGACTAAAAAAAAAAAAAAAAAAAAAAAAAAAAAAAAAAAAAAAAAAAAAAAAAAAAAAAAAAAAAA |
| 44 | ModA murine IFNα4 (RNA) | GGGCGAACUAGUAUUCUUCUGGUCCCCACAGACUCAGAGAGAACCCGCCACCAUGAGAGUGACCGCCCCAGAACCCUGAUCCUGCUG<br>CUGUCUGGCGCCCUGGCCCUGACAGAGACAUGGGCCGGAAGCGGAUCCUGUGACCUGCCUCACACUUAUAACCUCGGGAACAAGAGG<br>CCUUGACAGUCCUGGAAGAAAUGAGAAGACUCCCCCCUCUUUCCUGCCUGAAGGACAGGAAGGAUUUUGGAUUCCCCUUGGAGAAGGU<br>GGAUAACCAACAGAUCCAGAAGGCUCAAGCCAUCCUUGUGCUAAGAGAUCUUACCCAGCAGAUUUUGAACCUCUUCACAUCAAAAGAC<br>UUGUCUGCUACUUGGAAUGCAACUCUCCUAGACUCAUUCUGCAAUGACCUCCAUCAGCAGCUCAAUGAUCUCAAAGCCUGUGUGAUGC<br>AGGAACCUCCUCUGACCCAGGAAGACUCCCUGCUGGCUGUGAGGACAUACUUCCACAGGAUCACUGUGUACCUGAGAAAGAAGAAACA<br>CAGCCUCUGUGCCUGGGAGGUGAUCAGAGCAGAAGUCUGGAGAGCCCUCUCUUCCUCAACCAACUUGCUGGCAAGACUGAGUGAGGAG<br>AAGGAGUGAUAACUCGAGAGCUCGCUUUCUUGCUGUCCAAUUUCUAUUAAAGGUUCCUUUGUUCCCUAAGUCCAACUACUAAACUGGG<br>GGAUAUUAUGAAGGGCCUUGAGCAUCUGGAUUCUGCCUAAUAAAAACAUUUAUUUUCAUUGCUGCGUCGAGACCUGGUCCAGAGUCGCUAGCAAAAAAAAAAAAAAAAAAAAAAAAAAAAAA<br>GUCCAAUUUCUAUUAAAGGUUCCUUUGUUCCCUAAGUCCAACUACUAAACUGGGGGAUAUUAUGAAGGGCCUUGAGCAUCUGGAUUCU<br>GCCUAAUAAAAACAUUUAUUUUCAUUGCUGCGUCGAGACCUGGUCCAGAGUCGCUAGCAAAAAAAAAAAAAAAAAAAAAAAAAAAAAA<br>AGCAUAUGACUAAAAAAAAAAAAAAAAAAAAAAAAAAAAAAAAAAAAAAAAAAAAAAAAAAAAAAAAAAAAAA |

TABLE 2-continued

DESCRIPTION OF THE SEQUENCES (mouse sequences and other sequences of the invention)

| SEQ ID NO: | Description | SEQUENCE |
|---|---|---|
| 45 | ModB murine IFNα4 (amino acid) | MGAMAPRTLLLLLAAALAPTQTRAGPGSCDLPHTYNLGNKRALTVLEEMRRLPPLSCLKDRKDFGFPLEKVDNQQIQKAQAILVLRDL TQQILNLFTSKDLSATWNATLLDSFCNDLHQQLNDLKACVMQEPPLTQEDSLLAVRTYFHRITVYLRKKKHSLCAWEVIRAEVWRALS SSTNLLARLSEEKE |
| 46 | ModB murine IFNα4 (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCCATGGGCGCCATGGCCCCTAGAACATTGCTCC TGCTGCTGGCCGCTGCCCTGGCCCCTACACAGACAAGAGCTGGACCTGGATCCTGTGACCTGCCTCACACTTATAACCTCGGGAACAA GAGGGCCTTGACAGTCCTGGAAGAAATGAGAAGACTCCCCCCTCTTTCCTGCCTGAAGGACAGGAAGGATTTTGGATTCCCCTTGGAG AAGGTGGATAACCAACAGATCCAGAAGGCTCAAGCCATCCTTGTGCTAAGAGATCTTACCCAGCAGATTTTGAACCTCTTCACATCAA AAGACTTGTCTGCTACTTGGAATGCAACTCTCCTAGACTCATTCTGCAATGACCTCCATCAGCAGCTCAATGATCTCAAAGCCTGTGT GATGCAGGAACCTCCTCTGACCCAGGAAGACTCCCTGCTGGCTGTGAGGACATACTTCCACAGGATCACTGTGTACCTGAGAAAGAAG AAACACAGCCTCTGTGCCTGGGAGGTGATCAGAGCAGAAGTCTGGAGAGCCCTCTCTTCCTCAACCAACTTGCTGGCAAGACTGAGTG AGGAGAAGGAGTGATAACTCGACGTCCTGGTACTGCATGCACGCAATGCTAGCTGCCCCTTTCCCGTCCTGGGTACCCCGAGTCTCCC CCGACCTCGGGTCCCAGGTATGCTCCCACCTCCACCTGCCCCACTCACCACCTCTGCTAGTTCCAGACACCTCCCAAGCACGCAGCAA TGCAGCTCAAAACGCTTAGCCTAGCCACACCCCCACGGGAAACAGCAGTGATTAACCTTTAGCAATAAACGAAAGTTTAACTAAGCTA TACTAACCCCAGGGTTGGTCAATTTCGTGCCAGCCACACCCTCGAGCTAGCAAAAAAAAAAAAAAAAAAAAAAAAAAAAAAGCATATG ACTAAAAAAAAAAAAAAAAAAAAAAAAAAAAAAAAAAAAAAAAAAAAAAAAAAAAAAAAAAAA |
| 47 | ModB murine IFNα4 (RNA) | GGAAUAAACUAGUCUCAACACAACAUAUACAAAACAAACGAAUCUCAAGCAAUCAAGCAUUCUACUUCUAUUGCAGCAAUUUAAAUCA UUUCUUUUAAAGCAAAAGCAAUUUUCUGAAAAUUUUCACCAUUUACGAACGAUAGCCAUGGGCGCCAUGGCCCCUAGAACAUUGCUCC UGCUGCUGGCCGCUGCCCUGGCCCCUACACAGACAAGAGCUGGACCUGGAUCCUGUGACCUGCCUCACACUUAUAACCUCGGGAACAA GAGGGCCUUGACAGUCCUGGAAGAAAUGAGAAGACUCCCCCCUCUUUCCUGCCUGAAGGACAGGAAGGAUUUUGGAUUCCCCUUGGAG AAGGUGGAUAACCAACAGAUCCAGAAGGCUCAAGCCAUCCUUGUGCUAAGAGAUCUUACCCAGCAGAUUUUGAACCUCUUCACAUCAA AAGACUUGUCUGCUACUUGGAAUGCAACUCUCCUAGACUCAUUCUGCAAUGACCUCCAUCAGCAGCUCAAUGAUCUCAAAGCCUGUGU GAUGCAGGAACCUCCUCUGACCCAGGAAGACUCCCUGCUGGCUGUGAGGACAUACUUCCACAGGAUCACUGUGUACCUGAGAAAGAAG AAACACAGCCUCUGUGCCUGGGAGGUGAUCAGAGCAGAAGUCUGGAGAGCCCUCUCUUCCUCAACCAACUUGCUGGCAAGACUGAGUG AGGAGAAGGAGUGAUAACUCGACGUCCUGGUACUGCAUGCACGCAAUGCUAGCUGCCCCUUUCCCGUCCUGGGUACCCCGAGUCUCCC CCGACCUCGGGUCCCAGGUAUGCUCCCACCUCCACCUGCCCCACUCACCACCUCUGCUAGUUCCAGACACCUCCCAAGCACGCAGCAA UGCAGCUCAAAACGCUUAGCCUAGCCACACCCCCACGGGAAACAGCAGUGAUUAACCUUUAGCAAUAAACGAAAGUUUAACUAAGCUA UACUAACCCCAGGGUUGGUCAAUUUCGUGCCAGCCACACCCUCGAGCUAGCAAAAAAAAAAAAAAAAAAAAAAAAAAAAAAGCAUAUG ACUAAAAAAAAAAAAAAAAAAAAAAAAAAAAAAAAAAAAAAAAAAAAAAAAAAAAAAAAAAAA |

IL-15 sushi mouse

| 48 | ModA murine IL-15 sushi (amino acid) | MGAMAPRTLLLLLAAALAPTQTRAGPGSTTCPPPVSIEHADIRVKNYSVNSRERYVCNSGFKRKAGTSTLIECVINKNINVAHWTTPS LKCIRDPSLAGGSGGSGGSGGSGGSGGSGGNWIDVRYDLEKIESLIQSIHIDTTLYTDSDFHPSCKVTAMNCFLLELQVILHEYSNMT LNETVRNVLYLANSTLSSNKNVAESGCKECEELEEKTFTEFLQSFIRIVQMFINTS |
| 49 | ModA murine IL-15 sushi (DNA: 5' UTR-CDS-3' UTR) | GGGCGAACTAGTATTCTTCTGGTCCCCACAGACTCAGAGAGAACCCGCCACCATGGGCGCCATGGCCCCTAGAACATTGCTCCTGCTG CTGGCCGCTGCCCTGGCCCCTACACAGACAAGAGCTGGACCTGGATCCACCACGTGTCCACCTCCCGTATCTATTGAGCATGCTGACA TCCGGGTCAAGAATTACAGTGTGAACTCCAGGGAGAGGTATGTCTGTAACTCTGGCTTTAAGCGGAAAGCTGGAACATCCACCCTGAT TGAGTGTGTGATCAACAAGAACACAAATGTTGCCCACTGGACAACTCCCAGCCTCAAGTGCATCAGAGACCCCTCCCTAGCTGGAGGG AGCGGAGGCTCTGGCGGAAGCGGCGGGTCTGGAGGCTCCGGGGGAAGCGGCGGAAATTGGATCGACGTGCGCTACGACCTGGAAAAGA TCGAGAGCCTGATCCAGAGCATCCACATCGACACCACCCTGTACACCGACAGCGACTTCCACCCCAGCTGCAAAGTGACCGCTATGAA CTGCTTCCTGCTGGAACTGCAAGTGATCCTGCACGAGTACAGCAACATGACCCTGAACGAGACAGTGCGGAACGTGCTGTACCTGGCC AACAGCACCCTGAGCAGCAACAAGAACGTGGCCGAGAGCGGCTGCAAAGAGTGCGAGGAACTGGAAGAAAAGACCTTCACCGAGTTTC TGCAGAGCTTCATCAGGATCGTGCAGATGTTCATCAACACCTCTTGATGAGTCGACGTCCTGGTACTGCATGCACGCAATGCTAGCTG CCCCTTTCCCGTCCTGGGTACCCCGAGTCTCCCCCGACCTCGGGTCCCAGGTATGCTCCCACCTCCACCTGCCCCACTCACCACCTCT GCTAGTTCCAGACACCTCCCAAGCACGCAGCAATGCAGCTCAAAACGCTTAGCCTAGCCACACCCCCACGGGAAACAGCAGTGATTAA CCTTTAGCAATAAACGAAAGTTTAACTAAGCTATACTAACCCCAGGGTTGGTCAATTTCGTGCCAGCCACACCCTCGAGCTAGCAAAA AAAAAAAAAAAAAAAAAAAAAAAAAAAAGCATATGACTAAAAAAAAAAAAAAAAAAAAAAAAAAAAAAAAAAAAAAAAAAAAAAAAAA AAAAAAAAAAAAAAAA |
| 50 | ModA murine IL-15 sushi (RNA) | GGGCGAACUAGUAUUCUUCUGGUCCCCACAGACUCAGAGAGAACCCGCCACCAUGGGCGCCAUGGCCCCUAGAACAUUGCUCCUGCUG CUGGCCGCUGCCCUGGCCCCUACACAGACAAGAGCUGGACCUGGAUCCACCACGUGUCCACCUCCCGUAUCUAUUGAGCAUGCUGACA UCCGGGUCAAGAAUUACAGUGUGAACUCCAGGGAGAGGUAUGUCUGUAACUCUGGCUUUAAGCGGAAAGCUGGAACAUCCACCCUGAU UGAGUGUGUGAUCAACAAGAACACAAAUGUUGCCCACUGGACAACUCCCAGCCUCAAGUGCAUCAGAGACCCCUCCCUAGCUGGAGGG AGCGGAGGCUCUGGCGGAAGCGGCGGGUCUGGAGGCUCCGGGGGAAGCGGCGGAAAUUGGAUCGACGUGCGCUACGACCUGGAAAAGA UCGAGAGCCUGAUCCAGAGCAUCCACAUCGACACCACCCUGUACACCGACAGCGACUUCCACCCCAGCUGCAAAGUGACCGCUAUGAA CUGCUUCCUGCUGGAACUGCAAGUGAUCCUGCACGAGUACAGCAACAUGACCCUGAACGAGACAGUGCGGAACGUGCUGUACCUGGCC AACAGCACCCUGAGCAGCAACAAGAACGUGGCCGAGAGCGGCUGCAAAGAGUGCGAGGAACUGGAAGAAAAGACCUUCACCGAGUUUC UGCAGAGCUUCAUCAGGAUCGUGCAGAUGUUCAUCAACACCUCUUGAUGAGUCGACGUCCUGGUACUGCAUGCACGCAAUGCUAGCUG CCCCUUUCCCGUCCUGGGUACCCCGAGUCUCCCCCGACCUCGGGUCCCAGGUAUGCUCCCACCUCCACCUGCCCCACUCACCACCUCU GCUAGUUCCAGACACCUCCCAAGCACGCAGCAAUGCAGCUCAAAACGCUUAGCCUAGCCACACCCCCACGGGAAACAGCAGUGAUUAA CCUUUAGCAAUAAACGAAAGUUUAACUAAGCUAUACUAACCCCAGGGUUGGUCAAUUUCGUGCCAGCCACACCCUCGAGCUAGCAAAA AAAAAAAAAAAAAAAAAAAAAAAAAAAAGCAUAUGACUAAAAAAAAAAAAAAAAAAAAAAAAAAAAAAAAAAAAAAAAAAAAAAAAAA AAAAAAAAAAAAAAAA |

TABLE 2-continued

DESCRIPTION OF THE SEQUENCES (mouse sequences and other sequences of the invention)

| SEQ ID NO: | Description | SEQUENCE |
|---|---|---|
| 51 | ModB murine IL-15 sushi (amino acid) | MGAMAPRTLLLLLAAALAPTQTRAGPGSTTCPPPVSIEHADIRVKNYSVNSRERYVCNSGFKRKAGTSTLIECVINKNTNVAHWTTPS LKCIRDPSLAGGSGGSGGSGGSGGSGGSGGNWIDVRYDLEKIESLIQSIHIDTTLYTDSDFHPSCKVTAMNCFLLELQVILHEYSNMT LNETVRNVLYLANSTLSSNKNVAESGCKECEELEEKTFTEFLQSFIRIVQMFINTS |
| 52 | ModB murine IL-15 sushi (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCCATGGGCGCCATGGCCCCTAGAACATTGCTCC TGCTGCTGGCCGCTGCCCTGGCCCCTACACAGACAAGAGCTGGACCTGGATCCACCACGTGTCCACCTCCCGTATCTATTGAGCATGC TGACATCCGGGTCAAGAATTACAGTGTGAACTCCAGGGAGAGGTATGTCTGTAACTCTGGCTTTAAGCGGAAAGCTGGAACATCCACC CTGATTGAGTGTGTGATCAACAAGAACACAAATGTTGCCCACTGGACAACTCCCAGCCTCAAGTGCATCAGAGACCCCTCCCTAGCTG GAGGGAGCGGAGGCTCTGGCGGAAGCGGCGGGTCTGGAGGCTCCGGGGGAAGCGGCGGAAATTGGATCGACGTGCGCTACGACCTGGA AAAGATCGAGAGCCTGATCCAGAGCATCCACATCGACACCACCCTGTACACCGACAGCGACTTCCACCCCAGCTGCAAAGTGACCGCT ATGAACTGCTTCCTGCTGGAACTGCAAGTGATCCTGCACGAGTACAGCAACATGACCCTGAACGAGACAGTGCGGAACGTGCTGTACC TGGCCAACAGCACCCTGAGCAGCAACAAGAACGTGGCCGAGAGCGGCTGCAAAGAGTGCGAGGAACTGGAAGAAAAGACCTTCACCGA GTTTCTGCAGAGCTTCATCAGGATCGTGCAGATGTTCATCAACACCTCTTGATGAGTCGACGTCCTGGTACTGCATGCACGCAATGCT AGCTGCCCCTTTCCCGTCCTGGGTACCCCGAGTCTCCCCCGACCTCGGGTCCCAGGTATGCTCCCACCTCCACCTGCCCCACTCACCA CCTCTGCTAGTTCCAGACACCTCCCAAGCACGCAGCAATGCAGCTCAAAACGCTTAGCCTAGCCACACCCCCACGGGAAACAGCAGTG ATTAACCTTTAGCAATAAACGAAAGTTTAACTAAGCTATACTAACCCCAGGGTTGGTCAATTTCGTGCCAGCCACACCCTCGAGCTAG CAAAAAAAAAAAAAAAAAAAAAAAAAAAAAGCATATGACTAAAAAAAAAAAAAAAAAAAAAAAAAAAAAAAAAAAAAAAAAAAAAAAA AAAAAAAAAAAAAAAAAAAAAAA |
| 53 | ModB murine IL-15 sushi (RNA) | GGAAUAAACUAGUCUCAACACAACAUAUACAAAACAAACGAAUCUCAAGCAAUCAAGCAUUCUACUUCUAUUGCAGCAAUUUAAAUCA UUUCUUUUAAAGCAAAAGCAAUUUUCUGAAAAUUUUCACCAUUUACGAACGAUAGCCAUGGGCGCCAUGGCCCCUAGAACAUUGCUCC UGCUGCUGGCCGCUGCCCUGGCCCCUACACAGACAAGAGCUGGACCUGGAUCCACCACGUGUCCACCUCCCGUAUCUAUUGAGCAUGC UGACAUCCGGGUCAAGAAUUACAGUGUGAACUCCAGGGAGAGGUAUGUCUGUAACUCUGGCUUUAAGCGGAAAGCUGGAACAUCCACC CUGAUUGAGUGUGUGAUCAACAAGAACACAAAUGUUGCCCACUGGACAACUCCCAGCCUCAAGUGCAUCAGAGACCCCUCCCUAGCUG GAGGGAGCGGAGGCUCUGGCGGAAGCGGCGGGUCUGGAGGCUCCGGGGGAAGCGGCGGAAAUUGGAUCGACGUGCGCUACGACCUGGA AAAGAUCGAGAGCCUGAUCCAGAGCAUCCACAUCGACACCACCCUGUACACCGACAGCGACUUCCACCCCAGCUGCAAAGUGACCGCU AUGAACUGCUUCCUGCUGGAACUGCAAGUGAUCCUGCACGAGUACAGCAACAUGACCCUGAACGAGACAGUGCGGAACGUGCUGUACC UGGCCAACAGCACCCUGAGCAGCAACAAGAACGUGGCCGAGAGCGGCUGCAAAGAGUGCGAGGAACUGGAAGAAAAGACCUUCACCGA GUUUCUGCAGAGCUUCAUCAGGAUCGUGCAGAUGUUCAUCAACACCUCUUGAUGAGUCGACGUCCUGGUACUGCAUGCACGCAAUGCU AGCUGCCCCUUUCCCGUCCUGGGUACCCCGAGUCUCCCCCGACCUCGGGUCCCAGGUAUGCUCCCACCUCCACCUGCCCCACUCACCA CCUCUGCUAGUUCCAGACACCUCCCAAGCACGCAGCAAUGCAGCUCAAAACGCUUAGCCUAGCCACACCCCCACGGGAAACAGCAGUG AUUAACCUUUAGCAAUAAACGAAAGUUUAACUAAGCUAUACUAACCCCAGGGUUGGUCAAUUUCGUGCCAGCCACACCCUCGAGCUAG AAAAAAAAAAAAAAAAAAAAAAA |
| | GM-CSF mouse | |
| 54 | ModA murine GM-CSF (amino acid) | MWLQNLLFLGIVVYSLSAPTRSPITVTRPWKHVEAIKEALNLLDDMPVTLNEEVEVVSNEFSFKKLTCVQTRLKIFEQGLRGNFTKLK GALNMTASYYQTYCPPTPETDCETQVTTYADFIDSLKTFLTDIPFECKKPGQK |
| 55 | ModA murine GM-CSF (DNA: 5' UTR-CDS-3' UTR) | GGGCGAACTAGTATTCTTCTGGTCCCCACAGACTCAGAGAGAACCCGCCACCATGTGGCTGCAGAACCTGCTGTTCCTGGGCATCGTG GTGTACAGCCTGAGCGCCCCCACCAGGAGCCCCATCACCGTGACCAGGCCCTGGAAGCACGTGGAGGCCATCAAGGAGGCCCTGAACC TGCTGGACGACATGCCCGTGACCCTGAACGAGGAGGTGGAGGTGGTGAGCAACGAGTTCAGCTTCAAGAAGCTGACCTGCGTGCAGAC CAGGCTGAAGATCTTCGAGCAGGGCCTGAGGGGCAACTTCACCAAGCTGAAGGGCGCCCTGAACATGACCGCCAGCTACTACCAGACC TACTGCCCCCCCACCCCCGAGACCGACTGCGAGACCCAGGTGACCACCTACGCCGACTTCATCGACAGCCTGAAGACCTTCCTGACCG ACATCCCCTTCGAGTGCAAGAAGCCCGGCCAGAAGTGATGACTCGAGCTGGTACTGCATGCACGCAATGCTAGCTGCCCCTTTCCCGT CCTGGGTACCCCGAGTCTCCCCCGACCTCGGGTCCCAGGTATGCTCCCACCTCCACCTGCCCCACTCACCACCTCTGCTAGTTCCAGA CACCTCCCAAGCACGCAGCAATGCAGCTCAAAACGCTTAGCCTAGCCACACCCCCACGGGAAACAGCAGTGATTAACCTTTAGCAATA AACGAAAGTTTAACTAAGCTATACTAACCCCAGGGTTGGTCAATTTCGTGCCAGCCACACCGAGACCTGGTCCAGAGTCGCTAGCCGC GTCGCTAAAAAAAAAAAAAAAAAAAAAAAAAAAAGCATATGACTAAAAAAAAAAAAAAAAAAAAAAAAAAAAAAAAAAAAAAAAAAAA AAAAAAAAAAAAAAAAAAAAAAA |
| 56 | ModA murine GM-CSF (RNA) | GGGCGAACUAGUAUUCUUCUGGUCCCCACAGACUCAGAGAGAACCCGCCACCAUGUGGCUGCAGAACCUGCUGUUCCUGGGCAUCGUG GUGUACAGCCUGAGCGCCCCCACCAGGAGCCCCAUCACCGUGACCAGGCCCUGGAAGCACGUGGAGGCCAUCAAGGAGGCCCUGAACC UGCUGGACGACAUGCCCGUGACCCUGAACGAGGAGGUGGAGGUGGUGAGCAACGAGUUCAGCUUCAAGAAGCUGACCUGCGUGCAGAC CAGGCUGAAGAUCUUCGAGCAGGGCCUGAGGGGCAACUUCACCAAGCUGAAGGGCGCCCUGAACAUGACCGCCAGCUACUACCAGACC UACUGCCCCCCCACCCCCGAGACCGACUGCGAGACCCAGGUGACCACCUACGCCGACUUCAUCGACAGCCUGAAGACCUUCCUGACCG ACAUCCCCUUCGAGUGCAAGAAGCCCGGCCAGAAGUGAUGACUCGAGCUGGUACUGCAUGCACGCAAUGCUAGCUGCCCCUUUCCCGU CCUGGGUACCCCGAGUCUCCCCCGACCUCGGGUCCCAGGUAUGCUCCCACCUCCACCUGCCCCACUCACCACCUCUGCUAGUUCCAGA CACCUCCCAAGCACGCAGCAAUGCAGCUCAAAACGCUUAGCCUAGCCACACCCCCACGGGAAACAGCAGUGAUUAACCUUUAGCAAUA AACGAAAGUUUAACUAAGCUAUACUAACCCCAGGGUUGGUCAAUUUCGUGCCAGCCACACCGAGACCUGGUCCAGAGUCGCUAGCCGC GUCGCUAAAAAAAAAAAAAAAAAAAAAAAAAAAAGCAUAUGACUAAAAAAAAAAAAAAAAAAAAAAAAAAAAAAAAAAAAAAAAAAAA AAAAAAAAAAAAAAAAAAAAAAA |

TABLE 2-continued

DESCRIPTION OF THE SEQUENCES (mouse sequences and other sequences of the invention)

| SEQ ID NO: | Description | SEQUENCE |
|---|---|---|
| 57 | ModB murine GM-CSF (amino acid) | MWLQNLLFLGIVVYSLSAPTRSPITVTRPWKHVEAIKEALNLLDDMPVTLNEEVEVVSNEFSFKKLTCVQTRLKIFEQGLRGNFTKLK GALNMTASYYQTYCPPTPETDCETQVTTYADFIDSLKTFLTDIPFECKKPGQK |
| 58 | ModB murine GM-CSF (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCCATGTGGCTGCAGAACCTGCTGTTCCTGGGCA TCGTGGTGTACAGCCTGAGCGCCCCCACCAGGAGCCCCATCACCGTGACCAGGCCCTGGAAGCACGTGGAGGCCATCAAGGAGGCCCT GAACCTGCTGGACGACATGCCCGTGACCCTGAACGAGGAGGTGGAGGTGGTGAGCAACGAGTTCAGCTTCAAGAAGCTGACCTGCGTG CAGACCAGGCTGAAGATCTTCGAGCAGGGCCTGAGGGGCAACTTCACCAAGCTGAAGGGCGCCCTGAACATGACCGCCAGCTACTACC AGACCTACTGCCCCCCCACCCCCGAGACCGACTGCGAGACCCAGGTGACCACCTACGCCGACTTCATCGACAGCCTGAAGACCTTCCT GACCGACATCCCCTTCGAGTGCAAGAAGCCCGGCCAGAAGTGATGACTCGAGCTGGTACTGCATGCACGCAATGCTAGCTGCCCCTTT CCCGTCCTGGGTACCCCGAGTCTCCCCCGACCTCGGGTCCCAGGTATGCTCCCACCTCCACCTGCCCCACTCACCACCTCTGCTAGTT CCAGACACCTCCCAAGCACGCAGCAATGCAGCTCAAAACGCTTAGCCTAGCCACACCCCCACGGGAAACAGCAGTGATTAACCTTTAG CAATAAACGAAAGTTTAACTAAGCTATACTAACCCCAGGGTTGGTCAATTTCGTGCCAGCCACACCGAGACCTGGTCCAGAGTCGCTA GCCGCGTCGCTAAAAAAAAAAAAAAAAAAAAAAAAAAAAAGCATATGACTAAAAAAAAAAAAAAAAAAAAAAAAAAAAAAAAAAAAA AAAAAAAAAAAAAAAAAAAAAAAAAAAAAA |
| 59 | ModB murine GM-CSF (RNA) | GGAAUAAACUAGUCUCAACACAACAUAUACAAAACAAACGAAUCUCAAGCAAUCAAGCAUUCUACUUCUAUUGCAGCAAUUUAAAUCA UUUCUUUUAAAGCAAAAGCAAUUUUCUGAAAAUUUUCACCAUUUACGAACGAUAGCCAUGUGGCUGCAGAACCUGCUGUUCCUGGGCA UCGUGGUGUACAGCCUGAGCGCCCCCACCAGGAGCCCCAUCACCGUGACCAGGCCCUGGAAGCACGUGGAGGCCAUCAAGGAGGCCCU GAACCUGCUGGACGACAUGCCCGUGACCCUGAACGAGGAGGUGGAGGUGGUGAGCAACGAGUUCAGCUUCAAGAAGCUGACCUGCGUG CAGACCAGGCUGAAGAUCUUCGAGCAGGGCCUGAGGGGCAACUUCACCAAGCUGAAGGGCGCCCUGAACAUGACCGCCAGCUACUACC AGACCUACUGCCCCCCCACCCCCGAGACCGACUGCGAGACCCAGGUGACCACCUACGCCGACUUCAUCGACAGCCUGAAGACCUUCCU GACCGACAUCCCCUUCGAGUGCAAGAAGCCCGGCCAGAAGUGAUGACUCGAGCUGGUACUGCAUGCACGCAAUGCUAGCUGCCCCUUU CCCGUCCUGGGUACCCCGAGUCUCCCCCGACCUCGGGUCCCAGGUAUGCUCCCACCUCCACCUGCCCCACUCACCACCUCUGCUAGUU CCAGACACCUCCCAAGCACGCAGCAAUGCAGCUCAAAACGCUUAGCCUAGCCACACCCCCACGGGAAACAGCAGUGAUUAACCUUUAG CAAUAAACGAAAGUUUAACUAAGCUAUACUAACCCCAGGGUUGGUCAAUUUCGUGCCAGCCACACCGAGACCUGGUCCAGAGUCGCUA GCCGCGUCGCUAAAAAAAAAAAAAAAAAAAAAAAAAAAAAGCAUAUGACUAAAAAAAAAAAAAAAAAAAAAAAAAAAAAAAAAAAAA AAAAAAAAAAAAAAAAAAAAAAAAAAAAAA |
| | FLT3L mouse | |
| 60 | ModA FLT3L (amino acid, human FLT3L in combination with a mouse optimized secretion sequence)) | MGAMAPRTLLLLLAAALAPTQTRAGPGSTQDCSFQHSPISSDFAVKIRELSDYLLQDYPVTVASNLQDEELCGGLWRLVLAQRWMERL KTVAGSKMQGLLERVNTEIHFVTKCAFQPPPSCLRFVQTNISRLLQETSEQLVALKPWITRQNFSRCLELQCQPDSSTLPPPWSPRPL EATAPTAPQPP |
| 61 | ModA FLT3L (DNA: 5' UTR-CDS-3' UTR) | GGGCGAACTAGTATTCTTCTGGTCCCCACAGACTCAGAGAGAACCCGCCACCATGGGCGCCATGGCCCCTAGAACATTGCTCCTGCTG CTGGCCGCTGCCCTGGCCCCTACACAGACAAGAGCTGGACCTGGATCCACCCAGGACTGCAGCTTCCAGCACTCCCCTATCTCCTCCG ACTTCGCCGTGAAGATCCGGGAGCTGTCCGATTACCTGCTGCAGGACTACCCTGTGACCGTGGCCAGCAACCTGCAGGACGAAGAACT GTGTGGCGGCCTGTGGCGGCTGGTGCTGGCCCAGCGGTGGATGGAACGGCTGAAAACCGTGGCCGGCTCCAAGATGCAGGGCCTGCTC GAGCGGGTGAACACCGAGATCCACTTCGTGACCAAGTGCGCCTTCCAGCCTCCTCCTTCCTGCCTGCGGTTCGTGCAGACCAACATCT CCCGGCTGCTGCAGGAAACCTCCGAGCAGCTGGTCGCCCTGAAGCCTTGGATCACCCGGCAGAACTTCTCCCGGTGTCTGGAACTCCA GTGTCAGCCCGACTCCTCCACCCTGCCCTCCTCCCTGGTCCCCCAGGCCTCTGGAAGCCACCGCCCCTACCGCCCCACAGCCTCCTTGA TAGGTCGACGTCCTGGTACTGCATGCACGCAATGCTAGCTGCCCCTTTCCCGTCCTGGGTACCCCGAGTCTCCCCCGACCTCGGGTCC CAGGTATGCTCCCACCTCCACCTGCCCCACTCACCACCTCTGCTAGTTCCAGACACCTCCCAAGCACGCAGCAATGCAGCTCAAAACG CTTAGCCTAGCCACACCCCCACGGGAAACAGCAGTGATTAACCTTTAGCAATAAACGAAAGTTTAACTAAGCTATACTAACCCCAGGG TTGGTCAATTTCGTGCCAGCCACACCCTCGAGCTAGCAAAAAAAAAAAAAAAAAAAAAAAAAAAAAAGCATATGACTAAAAAAAAAAA AAAAAAAAAAAAAAAAAAAAAAAAAAAAAAAAAAAAAAAAAAAA |
| 62 | ModA FLT3L (RNA) | GGGCGAACUAGUAUUCUUCUGGUCCCCACAGACUCAGAGAGAACCCGCCACCAUGGGCGCCAUGGCCCCUAGAACAUUGCUCCUGCUG CUGGCCGCUGCCCUGGCCCCUACACAGACAAGAGCUGGACCUGGAUCCACCCAGGACUGCAGCUUCCAGCACUCCCCUAUCUCCUCCG ACUUCGCCGUGAAGAUCCGGGAGCUGUCCGAUUACCUGCUGCAGGACUACCCUGUGACCGUGGCCAGCAACCUGCAGGACGAAGAACU GUGUGGCGGCCUGUGGCGGCUGGUGCUGGCCCAGCGGUGGAUGGAACGGCUGAAAACCGUGGCCGGCUCCAAGAUGCAGGGCCUGCUC GAGCGGGUGAACACCGAGAUCCACUUCGUGACCAAGUGCGCCUUCCAGCCUCCUCCUUCCUGCCUGCGGUUCGUGCAGACCAACAUCU CCCGGCUGCUGCAGGAAACCUCCGAGCAGCUGGUCGCCCUGAAGCCUUGGAUCACCCGGCAGAACUUCUCCCGGUGUCUGGAACUCCA GUGUCAGCCCGACUCCUCCACCCUGCCCUCCUCCCUGGUCCCCCAGGCCUCUGGAAGCCACCGCCCCUACCGCCCCACAGCCUCCUUGA UAGGUCGACGUCCUGGUACUGCAUGCACGCAAUGCUAGCUGCCCCUUUCCCGUCCUGGGUACCCCGAGUCUCCCCCGACCUCGGGUCC CAGGUAUGCUCCCACCUCCACCUGCCCCACUCACCACCUCUGCUAGUUCCAGACACCUCCCAAGCACGCAGCAAUGCAGCUCAAAACG CUUAGCCUAGCCACACCCCCACGGGAAACAGCAGUGAUUAACCUUUAGCAAUAAACGAAAGUUUAACUAAGCUAUACUAACCCCAGGG |

TABLE 2-continued

DESCRIPTION OF THE SEQUENCES (mouse sequences and other sequences of the invention)

| SEQ ID NO: | Description | SEQUENCE |
|---|---|---|
| | | UUGGUCAAUUUCGUGCCAGCCACACCCUCGAGCUAGCAAAAAAAAAAAAAAAAAAAAAAAAAAAAAAAAAGCAUAUGACUAAAAAAAAAA AAAAAAAAAAAAAAAAAAAAAAAAAAAAAAAAAAAAAAAAAAAAAAAAAAAAA |
| 63 | ModB FLT3L (amino acid, human FLT3L in combination with a mouse optimized secretion sequence) | MGAMAPRTLLLLLAAALAPTQTRAGPGSTQDCSFQHSPISSDFAVKIRELSDYLLQDYPVTVASNLQDEELCGGLWRLVLAQRWMERL KTVAGSKMQGLLERVNTEIHFVTKCAFQPPPSCLRFVQTNISRLLQETSEQLVALKPWITRQNFSRCLELQCQPDSSTLPPPWSPRPL EATAPTAPQPP |
| 64 | ModB FLT3L (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCCATGGGCGCCATGGCCCCTAGAACATTGCTCC TGCTGCTGGCCGCTGCCCTGGCCCCTACACAGACAAGAGCTGGACCTGGATCCACCCAGGACTGCAGCTTCCAGCACTCCCCTATCTC CTCCGACTTCGCCGTGAAGATCCGGGAGCTGTCCGATTACCTGCTGCAGGACTACCCTGTGACCGTGGCCAGCAACCTGCAGGACGAA GAACTGTGTGGCGGCCTGTGGCGGCTGGTGCTGGCCCAGCGGTGGATGGAACGGCTGAAAACCGTGGCCGGCTCCAAGATGCAGGGCC TGCTCGAGCGGGTGAACACCGAGATCCACTTCGTGACCAAGTGCGCCTTCCAGCCTCCTCCTTCCTGCCTGCGGTTCGTGCAGACCAA CATCTCCCGGCTGCTGCAGGAAACCTCCGAGCAGCTGGTCGCCCTGAAGCCTTGGATCACCCGGCAGAACTTCTCCCGGTGTCTGGAA CTCCAGTGTCAGCCCGACTCCTCCACCCTGCCTCCTCCCTGGTCCCCCAGGCCTCTGGAAGCCACCGCCCCTACCGCCCCACAGCCTC CTTGATAGGTCGACGTCCTGGTACTGCATGCACGCAATGCTAGCTGCCCCTTTCCCGTCCTGGGTACCCCGAGTCTCCCCCGACCTCG GGTCCCAGGTATGCTCCCACCTCCACCTGCCCCACTCACCACCTCTGCTAGTTCCAGACACCTCCCAAGCACGCAGCAATGCAGCTCA AAACGCTTAGCCTAGCCACACCCCACGGGAAACAGCAGTGATTAACCTTTAGCAATAAACGAAAGTTTAACTAAGCTATACTAACCC CAGGGTTGGTCAATTTCGTGCCAGCCACACCCTCGAGCTAGCAAAAAAAAAAAAAAAAAAAAAAAAAAAAAAAAGCATATGACTAAAAA AAAAAAAAAAAAAAAAAAAAAAAAAAAAAAAAAAAAAAAAAAAAAAAAAAAAA |
| 65 | ModB murine FLT3L (RNA) | GGAAUAAACUAGUCUCAACACAACAUAUACAAAACAAACGAAUCUCAAGCAAUCAAGCAUUCUACUUCUAUUGCAGCAAUUUAAAUCA UGCUGCUGGCCGCUGCCCUGGCCCCUACACAGACAAGAGCUGGACCUGGAUCCACCCAGGACUGCAGCUUCCAGCACUCCCCUAUCUC CUCCGACUUCGCCGUGAAGAUCCGGGAGCUGUCCGAUUACCUGCUGCAGGACUACCCUGUGACCGUGGCCAGCAACCUGCAGGACGAA GAACUGUGUGGCGGCCUGUGGCGGCUGGUGCUGGCCCAGCGGUGGAUGGAACGGCUGAAAACCGUGGCCGGCUCCAAGAUGCAGGGCC UGCUCGAGCGGGUGAACACCGAGAUCCACUUCGUGACCAAGUGCGCCUUCCAGCCUCCUCCUUCCUGCCUGCGGUUCGUGCAGACCAA CAUCUCCCGGCUGCUGCAGGAAACCUCCGAGCAGCUGGUCGCCCUGAAGCCUUGGAUCACCCGGCAGAACUUCUCCCGGUGUCUGGAA CUCCAGUGUCAGCCCGACUCCUCCACCCUGCCUCCUCCCUGGUCCCCCAGGCCUCUGGAAGCCACCGCCCCUACCGCCCCACAGCCUC CUUGAUAGGUCGACGUCCUGGUACUGCAUGCACGCAAUGCUAGCUGCCCCUUUCCCGUCCUGGGUACCCCGAGUCUCCCCCGACCUCG GGUCCCAGGUAUGCUCCCACCUCCACCUGCCCCACUCACCACCUCUGCUAGUUCCAGACACCUCCCAAGCACGCAGCAAUGCAGCUCA AAACGCUUAGCCUAGCCACACCCCACGGGAAACAGCAGUGAUUAACCUUUAGCAAUAAACGAAAGUUUAACUAAGCUAUACUAACCC CAGGGUUGGUCAAUUUCGUGCCAGCCACACCCUCGAGCUAGCAAAAAAAAAAAAAAAAAAAAAAAAAAAAAAAAGCAUAUGACUAAAAA AAAAAAAAAAAAAAAAAAAAAAAAAAAAAAAAAAAAAAAAAAAAAAAAAAAAA |
| | 41BBL mouse | |
| 66 | ModA murine 41BBL (amino acid) | MDQHTLDVEDTADARHPAGTSCPSDAALLRDTGLLADAALLSDTVRPTNAALPTDAAYPAVNVRDREAAWPPALNFCSRHPKLYGLVA LVLLLLIAACVPIFTRTEPRPALTITTSPNLGTRENNADQVTPVSHIGCPNTTQQGSPVFAKLLAKNQASLCNTTLNWHSQDGAGSSY LSQGLRYEEDKKELVVDSPGLYYVFLELKLSPTFTNTGHKVQGWVSLVLQAKPQVDDFDNLALTVELFPCSMENKLVDRSWSQLLLLK AGHRLSVGLRAYLHGAQDAYRDWELSYPNTTSFGLFLVKPDNPWE |
| 67 | ModA murine 41BBL (DNA: 5' UTR-CDS-3' UTR) | GGGCGAACTAGTATTCTTCTGGTCCCCACAGACTCAGAGAGAACCCGCCACCATGGACCAGCACACACTTGATGTGGAGGATACCGCG GATGCCAGACATCCAGCAGGTACTTCGTGCCCCTCGGATGCGGCGCTCCTCAGAGATACCGGGCTCCTCGCGGACGCTGCGCTCCTCT CAGATACTGTGCGCCCCACAAATGCCGCGCTCCCCACGGATGCTGCCTACCCTGCGGTTAATGTTCGGGATCGCGAGGCCGCGTGGCC GCCTGCACTGAACTTCTGTTCCCGCCACCCAAAGCTCTATGGCCTAGTCGCTTTGGTTTTGCTGCTTCTGATCGCCGCCTGTGTTCCT ATCTTCACCCGCACCGAGCCTCGGCCAGCGCTCACAATCACCACCTCGCCCAACCTGGGTACCCGAGAGAATAATGCAGACCAGGTCA CCCCTGTTTCCCACATTGGCTGCCCCAACACTACACAACAGGGCTCTCCTGTGTTCGCCAAGCTACTGGCTAAAAACCAAGCATCGTT GTGCAATACAACTCTGAACTGGCACAGCCAAGATGGAGCTGGGAGCTCATACCTATCTCAAGGTCTGAGGTACGAAGAAGACAAAAAG GAGTTGGTGGTAGACAGTCCCGGGCTCTACTACGTATTTTTGAACTGAAGCTCAGTCCAACATTCACAAACACAGGCCACAAGGTGC AGGGCTGGGTCTCTCTTGTTTTGCAAGCAAAGCCTCAGGTAGATGACTTTGACAACTTGGCCCTGACAGTGGAACTGTTCCCTTGCTC CATGGAGAACAAGTTAGTGGACCGTTCCTGGAGTCAACTGTTCCTGAAGGCTGGCCACCGCCTCAGTGTGGGTCTGAGGGCTTAT CTGCATGGAGCCCAGGATGCATACAGAGACTGGGAGCTGTCTTATCCCAACACCACCAGCTTTGGACTCTTTCTTGTGAAACCCGACA ACCCATGGGAATGATAGGGATCCGATCTGGTACTGCATGCACGCAATGCTAGCTGCCCCTTTCCCGTCCTGGGTACCCCGAGTCTCCC CCGACCTCGGGTCCCAGGTATGCTCCCACCTCCACCTGCCCCACTCACCACCTCTGCTAGTTCCAGACACCTCCCAAGCACGCAGCAA TGCAGCTCAAAACGCTTAGCCTAGCCACACCCCACGGGAAACAGCAGTGATTAACCTTTAGCAATAAACGAAAGTTTAACTAAGCTA TACTAACCCCAGGGTTGGTCAATTTCGTGCCAGCCACACCCTCGAGCTAGCAAAAAAAAAAAAAAAAAAAAAAAAAAAAAAAGCATATG ACTAAAAAAAAAAAAAAAAAAAAAAAAAAAAAAAAAAAAAAAAAAAAAAAAAAAAAAAAAAAA |

TABLE 2-continued

DESCRIPTION OF THE SEQUENCES (mouse sequences and other sequences of the invention)

| SEQ ID NO: | Description | SEQUENCE |
|---|---|---|
| 68 | ModA murine 41BBL (RNA) | GGGCGAACUAGUAUUCUUCUGGUCCCCACAGACUCAGAGAGAACCCGCCACCAUGGACCAGCACACACUUGAUGUGGAGGAUACCGCG GAUGCCAGACAUCCAGCAGGUACUUCGUGCCCUCGGAUGCGGCGCUCCUCAGAGAUACCGGGCUCCUCGCGGACGCUGCGCUCCUCU CAGAUACUGUGCGCCCCACAAAUGCCGCGCUCCCCACGGAUGCUGCCUACCCUGCGGUUAAUGUUCGGGAUCGCGAGGCCGCGUGGCC GCCUGCACUGAACUUCUGUUCCCGCCACCCAAAGCUCUAUGGCCUAGUCGCUUUGGUUUUGCUGCUUCUGAUCGCCGCCUGUGUUCCU AUCUUCACCCGCACCGAGCCUCGGCCAGCGCUCACAAUCACCACCUCGCCCAACCUGGGUACCCGAGAGAAUAAUGCAGACCAGGUCA CCCCUGUUUCCCACAUUGGCUGCCCCAACACUACACAACAGGGCUCUCCUGUGUUCGCCAAGCUACUGGCUAAAAACCAAGCAUCGUU GUGCAAUACAACUCUGAACUGGCACAGCCAAGAUGGAGCUGGGAGCUCAUACCUAUCUCAAGGUCUGAGGUACGAAGAAGACAAAAAG GAGUUGGUGGUAGACAGUCCCGGGCUCUACUACGUAUUUUUGGAACUGAAGCUCAGUCCAACAUUCACAAACACAGGCCACAAGGUGC AGGGCUGGGUCUCUCUUGUUUUGCAAGCAAAGCCUCAGGUAGAUGACUUUGACAACUUGGCCCUGACAGUGGAACUGUUCCCUUGCUC CAUGGAGAACAAGUUAGUGGACCGUUCCUGGAGUCAACUGUUGCUCCUGAAGGCUGGCCACCGCCUCAGUGGGUCUGAGGGCUUUAU CUGCAUGGAGCCCAGGAUGCAUACAGAGACUGGGAGCUGUCUUAUCCCAACACCACCAGCUUUGGACUCUUUCUUGUGAAACCCGACA ACCCAUGGGAAUGAUAGGGAUCCGAUCUGGUACUGCAUGCACGCAAUGCUAGCUGCCCCUUUCCCGUCCUGGGUACCCCGAGUCUCCC CCGACCUCGGGUCCCAGGUAUGCUCCCACCUCCACCUGCCCCACUCACCACCUCUGCUAGUUCCAGACACCUCCCAAGCACGCAGCAA UGCAGCUCAAAACGCUUAGCCUAGCCACACCCCACGGGAAACAGCAGUGAUUAACCUUUAGCAAUAAACGAAAGUUUAACUAAGCUA UACUAACCCCAGGGUUGGUCAAUUUCGUGCCAGCCACACCCUCGAGCUAGCAAAAAAAAAAAAAAAAAAAAAAAAAAAAAAGCAUAUG ACUAAAAAAAAAAAAAAAAAAAAAAAAAAAAAAAAAAAAAAAAAAAAAAAAAAAAAAAA |
| 69 | ModB murine 41BBL (amino acid) | MDQHTLDVEDTADARHPAGTSCPSDAALLRDTGLLADAALLSDTVRPTNAALPTDAAYPAVNVRDREAAWPPALNFCSRHPKLYGLVA LVLLLLIAACVPIFTRTEPRPALTITTSPNLGTRENNADQVTPVSHIGCPNTTQQGSPVFAKLLAKNQASLCNTTLNWHSQDGAGSSY LSQGLRYEEDKKELVVDSPGLYYVFLELKLSPTFTNTGHKVQGWVSLVLQAKPQVDDFDNLALTVELFPCSMENKLVDRSWSQLLLLK AGHRLSVGLRAYLHGAQDAYRDWELSYPNTTSFGLFLVKPDNPWE |
| 70 | ModB murine 41BBL (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCCATGGACCAGCACACACTTGATGTGGAGGATA CCGCGGATGCCAGACATCCAGCAGGTACTTCGTGCCCTCGGATGCGGCGCTCCTCAGAGATACCGGGCTCCTCGCGGACGCTGCGCT CCTCTCAGATACTGTGCGCCCCACAAATGCCGCGCTCCCCACGGATGCTGCCTACCCTGCGGTTAATGTTCGGGATCGCGAGGCCGCG TGGCCGCCTGCACTGAACTTCTGTTCCCGCCACCCAAAGCTCTATGGCCTAGTCGCTTTGGTTTTGCTGCTTCTGATCGCCGCCTGTG TTCCTATCTTCACCCGCACCGAGCCTCGGCCAGCGCTCACAATCACCACCTCGCCCAACCTGGGTACCCGAGAGAATAATGCAGACCA GGTCACCCCTGTTTCCCACATTGGCTGCCCCAACACTACACAACAGGGCTCTCCTGTGTTCGCCAAGCTACTGGCTAAAAACCAAGCA TCGTTGTGCAATACAACTCTGAACTGGCACAGCCAAGATGGAGCTGGGAGCTCATACCTATCTCAAGGTCTGAGGTACGAAGAAGACA AAAAGGAGTTGGTGGTAGACAGTCCCGGGCTCTACTACGTATTTTTGGAACTGAAGCTCAGTCCAACATTCACAAACACAGGCCACAA GGTGCAGGGCTGGGTCTCTCTTGTTTTGCAAGCAAAGCCTCAGGTAGATGACTTTGACAACTTGGCCCTGACAGTGGAACTGTTCCCT TGCTCCATGGAGAACAAGTTAGTGGACCGTTCCTGGAGTCAACTGTTGCTCCTGAAGGCTGGCCACCGCCTCAGTGTGGGTCTGAGGG CTTATCTGCATGGAGCCCAGGATGCATACAGAGACTGGGAGCTGTCTTATCCCAACACCACCAGCTTTGGACTCTTTCTTGTGAAACC CGACAACCCATGGGAATGATAGGGATCCGATCTGGTACTGCATGCACGCAATGCTAGCTGCCCCTTTCCCGTCCTGGGTACCCCGAGT CTCCCCCGACCTCGGGTCCCAGGTATGCTCCCACCTCCACCTGCCCCACTCACCACCTCTGCTAGTTCCAGACACCTCCCAAGCACGC AGCAATGCAGCTCAAAACGCTTAGCCTAGCCACACCCCACGGGAAACAGCAGTGATTAACCTTTAGCAATAAACGAAAGTTTAACTA AGCTATACTAACCCCAGGGTTGGTCAATTTCGTGCCAGCCACACCCTCGAGCTAGCAAAAAAAAAAAAAAAAAAAAAAAAAAAAAAGC ATATGACTAAAAAAAAAAAAAAAAAAAAAAAAAAAAAAAAAAAAAAAAAAAAAAAAAAAAAAAA |
| 71 | ModB murine 41BBL (RNA) | GGAAUAAACUAGUCUCAACACAACAUAUACAAAACAAACGAAUCUCAAGCAAUCAAGCAUUCUACUUCUAUUGCAGCAAUUUAAAUCA UUUCUUUUAAAGCAAAAGCAAUUUUCUGAAAAUUUUCACCAUUUACGAACGAUAGCCAUGGACCAGCACACACUUGAUGUGGAGGAUA CCGCGGAUGCCAGACAUCCAGCAGGUACUUCGUGCCCUCGGAUGCGGCGCUCCUCAGAGAUACCGGGCUCCUCGCGGACGCUGCGCU CCUCUCAGAUACUGUGCGCCCCACAAAUGCCGCGCUCCCCACGGAUGCUGCCUACCCUGCGGUUAAUGUUCGGGAUCGCGAGGCCGCG UGGCCGCCUGCACUGAACUUCUGUUCCCGCCACCCAAAGCUCUAUGGCCUAGUCGCUUUGGUUUUGCUGCUUCUGAUCGCCGCCUGUG UUCCUAUCUUCACCCGCACCGAGCCUCGGCCAGCGCUCACAAUCACCACCUCGCCCAACCUGGGUACCCGAGAGAAUAAUGCAGACCA GGUCACCCCUGUUUCCCACAUUGGCUGCCCCAACACUACACAACAGGGCUCUCCUGUGUUCGCCAAGCUACUGGCUAAAAACCAAGCA UCGUUGUGCAAUACAACUCUGAACUGGCACAGCCAAGAUGGAGCUGGGAGCUCAUACCUAUCUCAAGGUCUGAGGUACGAAGAAGACA AAAAGGAGUUGGUGGUAGACAGUCCCGGGCUCUACUACGUAUUUUUGGAACUGAAGCUCAGUCCAACAUUCACAAACACAGGCCACAA GGUGCAGGGCUGGGUCUCUCUUGUUUUGCAAGCAAAGCCUCAGGUAGAUGACUUUGACAACUUGGCCCUGACAGUGGAACUGUUCCCU UGCUCCAUGGAGAACAAGUUAGUGGACCGUUCCUGGAGUCAACUGUUGCUCCUGAAGGCUGGCCACCGCCUCAGUGUGGGUCUGAGGG CUUAUCUGCAUGGAGCCCAGGAUGCAUACAGAGACUGGGAGCUGUCUUAUCCCAACACCACCAGCUUUGGACUCUUUCUUGUGAAACC CGACAACCCAUGGGAAUGAUAGGGAUCCGAUCUGGUACUGCAUGCACGCAAUGCUAGCUGCCCCUUUCCCGUCCUGGGUACCCCGAGU CUCCCCCGACCUCGGGUCCCAGGUAUGCUCCCACCUCCACCUGCCCCACUCACCACCUCUGCUAGUUCCAGACACCUCCCAAGCACGC AGCAAUGCAGCUCAAAACGCUUAGCCUAGCCACACCCCACGGGAAACAGCAGUGAUUAACCUUUAGCAAUAAACGAAAGUUUAACUA AGCUAUACUAACCCCAGGGUUGGUCAAUUUCGUGCCAGCCACACCCUCGAGCUAGCAAAAAAAAAAAAAAAAAAAAAAAAAAAAAAGC AUAUGACUAAAAAAAAAAAAAAAAAAAAAAAAAAAAAAAAAAAAAAAAAAAAAAAAAAAAAAAA |

TABLE 2-continued

DESCRIPTION OF THE SEQUENCES (mouse sequences and other sequences of the invention)

| SEQ ID NO: | Description | SEQUENCE |
|---|---|---|

CD27L-CD40L mouse

| 72 | ModA murine CD27L-CD40L (amino acid) Sequence annotations CAPS: CD27L; CAPS: linker; CAPS: CD40L | MRVTAPRTLILLLSGALALTETWAGSGSHPEPHTAELQLNLTVPRKDPTLRWGAGPALGRSFTHGPELEEGHLRIHQDGLYRLHIQVT<br>LANCSSPGSTLQHRATLAVGICSPAAHGISLLRGRFGQDCTVALQRLTYLVHGDVLCTNLTLPLLPSRNADETFFGVQWICPGGGSGG<br>GHPEPHTAELQLNLTVPRKDPTLRWGAGPALGRSFTHGPELEEGHLRIHQDGLYRLHIQVTLANCSSPGSTLQHRATLAVGICSPAAH<br>GISLLRGRFGQDCTVALQRLTYLVHGDVLCTNLTLPLLPSRNADETFFGVQWICPGGGSGGGHPEPHTAELQLNLTVPRKDPTLRWGA<br>GPALGRSFTHGPELEEGHLRIHQDGLYRLHIQVTLANCSSPGSTLQHRATLAVGICSPAAHGISLLRGRFGQDCTVALQRLTYLVHGD<br>VLCTNLTLPLLPSRNADETFFGVQWICPGGGSGGGSGGGGSGDEDPQIAAHVVSEANSNAASVLQWAKKGYYTMKSNLVMLENGKQ<br>LTVKREGLYYVYTQVTFCSNREPSSQRPFIVGLWLKPSSGSERILLKAANTHSSSQLCEQQSVHLGGVFELQAGASVFVNVTEASQVI<br>HRVGFSSFGLLKLGGGSGGGGDEDPQIAAHVVSEANSNAASVLQWAKKGYYTMKSNLVMLENGKQLTVKREGLYYVYTQVTFCSNREP<br>SSQRPFIVGLWLKPSSGSERILLKAANTHSSSQLCEQQSVHLGGVFELQAGASVFVNVTEASQVIHRVGFSSFGLLKLGGGSGGGGDE<br>DPQIAAHVVSEANSNAASVLQWAKKGYYTMKSNLVMLENGKQLTVKREGLYYVYTQVTFCSNREPSSQRPFIVGLWLKPSSGSERILL<br>KAANTHSSSQLCEQQSVHLGGVFELQAGASVFVNVTEASQVIHRVGFSSFGLLKL |
| 73 | ModA murine CD27L-CD40L (DNA: 5' UTR-CDS-3' UTR) | GGGCGAACTAGTATTCTTCTGGTCCCCACAGACTCAGAGAGAACCCGCCACCATGAGAGTGACCGCCCCAGAACCCTGATCCTGCTG<br>CTGTCTGGCGCCCTGGCCCTGACAGAGACATGGGCCGGAAGCGGATCCCACCCCGAGCCCCACACCGCCGAACTGCAGCTGAACCTGA<br>CCGTGCCCAGAAAGGACCCCACCCTGAGATGGGGAGCTGGCCCTGCTCTGGGCAGATCCTTTACACACGGCCCCGAGCTGGAAGAAGG<br>CCACCTGAGAATCCACCAGGACGGCCTGTACAGACTGCACATCCAAGTGACCCTGGCCAACTGCAGCAGCCCTGGCTCTACCCTGCAG<br>CACAGAGCCACACTGGCCGTGGGCATCTGTAGCCCTGCTGCTCACGGAATCAGCCTGCTGAGAGGCAGATTCGGCCAGGACTGTACCG<br>TGGCCCTGCAGAGGCTGACCTATCTGGTGCATGGCGACGTGCTGTGCACCAACCTGACACTGCCTCTGCTGCCCAGCAGAAACGCCGA<br>CGAAACATTCTTTGGAGTGCAGTGGATTTGTCCTGGCGGAGGGTCCGGGGGAGGACACCCAGAACCTCATACAGCTGAACTGCAGCTG<br>AACCTGACCGTGCCCAGAAAGGACCCCACCCTGAGATGGGGAGCTGGCCCTGCTCTGGGCAGATCCTTTACACACGGCCCCGAGCTGG<br>AAGAAGGCCACCTGAGAATCCACCAGGACGGCCTGTACAGACTGCACATCCAAGTGACCCTGGCCAACTGCAGCAGCCCTGGCTCTAC<br>CCTGCAGCACAGAGCCACACTGGCCGTGGGCATCTGTAGCCCTGCTGCTCACGGAATCAGCCTGCTGAGAGGCAGATTCGGCCAGGAC<br>TGTACCGTGGCCCTGCAGAGGCTGACCTATCTGGTGCATGGCGACGTGCTGTGCACCAACCTGACACTGCCTCTGCTGCCCAGCAGAA<br>ACGCCGACGAAACATTCTTTGGAGTGCAGTGGATTTGTCCTGGGGGAGGCTCCGGAGGCGGACACCCTGAACCTCATACAGCTGAACT<br>GCAGCTGAACCTGACCGTGCCCAGAAAGGACCCCACCCTGAGATGGGGAGCTGGCCCTGCTCTGGGCAGATCCTTTACACACGGCCCC<br>GAGCTGGAAGAAGGCCACCTGAGAATCCACCAGGACGGCCTGTACAGACTGCACATCCAAGTGACCCTGGCCAACTGCAGCAGCCCTG<br>GCTCTACCCTGCAGCACAGAGCCACACTGGCCGTGGGCATCTGTAGCCCTGCTGCTCACGGAATCAGCCTGCTGAGAGGCAGATTCGG<br>CCAGGACTGTACCGTGGCCCTGCAGAGGCTGACCTATCTGGTGCATGGCGACGTGCTGTGCACCAACCTGACACTGCCTCTGCTGCCC<br>AGCAGAAACGCCGACGAGACCTTCTTCGGCGTCCAGTGGATCTGCCCCGGAGGCGGTGGTAGTGGAGGTGGCGGGTCCGGTGGAGGTG<br>GAAGCGGCGACGAGGACCCCCAGATCGCCGCCCACGTGGTGTCTGAGGCCAACAGCAACGCCGCCTCTGTGCTGCAGTGGGCCAAGAA<br>AGGCTACTACACCATGAAGTCCAACCTCGTGATGCTGGAAAACGGCAAGCAGCTGACCGTGAAGCGCGAGGGCCTGTACTATGTGTAC<br>ACCCAAGTGACATTCTGCAGCAACCGCGAGCCCAGCAGCCAGAGGCCTTTTATCGTGGGCCTGTGGCTGAAGCCTAGCAGCGGCAGCG<br>AGAGAATCCTGCTGAAGGCCGCCAACACCCACAGCAGCTCTCAGCTGTGCGAGCAGCAGTCTGTGCACCTGGGAGGCGTGTTCGAGCT<br>GCAAGCTGGCGCTTCCGTGTTCGTGAACGTGACCGAGGCCAGCCAAGTGATCCACAGAGTGGGCTTCAGCAGCTTTGGACTGCTCAAA<br>CTGGGCGGAGGGTCCGGCGGAGGCGGAGATGAAGATCCTCAGATTGCTGCCCACGTGGTGTCTGAGGCCAACAGCAACGCCGCCTCTG<br>TGCTGCAGTGGGCCAAGAAAGGCTACTACACCATGAAGTCCAACCTCGTGATGCTGGAAAACGGCAAGCAGCTGACCGTGAAGCGCGA<br>GGGCCTGTACTATGTGTACACCCAAGTGACATTCTGCAGCAACCGCGAGCCCAGCAGCCAGAGGCCTTTTATCGTGGGCCTGTGGCTG<br>AAGCCTAGCAGCGGCAGCGAGAGAATCCTGCTGAAGGCCGCCAACACCCACAGCAGCTCTCAGCTGTGCGAGCAGCAGTCTGTGCACC<br>TGGGAGGCGTGTTCGAGCTGCAAGCTGGCGCTTCCGTGTTCGTGAACGTGACCGAGGCCAGCCAAGTGATCCACAGAGTGGGCTTCAG<br>CAGCTTTGGACTGCTCAAACTGGGAGGCGGCTCCGGAGGCGGAGGAGATGAAGATCCTCAGATTGCTGCCCACGTGGTGTCTGAGGCC<br>AACAGCAACGCCGCCTCTGTGCTGCAGTGGGCCAAGAAAGGCTACTACACCATGAAGTCCAACCTCGTGATGCTGGAAAACGGCAAGC<br>AGCTGACCGTGAAGCGCGAGGGCCTGTACTATGTGTACACCCAAGTGACATTCTGCAGCAACCGCGAGCCCAGCAGCCAGAGGCCTTT<br>TATCGTGGGCCTGTGGCTGAAGCCTAGCAGCGGCAGCGAGAGAATCCTGCTGAAGGCCGCCAACACCCACAGCAGCTCTCAGCTGTGC<br>GAGCAGCAGTCTGTGCACCTGGGAGGCGTGTTCGAGCTGCAAGCTGGCGCTTCCGTGTTCGTGAACGTGACCGAGGCCAGCCAAGTGA<br>TCCACAGAGTGGGCTTCTCCTCCTTCGGCCTCCTGAAGCTGTGACTCGAGAGCTCGCTTTCTTGCTGTCCAATTTCTATTAAAGGTTC<br>CTTTGTTCCCTAAGTCCAACTACTAAACTGGGGGATATTATGAAGGGCCTTGAGCATCTGGATTCTGCCTAATAAAAAACATTTATTT<br>TCATTGCTGCGTCGAGAGCTCGCTTTCTTGCTGTCCAATTTCTATTAAAGGTTCCTTTGTTCCCTAAGTCCAACTACTAAACTGGGGG<br>ATATTATGAAGGGCCTTGAGCATCTGGATTCTGCCTAATAAAAAACATTTATTTTCATTGCTGCGTCGAGACCTGGTCCAGAGTCGCT<br>AGCAAAAAAAAAAAAAAAAAAAAAAAAAAAAAAAAAGCATATGACTAAAAAAAAAAAAAAAAAAAAAAAAAAAAAAAAAAAAAAAAAA<br>AAAAAAAAAAAAAAAAAAAAAAAA |
| 74 | ModA murine CD27L-CD40L (RNA) | GGGCGAACUAGUAUUCUUCUGGUCCCCACAGACUCAGAGAGAACCCGCCACCAUGAGAGUGACCGCCCCAGAACCCUGAUCCUGCUG<br>CUGUCUGGCGCCCUGGCCCUGACAGAGACAUGGGCCGGAAGCGGAUCCCACCCCGAGCCCCACACCGCCGAACUGCAGCUGAACCUGA<br>CCGUGCCCAGAAAGGACCCCACCCUGAGAUGGGGAGCUGGCCCUGCUCUGGGCAGAUCCUUUACACACGGCCCCGAGCUGGAAGAAGG<br>CCACCUGAGAAUCCACCAGGACGGCCUGUACAGACUGCACAUCCAAGUGACCCUGGCCAACUGCAGCAGCCCUGGCUCUACCCUGCAG<br>CACAGAGCCACACUGGCCGUGGGCAUCUGUAGCCCUGCUGCUCACGGAAUCAGCCUGCUGAGAGGCAGAUUCGGCCAGGACUGUACCG<br>UGGCCCUGCAGAGGCUGACCUAUCUGGUGCAUGGCGACGUGCUGUGCACCAACCUGACACUGCCUCUGCUGCCCAGCAGAAACGCCGA<br>CGAAACAUUCUUUGGAGUGCAGUGGAUUUGUCCUGGCGGAGGGUCCGGGGGAGGACACCCAGAACCUCAUACAGCUGAACUGCAGCUG<br>AACCUGACCGUGCCCAGAAAGGACCCCACCCUGAGAUGGGGAGCUGGCCCUGCUCUGGGCAGAUCCUUUACACACGGCCCCGAGCUGG<br>AAGAAGGCCACCUGAGAAUCCACCAGGACGGCCUGUACAGACUGCACAUCCAAGUGACCCUGGCCAACUGCAGCAGCCCUGGCUCUAC<br>CCUGCAGCACAGAGCCACACUGGCCGUGGGCAUCUGUAGCCCUGCUGCUCACGGAAUCAGCCUGCUGAGAGGCAGAUUCGGCCAGGAC<br>UGUACCGUGGCCCUGCAGAGGCUGACCUAUCUGGUGCAUGGCGACGUGCUGUGCACCAACCUGACACUGCCUCUGCUGCCC |

TABLE 2-continued

DESCRIPTION OF THE SEQUENCES (mouse sequences and other sequences of the invention)

| SEQ ID NO: | Description | SEQUENCE |
|---|---|---|
| | | AGCAGAAACGCCGACGAGACCUUCUUCGGCGUCCAGUGGAUCUGCCCCGGAGGCGGUGGUAGUGGAGGUGGCGGGUCCGGUGGAGGUG GAAGCGGCGACGAGGACCCCCAGAUCGCCGCCCACGUGGUGGUCUGAGGCCAACAGCAACGCCGCCUCUGUGCUGCAGUGGGCCAAGAA AGGCUACUACACCAUGAAGUCCAACCUCGUGAUGCUGGAAAACGGCAAGCAGCUGACCGUGAAGCGCGAGGGCCUGUACUAUGUGUAC ACCCAAGUGACAUUCUGCAGCAACCGCGAGCCCAGCAGCCAGAGGCCUUUUAUCGUGGGCCUGUGGCUGAAGCCUAGCAGCGGCAGCG AGAGAAUCCUGCUGAAGGCCGCCAACACCCACAGCAGCUCUCAGCUGUGCGAGCAGCAGUCUGUGCACCUGGGAGGCGUGUUCGAGCU GCAAGCUGGCGCUUCCGUGUUCGUGAACGUGACCGAGGCCAGCCAAGUGAUCCACAGAGUGGGCUUCAGCAGCUUUGGACUGCUCAAA CUGGGCGGAGGGUCCGGCGGAGGCGGAGAUGAAGAUCCUCAGAUUGCUGCCCACGUGGUGUCUGAGGCCAACAGCAACGCCGCCUCUG UGCUGCAGUGGGCCAAGAAAGGCUACUACACCAUGAAGUCCAACCUCGUGAUGCUGGAAAACGGCAAGCAGCUGACCGUGAAGCGCGA GGGCCUGUACUAUGUGUACACCCAAGUGACAUUCUGCAGCAACCGCGAGCCCAGCAGCCAGAGGCCUUUUAUCGUGGGCCUGUGGCUG AAGCCUAGCAGCGGCAGCGAGAGAAUCCUGCUGAAGGCCGCCAACACCCACAGCAGCUCUCAGCUGUGCGAGCAGCAGUCUGUGCACC UGGGAGGCGUGUUCGAGCUGCAAGCUGGCGCUUCCGUGUUCGUGAACGUGACCGAGGCCAGCCAAGUGAUCCACAGAGUGGGCUUCAG CAGCUUUGGACUGCUCAAACUGGGAGGCGGAUCCGGAGGCGGAGAGAUGAAGAUCCUCAGAUUGCUGCCCACGUGGUGUCUGAGGCC AACAGCAACGCCGCCUCUGUGCUGCAGUGGGCCAAGAAAGGCUACUACACCAUGAAGUCCAACCUCGUGAUGCUGGAAAACGGCAAGC AGCUGACCGUGAAGCGCGAGGGCCUGUACUAUGUGUACACCCAAGUGACAUUCUGCAGCAACCGCGAGCCCAGCAGCCAGAGGCCUUU UAUCGUGGGCCUGUGGCUGAAGCCUAGCAGCGGCAGCGAGAGAAUCCUGCUGAAGGCCGCCAACACCCACAGCAGCUCUCAGCUGUGC GAGCAGCAGUCUGUGCACCUGGGAGGCGUGUUCGAGCUGCAAGCUGGCGCUUCCGUGUUCGUGAACGUGACCGAGGCCAGCCAAGUGA UCCACAGAGUGGGCUUCUCCUCCUUCGGCCUCCUGAAGCUGUGACUCGAGAGCUCGCUUUCUUGCUGUCCAAUUUCUAUUAAAGGUUC CUUUGUUCCCUAAGUCCAACUACUAAACUGGGGGAUAUUAUGAAGGGCCUUGAGCAUCUGGAUUCUGCCUAAUAAAAAACAUUUAUUU UCAUUGCUGCGUCGAGACUCGCUUUCUUGCUGUCCAAUUUCUAUUAAAGUCCAACUACUAAACUGGGGG AUAUUAUGAAGGGCCUUGAGCAUCUGGAUUCUGCCUAAUAAAAAACAUUUAUUUUCAUUGCUGCGUCGAGACCUGGUCCAGAGUCGCU AGCAAAAAAAAAAAAAAAAAAAAAAAAAAAGCAUAUGACUAAAAAAAAAAAAAAAAAAAAAAAAAAAAAAAAAAAAAAAAAAAAAAAAA AAAAAAAAAAAAAAAAAAAAAAAA |
| 75 | ModB murine CD27L-CD40L (amino acid) | MGAMAPRTLLLLLAAALAPTQTRAGPGSHPEPHTAELQLNLTVPRKDPTLRWGAGPALGRSFTHGPELEEGHLRIHQDGLYRLHIQVT LANCSSPGSTLQHRATLAVGICSPAAHGISLLRGRFGQDCTVALQRLTYLVHGDVLCTNLTLPLLPSRNADETFFGVQWICPGGGSGG GHPEPHTAELQLNLTVPRKDPTLRWGAGPALGRSFTHGPELEEGHLRIHQDGLYRLHIQVTLANCSSPGSTLQHRATLAVGICSPAAH GISLLRGRFGQDCTVALQRLTYLVHGDVLCTNLTLPLLPSRNADETFFGVQWICPGGGSGGGGHPEPHTAELQLNLTVPRKDPTLRWGA GPALGRSFTHGPELEEGHLRIHQDGLYRLHIQVTLANCSSPGSTLQHRATLAVGICSPAAHGISLLRGRFGQDCTVALQRLTYLVHGD VLCTNLTLPLLPSRNADETFFGVQWICPGGGSGGGGSGGGGSGDEDPQIAAHVVSEANSNAASVLQWAKKGYYTMKSNLVMLENGKQ LTVKREGLYYVYTQVTFCSNREPSSQRPFIVGLWLKPSSGSERILLKAANTHSSSQLCEQQSVHLGGVFELQAGASVFVNVTEASQVI HRVGFSSFGLLKLGGGSGGGGDEDPQIAAHVVSEANSNAASVLQWAKKGYYTMKSNLVMLENGKQLTVKREGLYYVYTQVTFCSNREP SSQRPFIVGLWLKPSSGSERILLKAANTHSSSQLCEQQSVHLGGVFELQAGASVFVNVTEASQVIHRVGFSSFGLLKLGGGSGGGGDE DPQIAAHVVSEANSNAASVLQWAKKGYYTMKSNLVMLENGKQLTVKREGLYYVYTQVTFCSNREPSSQRPFIVGLWLKPSSGSERILL KAANTHSSSQLCEQQSVHLGGVFELQAGASVFVNVTEASQVIHRVGFSSFGLLKL |
| 76 | ModB murine CD27L-CD40L (DNA: 5' UTR-CDS-3' UTR) | GGAATAAACTAGTCTCAACACAACATATACAAAACAAACGAATCTCAAGCAATCAAGCATTCTACTTCTATTGCAGCAATTTAAATCA TTTCTTTTAAAGCAAAAGCAATTTTCTGAAAATTTTCACCATTTACGAACGATAGCCATGGGCGCCATGGCCCCTAGAACATTGCTCC TGCTGCTGGCCGCTGCCCTGGCCCCTACACAGACAAGAGCTGGACCTGGATCCCACCCCGAGCCCCACACCGCCGAACTGCAGCTGAA CCTGACCGTGCCCAGAAAGGACCCCACCCTGAGATGGGGAGCTGGCCCTGCTCTGGGCAGATCCTTTACACACGGCCCCGAGCTGGAA GAAGGCCACCTGAGAATCCACCAGGACGGCCTGTACAGACTGCACATCCAAGTGACCCTGGCCAACTGCAGCAGCCCTGGCTCTACCC TGCAGCACAGAGCCACACTGGCCGTGGGCATCTGTAGCCCTGCTGCTCACGGAATCAGCCTGCTGAGAGGCAGATTCGGCCAGGACTG TACCGTGGCCCTGCAGAGGCTGACCTATCTGGTGCATGGCGACGTGCTGTGCACCAACCTGACACTGCCTCTGCTGCCCAGCAGAAAC GCCGACGAAACATTCTTTGGAGTGCAGTGGATTTGTCCTGGCGGAGGGTCCGGGGAGGACACCCAGAACCTCATACAGCTGAACTGC AGCTGAACCTGACCGTGCCCAGAAAGGACCCCACCCTGAGATGGGGAGCTGGCCCTGCTCTGGGCAGATCCTTTACACACGGCCCGA GCTGGAAGAAGGCCACCTGAGAATCCACCAGGACGGCCTGTACAGACTGCACATCCAAGTGACCCTGGCCAACTGCAGCAGCCCTGGC TCTACCCTGCAGCACAGAGCCACACTGGCCGTGGGCATCTGTAGCCCTGCTGCTCACGGAATCAGCCTGCTGAGAGGCAGATTCGGCC AGGACTGTACCGTGGCCCTGCAGAGGCTGACCTATCTGGTGCATGGCGACGTGCTGTGCACCAACCTGACACTGCCTCTGCTGCCCAG CAGAAACGCCGACGAAACATTCTTTGGAGTGCAGTGGATTTGTCCTGGGGGAGGCTCCGGAGGCGGAACCCCTCAGAACCTCATACAGCT GAACTGCAGCTGAACCTGACCGTGCCCAGAAAGGACCCCACCCTGAGATGGGGAGCTGGCCCTGCTCTGGGCAGATCCTTTACACACG GCCCCGAGCTGGAAGAAGGCCACCTGAGAATCCACCAGGACGGCCTGTACAGACTGCACATCCAAGTGACCCTGGCCAACTGCAGCAG CCCTGGCTCTACCCTGCAGCACAGAGCCACACTGGCCGTGGGCATCTGTAGCCCTGCTGCTCACGGAATCAGCCTGCTGAGAGGCAGA TTCGGCCAGGACTGTACCGTGGCCCTGCAGAGGCTGACCTATCTGGTGCATGGCGACGTGCTGTGCACCAACCTGACACTGCCTCTGC TGCCCAGCAGAAACGCCGACGAGACCTTCTTCGGCGTCCAGTGGATCTGCCCCGGAGGCGGTGGTAGTGGAGGTGGCGGGTCCGGTGG AGGTGGAAGCGGCGACGAGGACCCCCAGATCGCCGCCCACGTGGTGTCTGAGGCCAACAGCAACGCCGCCTCTGTGCTGCAGTGGGCC AAGAAAGGCTACTACACCATGAAGTCCAACCTCGTGATGCTGGAAAACGGCAAGCAGCTGACCGTGAAGCGCGAGGGCCTGTACTATG TGTACACCCAAGTGACATTCTGCAGCAACCGCGAGCCCAGCAGCCAGAGGCCTTTTATCGTGGGCCTGTGGCTGAAGCCTAGCAGCGG CAGCGAGAGAATCCTGCTGAAGGCCGCCAACACCCACAGCAGCTCTCAGCTGTGCGAGCAGCAGTCTGTGCACCTGGGAGGCGTGTTC GAGCTGCAAGCTGGCGCTTCCGTGTTCGTGAACGTGACCGAGGCCAGCCAAGTGATCCACAGAGTGGGCTTCAGCAGCTTTGGACTGC TCAAACTGGGCGGAGGGTCCGGCGGAGGCGGAGATGAAGATCCTCAGATTGCTGCCCACGTGGTGTCTGAGGCCAACAGCAACGCCGC CTCTGTGCTGCAGTGGGCCAAGAAAGGCTACTACACCATGAAGTCCAACCTCGTGATGCTGGAAAACGGCAAGCAGCTGACCGTGAAG CGCGAGGGCCTGTACTATGTGTACACCCAAGTGACATTCTGCAGCAACCGCGAGCCCAGCAGCCAGAGGCCTTTTATCGTGGGCCTGT GGCTGAAGCCTAGCAGCGGCAGCGAGAGAATCCTGCTGAAGGCCGCCAACACCCACAGCAGCTCTCAGCTGTGCGAGCAGCAGTCTGT GCACCTGGGAGGCGTGTTCGAGCTGCAAGCTGGCGCTTCCGTGTTCGTGAACGTGACCGAGGCCAGCCAAGTGATCCACAGAGTGGGC TTCAGCAGCTTTGGACTGCTCAAACTGGGAGGCGGTCCGGAGGCGGAGAGATGAAGATCCTCAGATTGCTGCCCACGTGGTGTCTG AGGCCAACAGCAACGCCGCCTCTGTGCTGCAGTGGGCCAAGAAAGGCTACTACACCATGAAGTCCAACCTCGTGATGCTGGAAAACGG CAAGCAGCTGACCGTGAAGCGCGAGGGCCTGTACTATGTGTACACCCAAGTGACATTCTGCAGCAACCGCGAGCCCAGCAGCCAGAGG CCTTTTATCGTGGGCCTGTGGCTGAAGCCTAGCAGCGGCAGCGAGAGAATCCTGCTGAAGGCCGCCAACACCCACAGCAGCTCTCAGC TGTGCGAGCAGCAGTCTGTGCACCTGGGAGGCGTGTTCGAGCTGCAAGCTGGCGCTTCCGTGTTCGTGAACGTGACCGAGGCCAGCCA AGTGATCCACAGAGTGGGCTTCTCCTCCTTCGGCCTCCTGAAGCTGTGACTCGAGCTGCATGCACGCAATGCTAGCTGC CCCTTTCCCGTCCTGGGTACCCGAGTCTCCCCCGACCTCGGGTCCCAGGTATGCTCCCACCTCCACCTGCCCCACTCACCACCTCTG CTAGTTCCAGACACCTCCCAAGCACGCAGCAATGCAGCTCAAAACGCTTAGCCTAGCCACACCCCCAGGGAAACAGCAGTGATTAAC CTTTAGCAATAAACGAAAGTTTAACTAAGCTATACTAACCCCAGGGTTGGTCAATTTCGTGCCAGCCACACCCTCGAGCTAGCAAAAA AAAAAAAAAAAAAAAAAAAAAAGCATATGACTAAAAAAAAAAAAAAAAAAAAAAAAAAAAAAAAAAAAAAAAAAAAAAAAAA AAAAAAAAAAAAAAAA |

TABLE 2-continued

DESCRIPTION OF THE SEQUENCES (mouse sequences and other sequences of the invention)

| SEQ ID NO: | Description | SEQUENCE |
|---|---|---|
| 77 | ModB murine CD27L-CD40L (RNA) | GGAAUAAACUAGUCUCAACACAACAUAUACAAAACAAACGAAUCUCAAGCAAUCAAGCAUUCUACUUCUAUUGCAGCAAUUUAAAUCA UUUCUUUUAAAGCAAAAGCAAUUUUCUGAAAAUUUUCACCAUUUACGAACGAUAGCCAUGGGCGCCAUGGCCCCUAGAACAUUGCUCC UGCUGCUGGCCGCUGCCCUGGCCCCUACACAGACAAGAGCUGGACCUGGAUCCCACCCCGAGCCCACACCGCCGAACUGCAGCUGAA CCUGACCGUGCCCAGAAAGGACCCCACCCUGAGAUGGGGAGCUGGCCCUGCUCUGGGCAGAUCCUUUACACACGGCCCCGAGCUGGAA GAAGGCCACCUGAGAAUCCACCAGGACGGCCUGUACAGACUGCACAUCCAAGUGACCCUGGCCAACUGCAGCAGCCCUGGCUCUACCC UGCAGCACAGAGCCACACUGGCCGUGGGCAUCUGUAGCCCUGCUGCUCACGGAAUCAGCCUGCUGAGAGGCAGAUUCGGCCAGGACUG UACCGUGGCCCUGCAGAGGCUGACCUAUCUGGUGCAUGGCGACGUGCUGUGCACCAACCUGACACUGCCUCUGCUGCCCAGCAGAAAC GCAGACGAAACAUUCUUUGGAGUGCAGUGGAUUUGUCCUGGCGGAGGGUCCGGGGGAGGACACCCAGAACUCAUACAGCUGAACUGC AGCUGAACCUGACCGUGCCCAGAAAGGACCCCACCCUGAGAUGGGGAGCUGGCCCUGCUCUGGGCAGAUCCUUUACACACGGCCCCGA GCUGGAAGAAGGCCACCUGAGAAUCCACCAGGACGGCCUGUACAGACUGCACAUCCAAGUGACCCUGGCCAACUGCAGCAGCCCUGGC UCUACCCUGCAGCACAGAGCCACACUGGCCGUGGGCAUCUGUAGCCCUGCUGCUCACGGAAUCAGCCUGCUGAGAGGCAGAUUCGGCC AGGACUGUACCGUGGCCCUGCAGAGGCUGACCUAUCUGGUGCAUGGCGACGUGCUGUGCACCAACCUGACACUGCCUCUGCUGCCCAG CAGAAACGCCGACGAAACAUUCUUUGGAGUGCAGUGGAUUUGUCCUGGGGGAGGCUCCGGAGGCGGACACCCUGAACCUCAUACAGCU GAACUGCAGCUGAACCUGACCGUGCCCAGAAAGGACCCCACCCUGAGAUGGGGAGCUGGCCCUGCUCUGGGCAGAUCCUUUACACACG GCCCCGAGCUGGAAGAAGGCCACCUGAGAAUCCACCAGGACGGCCUGUACAGACUGCACAUCCAAGUGACCCUGGCCAACUGCAGCAG CCCUGGCUCUACCCUGCAGCACAGAGCCACACUGGCCGUGGGCAUCUGUAGCCCUGCUGCUCACGGAAUCAGCCUGCUGAGAGGCAGA UUCGGCCAGGACUGUACCGUGGCCCUGCAGAGGCUGACCUAUCUGGUGCAUGGCGACGUGCUGUGCACCAACCUGACACUGCCUCUGC UGCCCAGCAGAAACGCCGACGAGACCUUCUUCGGCGUCCAGUGGAUCUGCCCCGGAGGCGGUGGUAGUGGAGGUGGCGGGUCCGGUGG AGGUGGAAGCGGCGACGAGGACCCCCAGAUCGCCGCCCACGUGGUGUCUGAGGCCAACAGCAACGCCGCCUCUGUGCUGCAGUGGGCC AAGAAAGGCUACUACACCAUGAAGUCCAACCUCGUGAUGCUGGAAAACGGCAAGCAGCUGACCGUGAAGCGCGAGGGCCUGUACUAUG UGUACACCCAAGUGCAUUCUGCAGCAACCGCGAGCCCAGCAGCCAGAGGCCUUUUAUCGUGGGCCUGUGGCUGAAGCCUAGCAGCGG CAGCGAGAGAAUCCUGCUGAAGGCCGCCAACACCCACAGCAGCUCUCAGCUGUGCGAGCAGCAGUCUGUGCACCUGGGAGGCGUGUUC GAGCUGCAAGCUGGCGCUUCCGUGUUCGUGAACGUGACCGAGGCCAGCCAAGUGAUCCACAGACUGGGCUUCAGCAGCUUUGGACUGC UCAAACUGGGCGAGGGUCCGGCGGAGGCGGAGAUGAAGAUCCUCAGAUUGCUGCCCACGUGGUGUCUGAGGCCAACAGCAACGCCGC CUCUGUGCUGCAGUGGGCCAAGAAAGGCUACUACACCAUGAAGUCCAACCUCGUGAUGCUGGAAAACGGCAAGCAGCUGACCGUGAAG CGCGAGGGCCUGUACUAUGUGUACACCCAAGUGACAUUCUGCAGCAACCGCGAGCCCAGCAGCCAGAGGCCUUUUAUCGUGGGCCUGU GGCUGAAGCCUAGCAGCGGCAGCGAGAGAAUCCUGCUGAAGGCCGCCAACACCCACAGCAGCUCUCAGCUGUGCGAGCAGCAGUCUGU GCACCUGGGAGGCGUGUUCGAGCUGCAAGCUGGCGCUUCCGUGUUCGUGAACGUGACCGAGGCCAGCCAAGUGAUCCACAGAGUGGGC UUCAGCAGCUUUGGACUGCUCAAACUGGGAGGCGGUCCGGAGGCGGAGGAGAUGAAGAUCCUCAGAUUGCUGCCCACGUGGUGUCUG AGGCCAACAGCACGCCGCCUCUGUGCUGCAGUGGGCCAAGAAAGGCUACUACACCAUGAAGUCCAACCUCGUGAUGCUYGGAAAACGG CAAGCAGCUGACCGUGAAGCGCGAGGGCCUGUACUAUGUGUACACCCAAGUGACAUUCUGCAGCAACCGCGAGCCCAGCAGCCAGAGG CCUUUUAUCGUGGGCCUGUGGCUGAAGCCUAGCAGCGGCAGCGAGAGAAUCCUGCUGAAGGCCGCCAACACCCACAGCAGCUCUCAGC UGUGCGAGCAGCAGUCUGUGCACCUGGGAGGCGUGUUCGAGCUGCAAGCUGGCGCUUCCGUGUUCGUGAACGUGACCGAGGCCAGCCA AGUGAUCCACAGAGUGGGCUUCUCCUCCUUCGGCCUCCUGAAGCUGUGACUCGACGUCCUGGUACUGCAUGCACGCAAUGCUAGCUGC CCCUUUCCCGUCCUGGGUACCCCGAGUCUCCCCCGACCUCGGGUCCCAGGUAUGCUCCCACCUCCACCUGCCCCACUCACCACCUCUG CUAGUUCCAGACACCUCCCAAGCACGCAGCAAUGCAGCUCAAAACGCUUAGCCUAGCCACACCCCACGGGAAACAGCAGUGAUUAAC CUUUAGCAAUAAACGAAAGUUUAACUAAGCUAUACUAACCCCAGGUUGGUCAAUUUCGUGCCAGCCACACCCUCGAGCUAGCAAAAA AAAAAAAAAAAAAAAAAAAAAAGCAUAUGACUAAAAAAAAAAAAAAAAAAAAAAAAAAAAAAAAAAAAAAAAAAAAAAAAAAAAAAAA AAAAAAAAAAAAAAAA |

Other sequences of the invention

| 78 | Poly-A | AAAAAAAAAAAAAAAAAAAAAAAAAAAAAAGCAUAUGACUAAAAAAAAAAAAAAAAAAAAAAAAAAAAAAAAAAAAAAAAAAAAAAAAAA AAAAAAAAAAAAAAAAAAAA |
| 79 | Anti-PD1 Mab heavy chain | EVQLLESGGV LVQPGGSLRL SCAASGFTFS NFGMTWVRQA PGKGLEWVSG ISGGGRDTYF ADSVKGRFTI SRDNSKNTLY LQMNSLKGED TAVYYCVKWG NIYFDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |

TABLE 2-continued

DESCRIPTION OF THE SEQUENCES (mouse sequences and other sequences of the invention)

| SEQ ID NO: | Description | SEQUENCE |
|---|---|---|
| 80 | Anti-PD1 Mab light chain | DIQMTQSPSS LSASVGDSIT ITCRASLSIN TFLNWYQQKP GKAPNLLIYA ASSLHGGVPS RFSGSGSGTD FTLTIRTLQP EDFATYYCQQ SSNTPFTFGP GTVVDFRRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSEN RGEC |
| 81 | HCDR1 | GFTFSNFG |
| 82 | HCDR2 | ISGGGRDT |
| 83 | HCDR3 | VKWGNIYFDY |
| 84 | LCDR1 | LSINTF |
| 85 | LCDR2 | AAS |
| 86 | LCDR3 | QQSSNTPFT |
| 87 | Anti-PD1 Mab VH | EVQLLESGGV LVQPGGSLRL SCAASGFTFS NFGMTWVRQA PGKGLEWVSG ISGGGRDTYF ADSVKGRFTI SRDNSKNTLY LQMNSLKGED TAVYYCVKWG NIYFDYWGQG TLVTVSS |
| 88 | Anti-PD1 Mab VL | DIQMTQSPSS LSASVGDSIT ITCRASLSIN TFLNWYQQKP GKAPNLLIYA ASSLHGGVPS RFSGSGSGTD FTLTIRTLQP EDFATYYCQQ SSNTPFTFGP GTVVDFR |

DETAILED DESCRIPTION

I. Definitions

The term "ModB" describes RNA comprising a modified nucleobase in place of at least one (e.g., every) uridine and further comprising a Cap1 structure at the 5' end of the RNA. In some embodiments, the 5' UTR of a ModB RNA comprises SEQ ID NOs: 4 or 6. ModB RNA has been processed to reduce double-stranded RNA (dsRNA). The "Cap1" structure may be generated after in-vitro translation by enzymatic capping or during in-vitro translation (co-transcriptional capping).

In some embodiments, the building block cap for ModB modified RNA is as follows, which is used when co-transcriptionally capping:

$m_2^{7,3'-O}Gppp(m_1^{2'-O})ApG$ (also sometimes referred to as $m_2^{7,3'-O}G(5')ppp(5')m^{2'-O}ApG$), which has the following structure:

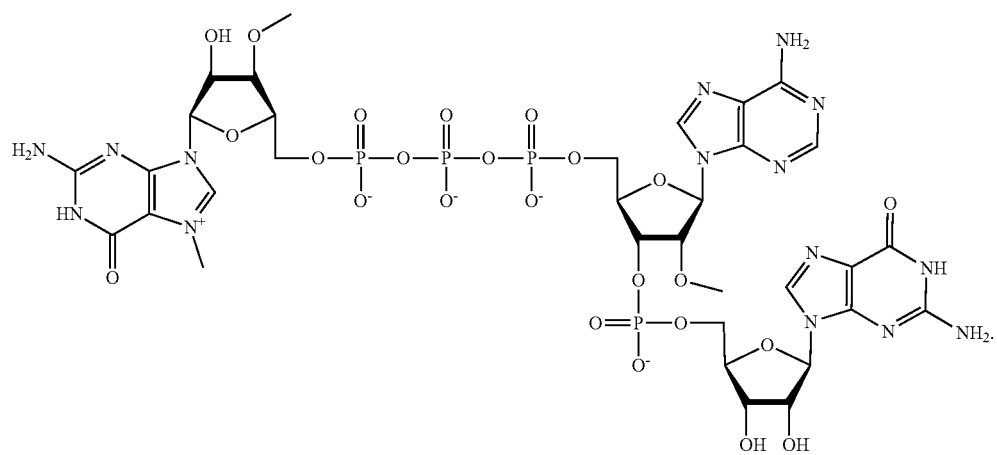

Below is an exemplary Cap1 RNA after co-transcriptional capping, which comprises RNA and $m_2^{7,3'-O}G(5')ppp(5')m^{2'-O}ApG$:

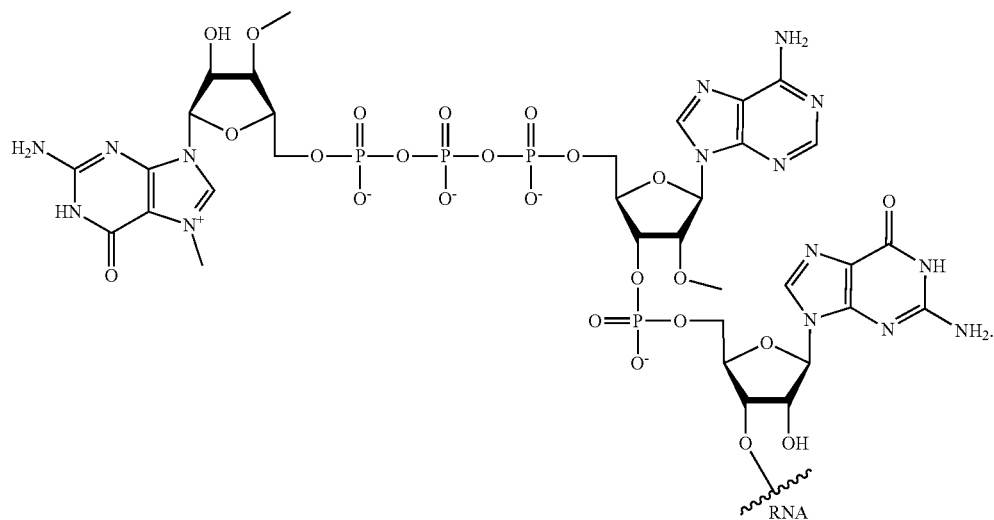

Below is another exemplary Cap1 RNA after enzymatic capping (no cap analog):

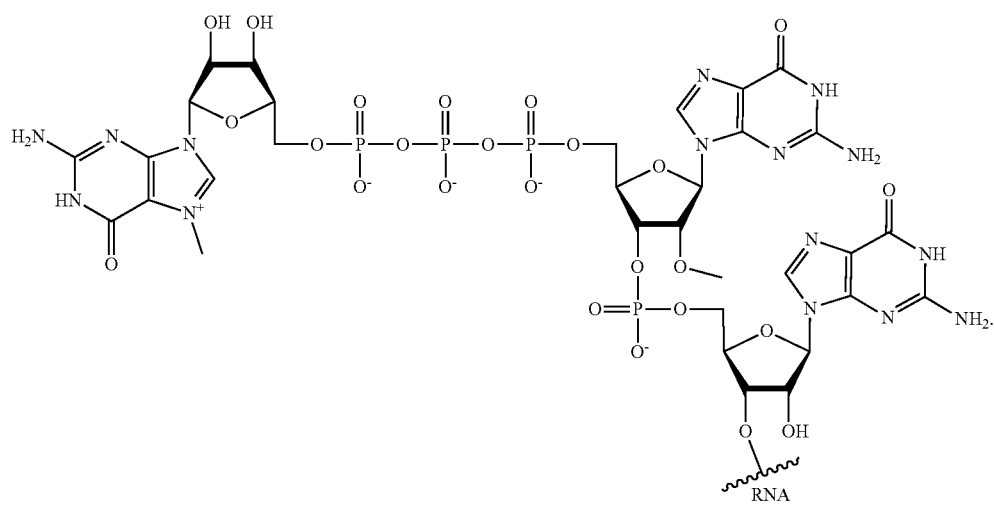

The term "ModA" describes RNA without dsRNA reduction that does not comprise a modified nucleobase in place of at least one uridine. ModA RNA comprises a Cap0 structure at the 5' end of the RNA. The 5' UTR of a ModA RNA may comprise SEQ ID NO: 2. "Cap0" structures are generated during in-vitro translation (co-transcriptional capping) using, in one embodiment, the cap analog anti-reverse cap (ARCA Cap ($m_2^{7,3'-O}G(5')ppp(5')G$)) with the structure:

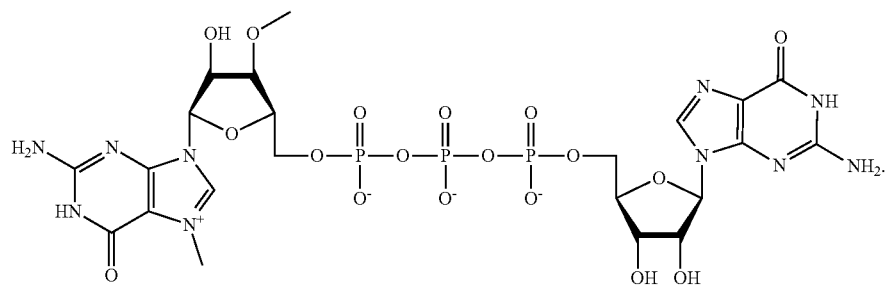
Below is an exemplary Cap0 RNA comprising RNA and $m_2^{7,3'-O}G(5')ppp(5')G$:
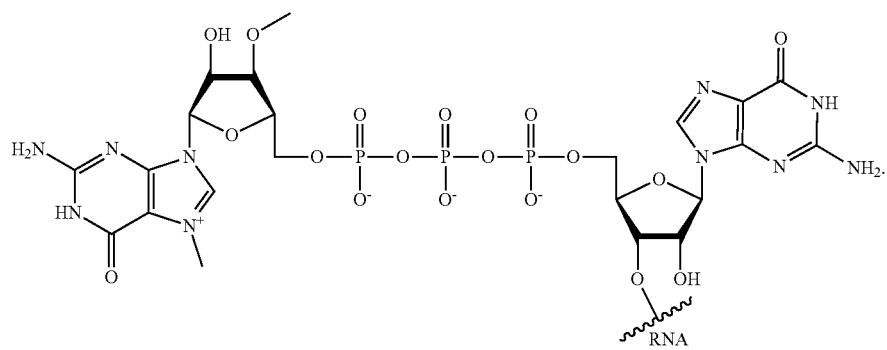
In some embodiments, the "Cap0" structures are generated during in-vitro translation (co-transcriptional capping) using the cap analog Beta-S-ARCA ($m_2^{7,2'-O}G(5')ppSp(5')G$) with the structure:
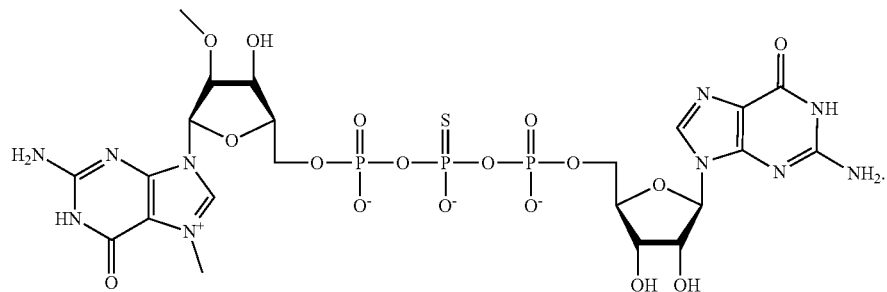

Below is an exemplary Cap0 RNA comprising Beta-S-ARCA ($m_2^{7,2'O}G(5')ppSp(5')G$) and RNA.

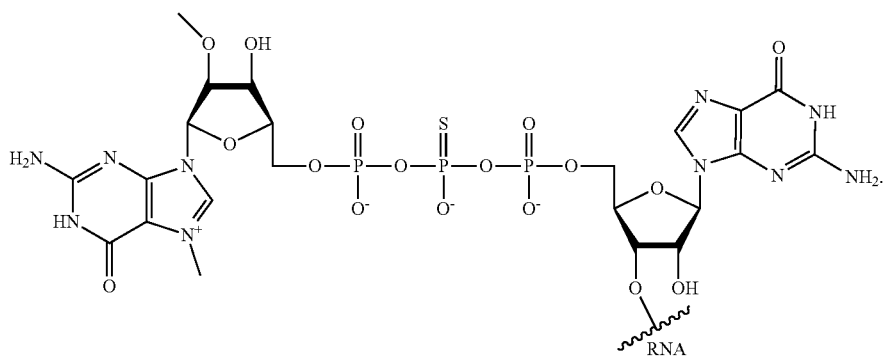

The term "uracil," as used herein, describes one of the nucleobases that can occur in the nucleic acid of RNA. The structure of uracil is:

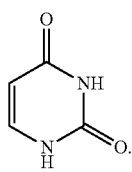

The term "uridine," as used herein, describes one of the nucleosides that can occur in RNA. The structure of uridine is:

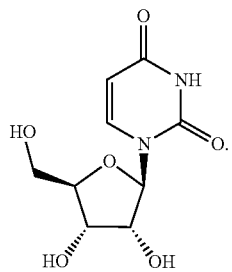 [SMILES: O=c1ccn([C@@H]2O[C@H](CO)[C@@H](O)[C@H]2O)c(=O)[nH]1]

UTP (uridine 5'-triphosphate) has the following structure:

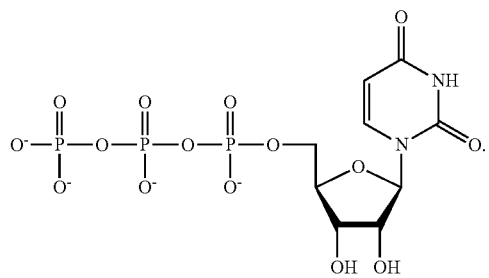

Pseudo-UTP (pseudouridine 5'-triphosphate) has the following structure:

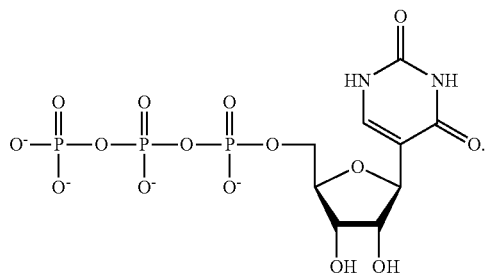

"Pseudouridine" is one example of a modified nucleoside that is an isomer of uridine, where the uracil is attached to the pentose ring via a carbon-carbon bond instead of a nitrogen-carbon glycosidic bond. Pseudouridine is described, for example, in Charette and Gray, Life; 49:341-351 (2000).

Another exemplary modified nucleoside is N1-methylpseudouridine (m1Ψ), which has the structure:

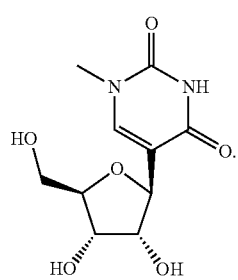 [SMILES: Cn1cc([C@@H]2O[C@H](CO)[C@@H](O)[C@H]2O)c(=O)[nH]c1=O]

N1-Methylpseudo-UTP has the following structure:

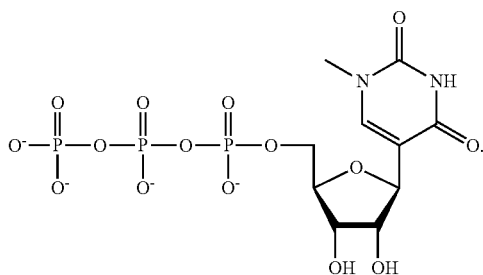

As used herein, the term "poly-A tail" or "poly-A sequence" refers to an uninterrupted or interrupted sequence of adenylate residues which is typically located at the 3' end of an RNA molecule. Poly-A tails or poly-A sequences are known to those of skill in the art, and may follow the 3' UTR in the RNAs described herein. An uninterrupted poly-A tail is characterized by consecutive adenylate residues. In nature, an uninterrupted poly-A tail is typical. RNAs disclosed herein can have a poly-A tail attached to the free 3' end of the RNA by a template-independent RNA polymerase after transcription or a poly-A tail encoded by DNA and transcribed by a template-dependent RNA polymerase.

It has been demonstrated that a poly-A tail of about 120 A nucleotides has a beneficial influence on the levels of RNA in transfected eukaryotic cells, as well as on the levels of protein that is translated from an open reading frame that is present upstream (5') of the poly-A tail (Holtkamp et al., 2006, Blood, vol. 108, pp. 4009-4017).

The poly-A tail may be of any length. In one embodiment, a poly-A tail comprises, essentially consists of, or consists of at least 20, at least 30, at least 40, at least 80, or at least 100 and up to 500, up to 400, up to 300, up to 200, or up to 150 A nucleotides, and, in particular, about 120 A nucleotides. In this context "essentially consists of" means that most nucleotides in the poly-A tail, typically at least 75%, at least 80%, at least 85%, at least 90%, at least 95%, at least 96%, at least 97%, at least 98%, or at least 99% by number of nucleotides in the poly-A tail are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly-A tail, i.e., 100% by number of nucleotides in the poly-A tail, are A nucleotides. The term "A nucleotide" or "A" refers to adenylate.

In some embodiments, a poly-A tail is attached during RNA transcription, e.g., during preparation of in vitro transcribed RNA, based on a DNA template comprising repeated dT nucleotides (deoxythymidylate) in the strand complementary to the coding strand. The DNA sequence encoding a poly-A tail (coding strand) is referred to as poly(A) cassette.

In one embodiment of the present invention, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present invention. A poly(A) cassette that essentially consists of dA nucleotides, but is interrupted by a random sequence having an equal distribution of the four nucleotides (dA, dC, dG, dT) and having a length of e.g. 5 to 50 nucleotides shows, on DNA level, constant propagation of plasmid DNA in E. coli and is still associated, on RNA level, with the beneficial properties with respect to supporting RNA stability and translational efficiency. Consequently, in one embodiment of the present invention, the poly-A tail contained in an RNA molecule described herein essentially consists of A nucleotides, but is interrupted by a random sequence of the four nucleotides (A, C, G, U). Such random sequence may be 5 to 50, 10 to 30, or 10 to 20 nucleotides in length.

In one embodiment of the invention, no nucleotides other than A nucleotides flank a poly-A tail at its 3' end, i.e., the poly-A tail is not masked or followed at its 3' end by a nucleotide other than A.

In some embodiments, a poly-A tail comprises the sequence:

```
                                       (SEQ ID NO: 78)
AAAAAAAAAAAAAAAAAAAAAAAAAAAAAAGCAUAUGACUAAAAAAAAAA

AAAAAAAAAAAAAAAAAAAAAAAAAAAAAAAAAAAAAAAAAAAAAAAAAA

AAAAAAAAAA,
``` which is also shown in Table 2 following the 3' UTR sequence.

"RNA" and "mRNA" are used interchangeably herein.

"IFNα" is used generically herein to describe any interferon alpha Type I cytokine, including IFNα2b and IFNα4. In the experiments described in the Example section, human IFNα2b and mouse IFNα4 were utilized. Any IFNα may be incorporated into the compositions and used in the methods described herein.

The term "treatment," as used herein, covers any administration or application of a therapeutic for disease in a subject, and includes inhibiting the disease, arresting its development, relieving one or more symptoms of the disease, curing the disease, or preventing reoccurrence of the disease. For example, treatment of a solid tumor may comprise alleviating symptoms of the solid tumor, decreasing the size of the solid tumor, eliminating the solid tumor, reducing further growth of the tumor, or reducing or eliminating recurrence of a solid tumor after treatment. Treatment may also be measured as a change in a biomarker of effectiveness or in an imaging or radiographic measure.

The term "prevention," as used herein, means inhibiting or arresting development of cancer, including solid tumors, in a subject deemed to be cancer free.

"Metastasis" means the process by which cancer spreads from the place at which it first arose as a primary tumor to other locations in the body.

The term "intra-tumorally," as used herein, means into the tumor. For example, intra-tumoral injection means injecting the therapeutic at any location that touches the tumor.

The term "peri-tumorally," or "peri-tumoral," as used herein, is an area that is about 2-mm wide and is adjacent to the invasive front of the tumor periphery. The peri-tumoral area comprises host tissue. See, for example, FIG. 36.

"Administering" means providing a pharmaceutical agent or composition to a subject, and includes, but is not limited to, administering by a medical professional and self-administering.

The disclosure describes nucleic acid sequences and amino acid sequences having a certain degree of identity to a given nucleic acid sequence or amino acid sequence, respectively (a reference sequence).

"Sequence identity" between two nucleic acid sequences indicates the percentage of nucleotides that are identical between the sequences. "Sequence identity" between two amino acid sequences indicates the percentage of amino acids that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions at which the sequences to be compared correspond, dividing this number by the number of positions compared (e.g., the number of positions in the reference sequence) and multiplying this result by 100.

In some embodiments, the degree of identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments in continuous nucleotides. In some embodiments, the degree of identity is given for the entire length of the reference sequence.

Nucleic acid sequences or amino acid sequences having a particular degree of identity to a given nucleic acid sequence or amino acid sequence, respectively, may have at least one functional property of said given sequence, e.g., and in some instances, are functionally equivalent to said given sequence. One important property includes the ability to act as a cytokine, in particular when administered to a subject. In some embodiments, a nucleic acid sequence or amino acid sequence having a particular degree of identity to a given nucleic acid sequence or amino acid sequence is functionally equivalent to said given sequence.

II. Compositions and Medical Preparations

A. Interleukin-2 (IL-2)

In some embodiments, the composition comprises a DNA sequence encoding interleukin-2 (IL-2) (SEQ ID NO: 9). In some embodiments, the DNA sequence encoding IL-2 is provided in SEQ ID NO: 10.

In some embodiments, the composition comprises a codon-optimized DNA sequence encoding IL-2. In some embodiments, the codon-optimized DNA sequence comprises or consists of the nucleotides of SEQ ID NOs: 11. In some embodiments, the DNA sequence comprises a codon-optimized DNA sequence with 83%, 84%, 85%, 90%, 95%, 96%, 97%, 98%, or 99% identity to SEQ ID NO: 11.

The alignment of codon optimized IL-2 to native IL-2 is shown below, where the "Q" is native IL-2 (NM_000586.3; SEQ ID NO: 10) and the "S" is codon optimized IL-2 (SEQ ID NO: 11). The percent identity is 82.79%.

```
Q:    1 ATGTACAGGATGCAACTCCTGTCTTGCATTGCACTAAGTCTTGCACTTGTCACAAACAGT   60
        |||||||| ||||| || |||||||||||| |||||| ||||| ||||| |||||    |
S:    1 ATGTACAGAATGCAGCTGCTGTCTTGCATTGCTCTTTCTCTTGCTCTTGTGACAAATTCT   60

Q:   61 GCACCTACTTCAAGTTCTACAAAGAAAACACAGCTACAACTGGAGCATTTACTGCTGGAT  120
        || || || ||   ||| |||||||||||||||| || ||||| || || || |  | || || |||
S:   61 GCTCCAACATCTTCTTCAACAAAGAAAACACAGCTTCAGCTTGAACACCTTCTTCTTGAT  120

Q:  121 TTACAGATGATTTTGAATGAATTAATAATTACAAGAATCCCAAACTCACCAGGATGCTC  180
        | |||||||||   ||||||||| || ||||||||| ||||| ||||| ||  |  |||||
S:  121 CTTCAGATGATTCTGAATGGAATCAACAATTACAAAAATCCAAAACTGACAAGAATGCTG  180

Q:  181 ACATTTAAGTTTTACATGCCCAAGAAGGCCACAGAACTGAAACATCTTCAGTGTCTAGAA  240
        |||||||| |||||||||||| ||||| || |||||||||||| ||||||| || |||
S:  181 ACATTTAAATTTTACATGCCAAAGAAAGCAACAGAACTGAAACACCTTCAGTGCCTTGAA  240

Q:  241 GAAGAACTCAAACCTCTGGAGGAAGTGCTAAATTTAGCTCAAAGCAAAAACTTTCACTTA  300
        |||||||| |||||||||||  ||||||||||||||  |||  | ||||| |||||||| ||||||  |
S:  241 GAAGAACTGAAACCTCTGGAAGAAGTGCTGAATCTGGCTCAGAGCAAAAATTTTCACCTG  300

Q:  301 AGACCCAGGGACTTAATCAGCAATATCAACGTAATAGTTCTGGAACTAAAGGGATCTGAA  360
        ||||| || ||  | ||||||||| |||| || || || ||||||||| || ||||||||||
S:  301 AGACCAAGAGATCTGATCAGCAACATCAATGTGATTGTGCTGGAACTGAAAGGATCTGAA  360

Q:  361 ACAACATTCATGTGTGAATATGCTGATGAGACAGCAACCATTGTAGAATTTCTGAACAGA  420
        |||||||||||||||||||||||||||||||| ||||||||  ||||| ||||||||||||||||
S:  361 ACAACATTCATGTGTGAATATGCTGATGAAACAGCAACAATTGTGGAATTTCTGAACAGA  420

Q:  421 TGGATTACCTTTTGTCAAAGCATCATCTCAACACTGACT                       459
        ||||| || |||||| |     ||||| ||||||||||||
S:  421 TGGATCACATTTTGCCAGTCAATCATTTCAACACTGACA                       459
```

In some embodiments, the composition comprises an RNA sequence transcribed from a DNA sequence encoding IL-2. In some embodiments, the RNA sequence is transcribed from a nucleotide sequence comprising SEQ ID NO: 10 or 11. In some embodiments, the RNA sequence comprises or consists of SEQ ID NOs: 12 or 13. In some embodiments, the RNA sequence comprises or consists of an RNA sequence with 70%, 75%, 80%, 85%, 90%, 95%, 96%, 97%, 98%, or 99% identity to SEQ ID NOs: 12 or 13.

In some embodiments, one or more uridine in the IL-2 RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the IL-2 RNA comprises an altered nucleotide at the 5' end. In some embodiments, the IL-2 RNA comprises a 5' cap. Any 5' cap known in the art may be used. In some embodiments, the 5' cap comprises a 5' to 5' triphosphate linkage. In some embodiments, the 5' cap comprises a 5' to 5' triphosphate linkage including thiophosphate modification. In some embodiments, the 5' cap comprises a 2'-O or 3'-O-ribose-methylated nucleotide. In some embodiments, the 5' cap comprises a modified guanosine nucleotide or modified adenosine nucleotide. In some embodiments, the 5' cap comprises 7-methylguanylate. In some embodiments, the 5' cap is Cap0 or Cap1. Exemplary cap structures include m7G(5')ppp(5')G, m7,2' O-mG(5')ppsp(5')G, m7G(5')ppp (5')2'O-mG, and m7,3' O-mG(5')ppp(5')2' O-mA.

In some embodiments, the IL-2 RNA comprises a 5' untranslated region (UTR). In some embodiments, the 5' UTR is upstream of the initiation codon. In some embodiments, the 5' UTR regulates translation of the RNA. In some embodiments, the 5' UTR is a stabilizing sequence. In some embodiments, the 5' UTR increases the half-life of RNA. Any 5' UTR known in the art may be used. In some embodiments, the 5' UTR RNA sequence is transcribed from a nucleotide sequence comprising SEQ ID NOs: 1, 3, or 5. In some embodiments, the 5' UTR RNA sequence comprises or consists of SEQ ID NOs: 2, 4, or 6. In some embodiments, the 5' UTR RNA sequence is at least 70%, 75%, 80%, 85%, 90%, 95%, 96%, 97%, 98%, or 99% identical to SEQ ID NOs: 2, 4, or 6.

In some embodiments, the IL-2 RNA comprises a 3' UTR. In some embodiments, the 3' UTR follows the translation termination codon. In some embodiments, the 3' UTR regulates polyadenylation, translation efficiency, localization, or stability of the RNA. In some embodiments, the 3' UTR RNA sequence is transcribed from a nucleotide sequence comprising SEQ ID NO: 7. In some embodiments, the 3' UTR RNA sequence comprises or consists of SEQ ID NO: 8. In some embodiments, the 3' UTR RNA sequence is at least 70%, 75%, 80%, 85%, 90%, 95%, 96%, 97%, 98%, or 99% identical to SEQ ID NO: 8.

In some embodiments, the IL-2 composition comprises both a 5' UTR and a 3' UTR. In some embodiments, the composition comprises only a 5' UTR. In some embodiments, the composition comprises only a 3' UTR.

In some embodiments, the IL-2 RNA comprises a poly-A tail. In some embodiments, the RNA comprises a poly-A tail of at least about 25, at least about 30, at least about 50, at least about 70, or at least about 100 nucleotides. In some embodiments, the poly-A tail comprises 200 or more nucleotides. In some embodiments, the poly-A tail comprises or consists of SEQ ID NO: 78.

In some embodiments, the RNA comprises a 5' cap, a 5' UTR, a nucleic acid encoding IL-2, a 3' UTR, and a poly-A tail, in that order.

In some embodiments, the composition comprises a DNA sequence comprising or consisting of a nucleic acid sequence that is at least 70%, 75%, 80%, 85%, 90%, 95%, 96%, 97%, 98%, 99%, or 100% identical to SEQ ID NOs: 10 or 11 and at least 70%, 75%, 80%, 85%, 90%, 95%, 96%, 97%, 98%, 99%, or 100% identical to SEQ ID NOs: 1, 3, or 5.

In some embodiments, the composition comprises an RNA sequence, that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 10 or 11 and at least 70%, 75%, 80%, 85%, 90%, 95%, 96%, 97%, 98%, 99%, or 100% identical to SEQ ID NOs: 1, 3, or 5. The RNA may also be recombinantly produced. In some embodiments, one or more uridine in the IL-2 RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the composition comprises a DNA sequence comprising or consisting of a nucleic acid sequence at least 70%, 75%, 80%, 85%, 90%, 95%, 96%, 97%, 98%, 99%, or 100% identical to SEQ ID NOs: 10 or 11 and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 10 or 11 and at least 70%, 75%, 80%, 85%, 90%, 95%, 96%, 97%, 98%, 99%, or 100% identical to SEQ ID NO: 7. In some embodiments, one or more uridine in the IL-2 RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the composition comprises a DNA sequence comprising or consisting of a nucleic acid sequence at least 70%, 75%, 80%, 85%, 90%, 95%, 96%, 97%, 98%, 99%, or 100% identical to SEQ ID NOs: 10 or 11; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 10 or 11; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7. The RNA may also be recombinantly produced.

In some embodiments, one or more uridine in the IL-2 RNA is replaced by a modified nucleoside as described herein. In some embodiments, the modified nucleoside replacing uridine is pseudouridine (ψ), N1-methyl-pseudouridine (m¹ψ) or 5-methyl-uridine (m⁵U). In some embodiments, the RNA comprises a modified nucleoside in place of each uridine. In some embodiments, the modified nucleoside is N1-methyl-pseudouridine (m¹ψ).

In some embodiments, the composition comprises an RNA sequence comprising or consisting of a nucleic acid sequence at least 70%, 75%, 80%, 85%, 90%, 95%, 96%, 97%, 98%, 99%, or 100% identical to SEQ ID NOs: 12 or 13; at least 70%, 75%, 80%, 85%, 90%, 95%, 96%, 97%, 98%, 99%, or 100% identical to SEQ ID NOs: 2, 4, or 6; and at least 70%, 75%, 80%, 85%, 90%, 95%, 96%, 97%, 98%, 99%, or 100% identical to SEQ ID NO: 8. In some embodiments, one or more uridine in the IL-2 RNA is replaced by a modified nucleoside as described herein. In some embodiments, the modified nucleoside replacing uridine is pseudouridine (ψ), N1-methyl-pseudouridine (m¹ψ) or 5-methyl-uridine (m⁵U). In some embodiments, the RNA comprises a modified nucleoside in place of each uridine. In some embodiments, the modified nucleoside is N1-methyl-pseudouridine (m¹ψ).

B. Interleukin-12 Single-Chain (IL-12sc)

In some embodiments, the composition comprises a DNA sequence encoding interleukin-12 single-chain (IL-12sc) (e.g., SEQ ID NO: 14), which comprises IL-12 p40 (sometimes referred to as IL-12B), a linker, such as a GS linker, and IL-12 p35 (sometimes referred to as IL-12A). In some embodiments, the IL-12p40, linker, and IL-12p35 are consecutive with no intervening nucleotides. An exemplary DNA sequence encoding IL-12sc is provided in SEQ ID NO: 15.

The alignment of codon optimized IL-12 p40 to native IL-12 p40 is shown below, where the "S" is native IL-12 p40 (NM 002187.2; nucleotides 1-984 of SEQ ID NO: 15) and the "Q" is codon optimized IL-12 p40 (nucleotides 1-984 of SEQ ID NO: 16). The percent identity is 77%.

```
Q:    1 ATGTGTCACCAGCAGCTGGTGATCTCATGGTTCTCCCTGGTATTTCTGGCATCTCCTCTT   60
        ||||||||||||||| ||| ||||| ||||| ||||||| |||||||||||||  ||
S:    1 ATGTGTCACCAGCAGTTGGTCATCTCTTGGTTTTCCCTGGTTTTTCTGGCATCTCCCCTC   60

Q:   61 GTCGCAATCTGGGAACTGAAGAAAGACGTGTATGTCGTTGAGCTCGACTGGTATCCGGAT  120
        || || || ||||||||||||||||| || ||||||| ||    || ||||||||||||
S:   61 GTGGCCATATGGGAACTGAAGAAAGATGTTTATGTCGTAGAATTGGATTGGTATCCGGAT  120

Q:  121 GCGCCTGGCGAGATGGTGGTGCTGACCTGTGACACCCCAGAGGAGGATGGGATCACTTGG  180
        || ||||| || |||||||| ||  ||||||||||| || || ||||| ||||| |||
S:  121 GCCCCTGGAGAAATGGTGGTCCTCACCTGTGACACCCCTGAAGAAGATGGTATCACCTGG  180

Q:  181 ACCCTTGATCAATCCTCCGAAGTGCTCGGGTCTGGCAAGACTCTGACCATACAAGTGAAA  240
        ||| | || ||    | ||||  | || |||||||||  ||||||||||| ||||||
S:  181 ACCTTGGACCAGAGCAGTGAGGTCTTAGGCTCTGGCAAAACCCTGACCATCCAAGTCAAA  240

Q:  241 GAGTTTGGCGATGCCGGGCAGTACACTTGCCATAAGGGCGGAGAAGTTCTGTCCCACTCA  300
        |||||||| ||||| || |||||||| || || || || || || |||||   ||| ||
S:  241 GAGTTTGGAGATGCTGGCCAGTACACCTGTCACAAGGGAGGCGAGGTTCTAAGCCATTCG  300

Q:  301 CTGCTGCTGCTGCACAAGAAAGAGGACGGAATTTGGAGTACCGATATCCTGAAAGATCAG  360
        || |||||||||| |||| || |||||||||||||| |  ||||||| | ||| ||
S:  301 CTCCTGCTGCTCTTCACAAAAAGGAAGATGGAATTTGGTCCACTGATATTTTAAAGGACCAG  360

Q:  361 AAAGAGCCCAAGAACAAAACCTTCTTGCGGTGCGAAGCCAAGAACTACTCAGGGAGATTT  420
        |||||  ||||| || ||||||    |  || |||||||||||| || ||  |  |||
S:  361 AAAGAACCCAAAAATAAGACCTTTCTAAGATGCGAGGCCAAGAATTATTCTGGACGTTTC  420

Q:  421 ACTTGTTGGTGGCTGACGACGATCAGCACCGATCTGACTTTCTCCGTGAAATCAAGTAGG  480
        || || ||||||||||||||| ||||| || |||| ||| ||| ||   || || ||
S:  421 ACCTGCTGGTGGCTGACGACAATCAGTACTGATTTGACATTCAGTGTCAAAAGCAGCAGA  480

Q:  481 GGATCATCTGACCCTCAAGGAGTCACATGTGGAGCGGCTACTCTGAGCGCTGAACGCGTA  540
        || || |||||||| ||||| || || || || ||||| || |||| || || | ||
S:  481 GGCTCTTCTGACCCCCAAGGGGTGACGTGCGGAGCTGCTACACTCTCTGCAGAGAGAGTC  540

Q:  541 AGAGGGGACAATAAGGAGTACGAGTATAGCGTTGAGTGCCAAGAGGATAGCGCATGCCCC  600
        |||||||||| |||||||| ||||| | |||||| ||||||||||||||| || |||||
S:  541 AGAGGGGACAACAAGGAGTATGAGTACTCAGTGGAGTGCCAGGAGGACAGTGCCTGCCCA  600

Q:  601 GCCGCCGA--AGAATCATTGCCCATTGAAGTGATGGTGGATGCTGTACACAAGCTGAAGT  658
        || || ||   ||| || | ||||||||| || ||||||||||| || ||||||| ||||
S:  601 GCTGCTGAGGAGAGTC-T-GCCCATTGAGGTCATGGTGGATGCCGTTCACAAGCTCAAGT  658

Q:  659 ATGAGAACTACACAAGCTCCTTCTTCATCCGTGACATCATCAAACCAGATCCTCCTAAGA  718
        |||| ||||||||| ||||||||||||| || ||||||||||||| || || || ||||
S:  659 ATGAAAACTACACCAGCAGCTTCTTCATCAGGGACATCATCAAACCTGACCCACCCAAGA  718

Q:  719 ACCTCCAGCTTAAACCTCTGAAGAACTCTAGACAGGTGGAAGTGTCTTGGGAGTATCCCG  778
        || | |||||| || || ||||| |||||| | ||||||||||||| |||||||| |||
S:  719 ACTTGCAGCTGAAGCCATTAAAGAATTCTCGGCAGGTGGAGGTCAGCTGGGAGTACCCTG  778

Q:  779 ACACCTGGTCTACACCACATTCCTACTTCAGTCTCACATTCTGCGTTCAGGTACAGGGCA  838
        |||||||   || ||||||||||||||| |   || || ||||||||||||| ||||||
S:  779 ACACCTGGAGTACTCCACATTCCTACTTCTCCCTGACATTCTGCGTTCAGGTCCAGGGCA  838
```

```
Q:  839 AGTCCAAAAGGGAGAAGAAGGATCGGGTCTTTACAGATAAAACAAGTGCCACCGTTATAT  898
        ||  ||| || ||  |||||  |||  ||||| || || || ||    |||||  || ||  |
S:  839 AGAGCAAGNGAGAAAAGAAAGATAGAGTCTTCACGGACAAGACCTCAGCCACGGTCATCT  898

Q:  899 GCCGGAAGAATGCCTCTATTTCTGTGCGTGCGCAGGACAGATACTATAGCAGCTCTTGGA  958
        ||||  || ||||||||     |||   |||||| || |||||||| |  ||||||||||||||
S:  899 GCCGCAAAAATGCCAGCATTAGCGTGCGGGCCCAGGACCGCTACTATAGCTCATCTTGGA  958

Q:  959 GTGAATGGGC--CAGTGTCCCATGTTCA                                  984
        |  ||||||||  |  ||| ||| || ||
S:  959 GCGAATGGGCATCTGTG-CCC-TG--CA                                  982
```

The alignment of codon optimized IL-12 p35 to native IL-12 p35 is shown below, where the "S" is native IL-12 p35 (NM_00882.3; nucleotides 1027-1623 of SEQ ID NO: 15) and the "Q" is codon optimized IL-12 p35 (nucleotides 1027-1623 of SEQ ID NO: 16). The percent identity is 80%.

```
Q:    1 AGAAATCTCCCTGTGGCTACACCTGATCCAGGCATGTTTCCCTGTTTGCACCATAGCCAA   60
        |||||  |||||  |||||| ||  ||  || ||||||  |||||  |  |  ||||||  ||||
S:    1 AGAAACCTCCCCGTGGCCACTCCAGACCCAGGAATGTTCCCATGCCTTCACCACTCCCAA   60

Q:   61 AACCTCCTGAGAGCAGTCAGCAACATGCTCCAGAAAGCTAGACAAACACTGGAATTCTAC  120
        |||||  |||||  || ||||||||||||||||||||  ||  ||||||||| |  |||||||  |||
S:   61 AACCTGCTGAGGGCCGTCAGCAACATGCTCCAGAAGGCCAGACAAACTCTAGAATTTTAC  120

Q:  121 CCATGCACCTCCGAGGAAATAGATCACGAGGATATCACTAAGGACAAAACAAGCACTGTC  180
        ||  ||||||  ||  ||  ||  ||||| ||  |||||||||| ||  || ||||| |||||  |||
S:  121 CCTTGCACTTCTGAAGAGATTGATCATGAAGATATCACAAAAGATAAAACCAGCACAGTG  180

Q:  181 GAAGCATGCCTTCCCTTGGAACTGACAAAGAACGAGAGTTGCCTTAATTCAAGAGAAACA  240
        ||  || ||   |  || |||||| |  || |||||  ||||||||||||  ||||| ||||||  ||
S:  181 GAGGCCTGTTTACCATTGGAATTAACCAAGAATGAGAGTTGCCTAAATTCCAGAGAGACC  240

Q:  241 TCTTTCATTACAAACGGTAGCTGCTTGGCAAGCAGAAAACATCTTTTATGATGGCCCTT  300
        ||||||||  || || || ||  || |||    ||||||  ||  |||||||||||||||||
S:  241 TCTTTCATAACTAATGGGAGTTGCCTGGCCTCCAGAAAGACCTCTTTTATGATGGCCCTG  300

Q:  301 TGTCTGAGCAGTATTTATGAGGATCTCAAAATGTACCAGGTGGAGTTTAAGACCATGAAT  360
        ||  || ||  ||||||||||  ||||   || ||||||||||||||||  |||||||||||||||||
S:  301 TGCCTTAGTAGTATTTATGAAGACTTGAAGATGTACCAGGTGGAGTTCAAGACCATGAAT  360

Q:  361 GCCAAGCTGCTGATGGACCCAAAGAGACAGATTTTCCTCGATCAGAATATGCTGGCTGTG  420
        ||  |||||  ||||||||||  ||||| |||||  || |||| | |||||| |||||||||  ||
S:  361 GCAAAGCTTCTGATGGATCCTAAGAGGCAGATCTTTCTAGATCAAAACATGCTGGCAGTT  420

Q:  421 ATTGATGAACTGATGCAGGCCTTGAATTTCAACAGCGAAACCGTTCCCCAGAAAAGCAGT  480
        |||||||| ||||||||||||| |||||||||||  | ||| ||| ||| ||  ||  |
S:  421 ATTGATGAGCTGATGCAGGCCCTGAATTTCAACAGTGAGACTGTGCCACAAAAATCCTCC  480

Q:  481 CTTGAAGAACCTGACTTTTATAAGACCAAGATCAAACTGTGTATTCTCCTGCATGCCTTT  540
        ||||||||||| || ||||||||  | ||||| ||||  ||||| ||||||||| |||| |
S:  481 CTTGAAGAACCGGATTTTTATAAAACTAAAATCAAGCTCTGCATACTTCTTCATGCTTTC  540

Q:  541 AGAATCAGAGCAGTCACTATAGATAGAGTGATGTCCTACCTGAATGCTTCC          591
        |||||   | |||| ||||| |||||||||||||   |||  ||||||||||||
S:  541 AGAATTCGGGCAGTGACTATTGATAGAGTGATGAGCTATCTGAATGCTTCC          591
```

In some embodiments, the composition comprises a codon-optimized DNA sequence encoding IL-12sc. In some embodiments, the composition comprises a codon-optimized DNA sequence encoding IL-12 p40. In some embodiments, the composition comprises a codon-optimized DNA sequence encoding IL-12 p35. In some embodiments, the codon-optimized DNA sequence comprises or consists of SEQ ID NO: 16. In some embodiments, the DNA sequence comprises a codon-optimized DNA sequence with 70%, 75%, 80%, 85%, 90%, 95%, 96%, 97%, 98%, or 99% identity to SEQ ID NO: 16. In some embodiments, the codon-optimized DNA sequence encoding IL-12 p40 comprises the nucleotides encoding the IL-12sc-p40 (nucleotides 1-984 of SEQ ID NO: 16). In some embodiments, the codon-optimized DNA sequence encoding IL-12 p35 comprises the nucleotides encoding the IL-12sc-p35 (nucleotides 1027-1623 of SEQ ID NO: 16). In some embodiments, the codon-optimized DNA sequence encoding IL-12sc comprises the nucleotides encoding the IL-12sc-p40 (nucleotides 1-984 of SEQ ID NO: 16) and -p35 (nucleotides 1027-1623 of SEQ ID NO: 16) portions of SEQ ID NO: 16 and further comprises nucleotides between the p40 and p35 portions (e.g., nucleotides 985-1026 of SEQ ID NO: 16) encoding a linker polypeptide connecting the p40 and p35 portions. Any linker known to those of skill in the art may be used. The p40 portion may be 5' or 3' to the p35 portion.

In some embodiments, the composition comprises an RNA sequence that is, for example, transcribed from a DNA sequence encoding IL-12sc. The RNA may also be recombinantly produced. In some embodiments, the RNA sequence is transcribed from a nucleotide sequence comprising SEQ ID NOs: 15 or 16. In some embodiments, the RNA sequence comprises or consists of SEQ ID NOs: 17 or 18. In some embodiments, the RNA sequence comprises or consists of an RNA sequence with 70%, 75%, 80%, 85%, 90%, 95%, 96%, 97%, 98%, or 99% identity to SEQ ID NOs: 17 or 18. In some embodiments, the RNA sequence comprises the nucleotides encoding the IL-12sc-p40 (nucleotides 1-984 of SEQ ID NOs: 17 or 18) and -p35 (nucleotides 1027-1623 of SEQ ID NOs: 17 or 18) portions of SEQ ID NOs: 17 or 18. In some embodiments, the codon-optimized RNA sequence encoding IL-12sc comprises the nucleotides encoding the IL-12sc-p40 (nucleotides 1-984 of SEQ ID NO: 18) and -p35 (nucleotides 1027-1623 of SEQ ID NO: 18) portions of SEQ ID NO: 18 and further comprises nucleotides between the p40 and p35 portions encoding a linker polypeptide connecting the p40 and p35 portions. Any linker known to those of skill in the art may be used.

In some embodiments, one or more uridine in the IL-12sc RNA is replaced by a modified nucleoside as described herein. In some embodiments, the modified nucleoside replacing uridine is pseudouridine ($\psi$), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the IL-12sc RNA comprises an altered nucleotide at the 5' end. In some embodiments, the RNA comprises a 5' cap. Any 5' cap known in the art may be used. In some embodiments, the 5' cap comprises a 5' to 5' triphosphate linkage. In some embodiments, the 5' cap comprises a 5' to 5' triphosphate linkage including thiophosphate modification. In some embodiments, the 5' cap comprises a 2'-O or 3'-O-ribose-methylated nucleotide. In some embodiments, the 5' cap comprises a modified guanosine nucleotide or modified adenosine nucleotide. In some embodiments, the 5' cap comprises 7-methylguanylate. In some embodiments, the 5' cap is Cap0 or Cap1. Exemplary cap structures include m7G(5')ppp(5')G, m7,2' O-mG(5') ppsp(5')G, m7G(5')ppp(5')2'O-mG, and m7,3' O-mG(5')ppp (5')2' O-mA.

In some embodiments, the IL-12sc RNA comprises a 5' untranslated region (UTR). In some embodiments, the 5' UTR is upstream of the initiation codon. In some embodiments, the 5' UTR regulates translation of the RNA. In some embodiments, the 5' UTR is a stabilizing sequence. In some embodiments, the 5' UTR increases the half-life of RNA. Any 5' UTR known in the art may be used. In some embodiments, the 5' UTR RNA sequence is transcribed from SEQ ID NOs: 1, 3, or 5. In some embodiments, the 5' UTR RNA sequence comprises or consists of SEQ ID NOs: 2, 4, or 6. In some embodiments, the 5' UTR RNA sequence is at least 70%, 75%, 80%, 85%, 90%, 95%, 96%, 97%, 98%, or 99% identical to SEQ ID NOs: 2, 4, or 6.

In some embodiments, the IL-12sc RNA comprises a 3' UTR. In some embodiments, the 3' UTR follows the translation termination codon. In some embodiments, the 3' UTR regulates polyadenylation, translation efficiency, localization, or stability of the RNA. In some embodiments, the 3' UTR RNA sequence is transcribed from SEQ ID NO: 7. In some embodiments, the 3' UTR RNA sequence comprises or consists of SEQ ID NO: 8. In some embodiments, the 3' UTR RNA sequence is at least 70%, 75%, 80%, 85%, 90%, 95%, 96%, 97%, 98%, or 99% identical to SEQ ID NO: 8.

In some embodiments, the IL-12sc composition comprises both a 5' UTR and a 3' UTR. In some embodiments, the IL-12sc composition comprises only a 5' UTR. In some embodiments, the IL-12sc composition comprises only a 3' UTR.

In some embodiments, the IL-12sc RNA comprises a poly-A tail. In some embodiments, the RNA comprises a poly-A tail of at least about 25, at least about 30, at least about 50 nucleotides, at least about 70 nucleotides, or at least about 100 nucleotides. In some embodiments, the poly-A tail comprises 200 or more nucleotides. In some embodiments, the poly-A tail comprises or consists of SEQ ID NO: 78.

In some embodiments, the RNA comprises a 5' cap, a 5' UTR, a nucleic acid encoding IL-12sc, a 3' UTR, and a poly-A tail, in that order.

In some embodiments, the composition comprises a DNA sequence comprising or consisting of a nucleic acid sequence that is at least 70%, 75%, 80%, 85%, 90%, 95%, 96%, 97%, 98%, 99%, or 100% identical to SEQ ID NOs: 15 or 16 and at least 70%, 75%, 80%, 85%, 90%, 95%, 96%, 97%, 98%, 99%, or 100% identical to SEQ ID NOs: 1, 3, or 5.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 15 or 16 and at least 70%, 75%, 80%, 85%, 90%, 95%, 96%, 97%, 98%, 99%, or 100% identical to SEQ ID NOs: 1, 3, or 5. The RNA may also be recombinantly produced. In some embodiments, one or more uridine in the IL-12sc RNA is replaced by a modified nucleoside as described herein. In some embodiments, the modified nucleoside replacing uridine is pseudouridine ($\psi$), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the composition comprises a DNA sequence comprising or consisting of a nucleic acid sequence at least 70%, 75%, 80%, 85%, 90%, 95%, 96%, 97%, 98%, 99%, or 100% identical to SEQ ID NOs: 15 or 16 and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 15 or 16 and at least 70%, 75%, 80%, 85%, 90%, 95%, 96%, 97%, 98%, 99%, or 100% identical to SEQ ID NO: 7. The RNA may also be recombinantly produced. In some embodiments, one or more uridine in the IL-12sc RNA is replaced by a modified nucleoside as described herein. In some embodiments, the modified nucleoside replacing uridine is pseudouridine ($\psi$), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the composition comprises a DNA sequence comprising or consisting of a nucleic acid sequence at least 70%, 75%, 80%, 85%, 90%, 95%, 96%, 97%, 98%, 99%, or 100% identical to SEQ ID NOs: 15 or 16; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 15 or 16; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7. The RNA may also be recombinantly produced. In some embodiments, one or more uridine in the IL-12sc RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ).

In some embodiments, the composition comprises an RNA sequence comprising or consisting of a nucleic acid sequence at least 70%, 75%, 80%, 85%, 90%, 95%, 96%, 97%, 98%, 99%, or 100% identical to SEQ ID NOs: 17 or 18; at least 70%, 75%, 80%, 85%, 90%, 95%, 96%, 97%, 98%, 99%, or 100% identical to SEQ ID NOs: 2, 4, or 6; and at least 70%, 75%, 80%, 85%, 90%, 95%, 96%, 97%, 98%, 99%, or 100% identical to SEQ ID NO: 8. In some embodiments, one or more uridine in the IL-12sc RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U).

C. Interferon Alpha (IFNα)

In some embodiments, the composition comprises a DNA sequence encoding interferon alpha (IFNα) (e.g., SEQ ID NO: 19). An exemplary DNA sequence encoding this IFNα is provided in SEQ ID NO: 20.

The alignment of codon optimized IFNα to native IFNα is shown below, where the "S" is native IFNα (NM_000605.3; SEQ ID NO: 20) and the "Q" is codon optimized IFNα (SEQ ID NO: 21). The percent identity is 79%.

```
Q:    1 ATGGCCCTGACTTTTGCCCTTCTCGTGGCTTTGTTGGTGCTGAGTTGCAAATCTTCCTGT    60
        ||||||  ||||  ||||||   |  ||  |||||  |     ||||||||  ||||||  ||  |||
S:    1 ATGGCCTTGACCTTTGCTTTACTGGTGGCCCTCCTGGTGCTCAGCTGCAAGTCAAGCTGC    60

Q:   61 AGTGTCGGATGTGATCTGCCTCAAACCCACAGTCTGGG-ATCTAGGAGAACACTGATGCT   119
        |||  ||  ||||||||||||||||||||||||||||||  |||||  |  |  |||||  ||   |||||||
S:   61 TCTGTGGGCTGTGATCTGCCTCAAACCCACAGCCTGGGTAGC-AGGAGGACCTTGATGCT   119

Q:  120 CTTGGCACAGATGAGGAGAAT-TAGC-CTCTTTTCCTGCCTGAAGGATAGACATGACTTC   177
        |||||||||||||||||||||  |   |  ||  ||||||  |||||||   |||||||||||
S:  120 CCTGGCACAGATGAGGAGAATCT--CTCTTTTCTCCTGCTTGAAGGACAGACATGACTTT   177

Q:  178 GGCTTTCCCCAAGAGGAGTTTGGCAATCAGTTCCAGAAAGCGGAAACGATTCCCGTTCTG   237
        ||  ||||||||  ||||||||||||||  ||||||||  ||  ||  |||||  ||  ||  ||
S:  178 GGATTTCCCCAGGAGGAGTTTGGCAACCAGTTCCAAAAGGCTGAAACCATCCCTGTCCTC   237

Q:  238 CACGAGATGATCCAGCAGATCTTCAACCTCTTTTCAAC-CAAAG-ACAGCTCAGCAGCCT   295
        ||  ||||||||||||||||||||||||||  |||||   ||  |  |||||  ||   |||  ||  |  |
S:  238 CATGAGATGATCCAGCAGATCTTCAATCTCTT--CAGCACAAAGGACTCATCTGCTGCTT   295

Q:  296 GGGATGAGACACTGCTGGACAAATTCTACACAGAACTGTATCAGCAGCTTAACGATCTGG   355
        |||||||||||  ||  ||  ||||||||||||||  |||||  ||  ||||||||  ||  ||  ||||
S:  296 GGGATGAGACCCTCCTAGACAAATTCTACACTGAACTCTACCAGCAGCTGAATGACCTGG   355

Q:  356 AGGCATGCGTGATCCAAGGGGTTGGTGTGACTGAAACTCCGCTTATGAAGGAGGACTCCA   415
        |  ||  ||  |||||  ||  |||||||  ||  |||||  ||  |||||||||||||||||||
S:  356 AAGCCTGTGTGATACAGGGGGTGGGGGTGACAGAGACTCCCCTGATGAAGGAGGACTCCA   415

Q:  416 TTCTGGCTGTACGGAAGTACTTCCAGAGAATAACCCTCTATCTGAAGGAGAAGAAGTACT   475
        |||||||||  ||||  ||||||||  ||  ||||||||||||  |||||||||  ||||||  |||
S:  416 TTCTGGCTGTGAGGAAATACTTCCAAAGAATCACTCTCTATCTGAAAGAGAAGAAATACA   475

Q:  476 CACCATGTGCTTGGGAAGTCGTGAGAGCCGAAATCATGAGATCCTTCAGCCTTAG-CACC   534
        || ||||| |||||  ||  ||  ||||| ||||||||||||||||||  ||   | ||  || |
S:  476 GCCCTTGTGCCTGGGAGGTTGTCAGAGCAGAAATCATGAGATC-TTTTC-TTTGTCAAC   533

Q:  535 AATC-TCCAGGAATCTCTGAGAAGCAAAGAG    564
        || |  ||  ||  |||  |  | |||||  || ||
S:  534 AAACTTGCAAGAAAGTTTAAGAAGTAAGGAA    564
```

In some embodiments, the composition comprises a codon-optimized DNA sequence encoding IFNα. In some embodiments, the codon-optimized DNA sequence comprises or consists of the nucleotides of SEQ ID NO: 21. In some embodiments, the DNA sequence comprises or consists of a codon-optimized DNA sequence with 70%, 75%, 80%, 85%, 90%, 95%, 96%, 97%, 98%, or 99% identity to SEQ ID NO: 21.

In some embodiments, the composition comprises an RNA sequence that is, for example, transcribed from a DNA sequence encoding IFNα. The RNA may also be recombinantly produced. In some embodiments, the RNA sequence is transcribed from a nucleotide sequence comprising SEQ ID NOs: 20 or 21. In some embodiments, the RNA sequence comprises or consists of SEQ ID NOs: 22 or 23. In some embodiments, the RNA sequence comprises or consists of an RNA sequence with 70%, 75%, 80%, 85%, 90%, 95%, 96%, 97%, 98%, or 99% identity to SEQ ID NOs: 22 or 23.

In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, each uridine in the RNA is modified. In some embodiments, each uridine in the RNA is modified with N1-methyl-pseudouridine (m$^1$ψ).

In some embodiments, the IFNα RNA comprises an altered nucleotide at the 5' end. In some embodiments, the IFNα RNA comprises a 5' cap. Any 5' cap known in the art may be used. In some embodiments, the 5' cap comprises a 5' to 5' triphosphate linkage. In some embodiments, the 5' cap comprises a 5' to 5' triphosphate linkage including thiophosphate modification. In some embodiments, the 5' cap comprises a 2'-O or 3'-O-ribose-methylated nucleotide. In some embodiments, the 5' cap comprises a modified guanosine nucleotide or modified adenosine nucleotide. In some embodiments, the 5' cap comprises 7-methylguanylate. In some embodiments, the 5' cap is Cap0 or Cap1. Exemplary cap structures include m7G(5')ppp(5')G, m7,2' O-mG(5')ppsp(5')G, m7G(5')ppp(5')2'O-mG and m7,3' O-mG(5')ppp(5')2' 0-mA.

In some embodiments, the IFNα RNA comprises a 5' untranslated region (UTR). In some embodiments, the 5' UTR is upstream of the initiation codon. In some embodiments, the 5' UTR regulates translation of the RNA. In some embodiments, the 5' UTR is a stabilizing sequence. In some embodiments, the 5' UTR increases the half-life of RNA. Any 5' UTR known in the art may be used. In some embodiments, the 5' UTR RNA sequence is transcribed from a nucleotide sequence comprising SEQ ID NOs: 1, 3, or 5. In some embodiments, the 5' UTR RNA sequence comprises or consists of SEQ ID NOs: 2, 4, or 6. In some embodiments, the 5' UTR RNA sequence is at least 70%, 75%, 80%, 85%, 90%, 95%, 96%, 97%, 98%, or 99% identical to SEQ ID NOs: 2, 4, or 6.

In some embodiments, the IFNα RNA comprises a 3' UTR. In some embodiments, the 3' UTR follows the translation termination codon. In some embodiments, the 3' UTR regulates polyadenylation, translation efficiency, localization, or stability of the RNA. In some embodiments, the 3' UTR RNA sequence is transcribed from a nucleotide sequence comprising SEQ ID NO: 7. In some embodiments, the 3' UTR RNA sequence comprises or consists of SEQ ID NO: 8. In some embodiments, the 3' UTR RNA sequence is at least 70%, 75%, 80%, 85%, 90%, 95%, 96%, 97%, 98%, or 99% identical to SEQ ID NO: 8.

In some embodiments, the IFNα composition comprises both a 5' UTR and a 3' UTR. In some embodiments, the composition comprises only a 5' UTR. In some embodiments, the composition comprises only a 3' UTR.

In some embodiments, the IFNα RNA comprises a poly-A tail. In some embodiments, the IFNα RNA comprises a poly-A tail of at least about 25, at least about 30, at least about 50 nucleotides, at least about 70 nucleotides, or at least about 100 nucleotides. In some embodiments, the poly-A tail comprises 200 or more nucleotides. In some embodiments, the poly-A tail comprises or consists of SEQ ID NO: 78.

In some embodiments, the RNA comprises a 5' cap, a 5' UTR, a nucleic acid encoding IFNα, a 3' UTR, and a poly-A tail, in that order.

In some embodiments, the composition comprises a DNA sequence comprising or consisting of a nucleic acid sequence that is at least 70%, 75%, 80%, 85%, 90%, 95%, 96%, 97%, 98%, 99%, or 100% identical to SEQ ID NOs: 20 or 21 and at least 70%, 75%, 80%, 85%, 90%, 95%, 96%, 97%, 98%, 99%, or 100% identical to SEQ ID NOs: 1, 3, or 5.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 20 or 21 and at least 70%, 75%, 80%, 85%, 90%, 95%, 96%, 97%, 98%, 99%, or 100% identical to SEQ ID NOs: 1, 3, or 5. The RNA may also be recombinantly produced. In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ).

In some embodiments, the composition comprises a DNA sequence comprising or consisting of a nucleic acid sequence at least 70%, 75%, 80%, 85%, 90%, 95%, 96%, 97%, 98%, 99%, or 100% identical to SEQ ID NOs: 20 or 21 and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 20 or 21 and at least 70%, 75%, 80%, 85%, 90%, 95%, 96%, 97%, 98%, 99%, or 100% identical to SEQ ID NO: 7. In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ).

In some embodiments, the composition comprises a DNA sequence comprising or consisting of a nucleic acid sequence at least 70%, 75%, 80%, 85%, 90%, 95%, 96%, 97%, 98%, 99%, or 100% identical to SEQ ID NOs: 20 or 21; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NOs: 20 or 21; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7. The RNA may also be recombinantly produced. In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ). In some embodiments, the composition comprises an RNA sequence comprising or consisting of a nucleic acid sequence at least 70%, 75%, 80%, 85%, 90%, 95%, 96%, 97%, 98%, 99%, or 100% identical to SEQ ID NOs: 22 or 23; at least 70%, 75%, 80%, 85%, 90%, 95%, 96%, 97%, 98%, 99%, or 100% identical to SEQ ID NOs: 2, 4, or 6; and at least 70%, 75%, 80%, 85%, 90%, 95%, 96%, 97%, 98%, 99%, or 100% identical to SEQ ID NO: 8. In some embodiments, one or more uridine in the IFNα RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$).

D. IL-15 Sushi

As used herein, the term "IL-15 sushi" describes a construct comprising the soluble interleukin 15 (IL-15) receptor alpha sushi domain and mature interleukin alpha (IL-15) as a fusion protein. In some embodiments, the composition comprises a DNA sequence encoding IL-15 sushi (SEQ ID NO: 24), which comprises the soluble IL-15 receptor alpha chain (sushi) followed by a glycine-serine (GS) linker followed by the mature sequence of IL-15. The DNA sequence encoding this IL-15 sushi is provided in SEQ ID NO: 25.

In some embodiments, the composition comprises an RNA sequence that is, for example, transcribed from a DNA sequence encoding IL-15 sushi. The RNA may also be recombinantly produced. In some embodiments, the RNA sequence is transcribed from a nucleotide sequence comprising SEQ ID NO: 25. In some embodiments, the nucleotides encoding the linker may be completely absent or replaced in part or in whole with any nucleotides encoding a suitable linker. In some embodiments, the RNA sequence comprises or consists of SEQ ID NO: 26. In some embodiments, the RNA sequence comprises an RNA sequence with 70%, 75%, 80%, 85%, 90%, 95%, 96%, 97%, 98%, or 99% identity to SEQ ID NO: 26. In some embodiments, the DNA or RNA sequence encoding IL-15 sushi comprises the nucleotides encoding the sushi domain of IL-15 receptor alpha (e.g., nucleotide 1-321 of SEQ ID NOs: 25 or 26) and mature IL-15 (e.g., nucleotide 382-729 of SEQ ID NO: 25 or 26). In some embodiments, the DNA or RNA sequence encoding IL-15 sushi comprises the nucleotides encoding the sushi domain of IL-15 receptor alpha (e.g., nucleotide 1-321 of SEQ ID NOs: 25 or 26) and mature IL-15 (e.g., nucleotide 382-729 of SEQ ID NOs: 25 or 26) and further comprises nucleotides between these portions encoding a linker polypeptide connecting the portions. In some embodiments, the linker comprises nucleotides 322-381 of SEQ ID Nos: 25 or 26. Any linker known to those of skill in the art may be used.

In some embodiments, one or more uridine in the IL-15 sushi RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the IL-15 sushi RNA comprises an altered nucleotide at the 5' end. In some embodiments, the IL-15 sushi RNA comprises a 5' cap. Any 5' cap known in the art may be used. In some embodiments, the 5' cap comprises a 5' to 5' triphosphate linkage. In some embodiments, the 5' cap comprises a 5' to 5' triphosphate linkage including thiophosphate modification. In some embodiments, the 5' cap comprises a 2'-O or 3'-O-ribose-methylated nucleotide. In some embodiments, the 5' cap comprises a modified guanosine nucleotide or modified adenosine nucleotide. In some embodiments, the 5' cap comprises 7-methylguanylate. In some embodiments, the 5' cap is Cap0 or Cap1. Exemplary cap structures include m7G(5')ppp(5') G, m7,2' O-mG(5')ppsp(5')G, m7G(5')ppp(5')2' O-mG and m7,3' O-mG(5')ppp(5')2' O-mA.

In some embodiments, the IL-15 sushi RNA comprises a 5' untranslated region (UTR). In some embodiments, the 5' UTR is upstream of the initiation codon. In some embodiments, the 5' UTR regulates translation of the RNA. In some embodiments, the 5' UTR is a stabilizing sequence. In some embodiments, the 5' UTR increases the half-life of RNA. Any 5' UTR known in the art may be used. In some embodiments, the 5' UTR RNA sequence is transcribed from SEQ ID NOs: 1, 3, or 5. In some embodiments, the 5' UTR RNA sequence comprises or consists of SEQ ID NOs: 2, 4, or 6. In some embodiments, the 5' UTR RNA sequence is at least 70%, 75%, 80%, 85%, 90%, 95%, 96%, 97%, 98%, or 99% identical to SEQ ID NOs: 2, 4, or 6.

In some embodiments, the IL-15 sushi RNA comprises a 3' UTR. In some embodiments, the 3' UTR follows the translation termination codon. In some embodiments, the 3' UTR regulates polyadenylation, translation efficiency, localization, or stability of the RNA. In some embodiments, the 3' UTR RNA sequence is transcribed from SEQ ID NO: 7. In some embodiments, the 3' UTR RNA sequence comprises or consists of SEQ ID NO: 8. In some embodiments, the 3' UTR RNA sequence is at least 70%, 75%, 80%, 85%, 90%, 95%, 96%, 97%, 98%, or 99% identical to SEQ ID NO: 8.

In some embodiments, the IL-15 sushi composition comprises both a 5' UTR and a 3' UTR. In some embodiments, the IL-15 sushi composition comprises only a 5' UTR. In some embodiments, the IL-15 sushi composition comprises only a 3' UTR.

In some embodiments, the IL-15 sushi RNA comprises a poly-A tail. In some embodiments, the RNA comprises a poly-A tail of at least about 25, at least about 30, at least about 50 nucleotides, at least about 70 nucleotides, or at least about 100 nucleotides. In some embodiments, the poly-A tail comprises 200 or more nucleotides. In some embodiments, the poly-A tail comprises or consists of SEQ ID NO: 78.

In some embodiments, the RNA comprises a 5' cap, a 5' UTR, a nucleic acid encoding IL-15 sushi, a 3' UTR, and a poly-A tail, in that order.

In some embodiments, the IL-15 sushi composition comprises a DNA sequence comprising or consisting of a nucleic acid sequence that is at least 70%, 75%, 80%, 85%, 90%, 95%, 96%, 97%, 98%, 99%, or 100% identical to SEQ ID NO: 25 and at least 70%, 75%, 80%, 85%, 90%, 95%, 96%, 97%, 98%, 99%, or 100% identical to SEQ ID NOs: 1, 3, or 5.

In some embodiments, the IL-15 sushi composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NO: 25 and at least 70%, 75%, 80%, 85%, 90%, 95%, 96%, 97%, 98%, 99%, or 100% identical to SEQ ID NOs: 1, 3, or 5. The RNA may also be recombinantly produced. In some embodiments, one or more uridine in the IFNα RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the IL-15 sushi composition comprises a DNA sequence comprising or consisting of a nucleic acid sequence at least 70%, 75%, 80%, 85%, 90%, 95%, 96%, 97%, 98%, 99%, or 100% identical to SEQ ID NO: 25 and at least 70%, 75%, 80%, 85%, 90%, 95%, 96%, 97%, 98%, 99%, or 100% identical to SEQ ID NO: 7.

In some embodiments, the IL-15 sushi composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NO: 25 and at least 70%, 75%, 80%, 85%, 90%, 95%, 96%, 97%, 98%, 99%, or 100% identical to SEQ ID NO: 7. The RNA may also be recombinantly produced. In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ).

In some embodiments, the IL-15 sushi composition comprises a DNA sequence comprising or consisting of a nucleic acid sequence at least 70%, 75%, 80%, 85%, 90%, 95%, 96%, 97%, 98%, 99%, or 100% identical to SEQ ID NO: 25; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7.

In some embodiments, the IL-15 sushi composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NO: 25; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7. In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ).

In some embodiments, the IL-15 sushi composition comprises an RNA sequence comprising or consisting of a nucleic acid sequence at least 70%, 75%, 80%, 85%, 90%, 95%, 96%, 97%, 98%, 99%, or 100% identical to SEQ ID NO: 26; at least 70%, 75%, 80%, 85%, 90%, 95%, 96%, 97%, 98%, 99%, or 100% identical to SEQ ID NOs: 2, 4, or 6; and at least 70%, 75%, 80%, 85%, 90%, 95%, 96%, 97%, 98%, 99%, or 100% identical to SEQ ID NO: 8. In some embodiments, one or more uridine in the IFNα RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U).

E. Granulocyte-Macrophage Colony-Stimulating Factor (GM-CSF)

In some embodiments, the composition comprises a DNA sequence encoding granulocyte-macrophage colony-stimulating factor (GM-CSF) (e.g., SEQ ID NO: 27). In some embodiments, the DNA sequence encoding GM-CSF is provided in SEQ ID NO: 28.

In some embodiments, the GM-CSF composition comprises an RNA sequence that is, for example, transcribed from a DNA sequence encoding GM-CSF. In some embodiments, the RNA sequence is transcribed from SEQ ID NO: 28. The RNA may also be recombinantly produced. In some embodiments, the RNA sequence comprises or consists of SEQ ID NO: 29. In some embodiments, the RNA sequence comprises an RNA sequence with 70%, 75%, 80%, 85%, 90%, 95%, 96%, 97%, 98%, or 99% identity to SEQ ID NOs: 29.

In some embodiments, one or more uridine in the GM-CSF RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, the RNA comprises a modified nucleoside in place of each uridine. In some embodiments, the modified nucleoside is N1-methyl-pseudouridine (m$^1$ψ). In some embodiments, the GM-CSF RNA comprises an altered nucleotide at the 5' end. In some embodiments, the RNA comprises a 5' cap. Any 5' cap known in the art may be used. In some embodiments, the 5' cap comprises a 5' to 5' triphosphate linkage. In some embodiments, the 5' cap comprises a 5' to 5' triphosphate linkage including thiophosphate modification. In some embodiments, the 5' cap comprises a 2'-O or 3'-O-ribose-methylated nucleotide. In some embodiments, the 5' cap comprises a modified guanosine nucleotide or modified adenosine nucleotide. In some embodiments, the 5' cap comprises 7-methylguanylate. In some embodiments, the 5' cap is Cap0 or Cap1. Exemplary cap structures include m7G(5')ppp(5')G, m7,2' O-mG(5')ppsp(5')G, m7G(5')ppp(5')2'O-mG and m7,3' O-mG(5')ppp(5')2' O-mA.

In some embodiments, the GM-CSF RNA comprises a 5' untranslated region (UTR). In some embodiments, the 5' UTR is upstream of the initiation codon. In some embodiments, the 5' UTR regulates translation of the RNA. In some embodiments, the 5' UTR is a stabilizing sequence. In some embodiments, the 5' UTR increases the half-life of RNA. Any 5' UTR known in the art may be used. In some embodiments, the 5' UTR RNA sequence is transcribed from SEQ ID NOs: 1, 3, or 5. In some embodiments, the 5' UTR RNA sequence comprises or consists of SEQ ID NOs: 2, 4, or 6. In some embodiments, the 5' UTR RNA sequence is at least 70%, 75%, 80%, 85%, 90%, 95%, 96%, 97%, 98%, or 99% identical to SEQ ID NOs: 2, 4, or 6.

In some embodiments, the GM-CSF RNA comprises a 3' UTR. In some embodiments, the 3' UTR follows the translation termination codon. In some embodiments, the 3' UTR regulates polyadenylation, translation efficiency, localization, or stability of the RNA. In some embodiments, the 3' UTR RNA sequence is transcribed from SEQ ID NO: 7. In some embodiments, the 3' UTR RNA sequence comprises or consists of SEQ ID NO: 8. In some embodiments, the 3' UTR RNA sequence is at least 70%, 75%, 80%, 85%, 90%, 95%, 96%, 97%, 98%, or 99% identical to SEQ ID NO: 8.

In some embodiments, the GM-CSF composition comprises both a 5' UTR and a 3' UTR. In some embodiments, the composition comprises only a 5' UTR. In some embodiments, the composition comprises only a 3' UTR.

In some embodiments, the GM-CSF RNA comprises a poly-A tail. In some embodiments, the RNA comprises a poly-A tail of at least about 25, at least about 30, at least about 50 nucleotides, at least about 70 nucleotides, or at least about 100 nucleotides. In some embodiments, the poly-A tail comprises 200 or more nucleotides. In some embodiments, the poly-A tail comprises or consists of SEQ ID NO: 78.

In some embodiments, the GM-CSF RNA comprises a 5' cap, a 5' UTR, nucleotides encoding GM-CSF, a 3' UTR, and a poly-A tail, in that order.

In some embodiments, the GM-CSF composition comprises a DNA sequence comprising or consisting of a nucleic acid sequence that is at least 70%, 75%, 80%, 85%, 90%, 95%, 96%, 97%, 98%, 99%, or 100% identical to SEQ ID NO: 28 and at least 70%, 75%, 80%, 85%, 90%, 95%, 96%, 97%, 98%, 99%, or 100% identical to SEQ ID NOs: 1, 3, or 5.

In some embodiments, the GM-CSF composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NO: 28 and at least 70%, 75%, 80%, 85%, 90%, 95%, 96%, 97%, 98%, 99%, or 100% identical to SEQ ID NOs: 1, 3, or 5. The RNA may also be recombinantly produced. In some embodiments, one or more uridine in the GM-CSF RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the GM-CSF composition comprises a DNA sequence comprising or consisting of a nucleic acid sequence at least 70%, 75%, 80%, 85%, 90%, 95%, 96%, 97%, 98%, 99%, or 100% identical to SEQ ID NO: 28 and at least 70%, 75%, 80%, 85%, 90%, 95%, 96%, 97%, 98%, 99%, or 100% identical to SEQ ID NO: 7.

In some embodiments, the GM-CSF composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NO: 28 and at least 70%, 75%, 80%, 85%, 90%, 95%, 96%, 97%, 98%, 99%, or 100% identical to SEQ ID NO: 7. The RNA may also be recombinantly produced. In some embodiments, one or more uridine in the GM-CSF RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the GM-CSF composition comprises a DNA sequence comprising or consisting of a nucleic acid sequence at least 70%, 75%, 80%, 85%, 90%, 95%, 96%, 97%, 98%, 99%, or 100% identical to SEQ ID NO: 28; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7.

In some embodiments, the composition comprises an RNA sequence that is, for example, transcribed from a DNA sequence comprising or consisting of a nucleic acid sequence at least 70%, 75%, 80%, 85%, 90%, 95%, 96%, 97%, 98%, 99%, or 100% identical to SEQ ID NO: 28; at least 70%, 75%, 80%, 85%, 90%, 95%, 96%, 97%, 98%, 99%, or 100% identical to SEQ ID NOs: 1, 3, or 5; and at least 70%, 75%, 80%, 85%, 90%, 95%, 96%, 97%, 98%, 99%, or 100% identical to SEQ ID NO: 7. The RNA may also be recombinantly produced. In some embodiments, one or more uridine in the GM-CSF RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$). In some embodiments, the RNA comprises a modified nucleoside in place of each uridine. In some embodiments, the modified nucleoside is N1-methyl-pseudouridine ($m^1\psi$).

In some embodiments, the GM-CSF composition comprises an RNA sequence comprising or consisting of a nucleic acid sequence at least 70%, 75%, 80%, 85%, 90%, 95%, 96%, 97%, 98%, 99%, or 100% identical to SEQ ID NO: 29; at least 70%, 75%, 80%, 85%, 90%, 95%, 96%, 97%, 98%, 99%, or 100% identical to SEQ ID NOs: 2, 4, or 6; and at least 70%, 75%, 80%, 85%, 90%, 95%, 96%, 97%, 98%, 99%, or 100% identical to SEQ ID NO: 8. In some embodiments, one or more uridine in the GM-CSF RNA is replaced by a modified nucleoside as described herein. In some embodiments, the modified nucleoside replacing uridine is pseudouridine (ψ), N1-methyl-pseudouridine ($m^1\psi$) or 5-methyl-uridine ($m^5U$).

F. Modifications

Each of the RNAs and compositions described herein may be modified in any way known to those of skill in the art. In some embodiments, the modifications are "ModA" or "ModB" modified as described herein.

In some embodiments, one or more uridine in the RNA is replaced by a modified nucleoside. In some embodiments, the modified nucleoside is a modified uridine.

In some embodiments, the modified uridine replacing uridine is pseudouridine (ψ), N1-methyl-pseudouridine (m1ψ), or 5-methyl-uridine (m5U).

In some embodiments, one or more cytosine, adenine or guanine in the RNA is replaced by modified nucleobase(s). In one embodiment, the modified nucleobase replacing cytosine is 5-methylcytosine ($m^5C$). In another embodiment, the modified nucleobase replacing adenine is $N^6$-methyladenine ($m^6A$). In another embodiment, any other modified nucleobase known in the art for reducing the immunogenicity of the molecule can be used.

The modified nucleoside replacing one or more uridine in the RNA may be any one or more of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine($\tau m5s2U$), 1-taurinomethyl-4-thio-pseudouridine), 5-methyl-2-thio-uridine ($m^5s^2U$), 1-methyl-4-thio-pseudouridine ($m^1s^4$) 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine (inm$^5$s$^2$U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

G. Combination Compositions

In some embodiments, the invention comprises a composition comprising more than one RNA as described herein. In some embodiments, the composition comprises two RNAs. In some embodiments, the composition comprises three RNAs. In some embodiments, the composition comprises four RNAs. In some embodiments, the composition comprises five RNAs. In some embodiments, any or all of the RNAs encoding IL-2, IL12sc, IL-15 sushi, GM-CSF, or IFNα may be replaced by IL-2, IL12sc, IL-15 sushi, GM-CSF, and/or IFNα polypeptides, e.g., in any of the compositions and formulations comprising these RNAs described herein.

In some embodiments, the modified or unmodified RNAs encoding IL-2, IL12sc, IL-15 sushi, GM-CSF, and/or IFNα may be replaced by modified or unmodified polycistronic RNAs encoding two or more polypeptides selected from IL-2, IL12sc, IL15 sushi, GM-CSF and IFNα polypeptides, e.g., in any of the compositions and formulations comprising these RNAs described herein.

Any of the combination compositions may further comprise an excipient or diluent. The excipient or diluent may be pharmaceutically acceptable for administration to a subject.

In some embodiments, a combination composition comprises RNAs with the same modifications. In some embodiments, a combination composition comprises RNAs with different modifications. In some embodiments, a combination composition comprises RNAs with ModA modification. In some embodiments, a combination composition comprises RNAs with ModB modification. In some embodiments, a combination composition comprises RNAs with ModA and ModB modifications.

In some embodiments, a composition comprising DNA or RNA encoding IL-2 and one or more of a DNA or RNA encoding IL-12sc, IFNα, IL-15 sushi, and GM-CSF is encompassed. In some embodiments, the composition comprises a DNA or RNA encoding IL-2 or codon-optimized IL-2 (SEQ ID NOs: 10-13) and one or more of a DNA or RNA encoding IL-12sc or optimized IL-12sc (SEQ ID Nos: 15-18), IFNα or optimized IFNα (SEQ ID Nos: 20-23), IL-15 sushi (SEQ ID NOs: 25-26), and GM-CSF (SEQ ID NOs: 28-29), as described herein. In some embodiments, one or more uridine in the RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, one or more of the RNAs in the composition further comprises a 5' cap, a 5' UTR, a 3' UTR, and a poly-A tail, as described herein in the composition section.

In some embodiments, a composition comprising DNA or RNA encoding IL-12sc and one or more of a DNA or RNA encoding IL-2, IFNα, IL-15 sushi, and GM-CSF is encompassed. In some embodiments, the composition comprises a DNA or RNA encoding IL-12sc or codon-optimized IL-12sc (SEQ ID NOs: 15-18) and one or more of a DNA or RNA encoding IL-2 or optimized IL-2 (SEQ ID NOs: 10-13), IFNα or optimized IFNα (SEQ ID NOs: 20-23), IL-15 sushi (SEQ ID NOs: 25-26), and GM-CSF (SEQ ID NOs: 28-29), as described herein. In some embodiments, one or more uridine in the RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U).

In some embodiments, one or more of the RNAs in the composition further comprises a 5' cap, a 5' UTR, a 3' UTR, and a poly-A tail, as described herein in the composition section.

In some embodiments, a composition comprising DNA or RNA encoding IFNα and one or more of a DNA or RNA encoding IL-2, IL-12sc, IL-15 sushi, and GM-CSF is encompassed. In some embodiments, the composition comprises a DNA or RNA encoding IFNα or codon-optimized IFNα (SEQ ID NOs: 20-23) and one or more of a DNA or RNA encoding IL-12sc or optimized IL-12sc (SEQ ID NOs: 15-18), IL-2 or optimized IL-2 (SEQ ID NOs: 10-13), IL-15 sushi (SEQ ID NOs: 25-26), and GM-CSF (SEQ ID NOs: 28-29), as described herein. In some embodiments, one or more uridine in the RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, one or more of the RNAs in the composition further comprises a 5' cap, a 5' UTR, a 3' UTR, and a poly-A tail as described herein in the composition section.

In some embodiments, a composition comprising DNA or RNA encoding IL-15 sushi and one or more of a DNA or RNA encoding IL-2, IL-12sc, IFNα, and GM-CSF is encompassed. In some embodiments, the composition comprises a DNA or RNA encoding IL-15 sushi (SEQ ID NOs: 25-26) and one or more of a DNA or RNA encoding IL-12sc or optimized IL-12sc (SEQ ID NOs: 15-18), IFNα or optimized IFNα (SEQ ID NOs: 20-23), IL-2 or optimized IL-2 (SEQ ID NOs: 10-13), and GM-CSF (SEQ ID NOs: 28-29), as described herein. In some embodiments, one or more uridine in the RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, one or more of the RNAs in the composition further comprises a 5' cap, a 5' UTR, a 3' UTR, and a poly-A tail as described herein in the composition section.

In some embodiments, a composition comprising DNA or RNA encoding GM-CSF and one or more of a DNA or RNA encoding IL-2, IL-12sc, IFNα, and IL-15 sushi is encompassed. In some embodiments, the composition comprises a DNA or RNA encoding GM-CSF (SEQ ID NOs: 28-29) and one or more of a DNA or RNA encoding IL-12sc or optimized IL-12sc (SEQ ID NOs: 15-18), IFNα or optimized IFNα (SEQ ID NOs: 20-23), IL-2 or optimized IL-2 (SEQ ID NOs: 10-13), and IL-15 sushi (SEQ ID NOs: 25-26), as described herein. In some embodiments, one or more uridine in the RNA is replaced by a modified nucleoside as described herein. In some embodiments, the modified nucleoside replacing uridine is pseudouridine (ψ), N1-methyl-pseudouridine (m$^1$ψ) or 5-methyl-uridine (m$^5$U). In some embodiments, one or more of the RNAs in the composition further comprises a 5' cap, a 5' UTR, a 3' UTR, and a poly-A tail as described herein in the composition section.

In some embodiments, the composition comprises GM-CSF, IL-2, and IL-12sc RNA. In some embodiments, the composition is modified, for example, as ModA or ModB. In some embodiments, the IL-12sc RNA is optimized as shown in SEQ ID NO: 18.

In some embodiments, the composition comprises GM-CSF, IL-15 sushi, and IL-12sc RNA. In some embodiments, the composition is modified, for example, as ModA or ModB. In some embodiments, the IL-12sc RNA is optimized as shown in SEQ ID NO: 18.

In some embodiments, the composition comprises GM-CSF, IL-2, IL-12sc, and IFNα RNA. In some embodiments, the composition is modified, for example, as ModA or ModB. In some embodiments, the IL-12sc RNA and IFNα RNA is optimized as shown in SEQ ID NOs: 18 and 23, respectively.

In some embodiments, the composition comprises GM-CSF, IL-15 sushi, IL-12sc, and IFNα RNA. In some embodiments, the composition is modified, for example, as ModA or ModB. In some embodiments, the IL-12sc RNA and IFNα RNA is optimized as shown in SEQ ID NOs: 18 and 23, respectively.

In some embodiments, the composition comprises GM-CSF, IL-15 sushi, IL-12sc, and IFNα RNA, wherein the RNAs comprise or consist of the nucleotides shown in SEQ ID Nos: 18 (IL-12sc), 23 (IFNα), 26 (IL-15 sushi), or 29 (GM-CSF). In some embodiments, the composition is modified, for example, as ModA or ModB.

In some embodiments, combinations of RNA are administered as a 1:1, 1:1:1, or 1:1:1:1 ratio based on equal RNA mass. For example, 20 µg of IL15-sushi, 20 µg of IL-12sc, 20 µg of IFNα2b and 20 µg GM-CSF. In some embodiments, the ratio is adjusted so that different ratios by mass are administered, for example, 1:10:1:10 ratio (20 µg, 200 µg, 20 µg, 200 µg). Likewise, in some embodiments, for example, a ratio of 1:2:3:4 (20 µg, 40 µg, 60 µg, 80 µg) is used. Alternatively, rather than basing the ratio on the mass of the RNA, the ratio may be based on the molarity of the RNA.

In some embodiments, a mixture of RNAs is administered with an equal ratio of each RNA of the mixture.

In some embodiments, a mixture of RNAs is administered with an unequal ratio of each RNA of the mixture. In some embodiments, one or more RNAs are administered at a ratio that is 1, 2, 3, 4, 5, 6, 7, 8, 9, or 10 times greater than another RNA in the mixture. In some embodiments, one or more RNAs are administered at a ratio that is 1, 2, 3, 4, 5, 6, 7, 8, 9, or 10 times less than another RNA in the mixture.

In some embodiments, the compositions described herein may be a medical preparation. In some embodiments, the medical preparation comprises a kit, wherein the included RNAs may be in the same or separate vials. In some embodiments, the medical preparation further comprising instructions for use of the composition for treating or preventing a solid tumor.

In some embodiments, a kit comprising the compositions described herein is provided, wherein the included RNAs may be in the same or separate vials. In some embodiments, the kit further comprising instructions for use of the composition for treating or preventing a solid tumor.

H. Effect of IFNα Addition to Modified mRNA Treatment

RNA can activate the immune system through stimulating various pattern recognition receptors (PRR) leading to production of Type I interferons (like IFNα). The incorporation of various modified nucleotides, or other alterations like reducing the amount of dsRNA administered, can reduce the immune stimulatory effects of RNA. Unexpectedly, as described in the Examples, inclusion of nucleotide-modified and dsRNA-reduced mRNA encoding interferon alpha improved anti-tumor activity relative to that of mRNA that was not nucleotide modified and dsRNA-reduced. The addition of mRNA encoding interferon alpha restored a portion of the immune stimulatory effects removed by the inclusion of modified nucleotides and the dsRNA purification.

In some embodiments, RNA encoding IFN (in any form or subtype) is provided, wherein the IFN RNA is altered to have reduced immunogenicity compared to un-altered RNA. In certain embodiments, the administration of this IFN improves the anti-tumor response of non-IFN encoding RNA. In some embodiments, RNA encoding IFNα improves the anti-tumor response of other RNAs, so long as the other RNAs have been altered to reduce immunogenicity. In one embodiment, the alteration to reduce immunogenicity is a reduction in the amount of dsRNA. In some aspects, the alteration to reduce immunogenicity is the replacement of one or more uridines with a modified nucleoside. In some aspects, the alteration to reduce immunogenicity is both a reduction in the amount of dsRNA and the replacement of one or more uridines with modified nucleoside. In some embodiments, the IFN is IFNα.

In some embodiments, IFN RNA improves the anti-tumor response of modified RNAs. In some embodiments, IFN RNA improves the anti-tumor response of RNAs comprising modified nucleotides. In some embodiments, IFN RNA improves the anti-tumor response of mRNAs comprising pseudouridine. In some embodiments, IFN RNA improves the anti-tumor response of RNAs with ModB modifications.

In some embodiments, IFN RNA improves the anti-tumor response of RNAs of IL-2 (SEQ ID NO: 12 or 13), IL-12sc (SEQ ID NO: 17 or 18), IL-15 sushi (SEQ ID NO: 26) or GM-CSF (SEQ ID NO: 29). In some embodiments, the RNAs comprise ModB modifications.

In some embodiments, the IFN is IFNα.

In some embodiments, the IFN RNA construct is SEQ ID NO: 22 or 23.

III. Methods and Uses

Any of the RNAs, compositions, medical preparations and combination compositions described herein may be administered to a subject to treat cancer or a solid tumor. In some embodiments, the cancer is a solid tumor. In some embodiments, the solid tumor is an abnormal mass of tissue that does not contain cysts or liquid areas. In some embodiments, the solid tumor may be benign or malignant. In some embodiments, the solid tumor is a pre-cancerous lesion. In some embodiments, the solid tumor occurs in lung, colon, ovary, cervix, uterus, peritoneum, testicles, penis, tongue, lymph node, pancreas, bone, breast, prostate, soft tissue, connective tissue, kidney, liver, brain, thyroid, or skin.

In some embodiments, the solid tumor is a sarcoma, carcinoma, or lymphoma. In some embodiments, the solid tumor is an epithelial tumor, Hodgkin lymphoma (HL), non-Hodgkin lymphoma, prostate tumor, ovarian tumor, renal cell tumor, gastrointestinal tract tumor, hepatic tumor, colorectal tumor, tumor with vasculature, mesothelioma tumor, pancreatic tumor, breast tumor, sarcoma tumor, lung tumor, colon tumor, brain tumor, melanoma tumor, basal cell carcinoma, squamous cell carcinoma, small cell lung tumor, neuroblastoma tumor, testicular tumor, carcinoma tumor, adenocarcinoma tumor, glioma tumor, seminoma tumor, retinoblastoma, or osteosarcoma tumor. In some embodiments, the solid tumor is a precancerous lesion such as actinic keratosis.

In some embodiments, the RNA compositions may be delivered via injection into (e.g., intra-tumorally) or near (peri-tumorally) the tumor. In some embodiments, the RNA compositions may be delivered at or near the site of a tumor removal.

In some embodiments, the RNA compositions may be delivered via a topical solution, ointment, or cream.

In some embodiments, the RNA compositions may be delivered via a virus. In some embodiments, the RNA compositions may be delivered by infection with a virus encoding the RNA compositions, such as an oncolytic virus. In some embodiments, the RNA compositions may be delivered by an oncolytic virus.

In some embodiments, more than one administration is delivered. In some embodiments, a catheter is placed into or near the site of the tumor for multiple administrations. In some embodiments, a catheter is placed at the site of removal of a tumor for multiple administrations.

In some embodiments, the subject is human. In some embodiments, the subject is a non-human mammal such as a dog, cat, mouse, rat, rabbit, sheep, cattle, horse and pig.

In some embodiments, RNA compositions are combined with another therapy. In some embodiments, RNA compositions are combined with more than one other therapy. In some embodiments, RNA compositions are combined in a multi-modal therapy.

In some embodiments, the other therapy is surgery to excise, resect, or debulk the tumor. In some embodiments, therapeutic RNA compositions are administered during a surgery to excise, resect, or debulk the tumor.

In some embodiments, the other therapy is radiotherapy. In some embodiments, the radiotherapy is external beam radiation therapy or particle beam radiation. In some embodiments, the radiotherapy is brachytherapy involving temporary or permanent implantation of radioactive isotopes directly into the tumor via catheter or large bore needle. In some embodiments, the radioactive isotope is 137Cesium, 192Iridium, or radioactive iodine. In some embodiments, the radiotherapy is radioisotope preparations administered intravenously. In some embodiments, the radioisotope preparations are radioactive iodine (131I), Strontium (89Sr), or Samarium (153Sm).

In some embodiments, the other therapy is chemotherapy. In some embodiments, the chemotherapy is an alkylating agent, an antimetabolite, an anti-microtubule agent, a topoisomerase inhibitor, or a cytotoxic antibody.

In some embodiments, the chemotherapy comprises anti-invasion agents (e.g., metalloproteinase inhibitors like marimastat and inhibitors of urokinase plasminogen activator receptor function). In some embodiments, the chemotherapy comprises inhibitors of growth factor function (e.g., platelet derived growth factor and hepatocyte growth factor), growth factor antibodies, or growth factor receptor antibodies, (e.g., anti-erbb2 antibody trastuzumab [Herceptin™] and the anti-erbb1 antibody Cetuximab™). In some embodiments, the chemotherapy is a farnesyl transferase inhibitor. In some embodiments, the chemotherapy is a tyrosine kinase inhibitor such as inhibitors of the epidermal growth factor family (e.g., EGFR family tyrosine kinase inhibitors such as gefitinib (Iressa™), erlotinib (Tarceva™), and Canertinib (CI 1033), or a serine/threonine kinase inhibitor).

In some embodiments, the chemotherapy comprises anti-proliferative/antineoplastic drugs such as antimetabolites (e.g., antifolates like methotrexate, fluoropyrimidines like 5-fluorouracil, tegafur, purine and adenosine analogues, cytosine arabinoside); antitumour antibiotics (e.g., anthracyclines like adriamycin, bleomycin, doxorubicin, daunomycin, epirubicin and idarubicin, mitomycin-C, dactinomycin, mithramycin); platinum derivatives (e.g., cisplatin, carboplatin); alkylating agents (e.g., nitrogen mustard, melphalan, chlorambucil, busulphan, cyclophosphamide, ifosfamide, nitrosoureas, thiotepa); antimitotic agents (e.g., *vinca* alkaloids like vincristine, vinblastine, vindesine, vinorelbine, and taxoids like taxol, taxotere); topoisomerase inhibitors (e.g., epipodophyllotoxins like etoposide and teniposide, amsacrine, topotecan, camptothecin and also irinotecan); or thymidylate synthase inhibitors (e.g., raltitrexed).

In some embodiments, the chemotherapy is an antibody-drug conjugate (ADC). In some embodiments, the ADC is an antibody linked to a cytotoxic (anticancer) drug. In some embodiments, the ADC allows targeted delivery of cytotoxic drugs to tumor cells. In some embodiments, the ADC allows preferential deliver of cytotoxic drugs to tumor cells versus normal tissue.

In some embodiments, the chemotherapy is combination chemotherapy with a combination of different agents. In some embodiments, the combination comprises different agents that have different mechanisms of action and/or different, non-overlapping toxicities.

In some embodiments, the other therapy is an immune stimulator or immunotherapy, such as, for example, a checkpoint modulator/inhibitor. Checkpoint modulators/inhibitors are well known in the art to prevent the host immune system from attacking itself, and include, for example, CTLA-4, PD1, PDL1, GITR, OX40, LAG-3, and TIM-3. In some embodiments, the immune stimulator, immunotherapy, or checkpoint modulator/inhibitor is a monoclonal antibody. In some embodiments, the monoclonal antibody is an antibody against PD1, PDL1, CTLA-4, LAG3, OX40, CD40, CD40L, 41BB, 41BBL, GITR, CD3, CD28, CD38, or TGFbeta. In some embodiments, the monoclonal antibody is a bispecific antibody. In some embodiments, the immune stimulator is a cell-based immunotherapy. In some embodiments, the immune stimulator is a cytokine or chemokine. In some embodiments, the immune stimulator is a cancer vaccine. As a wide range of immune stimulators would be known to scientists and clinicians skilled in the art, the invention is not limited to a specific combination with a particular immune stimulator.

In some instances, any of the RNAs, RNA compositions, medical preparations, and RNA combination compositions described herein may be administered in combination with an immune stimulator, immunotherapy, or checkpoint modulator. In some instances, the RNAs, RNA compositions, and RNA combination compositions described herein are administered in combination with an antibody to a subject to treat cancer, including solid tumors. In some embodiments, the antibody is an anti-PD1 antibody, an anti-CTLA4 antibody, or a combination of an anti-PD1 antibody and anti-CTLA4 antibody. In some embodiments, the antibody is a multi-specific antibody such as, for example, a tri-specific or bi-specific antibody.

In some embodiments, the anti-PD1 antibody is a chimeric, humanized or human antibody. In some embodiments, the anti-PD-1 antibody is isolated and/or recombinant. Examples of anti-PD-1 antibodies are nivolumab, pembrolizumab, cemiplimab, MEDI0608 (formerly AMP-514; see, e.g., WO 2012/145493 and U.S. Pat. No. 9,205,148), PDR001 (see, e.g., WO 2015/112900), PF-06801591 (see, e.g., WO 2016/092419), BGB-A317 (see, e.g., WO 2015/035606).

In some embodiments, the anti-PD-1 antibody is one of those disclosed in WO 2015/112800 (such as those referred to as H1M7789N, H1M7799N, H1M7800N, H2M7780N, H2M7788N, H2M7790N, H2M7791N, H2M7794N, H2M7795N, H2M7796N, H2M7798N, H4H9019P, H4xH9034P2, H4xH9035P2, H4xH9037P2, H4xH9045P2, H4xH9048P2, H4H9057P2, H4H9068P2, H4xH9119P2, H4xH9120P2, H4xH9128P2, H4xH9135P2, H4xH9145P2, H4xH8992P, H4xH8999P and H4xH9008P in Table 1 of the PCT publication, and those referred to as H4H7798N, H4H7795N2, H4H9008P and H4H9048P2 in Table 3 of the PCT publication). The disclosure of WO 2015/112800 is incorporated by reference herein in its entirety. For example, the antibodies disclosed in WO 2015/112800 and related antibodies, including antibodies and antigen-binding fragments having the CDRs, VH and VL sequences, or heavy and light chain sequences disclosed in that PCT publication, as well as antibodies and antigen-binding fragments binding to the same PD-1 epitope as the antibodies disclosed in that PCT publication, can be used in conjunction with the RNA compositions of the present invention to treat and/or prevent cancer.

```
HCDR1 =
                                            (SEQ ID NO: 81)
GFTFSNFG

HCDR2 =
                                            (SEQ ID NO: 82)
ISGGGRDT

HCDR3 =
                                            (SEQ ID NO: 83)
VKWGNIYFDY

LCDR1 =
                                            (SEQ ID NO: 84)
LSINTF

LCDR2 =
                                            (SEQ ID NO: 85)
AAS

LCDR3 =
                                            (SEQ ID NO: 86)
QQSSNTPFT.
```

An exemplary antibody comprising a heavy chain comprising the VH and VL sequences in SEQ ID NOs: 87 and 88 (shown in italics) is the fully human anti-PD-1 antibody known as REGN2810 (cemiplimab).

| Anti-PD-1 Mab heavy chain |
|---|
| *EVQLLESGGV LVQPGGSLRL SCAAS*GFTFS NFG*MTWVRQA PGKGLEWVSG* ISGGGRDT*YF* |
| *ADSVKGRFTI SRDNSKNTLY LQMNSLKGED TAVYYC*VKWG NIYFDY*WGQG TLVTVSSAST* |
| SLSSVVTVPS SSLGTKTYTC NVDHKPSNTK VDKRVESKYG PPCPPCPAPE FLGGPSVFLF |
| PPKPKDTLMI SRTPEVTCVV VDVSQEDPEV QFNWYVDGVE VHNAKTKPRE EQFNSTYRVV |
| SVLTVLHQDW LNGKEYKCKV SNKGLPSSIE KTISKAKGQP REPQVYTLPP SQEEMTKNQV |
| SLTCLVKGFY PSDIAVEWES NGQPENNYKT TPPVLDSDGS FFLYSRLTVD KSRWQEGNVF |
| SCSVMHEALH NHYTQKSLSL SLGK (SEQ ID NO: 79) |
| HCDR1 = GFTFSNFG (SEQ ID NO: 81) |
| HCDR2 = ISGGGRDT (SEQ ID NO: 82) |
| HCDR3 = VKWGNIYFDY (SEQ ID NO: 83) |
| Anti-PD-1 Mab light chain |
| *DIQMTQSPSS LSASVGDSIT ITCRAS*LSIN TF*LNWYQQKP GKAPNLLIY*A AS*SLHGGVPS* |
| *RFSGSGSGTD FTLTIRTLQP EDFATYYC*QQ SSNTPFT*FGP GTVVDFRRTV AAPSVFIFPP* |
| SDEQLKSGTA SVVCLLNNFY PREAKVQWKV DNALQSGNSQ ESVTEQDSKD STYSLSSTLT |
| LSKADYEKHK VYACEVTHQG LSSPVTKSEN RGEC (SEQ ID NO: 80) |
| LCDR1 = LSINTF (SEQ ID NO: 84) |
| LCDR2 = AAS (SEQ ID NO: 85) |
| LCDR3 = QQ SSNTPFT (SEQ ID NO: 86) |

In related embodiments, the anti-PD-1 antibody may comprise the heavy and light chain amino acid sequences shown below as SEQ ID NOs: 79 and 80, respectively; the VH and VL sequences in SEQ ID NOs: 87 and 88 (shown in italics), or one or more (e.g., all six) CDRs in SEQ ID NOs: 79 and 80 (shown in bold boxes). In some embodiments, an antibody comprising the following CDRs is encompassed:

In some embodiments, the RNAs, RNA compositions, and RNA combination compositions may be delivered via injection into the tumor (e.g., intratumorally), near the tumor (peri-tumorally), or near the site of a tumor removal, and the antibody may be delivered in the same manner or systemically, such as, for example, enteral or parenteral, including, via injection, infusion, and implantation. "Administered in combination" includes simultaneous or sequential administration. If sequential, administration can be in any order and at any appropriate time interval known to those of skill in the art.

In some embodiments, the other therapy is hormonal therapy. In some embodiments, the hormonal therapy is antiestrogen drugs for treatment of breast cancer or anti-androgen drugs for treating prostate cancer. Example agents include antiestrogens (e.g., tamoxifen, toremifene, raloxifene, droloxifene, iodoxyfene), estrogen receptor down regulators (e.g., fulvestrant), progestogens (e.g., megestrol acetate), aromatase inhibitors (e.g., anastrozole, letrazole, vorazole, exemestane), antiprogestogens, antiandrogens (e.g., flutamide, nilutamide, bicalutamide, cyproterone acetate), LHRH agonists and antagonists (e.g., goserelin acetate, luprolide, buserelin), and inhibitors of 5-alpha-reductase (e.g., finasteride).

In some embodiments, the other therapy is a targeted therapy. In some embodiments, the targeted therapy is a kinase inhibitor. In some embodiments, the targeted therapy is one that inhibits activity of a gene product of a proto-oncogene. In some embodiments, the targeted therapy is an anti-angiogenic agent. In some embodiments, the targeted therapy is one directed to modulate activity of VEGF, BCR-ABL, BRAF, EGFR, c-Met, MEK, ERK, mTOR, or ALK.

In some embodiments, the other therapy is stem cell transplantation.

In some embodiments, therapeutic RNA compositions are delivered at the same time as another therapy.

In some embodiments, therapeutic RNA compositions are delivered before another therapy.

In some embodiments, therapeutic RNA compositions are delivered after another therapy.

In some embodiments, therapeutic RNA compositions are delivered directly into the tumor, or near the tumor or the site of tumor removal together with another therapy. In some embodiments, therapeutic RNA compositions are delivered directly into the tumor, or near the tumor or site of tumor removal while another agent is delivered systemically.

IV. Pharmaceutical Formulations

In some embodiments, any of the DNAs, RNAs, and compositions described herein are pharmaceutical formulations. In some embodiments, the pharmaceutical formulations comprise a diluent, excipient, or other pharmaceutically acceptable carrier. Thus, provided herein are pharmaceutical compositions comprising the DNA, RNA, compositions, or combinations thereof provided herein, and a pharmaceutically acceptable excipient. In certain embodiments, the pharmaceutically acceptable excipient is an aqueous solution. In certain embodiments, the aqueous solution is a saline solution. As used herein, pharmaceutically acceptable excipients are understood to be sterile. In some embodiments, a pharmaceutical composition is administered in the form of a dosage unit. For example, in certain embodiments, a dosage unit is in the form of a tablet, capsule, implantable device, or a bolus injection.

In some embodiments, the pharmaceutical compositions provided herein may additionally contain other adjunct components conventionally found in pharmaceutical compositions. For example, the compositions may contain additional, compatible, pharmaceutically-active materials such as, for example, antipruritics, astringents, local anesthetics or anti-inflammatory agents. The compositions may also contain additional, compatible, pharmaceutically-inactive materials such as excipients, diluents, and carriers.

Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

Lipid moieties may be used to deliver the RNAs provided herein. In one method, the RNA is introduced into pre-formed liposomes or lipoplexes made of mixtures of cationic lipids and neutral lipids. In another method, RNA complexes with mono- or poly-cationic lipids are formed without the presence of a neutral lipid. In certain embodiments, a lipid moiety is selected to increase distribution of a pharmaceutical agent to a particular cell or tissue.

In some embodiments, a pharmaceutical composition provided herein comprises a polyamine compound or a lipid moiety complexed with the DNA or RNA provided herein.

In some embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

Certain pharmaceutical compositions for injection are presented in unit dosage form, e.g., in ampoules or in multi-dose containers. In certain embodiments, a pharmaceutical composition provided herein comprises a RNA or combination of RNAs in a therapeutically effective amount. In certain embodiments, the therapeutically effective amount is sufficient to treat or prevent cancer in the subject being treated.

The following clauses provide numerous embodiments and are non-limiting:

Clause 1. A composition comprising RNA encoding an IL-12sc protein, RNA encoding an IL-15 sushi protein, RNA encoding an IFNα protein, and RNA encoding a GM-CSF protein.

Clause 2. The composition of clause 1, wherein the IFNα protein is an IFNα2b protein.

Clause 3. The composition of clause 1, wherein (i) the RNA encoding an IL-12sc protein comprises the nucleotide sequence of SEQ ID NO: 17 or 18, or a nucleotide sequence having at least 99%, 98%, 97%, 96%, 95%, 90%, 85%, or 80% identity to the nucleotide sequence of SEQ ID NO: 17 or 18 and/or (ii) the IL-12sc protein comprises the amino acid sequence of SEQ ID NO: 14, or an amino acid sequence having at least 99%, 98%, 97%, 96%, 95%, 90%, 85%, or 80% identity to the amino acid sequence of SEQ ID NO: 14.

Clause 4. The composition of clause 1, wherein (i) the RNA encoding an IL-15 sushi protein comprises the nucleotide sequence of SEQ ID NO: 26, or a nucleotide sequence having at least 99%, 98%, 97%, 96%, 95%, 90%, 85%, or 80% identity to the nucleotide sequence of SEQ ID NO: 26 and/or (ii) the IL-15 sushi protein comprises the amino acid sequence of SEQ ID NO: 24, or an amino acid sequence having at least 99%, 98%, 97%, 96%, 95%, 90%, 85%, or 80% identity to the amino acid sequence of SEQ ID NO: 24.

Clause 5. The composition of clause 1, wherein (i) the RNA encoding an IFNα protein comprises the nucleotide sequence of SEQ ID NO: 22 or 23, or a nucleotide sequence having at least 99%, 98%, 97%, 96%, 95%, 90%, 85%, or 80% identity to the nucleotide sequence of SEQ ID NO: 22 or 23 and/or (ii) the IFNα protein comprises the amino acid sequence of SEQ ID NO: 19, or an amino acid sequence having at least 99%, 98%, 97%, 96%, 95%, 90%, 85%, or 80% identity to the amino acid sequence of SEQ ID NO: 19.

Clause 6. The composition of clause 1, wherein (i) the RNA encoding a GM-CSF protein comprises the nucleotide sequence of SEQ ID NO: 29, or a nucleotide sequence having at least 99%, 98%, 97%, 96%, 95%, 90%, 85%, or 80% identity to the nucleotide sequence of SEQ ID NO: 29 and/or (ii) the GM-CSF protein comprises the amino acid sequence of SEQ ID NO: 27, or an amino acid sequence having at least 99%, 98%, 97%, 96%, 95%, 90%, 85%, or 80% identity to the amino acid sequence of SEQ ID NO: 27.

Clause 7. The composition of clause 1, wherein at least one RNA comprises a modified nucleoside in place of at least one uridine, wherein the modified nucleoside is pseudouridine (ψ), N1-methyl-pseudouridine (m1ψ), 5-methyl-uridine (m5U), or a combination thereof.

Clause 8. The composition of clause 1, wherein each RNA comprises a modified nucleoside in place of at least one uridine, wherein the modified nucleoside is pseudouridine (ψ), N1-methyl-pseudouridine (m1ψ), 5-methyl-uridine (m5U), or a combination thereof.

Clause 9. The composition of clause 1, wherein at least one RNA comprises the 5' cap $m_2^{7,3'-O}Gppp(m_1^{2'-O})ApG$, or 3'-O-Me-m$^7$G(5')ppp(5')G, or $m_2^{7,3'-O}Gppp(m_1^{2'-O})ApG$, or 3'-O-Me-m$^7$G(5')ppp(5')G.

Clause 10. The composition of clause 1, wherein at least one RNA comprises a 5' UTR comprising (i) a nucleotide sequence selected from the group consisting of SEQ ID NOs: 2, 4, and 6, or (ii) a nucleotide sequence having at least 99%, 98%, 97%, 96%, 95%, 90%, 85%, or 80% identity to a nucleotide sequence selected from the group consisting of SEQ ID NOs: 2, 4, and 6 and/or a 3' UTR comprising (i) the nucleotide sequence of SEQ ID NO: 8, or (ii) a nucleotide sequence having at least 99%, 98%, 97%, 96%, 95%, 90%, 85%, or 80% identity to the nucleotide sequence of SEQ ID NO: 8.

Clause 11. The composition of clause 1, wherein at least one RNA comprises a poly-A tail of at least 100 nucleotides.

Clause 12. The composition of clause 11, wherein the poly-A tail comprises the poly-A tail shown in SEQ ID NO: 78.

Clause 13. The composition of clause 1, wherein one or more RNA comprises:
a 5' cap comprising $m_2^{7,3'-O}Gppp(m_1^{2'-O})ApG$ or 3'-O-Me-m$^7$G(5')ppp(5')G;
a 5' UTR comprising (i) a nucleotide sequence selected from the group consisting of SEQ ID NOs: 2, 4, and 6, or (ii) a nucleotide sequence having at least 99%, 98%, 97%, 96%, 95%, 90%, 85%, or 80% identity to a nucleotide sequence selected from the group consisting of SEQ ID NOs: 2, 4, and 6;
a 3' UTR comprising (i) the nucleotide sequence of SEQ ID NO: 8, or (ii) a nucleotide sequence having at least 99%, 98%, 97%, 96%, 95%, 90%, 85%, or 80% identity to the nucleotide sequence of SEQ ID NO:8; and
a poly-A tail comprising at least 100 nucleotides.

Clause 14. The composition of clause 13, wherein the poly-A tail comprises SEQ ID NO: 78.

Clause 15. A pharmaceutical composition comprising the composition of clause 1 and a pharmaceutically acceptable carrier, diluent and/or excipient.

Clause 16. A method for treating or reducing the likelihood of a solid tumor comprising administering to a subject in need thereof the composition of clause 1.

Clause 17. A method for treating or reducing the likelihood of a solid tumor comprising administering to a subject in need thereof a first RNA, wherein the first RNA encodes an IL-12sc protein, an IL-15 sushi protein, an IFNα protein, or a GM-CSF protein, and additional RNA, wherein:
if the first RNA encodes an IL-12sc protein, then the additional RNA encodes an IL-15 sushi protein, an IFNα protein, and a GM-CSF protein;
if the first RNA encodes an IL-15 sushi protein, then the additional RNA encodes an IL-12sc protein, an IFNα protein, and a GM-CSF protein;
if the first RNA encodes an IFNα protein, then the additional RNA encodes an IL-15 sushi protein, an IL-12sc protein, and a GM-CSF protein; and
if the first RNA encodes a GM-CSF protein, then the additional RNA encodes an IL-15 sushi protein, an IFNα protein, and an IL-12sc protein.

Clause 18. The method of clause 17, wherein the first RNA is administered to the subject at the same time as the additional RNA.

Clause 19. The method of clause 17, wherein the RNA is administered intra-tumorally or peri-tumorally.

Clause 20. The method of clause 17, wherein the subject is further treated with an additional therapy comprising (i) surgery to excise, resect, or debulk a tumor, (ii) immunotherapy, (iii) radiotherapy, or (iv) chemotherapy.

Clause 21. The method of clause 17, wherein the subject is further treated with a checkpoint modulator.

Clause 22. The method of clause 21, wherein the checkpoint modulator is an anti-PD1 antibody, an anti-CTLA-4 antibody, or a combination of an anti-PD1 antibody and an anti-CTLA-4 antibody.

Clause 23. The method of clause 21, wherein the RNA is administered intra-tumorally or peri-tumorally via injection, and the checkpoint modulator is administered systemically.

Clause 24. The method of clause 17, wherein the solid tumor is a sarcoma, carcinoma, or lymphoma.

Clause 25. The method of clause 17, wherein the solid tumor is in the lung, colon, ovary, cervix, uterus, peritoneum, testicles, penis, tongue, lymph node, pancreas, bone, breast, prostate, soft tissue, connective tissue, kidney, liver, brain, thyroid, or skin.

Clause 26. The method of clause 17, wherein the solid tumor is an epithelial tumor, Hodgkin lymphoma (HL), non-Hodgkin lymphoma, prostate tumor, ovarian tumor, renal cell tumor, gastrointestinal tract tumor, hepatic tumor, colorectal tumor, tumor with vasculature, mesothelioma tumor, pancreatic tumor, breast tumor, sarcoma tumor, lung tumor, colon tumor, brain tumor, melanoma tumor, small cell lung tumor, neuroblastoma tumor, testicular tumor, carcinoma tumor, adenocarcinoma tumor, glioma tumor, seminoma tumor, retinoblastoma, or osteosarcoma tumor.

Clause 27. The method of clause 17, wherein treating or reducing the likelihood of the solid tumor comprises reducing the size of a tumor, reducing the likelihood of a reoccurrence of cancer in remission, or reducing the likelihood of cancer metastasis in the subject.

Clause 28. A combination therapy method for treating or reducing the likelihood of a solid tumor, comprising administering to a subject in need thereof RNAs and a further therapy, wherein the RNAs encode an IL-12sc protein, an IL-15 sushi protein, an IFNα protein, and a GM-CSF protein, and the further therapy comprises immunotherapy, chemotherapy, or a checkpoint modulator.

Clause 29. The combination therapy method of clause 28, wherein the further therapy comprises an anti-PD1 antibody, an anti-CTLA-4 antibody, or a combination of an anti-PD1 antibody and an anti-CTLA-4 antibody.

Clause 30. An isolated nucleic acid comprising a sequence encoding an IL-12sc protein, wherein:
the sequence encoding the IL-12sc protein comprises a) contiguous nucleotides having at least 99%, 98%, 97%, 96%, 95%, 90%, 85%, 80%, or 78% identity to nucleotides 1-984 of SEQ ID NO: 16 or 18, b) contiguous nucleotides having at least 99%, 98%, 97%, 96%, 95%, 90%, 85%, or 81% identity to nucleotides 1027-1623 of SEQ ID NO: 16 or 18, and c) nucleotides encoding a linker between the nucleotides of a) and b).

Clause 31. The nucleic acid of clause 30, which is a DNA.

Clause 32. The nucleic acid of clause 30, which is an RNA.

Clause 33. An isolated nucleic acid comprising a sequence encoding an IFNα protein, wherein:
the sequence encoding the IFNα protein has at least 99%, 98%, 97%, 96%, 95%, 90%, 85%, or 80% identity to the nucleotide sequence of SEQ ID NO: 21 or 23.

Clause 34. The nucleic acid of clause 33, which is a DNA.

Clause 35. The nucleic acid of clause 33, which is an RNA.

Clause 36. A method for treating or reducing the likelihood of a solid tumor comprising administering to a subject in need thereof the RNA of clause 34, wherein: the subject is further treated with additional RNA encoding an IL-15 sushi protein, an IFNα protein, and a GM-CSF protein.

Clause 37. A method for treating or reducing the likelihood of a solid tumor comprising administering to a subject in need thereof the RNA of clause 35, wherein: the subject is further treated with additional RNA encoding an IL-15 sushi protein, an IL-12sc protein, and a GM-CSF protein.

Clause 38. A method of producing an RNA encoding IL-12sc, comprising contacting an expression construct comprising the nucleic acid of clause 32 operably linked to a promoter with an RNA polymerase under conditions permissive for transcription.

Clause 39. A method of producing an RNA encoding IFNα, comprising contacting an expression construct comprising the nucleic acid of clause 35 operably linked to a promoter with an RNA polymerase under conditions permissive for transcription.

Clause 40. A kit comprising the composition of clause 1.

Clause 41. A kit comprising RNA encoding an IL-12sc protein, RNA encoding an IL-15 sushi protein, RNA encoding an IFNα protein, and RNA encoding a GM-CSF protein, wherein the RNAs are not in the same container.

Clause 42. The kit of clause 41, wherein each RNA is in a separate container.

Clause 43. The kit of any one of clause 40-42, further comprising instructions for use of the composition or RNAs for treating or reducing the likelihood of a solid tumor.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1—Materials and Methods

B16F10 Tumor Model: Female C57BL/6J mice (Jackson Laboratory; Bar Harbor, Me.), 6-8 weeks-old and weighing between 17.0 and 20.9 g were acclimated for at least three days prior to study enrollment. Mice had free access to food (Harlan 2916 rodent diet, Massachusetts, USA) and sterile water and housed on 12 hours light/dark cycle at 22° C.±2° C. with a relative humidity of 55%±15%. B16F10 cells were obtained from the American Type Culture Collection (ATCC) (Manassas, Va. USA) (Cat No. CRL-6475) and cultured in Dulbecco's Modified Eagle's Medium (DMEM) (Life technologies, Cat No. 11995) supplemented with 10% heat inactivated Fetal Bovine Serum (HI FBS) (Life technologies, Cat No. 10082-147) in 5% CO2 at 37° C. The cells were harvested using 0.25% Trypsin-EDTA (Life technologies, Cat No. 25200-056), resuspended in Dulbecco's phosphate-buffered saline (DPBS) (Life technologies, Cat No. 14190-144), and 0.5×10^6 cells/200 µl per mouse subcutaneously (SC) implanted into the right flank of female C57BL/6J mice. For dual flank tumor models on day 0, 0.5×10^6 B16F10 cells/200 µl per mouse were subcutaneously (SC) implanted into the right flank and 0.25×10^6 B16F10 cells/200 µl per mouse were SC implanted into the left flank. To test whether local administration of cytokine mRNA can have distant effects (see FIG. 19), female C57BL/6JOlaHsd mice (Envigo, Rossdorf, Germany), 6-8 weeks of age, with a weight between 17 and 24 g, were acclimated for at least six days prior to study enrollment. Mice had free access to food (ssniff M-Z autoclavable Soest, Germany) and sterile water and housed on 12 hours light/dark cycle at 22° C.±2° C. with a relative humidity of 55%±10%. B16F10 cells were obtained from the American Type Culture Collection (ATCC® CRL-6475™) and cultured in DMEM, high glucose, GlutaMAX™ (Life technologies, Cat No. 31966047) supplemented with 10% Fetal Bovine Serum (FBS) (Biochrom, Cat No. S 0115) in 7.5% $CO_2$ at 37° C. The cells were harvested using StemPro® Accutase® Cell Dissociation Reagent (Life technologies, Cat No. A1110501), re-suspended in Dulbecco's phosphate-buffered saline (DPBS) (Life technologies, Cat No. 14190-169), and $0.3 \times 10^6$ cells/100 μl per mouse subcutaneously (SC) were implanted into the right shaven flank of female C57BL/6J mice. For seeding of distant lung tumors, B16F10_luc-gfp cells were used. These cells were derived from B16F10 by stable transfection with a plasmid coding for Luciferase and GFP. B16F10_luc-gfp cells were cultured with the same conditions as the B16F10; only 0.5 μg/mL Puromycin was added to the culture medium. One day after SC implantation $0.3 \times 10^6$ cells/200 μl of B16F10_luc-gfp cells were injected per mouse intravenously (IV) into the tail vein. Intratumoral mRNA injections were initiated 10-14 days after SC inoculation of the tumors. Tumor growth was assessed by caliper measurements every 2-3 days and is expressed as the product of the perpendicular diameters using the following formula: $a^2 \ast b/2$, with $a<b$. Engraftment of luciferase-positive tumor cells in the lung was analyzed by in vivo bioluminescence imaging using the Xenogen IVIS Spectrum imaging system (Caliper Life Sciences). An aqueous solution of L-luciferin (250 μl, 1.6 mg; BD Biosciences) was injected intraperitoneally. Emitted photons from live animals quantified 10 min later with an exposure time of 1 min. Regions of interest (ROI) were quantified as average radiance (photons $s^{-1}$ $cm^{-2}sr^{-1}$, represented by as color-scaled images superimposed on grayscale photos of mice using the Living Image software from Caliper Life Sciences). For absolute quantification, the bioluminescence signal was blotted as total flux (photons $s^{-1}$). For studies performed in FIGS. 20C-G and 21E-I the above described model of C57BL/6JOlaHsd mice (Envigo, Rossdorf, Germany) without seeding of lung metastasis was used as well.

CT26 tumor model: For studies performed in FIGS. 2, 3, 7D-F, 8, 9, 12D and 21, female Balb/c Rj mice (Janvier, Genest-St.-Isle, France), 6-8 weeks of age, with a weight between 17 and 24 g, were acclimated for at least six days prior to study enrollment. Mice had free access to food (ssniff M-Z autoclavable Soest, Germany) and sterile water and housed on 12 hours light/dark cycle at 22° C.±2° C. with a relative humidity of 55%±10%. CT26 cells were obtained from the (ATCC® CRL-2638™) and cultured in Roswell Park Memorial Institute medium (RPMI) 1640 Medium, GlutaMAX™ (Life technologies, Cat No. 61870-044) supplemented with 10% Fetal Bovine Serum (FBS) (Biochrom, Cat No. S 0115) in 5% $CO_2$ at 37° C. The cells were harvested using StemPro® Accutase® Cell Dissociation Reagent (Life technologies, Cat No. A1110501), resuspended in DPBS (Life technologies, Cat No. 14190-169), and $0.5 \times 10^6$ cells/100 μl per mouse SC implanted into the right shaven flank of female Balb/c Rj mice. Intratumoral RNA injections were initiated 13-19 days after inoculation of the tumors. Tumor growth was assessed by caliper measurements every 2-3 days and is expressed as the product of the perpendicular diameters using the following formula: $a^2 \ast b/2$ where b is the longer of the two diameters (a<b).

For studies performed in FIGS. 6, and 7A-C female BALB/c mice (Jackson Laboratory; Bar Harbor, Me.), 6-8 weeks-old and weighing between 17.0 and 20.9 g were acclimated for at least three days prior to study enrollment. Mice had free access to food (Harlan 2916 rodent diet, Massachusetts, USA) and sterile water and housed on 12 hours light/dark cycle at a temperature (22° C.±2° C.), relative humidity (55%±15%). CT26 cells were obtained from the ATCC (Manassas, Va. USA) (Cat No. CRL-2638) and cultured in RPMI-1640 (Life technologies, Cat No. 11875-093) supplemented with 10% HI FBS (Life technologies, Cat No. 10082-147) in 5% $CO_2$ at 37° C. The cells were harvested using 0.25% Trypsin-EDTA (Life technologies, Cat No. 25200-056), re-suspended in DPBS (Life technologies, Cat No. 14190-144), and $0.5 \times 10^6$ cells/200 μl per mouse SC implanted into the right flank of BALB/c female mice.

In CT26 tumor model in addition to tumor growth gp70-reactive CD8+ T-cells were measured in blood where indicated. Blood samples were taken using EDTA-coated tubes. 100 μL of blood was transferred to FACS tubes and antibody mixture was added containing T-Select H-2Ld MuLV gp70 Tetramer-SPSYVYHQF-APC (MBL (TS-M-521-2), 4 μL for 100 μL blood), anti-CD8a FITC (life technologies (MCD801), 1 μL for 100 μL blood)) and anti-CD45 V500 (BD (561487), 1 μL for 100 μL blood)). After 20 min incubation at room temperature Blood Lysis Buffer (BD (349202), 300 μL per tube) was added and incubated for further 6 min. Then samples were washed twice with PBS-EDTA buffer. FACS samples were analyzed on a FACS Canto II flow cytometer.

MC38 tumor model: Female C57BL/6J mice (Jackson Laboratory; Bar Harbor, Me.), 6-8 weeks-old and weighing between 17.0 and 20.9 g were acclimated for at least three days prior to study enrollment. Mice had free access to food (Harlan 2916 rodent diet, Massachusetts, USA) and sterile water and housed on 12 hours light/dark cycle at 22° C.±2° C. with a relative humidity of 55%±15%. MC38 cells were generous gifts from Dr S. A. Rosenberg (National Institute of Health, Bethesda, Md., USA). The cell line was cultured in RPMI-1640 with L-glutamine (Gibco, Cat No. 11875) supplemented with 10% HI FBS (Gibco, Cat No. 100082) in 5% $CO_2$ at 37° C. The cells were harvested, re-suspended in DPBS (Gibco, Cat No. 14190), and $1 \times 10^6$ cells/200 μl per mouse SC implanted into the right flank of female C57BL/6J mice.

A375 tumor model: Female severe combined immune deficiency (SCID) mice (Jackson Laboratory; Bar Harbor, Me.), 6-8 weeks-old and weighing between 17.0 and 20.9 g were acclimated for at least three days prior to study enrollment. Mice had free access to food (Harlan 2916 rodent diet, Massachusetts, USA), sterile water and housed on 12 hours light/dark cycle at 22° C.±2° C. with a relative humidity of 55%±15%. A375 cells were obtained from the ATCC (Manassas, Va. USA) (Cat No. CRL-1619). The cell line was cultured in DMEM (Life technologies, Cat No. 11995) supplemented with 10% HI FBS (Life technologies, Cat No. 10082-147) in 5% $CO_2$ at 37° C. The cells were harvested using 0.25% Trypsin-EDTA (Life technologies, Cat No. 25200-056), re-suspended in DPBS (Life technologies, Cat No. 14190-144), and $3.0 \times 10^6/100$ μl PBS were mixed with 100 ul BD Matrigel Matrix (BD, Cat No. 354234) and implanted SC into the right flank of female SCID mice.

KM12 (CRC) Xenograft Model: Female NOD.CB17-Prkdcscid/SCID mice (Jackson Laboratory, Bar Harbor, Me.), 10-weeks-old and weighing between 17.3 g and 21.9 g were acclimated for at least three days prior to study enrollment. Mice had free access to food (Harlan 2916 rodent diet, Massachusetts, USA), sterile water and were housed on 12 hours light/dark cycle at (22±2° C.) with a relative humidity (55±15%). KM-12 cells were obtained from the American National Cancer Institute (NCI) (Cat No. 507345). The cells were grown in RPMI medium 1640 with L-glutamine (Gibco, Cat No. 11875) supplemented with 10% HI FBS (Gibco, Cat No. 10082), and incubated at 37° C. with 5% CO2. The cells were harvested using 0.25% Trypsin-EDTA (Gibco, Cat No. 25200), re-suspended in DPBS (Gibco, Cat No. 14190), and for each mouse 5.0×106 cells in 200 pl DPBS with 50% matrigel (BD, Cat No. 356234) were SC implanted into the right flank of female SCID mice.

RPMI8226 (Myeloma) Xenograft Model: Female NSG mice (Jackson Laboratory, Bar Harbor, Me.), 12-weeks-old and weighing between 19.8 g and 26.6 g were acclimated for at least three days prior to study enrollment. Mice had free access to food (Harlan 2916 rodent diet, Massachusetts, USA), sterile water and were housed on 12 hours light/dark cycle at (22±2° C.) with a relative humidity (55±15%). RPMI8226 cells were obtained from the ATCC (Cat No. CCL-155). The cells were grown in RPMI medium 1640 with L-glutamine (Gibco, Cat No. 11875) supplemented with 10% HI FBS (Gibco, Cat No. 10082), and incubated at 37° C. with 5% CO2. The cells were harvested using 0.25% Trypsin-EDTA (Gibco, Cat No. 25200), re-suspended in DPBS (Gibco, Cat No. 14190), and for each mouse 5.0×106 cells in 200 µl DPBS with 50% matrigel (BD, Cat No. 356234) were SC implanted into the right flank of female NSG mice.

NCI-N87 (Gastric) Xenograft Model: Female NOD.CB17-Prkdcscid/SCID (Jackson Laboratory, Bar Harbor, Me.), 11-weeks-old and weighing between 18.3 and 22.7 g were acclimated for at least three days before the study enrollment. Mice had free access to food (Harlan 2916 rodent diet, Massachusetts, USA), sterile water and were housed on 12 hours light/dark cycle at (22±2° C.) with a relative humidity (55±15%). NCI-N87 cells were obtained from the ATCC (Cat No. CRL-5822). The cells were grown in RPMI medium 1640 with L-glutamine (Gibco, Cat No. 11875) supplemented with 10% HI FBS (Gibco, Cat No. 10082), and incubated at 37° C. with 5% CO2. The cells were harvested using 0.25% Trypsin-EDTA (Gibco, Cat No. 25200), re-suspended in DPBS (Gibco, Cat No. 14190), and for each mouse 3.0×106 cells in 200 µl DPBS with 50% matrigel (BD, Cat No. 356234) were SC implanted into the right flank of female SCID mice.

NCI-H1975 (NSCLC) Xenograft Model: Female NSG mice (Jackson Laboratory, Bar Harbor, Me.), 10-weeks-old and weighed between 18.8 g and 26.0 g were allowed to acclimate for at least three days before study enrollment. Mice had free access to food (Harlan 2916 rodent diet, Massachusetts, USA), sterile water and were housed on 12 hours light/dark cycle at (22±2° C.) with a relative humidity (55±15%). NCI-H1975 cells were obtained from the ATCC (Cat No. CRL-5908) and cultured in RPMI medium 1640 with L-glutamine (Gibco, Cat No. 11875) supplemented with 10% HI FBS (Gibco, Cat No. 10082), and incubated at 37° C. with 5% CO2. The cells were harvested using 0.25% Trypsin-EDTA (Gibco, Cat No. 25200), re-suspended in DPBS (Gibco, Cat No. 14190), and for each mouse 5.0×106 cells in 200 µl DPBS with 50% matrigel (BD, Cat No. 356234) were SC implanted into the right flank of female NSG mice.

Tumor re-challenge: Female C57BL/6J mice were implanted with B16F10 cells as described above. Mice were treated with 4 intratumoral injections (80 µg mRNA/20 µg per target) on days 11, 13, 15, and 17 with ModB cytokine mRNA mixture (IL-15sushi, IL-12sc, GM-CSF, IFNα). After cytokine mRNA treatment 8 mice were tumor free. Four weeks after the last cytokine mRNA treatment tumor free mice were re-challenged with 0.5×10^6 B16F10 cells/200 µl per mouse by SC injection and tumor growth was monitored.

Tumor monitoring: Tumors were measured with a caliper twice weekly until final sacrifice. When a tumor size reached approximately 2000 mm$^3$ or there are animal health issues (20% area of a tumor ulcerated), animals were euthanized. Tumor regression was defined as i) tumor volume <20 mm3 at the end of the study or ii) $T^F/T^0<1$, where the $T^F$ equals the final tumor volume and $T^0$ equals tumor volume on the day of the first intratumoral mRNA injection.

mRNA modification A (ModA): Synthetic DNA fragments coding for the gene of interest were cloned into a common starting vector, comprising a 5'-UTR (corresponding in some cases to SEQ ID NO: 1), a 3' UTR consisting of two elements called F and I (corresponding in some cases to SEQ ID NO: 7), and a poly(A)-tail of 110 nucleotides in total (A30-linker-A70 structure; corresponding in some cases to SEQ ID NO: 78). Linearization of plasmid DNA was performed downstream of the poly(dA:dT) with a classIIS restriction enzyme to generate a template with no additional nucleotide beyond the poly(dA:dT) (see Holtkamp et al., *Blood* 108(13):4009-172006 (2006)). Linearized plasmid DNA was subjected to in vitro transcription with T7 RNA polymerase (Thermo Fisher) as previously described (see Grudzien-Nogalska E et al., *Methods Mol Biol.* 969:55-72 (2013)) in the presence of 7.5 mM ATP, CTP, UTP, GTP and 6 mM D1, a beta-S-antireverse cap analogue (beta-S-ARCA, Cap0) (see Kuhn A N et al, *Gene Ther.* 17(8):961-71 (2010)). RNA was purified using magnetic particles (see Berensmeier S. *Appl Microbiol Biotechnol.* 73(3):495-504 (2006)), and RNA concentration and quality were assessed spectrophotometry and analyzed by capillary gel electrophoresis systems, respectively.

mRNA modification B (ModB): Synthetic DNA fragments coding for the gene of interest were cloned into a common starting vector, comprising a 5'-UTR (corresponding in some cases to the Tobacco Etch Viral leader sequences TEV, SEQ ID NO: 3), a 3' UTR consisting of two elements called F and I (corresponding is some cases to SEQ ID NO: 7), and a poly(A)-tail of 110 nucleotides in total (A30-Linker-A70 structure). Upon linearization of plasmid DNA as described above, in vitro transcription with T7 RNA polymerase (Thermo Fisher) was performed. This was carried out as described for ModA, but no cap structure was added to the reaction and UTP was substituted for N1-methyl-pseudouridinetriphosphate. RNA was then purified using magnetic particles (Berensmeier 2006), and subsequently Cap1 structure was enzymatically introduced using a commercially available system based on the Vaccinia virus capping enzyme (NEB) and addition of mRNA Cap 2'-O-methyltransferase (NEB). Afterwards, the RNA was subjected to a further purification procedure by Cellulose-based chromatography to remove double-stranded RNA impurities (see Day P R et al, *Phytopathology* 67:1393 (1977); Morris T J et al., *Phytopathology* 69:854-858 (1979); and Castillo A et al., *Virol J.* 8:38 (2011)). RNA concentration and quality were assessed spectrophotometry and analyzed by capillary gel electrophoresis systems, respectively. Presence of dsRNA was assessed in a Northwestern dot-blot assay using dsRNA-specific J2 mAb (English & Scientific Consulting) as described in Karikó et al. Nucleic Acids Res. 39(21):e142 (2011).

mRNA codon optimization: The coding sequence of a protein may influence the efficiency as well as the accuracy of protein translation (see Bossi L et al., Nature. 286(5769): 123-7 (1980) and Irwin et al., J Biol Chem. 270(39):22801-6 (1995)).

Therefore, different codon variants of each target were designed and tested. The design of the different codon variants for each target utilized publicly available software from Life Technologies GmbH GeneArt® (Regensburg, Germany) (see Raab D et al., Syst Synth Biol. 4(3):215-25 (2010)) and Eurofins MWG Operon (Ebersberg, Germany). In addition, codon optimization was performed manually editing each codon separately. A GC-content comparable to the wild type sequence was maintained during the optimization process.

Evaluation and selection of constructs was determined by in vitro expression performed using: (i) mRNA lipofection of HEK293T/17 cells and (ii) mRNA electroporation K562 cells.

Forty thousand (40,000) HEK293T/17 cells (ATCC® CRL-11268™) were seeded in flat bottom 96-well plates (VWR International, Cat No. 734-1794) in DMEM, high glucose, GlutaMAX™ (Life technologies, Cat No. 31966047) containing 0.5% FBS (Biochrom, Cat No. S 0115). Seeded cells in 96-well plates were incubated at 37° C., 7.5% CO2 for 16-18 hours. Adherent HEK293T/17 cells were transfected with RNA using Lipofectamine™ Messenger MAX Reagent (Invitrogen, Cat No. LMRNA) according to the manufacturer's protocol by adding 1.2 µl of the transfection reagent to 20 µl of OptiMEM (Thermo Fisher, Cat No. 31985070) in an RNAse-free 1.5 ml Safe-Lock tube biopur (Eppendorf, Germany, Cat No. 0030121589); in a second tube the indicated RNA was added to 20 µl of OptiMEM. After 10 minutes of incubation the tube containing the RNA was diluted into the tube containing the Lipofectamine™ Messenger MAX and incubated an additional 5 minutes prior to adding 10 µl of the RNA-lipid-complex drop wise to one well of the 96-well plate containing the HEK293T/17 cell layer in 100 µl medium. The 10 µl RNA-lipid-complex contained 5 ng, 25 ng and 100 ng of target RNA respectively. The plates were placed into the incubator for 3h before an additional 140 µl of fresh medium (DMEM+0.5% FBS) was added. The transfected cells were incubated for 15-18 hours and the supernatants were collected and analyzed for protein content by ELISA as described herein.

K562, a human cell line derived from chronic myeloid leukemia (ATCC® CCL-243™) was cultivated in RPMI 1640 Medium, GlutaMAX™ (Life technologies, Cat No. 61870-044) supplemented with 5% FBS. K562 were electroporated in a 96-well plate system as follows. Cells were washed once in X-VIVO15 medium (Lonza, Cat No. BE02-060Q) and suspended to a final concentration of two hundred fifty thousand (250,000) cells/150 µl in X-VIVO15. A 150 µl of cell suspension was added per well of a 96-well plate containing 5 ng, 25 ng, or 100 ng of RNA. Cells and RNA were mixed and electroporation was performed in a 96 well Gene Pulser MX cell electroporation system from Biorad (250 V, 1×30 ms pulse). Immediately following electroporation, cells were transferred into a new culture plate with fresh medium without antibiotics and rested for 1 hour in the incubator at 37° C. The medium was exchanged for fresh RPMI 1640 GlutaMAX supplemented with 0.5% FCS and incubated 15-18 hours. Supernatants were harvested and analyzed for protein content by ELISA as described herein.

Protein concentrations were determined by ELISAs specific for the RNA encoded cytokine according to the manufacturer's protocol. (i) Human IL-15 sushi/IL-15 sushi R alpha Complex DuoSet ELISA (ii) Mouse IL-12sc Duo Set Development System (DY419-05) (iii) Mouse GM-CSF DuoSet ELISA Development Systems (DY415), all obtained from RnD systems, and mouse IFNα ELISA Kit (TCM) (PBL assay science, 42120-2).

For each mRNA target, the protein expression was evaluated for the wt-sequence and the different codon-optimized variants. Both data sets from lipofection of HEK293T/17 and electroporation of K562 each tested with the three different amounts of modified RNA were considered for selection of the protein coding sequence. A codon-optimized sequence was selected if an at least 1.5-fold increase of protein expression compared to WT sequence was measured. If this was not the case, the WT sequence was selected. For all constructs Earl-restriction sequences were eliminated by mutating the DNA recognition sequence (5'-CTCTTC-3'), while preserving the WT amino acid.

Cell lines: HEK293 (ATCC CRL-1573) cell line and human melanoma cell lines, A101D (ATCC CRL-7798), A375 (ATCC CRL-1619), A2058 (ATCC CRL-11147), and Hs294T (ATCC HTB-140), were obtained from ATCC and cultured in DMEM (ThermoFisher Scientific, Cat 11885-084) supplemented with 10% FBS HI FBS Life Technologies, Cat. 10082) in a humidified atmosphere of 5% CO2 at 37° C.

mRNA transfection: Cells were transfected using Lipofectamine™ MessengerMAX Reagent (Invitrogen, Cat #LMRNA001) according to the manufacturer protocol. Briefly, for each well 0.3 µl of the transfection reagent was diluted with 5 µl of the Opti-MEM™ media (Life Technologies, Cat. 31985062) and incubated for 10 min at room temperature; mRNA mixtures were diluted with Opti-MEM™ media (5 µl per well) and mixed with diluted MessengerMax reagent, incubated for 5 min at room temperature and aliquoted to the 96-well plate. Cells were diluted in complete growth media and 40,000 cells per well were added to the transfection mixtures. Cells were incubated for 24 hours at 37° C. in a CO2 incubator then media was collected and cytokine concentration was determined by Meso Scale Discovery (MSD) assay.

Meso Scale Discovery Assay: Cytokine concentration was determine using MSD assays: Proinflammatory Panel 1 (human) MSD kit (catalog N05049A-1) for IL12p70, Cytokine Panel 1 (human) MSD kit (catalog N05050A-1) for GM-CSF and IL-15 sushi, and Human IFN-α 2a Ultrasensitive Kit (catalog N05050A-1) for IFNα. Data were analyzed using MSD Discovery Workbench V. 4.0.12 software and GraphPad Prism V.6.00 software.

PBMC isolation and treatment: Peripheral Blood Mononuclear Cells (PBMCs) were isolated by density gradient media (Ficoll-Paque) from a leukopak (Research Blood Components). 600,000 PBMCs were added per well of a 96-well plate. Cells were treated with a cytokine mixture for 24 hrs and IFNγ production was measured in the cell culture media using Human IFNγ 384-Tissue Culture MSD Assay.

Measuring CD8 response: B16F10 tumor bearing mice received a single intratumoral injection of Immuno mRNA (IFNα, IL-15 sushi, GM-CSF, and IL-12sc, ModB) or control luciferase mRNA (Placebo). Seven days after intratumoral mRNA injection tumors were excised, processed for immunofluorescence and stained with an antibody for CD8 (gray). As shown in FIG. 25, CD8 cells were present after cytokine mRNA intratumoral injection.

Preparation of mRNA for in vivo studies: The respective mRNA mixtures were prepared for in vivo studies by mixing equal quantities (micrograms) of mRNA in water at 2× the intended dose. The mRNA mixture was frozen at −80 C until the day of intratumoral injection. On the day of injection, mRNA was thawed and mixed with an equal volume of 2× sterile Ringer's solution. The resulting 1×mRNA/Ringer solution was used for intratumoral injection.

Gene expression analysis: A375 tumors were homogenized in the RLT Buffer (Qiagen) using Precellys 24 homogenizer (Bertin Instruments). Total RNA was isolated with the RNeasy-96 Kit (Qiagen), following the spin protocol with the DNase treatment. RNA was eluted with nuclease-free water and quantified by ultraviolet absorbance using a NanoDrop 8000 (Thermo Scientific). cDNA synthesis was performed with the High Capacity RNA to cDNA Kit (Applied Biosystems) according to the manufacturer's recommendations. Real-time PCR were performed on a ViiA™7 (Applied Biosystems) according to standard protocol. Amplification was performed using the TaqMan Gene Expression Master Mix (Applied Biosystems) and predesigned Taqman Assays (Applied Biosystems). Gene expression was normalized to the endogenous control GAPDH. Comparative ddCT method was used to evaluate gene expression.

TABLE 3

| Gene | Assay ID | Lot Number | Fluorescent dye |
|---|---|---|---|
| ISG15 | Hs01921425_s1 | 1548867 | FAM |
| ISG54 | Hs01922738_s1 | 1532771 | FAM |
| Mx1 | Hs00895608_m1 | 1539223 | FAM |
| hGAPDH | 4326317E | 1311049 | VIC |

Example 2—Combinations of Three mRNAs Reduce Tumor Volume In Vivo

Figure 1A:
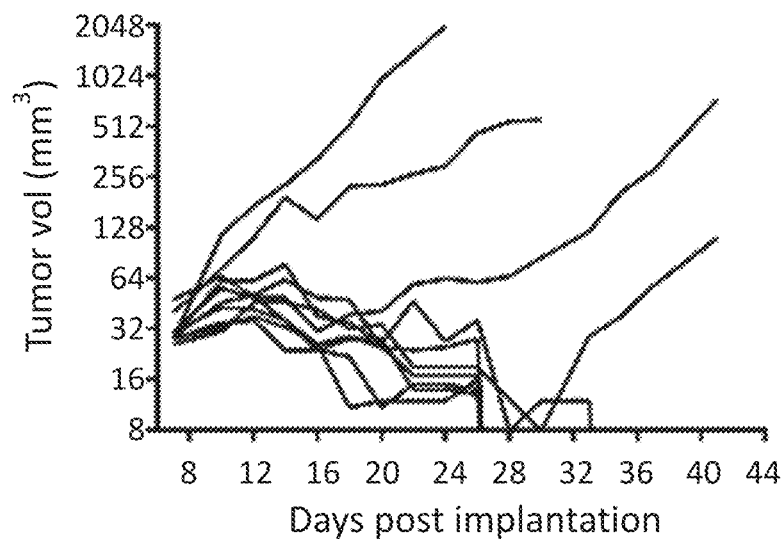
Figure 1B:
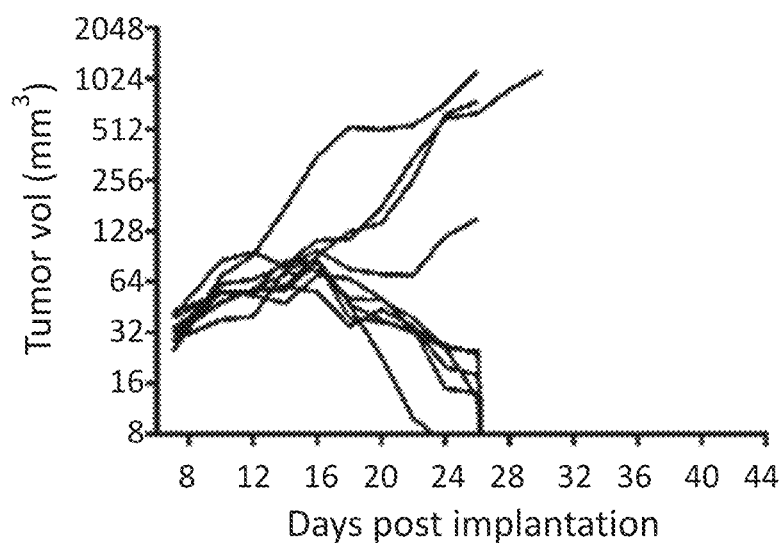
Figure 1C:
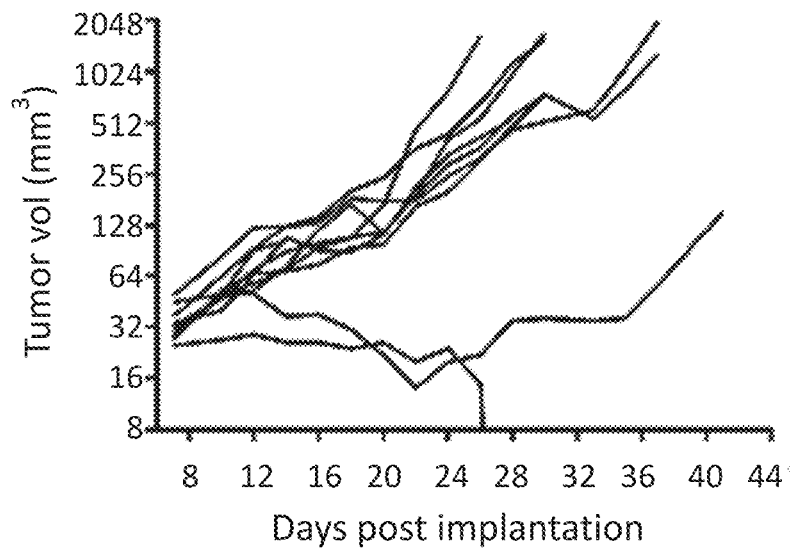
Figure 1D:
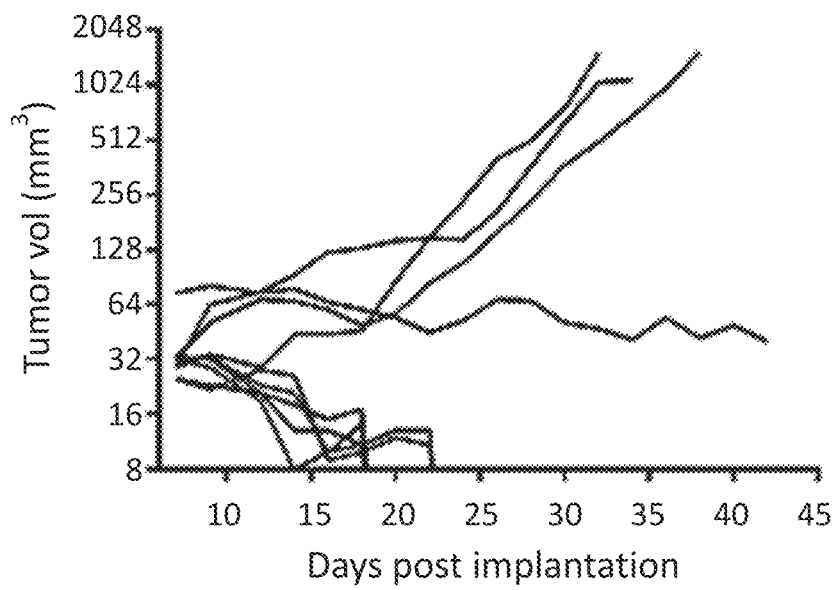
Figure 1E:
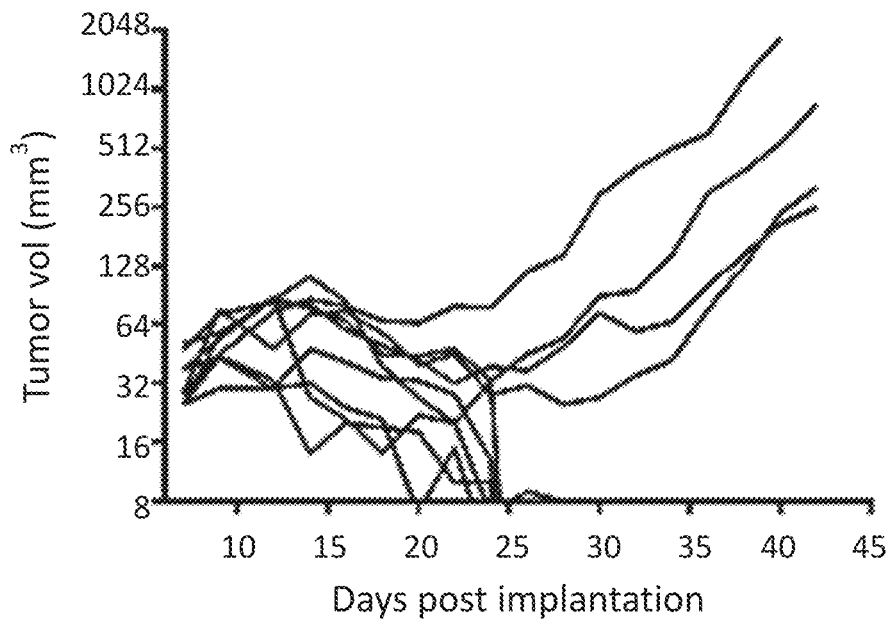
Figure 1F:
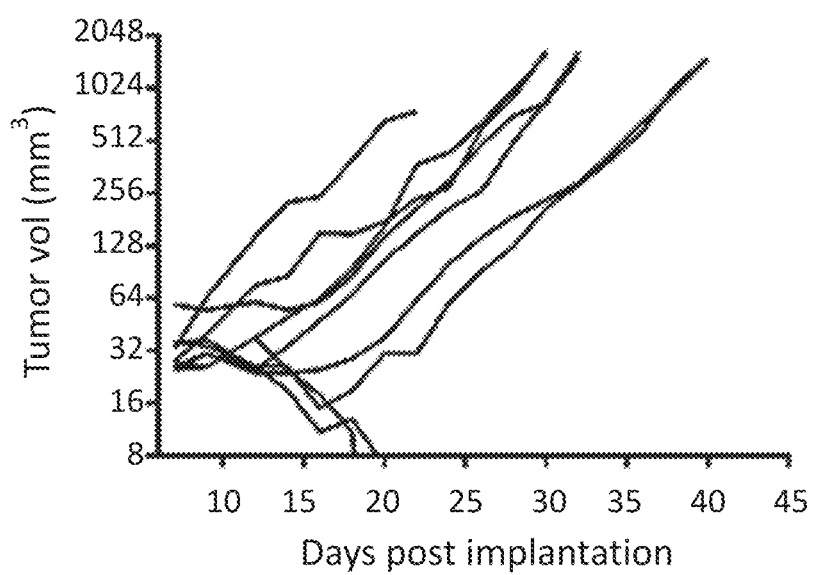
Figure 1G:
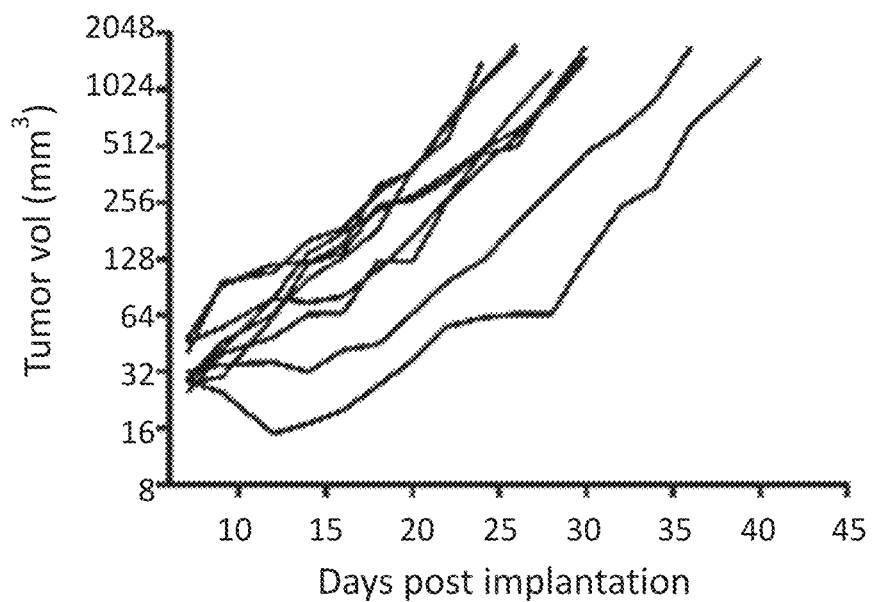

A mixture of modified mRNAs encoding GM-CSF, IL-2, and IL-12sc was injected into B16F10 tumor bearing mice and tumor growth was monitored to day 41. As shown in FIG. 1, intratumoral injection of a combination of three mRNAs encoding GM-CSF, IL-2, and IL-12sc having ModA (SEQ ID NOs: 32, 38, and 56; FIG. 1A), or a combination of three mRNAs encoding GM-CSF, IL-2, and IL-12sc having ModB (SEQ ID NOs: 35, 41, and 59; FIG. 1B) induced regression in 6 out of the 10 mice, while mice treated with a control mRNA encoding luciferase (ModA) displayed tumor regression in 1 of 10 animals (FIG. 1C). These data were confirmed in a repeat study of similar design (FIG. 1D-1G). In the repeat experiment, a mixture of cytokine mRNA (GM-CSF, IL-2, IL-12sc) with ModA or ModB lead to tumor regression in 5 of 9 mice, while treatment with control mRNA in ModA and ModB displayed 2 of 9 and 0 of 9 tumor regressions, respectively.

Figure 2A:
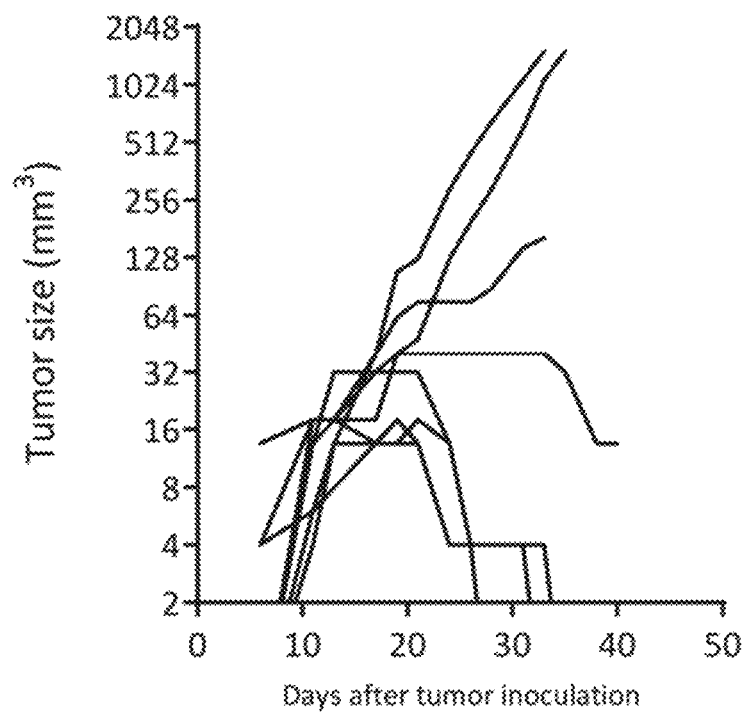
Figure 2B:
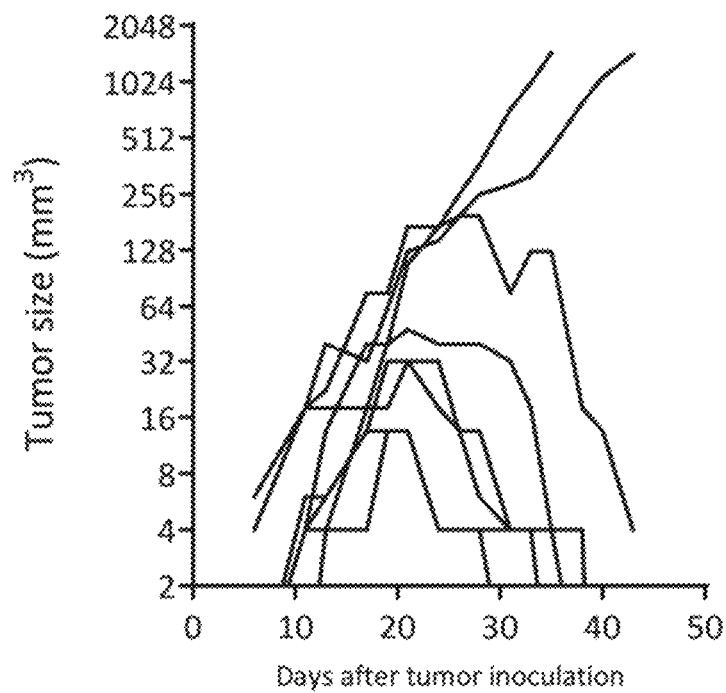
Figure 2C:
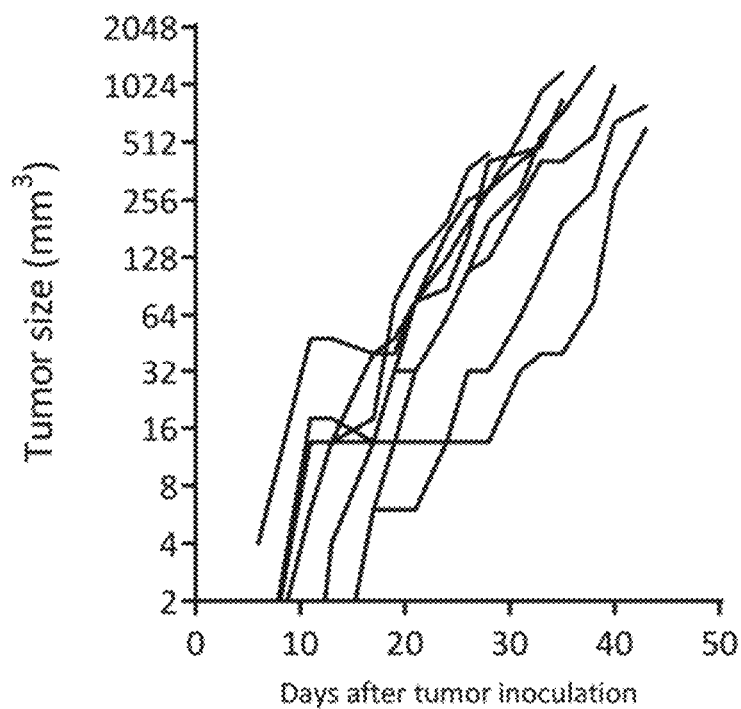
Figure 2D:
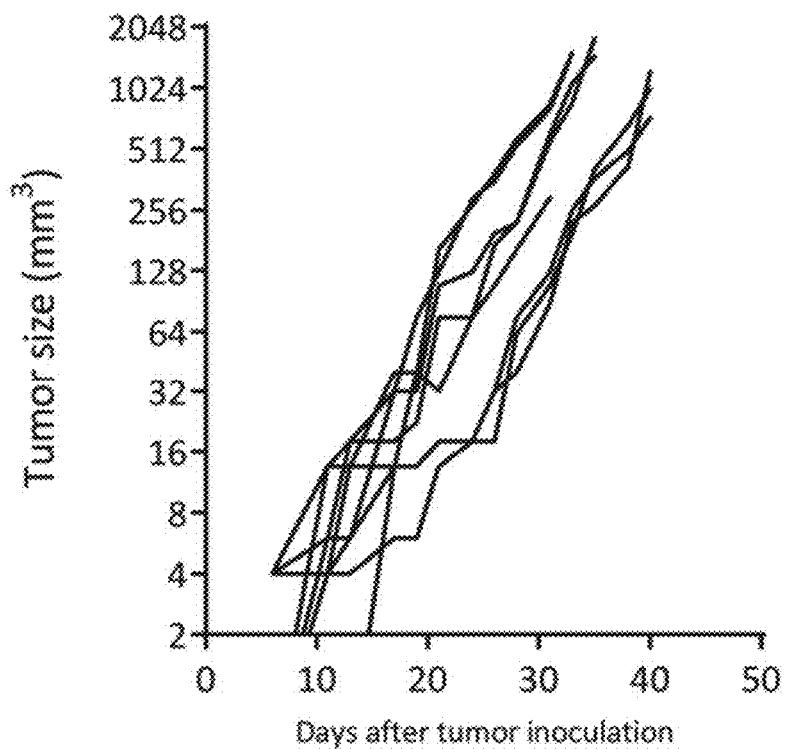

The effects of cytokine mRNA treatment were evaluated in CT26 tumors. Mice with established CT26 tumors were injected with a cytokine mRNA mixture encoding GM-CSF, IL-2, and IL-12sc in ModA and ModB formats, respectively. Two control groups were included: i) mRNA Ringer's diluent and ii) ModA mRNA encoding firefly luciferase. A total of 6 intratumoral injections were administered on days 19, 21, 24, 26, 28 and 31. As shown in FIG. 2, both GM-CSF, IL-2, and IL-12sc mRNA ModA (SEQ ID NOs: 56, 32, and 38; FIG. 2A) and ModB (SEQ ID NOs: 59, 35, and 41; FIG. 2B) resulted in tumor regression in 5 and 6 out of 8 mice, respectively, while no tumors treated with control mRNA in ModA (FIG. 2C) or Ringer's solution (FIG. 2D) displayed tumor regression.

Figure 3A:
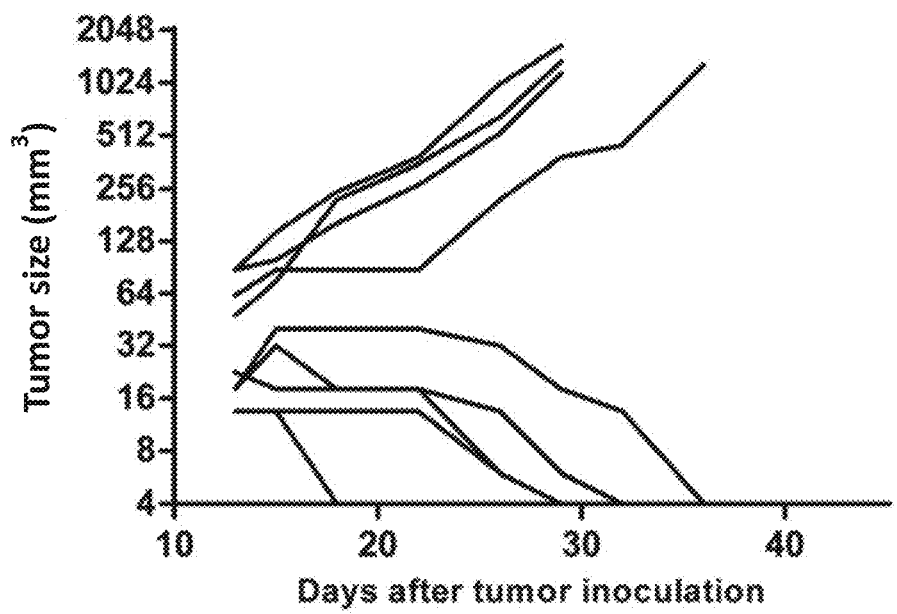
Figure 3B:
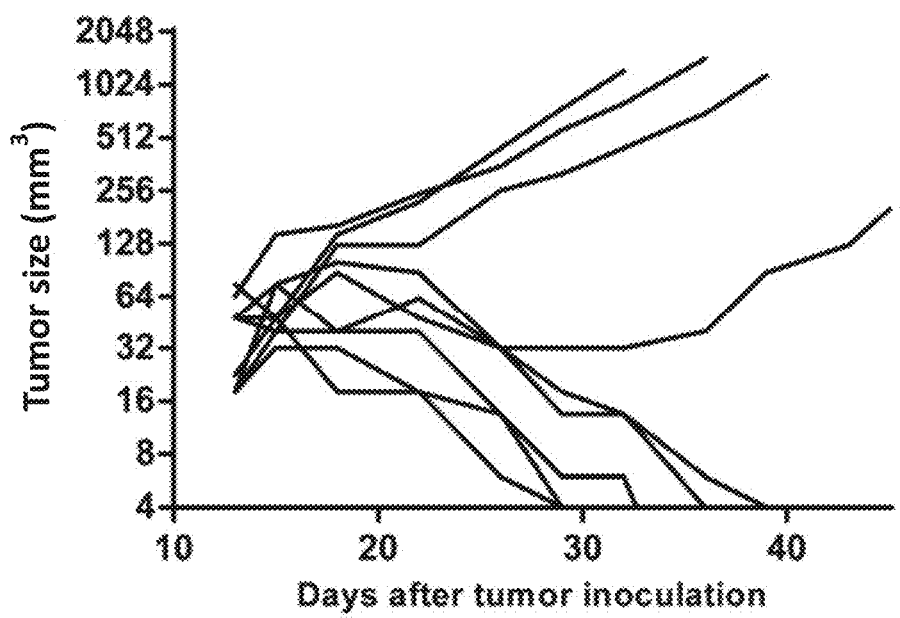
Figure 3C:
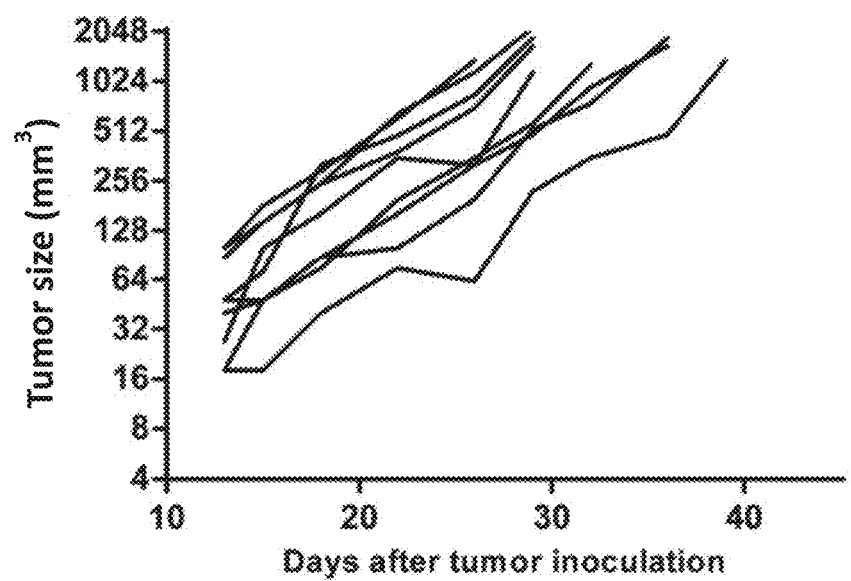

The cytokine mRNA mixture encoding IL-15 sushi, GM-CSF and IL-12sc (ModB; SEQ ID NOs: 53, 59, and 41) and IL-2, GM-CSF and IL-12sc (ModB; SEQ ID NOs: 35, 59, and 41) were evaluated for anti-tumor activity in the CT26 tumor model. Tumors received intratumoral mRNA injections on days 13, 15, 18, 20 and 22 after tumor inoculation. As shown in FIG. 3, intratumoral injection of either the IL-2 mixture (FIG. 3A) or IL-15 sushi mixture (FIG. 3B) resulted in tumor regression in 5 out of 10 or 11 tumor-bearing animals, respectively (FIGS. 3A and B), whereas in the control group injected with luciferase mRNA (ModB) no tumor regression was observed (FIG. 3C).

Figure 4A:
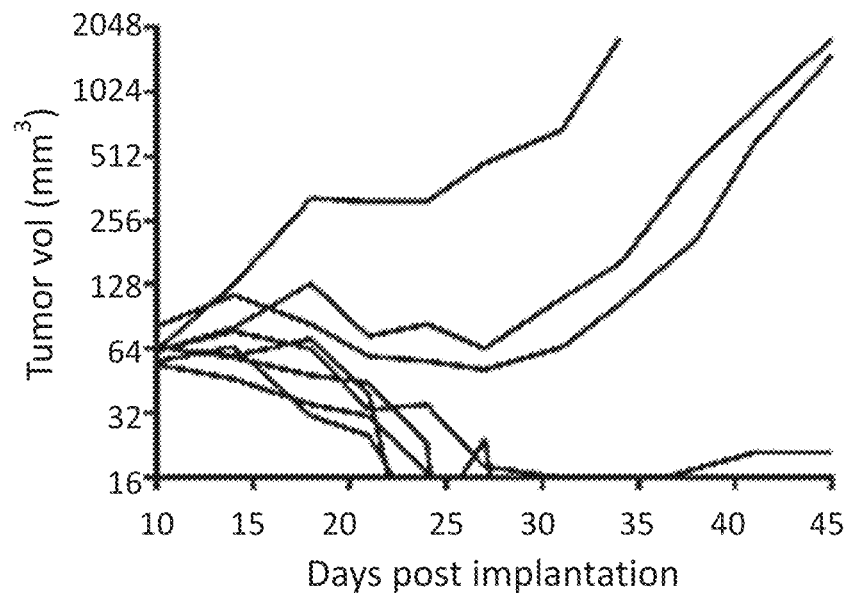
Figure 4B:
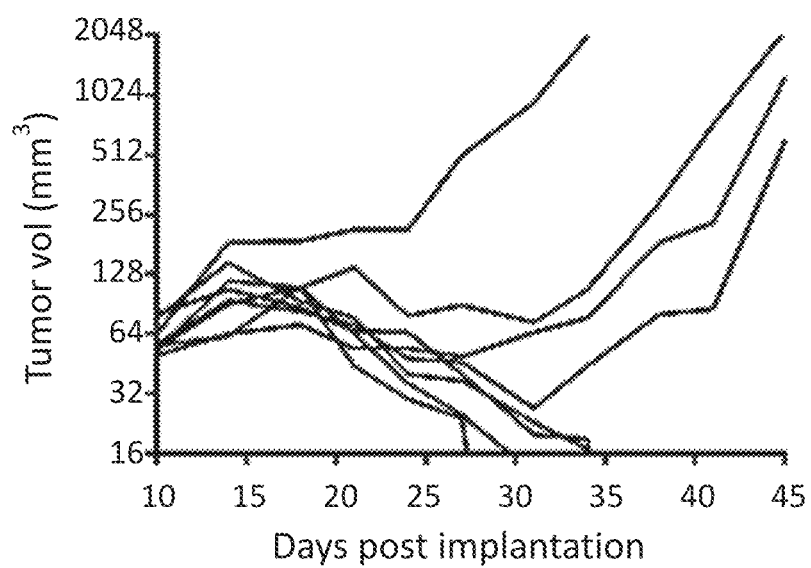
Figure 4C:
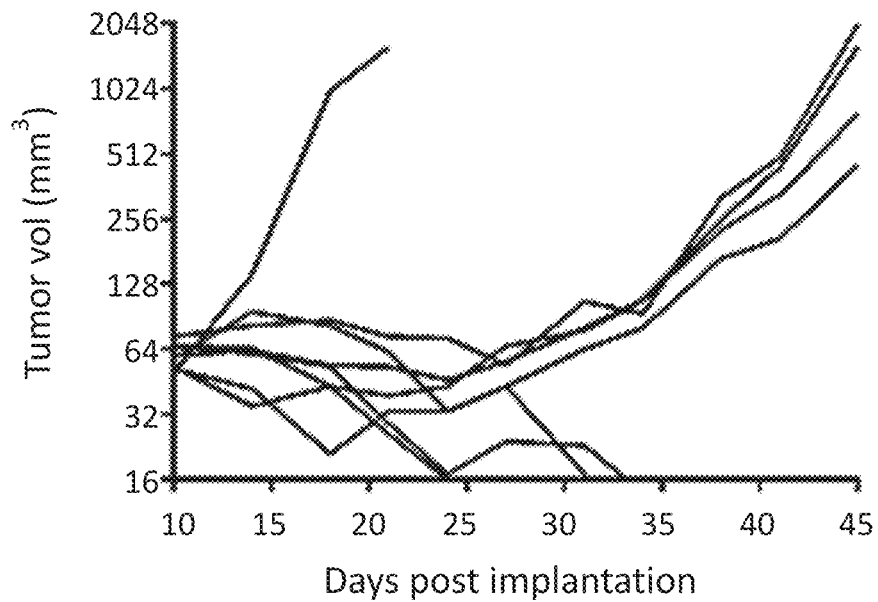
Figure 4D:
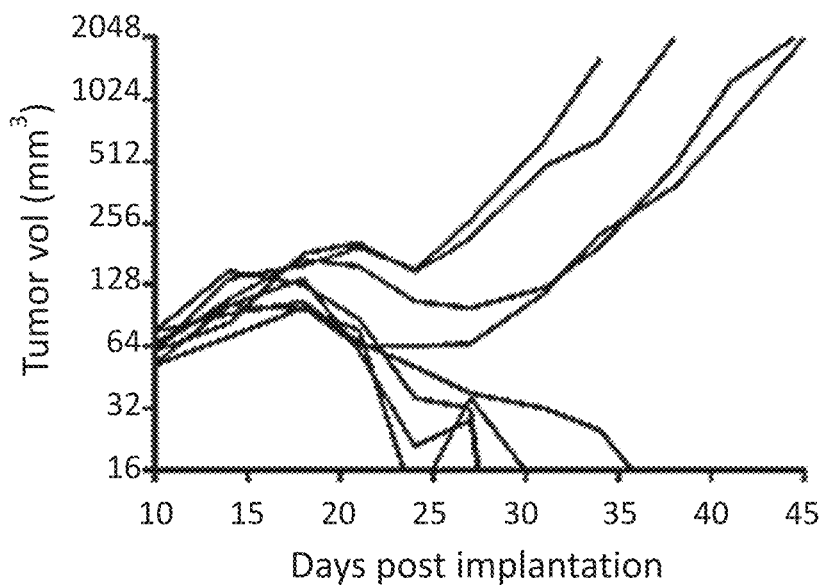
Figure 4E:
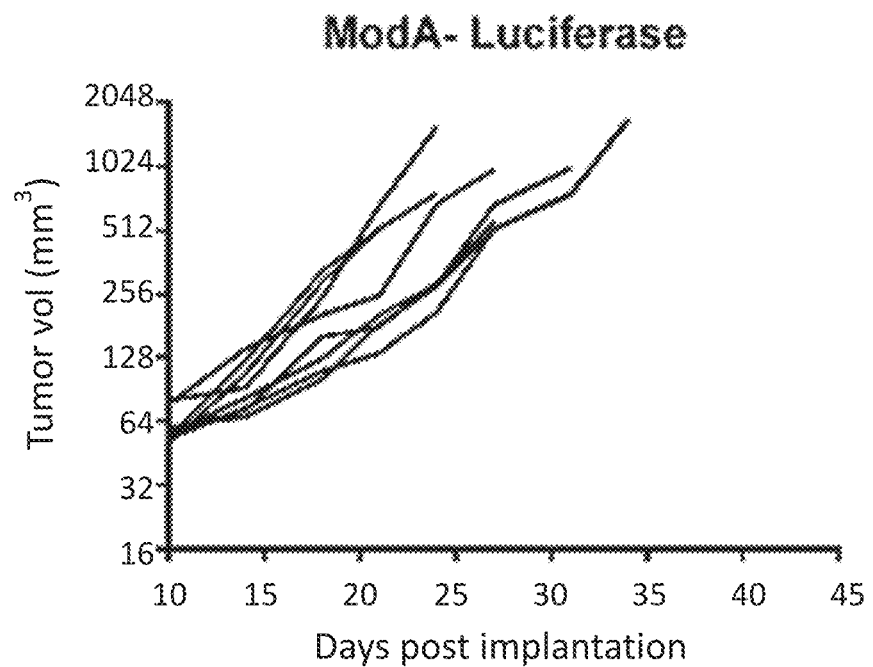
Figure 4F:
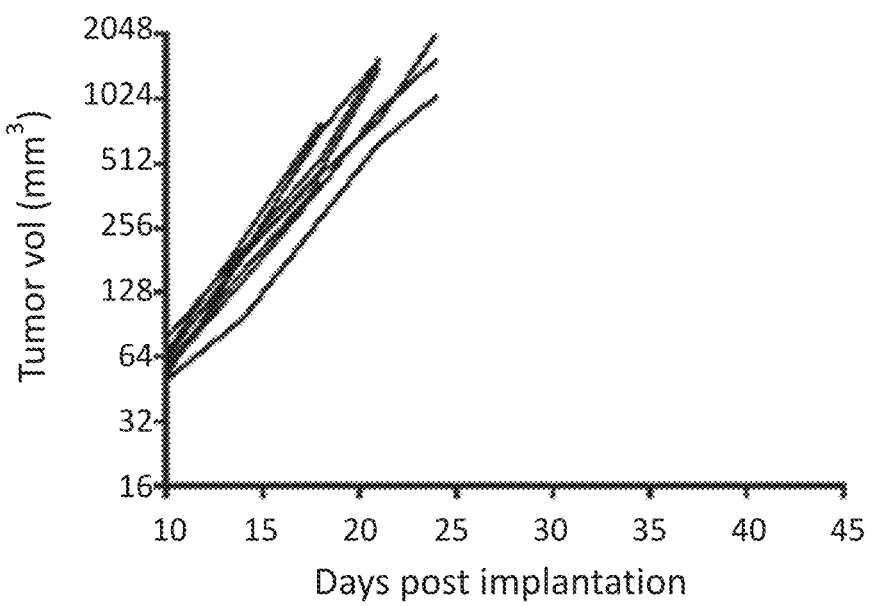

Anti-tumor activity of the mRNA mixture of IL-2, IL-12sc, and GM-CSF (FIG. 4A-ModA [SEQ ID NOs: 32, 38, and 56], 4B-ModB [SEQ ID NOs: 35, 41, and 59]), or IL-15 sushi, IL-12sc, and GM-CSF or (FIG. 4C-ModA [SEQ ID NOs: 50, 38, and 56], 4D-ModB [SEQ ID NOs: 53, 41, and 59) was further evaluated in the B16F10 tumor model. Mice with B16F10 tumors were injected intratumorally with mRNA on days 11, 13, 15, and 17. Treatment of B16F10 tumors with the cytokine mRNA mixture that encoded IL-15 sushi, IL-12sc, GM-CSF resulted in tumor regression in 3 and 4 of 8 mice in ModA and ModB, respectively. Tumors treated with an mRNA mixture of IL-2, IL-12sc, and GM-CSF (ModA or ModB) had tumor regression in 4 out of 8 mice, while no tumor regression was noted for mice treated with ModA or ModB mRNA encoding luciferase (FIG. 4E-ModA, FIG. 4F-ModB).

Example 3—Combinations of Four mRNAs Reduce Tumor Volume In Vivo

Figure 5A:
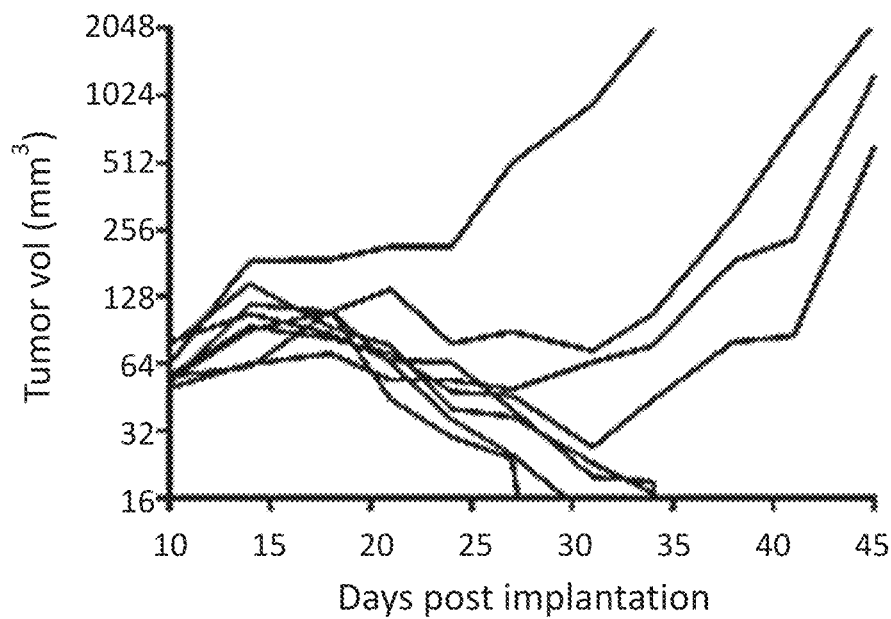
Figure 5B:
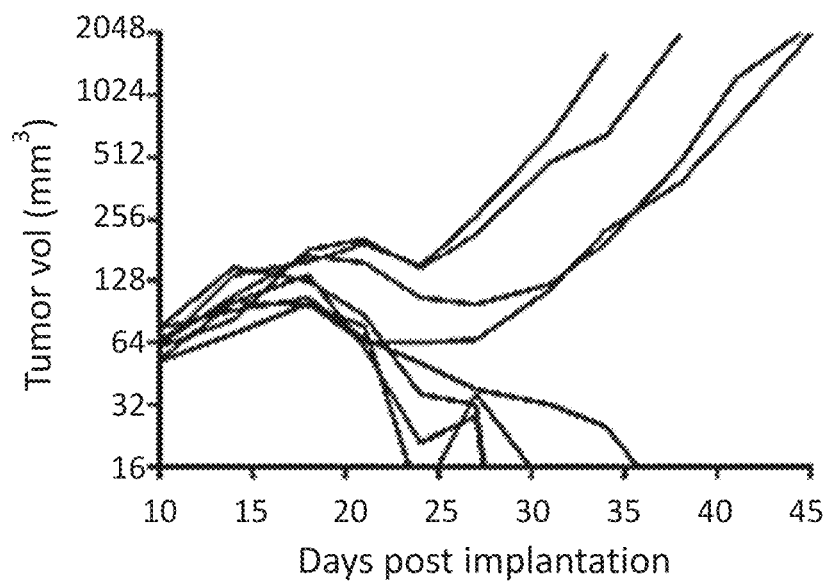
Figure 5C:
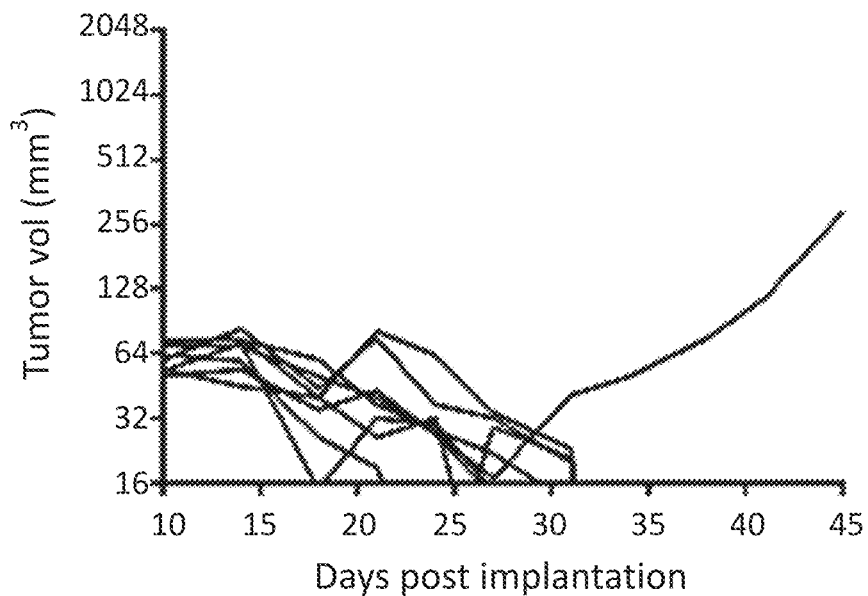
Figure 5D:
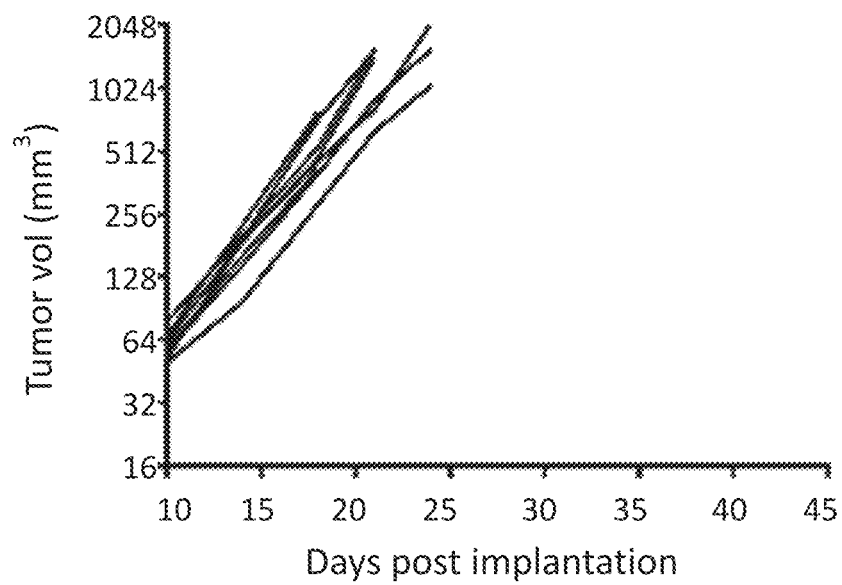

We next tested the effect of adding a fourth mRNA to the cytokine mRNA mixture. B16F10 tumor bearing mice received four intratumoral injections of ModB cytokine mRNA mixture encoding: i) GM-CSF, IL-2, IL-12sc (SEQ ID NOs: 59, 35, and 41; FIG. 5A), ii) GM-CSF, IL-15 sushi, IL-12sc (SEQ ID NOs: 59, 53, and 41; FIG. 5B) and iii) GM-CSF, IL-15 sushi, IL-12sc, IFNα (SEQ ID NOs: 59, 53, 41, and 47; FIG. 5C), and tumor growth was monitored to day 45. Each of the cytokine mRNA mixtures had an anti-tumor effect with 4 out of 8 tumors regressing following intratumoral injection of cytokine mRNA mixtures of GM-CSF, IL-2, and IL-12sc or GM-CSF, IL-15 sushi, and IL-12sc, and 7 out of 8 tumors regressed upon treatment with GM-CSF, IL-15 sushi, IL-12sc, and IFNα. Mice treated with control mRNA (ModB) exhibited no tumor regression (FIG. 5D).

Figure 6A:
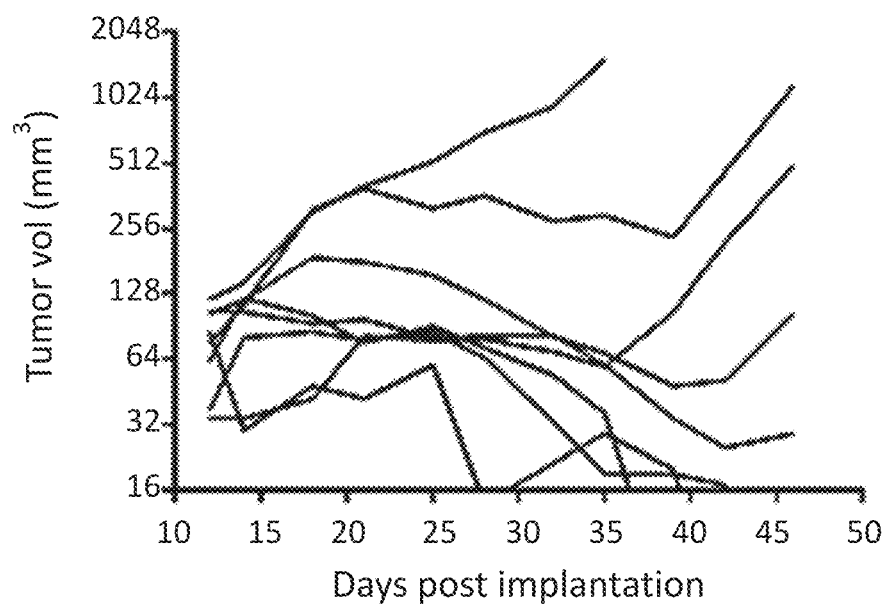
Figure 6B:
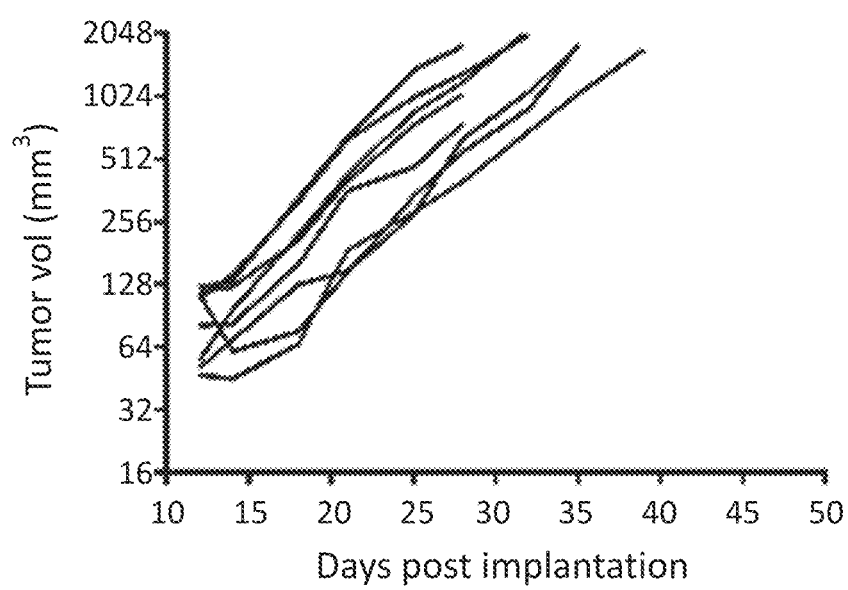
Figure 6C:
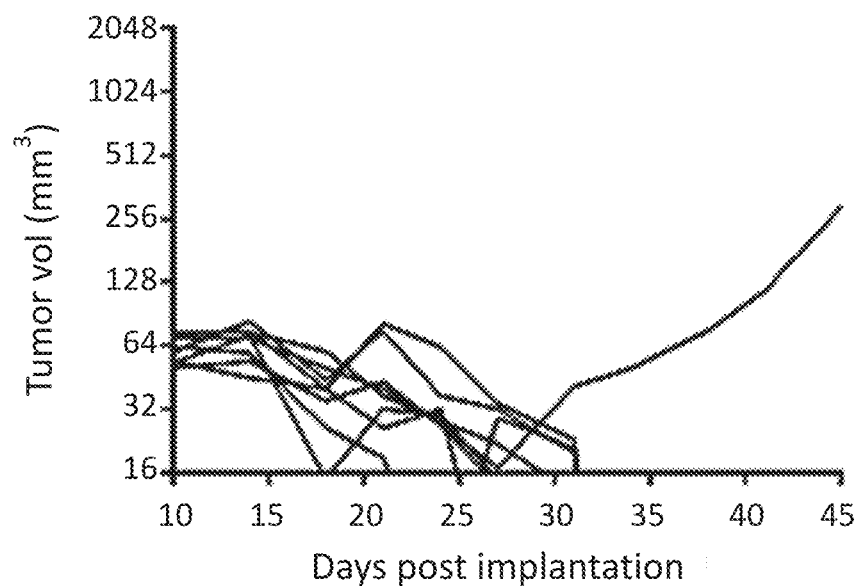
Figure 6D:
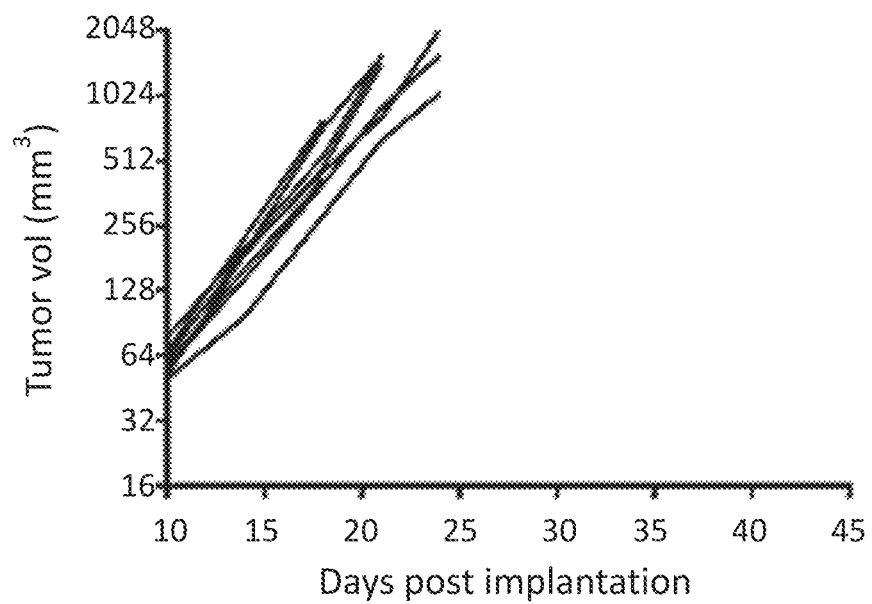
Figure 6E:
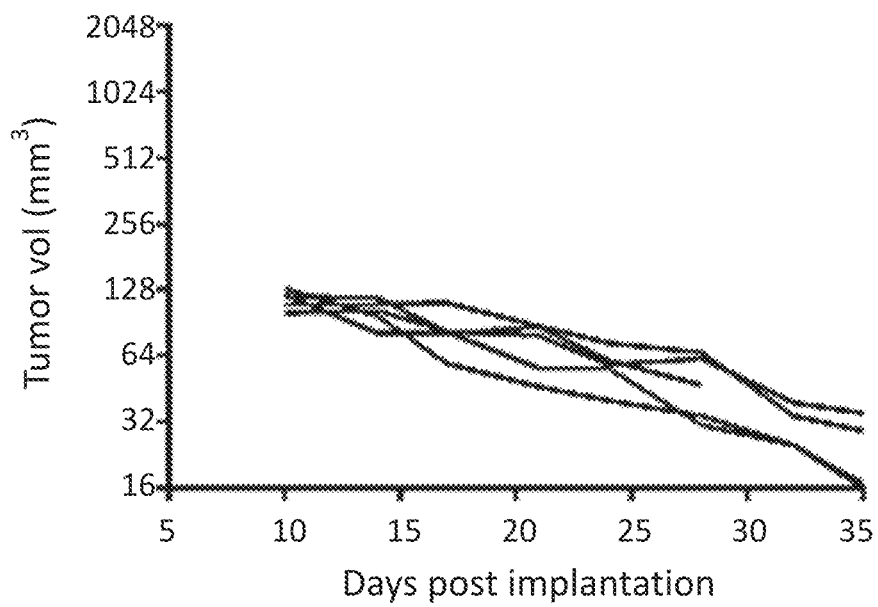
Figure 6F:
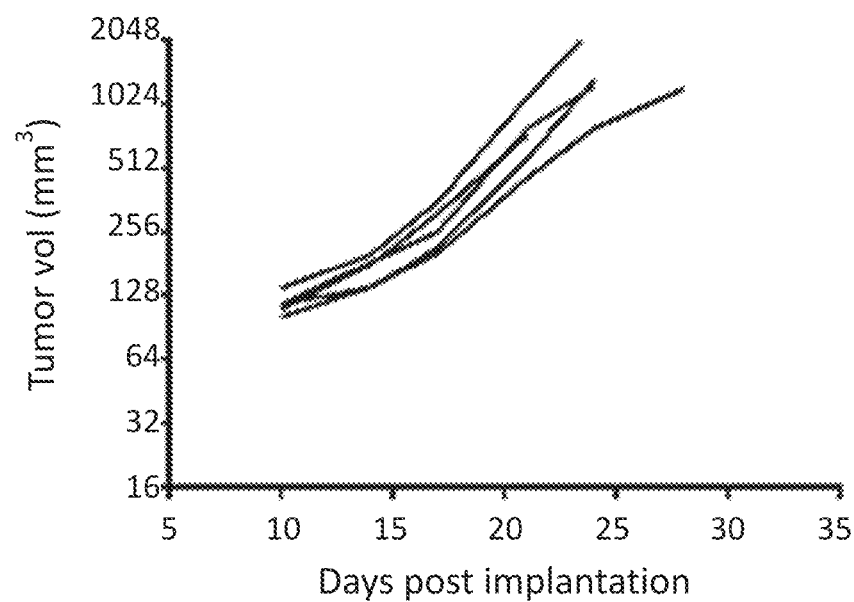

The anti-tumor activity of GM-CSF, IL-2, IL-12sc, and IFNα was examined in three different murine in vivo tumor models, CT26, B16F10 and MC38. Tumor bearing mice received 4-6 intratumoral injections of ModB cytokine mRNA encoding IL-2, IL-12sc, GM-CSF and IFNα (SEQ ID NOs: 35, 41, 59, and 47) or a control ModB mRNA encoding firefly luciferase. Anti-tumor activity was assessed in each tumor model. Mice treated with this combination of cytokine mRNA had 4/8, 7/8 and 5/5 regressing tumors in the CT26 (FIG. 6A), B16F10 (FIG. 6C) and MC38 (FIG. 6E) models, respectively. No tumor regression was observed in the comparator tumor bearing mice treated with luciferase mRNA (FIGS. 6B [CT26], 6D [B16F10], and 6F [MC38]).

Figure 7A:
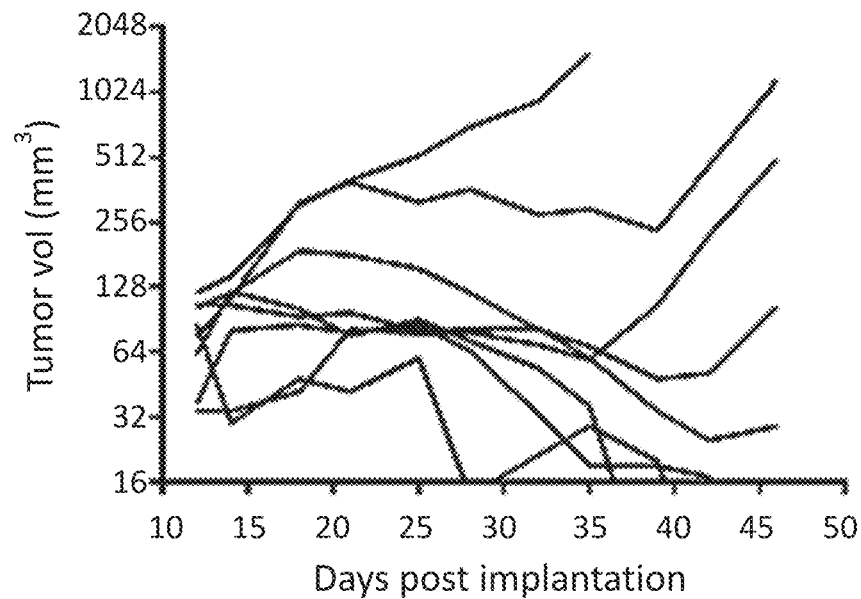
Figure 7B:
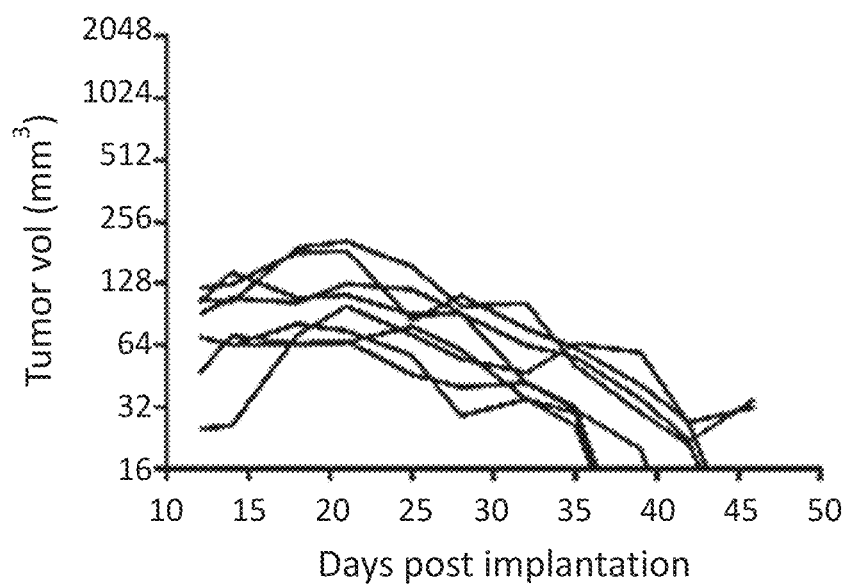
Figure 7C:
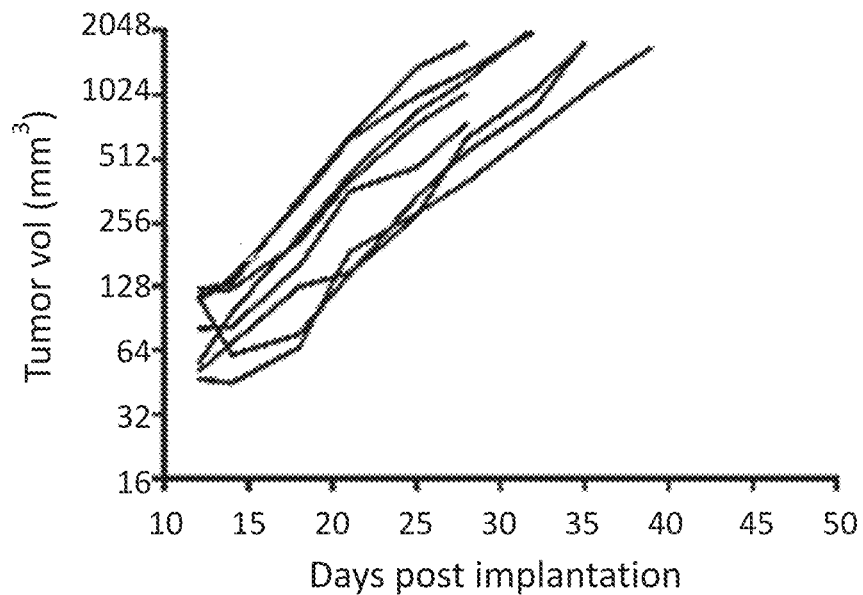
Figure 7D:
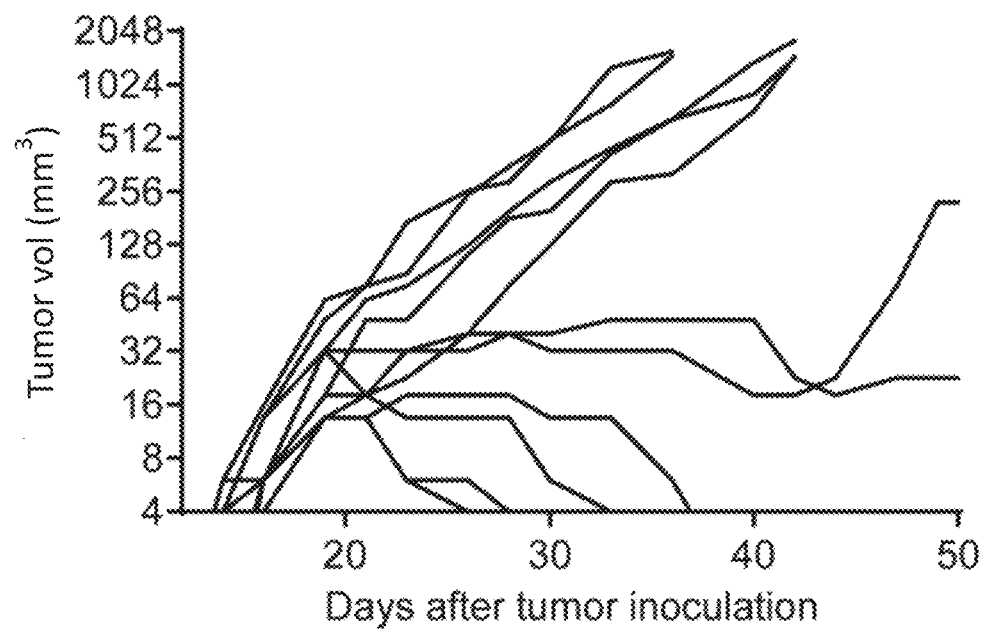
Figure 7E:
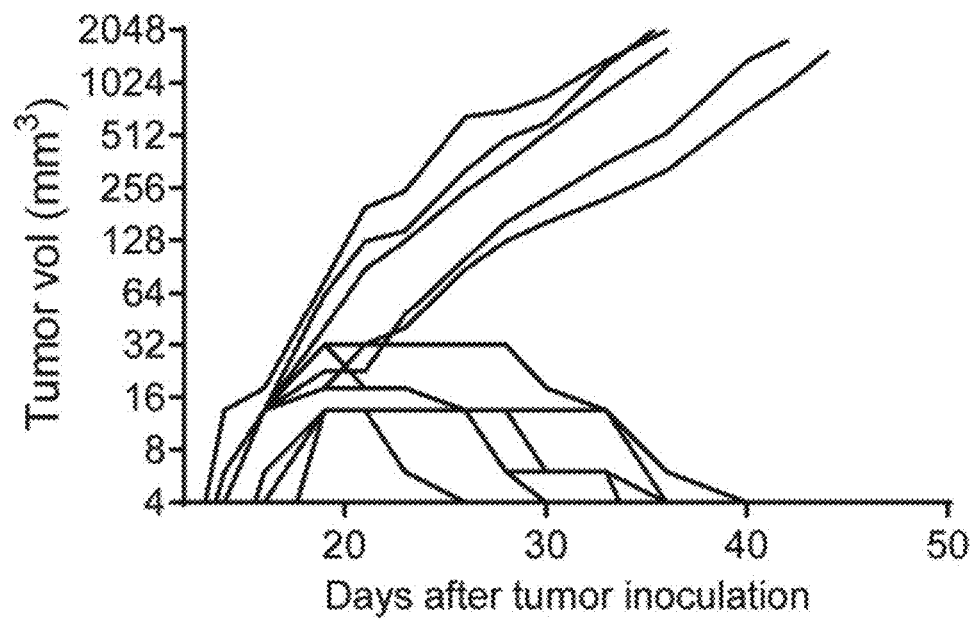
Figure 7F:
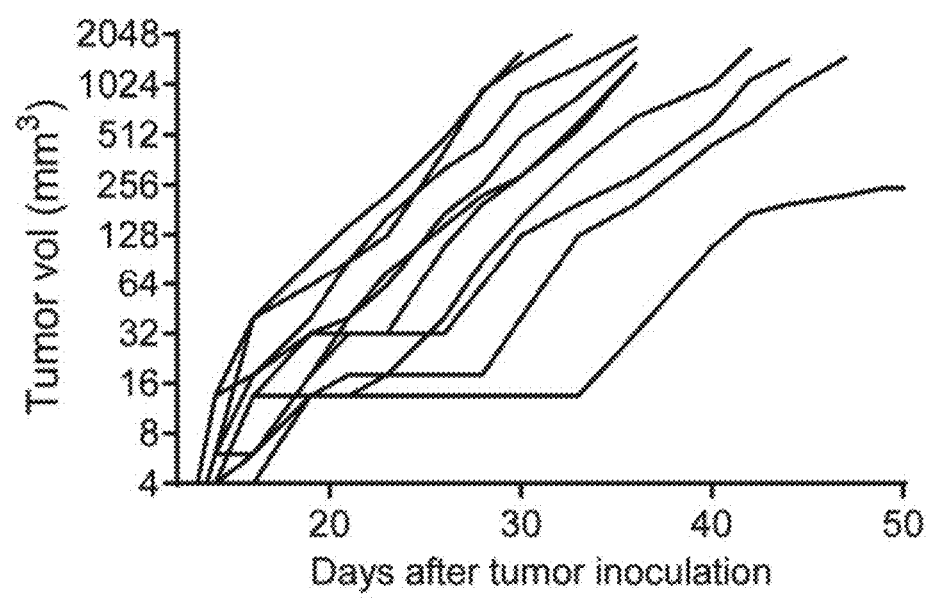

The anti-tumor activity of a four-component cytokine mRNA mixture encoding each of IL-2, IL-12sc, GM-CSF and IFNα (ModB, SEQ ID NOs: 35, 41, 59, and 47) or IL-15 sushi, IL-12sc, GM-CSF and IFNα (ModB, SEQ ID NOs: 53, 41, 59, and 47) was evaluated in the CT26 tumor model. Tumor bearing mice were treated with 6 intratumoral injections and tumor growth was monitored. Treatment with both IL-2, IL-12sc, GM-CSF and IFNα (FIG. 7A) and IL-15 sushi, IL-12sc, GM-CSF and IFNα (FIG. 7B) effectively induced tumor regression in 4/8 and 8/8 mice, respectively, while no tumor regressions were observed for mice treated with the control mRNA (FIG. 7C). These data were confirmed in a repeat study of similar design (FIG. 7D-F).

Figure 8A:
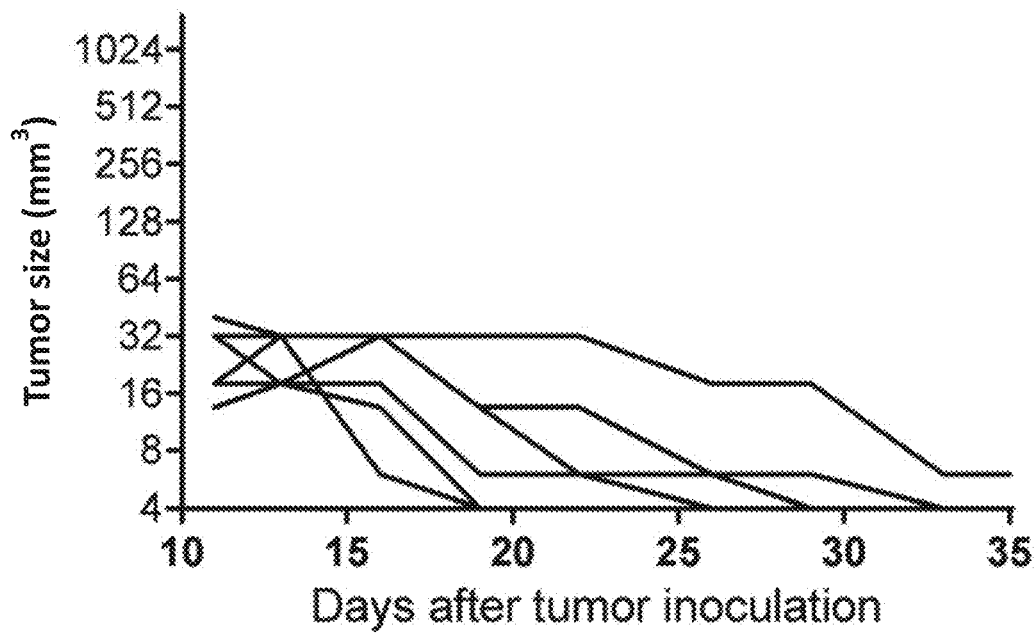
Figure 8B:
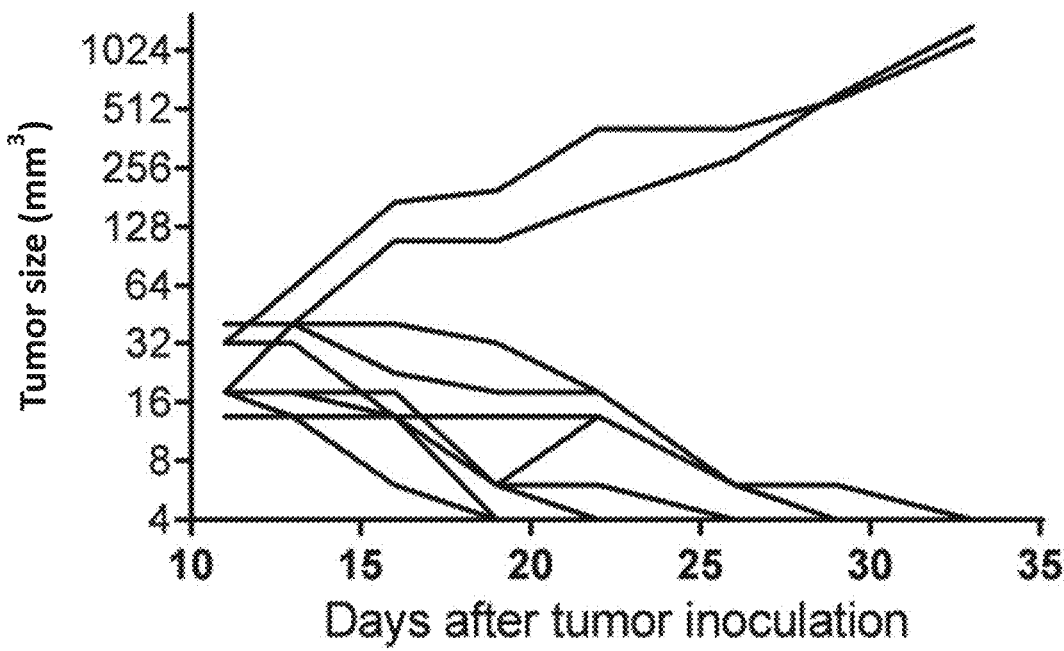
Figure 8C:
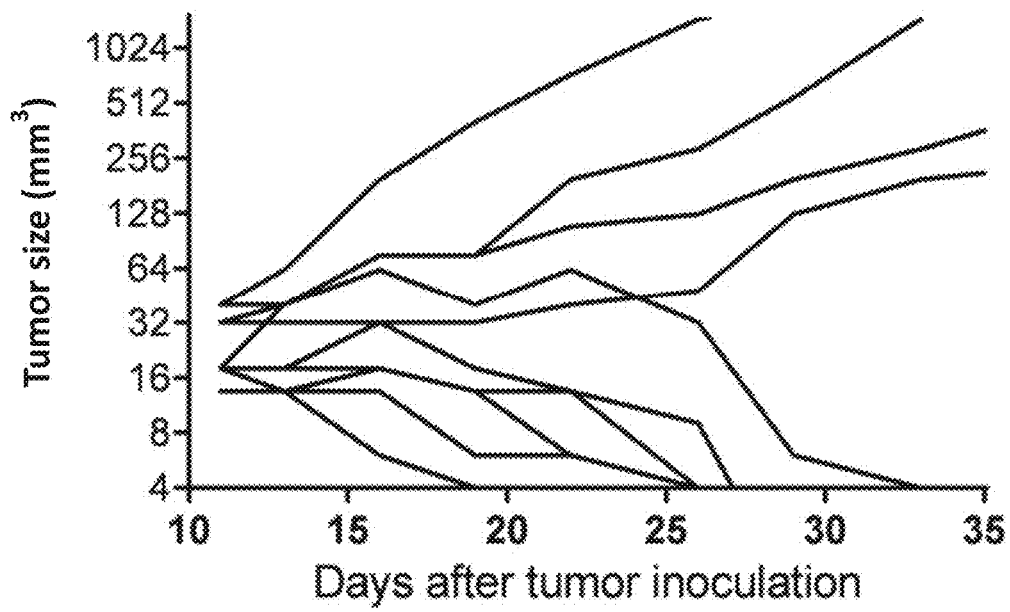
Figure 8D:
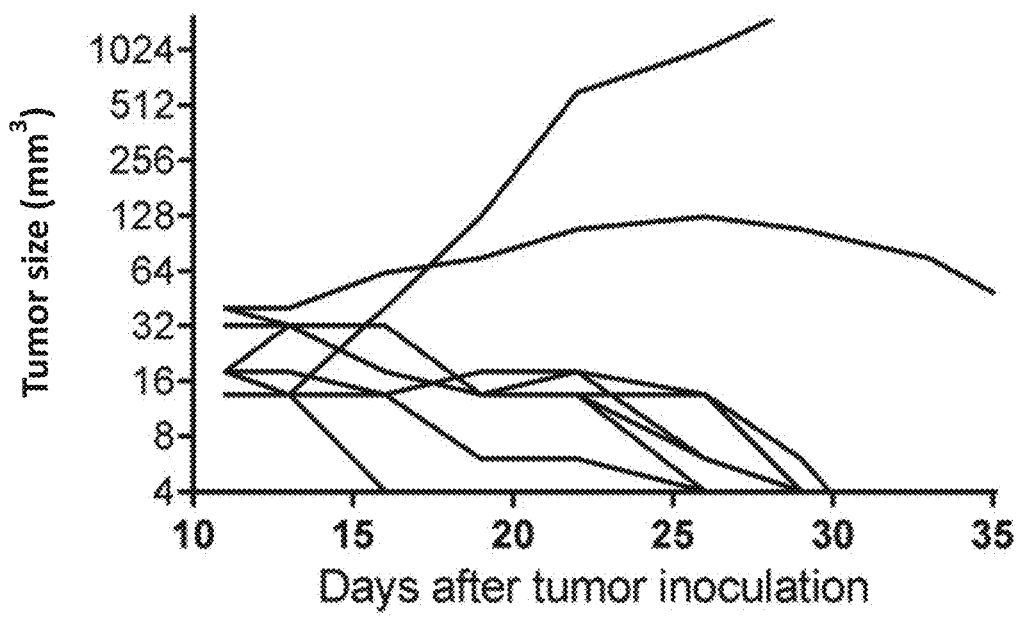
Figure 8E:
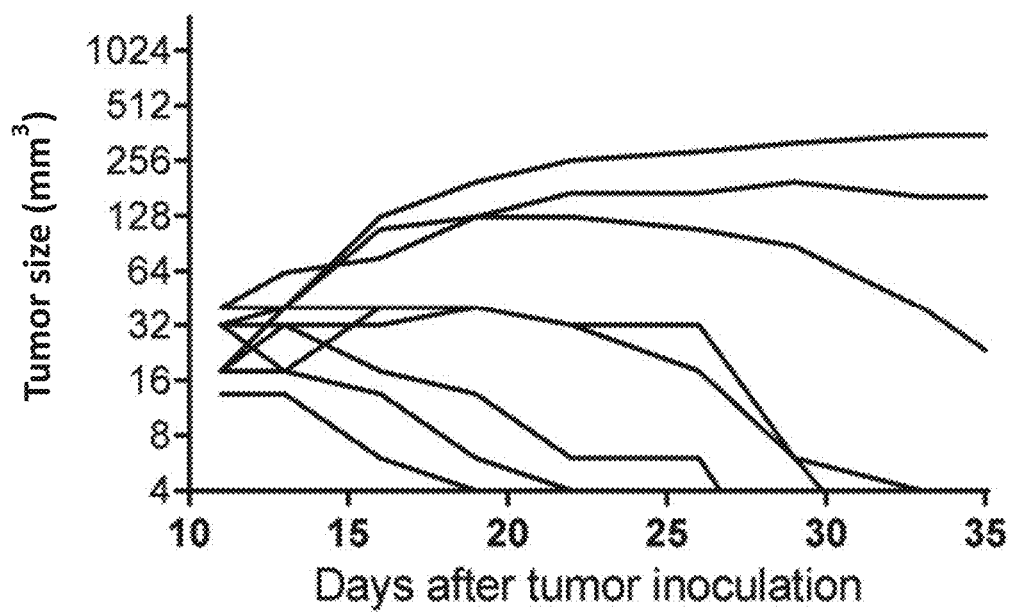
Figure 8F:
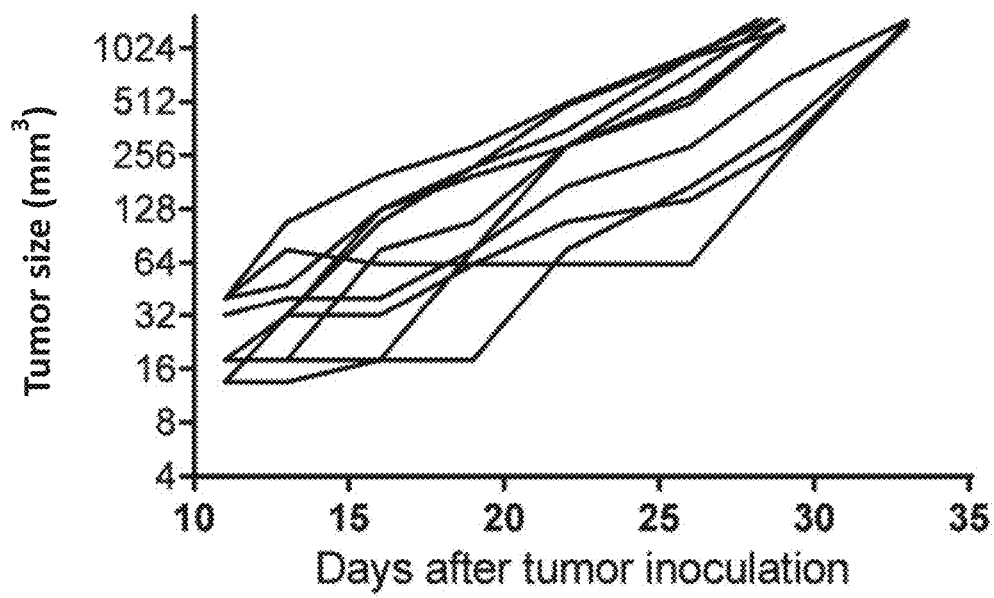
Figure 8G:
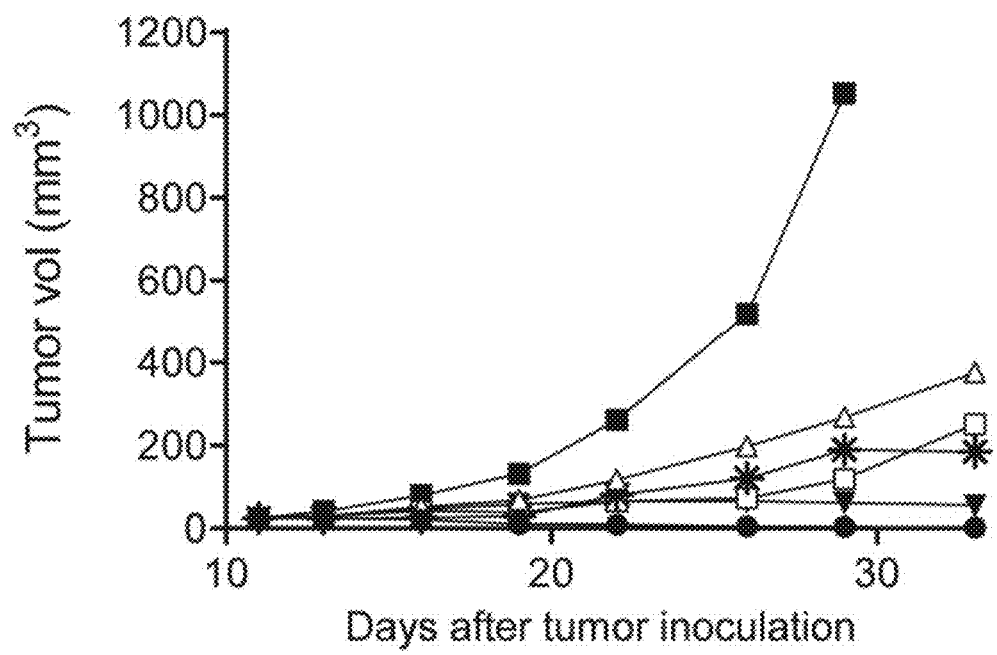
Figure 8H:
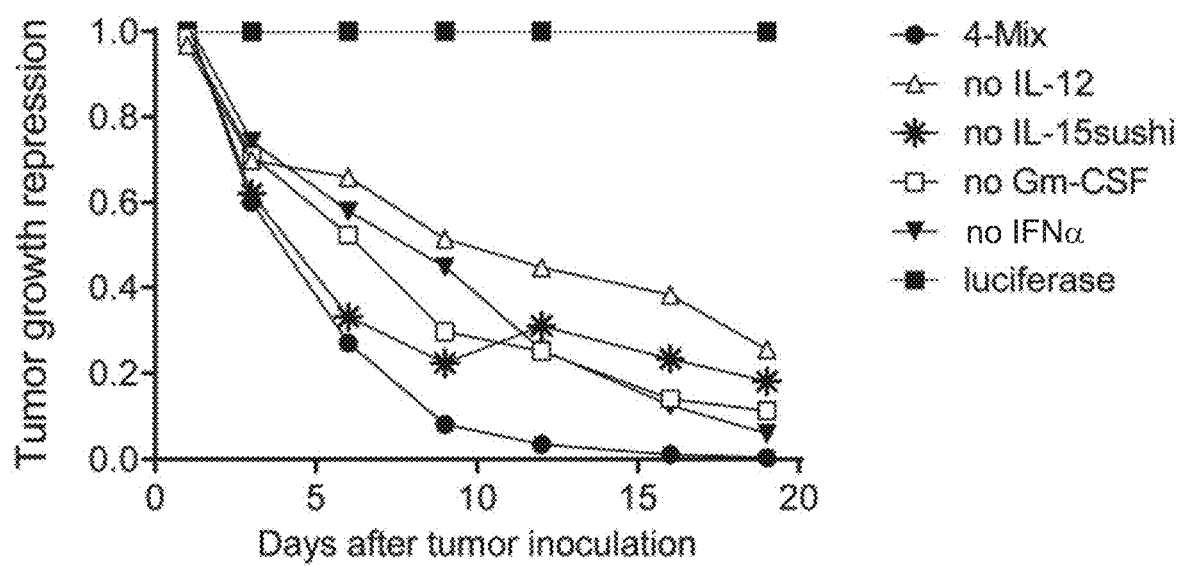

A study in CT26 tumor model was conducted in which individual components were systematically removed from the mRNA mixture of IL-15 sushi, IL-12sc, GM-CSF and IFNα (ModB, SEQ ID NOs: 53, 41, 59, and 47). CT26 tumors were injected with cytokine mRNA on days 12, 15, 19 and 22 after inoculation. Tumors treated with four injections of mRNA encoding IL-15 sushi, IL-12sc, GM-CSF and IFNα induced regression in all 10 treated tumors (FIG. 8A). Tumors treated with the ModB mRNA mixtures of i) IL-15 sushi, IL-12sc and IFNα, ii) IL-15 sushi, GM-CSF and IFNα, iii) IL-12sc, GM-CSF and IFNα, iv) IL-15 sushi, IL-12sc, and GM-CSF resulted in regression of 8, 6, 8, 7 out of 10 tumors, respectively (FIG. 8B-E). No tumors treated with control mRNA (ModB) displayed tumor regression (FIG. 8F). To analyze tumor growth kinetics, mean tumor volumes were calculated for each treatment group up to day 33 (FIG. 8G). The smallest mean tumor volume was observed for mice treated with the mixture of IL-15 sushi, IL-12sc, GM-CSF and IFNα, while the largest mean tumor volume was observed in the luciferase treated animals. Tumor growth repression T/C (Tumor/Control based on mean tumor volume) was plotted to day 19 (FIG. 8H) for each of the treatment groups. The four-component mixture of IL-15 sushi, IL-12sc, GM-CSF and IFNα exhibited the largest T/C.

Figure 9A:
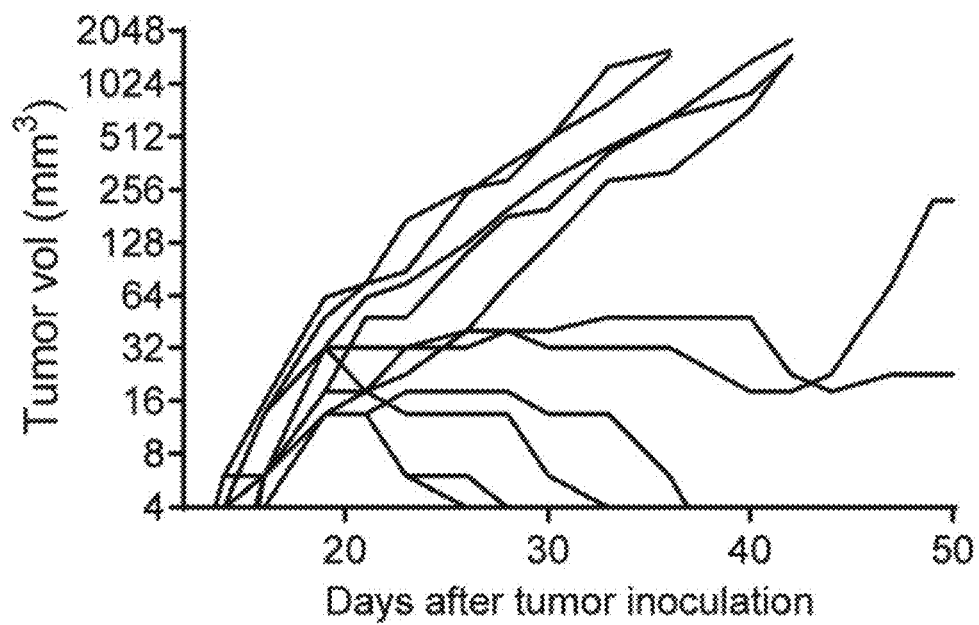
Figure 9B:
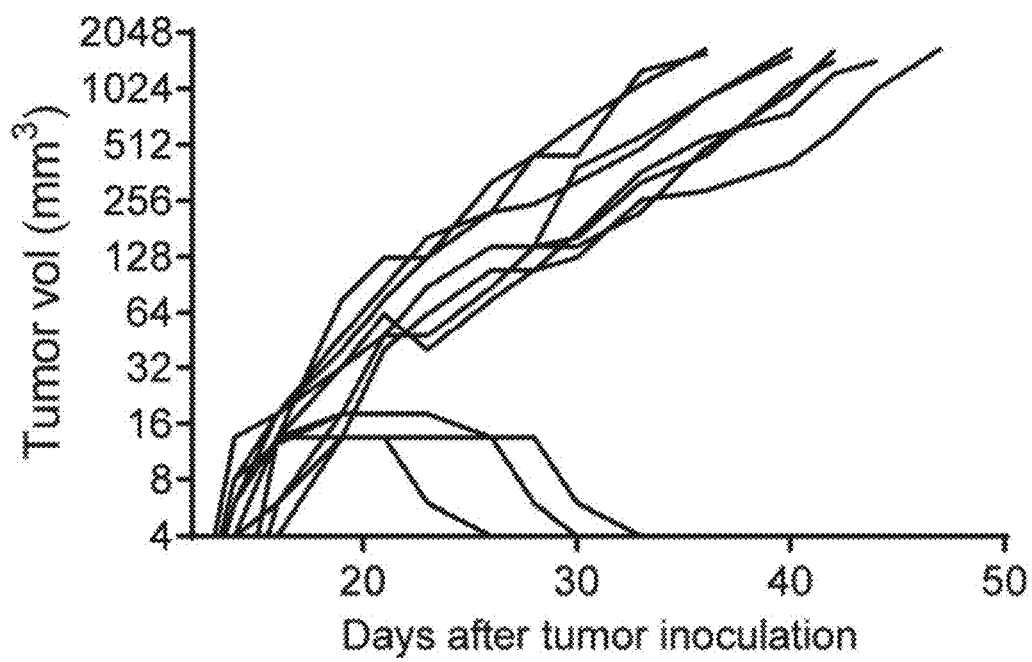
Figure 9C:
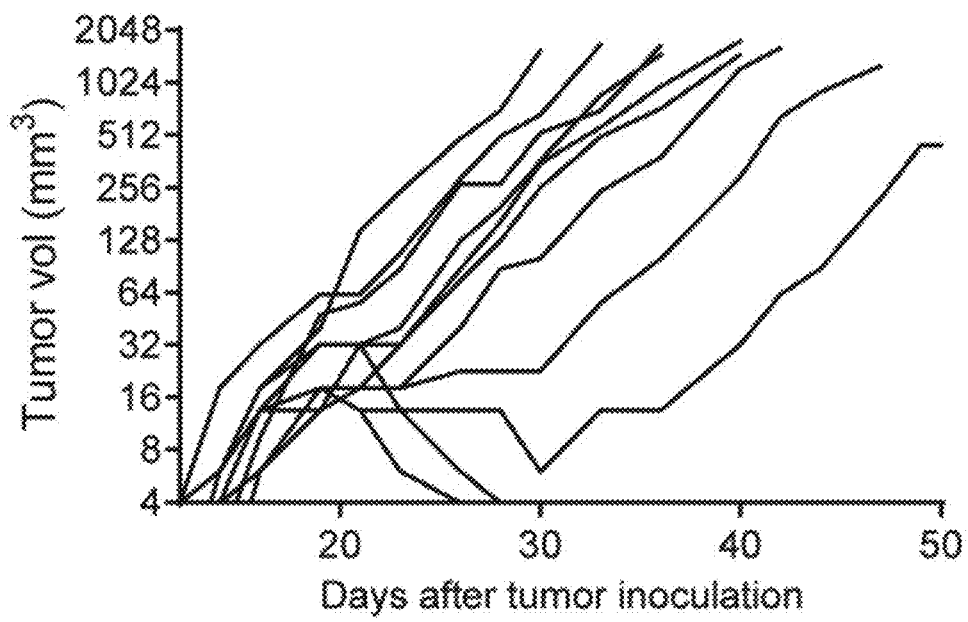
Figure 9D:
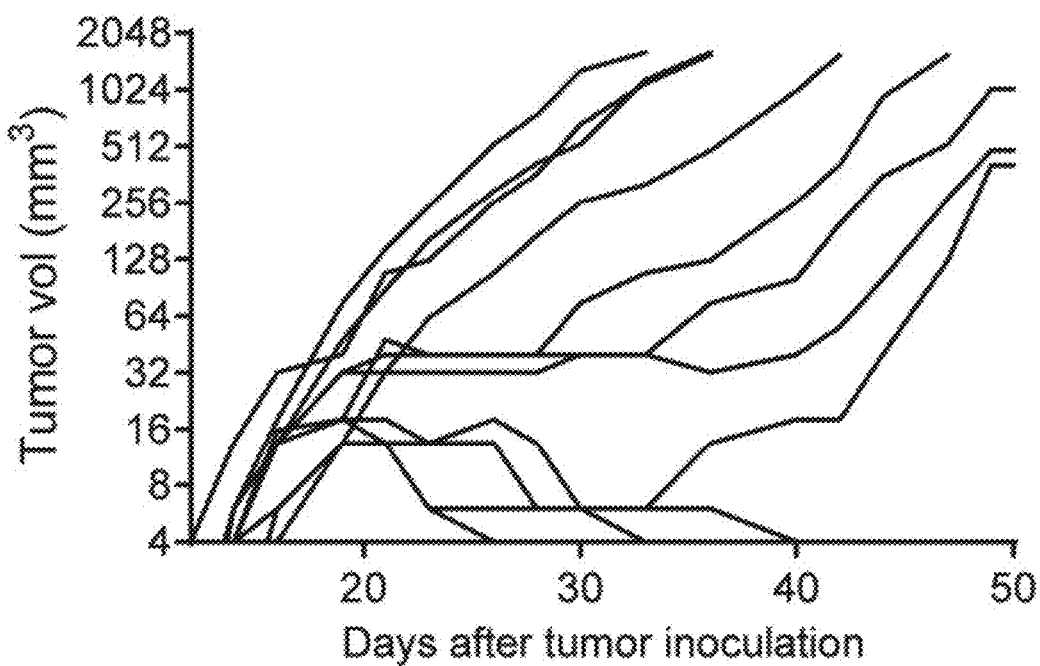
Figure 9E:
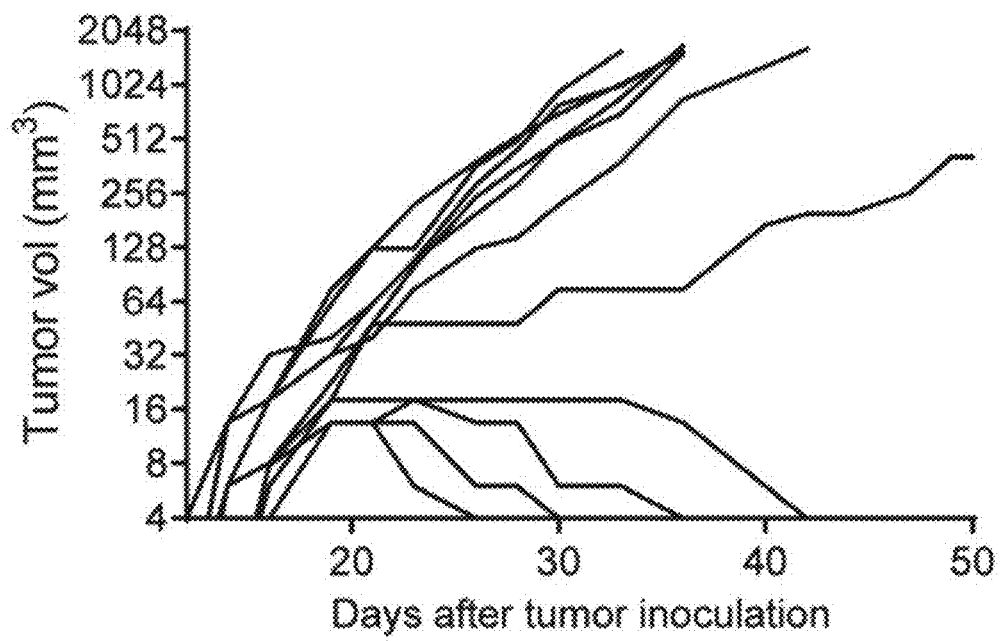
Figure 9F:
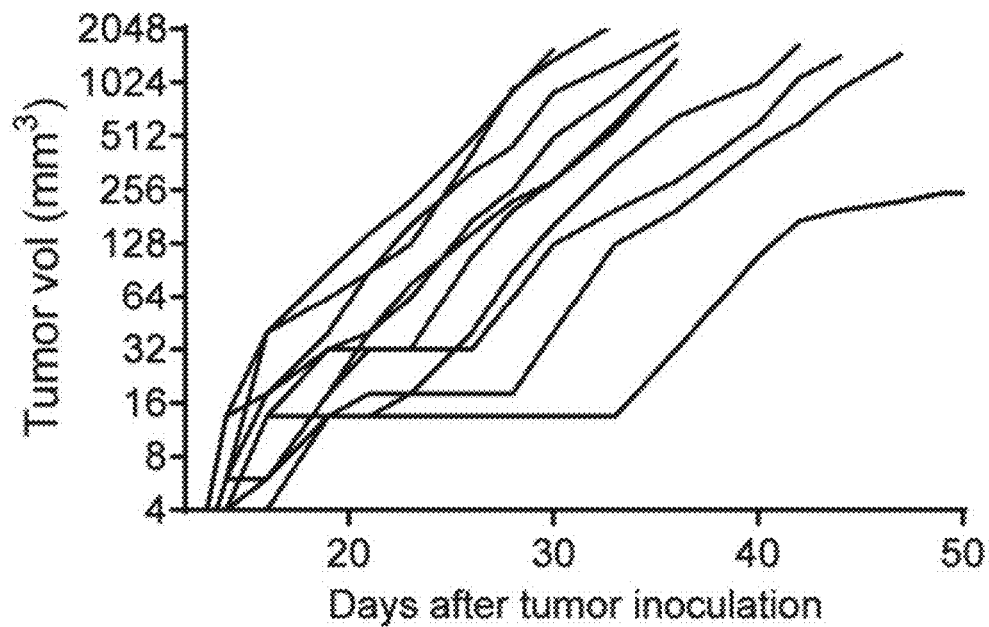

Analogous to the study shown in FIG. 8, a study was conducted in which individual components were systematically removed from the mRNA mixture of IL-2, IL-12sc, GM-CSF and IFNα (ModB; SEQ ID NOs: 35, 41, 59, and 47). CT26 tumors received 6 intratumoral mRNA injections on days 19, 21, 23, 26, 28 and 30. Treatment with the cytokine mRNA mixture of IL-2, IL-12sc, GM-CSF and IFNα resulted in tumor regression in 4 of 10 animals led to complete tumor regression in 4 animals and stable disease beyond day 40 in two individuals (FIG. 9A). Tumors treated with the ModB 3-component mRNA mixtures of i) IL-2, IL-12sc, and IFNα, ii) IL-2, GM-CSF and IFNα, iii) IL-12sc, GM-CSF and IFNα, and iv) IL-12sc, GM-CSF and IL-2 resulted in regression of 2, 3, 3 and 4 tumors, respectively (FIG. 9B-E) and CT26 tumors treated with a control luciferase mRNA displayed no tumor regression (FIG. 9F).

Figure 10A:
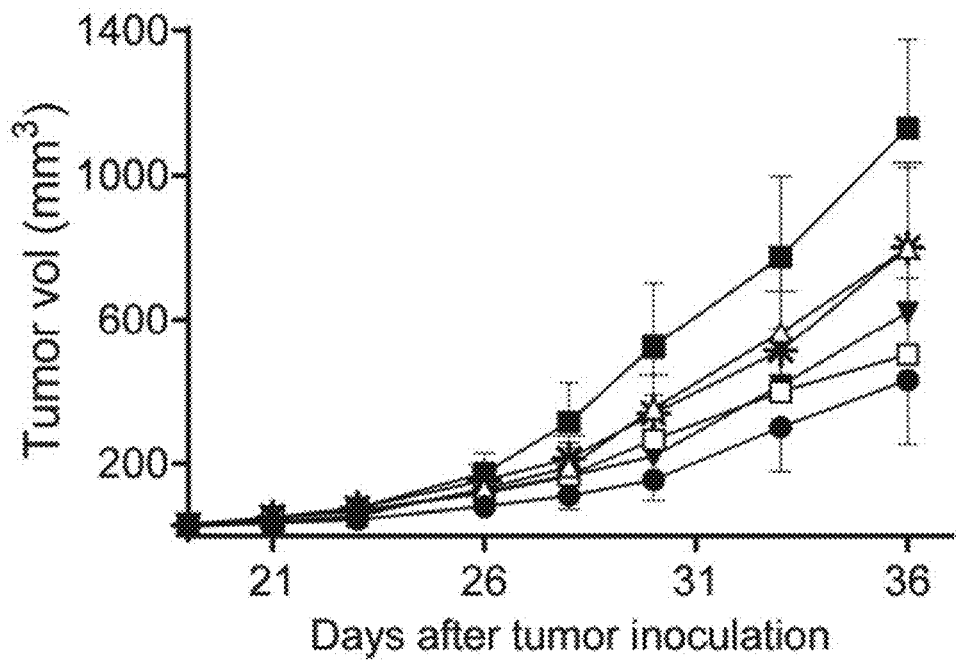
Figure 10B:
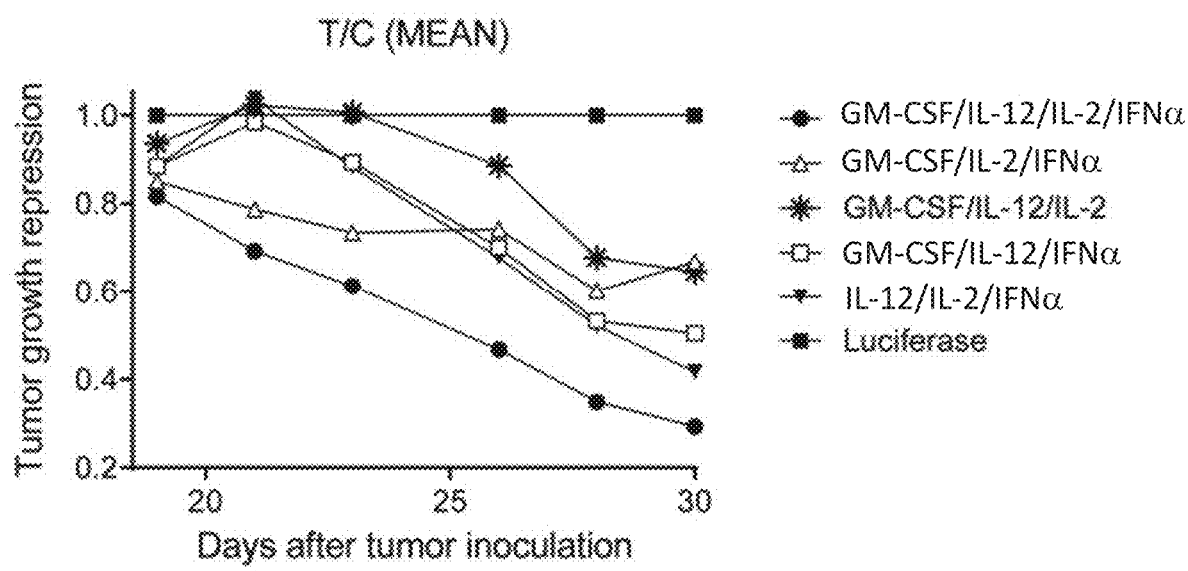

To analyze tumor growth kinetics, mean tumor volumes were calculated for each treatment group up to day 36. The smallest mean tumor volume was observed for mice treated with the mixture of IL-2, IL-12sc, GM-CSF and IFNα, while the largest mean tumor volume was observed in the luciferase treated animals (FIG. 10 A). Tumor growth repression T/C (Tumor/Control based on mean tumor volume) was plotted to day 30 (FIG. 10B) for each of the treatment groups. The four-component mixture of IL-2, IL-12sc, GM-CSF and IFNα exhibited the largest T/C.

Figure 11:
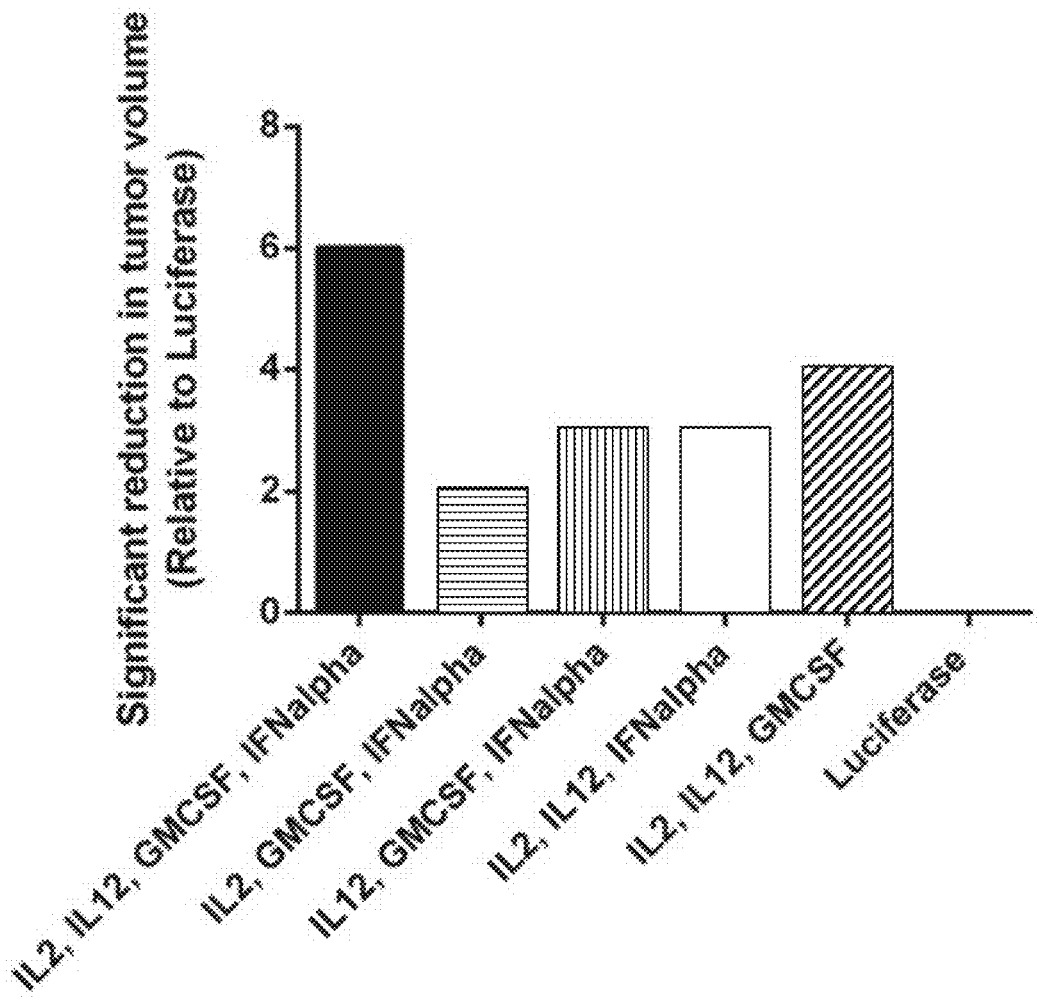

The anti-tumor response from the different cytokine mRNA mixtures in FIG. 9 were further analyzed as follows: The tumor volume change ($\Delta V$) as defined by the difference in tumor volume between the measurement at the end of experiment or termination ($V_t$) and the measurement at the beginning of the experiment ($V_b$) ($\Delta V = V_t - V_b$), was calculated for all mice in each of the six treatment groups, including mice treated with 4 component cytokine mRNA mixture (IL-2, IL-12sc, GM-CSF and IFNα), mice treated with 3 component mixture missing one of the four cytokines and mice treated with control luciferase mRNA. Mean ($\mu$) and standard deviation ($\sigma$) of a trimmed data (removing top and bottom 10% of the original data) on tumor volume change was calculated for control luciferase group and the Shapiro-Wilk normality test of this trimmed data showed it approximately followed a normal distribution. A Z score ($Z=(\Delta V-\mu)/\sigma$) was then calculated for tumor volume change data in each individual mouse from all treatment groups. A ratio (R) between each tumor volume change value and the trimmed mean of control group was calculated ($R=\Delta V/\mu$). Given the definitions, we consider the Z score as "significance of tumor volume reduction" and R as "extent of tumor volume reduction". To identify a mouse that shows a significantly smaller tumor volume increase than that in control luciferase group (in other words "significant tumor reduction" as compared with control group), a cutoff of $Z<=-1.645$ ($p(Z<=-1.645)=0.05$) and $R<=0.15$ was applied. The results showed that the number of mice in each treatment group that has significantly smaller tumor volume increase than control group as follows: i) 6 out of 8 mice for the cytokine mRNA mixture of IL-2, IL-12sc, GM-CSF and IFNα (ModB). ii) 2 of 8 mice for IL-2, GM-CSF and IFNα (ModB), iii) 3 of 8 for IL-12sc, GM-CSF and IFNα and IL-2, IL-12sc, and IFNα and iv) 4 of 8 mice treated with the cytokine mRNA mixture of IL-2, IL-12sc, and GM-CSF (ModB) (FIG. 11).

Female C57BL/6J mice were implanted with B16F10 cells as described above. Mice were treated with 4 intratumoral injection (8 μg mRNA/2 μg per target) on days 11, 15, 19, and 23 with ModB cytokine mRNA mixture (IL-15 sushi, IL-12sc, GM-CSF, IFNα) or control luciferase mRNA. Treatment with the 4-component mixture of cytokine mRNA resulted in tumor rejection in 6/10 treated mice. See, FIG. 24B. In comparison, no tumor free mice were observed in any of the groups treated with a single mRNA (FIGS. 24C-F). The combination of IL-15 sushi, IL-12sc, GM-CSF, IFNα led to increased overall survival with 60% of the mice tumor free at Day 70, while all tumors of mice treated with a single cytokine mRNA progressing to the stage where the animals needed to be euthanized (FIG. 24G). Luciferase control is shown in FIG. 24A.

Example 4—Cytokine mRNA Protects Against Tumor Re-Challenge

Figure 12A:
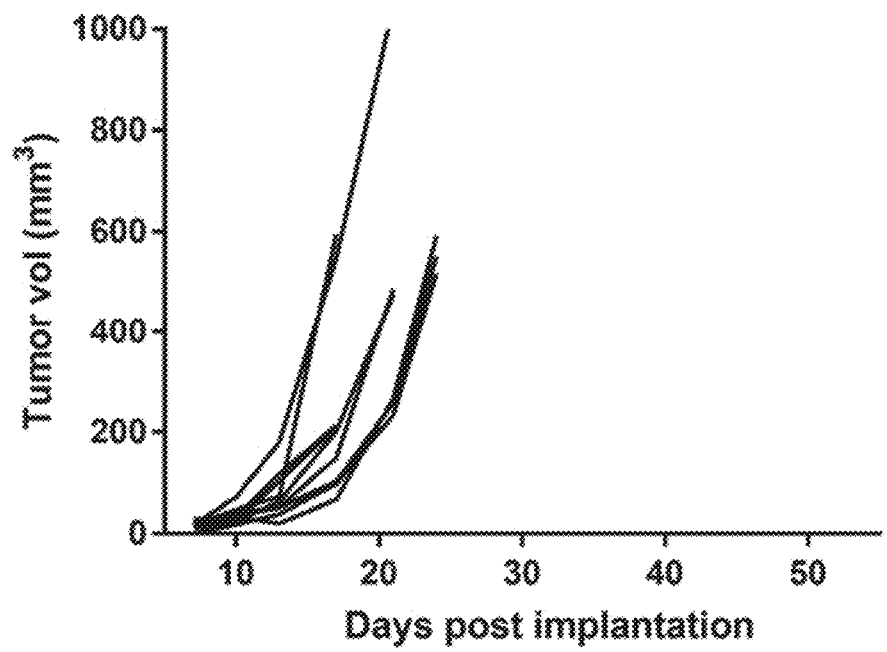
Figure 12B:
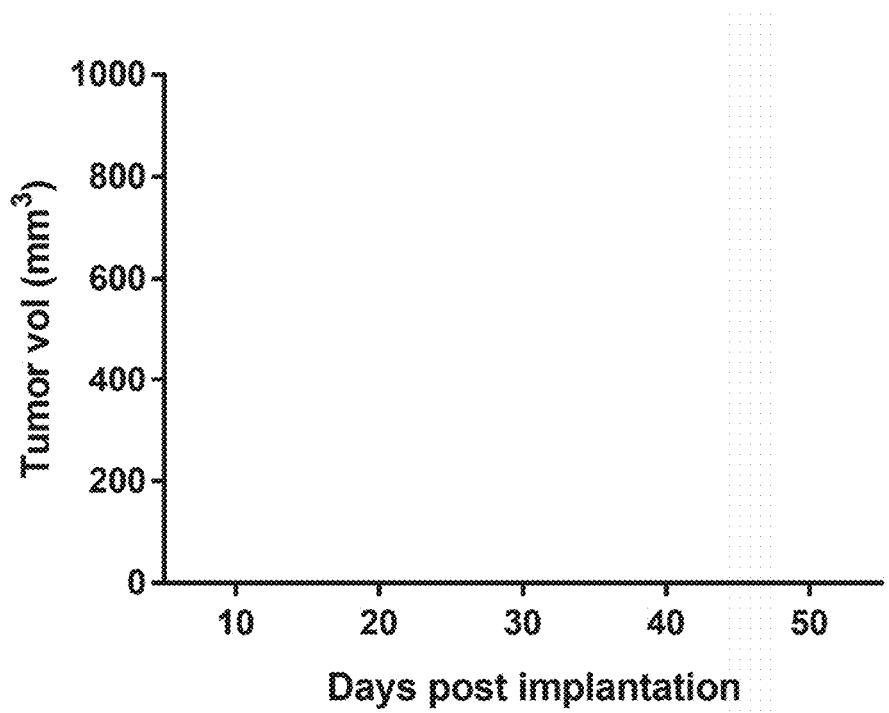
Figure 12C:
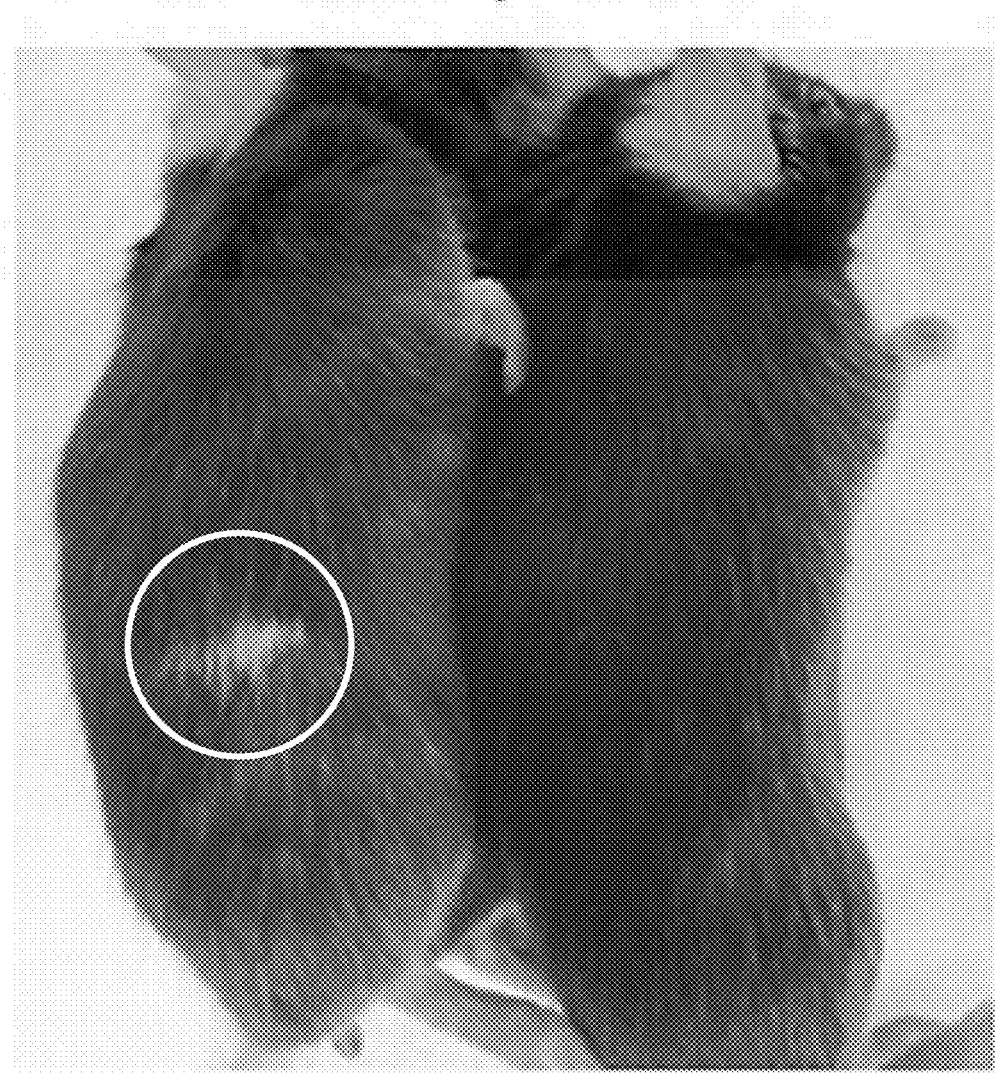

To evaluate the effect of the cytokine mRNA mixture on the development of immunological memory, re-challenge experiments were performed. Briefly, B16F10 tumor bearing mice were treated with a cytokine mRNA mixture of IL-15sushi, IL-12sc, GM-CSF, and IFNα (Mod B; SEQ ID NOs: 53, 41, 59, and 47). A portion of the cytokine mRNA treatment B16F10 tumors completely regressed leading to tumor free animals. These tumor free animals were then re-challenged with B16F10 cells as a way to assess adaptive immune memory and 9 naïve mice were implanted with B16F10 tumor cells as a positive control for tumor engraftment (FIG. 12A). All 9 naïve mice engrafted with B16F10 cells developed tumors, whereas all eight tumor-free mice rejected the B16F10 cells and did not exhibit growth of B16F10 tumors (FIG. 12B). A portion of mice previously treated with cytokine mRNA develop localized vitiligo at the original site of the tumor (FIG. 12C). This experiment was essentially repeated and results are shown in FIG. 33.

Figure 12D:
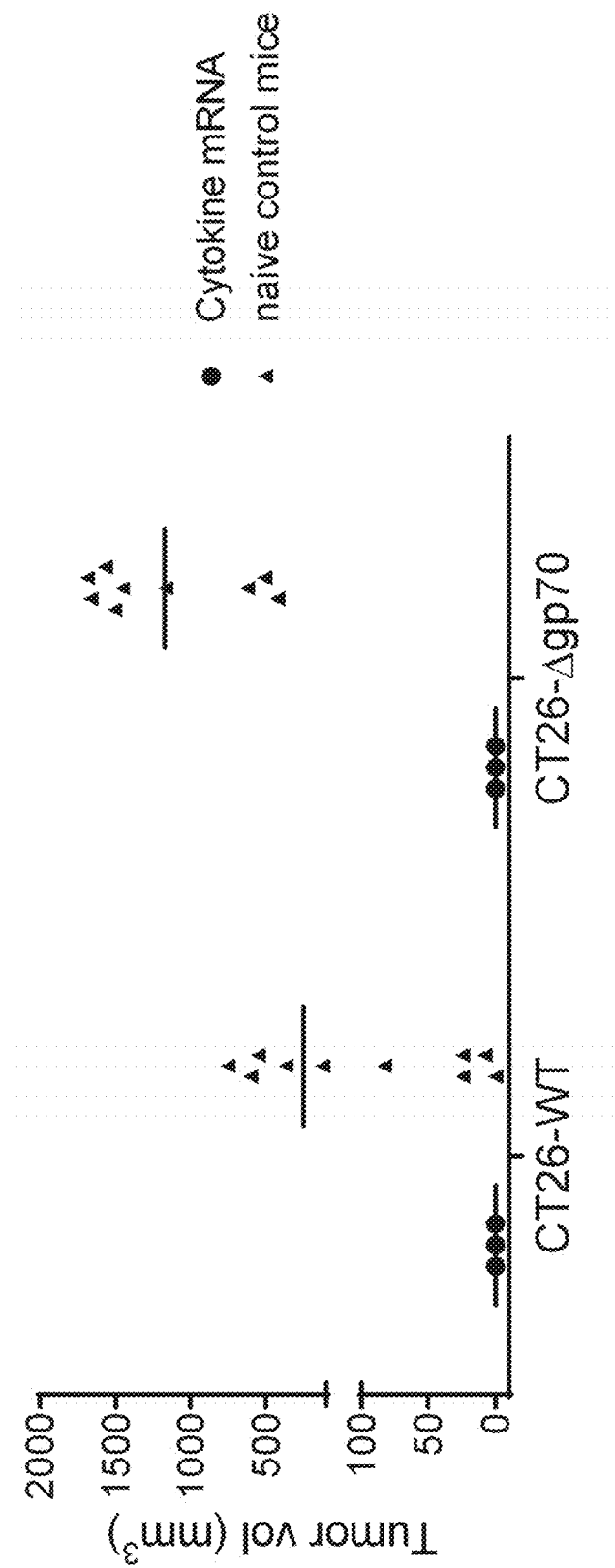

To evaluate the effect of the cytokine mRNA mixture on the development of immunological memory, a re-challenge experiment was performed using the CT26 tumor model. Therefore, CT26 tumor bearing mice were treated with a cytokine mRNA mixture of IL-15sushi, IL-12sc, GM-CSF, and IFNα (Mod B; SEQ ID NOs: 53, 41, 59, and 47). A portion of the cytokine mRNA treatment CT26 tumors completely regressed leading to tumor free animals. Three tumor free animals were then re-challenged with CT26 tumor cells and three tumor free animals were then re-challenged with CT26 tumor cells, in which the gp70 epitope (CT26-Δgp70) was knocked out. 9 and 10, respectively, naïve mice were implanted with CT26 tumor cells and CT26-Δgp70 as a positive control for tumor engraftment. On day 21 after tumor inoculation 8 out of 9 naïve mice had engrafted with CT26 tumor cells developed tumors and all 10 naïve mice engrafted with CT26-Δgp70 tumor cells developed tumors whereas all three tumor-free mice in each group rejected the CT26 and CT26-Δgp70 cells and did not exhibit growth of CT26 tumors and CT26-Δgp70, respectively (FIG. 12D). This experiment shows that immunological memory upon cytokine mRNA injection in the CT26 tumor model is not restricted to T-cells specific for the immunodominant epitope gp70.

Example 5—Systemic Anti-Tumor Activity of Cytokine mRNA

Figure 13A:
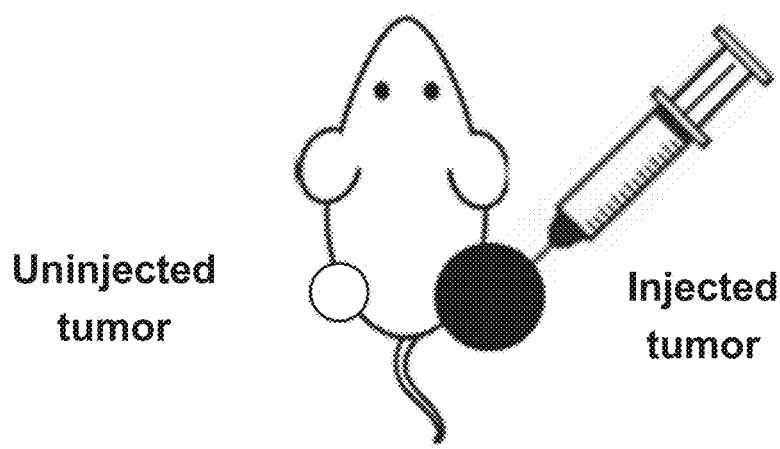
Figure 13B:
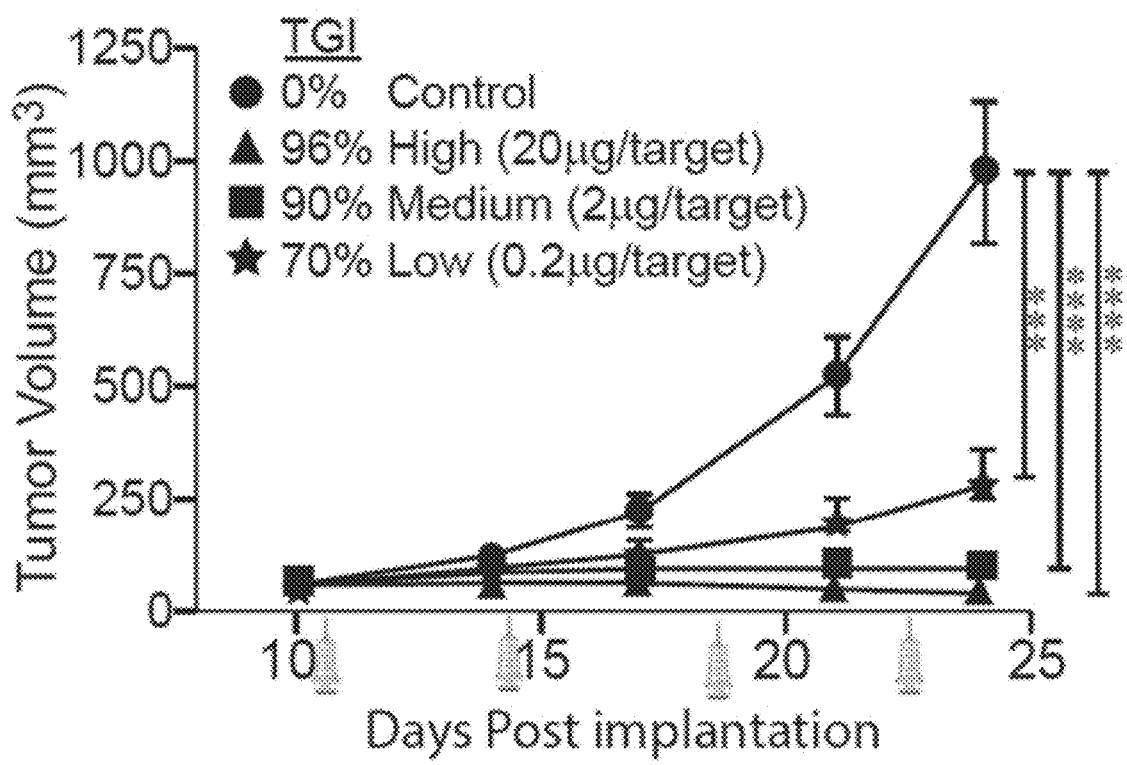
Figure 13C:
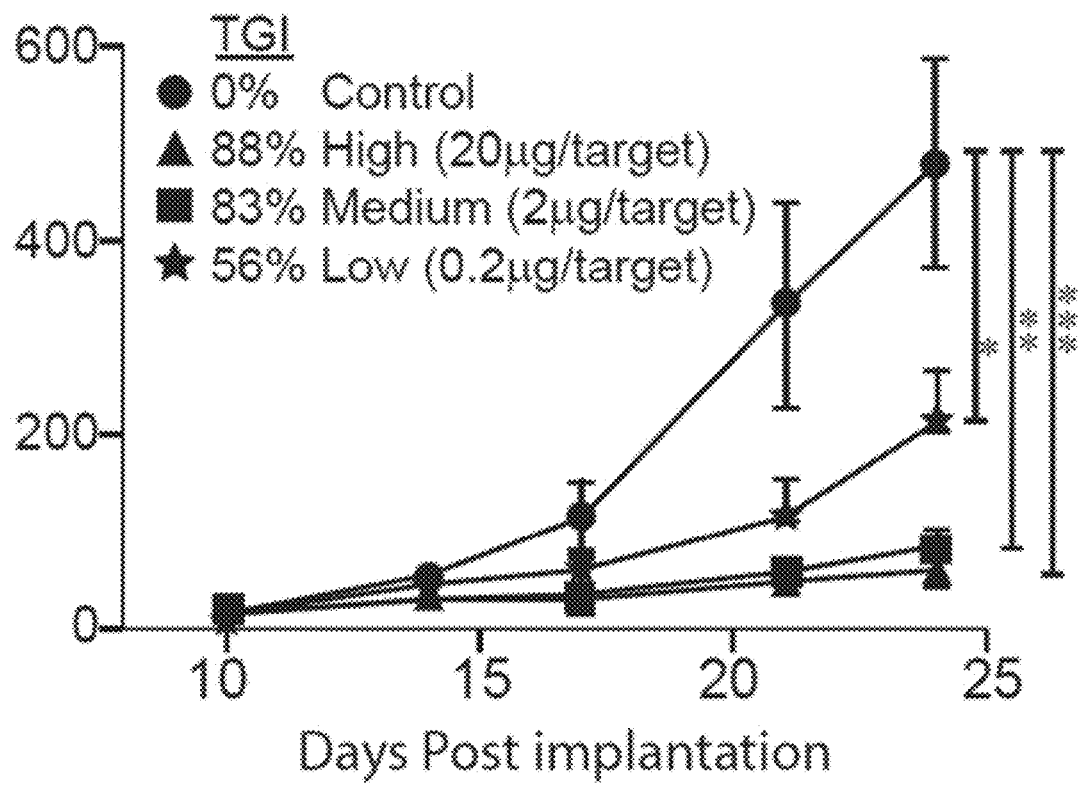
Figure 13D:
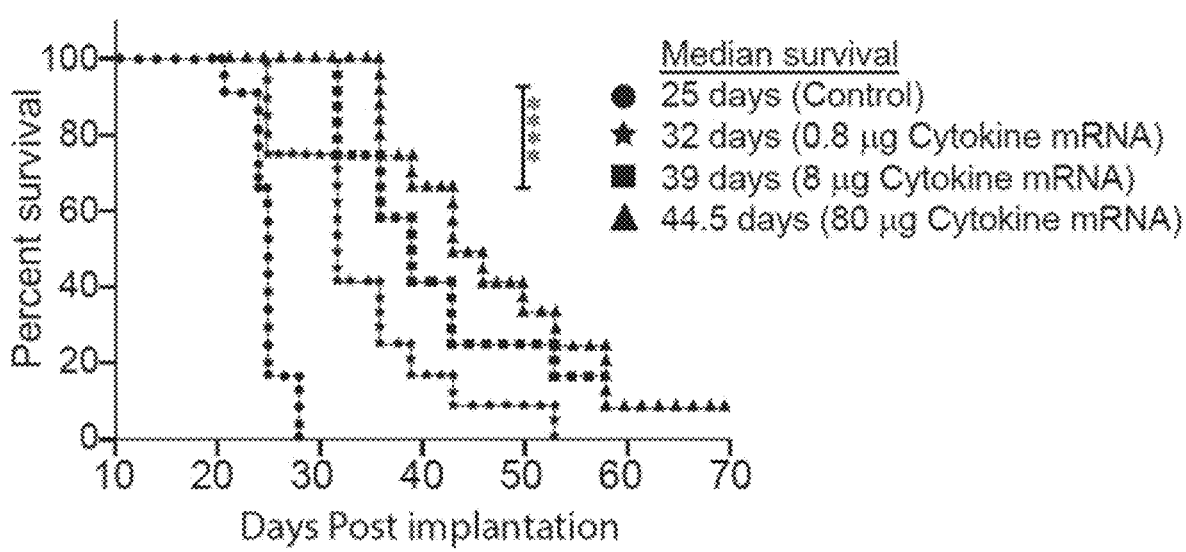

To evaluate the ability of local intratumoral cytokine mRNA to exert a systemic anti-tumor response, mice were engrafted with B16F10 tumor cells on both the left and right flanks (FIG. 13A). Mice bearing bilateral B16F10 tumors received four intratumoral injections with control mRNA encoding luciferase or a cytokine mRNA mixture encoding IL-15 sushi, IL-12sc, GM-CSF and IFNα (ModB; SEQ ID NOs: 53, 41, 59, and 47). The right tumor was injected with mRNA at three different dose levels (80 μg, 8 μg, and 0.8 μg mRNA corresponding to 20 μg, 2 μg and 0.2 μg mRNA/target), while tumors on the left flank were untreated. Dose dependent anti-tumor activity was observed in both the injected (FIG. 13B) and uninjected (FIG. 13C) tumors with tumor growth inhibition ranging from 88% in the uninjected tumor to 96% in the injected tumor. Groups treated with cytokine mRNA treatment had increased median survival compared to groups treated with the Luciferase control mRNA (FIG. 13D).

Figure 19A:
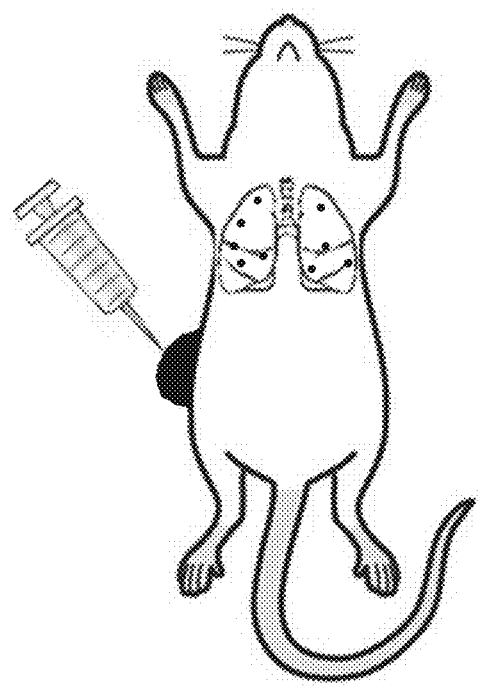
Figure 19B:
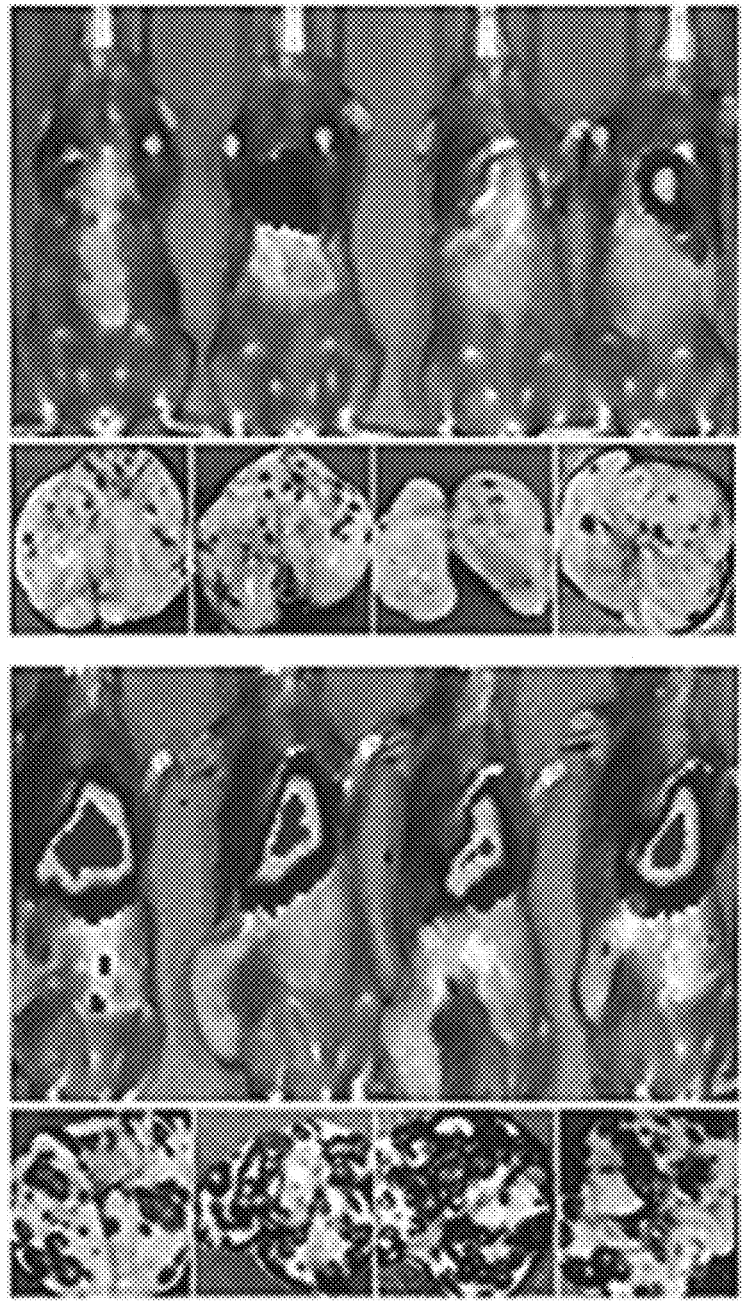
Figure 19C:
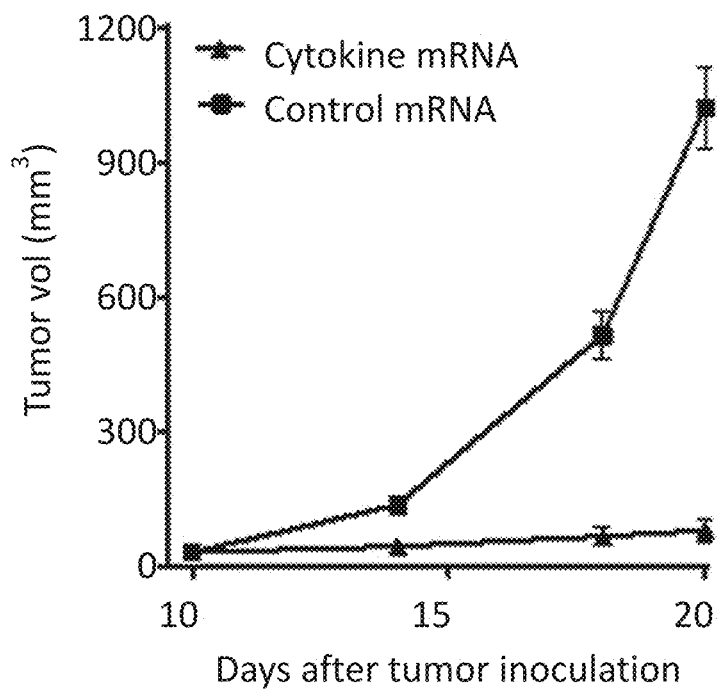
Figure 19D:
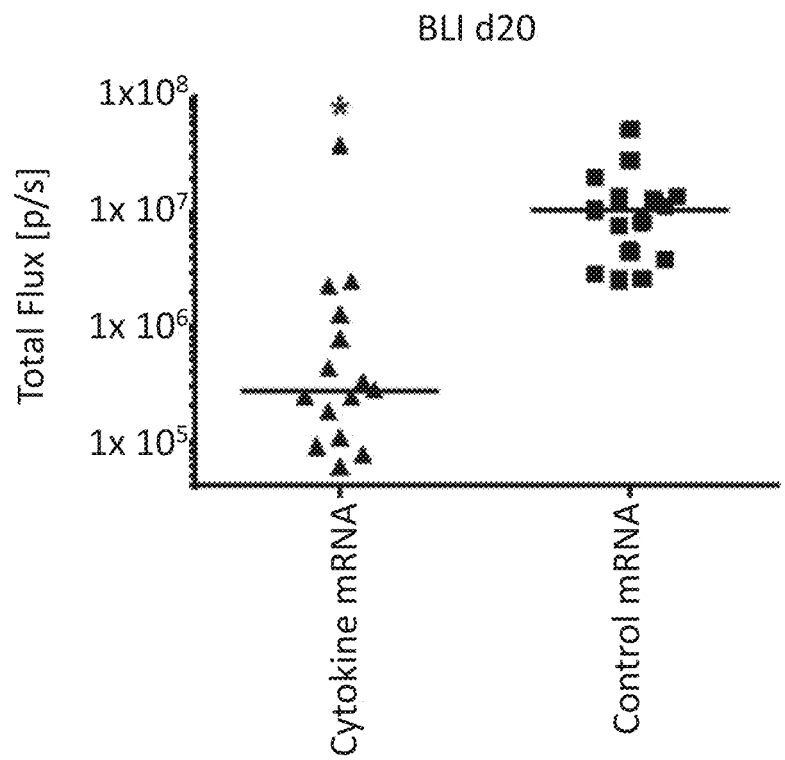
Figure 19E:
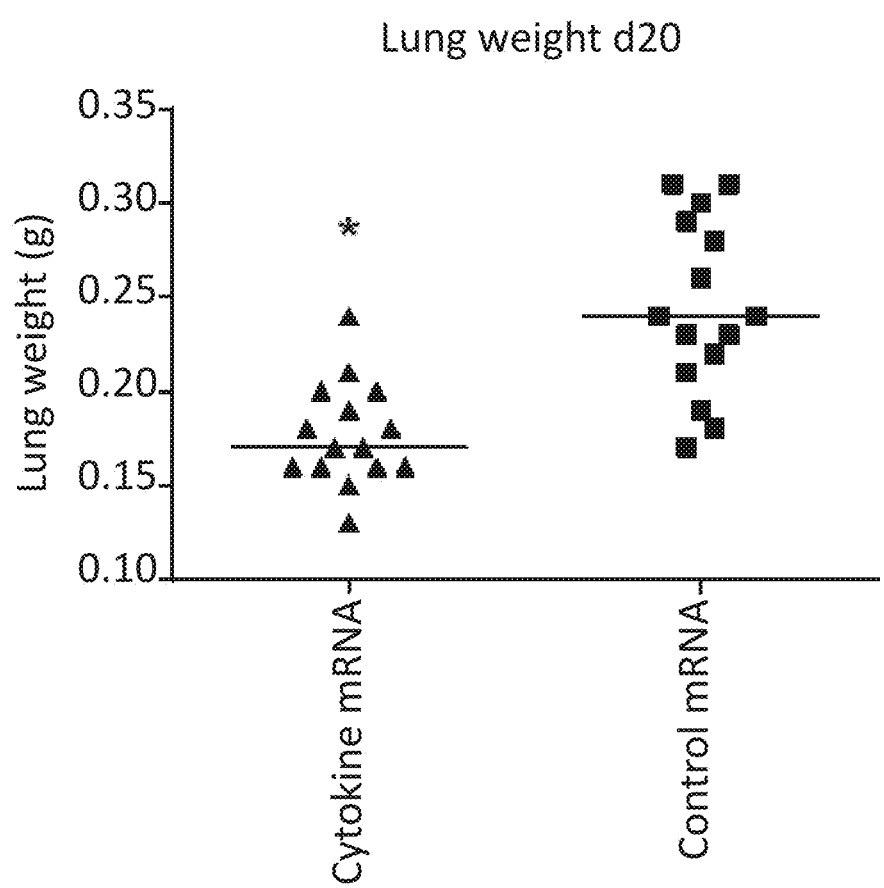

To further evaluate the ability of local intratumoral cytokine mRNA to exert a systemic anti-tumor response, mice were engrafted with B16F10 tumor cells on the right flank and received an IV injection of Luciferase-expressing B16F10 cells for induction of tumors in the lung (FIG. 19A). On day 11, 14 and 18 after SC tumor implantation mice bearing B16F10 tumors received in total three intratumoral injections with cytokine mRNA mixture of IL-15 sushi, IL-12sc, GM-CSF and IFNα (ModB; SEQ ID NOs: 53, 41, 59, and 47) into the flank tumor only, while tumors in the lung were untreated. The control group received intratumoral injection of equal amounts of control mRNA without any coding sequence. Mice were sacrificed for endpoint analysis on day 20, at which time lungs were taken out and weighed. FIG. 19B shows exemplarily bioluminescence measurements of four animals and pictures of the according lungs taken out in order to visualize the dark tumor nodes. Tumor growth of SC tumors was strongly suppressed by injection of cytokine mRNA mixture, whereas tumors injected with control mRNA grew progressively as depicted in FIG. 19C showing mean tumor volume of 15 mice in each group. Lung tumor growth was suppressed in animals which received intratumoral cytokine mRNA injection in SC tumors when compared to animals treated with control mRNA; FIG. 19D shows total flux analysis of bioluminescence measurements of all 15 animals per group on day 20, which is a correlate for tumor burden due to Luciferase-expressing tumor cells; line indicates median and asterisk indicates p<0.05 analyzed by T-test. Additionally, lungs of animals treated with cytokine mRNA had significantly less weight (FIG. 19E, line indicates median). Higher weight of lungs of animals treated with control RNA resulted from higher tumor burden.

Example 6—Human Cytokine mRNA

Figure 14A:
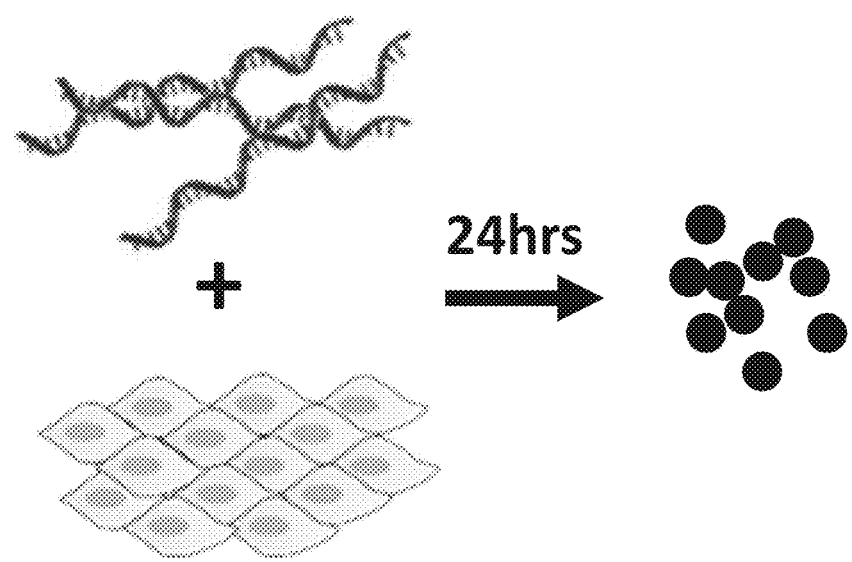
Figure 14B:
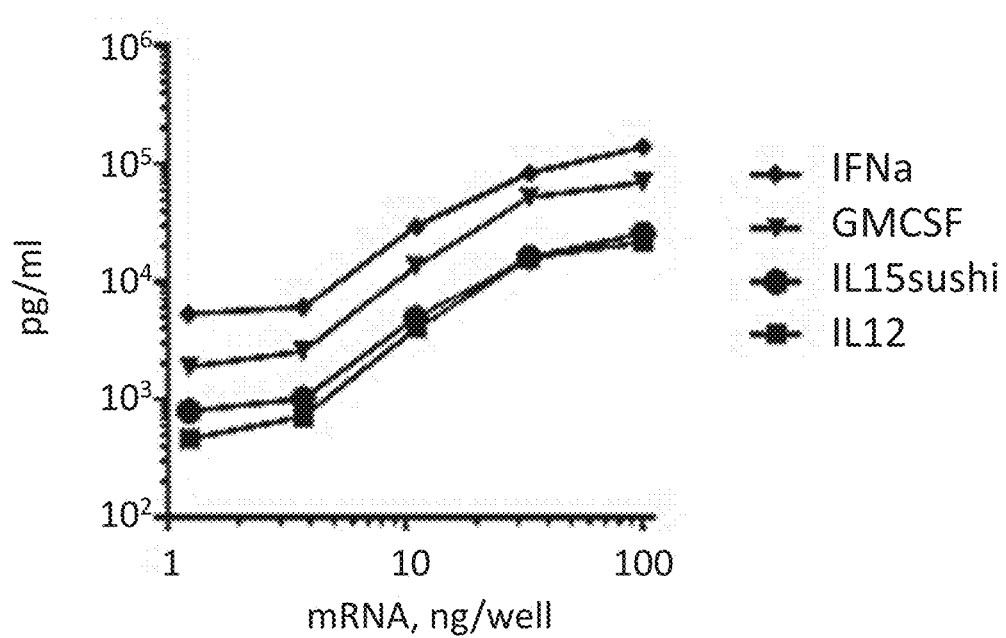
Figure 14C:
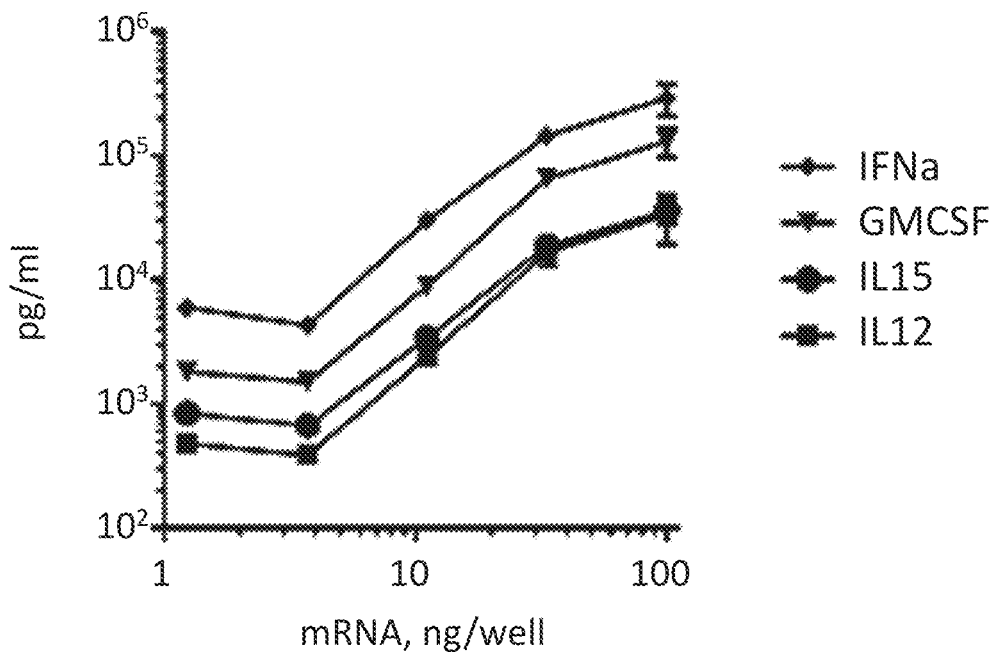
Figure 14D:
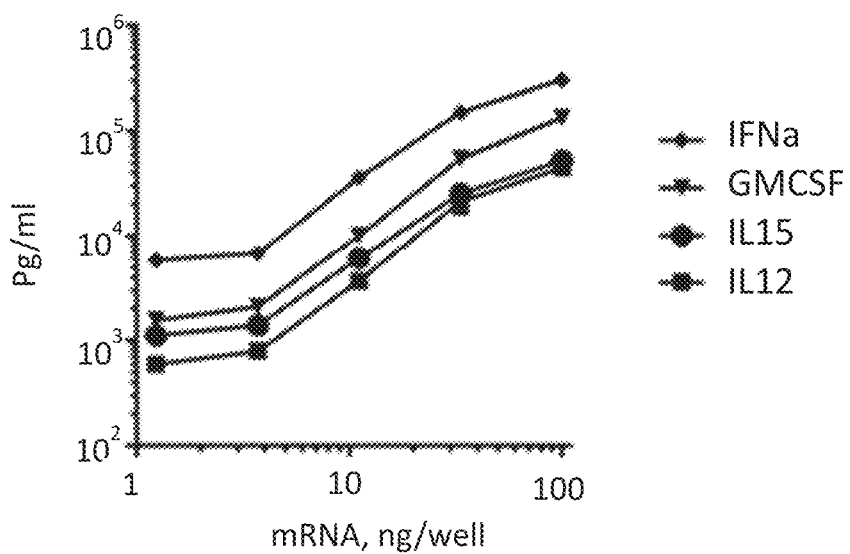
Figure 14E:
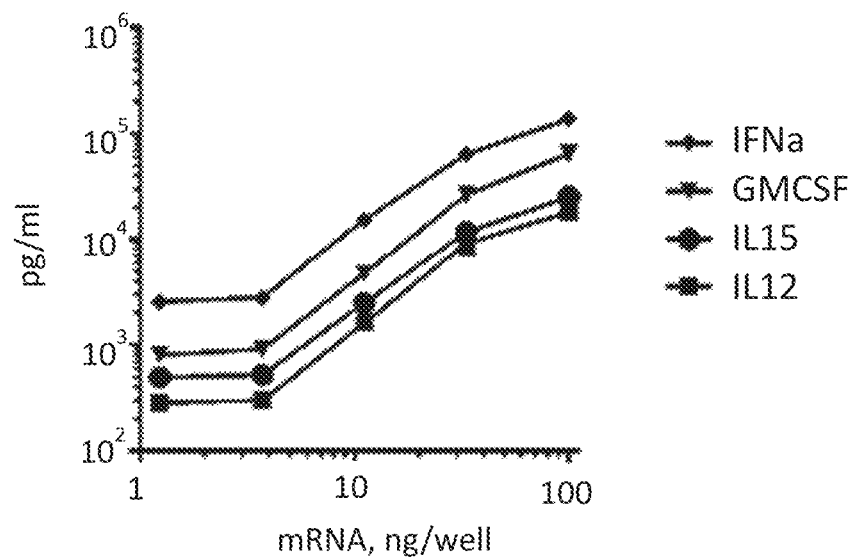
Figure 14F:
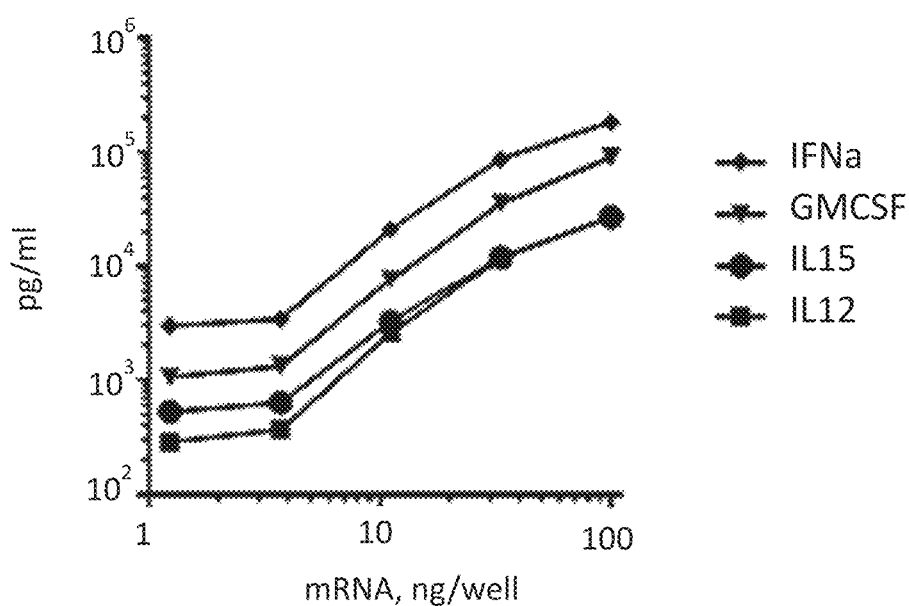

To evaluate in vitro expression of the human cytokine mRNA, an mRNA mixture encoding the human cytokines IL-15 sushi, IL-12sc, GM-CSF, and IFNα2b (SEQ ID Nos: 26, 18, 29, and 23) (ModB) were transfected into the HEK293 cell line along with four melanoma tumor cell lines (A375, A101D, A2058 and Hs294T) (FIG. 14A). The cytokine mRNA mixture exhibited dose dependent expression and secretion across a panel of five human cell lines (FIG. 14B-F).

Figure 15A:
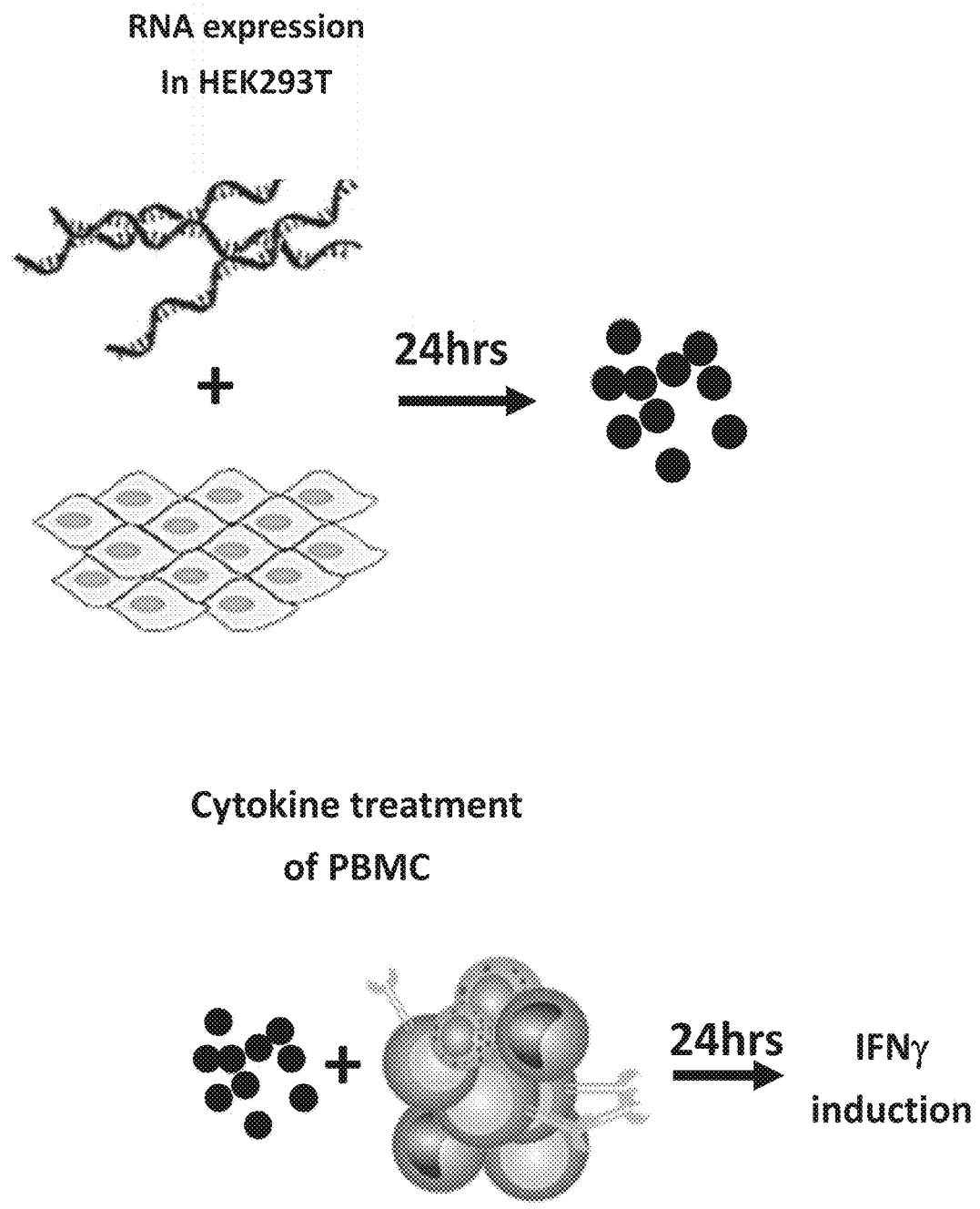
Figure 15B:
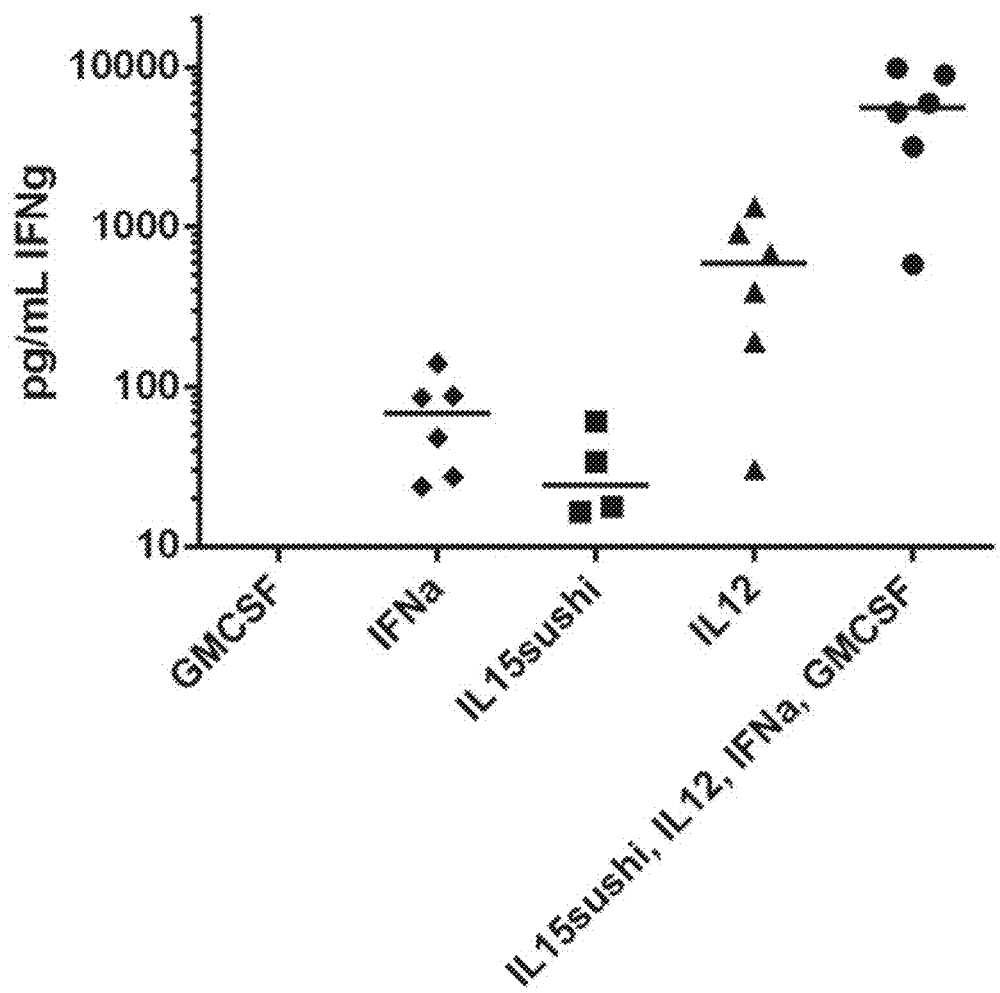

The pharmacodynamic effects of the human mRNA mixture of IL-15 sushi, IL-12sc, GM-CSF and IFNα2b were evaluated in vitro with human peripheral blood mononuclear cells (PBMC). In short, human cytokine mRNA mixture of IL-15 sushi, IL-12sc, GM-CSF and IFNα2b (ModB) or the individual cytokine mRNAs encoding IL-12sc, IFNα2b, IL-15 sushi or GM-CSF (ModB) were transfected in HEK293 cells and the conditioned media was collected at 24 hrs, diluted and added to human PBMC (FIG. 15A). The median IFNγ levels from 6 donors treated with the cytokine mRNA mixture of IL-15 sushi, IL-12sc, GM-CSF and IFNα2b was 5623 pg/mL, while treatment with the individual cytokine mRNA for IL-12sc, IFNα2b, IL-15 sushi or GM-CSF induced median IFNγ levels of 534, 67, 17, and 4 pg/mL, respectively (FIG. 15B).

Figure 16A:
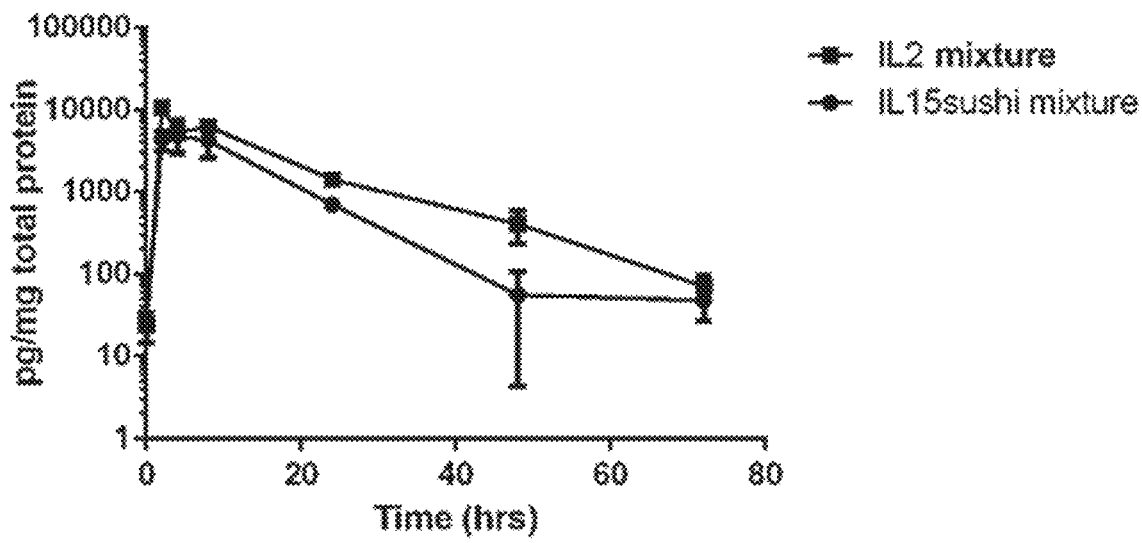
Figure 16B:
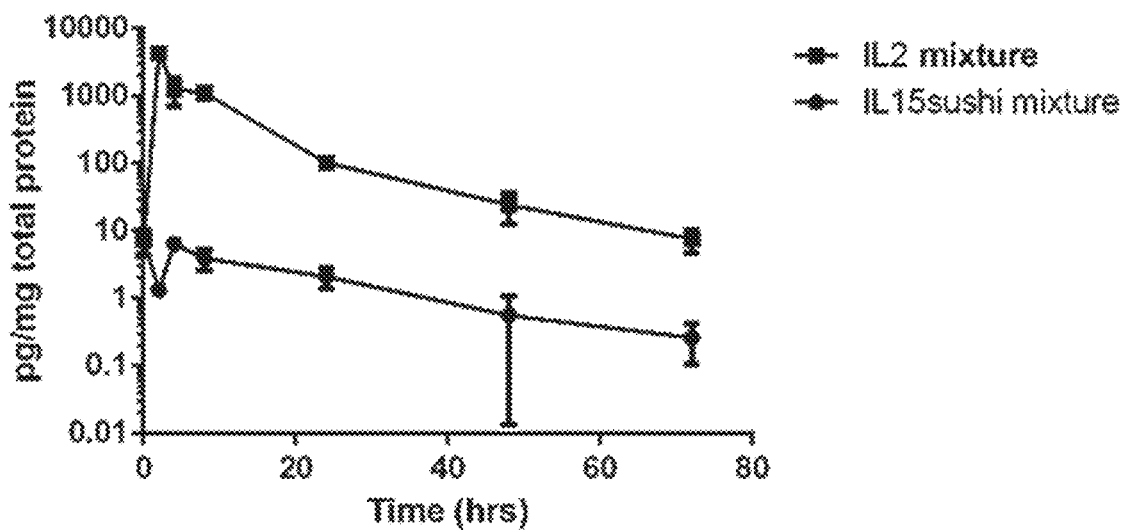
Figure 16C:
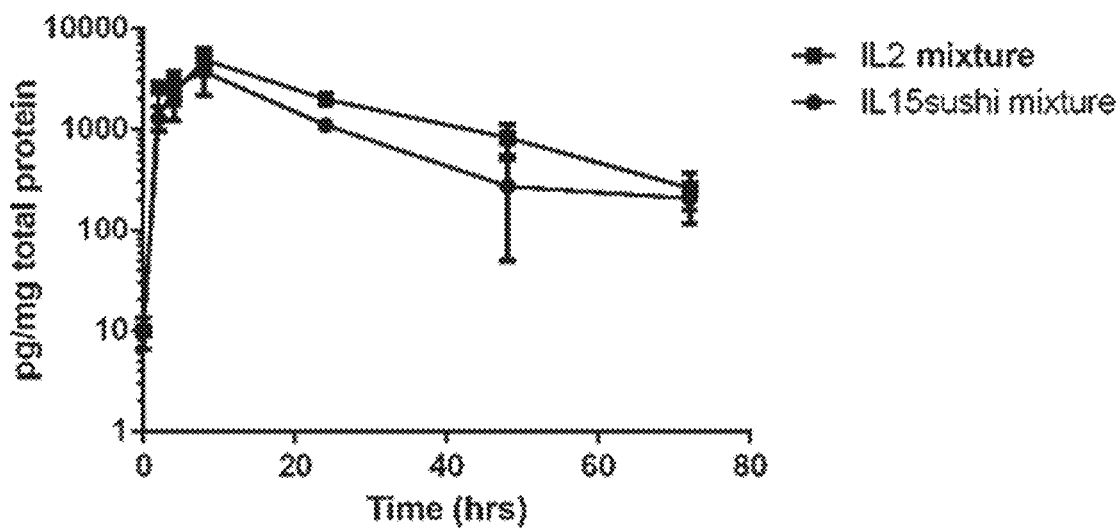
Figure 16D:
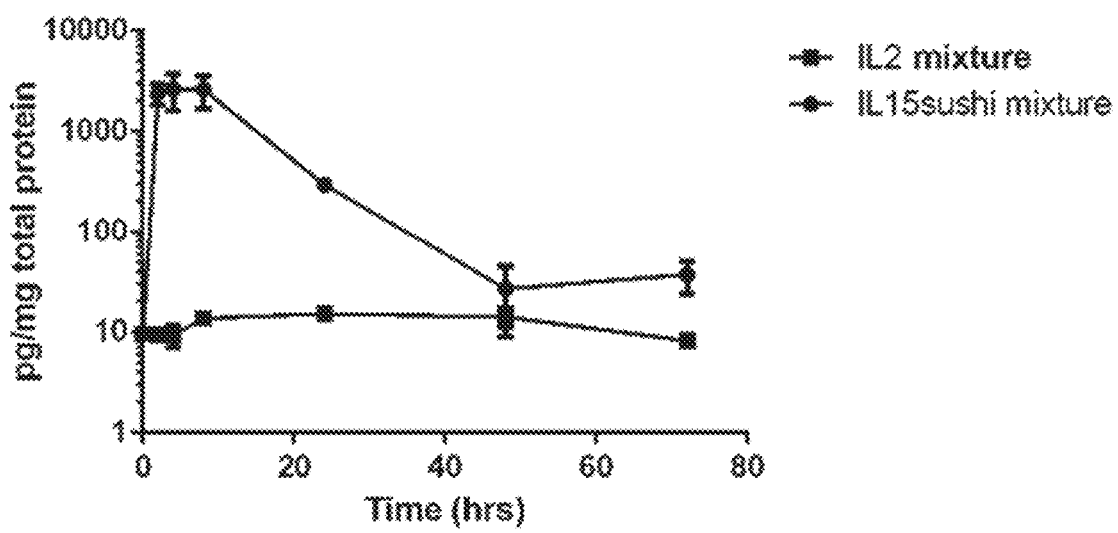
Figure 16E:
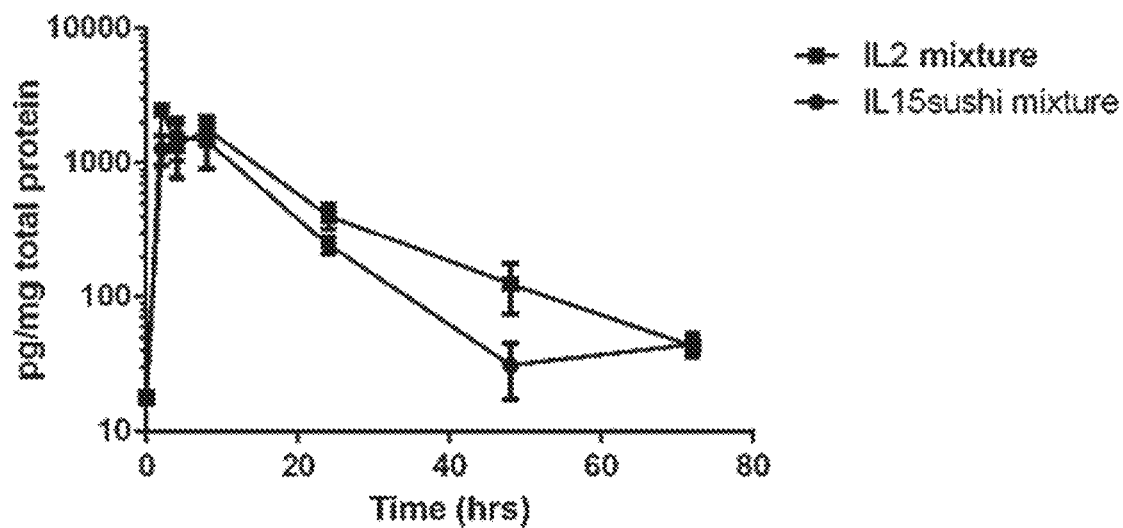

In vivo expression of the human cytokine mRNA mixture of IL-15 sushi, IL-12sc, GM-CSF and IFNα2b (ModB) and IL-2, IL-12sc, GM-CSF and IFNα2b (ModB) was monitored in the A375 human melanoma xenograft. Tumor bearing mice received a single injection of cytokine mRNA and tumor samples were collected at 2 hrs, 4 hrs, 8 hrs, 24 hrs, 48 hrs and 72 hrs after mRNA injection. Tumor lysates were prepared and expression of the individual human cytokines IFNα2b (FIG. 16A), IL-2 (FIG. 16B), IL-12sc (FIG. 16C), IL-15 sushi (FIG. 16D), GM-CSF (FIG. 16E) were evaluated.

Time dependent expression was observed for each of the individual cytokines with the maximal concentration (Cmax) occurring between 2-8 hrs for the mixtures of IL-15 sushi, IL-12sc, GM-CSF and IFNα2b (Table 4) and IL-2, IL-12sc, GM-CSF and IFNα2b (Table 5).

TABLE 4

Pharmacokinetic results for the IL-15 sushi mixture

| Tumor | GM-CSF | IFNα2b | IL-12sc | IL-15sushi |
|---|---|---|---|---|
| $t_{1/2}$ (hrs) | 12.4 | 9.59 | 15.2 | 10.2 |
| Tmax (hrs) | 4 | 4 | 8 | 4 |
| Cmax (pg/mg) | 1591 | 4862 | 3767 | 2639 |

TABLE 5

Pharmacokinetic results for the IL-2 mixture

| Tumor | GM-CSF | IFNα2b | IL-12sc | IL-2 |
|---|---|---|---|---|
| $t_{1/2}$ (hrs) | 14.8 | 10.2 | 15.5 | 12.8 |
| Tmax (hrs) | 2 | 2 | 8 | 2 |
| Cmax (pg/mg) | 2487 | 10685 | 4961 | 4271 |

Figure 17A:
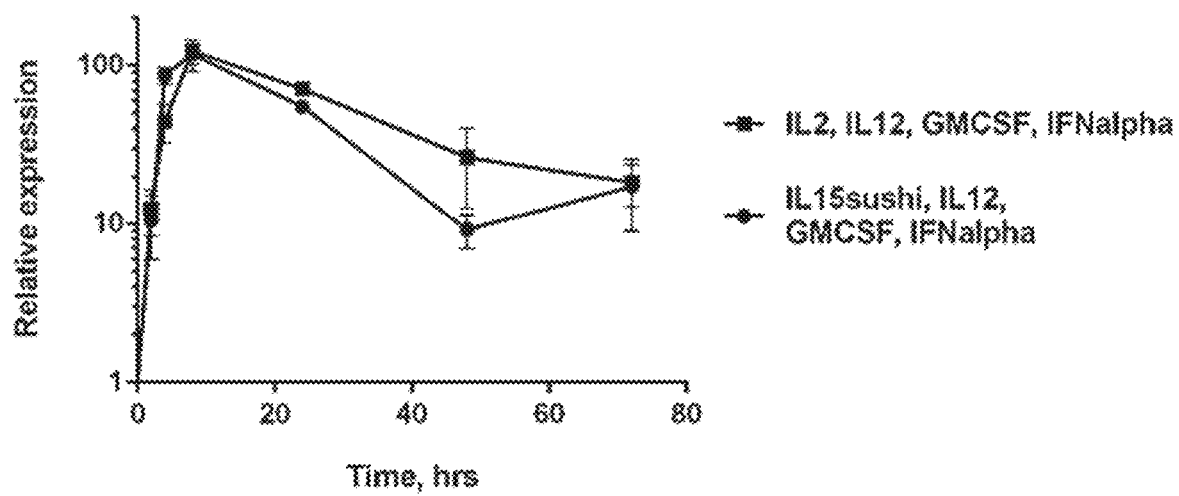
Figure 17B:
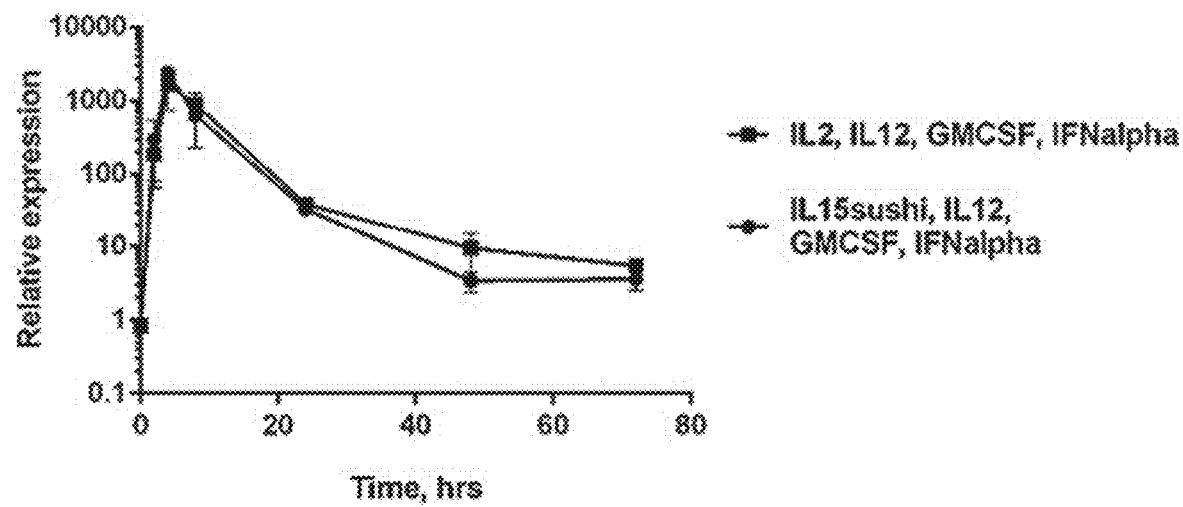
Figure 17C:
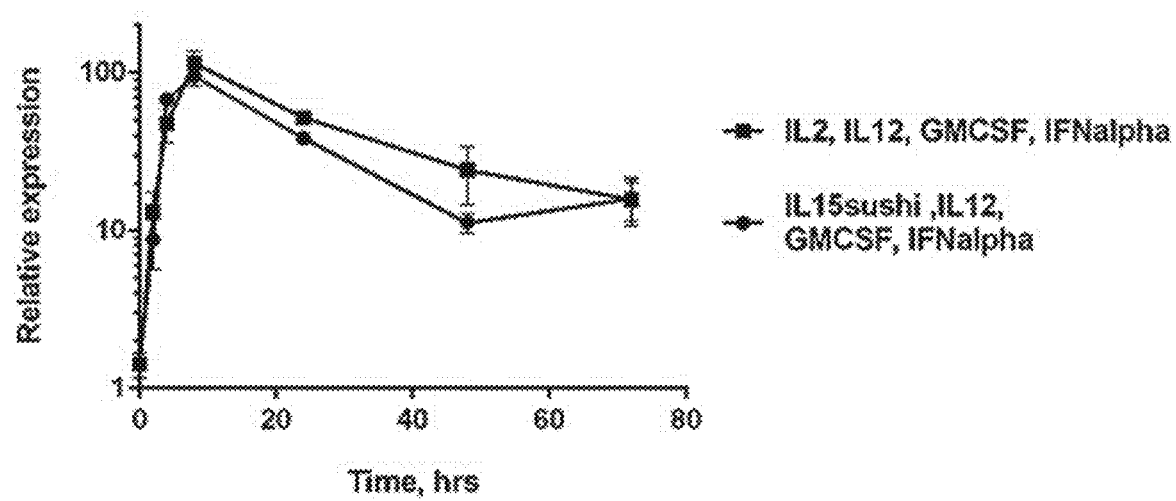

Induction of the human interferon alpha genes ISG15, ISG54 and MX1 were monitored in the A375 tumors as a pharmacodynamics marker at 2 h, 4 h, 8 h, 24 h, 48 h and 72 h following mRNA injection of the cytokine mRNA mixtures of IL-15 sushi, IL-12sc, GM-CSF and IFNα2b (ModB) and IL-2, IL-12sc, GM-CSF and IFNα2b (ModB). Compared to control treated tumors, A375 tumors treated with cytokine mRNA displayed greater than 100-fold induction of ISG15 (FIG. 17A), ISG54 (FIG. 17B) and MX1 (FIG. 17C) with peak induction occurring by 8 hrs after intratumoral mRNA injection.

Example 7—Interferon Effect

Figure 18A:
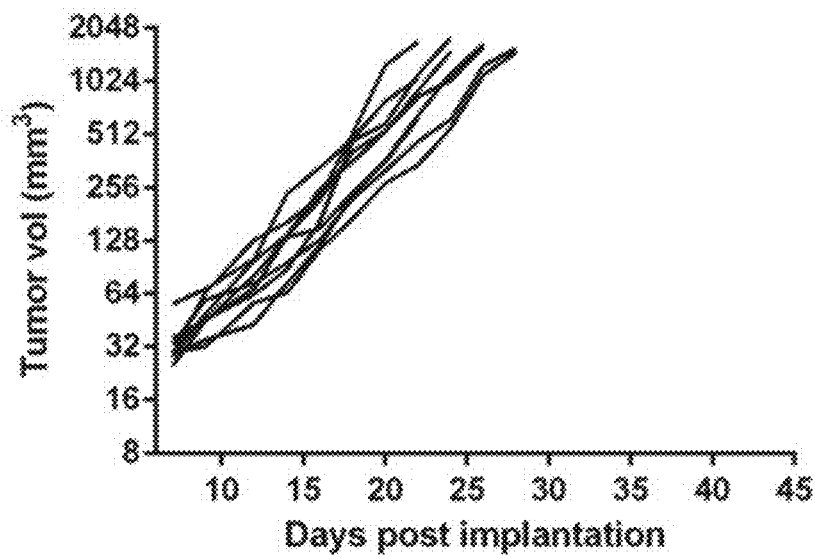
Figure 18B:
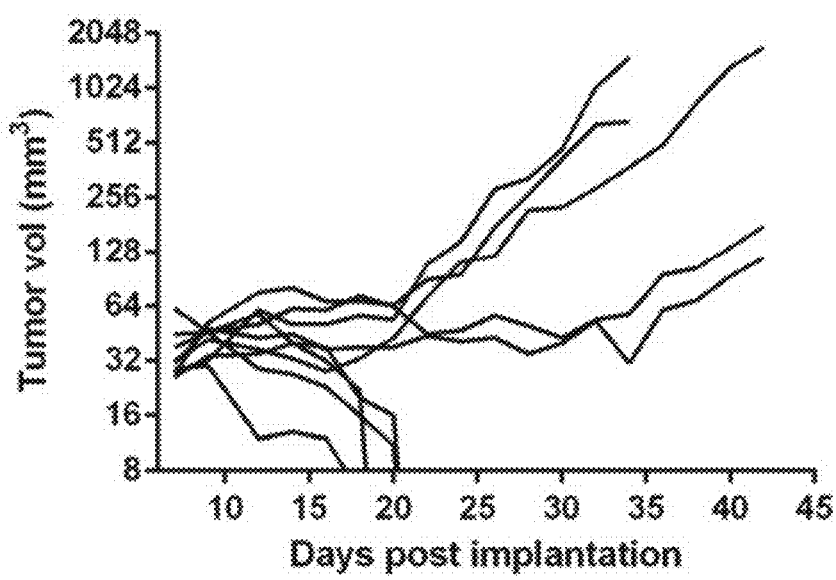
Figure 18C:
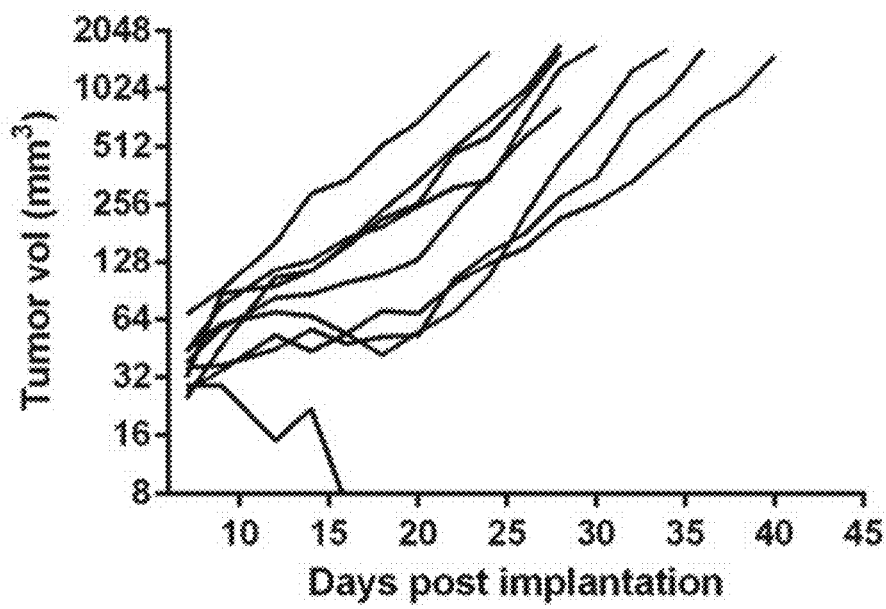
Figure 18D:
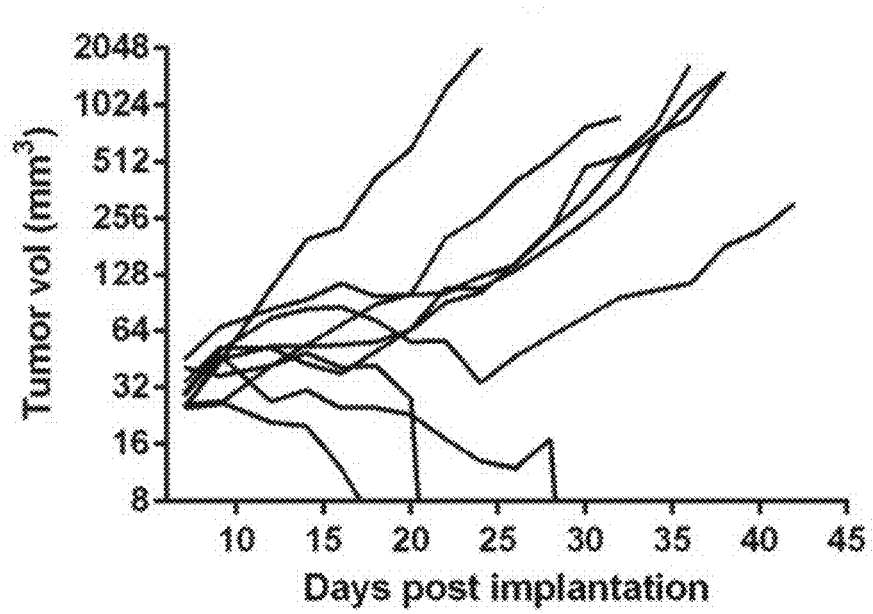
Figure 18E:
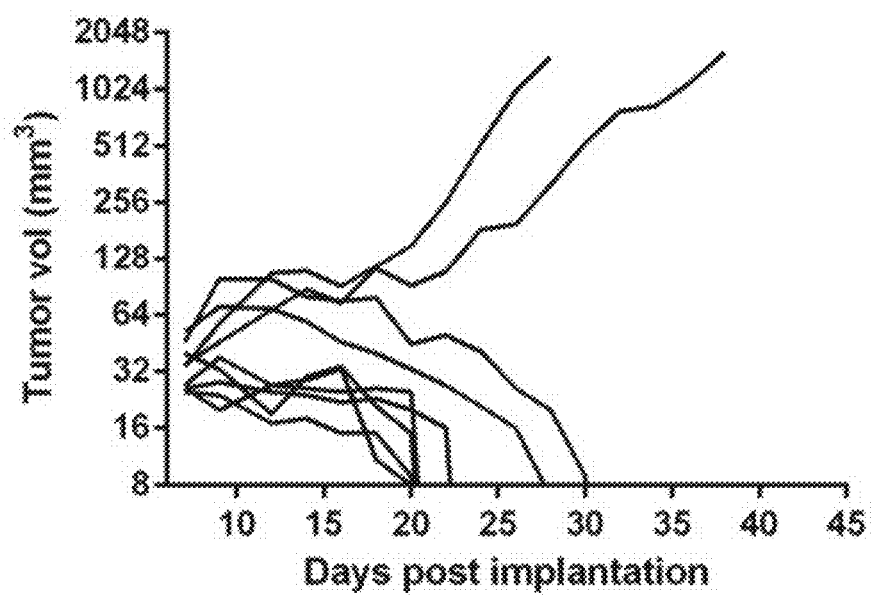

B16F10-tumor-bearing mice received intratumoral injections of ModA ("standard") cytokine mRNA encoding IL-2, Flt3 ligand (FLT3L), 41BBL (also known as CD137L or tumor necrosis factor superfamily member 9), and CD27L-CD40L (this comprises a fusion protein of the soluble domain of CD27L also known as CD70, and CD40L; both the CD27L and the CD40L is comprised of three soluble domains of either CD27L or CD40L, all separated by GS-Linker sequences (FIG. 18A, SEQ ID NOs: 32, 62, 68, and 74) or ModB ("modified") cytokine mRNA encoding IL-2, FLT3L, 41BBL, and CD27L-CD40L (FIG. 18B, SEQ ID NOs: 35, 65, 71, and 77). In addition, either ModA mRNA encoding IFNα (SEQ ID NO: 44) or ModB mRNA encoding IFNα (SEQ ID No: 47) was added to the ModA or ModB mRNA mixes, respectively (FIGS. 18D and 18E). Anti-tumor activity was assessed.

Mice treated with this combination of ModA mRNA had 4/9 mice tumor-free without IFNα (FIG. 18B) and 3/9 mice tumor-free with IFNα (FIG. 18D). Therefore, treatment with IFNα mRNA did not appear to increase the response to the cytokines when mRNA was dosed in the ModA form.

In contrast, mice treated with the combination of ModB mRNA had 1/9 mice tumor-free without IFNα (FIG. 18C) and 7/9 mice tumor-free with IFNα (FIG. 18E). Thus, treatment with IFNα mRNA increased the response to the mixture of cytokines when mRNA was dosed in the ModB form.

Example 8—Cytokine mRNA in Combination with Antibodies

Figures 20A, 20B:
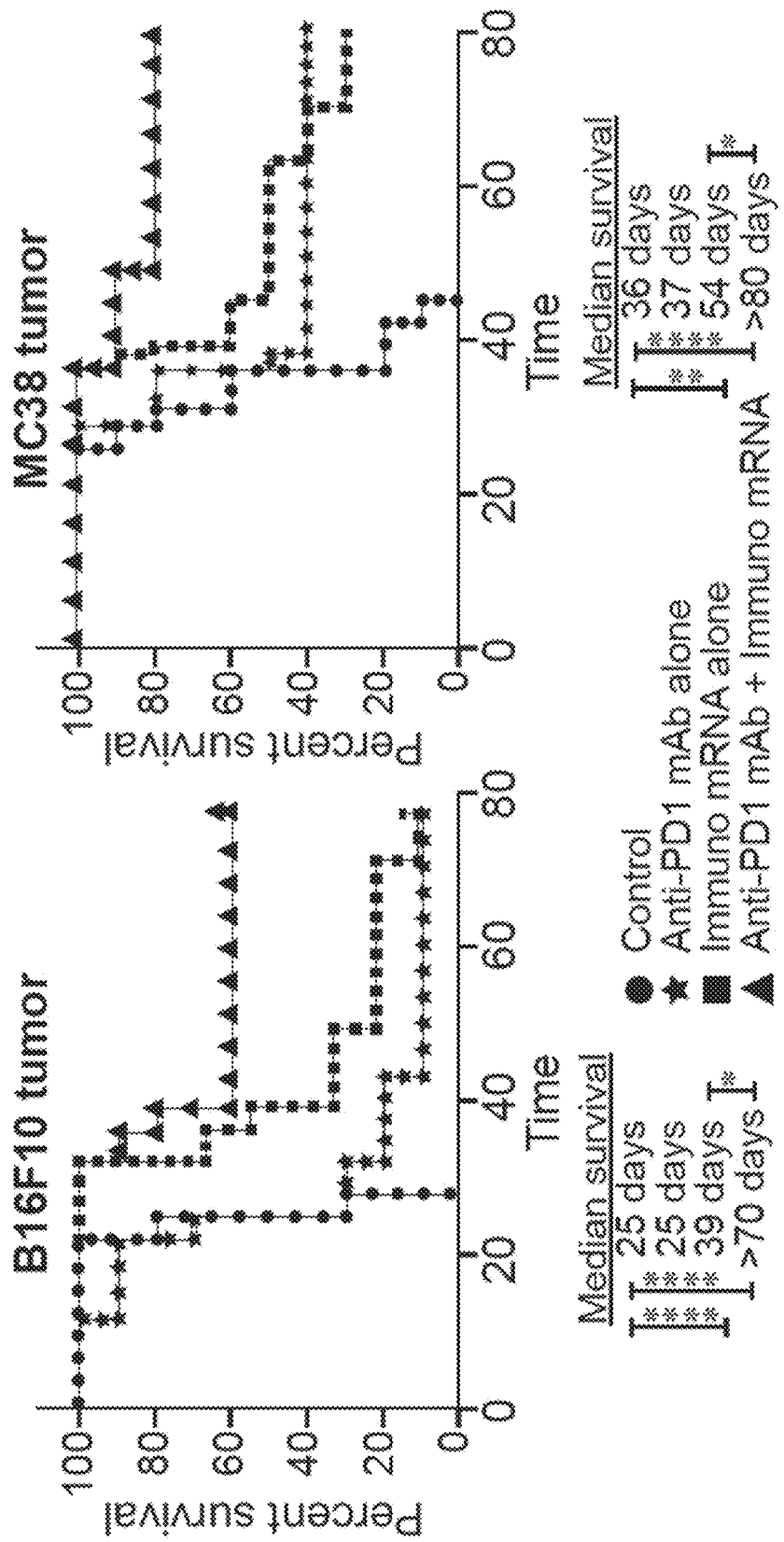
Figure 20C:
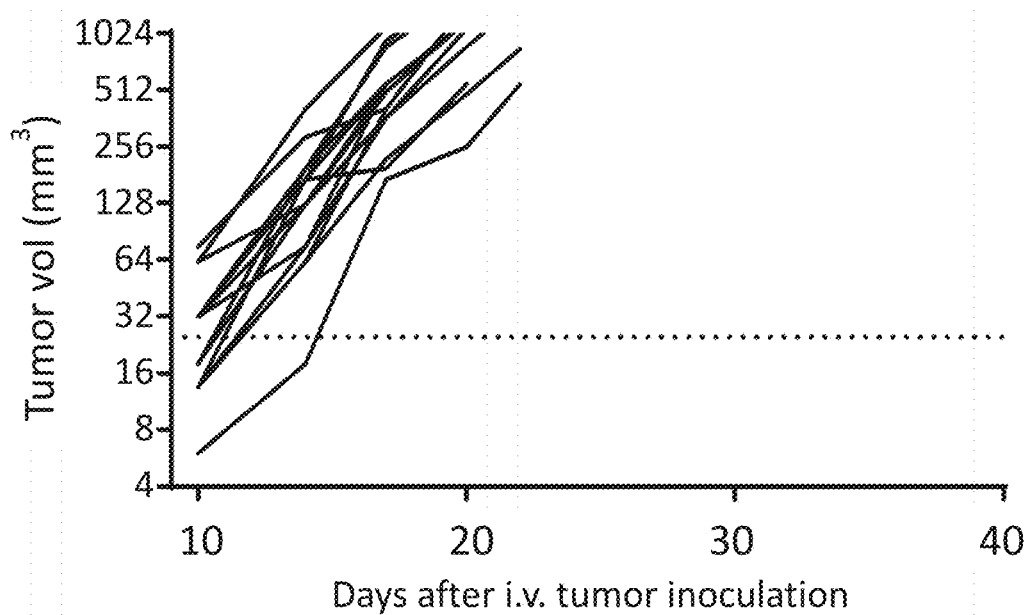
Figure 20D:
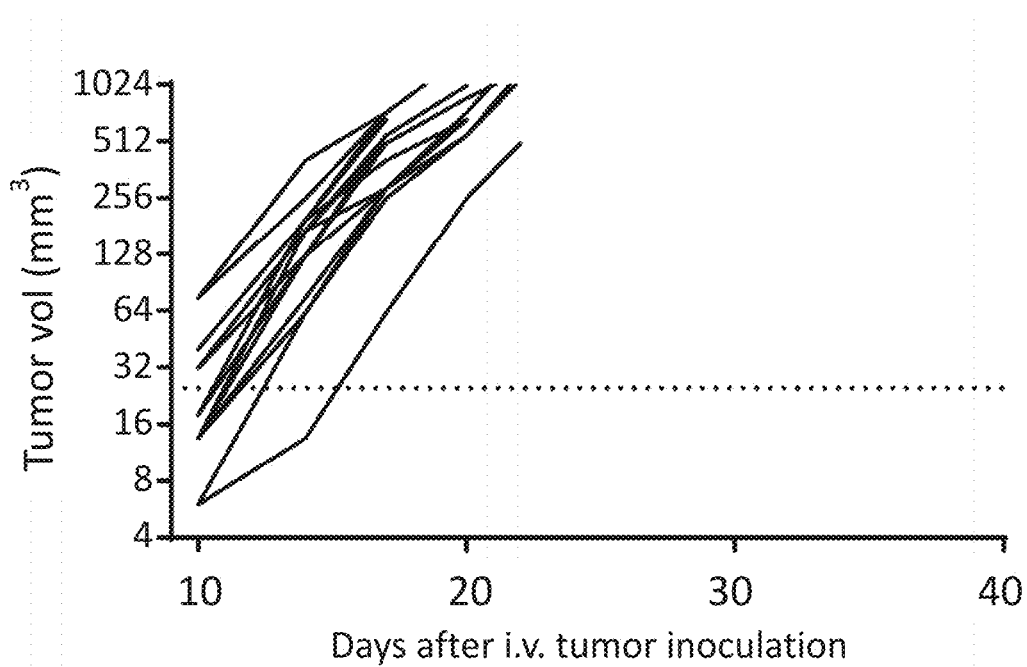
Figure 20E:
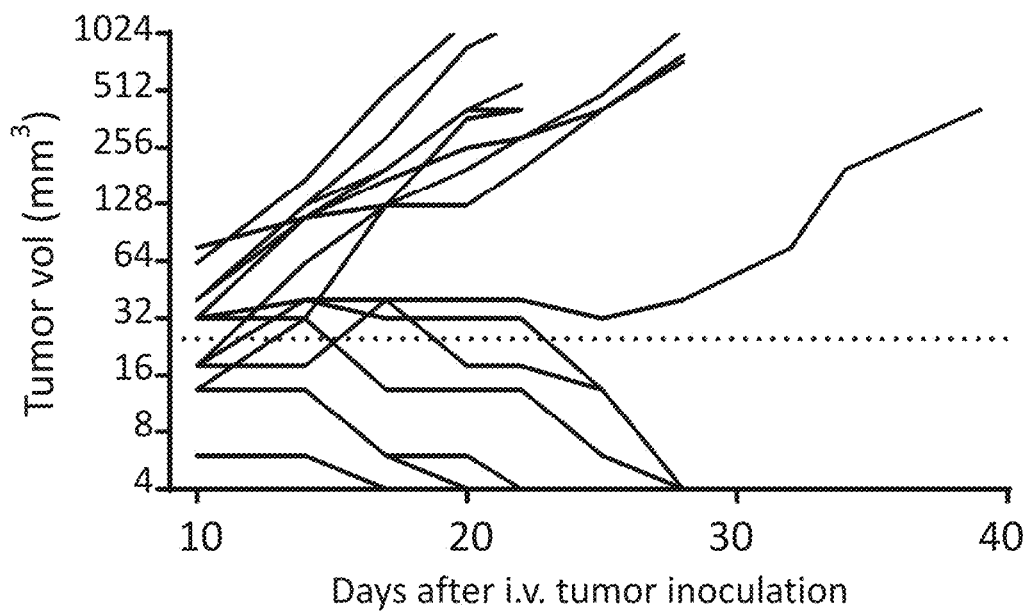

To evaluate the effect of intratumoral injection of cytokine mRNA in combination with systemic administration of antibodies, mice were engrafted with B16F10 or MC38 tumor cells on both the left and right flanks. Mice received four intratumoral injections with cytokine mRNA mixture of IL-15 sushi, IL-12sc, GM-CSF and IFNα (ModB; SEQ ID NOs: 53, 41, 59, and 47) into only one of the flank tumors on Days 11, 15, 19, 23, while the other flank tumor was left untreated. Mice also received intraperitoneal injection anti-PD1 antibody (Sanofi murinized version of rat IgG2a anti-mouse PD-1 clone RMP1-14 at 5 mg/kg) on Days 10, 13, 16, 19, 22, 25. Groups were as follows: 1) control mRNA (80 µg total mRNA; 50 µL intratumoral injection at 1.6 mg/mL plus control isotype antibody (clone MOPC-21 (BioLegend); 5 mg/kg): 2) control mRNA plus anti-PD1 antibody; 3) cytokine mRNA plus control isotype antibody; and 4) cytokine mRNA plus anti-PD1. Overall survival was monitored in both the B16F10 (FIG. 20A) and MC38 (FIG. 20B) tumor models. In both tumor models the highest overall survival was observed with the combination of cytokine mRNA and anti-PD-1 treatment with 60% of mice bearing B16F10 and 80% of MC38 bearing mice tumor free at the end of the study. In the B16F10 tumor model 10% of mice treated with anti-PD-1 or cytokine mRNA alone were tumor free, while in the MC38 model 40% of mice treated with anti-PD-1 and 30% of mice treated with cytokine alone were tumor free. The results indicate strong antitumor activity associated with cytokine mRNA and PD-1 combination.

Figure 20F:
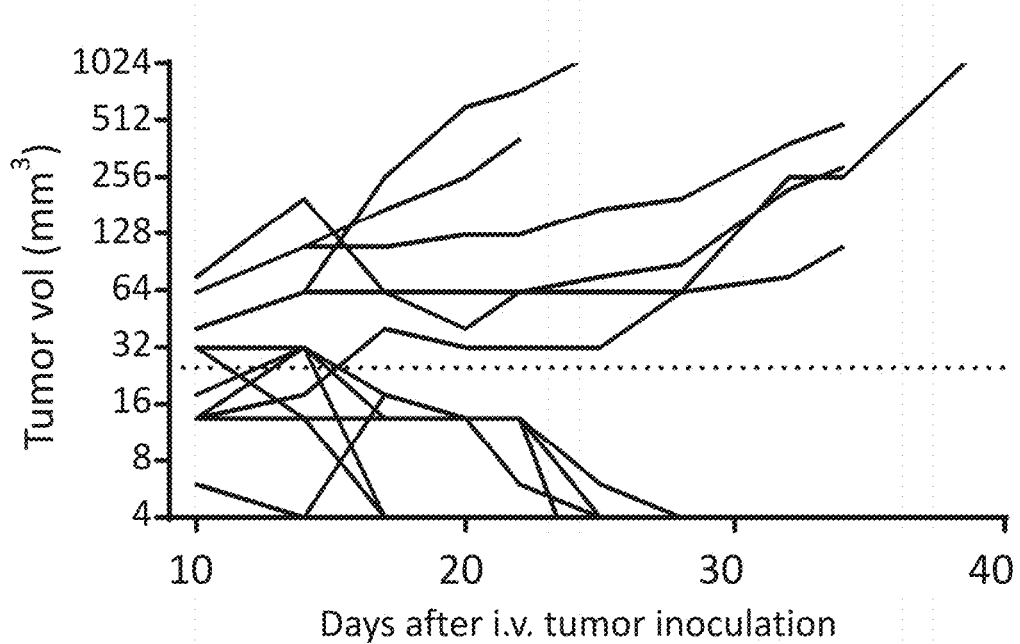
Figure 20G:
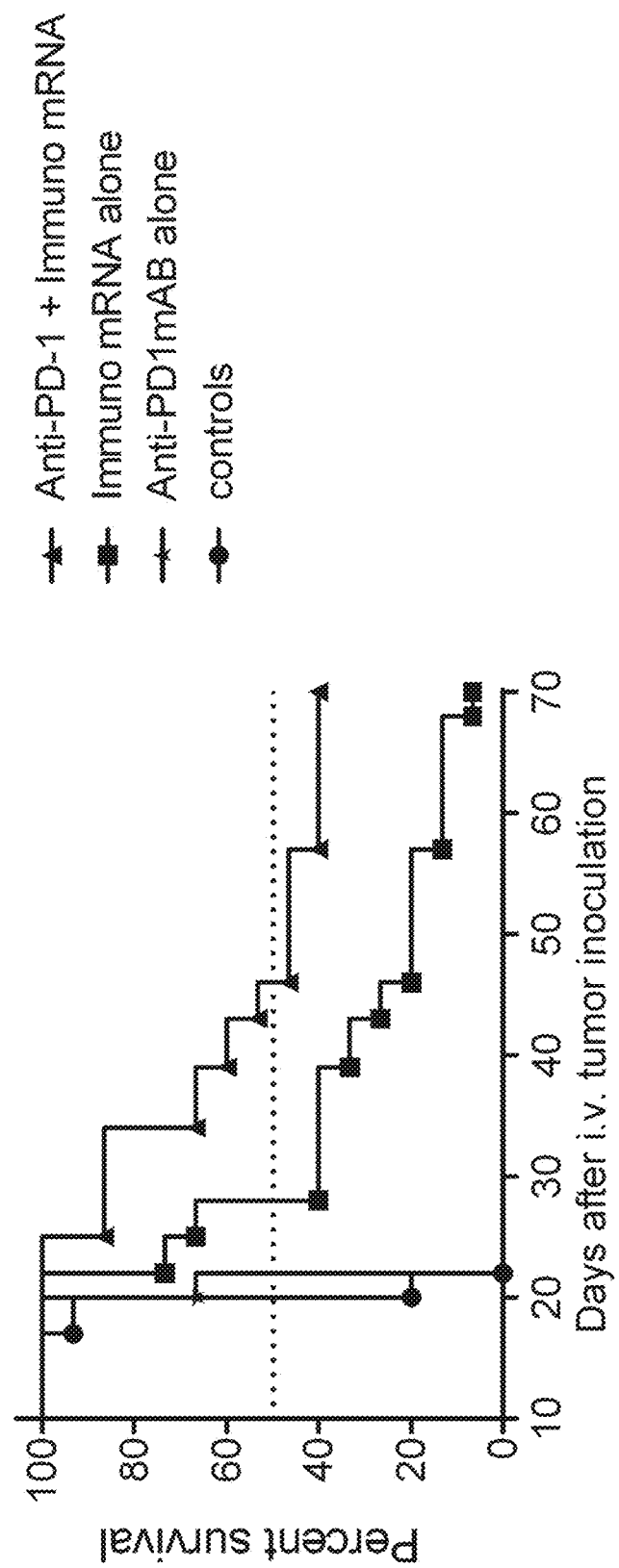

To further evaluate the ability of local intratumoral cytokine mRNA in combination with the PD-1 antibody to exert a systemic anti-tumor response, mice were engrafted with B16F10 tumor cells on the right flank and received one day later an IV injection of Luciferase-expressing B16F10 cells for induction of lung metastasis. On day 11, 14 and 17 after IV tumor implantation mice bearing B16F10 tumors received in total three intratumoral injections with cytokine mRNA mixture of IL-15 sushi, IL-12sc, GM-CSF and IFNα (ModB; SEQ ID NOs: 53, 41, 59, and 47) into the flank tumor only, while tumors in the lung were untreated. On the same day mice also received intraperitoneal (IP) injections of PD-1 antibody (Sanofi murinized version of rat IgG2a anti-mouse PD-1 clone RMP1-14 at 10 mg/kg). Groups were as follows: 1) control mRNA (40 µg total mRNA; 50 µL intratumoral injection of control isotype antibody (clone MOPC-21 (BioLegend); 10 mg/kg) (FIG. 20C); 2) control mRNA plus anti-PD1 antibody (FIG. 20D); 3) cytokine mRNA plus control isotype antibody (FIG. 20E); and 4) cytokine mRNA plus anti-PD1 (FIG. 20F). Tumor growth of SC tumors was monitored (FIGS. 20C-F) as well as survival (FIG. 20G). Overall survival in this model was determined by tumor burden due to SC tumors as well as lung pseudo-metastasis tumor (not shown in this Figure); in some mice the SC tumor was rejected, while lung metastasis grew progressively. The highest overall survival was observed with the combination of cytokine mRNA and anti-PD-1 treatment. 6-7% of mice treated with cytokine mRNA alone were tumor free, while mice that had received anti-PD-1 alone or control mRNA+isotype antibody were all sacrificed at day 22 due to high tumor burden. The results indicate strong antitumor activity associated with cytokine mRNA and PD-1 combination in this B16F10 tumor model with lung pseudo-metastasis, while anti-PD-1 antibody alone did not show any anti-tumor activity.

Figure 21A:
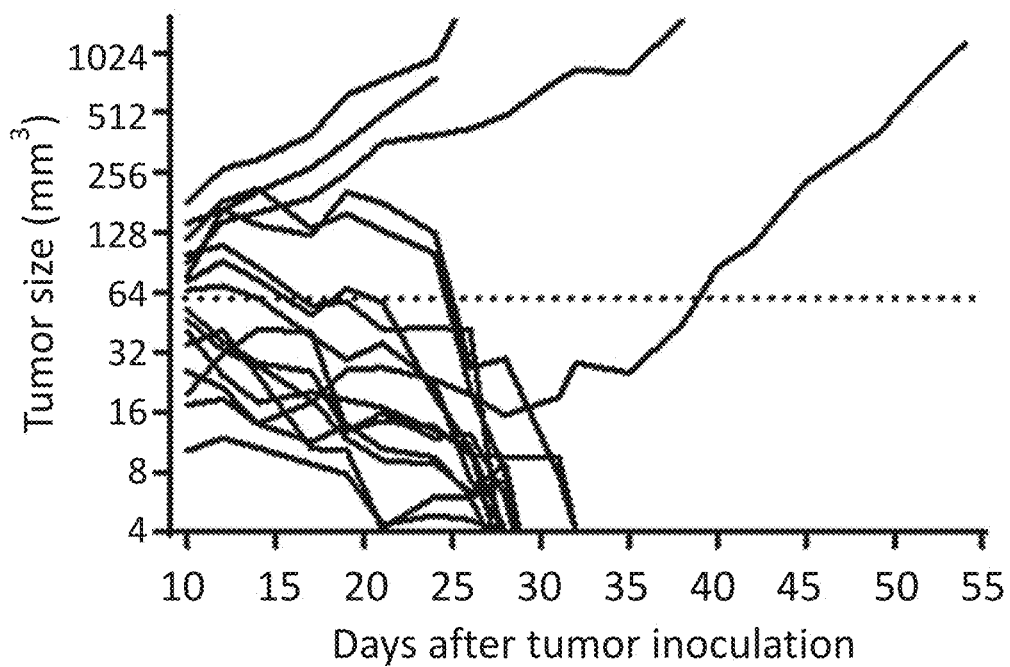
Figure 21B:
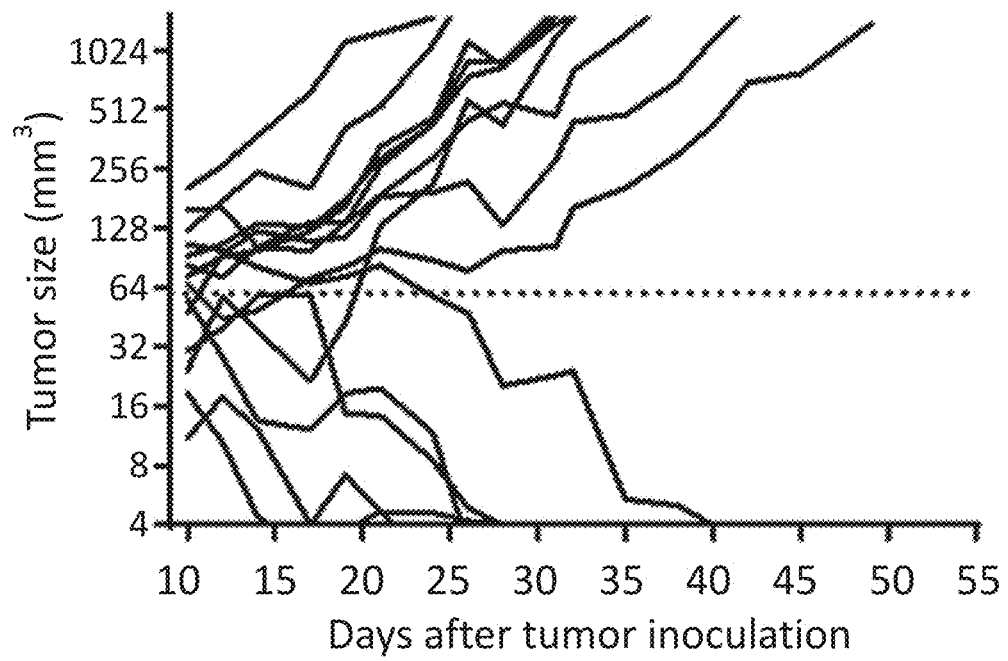
Figure 21C:
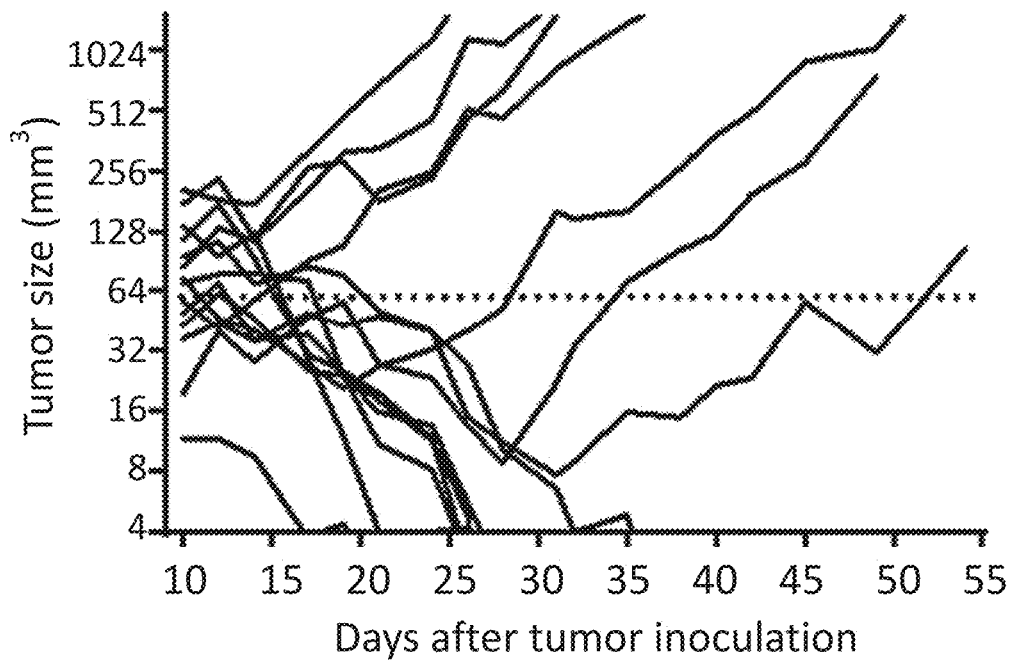
Figure 21D:
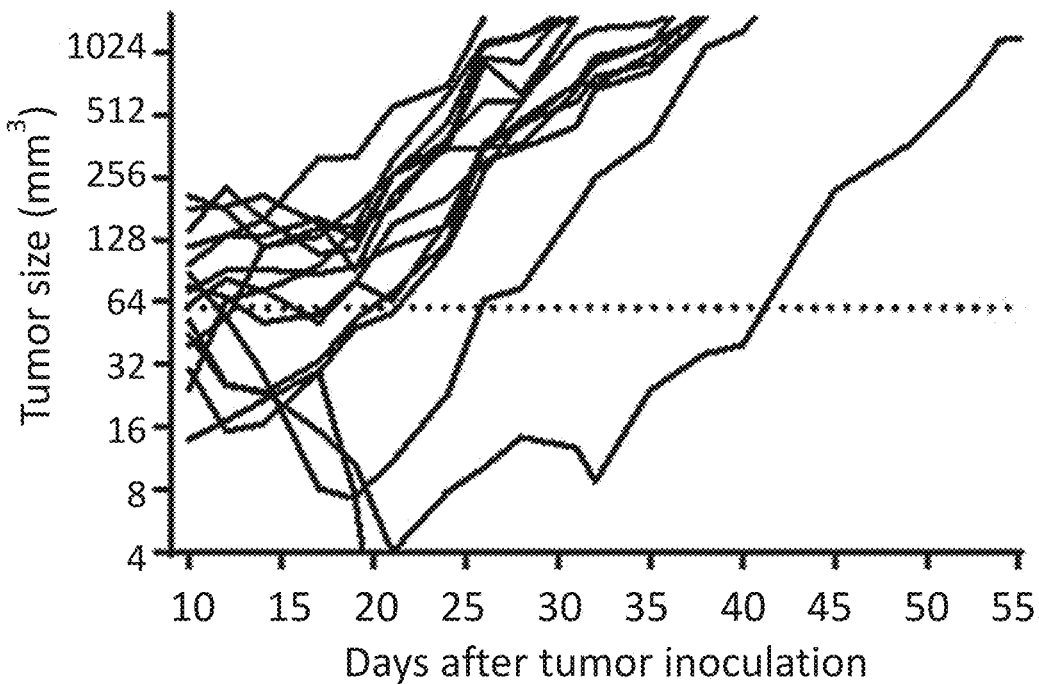

To further evaluate the effect of intratumoral injection of cytokine mRNA in combination with systemic administration of antibodies, mice were engrafted with CT26 tumor cells on right flanks. Mice received four intratumoral injections with cytokine mRNA mixture of IL-15 sushi, IL-12sc, GM-CSF and IFNα (ModB; SEQ ID NOs: 53, 41, 59, and 47) on day 11, 14, 18 and 21 after tumor inoculation. On the same day mice also received intraperitoneal (IP) injections of an anti-CTLA-4 antibody (100 µg/200 µL per mouse; clone 9H10 from InVivoMAb) or the isotype control antibody (100 µg/200 µL per mouse; Armenian hamster IgG from BioXCell). Groups were as follows: 1) cytokine mRNA plus anti-CTLA-4 antibody (FIG. 21A); 2) cytokine mRNA plus isotype control antibody (FIG. 21B); 3) control mRNA plus anti-CTLA-4 antibody (FIG. 21C) and 4) control mRNA plus isotype control antibody (FIG. 21D). Combination therapy of intratumoral cytokine mRNA and IP-injected anti-CTLA-4 resulted in strongest anti-tumoral activity with 12 tumor-free mice out of 16 mice on day 55 after tumor inoculation (FIG. 21A). Treatment with either cytokine mRNA plus isotype control antibody (FIG. 21B) or control mRNA plus anti-CTLA-4 antibody (FIG. 21C) induced less anti-tumoral activity with 5 and 7 tumor-free mice at the end of the study, respectively. In comparison, in the group that received control mRNA plus isotype control antibody (FIG. 21D), only one tumor-free mouse remained at the conclusion of the study.

Figure 21E:
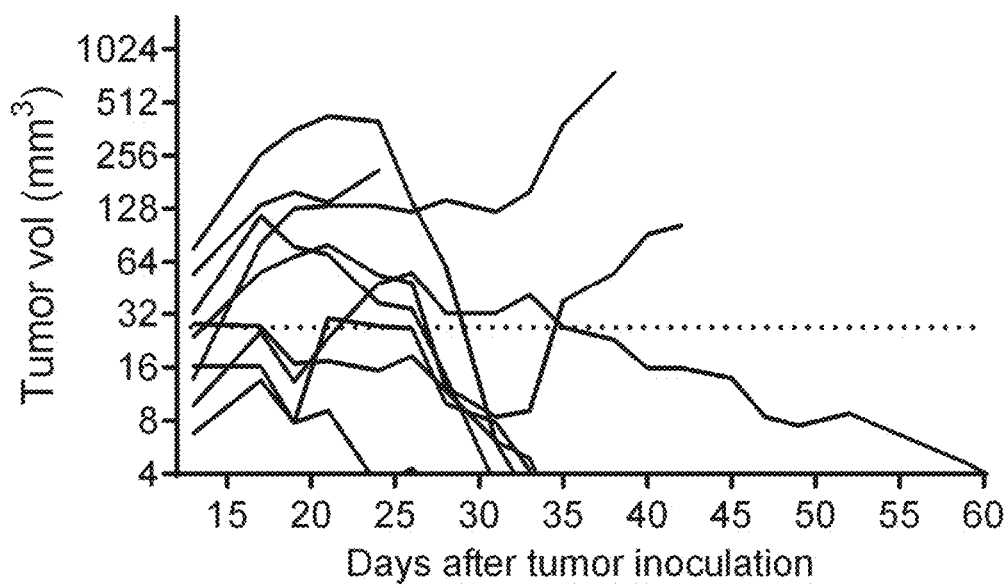
Figure 21F:
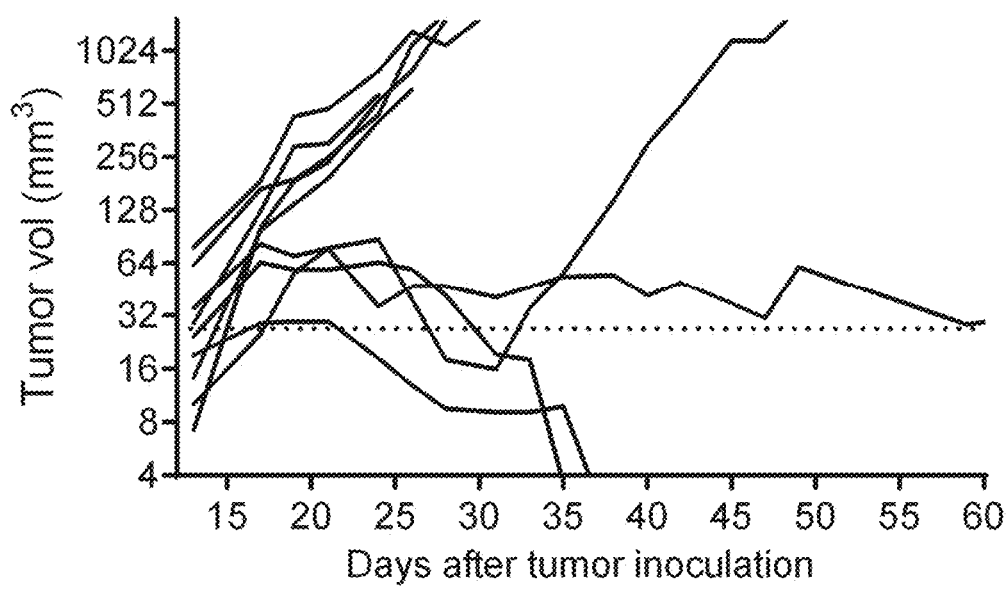
Figure 21G:
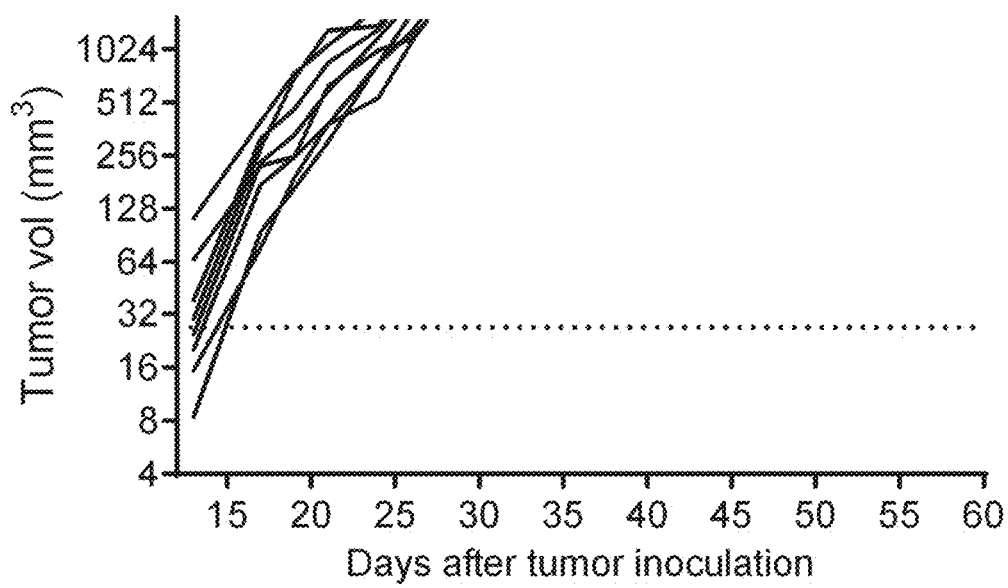
Figure 21H:
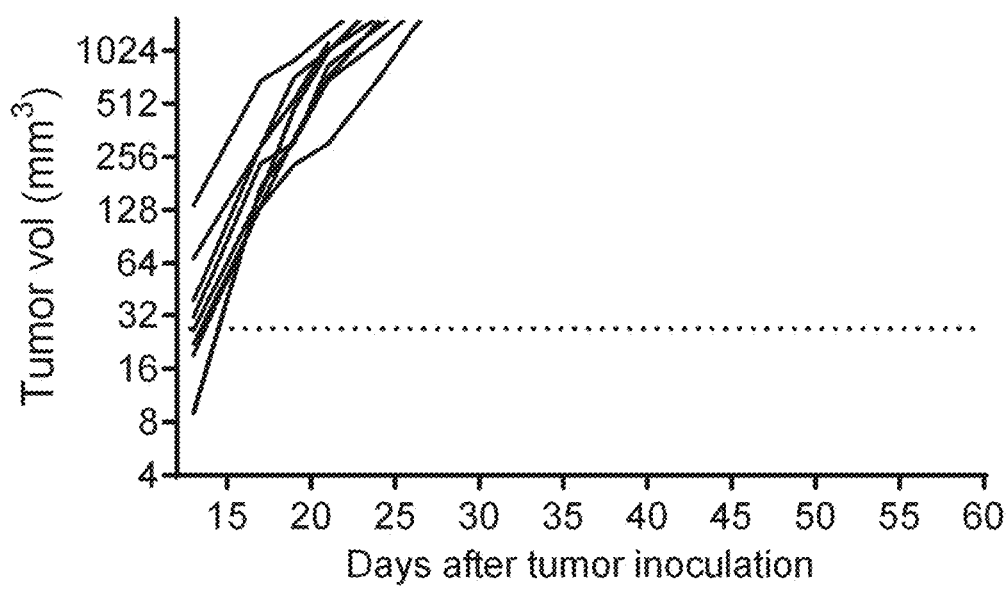
Figure 21I:
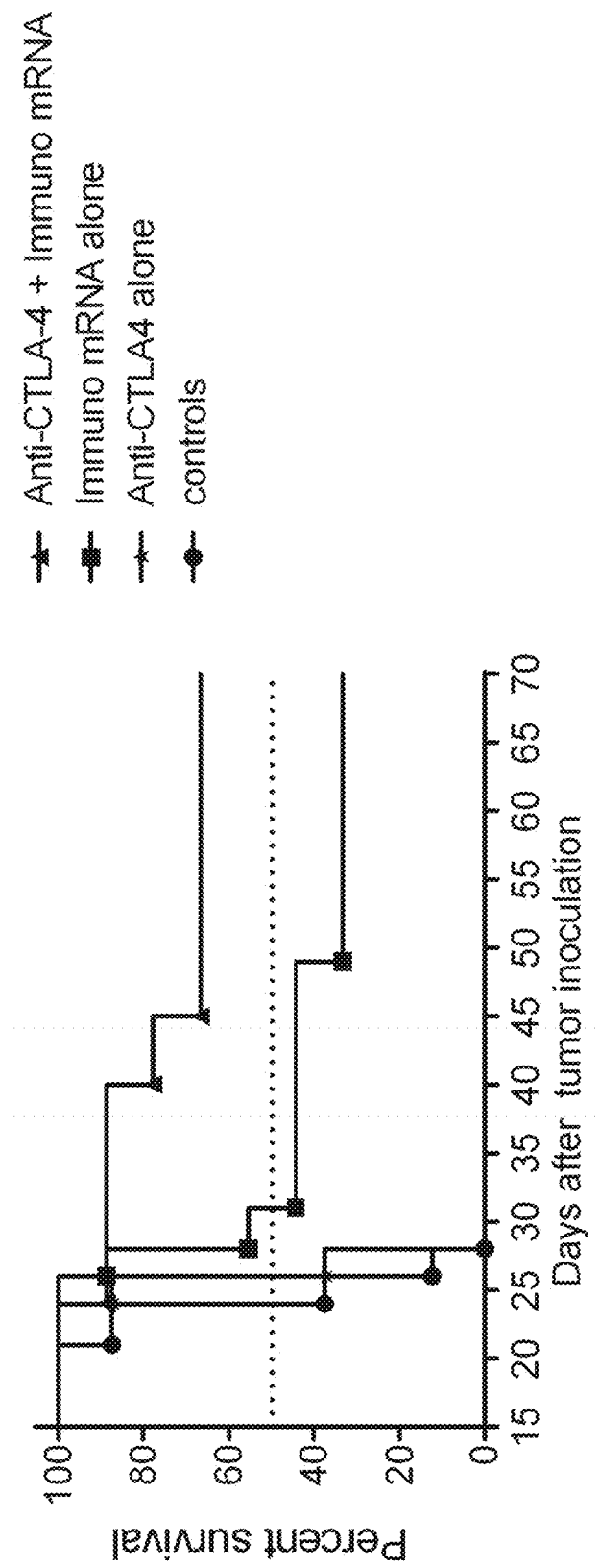

To further evaluate the effect of intratumoral injection of cytokine mRNA in combination with an anti-CTLA-4 antibody, mice were engrafted with B16F10 tumor cells on right flanks. Mice received three intratumoral injections with cytokine mRNA mixture of IL-15 sushi, IL-12sc, GM-CSF and IFNα (ModB; SEQ ID NOs: 53, 41, 59, and 47) on day 13, 17 and 20 after tumor inoculation. On day 13, 17, 20 and 24 after tumor inoculation mice also received intraperitoneal (IP) injections of an anti-CTLA-4 antibody (100 µg/200 µl per mouse; clone 9H10 from InVivoMAb) or the isotype control antibody (100 µg/200 µl per mouse; Armenian hamster IgG from BioXCell). Tumor growth of SC tumors as well as survival was monitored. Groups were as follows: 1) cytokine mRNA plus anti-CTLA-4 antibody (FIG. 21 E); 2) cytokine mRNA plus isotype control antibody (FIG. 21F); 3) control mRNA plus anti-CTLA-4 antibody (FIG. 21G) and 4) control mRNA plus isotype control antibody (FIG. 21H). Combination therapy of intratumoral cytokine mRNA and IP-injected anti-CTLA-4 resulted in strongest anti-tumoral activity with 6 tumor-free mice out of 9 mice on day 60 after tumor inoculation (FIG. 21E). Treatment with cytokine mRNA plus isotype control antibody (FIG. 21F) induced less anti-tumoral activity with 2 tumor-free mice out of 9 mice. In comparison, in the two groups that either received control mRNA plus anti-CTLA-4 antibody (FIG. 21G) or control mRNA plus isotype control antibody (FIG. 21H), no tumor-free mouse remained at the conclusion of the study. Percent survival is depicted in FIG. 21I, showing the highest overall survival in the combination of cytokine mRNA and anti-CTLA-4 treatment with 67% of mice bearing tumors at the end of the study (day 70), while 33% of mice treated with cytokine mRNA alone were tumor free. The results indicate strong antitumor activity associated with cytokine mRNA alone and cytokine mRNA and anti-CTLA-4 antibody in this B16F10 tumor model, in which anti-CTLA-4 antibody alone did not show any anti-tumor activity.

Example 9—mRNA Cytokine Injection in Multiple Cancer Types

Figure 22A:
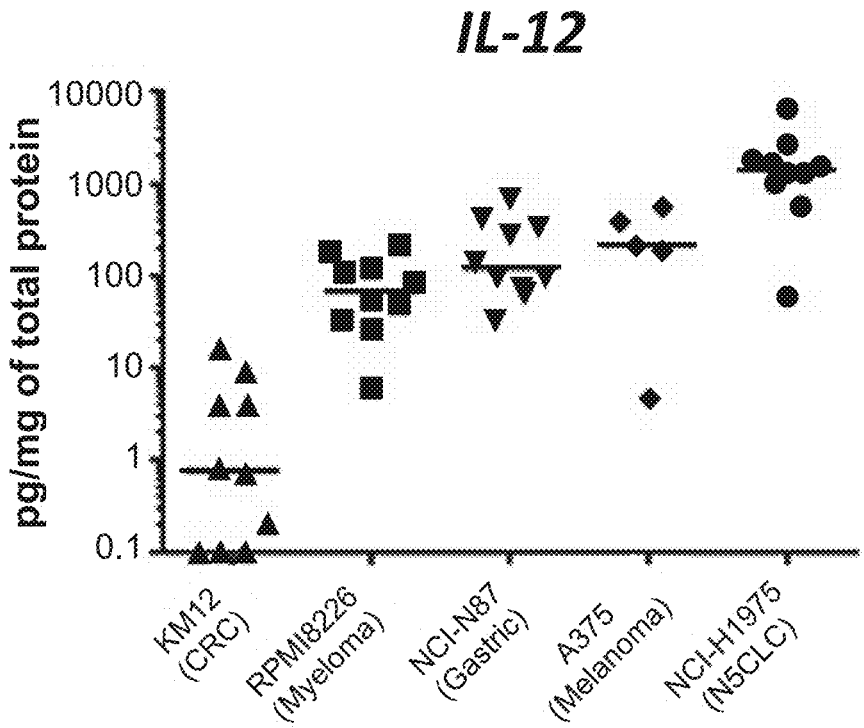
FIGS. 22A-22D shows the results of experiments designed to evaluate the effect of intratumoral injection of cytokine mRNA (Mod B) in human tumor xenografts of different human cancers. Intratumoral expression of each of the 4 mRNA encoded cytokines is shown: IL-12sc (FIG. 22A), IFNα2b (FIG. 22B), GM-CSF (FIG. 22C), and IL-15 sushi (FIG. 22D).
Figure 22B:
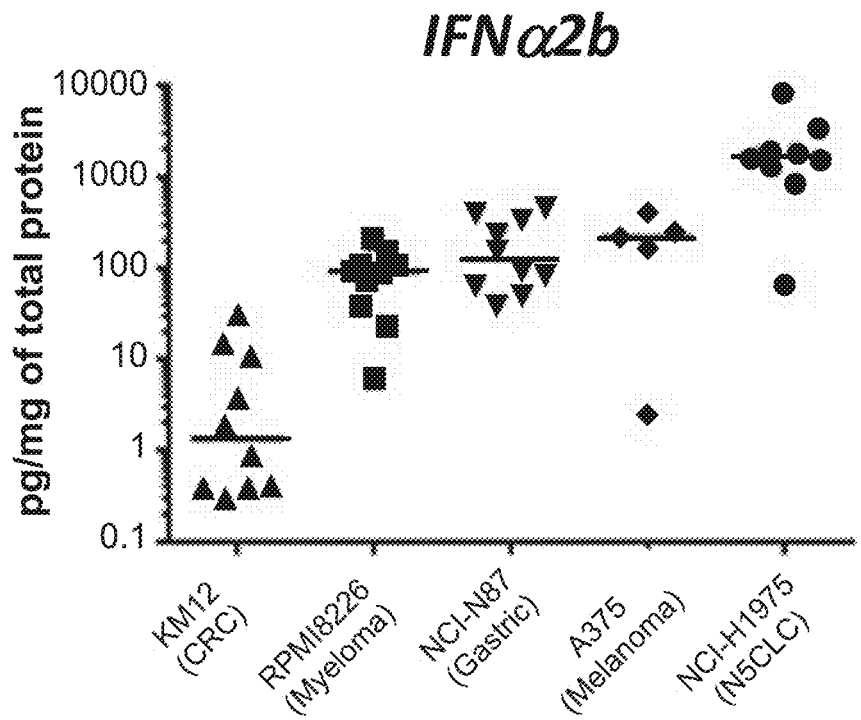
Figure 22C:
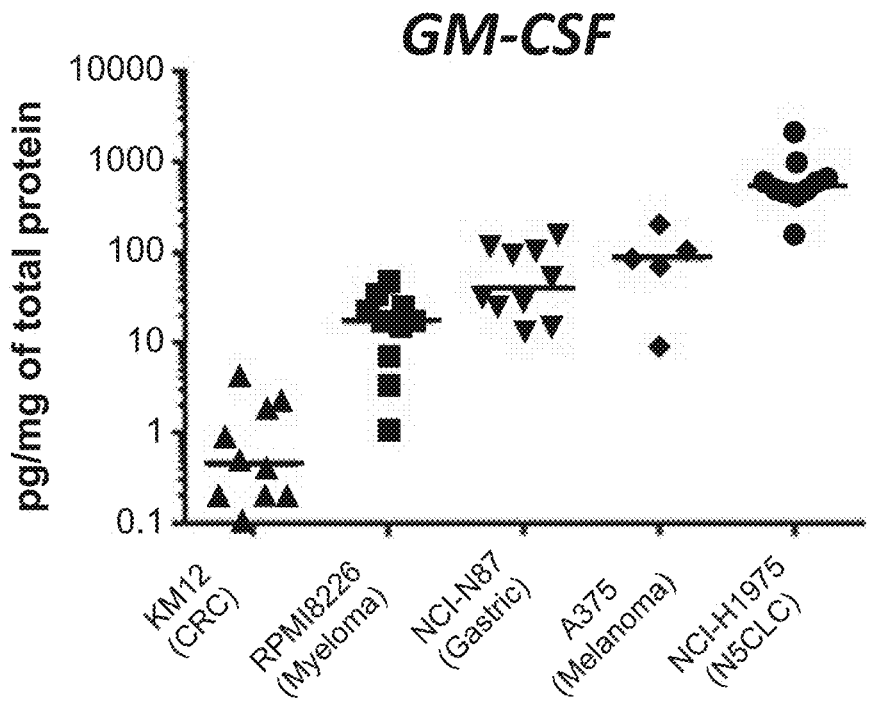
Figure 22D:
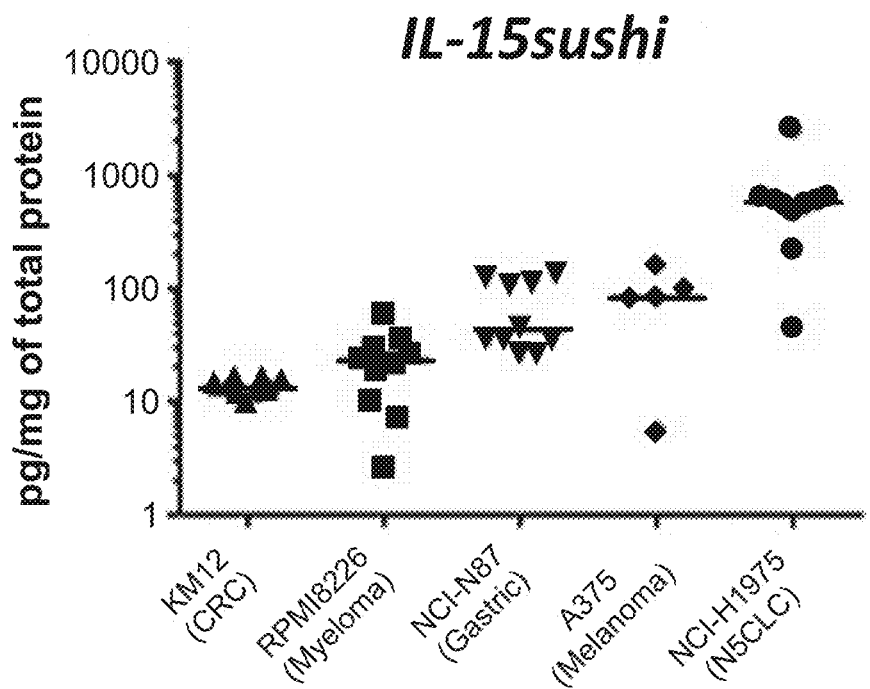
Figure 23A:
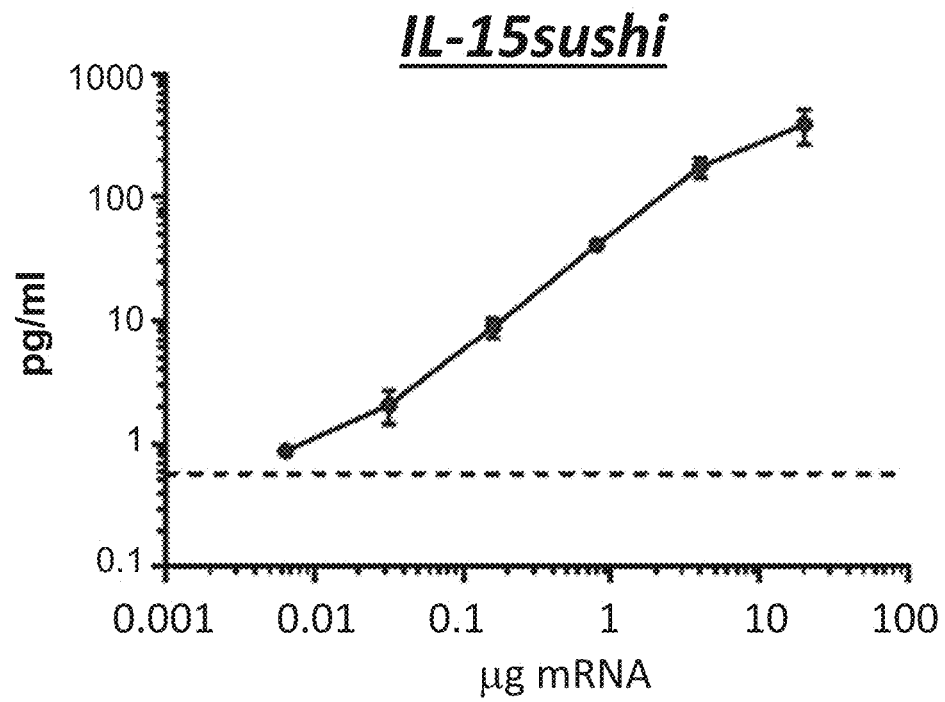
FIGS. 23A-23D show the results of experiments designed to evaluate the effect of different intratumoral mRNA doses on the expression of the encoded cytokines: IL-15 sushi (FIG. 23A), IL-12sc (FIG. 23B), GM-CSF (FIG. 23C) and IFNα2b (FIG. 23D).
Figure 23B:
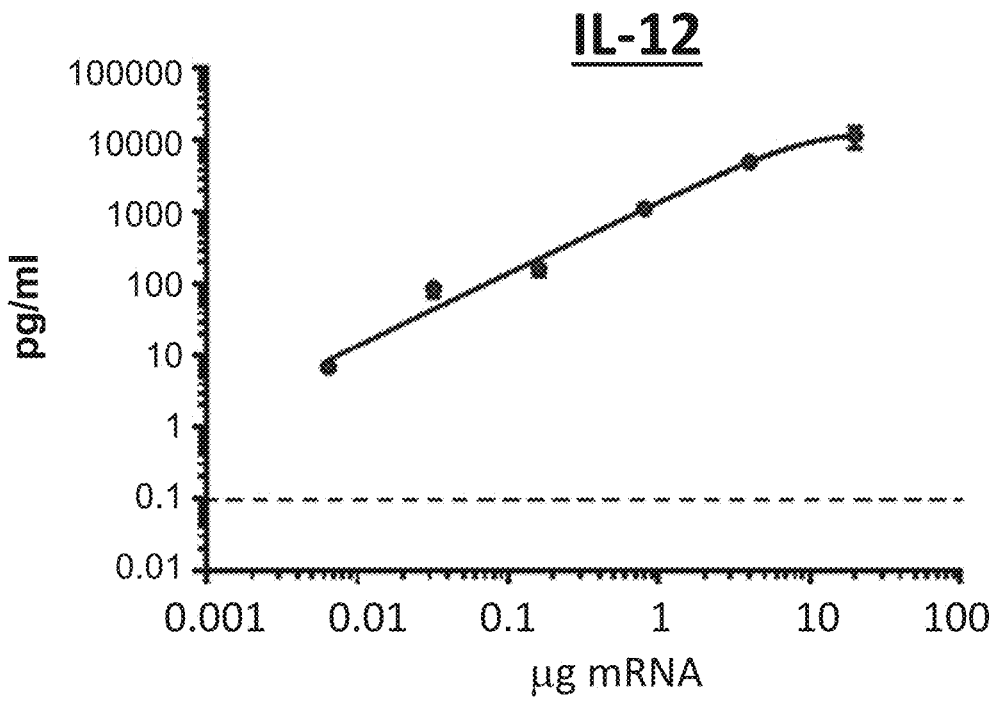
Figure 23C:
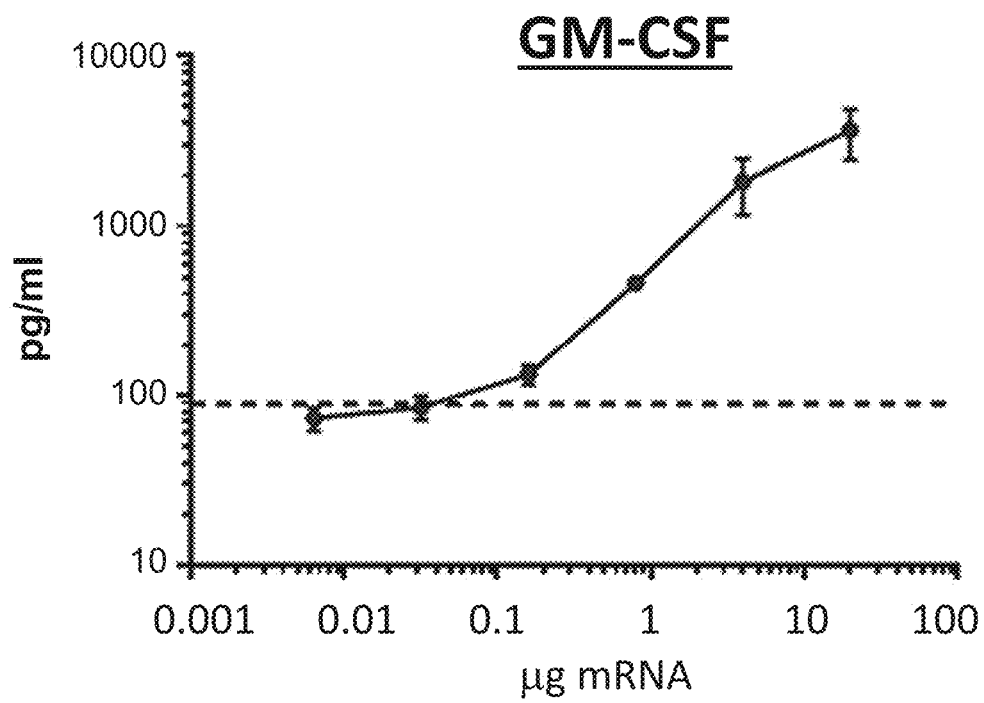
Figure 23D:
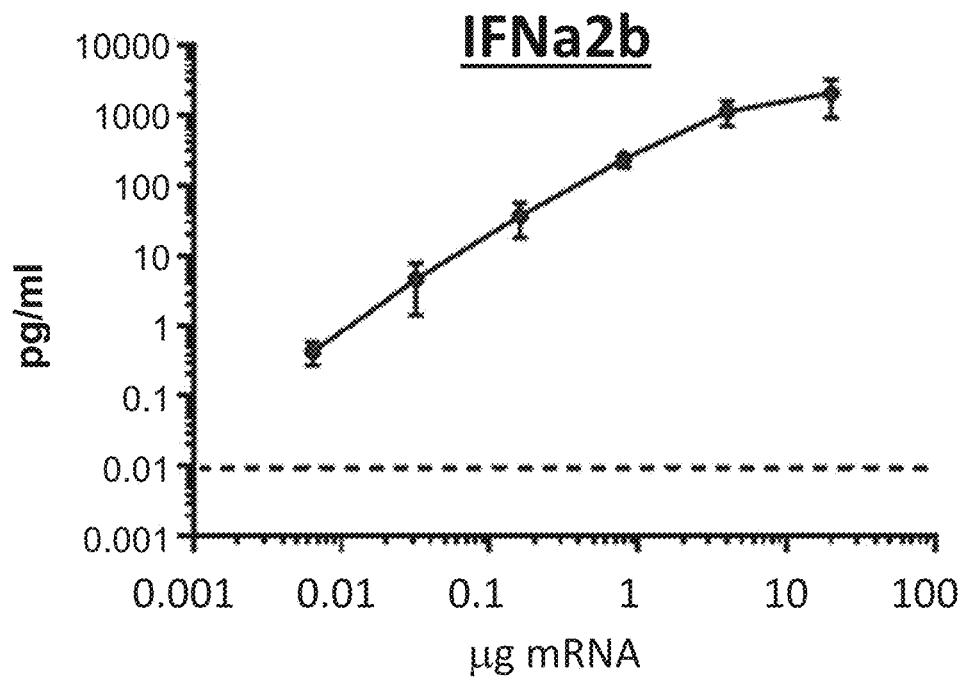

To evaluate the effect of intratumoral injection of cytokine mRNA in various types of cancer, five xenograft mouse models—KM12 (CRC), RPMI8226 (Myeloma), NCI-N87 (Gastric), A375 (Melanoma), and NCI-H1975 (NSCLC)—were tested as described in Example 1. Mice bearing KM12 (CRC), RPMI8226 (Myeloma), NCI-N87 (Gastric), A375 (Melanoma), and NCI-H1975 (NSCLC) tumors received a single intratumoral injection with 8 µg (2 µg/target) human cytokine mRNA mixture of IL-15 sushi, IL-12sc, GM-CSF and IFNα (ModB; SEQ ID NOs: 26, 18, 29, and 23) and the encoded cytokines were assessed in the tumor at 24 hours. Expression of each of the 4 cytokines of IL-15 sushi (FIG. 22D), IL-12sc (FIG. 22A), GM-CSF (FIG. 22C) and IFNα (FIG. 22B) was detected in all five of the xenograft models with the highest cytokines levels observed in NCI-H1975, followed by A375, NCI-N87, RPMI8226, and KM12.

Example 10—Dose Dependent Serum Expression of Cytokines after Intratumoral mRNA Cytokine Injection The effect of different intratumoral mRNA doses on the expression of the encoded cytokines was examined in the serum of mice engrafted with a single A375 tumor on the right flank. Mice received a single intratumoral injection of a cytokine mRNA mixture of human IL-15 sushi, IL-12sc, GM-CSF and IFNα (ModB; SEQ ID NOs: 26, 18, 29, and 23). At 6 hours after intratumoral mRNA injection, serum was collected and cytokine expression was analyzed by Meso Scale Discovery assay. Dose dependent expression of each of the mRNA encoded cytokines was observed in the serum from the highest dose of 80 µg (20 µg) to the lowest dose of 0.0256 µg (0.0064 µg). Results are shown in FIGS. 23A-D.

Example 11—Cytokine mRNA Leads to Expansion of Gp70+ CD8 T Cells

Mice bearing a single CT26 tumor on one flank received a four intratumoral injections of a cytokine mRNA mixture of IL-15 sushi, GM-CSF, IFNα, and IL-12sc (ModB; SEQ ID NOs: 53, 41, 59, and 47). Blood was collected 13 days after first intratumoral mRNA administration and T cells specific for the gp70 tumor antigen were quantified by flow cytometry. Frequency of T cells specific for the gp70 tumor antigen in blood were strongly increased in mice upon intratumoral injection of mRNA cytokines compared to mice that had received control RNA.

Example 12—Cytokine mRNA Induces Multiple Pro-Inflammatory Pathways and Increases Immune Infiltrate in Both Treated and Untreated Tumors Mice bearing B16F10 tumors on the left and right flank received a single intratumoral injection of 80 µg of mRNA (20 µg/target) into right tumor which was initiated with 0.5×10^6 cells (treated), while the tumor initiated with 0.25×10^6 cells remained untreated. At seven days after intratumoral injection of mRNA, both tumors were collected, and RNA was isolated and subjected to RNA sequencing analysis. As shown in FIGS. 27A-C, treatment with a cytokine mRNA mixture of IL-15 sushi, GM-CSF, IFNα, and IL-12sc (SEQ ID NOs: 59, 53, 41, and 47) upregulated multiple proinflammatory pathways including a range of IFNgamma response genes. The upregulation of proinflammatory/IFNgamma related pathways occurred in both the treated and untreated tumors, supporting the notion that local intratumoral treatment has systemic immune modulatory effects.

Causal network analysis (part of Ingenuity pathway analysis tool) was performed on 3298 genes that were differentially expressed (1699 up-regulated and 1599 down-regulated) between cytokine mRNA treatment and control in injected flank and 4973 genes (2546 up-regulated and 2427 down-regulated) in un-injected flank to identify changes in signaling pathways that could explain the observed changes in gene expression. Z scores were calculated to indicate the changes in pathways, with signs of score indicating the direction of change (positive sign suggests the activation whereas negative sign suggests inhibition).

Hierarchical clustering on expression of 328 genes regulated by IFNG (295 up-regulation and 33 down-regulation) was performed in both control and cytokine mRNA treated samples in both injected and un-injected tumors. Expression of each gene across samples were z-score normalized. The similarity metric is based on Pearson's correlation coefficient and complete-linkage is used to generate dendrogram. See, Table 6.

Relative abundance of infiltrated immune cells is determined by calculating the average expression of immune cell-type specific gene signatures.

TABLE 6

| Gene | IFNG_regulation | Treated_cytokine mRNA mix/IgG1 vs Luc mRNA/IgG1. FoldChange | Treated_cytokine mRNA mix/IgG1 vs Luc mRNA/IgG1. RawPValue | Treated_cytokine mRNA mix/IgG1 vs Luc mRNA/IgG1. FDR_BH | Untreated_cytokine mRNA mix/IgG1 vs Luc mRNA/IgG1. Foldchange | Untreated_cytokine mRNA mix/IgG1 vs Luc mRNA/IgG1. RawPValue | Untreated_cytokine mRNA mix/IgG1 vs Luc mRNA/IgG1. FDR_BH |
|---|---|---|---|---|---|---|---|
| ABI1 | Activate | 1.6776 | 0.0073 | 0.0995 | 1.5218 | 0.0354 | 0.1551 |
| ACOD1 | Activate | 31.6293 | 3.9652E−06 | 0.0024 | 6.1017 | 0.0096 | 0.0911 |
| ADGRG2 | Activate | 1.8174 | 0.0248 | 0.2076 | 1.3902 | 0.2293 | 0.4662 |
| ADORA2B | Activate | 2.9657 | 0.0044 | 0.0752 | 1.4261 | 0.352 | 0.6138 |
| AIF1 | Activate | 6.0406 | 0.0005 | 0.0201 | 4.7598 | 0.0032 | 0.057 |
| AIM2 | Activate | 9.9707 | 0.000085324 | 0.0086 | 3.4835 | 0.0276 | 0.1361 |
| ANGPTL4 | Activate | 2.0707 | 0.0293 | 0.2265 | 2.0904 | 0.0368 | 0.1586 |
| APOL6 | Activate | 10.3994 | 0.0017 | 0.0418 | 10.1341 | 0.0031 | 0.0564 |
| APP | Activate | 2.0312 | 0.0006 | 0.0238 | 2.2382 | 0.0003 | 0.0276 |
| ARFGAP3 | Activate | 1.6535 | 0.0146 | 0.1517 | 1.0201 | 0.9237 | 1 |
| ASS1 | Activate | 3.5414 | 0.0084 | 0.1093 | −1.0202 | 0.9668 | 1 |
| ATF3 | Activate | 5.5284 | 0.0006 | 0.0231 | −1.1007 | 0.8409 | 1 |
| B2M | Activate | 4.7005 | 0.000092097 | 0.0089 | 2.7946 | 0.0085 | 0.0859 |
| BACH1 | Activate | 2.2944 | 0.0098 | 0.1179 | 1.3281 | 0.3821 | 0.6482 |
| BATF2 | Activate | 4.0479 | 0.0211 | 0.1885 | 1.6468 | 0.4201 | 0.6889 |
| BCL2L11 | Activate | 4.2973 | 0.0057 | 0.0868 | 1.1465 | 0.7946 | 1 |
| BCL3 | Activate | 4.4411 | 0.0167 | 0.1639 | 2.5676 | 0.1413 | 0.3455 |
| BLNK | Activate | 4.2753 | 0.0003 | 0.0158 | 3.2008 | 0.0044 | 0.0643 |
| BST1 | Activate | 16.9081 | 1.3371E−06 | 0.0016 | 6.6164 | 0.0007 | 0.0334 |
| BTG1 | Activate | 3.5307 | 0.0001 | 0.0102 | −1.1775 | 0.5968 | 0.8607 |
| C1QA | Activate | 5.3999 | 0.0029 | 0.0588 | 1.3506 | 0.5911 | 0.8558 |
| C1QB | Activate | 5.955 | 0.0104 | 0.1219 | 3.531 | 0.0786 | 0.2408 |
| C1QC | Activate | 6.2282 | 0.0009 | 0.0307 | 2.7013 | 0.0707 | 0.2284 |
| C2 | Activate | 2.2866 | 0.0367 | 0.2598 | 2.5908 | 0.0242 | 0.1281 |
| C3 | Activate | 10.2057 | 0.0043 | 0.0734 | 11.6428 | 0.0044 | 0.0648 |
| C4B | Activate | 3.3143 | 0.0154 | 0.1562 | 1.3973 | 0.5045 | 0.7768 |
| C5AR1 | Activate | 6.4343 | 0.000061281 | 0.0074 | 1.8122 | 0.1729 | 0.3925 |
| CAMK4 | Activate | 2.5261 | 0.0011 | 0.0335 | 2.0726 | 0.012 | 0.1009 |
| CASP1 | Activate | 8.2891 | 0.0079 | 0.1049 | 6.7759 | 0.0214 | 0.1263 |
| CASP4 | Activate | 3.9281 | 0.0015 | 0.0389 | 1.2492 | 0.5969 | 0.8608 |
| CCL11 | Activate | 6.225 | 0.0028 | 0.0579 | 9.5207 | 0.0007 | 0.0334 |
| CCL17 | Activate | 3.9738 | 0.0268 | 0.2146 | 3.0432 | 0.0868 | 0.2549 |
| CCL2 | Activate | 5.0444 | 0.0331 | 0.2446 | 1.9159 | 0.4045 | 0.6716 |
| CCL22 | Activate | 5.4223 | 0.000050981 | 0.0069 | 3.6151 | 0.002 | 0.0467 |
| CCL3 | Activate | 8.2215 | 0.0007 | 0.0259 | 4.7966 | 0.0129 | 0.1045 |
| CCL4 | Activate | 8.7234 | 0.0008 | 0.0287 | 2.8285 | 0.1042 | 0.2846 |
| CCL5 | Activate | 19.1375 | 0.000004935 | 0.0027 | 9.4224 | 0.0004 | 0.0299 |
| CCL7 | Activate | 4.7053 | 0.0068 | 0.0952 | −1.2497 | 0.6964 | 0.9457 |
| CCL8 | Activate | 9.3589 | 0.0113 | 0.1283 | 3.9524 | 0.1286 | 0.3243 |
| CCR1 | Activate | 5.333 | 0.0012 | 0.0349 | 1.7221 | 0.2823 | 0.5325 |
| CCR2 | Activate | 5.8007 | 0.0025 | 0.0546 | 2.1931 | 0.1766 | 0.3975 |
| CCR5 | Activate | 10.8409 | 0.000010504 | 0.004 | 4.8697 | 0.0025 | 0.0512 |
| CCRL2 | Activate | 3.9822 | 0.002 | 0.0465 | 3.6428 | 0.0056 | 0.071 |
| CD14 | Activate | 5.6413 | 0.0025 | 0.0546 | 1.413 | 0.5406 | 0.8104 |
| CD2 | Activate | 13.539 | 0.0001 | 0.0095 | 5.0981 | 0.0138 | 0.1086 |
| CD274 | Activate | 11.0684 | 0.000096803 | 0.0091 | 3.4411 | 0.038 | 0.1616 |
| CD38 | Activate | 5.5697 | 0.0005 | 0.0212 | 1.4645 | 0.4221 | 0.6908 |
| CD40 | Activate | 11.0285 | 0.0003 | 0.0158 | 1.2537 | 0.7201 | 0.9637 |
| CD40LG | Activate | 3.1168 | 0.0068 | 0.0952 | 1.1976 | 0.6673 | 0.9224 |
| CD68 | Activate | 6.1325 | 0.000040468 | 0.0063 | 3.6801 | 0.0029 | 0.0544 |
| CD74 | Activate | 30.4664 | 0.000057089 | 0.0072 | 5.9291 | 0.0291 | 0.1392 |
| CD80 | Activate | 4.1003 | 0.0005 | 0.0217 | 3.5579 | 0.0026 | 0.0517 |
| CD86 | Activate | 6.3927 | 0.0008 | 0.027 | 8.2257 | 0.0004 | 0.0289 |
| CDKN2A | Activate | 1.9017 | 0.0117 | 0.1312 | −1.2679 | 0.3579 | 0.6202 |
| CEBPB | Activate | 4.4389 | 0.0007 | 0.0253 | 2.1429 | 0.0784 | 0.2404 |
| CELSR1 | Activate | 1.6953 | 0.0001 | 0.0107 | 1.1455 | 0.3001 | 0.5534 |
| CERS6 | Activate | 2.2538 | 0.0064 | 0.0927 | 1.717 | 0.0763 | 0.2363 |
| CFB | Activate | 9.003 | 0.0001 | 0.0109 | 6.2886 | 0.0018 | 0.0444 |
| CH25H | Activate | 4.3757 | 0.007 | 0.097 | 1.9042 | 0.2435 | 0.4858 |
| CHRNE | Activate | 1.6587 | 0.0293 | 0.2263 | 1.0536 | 0.8254 | 1 |

TABLE 6-continued

| Gene | IFNG_regulation | Treated_cytokine mRNA mix/IgG1 vs Luc mRNA/IgG1. FoldChange | Treated_cytokine mRNA mix/IgG1 vs Luc mRNA/IgG1. RawPValue | Treated_cytokine mRNA mix/IgG1 vs Luc mRNA/IgG1. FDR_BH | Untreated_cytokine mRNA mix/IgG1 vs Luc mRNA/IgG1. Foldchange | Untreated_cytokine mRNA mix/IgG1 vs Luc mRNA/IgG1. RawPValue | Untreated_cytokine mRNA mix/IgG1 vs Luc mRNA/IgG1. FDR_BH |
|---|---|---|---|---|---|---|---|
| CIITA | Activate | 6.2751 | 0.0008 | 0.0287 | 2.736 | 0.0651 | 0.2172 |
| CLEC2D | Activate | 4.9639 | 0.0002 | 0.0135 | 2.6567 | 0.0223 | 0.1263 |
| CLEC4E | Activate | 25.396 | 2.9823E−07 | 0.001 | 7.0201 | 0.0009 | 0.0355 |
| CLIC4 | Activate | 2.2909 | 0.000025847 | 0.0053 | 1.4654 | 0.0399 | 0.1658 |
| CMPK2 | Activate | 2.6988 | 0.0048 | 0.0785 | 1.9213 | 0.0687 | 0.2249 |
| CORO1A | Activate | 5.8653 | 0.0076 | 0.1019 | 2.1612 | 0.2494 | 0.4929 |
| CP | Activate | 2.7012 | 0.0222 | 0.1945 | 1.2703 | 0.5885 | 0.8544 |
| CSF1 | Activate | 5.3648 | 0.0071 | 0.0977 | 2.9314 | 0.0916 | 0.2624 |
| CSF2 | Activate | 2.4249 | 0.0053 | 0.0828 | 1.8261 | 0.0635 | 0.2145 |
| CSF2RB | Activate | 7.8798 | 0.000014063 | 0.0041 | 3.3417 | 0.008 | 0.0833 |
| CTSB | Activate | 2.9396 | 0.0192 | 0.1786 | −1.5854 | 0.3271 | 0.5867 |
| CTSD | Activate | 1.7662 | 0.0058 | 0.0873 | 1.5654 | 0.0351 | 0.1546 |
| CTSH | Activate | 6.6723 | 0.0004 | 0.0189 | 3.0998 | 0.0341 | 0.1523 |
| CTSS | Activate | 14.2913 | 0.000052305 | 0.0069 | 2.0554 | 0.2402 | 0.4813 |
| CXCL1 | Activate | 2.4631 | 0.0443 | 0.2909 | 2.3701 | 0.0679 | 0.223 |
| CXCL10 | Activate | 4.0615 | 0.0183 | 0.174 | 3.84 | 0.0314 | 0.1453 |
| CXCL11 | Activate | 6.3825 | 0.0032 | 0.0623 | 2.1745 | 0.2167 | 0.4494 |
| CXCL12 | Activate | 4.1992 | 0.0099 | 0.1191 | 3.9497 | 0.0188 | 0.1263 |
| CXCL16 | Activate | 11.7476 | 0.000012898 | 0.0041 | 2.7724 | 0.052 | 0.1919 |
| CXCL2 | Activate | 17.8737 | 0.000065478 | 0.0076 | 2.0435 | 0.2897 | 0.5414 |
| CXCL3 | Activate | 2.5623 | 0.0157 | 0.1584 | −1.1159 | 0.7808 | 1 |
| CXCL9 | Activate | 10.5652 | 0.002 | 0.0475 | 6.7433 | 0.0152 | 0.1139 |
| CYBB | Activate | 10.2429 | 0.0001 | 0.0102 | 2.4115 | 0.1288 | 0.3246 |
| CYLD | Activate | 2.1952 | 0.0005 | 0.0217 | 1.0366 | 0.8685 | 1 |
| CYSLTR2 | Activate | 4.6876 | 0.0015 | 0.0389 | −1.3886 | 0.4896 | 0.7624 |
| DAPK1 | Activate | 2.9566 | 0.0202 | 0.1837 | 2.3734 | 0.0752 | 0.2341 |
| DAXX | Activate | 2.5923 | 0.0255 | 0.2101 | 2.7152 | 0.0271 | 0.1349 |
| DDIT3 | Activate | 2.2027 | 0.0286 | 0.2233 | 2.4229 | 0.0212 | 0.1263 |
| DDX58 | Activate | 2.2084 | 0.0054 | 0.084 | 1.2566 | 0.422 | 0.6908 |
| DPP4 | Activate | 4.4101 | 0.047 | 0.3002 | 2.2805 | 0.2869 | 0.5383 |
| DTX3L | Activate | 3.4716 | 0.000027857 | 0.0053 | 1.6387 | 0.0759 | 0.2356 |
| EBI3 | Activate | 5.2118 | 0.0003 | 0.0153 | 2.8451 | 0.0203 | 0.1263 |
| ECE1 | Activate | 3.9089 | 0.0033 | 0.0624 | 1.8673 | 0.1782 | 0.3996 |
| EGLN3 | Activate | 2.9572 | 0.0465 | 0.2989 | 1.0391 | 0.9453 | 1 |
| EGR2 | Activate | 2.4479 | 0.0155 | 0.157 | 2.5764 | 0.0158 | 0.1159 |
| ERAP1 | Activate | 2.5669 | 0.0033 | 0.0634 | 2.2811 | 0.0134 | 0.1068 |
| FAM26F | Activate | 14.7052 | 0.0008 | 0.0279 | 26.6887 | 0.0002 | 0.0227 |
| FAS | Activate | 7.0896 | 0.0003 | 0.0169 | 4.7216 | 0.0052 | 0.0695 |
| FCER1G | Activate | 6.7045 | 0.0007 | 0.0254 | 4.8631 | 0.0059 | 0.0728 |
| FGF2 | Activate | 2.9272 | 0.0257 | 0.2106 | 1.8257 | 0.2249 | 0.4606 |
| FGL2 | Activate | 12.456 | 9.3027E−06 | 0.0038 | 4.9116 | 0.0036 | 0.0599 |
| FPR2 | Activate | 26.1833 | 0.000096227 | 0.0091 | 4.1758 | 0.0744 | 0.2328 |
| FTH1 | Activate | 1.6855 | 0.0413 | 0.2791 | 2.2166 | 0.0045 | 0.0657 |
| GBP2 | Activate | 7.2783 | 0.0007 | 0.0248 | 6.7229 | 0.0017 | 0.0437 |
| GBP3 | Activate | 6.2795 | 0.0006 | 0.0222 | 3.0356 | 0.0358 | 0.156 |
| GBP4 | Activate | 18.7632 | 0.0002 | 0.0139 | 6.7981 | 0.0154 | 0.1146 |
| GBP5 | Activate | 18.254 | 0.0003 | 0.0157 | 7.5534 | 0.0118 | 0.1 |
| GBP6 | Activate | 6.4537 | 0.0004 | 0.0187 | 8.0969 | 0.0002 | 0.0266 |
| GBP7 | Activate | 4.3285 | 0.0017 | 0.0427 | 2.3295 | 0.0713 | 0.2296 |
| GCH1 | Activate | 3.9933 | 0.0057 | 0.0867 | −2.2318 | 0.1144 | 0.3009 |
| GNA13 | Activate | 1.843 | 0.0129 | 0.1403 | 1.2404 | 0.3874 | 0.6539 |
| GSDMD | Activate | 5.5069 | 0.000067203 | 0.0076 | 4.0075 | 0.0013 | 0.0403 |
| GZMB | Activate | 10.9342 | 0.001 | 0.0323 | 11.0118 | 0.0018 | 0.0442 |
| H2-M3 | Activate | 6.3613 | 0.0003 | 0.0169 | −1.2831 | 0.6129 | 0.8754 |
| H2-Q7 | Activate | 13.035 | 0.00007123 | 0.0078 | 13.2107 | 0.0001 | 0.0209 |
| H2-T23 | Activate | 9.9835 | 0.0035 | 0.0651 | 1.093 | 0.9091 | 1 |
| HCAR2 | Activate | 5.1405 | 0.0007 | 0.0254 | 3.0731 | 0.0206 | 0.1263 |
| HCK | Activate | 7.0952 | 0.000025322 | 0.0053 | 4.1767 | 0.0019 | 0.0455 |
| HIF1A | Activate | 1.661 | 0.0261 | 0.2122 | 1.117 | 0.6345 | 0.8942 |
| HMOX1 | Activate | 2.9191 | 0.0049 | 0.0797 | 2.2892 | 0.0345 | 0.1532 |
| ICAM1 | Activate | 5.8185 | 0.0005 | 0.0217 | 4.9939 | 0.0023 | 0.0487 |
| ICOSL | Activate | 1.9545 | 0.0086 | 0.1107 | 1.8592 | 0.0203 | 0.1263 |
| IDO1 | Activate | 2.1676 | 0.007 | 0.097 | 1.5151 | 0.1535 | 0.3644 |
| IFI27 | Activate | 2.1198 | 0.0058 | 0.088 | 1.1685 | 0.5669 | 0.8345 |
| IFI44 | Activate | 10.2739 | 0.0001 | 0.0093 | 5.8893 | 0.0032 | 0.057 |
| IFIH1 | Activate | 3.3922 | 0.0001 | 0.0093 | 1.8886 | 0.0369 | 0.1588 |
| IFIT1 | Activate | 4.7651 | 0.000038724 | 0.0062 | 2.3488 | 0.0191 | 0.1263 |
| IFIT2 | Activate | 2.6547 | 0.0381 | 0.266 | 1.6098 | 0.3269 | 0.5865 |
| IFIT3 | Activate | 6.6433 | 0.0003 | 0.0153 | 2.3076 | 0.0981 | 0.2746 |
| IFITM1 | Activate | 13.8818 | 0.0017 | 0.0427 | 4.0409 | 0.096 | 0.2703 |
| IFITM3 | Activate | 5.3416 | 0.000049885 | 0.0069 | 4.6318 | 0.0003 | 0.0278 |
| IFNG | Activate | 15.8295 | 0.000030559 | 0.0055 | 5.3984 | 0.0086 | 0.0862 |

TABLE 6-continued

| Gene | IFNG_regulation | Treated_cytokine mRNA mix/IgG1 vs Luc mRNA/IgG1. FoldChange | Treated_cytokine mRNA mix/IgG1 vs Luc mRNA/IgG1. RawPValue | Treated_cytokine mRNA mix/IgG1 vs Luc mRNA/IgG1. FDR_BH | Untreated_cytokine mRNA mix/IgG1 vs Luc mRNA/IgG1. Foldchange | Untreated_cytokine mRNA mix/IgG1 vs Luc mRNA/IgG1. RawPValue | Untreated_cytokine mRNA mix/IgG1 vs Luc mRNA/IgG1. FDR_BH |
|---|---|---|---|---|---|---|---|
| IFNGR1 | Activate | 4.6529 | 0.0003 | 0.0169 | 1.1624 | 0.713 | 0.9579 |
| IKBKE | Activate | 3.6191 | 0.000070796 | 0.0078 | 2.1509 | 0.0151 | 0.1135 |
| IL10RA | Activate | 6.6362 | 0.0006 | 0.0225 | 2.2744 | 0.1259 | 0.3198 |
| IL12B | Activate | 1.5869 | 0.0237 | 0.2019 | 1.3356 | 0.1698 | 0.3882 |
| IL12RB1 | Activate | 3.6563 | 0.0032 | 0.0623 | 2.7374 | 0.0261 | 0.1323 |
| IL12RB2 | Activate | 10.8737 | 0.0001 | 0.0105 | 2.7693 | 0.0898 | 0.2596 |
| IL15RA | Activate | 5.6222 | 0.0002 | 0.0124 | 3.263 | 0.01 | 0.0929 |
| IL18BP | Activate | 13.3799 | 0.000016505 | 0.0045 | 2.6518 | 0.0808 | 0.2445 |
| IL18R1 | Activate | 10.5794 | 0.0004 | 0.0172 | 4.1773 | 0.0288 | 0.1387 |
| IL18RAP | Activate | 12.8979 | 1.6368E−06 | 0.0016 | 3.9032 | 0.0058 | 0.0721 |
| IL1A | Activate | 5.0611 | 0.0002 | 0.014 | 2.016 | 0.1006 | 0.2792 |
| IL1B | Activate | 7.1785 | 0.0017 | 0.0427 | 2.9628 | 0.0846 | 0.2505 |
| IL1RL1 | Activate | 3.2501 | 0.0421 | 0.2825 | 2.7191 | 0.0999 | 0.2778 |
| IL1RN | Activate | 11.4696 | 0.000016637 | 0.0045 | 3.5493 | 0.0183 | 0.1256 |
| IL27 | Activate | 5.0377 | 0.0003 | 0.0145 | 2.9655 | 0.0136 | 0.1077 |
| IL2RA | Activate | 12.629 | 0.000036735 | 0.0059 | 9.0232 | 0.0004 | 0.03 |
| IL3RA | Activate | 2.0071 | 0.0463 | 0.2977 | −2.3554 | 0.0222 | 0.1263 |
| INHBA | Activate | 7.0079 | 0.0006 | 0.0238 | 8.1176 | 0.0005 | 0.0316 |
| IRF1 | Activate | 4.8896 | 0.0002 | 0.0136 | 4.2429 | 0.0011 | 0.0383 |
| IRF2 | Activate | 3.0856 | 0.0001 | 0.0102 | 2.3475 | 0.0038 | 0.0609 |
| IRF4 | Activate | 3.6001 | 0.0009 | 0.0303 | 2.7396 | 0.0107 | 0.0955 |
| IRF5 | Activate | 6.3959 | 0.0039 | 0.0697 | 6.2724 | 0.0066 | 0.0767 |
| IRF7 | Activate | 4.6951 | 0.0016 | 0.0408 | 2.6708 | 0.0468 | 0.1806 |
| IRGM1 | Activate | 3.5604 | 0.0205 | 0.1855 | 3.8887 | 0.0196 | 0.1263 |
| ISG15 | Activate | 6.1635 | 0.0003 | 0.0158 | 2.64 | 0.0488 | 0.1845 |
| ISG20 | Activate | 3.3567 | 0.0012 | 0.0349 | 3.9719 | 0.0006 | 0.0322 |
| ITGA4 | Activate | 2.0304 | 0.0397 | 0.272 | 2.0083 | 0.055 | 0.1984 |
| ITGAL | Activate | 16.3545 | 0.000032377 | 0.0056 | 6.1759 | 0.0055 | 0.0707 |
| ITGAM | Activate | 8.5704 | 0.0093 | 0.1151 | 3.5033 | 0.1371 | 0.3385 |
| ITGAX | Activate | 3.9189 | 0.0101 | 0.1202 | 2.0482 | 0.185 | 0.4084 |
| ITGB2 | Activate | 7.7479 | 0.0002 | 0.0124 | 6.9547 | 0.0006 | 0.0332 |
| JAK2 | Activate | 1.6647 | 0.0461 | 0.2976 | 1.3678 | 0.2378 | 0.4779 |
| JUN | Activate | 1.7589 | 0.0035 | 0.0649 | −1.1739 | 0.4037 | 0.6708 |
| KLF4 | Activate | 1.907 | 0.0409 | 0.2778 | 1.156 | 0.6546 | 0.9116 |
| KLF6 | Activate | 2.4625 | 0.0037 | 0.0672 | 2.1351 | 0.0182 | 0.125 |
| KYNU | Activate | 3.8871 | 0.008 | 0.1057 | 4.8859 | 0.0039 | 0.061 |
| LAG3 | Activate | 7.4221 | 0.0002 | 0.0114 | 2.156 | 0.1298 | 0.3262 |
| LAT2 | Activate | 2.6441 | 0.028 | 0.2208 | 1.5322 | 0.3475 | 0.6094 |
| LCN2 | Activate | 4.3524 | 0.0296 | 0.2275 | 16.3586 | 0.0003 | 0.0276 |
| LCP2 | Activate | 8.4235 | 0.0004 | 0.0193 | 4.07 | 0.0205 | 0.1263 |
| LGALS9 | Activate | 1.6825 | 0.0051 | 0.0817 | 1.6728 | 0.0085 | 0.086 |
| LST1 | Activate | 7.6841 | 0.02 | 0.1832 | 1.6707 | 0.5648 | 0.8328 |
| LTA | Activate | 2.7386 | 0.0055 | 0.0851 | 2.4968 | 0.0157 | 0.1157 |
| LTB | Activate | 8.1723 | 0.0014 | 0.0379 | 2.3655 | 0.1846 | 0.4079 |
| LY6E | Activate | 5.1119 | 0.0028 | 0.0572 | 2.8148 | 0.061 | 0.2104 |
| LY96 | Activate | 2.4218 | 0.0302 | 0.2305 | 1.5311 | 0.3103 | 0.5661 |
| LYN | Activate | 5.1219 | 0.001 | 0.0325 | 1.6841 | 0.2851 | 0.536 |
| MAP3K8 | Activate | 7.131 | 0.0009 | 0.0302 | 1.0205 | 0.9717 | 1 |
| MEFV | Activate | 10.8378 | 0.000019758 | 0.0047 | 2.3756 | 0.0951 | 0.2688 |
| MMP12 | Activate | 6.4662 | 0.0035 | 0.0647 | 5.0068 | 0.015 | 0.1131 |
| MX1 | Activate | 6.1489 | 0.0128 | 0.1395 | 2.6469 | 0.1916 | 0.4171 |
| MX2 | Activate | 3.9804 | 0.0005 | 0.0205 | 1.8666 | 0.1068 | 0.2889 |
| NAMPT | Activate | 2.341 | 0.0066 | 0.0943 | −1.4194 | 0.2673 | 0.514 |
| NAPSA | Activate | 4.3452 | 0.0003 | 0.0149 | 4.7434 | 0.0003 | 0.0272 |
| NEURL3 | Activate | 5.943 | 0.0009 | 0.0291 | 1.9354 | 0.2066 | 0.4363 |
| NFKB1 | Activate | 1.8089 | 0.0051 | 0.0815 | 1.0738 | 0.7351 | 0.9751 |
| NFKBIA | Activate | 4.9409 | 0.000013016 | 0.0041 | 2.4668 | 0.0097 | 0.0912 |
| NFKBIZ | Activate | 2.328 | 0.0073 | 0.0995 | 2.0257 | 0.0308 | 0.1436 |
| NGF | Activate | 3.1687 | 0.0065 | 0.0933 | 3.4968 | 0.0055 | 0.0706 |
| NLRC5 | Activate | 3.4173 | 0.0109 | 0.1261 | 2.2706 | 0.0985 | 0.2752 |
| NLRP3 | Activate | 5.11 | 0.0007 | 0.0254 | 3.4525 | 0.0111 | 0.0975 |
| NMI | Activate | 2.0435 | 0.0228 | 0.1979 | 1.6117 | 0.1416 | 0.3459 |
| NOD2 | Activate | 3.5157 | 0.000018135 | 0.0045 | 2.5449 | 0.0013 | 0.0396 |
| NOS2 | Activate | 26.5216 | 2.2445E−06 | 0.0017 | 24.8128 | 7.9556E−06 | 0.0117 |
| NOTCH1 | Activate | 2.2952 | 0.0301 | 0.2303 | 1.4949 | 0.3078 | 0.5625 |
| NR1D1 | Activate | 1.7995 | 0.0049 | 0.0799 | 1.8784 | 0.0045 | 0.065 |
| NUPR1 | Activate | 2.8421 | 0.001 | 0.0318 | 1.7353 | 0.0807 | 0.2444 |
| OAS2 | Activate | 3.8997 | 0.0003 | 0.0154 | 2.3682 | 0.0204 | 0.1263 |
| OAS3 | Activate | 14.5317 | 7.7153E−06 | 0.0034 | 4.0924 | 0.0123 | 0.1019 |
| P2RY14 | Activate | 16.6314 | 0.0005 | 0.0204 | 4.8513 | 0.0471 | 0.1812 |
| P2RY6 | Activate | 5.352 | 0.0001 | 0.0103 | 2.2094 | 0.0606 | 0.2093 |
| PARP9 | Activate | 3.1267 | 0.0179 | 0.1716 | −1.1573 | 0.7644 | 0.9977 |

TABLE 6-continued

| Gene | IFNG_regulation | Treated_cytokine mRNA mix/IgG1 vs Luc mRNA/IgG1. FoldChange | Treated_cytokine mRNA mix/IgG1 vs Luc mRNA/IgG1. RawPValue | Treated_cytokine mRNA mix/IgG1 vs Luc mRNA/IgG1. FDR_BH | Untreated_cytokine mRNA mix/IgG1 vs Luc mRNA/IgG1. Foldchange | Untreated_cytokine mRNA mix/IgG1 vs Luc mRNA/IgG1. RawPValue | Untreated_cytokine mRNA mix/IgG1 vs Luc mRNA/IgG1. FDR_BH |
|---|---|---|---|---|---|---|---|
| PARVG | Activate | 6.3047 | 0.0025 | 0.0539 | 1.2154 | 0.7444 | 0.9822 |
| PDCD1LG2 | Activate | 11.6201 | 2.1928E−06 | 0.0017 | 3.9612 | 0.0045 | 0.065 |
| PF4 | Activate | 6.7372 | 0.0284 | 0.2226 | −2.2437 | 0.3655 | 0.6285 |
| PIM1 | Activate | 4.0708 | 0.0003 | 0.0169 | 2.0732 | 0.0575 | 0.2034 |
| PLA2G16 | Activate | 4.8619 | 0.001 | 0.0309 | 1.3802 | 0.4886 | 0.7613 |
| PLAU | Activate | 3.8214 | 0.00003401 | 0.0058 | 2.1662 | 0.0131 | 0.1056 |
| PLEK | Activate | 5.9274 | 0.0049 | 0.0805 | 2.9561 | 0.0921 | 0.2632 |
| PMAIP1 | Activate | 3.4224 | 0.0002 | 0.0134 | 2.6199 | 0.0041 | 0.0627 |
| PRDM1 | Activate | 3.5702 | 0.0297 | 0.2283 | 4.0335 | 0.0251 | 0.13 |
| PRKCD | Activate | 4.5574 | 2.2524E−07 | 0.001 | 2.0325 | 0.0066 | 0.0768 |
| PRKCQ | Activate | 2.1379 | 0.0065 | 0.0932 | 2.1615 | 0.0089 | 0.087 |
| PSMB10 | Activate | 3.6197 | 0.005 | 0.0807 | 1.4724 | 0.3976 | 0.6643 |
| PSMB8 | Activate | 3.9093 | 0.0032 | 0.0615 | 2.652 | 0.0388 | 0.1637 |
| PSMB9 | Activate | 7.4132 | 0.0005 | 0.0197 | 4.5308 | 0.009 | 0.0877 |
| PSME1 | Activate | 6.1609 | 0.0001 | 0.0096 | 3.9584 | 0.0037 | 0.06 |
| PTAFR | Activate | 8.5218 | 0.000052564 | 0.0069 | 2.2614 | 0.1024 | 0.2821 |
| PTGES | Activate | 3.3225 | 0.0241 | 0.2039 | 1.61 | 0.3819 | 0.6479 |
| PTGS2 | Activate | 10.9036 | 0.0075 | 0.1017 | 3.9538 | 0.1309 | 0.3282 |
| PTX3 | Activate | 5.271 | 0.0253 | 0.2091 | 1.8833 | 0.4052 | 0.672 |
| RAB20 | Activate | 2.29 | 0.0257 | 0.2106 | 1.1261 | 0.7537 | 0.9893 |
| RAC2 | Activate | 7.9519 | 0.000098427 | 0.0091 | 3.7008 | 0.0123 | 0.1021 |
| RIPK1 | Activate | 1.6822 | 0.0456 | 0.2959 | −1.1344 | 0.6373 | 0.8964 |
| RSAD2 | Activate | 3.916 | 0.0003 | 0.0152 | 1.6141 | 0.184 | 0.407 |
| RTP4 | Activate | 4.8033 | 0.0025 | 0.0537 | 2.5839 | 0.0696 | 0.2269 |
| RUNX2 | Activate | 5.3191 | 0.0001 | 0.0095 | 2.2697 | 0.0491 | 0.185 |
| RUNX3 | Activate | 5.5652 | 0.0012 | 0.0354 | 5.5875 | 0.002 | 0.0467 |
| S100A10 | Activate | 2.1419 | 0.001 | 0.0318 | −1.0647 | 0.7799 | 1 |
| S100A8 | Activate | 10.9785 | 0.0065 | 0.0931 | 11.8118 | 0.0079 | 0.0832 |
| S100A9 | Activate | 5.1245 | 0.0058 | 0.0879 | 4.0622 | 0.0228 | 0.1263 |
| S1PR3 | Activate | 2.8084 | 0.0426 | 0.2844 | 4.3054 | 0.0083 | 0.0851 |
| SAMHD1 | Activate | 6.8165 | 0.000028539 | 0.0053 | 5.2676 | 0.0004 | 0.0289 |
| SELL | Activate | 9.0266 | 0.000036704 | 0.0059 | 2.6848 | 0.0503 | 0.1879 |
| SEMA4A | Activate | 4.5461 | 0.0002 | 0.0134 | 7.1376 | 0.000014188 | 0.0118 |
| SEPT3 | Activate | 1.9813 | 0.0021 | 0.0484 | 1.2827 | 0.2581 | 0.5036 |
| SERPINB9 | Activate | 3.6968 | 0.0068 | 0.0955 | 1.3544 | 0.5306 | 0.8014 |
| SERPINE1 | Activate | 2.7348 | 0.0131 | 0.142 | 1.0382 | 0.9268 | 1 |
| SERPING1 | Activate | 8.5956 | 0.0003 | 0.0154 | 5.6206 | 0.0042 | 0.063 |
| SHARPIN | Activate | 1.8222 | 0.0003 | 0.0169 | −1.1856 | 0.2897 | 0.5414 |
| SLAMF1 | Activate | 4.2282 | 0.000066073 | 0.0076 | 1.8422 | 0.0753 | 0.2344 |
| SLC11A1 | Activate | 8.1631 | 0.0002 | 0.0114 | 6.6594 | 0.0009 | 0.0364 |
| SLC15A3 | Activate | 13.0122 | 0.0001 | 0.0093 | 4.2688 | 0.0238 | 0.1278 |
| SLC16A9 | Activate | 2.2466 | 0.0273 | 0.2172 | 1.6072 | 0.21 | 0.4406 |
| SLC28A2 | Activate | 6.903 | 0.0001 | 0.0096 | 1.4304 | 0.4466 | 0.7176 |
| SLFN5 | Activate | 3.7058 | 0.0022 | 0.0493 | 2.1361 | 0.0772 | 0.2383 |
| SMAD7 | Activate | 3.1247 | 0.0209 | 0.187 | −1.1526 | 0.7767 | 1 |
| SOCS1 | Activate | 3.9437 | 0.011 | 0.1267 | 3.3365 | 0.0325 | 0.1481 |
| SOD2 | Activate | 2.6759 | 0.0047 | 0.0774 | 3.1489 | 0.0021 | 0.0475 |
| SOD3 | Activate | 2.1257 | 0.0158 | 0.1591 | 1.4255 | 0.2663 | 0.5128 |
| SP100 | Activate | 4.8282 | 7.0055E−06 | 0.0032 | 2.8699 | 0.0019 | 0.0452 |
| SP110 | Activate | 3.7976 | 0.0057 | 0.0867 | 1.1957 | 0.71 | 0.9556 |
| SPI1 | Activate | 10.5793 | 0.000055966 | 0.0071 | 6.5856 | 0.0014 | 0.0409 |
| SPP1 | Activate | 2.5268 | 0.0212 | 0.1893 | 2.4021 | 0.0384 | 0.1624 |
| STAT1 | Activate | 4.2736 | 0.0089 | 0.1122 | 3.9844 | 0.0176 | 0.1229 |
| STAT2 | Activate | 5.4847 | 0.000013182 | 0.0041 | 3.019 | 0.0035 | 0.0589 |
| STAT4 | Activate | 6.3819 | 0.0038 | 0.069 | 1.1576 | 0.8175 | 1 |
| STAT6 | Activate | 1.7399 | 0.0097 | 0.1171 | 1.7712 | 0.0116 | 0.0993 |
| STX11 | Activate | 3.6303 | 0.0058 | 0.088 | 1.7593 | 0.2306 | 0.4679 |
| TAP1 | Activate | 4.588 | 0.001 | 0.0323 | 2.7092 | 0.0329 | 0.1493 |
| TAP2 | Activate | 2.8268 | 0.0148 | 0.1526 | 1.5315 | 0.3257 | 0.585 |
| TAPBP | Activate | 2.5416 | 0.0274 | 0.2176 | 1.7971 | 0.1801 | 0.4019 |
| TAPBPL | Activate | 3.0796 | 0.0031 | 0.0609 | 2.4014 | 0.0251 | 0.13 |
| TBX21 | Activate | 3.8788 | 0.0008 | 0.0273 | 4.1566 | 0.0008 | 0.0354 |
| TCIRG1 | Activate | 2.7899 | 0.0005 | 0.0217 | 1.2508 | 0.4321 | 0.7008 |
| TGFBR2 | Activate | 1.9044 | 0.031 | 0.2346 | 1.2596 | 0.451 | 0.7222 |
| THBS1 | Activate | 2.8135 | 0.005 | 0.0807 | 2.9522 | 0.0055 | 0.0707 |
| THEMIS2 | Activate | 9.3368 | 0.0011 | 0.0339 | 6.5099 | 0.0079 | 0.0832 |
| THY1 | Activate | 5.5745 | 0.0036 | 0.0666 | 3.0999 | 0.0597 | 0.2073 |
| TLR1 | Activate | 3.9534 | 0.0044 | 0.0751 | 4.9709 | 0.002 | 0.0463 |
| TLR2 | Activate | 4.2854 | 0.0004 | 0.0173 | 1.0613 | 0.8785 | 1 |
| TLR7 | Activate | 3.6076 | 0.0317 | 0.2384 | 1.1789 | 0.7874 | 1 |
| TLR8 | Activate | 7.9426 | 0.0012 | 0.0349 | 1.5453 | 0.4846 | 0.7574 |
| TLR9 | Activate | 7.0125 | 0.0004 | 0.0182 | 5.5003 | 0.0026 | 0.052 |

TABLE 6-continued

| Gene | IFNG_ regulation | Treated_ cytokine mRNA mix/IgG1 vs Luc mRNA/IgG1. FoldChange | Treated_ cytokine mRNA mix/IgG1 vs Luc mRNA/IgG1. RawPValue | Treated_ cytokine mRNA mix/IgG1 vs Luc mRNA/IgG1. FDR_BH | Untreated_ cytokine mRNA mix/IgG1 vs Luc mRNA/IgG1. Foldchange | Untreated_ cytokine mRNA mix/IgG1 vs Luc mRNA/IgG1. RawPValue | Untreated_ cytokine mRNA mix/IgG1 vs Luc mRNA/IgG1. FDR_BH |
|---|---|---|---|---|---|---|---|
| TMEM50B | Activate | 2.2646 | 0.0029 | 0.0584 | 1.6005 | 0.089 | 0.2584 |
| TNF | Activate | 15.5761 | 0.000001549 | 0.0016 | 3.6025 | 0.014 | 0.1094 |
| TNFAIP2 | Activate | 4.2629 | 0.0043 | 0.0737 | 1.3184 | 0.5837 | 0.8504 |
| TNFRSF11A | Activate | 3.7342 | 0.0089 | 0.1124 | 3.2927 | 0.0236 | 0.1273 |
| TNFRSF14 | Activate | 3.3507 | 0.0151 | 0.1547 | 2.0443 | 0.1615 | 0.3761 |
| TNFRSF1B | Activate | 6.9767 | 0.0004 | 0.0187 | 3.0014 | 0.0433 | 0.1723 |
| TNFSF10 | Activate | 5.9466 | 0.0008 | 0.0286 | 2.8254 | 0.0505 | 0.1883 |
| TNFSF12 | Activate | 4.0396 | 0.0003 | 0.0145 | 3.0636 | 0.0039 | 0.061 |
| TNFSF13 | Activate | 3.7405 | 0.0229 | 0.1979 | −1.7547 | 0.3434 | 0.6048 |
| TNFSF13B | Activate | 4.2939 | 0.00009167 | 0.0089 | 1.0175 | 0.96 | 1 |
| TRAFD1 | Activate | 7.5123 | 0.000066493 | 0.0076 | 1.4364 | 0.4415 | 0.7113 |
| TRIM21 | Activate | 3.1067 | 0.0069 | 0.096 | −1.1129 | 0.7984 | 1 |
| TXK | Activate | 3.1599 | 0.0017 | 0.0418 | 1.8261 | 0.0992 | 0.2766 |
| UBD | Activate | 39.4489 | 3.1101E−06 | 0.0021 | 20.5238 | 0.0001 | 0.0203 |
| UBE2L6 | Activate | 3.418 | 0.002 | 0.0464 | 4.4962 | 0.0005 | 0.031 |
| USP18 | Activate | 5.4886 | 0.0004 | 0.0192 | 1.697 | 0.258 | 0.5036 |
| VCAM1 | Activate | 7.3103 | 0.0003 | 0.0163 | 1.2409 | 0.6812 | 0.9337 |
| WARS | Activate | 1.5033 | 0.0098 | 0.1179 | 1.8802 | 0.0003 | 0.0284 |
| ZFP36 | Activate | 3.0067 | 0.0051 | 0.0815 | −1.1887 | 0.6585 | 0.9153 |
| AHCY | Inhibit | −2.0639 | 0.0374 | 0.2628 | −1.8643 | 0.0878 | 0.2566 |
| AQP1 | Inhibit | −2.6893 | 0.0012 | 0.0354 | −2.9843 | 0.0008 | 0.0346 |
| AZGP1 | Inhibit | −3.6306 | 0.0039 | 0.0701 | −3.72 | 0.0054 | 0.0705 |
| CSE1L | Inhibit | −1.9528 | 0.0448 | 0.2931 | −4.9001 | 0.000053442 | 0.0177 |
| DHX9 | Inhibit | −1.9049 | 0.0192 | 0.1787 | −1.3891 | 0.2439 | 0.4863 |
| EMID1 | Inhibit | −2.5566 | 0.047 | 0.3003 | −1.9661 | 0.1701 | 0.3887 |
| FKBP6 | Inhibit | −4.1867 | 0.0043 | 0.0733 | −2.2618 | 0.1075 | 0.2898 |
| FLT4 | Inhibit | −1.7478 | 0.0248 | 0.2076 | −1.6367 | 0.0588 | 0.2058 |
| GMPR | Inhibit | −2.9853 | 0.027 | 0.2154 | −5.5877 | 0.0017 | 0.0432 |
| GNAO1 | Inhibit | −2.2497 | 0.0179 | 0.1721 | −1.0647 | 0.8565 | 1 |
| HSP90AB1 | Inhibit | −1.9951 | 0.007 | 0.0974 | −1.1404 | 0.6083 | 0.8715 |
| IDI1 | Inhibit | −2.9218 | 0.004 | 0.0713 | −2.402 | 0.023 | 0.1263 |
| IGFBP4 | Inhibit | −3.3872 | 0.0211 | 0.1885 | −3.0044 | 0.0473 | 0.1815 |
| MIF | Inhibit | −3.5707 | 0.0052 | 0.0828 | −1.3189 | 0.5425 | 0.8124 |
| MSH2 | Inhibit | −1.909 | 0.0328 | 0.2435 | −1.7932 | 0.0664 | 0.2198 |
| MYC | Inhibit | −1.8764 | 0.0225 | 0.1962 | −1.5059 | 0.1507 | 0.36 |
| PBK | Inhibit | −4.8198 | 0.0008 | 0.0287 | −10.4275 | 0.000012076 | 0.0117 |
| PCDH17 | Inhibit | −2.2868 | 0.0029 | 0.0588 | −1.1447 | 0.6223 | 0.8835 |
| PLCG1 | Inhibit | −1.6389 | 0.0439 | 0.2895 | 1.263 | 0.3564 | 0.6189 |
| POLR2F | Inhibit | −1.7137 | 0.0139 | 0.1473 | −2.1058 | 0.0019 | 0.0456 |
| POMP | Inhibit | −1.5182 | 0.047 | 0.3002 | −1.3884 | 0.1354 | 0.336 |
| PRPF8 | Inhibit | −2.0788 | 0.0159 | 0.1593 | −2.1397 | 0.0179 | 0.1239 |
| PTGES2 | Inhibit | −1.9137 | 0.0278 | 0.2201 | −1.0746 | 0.811 | 1 |
| RAD18 | Inhibit | −2.1129 | 0.0032 | 0.0615 | −1.7251 | 0.0354 | 0.1551 |
| SF3A1 | Inhibit | −1.598 | 0.0042 | 0.0729 | −1.2281 | 0.2111 | 0.4418 |
| SLC12A2 | Inhibit | −2.8366 | 0.0039 | 0.0697 | −3.5987 | 0.0011 | 0.0373 |
| SMTN | Inhibit | −1.8432 | 0.0398 | 0.2725 | −1.2994 | 0.3927 | 0.6593 |
| SQLE | Inhibit | −4.0941 | 0.0396 | 0.2717 | −4.8892 | 0.0296 | 0.1404 |
| SREBF2 | Inhibit | −2.3929 | 0.0032 | 0.0615 | −3.5164 | 0.0001 | 0.0209 |
| SSBP1 | Inhibit | −1.5752 | 0.0094 | 0.1156 | 1.0074 | 0.9665 | 1 |
| TMEM158 | Inhibit | −1.6002 | 0.044 | 0.2897 | 1.4394 | 0.1352 | 0.3357 |
| TYMP | Inhibit | −2.6432 | 0.0448 | 0.2928 | 1.469 | 0.4412 | 0.7111 |
| UNC5B | Inhibit | −2.3093 | 0.0267 | 0.2143 | −1.5396 | 0.2666 | 0.5132 |

Example 13—Cytokine mRNA Increases CD4+ and CD8+ T Cells in Both Treated and Untreated Tumors Mice bearing B16F10 tumors on the left and right flank received a single intratumoral injection of 80 µg of mRNA (20 µg/target) into right tumor which was initiated with 0.5×10^6 cells only one of the tumors (treated), while the other tumor initiated with 0.25×10^6 cells remained untreated. At seven days post intratumoral mRNA injection, both the tumors were collected and processed for IHC (Immunofluorescence microscopy) staining with antibodies for CD4+, CD8+, and FoxP3+ cells. Mice from tumors in FIGS. 28A and 28B were treated with cytokine mRNA, while mice from tumors in FIGS. 28C and D were treated with control mRNA. Panels A and C are from the tumors injected with mRNA, while panels B and D are from the corresponding contralateral tumor not injected. (FIGS. 28A-D). For both the cytokine mRNA treated and control mRNA treated groups 5 tumors injected with RNA and the corresponding 5 contralateral tumors uninjected were subjected to immunofluorescent staining for CD4+, CD8+, FOXP3+ cells. The relative frequency and ratio of cells are plotted in FIGS. 28E, F, G. The results indicate that a cytokine mRNA mixture of IL-15 sushi, GM-CSF, IFNα, and IL-12sc (SEQ ID NOs: 59, 53, 41, and 47) increases CD8+ and CD4+ T cells infiltration leading to altering the CD8+/Treg ratio. An increase in immune infiltration occurred in both the treated and untreated tumors, supporting the notion that local intratumoral treatment has systemic immune modulatory effects.

Example 14—mRNA is Expressed in Both Tumor and Infiltrating Immune Cells

Mice bearing a single B16F10 tumor received a single intratumoral injection with mRNA encoding the Thy1.1 protein (FIG. 29A-G). Approximately 18 hrs after intratumoral injection the tumor was dissociated, stained with a panel of antibodies and flow cytometry was performed to define cells expressing Thy1.1 protein. The results indicate that both tumor and immune cells take up and express the mRNA.

Example 15—Dose Dependent Tumor Expression and PD Response Following Intratumoral Cytokine mRNA Injection Mice bearing B16F10 tumors received a single mRNA injection with 80, 8 or 0.8 µg of a cytokine mRNA mixture of IL-15 sushi, GM-CSF, IFNα, and IL-12sc (SEQ ID Nos: 59, 53, 41, and 47). Approximately 6 hrs after the intratumoral injection, the tumor was removed and lysed, and levels of IL-15 sushi, GM-CSF, IFNα, and IL-12sc, IFN-gamma and IP-10 were quantified in the tumor lysate. FIGS. 30A-F show that the cytokine mRNA was expressed intratumorally in a dose-dependent manner.

In a separate experiment, mice bearing B16F10 tumors received a single mRNA injection with 80, 8 or 0.8 ug of a cytokine mRNA mixture of IL-15 sushi, GM-CSF, IFNα, and IL-12sc (SEQ ID Nos: 59, 53, 41, and 47). At seven days following intratumoral cytokine mRNA injection, the tumors were dissociated, stained with a panel of antibodies, and analyzed by flow cytometry. The antibodies used were against murine: CD45, CD4, CD3, CD8, CD279, IFN-gamma, TNFalpha, FOXP3, Granzyme B). The results indicate that treatment with the cytokine mRNA mixture altered the CD8+/Treg ratio (FIG. 31A-B), led to increased frequency of polyfunctional CD8+ T cells in the tumor microenvironment (FIG. 31C-D), increased PD-L1 on infiltrating myeloid cells (FIG. 31E), and increased levels of PD-1 on infiltrating CD8+ T cells (FIG. 31F).

In a further experiment, mice bearing B16F10 tumors on the left and right flank received a single intratumoral injection of a cytokine mRNA mixture of IL-15 sushi, GM-CSF, IFNα, and IL-12sc (SEQ ID Nos: SEQ ID NOs: 59, 53, 41, and 47) or control mRNA into only one of the tumors (treated), while the other tumor remained untreated. At seven days post intratumoral mRNA injection, the injected tumor was collected and processed for flow cytometry staining with antibodies for CD45+, CD8+, CD3+, and Granzyme B. The results indicate that the cytokine mRNA mixture increased the frequency of intratumoral Granzyme B CD8+ T cells in the tumor (FIG. 31G-H).

Example 16—Intratumorally Injected mRNA is Primarily Expressed in the Tumor

Mice bearing B16F10 tumors received a single intratumoral injection of 50 µg mRNA encoding firefly luciferase. At 6 and 24-hour time points, 3 mice were sacrificed and tumor, liver, spleen, tumor draining lymph node (TDLN) and non-tumor draining lymph node (NDLN) were analyzed ex vivo for luciferase expression. FIGS. 32A-B show that luciferase expression was highest in the tumor, in which expression was greater than 100-fold above any other tissue.

Example 17—CD4+, CD8+, and NK Cells Contribute to the Anti-Tumor Activity of Cytokine mRNA in B16F10 Model Groups of mice bearing B16F10 tumors were treated with 100 µg of depleting antibodies (anti-CD4, anti-CD8, anti-NK1.1) by intraperitoneal injection once a week for 4 weeks total. Antibody mediated cellular depletion was initiated one day prior to treatment with an 80 µg cytokine mRNA mixture of IL-15 sushi, GM-CSF, IFNα, and IL-12sc (SEQ ID Nos: 59, 53, 41, and 47). The effect of antibody depletion on overall survival was monitored. The results, shown in FIG. 34, indicate that individual depletion CD8+, CD4+, or NK cells reduced, to varying degrees, the anti-tumor activity and overall survival of the cytokine mRNA.

Example 18—Antitumor Activity of Cytokine mRNAs is not Observed in IFN-Gamma-Deficient Mice WT C57BL6J mice and C57BL6J mice deficient for the murine IFNγ (IFNγ KO) were implanted with B16F10 tumor cells as described in Example 1. Mice were treated by intratumoral injection with 80 µg (20 µg/target) cytokine mRNA mixture of IL-15 sushi, GM-CSF, IFNα, and IL-12sc (SEQ ID Nos: 59, 53, 41, and 47) or 80 µg control mRNA, and overall survival was monitored. The results, depicted in FIG. 35, indicate that mice lacking IFNγ did not exhibit a detectable antitumor response when treated with the cytokine mRNA.

We claim:

1. A composition comprising RNA encoding an IL-12sc protein, RNA encoding an IL-15 sushi protein, RNA encoding an IFNα protein, and RNA encoding a GM-CSF protein, wherein each RNA comprises a modified nucleoside in place of each uridine, wherein the modified nucleoside is pseudouridine (ψ), N1-methyl-pseudouridine (m1ψ), 5-methyl-uridine (m5U), or a combination thereof, and wherein the IL-12sc protein comprises an amino acid sequence having at least 95% identity to the amino acid sequence of SEQ ID NO: 14;

the IL-15 sushi protein comprises an amino acid sequence having at least 95% identity to the amino acid sequence of SEQ ID NO: 24 the IFNα protein comprises an amino acid sequence having at least 95% identity to the amino acid sequence of SEQ ID NO: 19; and the GM-CSF protein comprises an amino acid sequence having at least 95% identity to the amino acid sequence of SEQ ID NO: 27.

2. The composition of claim 1, wherein each of the RNAs in the composition encodes a cytokine, and the cytokines encoded by the RNAs in the composition consist of the IL-12sc protein, the IL-15 sushi protein, the IFNα protein, and the GM-CSF protein.

3. The composition of claim 1, wherein the IFNα protein is an IFNα2b protein.

4. The composition of claim 1, wherein the RNA encoding an IL-12sc protein comprises a nucleotide sequence having at least 95% identity to the nucleotide sequence of SEQ ID NO: 17 or 18.

5. The composition of claim 1, wherein (i) the RNA encoding an IL-12sc protein comprises the nucleotide sequence of SEQ ID NO: 18; and/or (ii) the IL-12sc protein comprises the amino acid sequence of SEQ ID NO: 14.

6. The composition of claim 1, wherein the RNA encoding an IL-12sc protein comprises the nucleotide sequence of SEQ ID NO: 18 with an N1-methyl-pseudouridine (m1ψ) in place of each uridine.

7. The composition of claim 1, wherein the RNA encoding an IL-15 sushi protein comprises a nucleotide sequence having at least 95% identity to the nucleotide sequence of SEQ ID NO: 26.

8. The composition of claim 1, wherein (i) the RNA encoding an IL-15 sushi protein comprises the nucleotide sequence of SEQ ID NO: 26; and/or (ii) the IL-15 sushi protein comprises the amino acid sequence of SEQ ID NO: 24.

9. The composition of claim 1, wherein the RNA encoding an IL-15 sushi protein comprises the nucleotide sequence of SEQ ID NO: 26 with an N1-methyl-pseudouridine (m1ψ) in place of each uridine.

10. The composition of claim 1, wherein the RNA encoding an IFNα protein comprises a nucleotide sequence having at least 95% identity to the nucleotide sequence of SEQ ID NO: 22 or 23.

11. The composition of claim 1, wherein (i) the RNA encoding an IFNα protein comprises the nucleotide sequence of SEQ ID NO: 23; and/or (ii) the IFNα protein comprises the amino acid sequence of SEQ ID NO: 19.

12. The composition of claim 1, wherein the RNA encoding an IFNα protein comprises the nucleotide sequence of SEQ ID NO: 23 with an N1-methyl-pseudouridine (m1ψ) in place of each uridine.

13. The composition of claim 1, wherein the RNA encoding a GM-CSF protein comprises a nucleotide sequence having at least 95% identity to the nucleotide sequence of SEQ ID NO: 29.

14. The composition of claim 1, wherein (i) the RNA encoding a GM-CSF protein comprises the nucleotide sequence of SEQ ID NO: 29; and/or (ii) the GM-CSF protein comprises the amino acid sequence of SEQ ID NO: 27.

15. The composition of claim 1, wherein the RNA encoding a GM-CSF protein comprises the nucleotide sequence of SEQ ID NO: 29 with an N1-methyl-pseudouridine (m1ψ) in place of each uridine.

16. The composition of claim 1, wherein each RNA comprises an N1-methyl-pseudouridine (m1ψ) in place of each uridine.

17. The composition of claim 1, wherein at least one of the RNAs comprises a 5' cap comprising $m_2^{7,3'\text{-}O}Gppp(m_1^{2'\text{-}O})ApG$ or 3'-O-Me-m$^7$G(5')ppp(5')G.

18. The composition of claim 1, wherein at least one of the RNAs comprises a 5' UTR comprising a nucleotide sequence having at least 80% identity to a nucleotide sequence of SEQ ID NO: 2, 4, or 6.

19. The composition of claim 1, wherein at least one of the RNAs comprises a 3' UTR comprising a nucleotide sequence having at least 80% identity to the nucleotide sequence of SEQ ID NO: 8.

20. The composition of claim 1, wherein at least one RNA comprises a poly-A tail of at least 100 nucleotides.

21. The composition of claim 20, wherein the poly-A tail comprises the poly-A tail shown in SEQ ID NO: 78.

22. The composition of claim 2, wherein the coding sequence of the RNA encoding an IL-12sc protein consists of the sequence of SEQ ID NO: 18 with an N1-methyl-pseudouridine (m1ψ) in place of each uridine, the coding sequence of the RNA encoding an IL-15 sushi protein consists of the sequence of SEQ ID NO: 26 with an N1-methyl-pseudouridine (m1ψ) in place of each uridine, the coding sequence of the RNA encoding an IFNα protein consists of the sequence of SEQ ID NO: 23 with an N1-methyl-pseudouridine (m1ψ) in place of each uridine, and the coding sequence of the RNA encoding a GM-CSF protein consists of the sequence of SEQ ID NO: 29 with an N1-methyl-pseudouridine (m1ψ) in place of each uridine,
wherein each of the RNAs comprises:
a 5' cap comprising $m_2^{7,3'\text{-}P}Gppp(m_1^{2'\text{-}O})ApG$ or 3'-O-Me-m$^7$G(5')ppp(5')G;
a 5' UTR comprising the nucleotide sequence of SEQ ID NO: 2, 4, or 6;
a 3' UTR comprising the nucleotide sequence of SEQ ID NO: 8; and
a poly-A tail comprising the nucleotide sequence of SEQ ID NO: 78; and
wherein the molar ratio or weight ratio of the RNAs in the composition is 1:1:1:1.

23. A pharmaceutical composition comprising the composition of claim 1 and a pharmaceutically acceptable carrier, diluent, and/or excipient.

24. The pharmaceutical composition of claim 23 comprising a pharmaceutically acceptable aqueous solution.

25. The pharmaceutical composition of claim 24, wherein the pharmaceutically acceptable aqueous solution is Ringer's solution.

26. The pharmaceutical composition of claim 23, comprising a lipid moiety complexed with the RNAs.

27. The pharmaceutical composition of claim 26, wherein the lipid moiety is a liposome or lipoplex comprising a cationic lipid and a neutral lipid.

28. A kit comprising the composition of claim 1.

29. A kit comprising RNA encoding an IL-12sc protein, RNA encoding an IL-15 sushi protein, RNA encoding an IFNα protein, and RNA encoding a GM-CSF protein, wherein the RNAs are not in the same container, wherein each RNA comprises a modified nucleoside in place of each uridine, wherein the modified nucleoside is pseudouridine (ψ), N1-methyl-pseudouridine (m1ψ), 5-methyl-uridine (m5U), or a combination thereof, and wherein
the IL-12sc protein comprises an amino acid sequence having at least 95% identity to the amino acid sequence of SEQ ID NO: 14;
the IL-15 sushi protein comprises an amino acid sequence having at least 95% identity to the amino acid sequence of SEQ ID NO: 24
the IFNα protein comprises an amino acid sequence having at least 95% identity to the amino acid sequence of SEQ ID NO: 19; and
the GM-CSF protein comprises an amino acid sequence having at least 95% identity to the amino acid sequence of SEQ ID NO: 27.

30. The composition of claim 16, wherein
the IL-12sc protein comprises an amino acid sequence having the amino acid sequence of SEQ ID NO: 14;
the IL-15 sushi protein comprises an amino acid sequence having the amino acid sequence of SEQ ID NO: 24;
the IFNα protein comprises an amino acid sequence having the amino acid sequence of SEQ ID NO: 19; and
the GM-CSF protein comprises an amino acid sequence having the amino acid sequence of SEQ ID NO: 27.

* * * * *